United States Patent
Martin et al.

(10) Patent No.: US 9,795,140 B2
(45) Date of Patent: *Oct. 24, 2017

(54) MOLECULES HAVING PESTICIDAL UTILITY, AND INTERMEDIATES, COMPOSITIONS, AND PROCESSES, RELATED THERETO

(71) Applicant: Dow AgroSciences LLC, Indianapolis, IN (US)

(72) Inventors: Timothy P. Martin, Noblesville, IN (US); Joseph D. Eckelbarger, Carmel, IN (US); Ronald Ross, Jr., Zionsville, IN (US); Kyle DeKorver, Grandville, MI (US); Ronald J. Heemstra, Fishers, IN (US); Daniel I. Knueppel, Zionsville, IN (US); Peter Vednor, Carmel, IN (US); Ricky Hunter, Westfield, IN (US); David A. Demeter, Fishers, IN (US); Tony K. Trullinger, Westfield, IN (US); Erich Baum, Greenwood, IN (US); Zoltan Benko, Indianapolis, IN (US); Nakyen Choy, Carmel, IN (US); Gary Crouse, Noblesville, IN (US); John F. Daeuble, Sr., Carmel, IN (US); Fangzheng Li, Carmel, IN (US); Jeff Nissen, Indianapolis, IN (US); Michelle Riener, Newtonville, MA (US); Tom Sparks, Greenfield, IN (US); Frank Wessels, Indianapolis, IN (US); Maurice Yap, Zionsville, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/092,646

(22) Filed: Apr. 7, 2016

(65) Prior Publication Data

US 2016/0302418 A1 Oct. 20, 2016

Related U.S. Application Data

(60) Provisional application No. 62/148,818, filed on Apr. 17, 2015, provisional application No. 62/148,824, (Continued)

(51) Int. Cl.
*A01N 53/00* (2006.01)
*A01N 43/90* (2006.01)
(Continued)

(52) U.S. Cl.
CPC ............ *A01N 53/00* (2013.01); *A01N 37/22* (2013.01); *A01N 37/34* (2013.01); *A01N 41/10* (2013.01); *A01N 43/40* (2013.01); *A01N 43/60* (2013.01); *A01N 43/653* (2013.01); *A01N 43/707* (2013.01); *A01N 43/82* (2013.01); *A01N 43/90* (2013.01); *C07C 233/63* (2013.01); *C07C 233/65* (2013.01); *C07C 237/22* (2013.01);
(Continued)

(58) Field of Classification Search
None
See application file for complete search history.

(56) References Cited

U.S. PATENT DOCUMENTS 7,754,717 B2 * 7/2010 Dimauro ............. C07D 213/75
514/248
8,067,599 B2 * 11/2011 Honold ............... C07D 471/04
546/113

(Continued)

FOREIGN PATENT DOCUMENTS

| WO | 2016168056 A1 | 10/2016 |
| WO | 2016168058 A1 | 10/2016 |
| WO | 2016168059 A1 | 10/2016 |

OTHER PUBLICATIONS

A. E. Sheshenev, et. al.: "Generation and stereoselective transformations of 3-phenylcyclopropene", Tetrahedron, vol. 65, No. 48, Sep. 30, 2009, pp. 10036 to 10046, Elsevier Science Publishers, Amsterdam, NL.

*Primary Examiner* — Brian J Davis
(74) *Attorney, Agent, or Firm* — Carl D. Corvin

(57) ABSTRACT

This disclosure relates to the field of molecules having pesticidal utility against pests in Phyla Arthropoda, Mollusca, and Nematoda, processes to produce such molecules, intermediates used in such processes, pesticidal compositions containing such molecules, and processes of using such pesticidal compositions against such pests. These pesticidal compositions may be used, for example, as acaricides, insecticides, miticides, molluscicides, and nematicides. This document discloses molecules having the following formula ("Formula One").

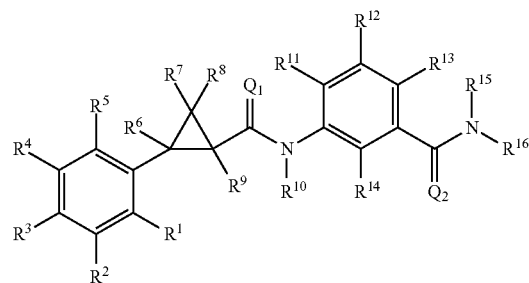

Formula One

20 Claims, No Drawings

Related U.S. Application Data filed on Apr. 17, 2015, provisional application No. 62/148,830, filed on Apr. 17, 2015, provisional application No. 62/148,837, filed on Apr. 17, 2015, provisional application No. 62/148,809, filed on Apr. 17, 2015, provisional application No. 62/148,814, filed on Apr. 17, 2015.

(51) Int. Cl.

| | |
|---|---|
| C07D 207/273 | (2006.01) |
| A01N 43/82 | (2006.01) |
| C07D 307/33 | (2006.01) |
| C07D 277/36 | (2006.01) |
| C07D 263/26 | (2006.01) |
| C07D 261/12 | (2006.01) |
| C07D 333/48 | (2006.01) |
| C07D 307/52 | (2006.01) |
| C07D 277/30 | (2006.01) |
| C07D 213/56 | (2006.01) |
| C07C 237/22 | (2006.01) |
| C07D 333/60 | (2006.01) |
| C07D 233/80 | (2006.01) |
| C07D 487/04 | (2006.01) |
| A01N 43/707 | (2006.01) |
| A01N 43/653 | (2006.01) |
| A01N 43/60 | (2006.01) |
| A01N 43/40 | (2006.01) |
| A01N 41/10 | (2006.01) |
| A01N 37/34 | (2006.01) |
| A01N 37/22 | (2006.01) |
| C07D 253/07 | (2006.01) |
| C07D 241/20 | (2006.01) |
| C07C 317/14 | (2006.01) |
| C07C 233/65 | (2006.01) |
| C07C 233/63 | (2006.01) |
| C07D 209/49 | (2006.01) |
| C07C 381/10 | (2006.01) |
| C07D 205/04 | (2006.01) |
| C07C 237/42 | (2006.01) |
| C07D 207/10 | (2006.01) |
| C07D 207/452 | (2006.01) |
| C07C 255/29 | (2006.01) |
| C07C 255/57 | (2006.01) |
| C07D 285/06 | (2006.01) |
| C07D 295/32 | (2006.01) |
| C07D 305/08 | (2006.01) |
| C07C 255/46 | (2006.01) |
| C07D 213/75 | (2006.01) |
| C07C 255/60 | (2006.01) |
| C07C 259/10 | (2006.01) |
| C07D 213/81 | (2006.01) |
| C07D 213/84 | (2006.01) |
| C07D 309/14 | (2006.01) |
| C07D 213/89 | (2006.01) |
| C07D 215/227 | (2006.01) |
| C07C 271/28 | (2006.01) |
| C07C 271/66 | (2006.01) |
| C07D 231/12 | (2006.01) |
| C07D 331/04 | (2006.01) |
| C07D 231/56 | (2006.01) |
| C07D 333/36 | (2006.01) |
| C07D 233/36 | (2006.01) |
| C07C 311/08 | (2006.01) |
| C07C 311/46 | (2006.01) |
| C07D 235/30 | (2006.01) |
| C07C 317/28 | (2006.01) |
| C07C 317/40 | (2006.01) |
| C07C 317/50 | (2006.01) |
| C07C 323/41 | (2006.01) |
| C07C 323/42 | (2006.01) |
| C07C 323/59 | (2006.01) |
| C07D 249/08 | (2006.01) |
| C07C 331/12 | (2006.01) |
| C07D 215/38 | (2006.01) |

(52) U.S. Cl.
CPC .......... *C07C 237/42* (2013.01); *C07C 255/29* (2013.01); *C07C 255/46* (2013.01); *C07C 255/57* (2013.01); *C07C 255/60* (2013.01); *C07C 259/10* (2013.01); *C07C 271/28* (2013.01); *C07C 271/66* (2013.01); *C07C 311/08* (2013.01); *C07C 311/46* (2013.01); *C07C 317/14* (2013.01); *C07C 317/28* (2013.01); *C07C 317/40* (2013.01); *C07C 317/50* (2013.01); *C07C 323/41* (2013.01); *C07C 323/42* (2013.01); *C07C 323/59* (2013.01); *C07C 331/12* (2013.01); *C07C 381/10* (2013.01); *C07D 205/04* (2013.01); *C07D 207/10* (2013.01); *C07D 207/273* (2013.01); *C07D 207/452* (2013.01); *C07D 209/49* (2013.01); *C07D 213/56* (2013.01); *C07D 213/75* (2013.01); *C07D 213/81* (2013.01); *C07D 213/84* (2013.01); *C07D 213/89* (2013.01); *C07D 215/227* (2013.01); *C07D 215/38* (2013.01); *C07D 231/12* (2013.01); *C07D 231/56* (2013.01); *C07D 233/36* (2013.01); *C07D 233/80* (2013.01); *C07D 235/30* (2013.01); *C07D 241/20* (2013.01); *C07D 249/08* (2013.01); *C07D 253/07* (2013.01); *C07D 261/12* (2013.01); *C07D 263/26* (2013.01); *C07D 277/30* (2013.01); *C07D 277/36* (2013.01); *C07D 285/06* (2013.01); *C07D 295/32* (2013.01); *C07D 305/08* (2013.01); *C07D 307/33* (2013.01); *C07D 307/52* (2013.01); *C07D 309/14* (2013.01); *C07D 331/04* (2013.01); *C07D 333/36* (2013.01); *C07D 333/48* (2013.01); *C07D 333/60* (2013.01); *C07D 487/04* (2013.01); *C07C 2601/02* (2017.05); *C07C 2601/04* (2017.05); *C07C 2601/08* (2017.05); *C07C 2601/14* (2017.05)

(56) References Cited

U.S. PATENT DOCUMENTS

| | | | |
|---|---|---|---|
| 8,492,404 B2 * | 7/2013 | Martin | ................ C07D 213/75 514/313 |
| 2002/0068838 A1 | 6/2002 | Demassey et al. | |
| 2014/0171308 A1 | 6/2014 | Lo et al. | |

\* cited by examiner

MOLECULES HAVING PESTICIDAL UTILITY, AND INTERMEDIATES, COMPOSITIONS, AND PROCESSES, RELATED THERETO

CROSS-REFERENCES TO RELATED APPLICATIONS

This application claims the benefit of, and priority from, U.S. provisional application Ser. Nos. 62/148,830; 62/148,837; 62/148,809; 62/148,814; 62/148,818; and 62/148,824; all of which were filed on Apr. 17, 2015. The entire contents of all of the above-identified applications are hereby incorporated by reference into this Application.

FIELD OF THIS DISCLOSURE

This disclosure relates to the field of molecules having pesticidal utility against pests in Phyla Arthropoda, Mollusca, and Nematoda, processes to produce such molecules, intermediates used in such processes, pesticidal compositions containing such molecules, and processes of using such pesticidal compositions against such pests. These pesticidal compositions may be used, for example, as acaricides, insecticides, miticides, molluscicides, and nematicides.

BACKGROUND OF THIS DISCLOSURE

"Many of the most dangerous human diseases are transmitted by insect vectors" (Rivero et al.). "Historically, malaria, dengue, yellow fever, plague, filariasis, louse-borne typhus, trypanomiasis, leishmaniasis, and other vector borne diseases were responsible for more human disease and death in the 17th through the early 20th centuries than all other causes combined" (Gubler). Vector-borne diseases are responsible for about 17% of the global parasitic and infectious diseases. Malaria alone causes over 800,000 deaths a year, 85% of which occur in children under five years of age. Each year there are about 50 to about 100 million cases of dengue fever. A further 250,000 to 500,000 cases of dengue hemorrhagic fever occur each year (Matthews). Vector control plays a critical role in the prevention and control of infectious diseases. However, insecticide resistance, including resistance to multiple insecticides, has arisen in all insect species that are major vectors of human diseases (Rivero et al.). Recently, more than 550 arthropod species have developed resistance to at least one pesticide (Whalon et al.). Furthermore, the cases of insect resistance continue to exceed by far the number of cases of herbicide and fungicide resistance (Sparks et al.).

Each year insects, plant pathogens, and weeds, destroy more than 40% of all food production. This loss occurs despite the application of pesticides and the use of a wide array of non-chemical controls, such as, crop rotations, and biological controls. If just some of this food could be saved, it could be used to feed the more than three billion people in the world who are malnourished (Pimental).

Plant parasitic nematodes are among the most widespread pests, and are frequently one of the most insidious and costly. It has been estimated that losses attributable to nematodes are from about 9% in developed countries to about 15% in undeveloped countries. However, in the United States of America a survey of 35 States on various crops indicated nematode-derived losses of up to 25% (Nicol et al.).

It is noted that gastropods (slugs and snails) are pests of less economic importance than other arthropods or nematodes, but in certain places, they may reduce yields substantially, severely affecting the quality of harvested products, as well as, transmitting human, animal, and plant diseases. While only a few dozen species of gastropods are serious regional pests, a handful of species are important pests on a worldwide scale. In particular, gastropods affect a wide variety of agricultural and horticultural crops, such as, arable, pastoral, and fiber crops; vegetables; bush and tree fruits; herbs; and ornamentals (Speiser).

Termites cause damage to all types of private and public structures, as well as to agricultural and forestry resources. In 2005, it was estimated that termites cause over US$50 billion in damage worldwide each year (Korb).

Consequently, for many reasons, including those mentioned above, there is an on-going need for the costly (estimated to be about US$256 million per pesticide in 2010), time-consuming (on average about 10 years per pesticide), and difficult, development of new pesticides (CropLife America).

CERTAIN REFERENCES CITED IN THIS DISCLOSURE

CropLife America, The Cost of New Agrochemical Product Discovery, Development & Registration, and Research & Development predictions for the Future, 2010.

Drewes, M., Tietjen, K., Sparks, T. C., High-Throughput Screening in Agrochemical Research, *Modern Methods in Crop Protection Research*, Part I, *Methods for the Design and Optimization of New Active Ingredients*, Edited by Jeschke, P., Kramer, W., Schirmer, U., and Matthias W., p. 1-20, 2012.

Gubler, D., Resurgent Vector-Borne Diseases as a Global Health Problem, Emerging Infectious Diseases, Vol. 4, No. 3, p. 442-450, 1998.

Korb, J., Termites, *Current Biology*, Vol. 17, No. 23, 2007.

Matthews, G., Integrated Vector Management: Controlling Vectors of Malaria and Other Insect Vector Borne Diseases, Ch. 1, p. 1, 2011.

Nicol, J., Turner S., Coyne, L., den Nijs, L., Hocksland, L., Tahna-Maafi, Z., Current Nematode Threats to World Agriculture, *Genomic and Molecular Genetics of Plant—Nematode Interactions*, p. 21-43, 2011.

Pimental, D., Pest Control in World Agriculture, *Agricultural Sciences*—Vol. II, 2009.

Rivero, A., Vezilier, J., Weill, M., Read, A., Gandon, S., Insect Control of Vector-Borne Diseases: When is Insect Resistance a Problem? *Public Library of Science Pathogens*, Vol. 6, No. 8, p. 1-9, 2010.

Sparks T. C., Nauen R., IRAC: Mode of action classification and insecticide resistance management, *Pesticide Biochemistry and Physiology* (2014) available online 4 Dec. 2014.

Speiser, B., Molluscicides, *Encyclopedia of Pest Management*, Ch. 219, p. 506-508, 2002.

Whalon, M., Mota-Sanchez, D., Hollingworth, R., Analysis of Global Pesticide Resistance in Arthropods, *Global Pesticide Resistance in Arthropods*, Ch. 1, p. 5-33, 2008.

DEFINITIONS USED IN THIS DISCLOSURE

The examples given in these definitions are generally non-exhaustive and must not be construed as limiting this disclosure. It is understood that a substituent should comply with chemical bonding rules and steric compatibility constraints in relation to the particular molecule to which it is attached. These definitions are only to be used for the purposes of this disclosure.

The phrase "active ingredient" means a material having activity useful in controlling pests, and/or that is useful in helping other materials have better activity in controlling pests, examples of such materials include, but are not limited to, acaricides, algicides, antifeedants, avicides, bactericides, bird repellents, chemosterilants, fungicides, herbicide safeners, herbicides, insect attractants, insect repellents, insecticides, mammal repellents, mating disrupters, molluscicides, nematicides, plant activators, plant growth regulators, rodenticides, synergists, and virucides (see alanwood.net). Specific examples of such materials include, but are not limited to, the materials listed in active ingredient group alpha.

The phrase "active ingredient group alpha" (hereafter "AIGA") means collectively the following materials:

(1) (3-ethoxypropyl)mercury bromide, 1,2-dibromoethane, 1,2-dichloroethane, 1,2-dichloropropane, 1,3-dichloropropene, 1-MCP, 1-methylcyclopropene, 1-naphthol, 2-(octylthio)ethanol, 2,3,3-TPA, 2,3,5-tri-iodobenzoic acid, 2,3,6-TBA, 2,4,5-T, 2,4,5-TB, 2,4,5-TP, 2,4-D, 2,4-DB, 2,4-DEB, 2,4-DEP, 2,4-DES, 2,4-DP, 2,4-MCPA, 2,4-MCPB, 2iP, 2-methoxyethylmercury chloride, 2-phenylphenol, 3,4-DA, 3,4-DB, 3,4-DP, 3,6-dichloropicolinic acid, 4-aminopyridine, 4-CPA, 4-CPB, 4-CPP, 4-hydroxyphenethyl alcohol, 8-hydroxyquinoline sulfate, 8-phenylmercurioxyquinoline, abamectin, abamectin-aminomethyl, abscisic acid, ACC, acephate, acequinocyl, acetamiprid, acethion, acetochlor, acetofenate, acetophos, acetoprole, acibenzolar, acifluorfen, aclonifen, ACN, acrep, acrinathrin, acrolein, acrylonitrile, acypetacs, afidopyropen, afoxolaner, alachlor, alanap, alanycarb, albendazole, aldicarb, aldicarb sulfone, aldimorph, aldoxycarb, aldrin, allethrin, allicin, allidochlor, allosamidin, alloxydim, allyl alcohol, allyxycarb, alorac, alpha-cypermethrin, alpha-endosulfan, alphamethrin, altretamine, aluminium phosphide, aluminum phosphide, ametoctradin, ametridione, ametryn, ametryne, amibuzin, amicarbazone, amicarthiazol, amidithion, amidoflumet, amidosulfuron, aminocarb, aminocyclopyrachlor, aminopyralid, aminotriazole, amiprofos-methyl, amiprophos, amiprophos-methyl, amisulbrom, amiton, amitraz, amitrole, ammonium sulfamate, amobam, amorphous silica gel, amorphous silicon dioxide, ampropylfos, AMS, anabasine, ancymidol, anilazine, anilofos, anisuron, anthraquinone, antu, apholate, aramite, arprocarb, arsenous oxide, asomate, aspirin, asulam, athidathion, atraton, atrazine, aureofungin, avermectin B1, AVG, aviglycine, azaconazole, azadirachtin, azafenidin, azamethiphos, azidithion, azimsulfuron, azinphosethyl, azinphos-ethyl, azinphosmethyl, azinphos-methyl, aziprotryn, aziprotryne, azithiram, azobenzene, azocyclotin, azothoate, azoxystrobin, bachmedesh, barban, barbanate, barium hexafluorosilicate, barium polysulfide, barium silicofluoride, barthrin, basic copper carbonate, basic copper chloride, basic copper sulfate, BCPC, beflubutamid, benalaxyl, benalaxyl-M, benazolin, bencarbazone, benclothiaz, bendaqingbingzhi, bendiocarb, bendioxide, benefin, benfluralin, benfuracarb, benfuresate, benmihuangcaoan, benodanil, benomyl, benoxacor, benoxafos, benquinox, bensulfuron, bensulide, bensultap, bentaluron, bentazon, bentazone, benthiavalicarb, benthiazole, benthiocarb, bentranil, benzadox, benzalkonium chloride, benzamacril, benzamizole, benzamorf, benzene hexachloride, benzfendizone, benzimine, benzipram, benzobicyclon, benzoepin, benzofenap, benzofluor, benzohydroxamic acid, benzomate, benzophosphate, benzothiadiazole, benzovindiflupyr, benzoximate, benzoylprop, benzthiazuron, benzuocaotong, benzyl benzoate, benzyladenine, berberine, beta-cyfluthrin, beta-cypermethrin, bethoxazin, BHC, bialaphos, bicyclopyrone, bifenazate, bifenox, bifenthrin, bifujunzhi, bilanafos, binapacryl, bingqingxiao, bioallethrin, bioethanomethrin, biopermethrin, bioresmethrin, biphenyl, bisazir, bismerthiazol, bismerthiazol-copper, bisphenylmercury methylenedi(x-naphthalene-y-sulphonate), bispyribac, bistrifluron, bisultap, bitertanol, bithionol, bixafen, blasticidin-S, borax, Bordeaux mixture, boric acid, boscalid, BPPS, brassinolide, brassinolide-ethyl, brevicomin, brodifacoum, brofenprox, brofenvalerate, broflanilide, brofluthrinate, bromacil, bromadiolone, bromchlophos, bromethalin, bromethrin, bromfenvinfos, bromoacetamide, bromobonil, bromobutide, bromociclen, bromocyclen, bromo-DDT, bromofenoxim, bromofos, bromomethane, bromophos, bromophos-ethyl, bromopropylate, bromothalonil, bromoxynil, brompyrazon, bromuconazole, bronopol, BRP, BTH, bucarpolate, bufencarb, buminafos, bupirimate, buprofezin, Burgundy mixture, busulfan, busulphan, butacarb, butachlor, butafenacil, butam, butamifos, butane-fipronil, butathiofos, butenachlor, butene-fipronil, butethrin, buthidazole, buthiobate, buthiuron, butifos, butocarboxim, butonate, butopyronoxyl, butoxycarboxim, butralin, butrizol, butroxydim, buturon, butylamine, butylate, butylchlorophos, butylene-fipronil, cacodylic acid, cadusafos, cafenstrole, calciferol, calcium arsenate, calcium chlorate, calcium cyanamide, calcium cyanide, calcium polysulfide, calvinphos, cambendichlor, camphechlor, camphor, captafol, captan, carbam, carbamorph, carbanolate, carbaril, carbaryl, carbasulam, carbathion, carbendazim, carbendazol, carbetamide, carbofenotion, carbofuran, carbon disulfide, carbon tetrachloride, carbonyl sulfide, carbophenothion, carbophos, carbosulfan, carboxazole, carboxide, carboxin, carfentrazone, carpropamid, cartap, carvacrol, carvone, CAVP, CDAA, CDEA, CDEC, cellocidin, CEPC, ceralure, cerenox, cevadilla, Cheshunt mixture, chinalphos, chinalphos-methyl, chinomethionat, chinomethionate, chiralaxyl, chitosan, chlobenthiazone, chlomethoxyfen, chloralose, chloramben, chloramine phosphorus, chloramphenicol, chloraniformethan, chloranil, chloranocryl, chlorantraniliprole, chlorazifop, chlorazine, chlorbenside, chlorbenzuron, chlorbicyclen, chlorbromuron, chlorbufam, chlordane, chlordecone, chlordimeform, chlorempenthrin, chloretazate, chlorethephon, chlorethoxyfos, chloreturon, chlorfenac, chlorfenapyr, chlorfenazole, chlorfenethol, chlorfenidim, chlorfenprop, chlorfenson, chlorfensulphide, chlorfenvinphos, chlorfenvinphos-methyl, chlorfluazuron, chlorflurazole, chlorflurecol, chlorfluren, chlorflurenol, chloridazon, chlorimuron, chlorinate, chlor-IPC, chlormephos, chlormequat, chlormesulone, chlormethoxynil, chlornidine, chlornitrofen, chloroacetic acid, chlorobenzilate, chlorodinitronaphthalenes, chlorofénizon, chloroform, chloromebuform, chloromethiuron, chloroneb, chlorophacinone, chlorophos, chloropicrin, chloropon, chloropropylate, chlorothalonil, chlorotoluron, chloroxifenidim, chloroxuron, chloroxynil, chlorphonium, chlorphoxim, chlorprazophos, chlorprocarb, chlorpropham, chlorpyrifos, chlorpyrifos-methyl, chlorquinox, chlorsulfuron, chlorthal, chlorthiamid, chlorthiophos, chlortoluron, chlozolinate, chltosan, cholecalciferol, choline chloride, chromafenozide, cicloheximide, cimectacarb, cimetacarb, cinerin I, cinerin II, cinerins, cinidon-ethyl, cinmethylin, cinosulfuron, cintofen, ciobutide, cisanilide, cismethrin, clacyfos, clefoxydim, clenpirin, clenpyrin, clethodim, climbazole, cliodinate, clodinafop, cloethocarb, clofencet, clofenotane, clofentezine, clofenvinfos, clofibric acid, clofop, clomazone, clomeprop, clonitralid, cloprop, cloproxydim, clopyralid, cloquintocet, cloransulam, closantel, clothianidin, clotrimazole, cloxyfonac, cloxylacon, clozylacon, CMA, CMMP, CMP, CMU, codlelure, colecalciferol, colophonate, copper 8-quinolinolate, copper acetate, copper acetoarsenite, copper arsenate, copper carbonate, basic, copper hydroxide, copper naphthenate, copper oleate, copper oxychloride, copper silicate, copper sulfate, copper sulfate, basic, copper zinc chromate, coumachlor, coumafène, coumafos, coumafuryl, coumaphos, coumatetralyl, coumethoxystrobin, coumithoate, coumoxystrobin, CPMC, CPMF, CPPC, credazine, cresol, cresylic acid, crimidine, crotamiton, crotoxyfos, crotoxyphos, crufomate, cryolite, cue-lure, cufraneb, cumyleron, cumyluron, cuprobam, cuprous oxide, curcumenol, CVMP, cyanamide, cyanatryn, cyanazine, cyanofenphos, cyanogen, cyanophos, cyanthoate, cyantraniliprole, cyanuric acid, cyazofamid, cybutryne, cyclafuramid, cyclanilide, cyclaniliprole, cyclethrin, cycloate, cycloheximide, cycloprate, cycloprothrin, cyclopyrimorate, cyclosulfamuron, cycloxydim, cycluron, cyenopyrafen, cyflufenamid, cyflumetofen, cyfluthrin, cyhalofop, cyhalothrin, cyhexatin, cymiazole, cymoxanil, cyometrinil, cypendazole, cypermethrin, cyperquat, cyphenothrin, cyprazine, cyprazole, cyproconazole, cyprodinil, cyprofuram, cypromid, cyprosulfamide, cyromazine, cythioate, cytrex, daimuron, dalapon, daminozide, dayoutong, dazomet, DBCP, d-camphor, DCB, DCIP, DCPA, DCPTA, DCU, DDD, DDPP, DDT, DDVP, debacarb, decafentin, decamethrin, decarbofuran, deet, dehydroacetic acid, deiquat, delachlor, delnav, deltamethrin, demephion, demephion-O, demephion-S, demeton, demeton-methyl, demeton-O, demeton-O-methyl, demeton-S, demeton-S-methyl, demeton-S-methyl sulphone, demeton-S-methylsulphon, DEP, depalléthrine, derris, desmedipham, desmetryn, desmetryne, d-fanshiluquebingjuzhi, diafenthiuron, dialifor, dialifos, diallate, diamidafos, dianat, diatomaceous earth, diatomite, diazinon, dibrom, dibutyl phthalate, dibutyl succinate, dicamba, dicapthon, dichlobenil, dichlofenthion, dichlofluanid, dichlone, dichloralurea, dichlorbenzuron, dichlorfenidim, dichlorflurecol, dichlorflurenol, dichlormate, dichlormid, dichloromethane, dicloromezotiaz, dichlorophen, dichlorprop, dichlorprop-P, dichlorvos, dichlozolin, dichlozoline, diclobutrazol, diclocymet, diclofop, diclomezine, dicloran, diclosulam, dicofol, dicophane, dicoumarol, dicresyl, dicrotophos, dicryl, dicumarol, dicyclanil, dicyclonon, dieldrin, dienochlor, diethamquat, diethatyl, diethion, diéthion, diethofencarb, dietholate, diéthon, diethyl pyrocarbonate, diethyltoluamide, difenacoum, difenoconazole, difenopenten, difenoxuron, difenzoquat, difethialone, diflovidazin, diflubenzuron, diflufenican, diflufenicanil, diflufenzopyr, diflumetorim, dikegulac, dilor, dimatif, dimefluthrin, dimefox, dimefuron, dimehypo, dimepiperate, dimetachlone, dimetan, dimethacarb, dimethachlone, dimethachlor, dimethametryn, dimethenamid, dimethenamid-P, dimethipin, dimethirimol, dimethoate, dimethomorph, dimethrin, dimethyl carbate, dimethyl disulfide, dimethyl phthalate, dimethylvinphos, dimetilan, dimexano, dimidazon, dimoxystrobin, dimpylate, dimuron, dinex, dingjunezuo, diniconazole, diniconazole-M, dinitramine, dinitrophenols, dinobuton, dinocap, dinocap-4, dinocap-6, dinocton, dinofenate, dinopenton, dinoprop, dinosam, dinoseb, dinosulfon, dinotefuran, dinoterb, dinoterbon, diofenolan, dioxabenzofos, dioxacarb, dioxathion, dioxation, diphacin, diphacinone, diphenadione, diphenamid, diphenamide, diphenyl sulfone, diphenylamine, diphenylsulphide, diprogulic acid, dipropalin, dipropetryn, dipterex, dipymetitrone, dipyrithione, diquat, disodium tetraborate, disosultap, disparlure, disugran, disul, disulfiram, disulfoton, ditalimfos, dithianon, dithicrofos, dithioether, dithiometon, dithiopyr, diuron, dixanthogen, d-limonene, DMDS, DMPA, DNOC, dodemorph, dodicin, dodine, dofenapyn, doguadine, dominicalure, doramectin, DPC, drazoxolon, DSMA, d-trans-allethrin, d-trans-resmethrin, dufulin, dymron, EBEP, EBP, ebufos, ecdysterone, echlomezol, EDB, EDC, EDDP, edifenphos, eglinazine, emamectin, EMPC, empenthrin, enadenine, endosulfan, endothal, endothall, endothion, endrin, enestroburin, enilconazole, enoxastrobin, ephirsulfonate, EPN, epocholeone, epofenonane, epoxiconazole, eprinomectin, epronaz, EPTC, erbon, ergocalciferol, erlujixiancaoan, esdépalléthrine, esfenvalerate, ESP, esprocarb, etacelasil, etaconazole, etaphos, etem, ethaboxam, ethachlor, ethalfluralin, ethametsulfuron, ethaprochlor, ethephon, ethidimuron, ethiofencarb, ethiolate, ethion, ethiozin, ethiprole, ethirimol, ethoatemethyl, ethobenzanid, ethofumesate, ethohexadiol, ethoprop, ethoprophos, ethoxyfen, ethoxyquin, ethoxysulfuron, ethychlozate, ethyl formate, ethyl pyrophosphate, ethylan, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, ETM, etnipromid, etobenzanid, etofenprox, etoxazole, etridiazole, etrimfos, étrimphos, eugenol, EXD, famoxadone, famphur, fenac, fenamidone, fenaminosulf, fenaminstrobin, fenamiphos, fenapanil, fenarimol, fenasulam, fenazaflor, fenazaquin, fenbuconazole, fenbutatin oxide, fenchlorazole, fenchlorphos, fenclofos, fenclorim, fenethacarb, fenfluthrin, fenfuram, fenhexamid, fenidin, fenitropan, fenitrothion, fénizon, fenjuntong, fenobucarb, fenolovo, fenoprop, fenothiocarb, fenoxacrim, fenoxanil, fenoxaprop, fenoxaprop-P, fenoxasulfone, fenoxycarb, fenpiclonil, fenpirithrin, fenpropathrin, fenpropidin, fenpropimorph, fenpyrazamine, fenpyroximate, fenquinotrione, fenridazon, fenson, fensulfothion, fenteracol, fenthiaprop, fenthion, fenthion-ethyl, fentiaprop, fentin, fentrazamide, fentrifanil, fenuron, fenuron-TCA, fenvalerate, ferbam, ferimzone, ferric phosphate, ferrous sulfate, fipronil, flamprop, flamprop-M, flazasulfuron, flocoumafen, flometoquin, flonicamid, florasulam, fluacrypyrim, fluazifop, fluazifop-P, fluazinam, fluazolate, fluazuron, flubendiamide, flubenzimine, flubrocythrinate, flucarbazone, flucetosulfuron, fluchloralin, flucofuron, flucycloxuron, flucythrinate, fludioxonil, fluénéthyl, fluenetil, fluensulfone, flufenacet, flufenerim, flufenican, flufenoxuron, flufenoxystrobin, flufenprox, flufenpyr, flufenzine, flufiprole, fluhexafon, flumethrin, flumetover, flumetralin, flumetsulam, flumezin, flumiclorac, flumioxazin, flumipropyn, flumorph, flumeturon, fluopicolide, fluopyram, fluorbenside, fluoridamid, fluoroacetamide, fluoroacetic acid, fluorochloridone, fluorodifen, fluoroglycofen, fluoroimide, fluoromide, fluoromidine, fluoronitrofen, fluoroxypyr, fluothiuron, fluotrimazole, fluoxastrobin, flupoxam, flupropacil, flupropadine, flupropanate, flupyradifurone, flupyrsulfuron, fluquinconazole, fluralaner, flurazole, flurecol, flurenol, fluridone, flurochloridone, fluromidine, fluroxypyr, flurprimidol, flursulamid, flurtamone, flusilazole, flusulfamide, flutenzine, fluthiacet, fluthiamide, flutianil, flutolanil, flutriafol, fluvalinate, fluxapyroxad, fluxofenim, folpel, folpet, fomesafen, fonofos, foramsulfuron, forchlorfenuron, formaldehyde, formetanate, formothion, formparanate, fosamine, fosetyl, fosmethilan, fospirate, fosthiazate, fosthietan, frontalin, fthalide, fuberidazole, fucaojing, fucaomi, fujunmanzhi, fulumi, fumarin, funaihecaoling, fuphenthiourea, furalane, furalaxyl, furamethrin, furametpyr, furan tebufenozide, furathiocarb, furcarbanil, furconazole, furconazole-cis, furethrin, furfural, furilazole, furmecyclox, furophanate, furyloxyfen, gamma-BHC, gamma-cyhalothrin, gamma-HCH, genit, gibberellic acid, gibberellin A3, gibberellins, gliftor, glitor, glucochloralose, glufosinate, glufosinate-P, glyodin, glyoxime, glyphosate, glyphosine, gossyplure, grandlure, griseofulvin, guanoctine, guazatine, halacrinate, halauxifen, halfenprox, halofenozide, halosafen, halosulfuron, haloxydine, haloxyfop, haloxyfop-P, haloxyfop-R, HCA, HCB, HCH, hemel, hempa, HEOD, heptachlor, heptafluthrin, heptenophos, heptopargil, herbimycin, herbimycin A, heterophos, hexachlor, hexachloran, hexachloroacetone, hexachlorobenzene, hexachlorobutadiene, hexachlorophene, hexaconazole, hexaflumuron, hexafluoramin, hexaflurate, hexalure, hexamide, hexazinone, hexylthiofos, hexythiazox, HHDN, holosulf, homobrassinolide, huancaiwo, huanchongjing, huangcaoling, huanjunzuo, hydramethylnon, hydrargaphen, hydrated lime, hydrogen cyanamide, hydrogen cyanide, hydroprene, hydroxyisoxazole, hymexazol, hyquincarb, IAA, IBA, IBP, icaridin, imazalil, imazamethabenz, imazamox, imazapic, imazapyr, imazaquin, imazethapyr, imazosulfuron, imibenconazole, imicyafos, imidacloprid, imidaclothiz, iminoctadine, imiprothrin, inabenfide, indanofan, indaziflam, indoxacarb, inezin, infusorial earth, iodobonil, iodocarb, iodofenphos, iodomethane, iodosulfuron, iofensulfuron, ioxynil, ipazine, IPC, ipconazole, ipfencarbazone, iprobenfos, iprodione, iprovalicarb, iprymidam, ipsdienol, ipsenol, IPSP, IPX, isamidofos, isazofos, isobenzan, isocarbamid, isocarbamide, isocarbophos, isocil, isodrin, isofenphos, isofenphos-methyl, isofetamid, isolan, isomethiozin, isonoruron, isopamphos, isopolinate, isoprocarb, isoprocil, isopropalin, isopropazol, isoprothiolane, isoproturon, isopyrazam, isopyrimol, isothioate, isotianil, isouron, isovaledione, isoxaben, isoxachlortole, isoxadifen, isoxaflutole, isoxapyrifop, isoxathion, isuron, ivermectin, ixoxaben, izopamfos, izopamphos, japonilure, japothrins, jasmolin I, jasmolin II, jasmonic acid, jiahuangchongzong, jiajizengxiaolin, jiaxiangjunzhi, jiecaowan, jiecaoxi, jinganmycin A, jodfenphos, juvenile hormone I, juvenile hormone II, juvenile hormone III, kadethrin, kappa-bifenthrin, kappa-tefluthrin, karbutilate, karetazan, kasugamycin, kejunlin, kelevan, ketospiradox, kieselguhr, kinetin, kinoprene, kiralaxyl, kresoxim-methyl, kuicaoxi, lactofen, lambda-cyhalothrin, latilure, lead arsenate, lenacil, lepimectin, leptophos, lianbenjingzhi, lime sulfur, lindane, lineatin, linuron, lirimfos, litlure, looplure, lufenuron, lüxiancaolin, lvdingjunzhi, lvfumijvzhi, lvxiancaolin, lythidathion, M-74, M-81, MAA, magnesium phosphide, malathion, maldison, maleic hydrazide, malonoben, maltodextrin, MAMA, mancopper, mancozeb, mandestrobin, mandipropamid, maneb, matrine, mazidox, MCC, MCP, MCPA, MCPA-thioethyl, MCPB, MCPP, mebenil, mecarbam, mecarbinzid, mecarphon, mecoprop, mecoprop-P, medimeform, medinoterb, medlure, mefenacet, mefenoxam, mefenpyr, mefluidide, megatomoic acid, melissyl alcohol, melitoxin, MEMC, menazon, MEP, mepanipyrim, meperfluthrin, mephenate, mephosfolan, mepiquat, mepronil, meptyldinocap, mercaptodimethur, mercaptophos, mercaptophos thiol, mercaptothion, mercuric chloride, mercuric oxide, mercurous chloride, merphos, merphos oxide, mesoprazine, mesosulfuron, mesotrione, mesulfen, mesulfenfos, mesulphen, metacresol, metaflumizone, metalaxyl, metalaxyl-M, metaldehyde, metam, metamifop, metamitron, metaphos, metaxon, metazachlor, metazosulfuron, metazoxolon, metconazole, metepa, metflurazon, methabenzthiazuron, methacrifos, methalpropalin, metham, methamidophos, methasulfocarb, methazole, methfuroxam, methibenzuron, methidathion, methiobencarb, methiocarb, methiopyrisulfuron, methiotepa, methiozolin, methiuron, methocrotophos, métholcarb, methometon, methomyl, methoprene, methoprotryn, methoprotryne, methoquin-butyl, methothrin, methoxychlor, methoxyfenozide, methoxyphenone, methyl apholate, methyl bromide, methyl eugenol, methyl iodide, methyl isothiocyanate, methyl parathion, methylacetophos, methylchloroform, methyldithiocarbamic acid, methyldymron, methylene chloride, methyl-isofenphos, methylmercaptophos, methylmercaptophos oxide, methylmercaptophos thiol, methylmercury benzoate, methylmercury dicyandiamide, methylmercury pentachlorophenoxide, methylneodecanamide, methylnitrophos, methyltriazothion, metiozolin, metiram, metiram-zinc, metobenzuron, metobromuron, metofluthrin, metolachlor, metolcarb, metometuron, metominostrobin, metosulam, metoxadiazone, metoxuron, metrafenone, metriam, metribuzin, metrifonate, metriphonate, metsulfovax, metsulfuron, mevinphos, mexacarbate, miechuwei, mieshuan, miewenjuzhi, milbemectin, milbemycin oxime, milneb, mima2nan, mipafox, MIPC, mirex, MNAF, moguchun, molinate, molosultap, momfluorothrin, monalide, monisuron, monoamitraz, monochloroacetic acid, monocrotophos, monolinuron, monomehypo, monosulfiram, monosulfuron, monosultap, monuron, monuron-TCA, morfamquat, moroxydine, morphothion, morzid, moxidectin, MPMC, MSMA, MTMC, muscalure, myclobutanil, myclozolin, myricyl alcohol, N-(ethylmercury)-p-toluenesulphonanilide, NAA, NAAm, nabam, naftalofos, naled, naphthalene, naphthaleneacetamide, naphthalic anhydride, naphthalophos, naphthoxyacetic acids, naphthylacetic acids, naphthylindane-1,3-diones, naphthyloxyacetic acids, naproanilide, napropamide, napropamide-M, naptalam, natamycin, NBPOS, neburea, neburon, nendrin, neonicotine, nichlorfos, niclofen, niclosamide, nicobifen, nicosulfuron, nicotine, nicotine sulfate, nifluridide, nikkomycins, NIP, nipyraclofen, nipyralofen, nitenpyram, nithiazine, nitralin, nitrapyrin, nitrilacarb, nitrofen, nitrofluorfen, nitrostyrene, nitrothal-isopropyl, nobormide, nonanol, norbormide, norea, norflurazon, nornicotine, noruron, novaluron, noviflumuron, NPA, nuarimol, nuranone, OCH, octachlorodipropyl ether, octhilinone, o-dichlorobenzene, ofurace, omethoate, o-phenylphenol, orbencarb, orfralure, orthobencarb, ortho-dichlorobenzene, orthosulfamuron, oryctalure, orysastrobin, oryzalin, osthol, osthole, ostramone, ovatron, ovex, oxabetrinil, oxadiargyl, oxadiazon, oxadixyl, oxamate, oxamyl, oxapyrazon, oxapyrazone, oxasulfuron, oxathiapiprolin, oxaziclomefone, oxine-copper, oxine-Cu, oxolinic acid, oxpoconazole, oxycarboxin, oxydemeton-methyl, oxydeprofos, oxydisulfoton, oxyenadenine, oxyfluorfen, oxymatrine, oxytetracycline, oxythioquinox, PAC, paclobutrazol, paichongding, palléthrine, PAP, para-dichlorobenzene, parafluron, paraquat, parathion, parathion-methyl, parinol, Paris green, PCNB, PCP, PCP-Na, p-dichlorobenzene, PDJ, pebulate, pédinex, pefurazoate, pelargonic acid, penconazole, pencycuron, pendimethalin, penfenate, penflufen, penfluron, penoxalin, penoxsulam, pentachlorophenol, pentachlorophenyl laurate, pentanochlor, penthiopyrad, pentmethrin, pentoxazone, perchlordecone, perfluidone, permethrin, pethoxamid, PHC, phenamacril, phenamacril-ethyl, phénaminosulf, phenazine oxide, phénétacarbe, phenisopham, phenkapton, phenmedipham, phenmedipham-ethyl, phenobenzuron, phenothiol, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosametine, phosazetim, phosazetin, phoscyclotin, phosdiphen, phosethyl, phosfolan, phosfolan-methyl, phosglycin, phosmet, phosnichlor, phosphamide, phosphamidon, phosphine, phosphinothricin, phosphocarb, phosphorus, phostin, phoxim, phoxim-methyl, phthalide, phthalophos, phthalthrin, picarbutrazox, picaridin, picloram, picolinafen, picoxystrobin, pimaricin, pindone, pinoxaden, piperalin, piperazine, piperonyl butoxide, piperonyl cyclonene, piperophos, piproctanly, piproctanyl, piprotal, pirimetaphos, pirimicarb, piriminil, pirimioxyphos, pirimiphos-ethyl, pirimiphos-methyl, pival, pivaldione, plifenate, PMA, PMP, polybutenes, polycarbamate, polychlorcamphene, polyethoxyquinoline, polyoxin D, polyoxins, polyoxorim, polythialan, potassium arsenite, potassium azide, potassium cyanate, potassium ethylxanthate, potassium naphthenate, potassium polysulfide, potassium thiocyanate, pp'-DDT, prallethrin, precocene I, precocene II, precocene III, pretilachlor, primidophos, primisulfuron, probenazole, prochloraz, proclonol, procyazine, procymidone, prodiamine, profenofos, profluazol, profluralin, profluthrin, profoxydim, profurite-aminium, proglinazine, prohexadione, prohydrojasmon, promacyl, promecarb, prometon, prometryn, prometryne, promurit, pronamide, propachlor, propafos, propamidine, propamocarb, propanil, propaphos, propaquizafop, propargite, proparthrin, propazine, propetamphos, propham, propiconazole, propidine, propineb, propisochlor, propoxur, propoxycarbazone, propyl isome, propyrisulfuron, propyzamide, proquinazid, prosuler, prosulfalin, prosulfocarb, prosulfuron, prothidathion, prothiocarb, prothioconazole, prothiofos, prothoate, protrifenbute, proxan, prymidophos, prynachlor, psoralen, psoralene, pydanon, pyflubumide, pymetrozine, pyracarbolid, pyraclofos, pyraclonil, pyraclostrobin, pyraflufen, pyrafluprole, pyramat, pyrametostrobin, pyraoxystrobin, pyrasulfotole, pyraziflumid, pyrazolate, pyrazolynate, pyrazon, pyrazophos, pyrazosulfuron, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridaphenthione, pyridate, pyridinitril, pyrifenox, pyrifluquinazon, pyriftalid, pyrimétaphos, pyrimethanil, pyrimicarbe, pyrimidifen, pyriminobac, pyriminostrobin, pyrimiphos-éthyl, pyrimiphos-methyl, pyrimisulfan, pyrimitate, pyrinuron, pyriofenone, pyriprole, pyripropanol, pyriproxyfen, pyrisoxazole, pyrithiobac, pyrolan, pyroquilon, pyroxasulfone, pyroxsulam, pyroxychlor, pyroxyfur, qincaosuan, qingkuling, quassia, quinacetol, quinalphos, quinalphos-methyl, quinazamid, quinclorac, quinconazole, quinmerac, quinoclamine, quinomethionate, quinonamid, quinothion, quinoxyfen, quintiofos, quintozene, quizalofop, quizalofop-P, quwenzhi, quyingding, rabenzazole, rafoxanide, R-diniconazole, rebemide, reglone, renriduron, rescalure, resmethrin, rhodethanil, rhodojaponin-III, ribavirin, rimsulfuron, rizazole, R-metalaxyl, rodéthanil, ronnel, rotenone, ryania, sabadilla, saflufenacil, saijunmao, saisentong, salicylanilide, salifluofen, sanguinarine, santonin, S-bioallethrin, schradan, scilliroside, sebuthylazine, secbumeton, sedaxane, selamectin, semiamitraz, sesamex, sesamolin, sesone, sethoxydim, sevin, shuangjiaancaolin, shuangjianancaolin, S-hydroprene, siduron, sifumijvzhi, siglure, silafluofen, silatrane, silica aerogel, silica gel, silthiofam, silthiopham, silthiophan, silvex, simazine, simeconazole, simeton, simetryn, simetryne, sintofen, S-kinoprene, slaked lime, SMA, S-methoprene, S-metolachlor, sodium arsenite, sodium azide, sodium chlorate, sodium cyanide, sodium fluoride, sodium fluoroacetate, sodium hexafluorosilicate, sodium naphthenate, sodium o-phenylphenoxide, sodium orthophenylphenoxide, sodium pentachlorophenate, sodium pentachlorophenoxide, sodium polysulfide, sodium silicofluoride, sodium tetrathiocarbonate, sodium thiocyanate, solan, sophamide, spinetoram, spinosad, spirodiclofen, spiromesifen, spirotetramat, spiroxamine, stirofos, streptomycin, strychnine, sulcatol, sulcofuron, sulcotrione, sulfallate, sulfentrazone, sulfiram, sulfluramid, sulfodiazole, sulfometuron, sulfosate, sulfosulfuron, sulfotep, sulfotepp, sulfoxaflor, sulfoxide, sulfoxime, sulfur, sulfuric acid, sulfuryl fluoride, sulglycapin, sulphosate, sulprofos, sultropen, swep, tau-fluvalinate, tavron, tazimcarb, TBTO, TBZ, TCA, TCBA, TCMTB, TCNB, TDE, tebuconazole, tebufenozide, tebufenpyrad, tebufloquin, tebupirimfos, tebutam, tebuthiuron, tecloftalam, tecnazene, tecoram, tedion, teflubenzuron, tefluthrin, tefuryltrione, tembotrione, temefos, temephos, tepa, TEPP, tepraloxydim, teproloxydim, terallethrin, terbacil, terbucarb, terbuchlor, terbufos, terbumeton, terbuthylazine, terbutol, terbutryn, terbutryne, terraclor, terramicin, terramycin, tetcyclacis, tetrachloroethane, tetrachlorvinphos, tetraconazole, tetradifon, tetradisul, tetrafluron, tetramethrin, tetra methylfluthrin, tetramine, tetranactin, tetraniliprole, tetrapion, tetrasul, thallium sulfate, thallous sulfate, thenylchlor, theta-cypermethrin, thiabendazole, thiacloprid, thiadiazine, thiadifluor, thiamethoxam, thiameturon, thiapronil, thiazafluron, thiazfluron, thiazone, thiazopyr, thicrofos, thicyofen, thidiazimin, thidiazuron, thiencarbazone, thifensulfuron, thifluzamide, thimerosal, thimet, thiobencarb, thiocarboxime, thiochlorfenphim, thiochlorphenphime, thiocyanatodinitrobenzenes, thiocyclam, thiodan, thiodiazole-copper, thiodicarb, thiofanocarb, thiofanox, thiofluoximate, thiohempa, thiomersal, thiometon, thionazin, thiophanate, thiophanate-ethyl, thiophanate-methyl, thiophos, thioquinox, thiosemicarbazide, thiosultap, thiotepa, thioxamyl, thiram, thiuram, thuringiensin, tiabendazole, tiadinil, tiafenacil, tiaojiean, TIBA, tifatol, tiocarbazil, tioclorim, tioxazafen, tioxymid, tirpate, TMTD, tolclofos-methyl, tolfenpyrad, tolprocarb, tolpyralate, tolyfluanid, tolylfluanid, tolylmercury acetate, tomarin, topramezone, toxaphene, TPN, tralkoxydim, tralocythrin, tralomethrin, tralopyril, transfluthrin, transpermethrin, tretamine, triacontanol, triadimefon, triadimenol, triafamone, triallate, triallate, triamiphos, triapenthenol, triarathene, triarimol, triasulfuron, triazamate, triazbutil, triaziflam, triazophos, triazothion, triazoxide, tribasic copper chloride, tribasic copper sulfate, tribenuron, tribufos, tributyltin oxide, tricamba, trichlamide, trichlopyr, trichlorfon, trichlormetaphos-3, trichloronat, trichloronate, trichlorotrinitrobenzenes, trichlorphon, triclopyr, triclopyricarb, tricresol, tricyclazole, tricyclohexyltin hydroxide, tridemorph, tridiphane, trietazine, trifenmorph, trifenofos, trifloxystrobin, trifloxysulfuron, trifludimoxazin, triflumezopyrim, triflumizole, triflumuron, trifluralin, triflusulfuron, trifop, trifopsime, triforine, trihydroxytriazine, trimedlure, trimethacarb, trimeturon, trinexapac, triphenyltin, triprene, tripropindan, triptolide, tritac, trithialan, triticonazole, tritosulfuron, trunc-call, tuoyelin, uniconazole, uniconazole-P, urbacide, uredepa, valerate, validamycin, validamycin A, valifenalate, valone, vamidothion, vangard, vaniliprole, vernolate, vinclozolin, vitamin D3, warfarin, xiaochongliulin, xinjunan, xiwojunan, xiwojunzhi, XMC, xylachlor, xylenols, xylylcarb, xymiazole, yishijing, zarilamid, zeatin, zengxiaoan, zengxiaolin, zetacypermethrin, zinc naphthenate, zinc phosphide, zinc thiazole, zinc thiozole, zinc trichlorophenate, zinc trichlorophenoxide, zineb, ziram, zolaprofos, zoocoumarin, zoxamide, zuoanjunzhi, zuocaoan, zuojunzhi, zuomihuanglong, α-chlorohydrin, α-ecdysone, α-multistriatin, α-naphthaleneacetic acids, and β-ecdysone;

(2) the following molecules
(a) N-(3-chloro-1-(pyridin-3-yl)-1H-pyrazol-4-yl)-N-ethyl-3-((3,3,3-trifluoropropyl)thio)propanamide (hereafter "AI-1")

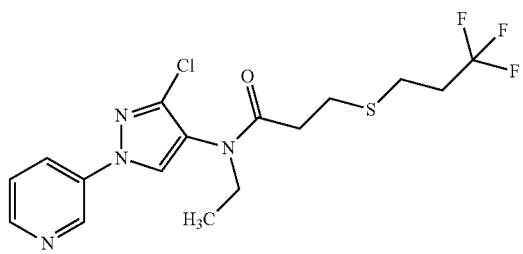 [SMILES: CCN(C(=O)CCSCCC(F)(F)F)c1cn(-c2cccnc2)nc1Cl]

(b) (3S,6S,7R,8R)-8-benzyl-3-(3-((isobutyryloxy)methoxy)-4-methoxypicolinamido)-6-methyl-4,9-dioxo-1,5-dioxonan-7-yl isobutyrate (hereafter "AI-2")

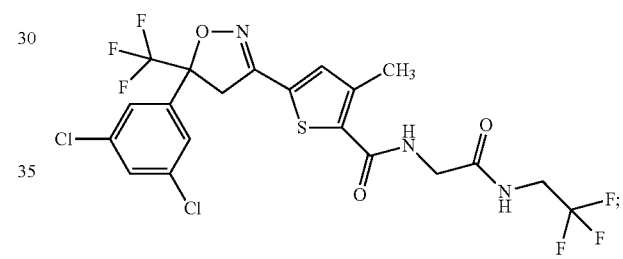

(3) a molecule known as Lotilaner that has the following structure

F F
F—⟨⟩—O—N
       ‖
Cl—⟨⟩—  CH₃
        S
    Cl      C(O)NH—CH₂—C(O)NH—CH₂CF₃ and
(4) the following molecules in Table A

TABLE A

Structure of M# - active ingredients

| M# | Structure |
|---|---|
| M1 | R≡ ... (bicyclic structure) N−CH(R₁)−C≡CH; R = CH, N; R₁ = H, Me |
| M2 | X—pyridine—CH₂—N—pyridine=N—C(O)—CF₂R; X = F, Cl; R = H, F |

TABLE A-continued

Structure of M# - active ingredients

| M# | Structure |
|---|---|
| M3 | 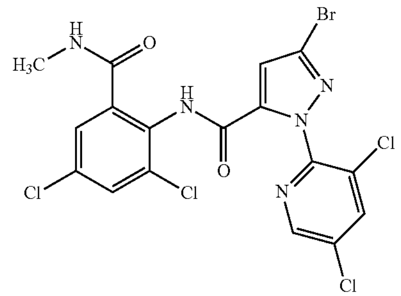 [SMILES: CNC(=O)c1cc(Cl)cc(Cl)c1NC(=O)c1cc(Br)nn1-c1ncc(Cl)cc1Cl] |
| M4 | 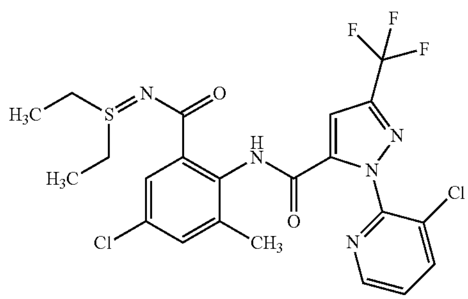 [SMILES: CCS(CC)=NC(=O)c1cc(Cl)cc(C)c1NC(=O)c1cc(C(F)(F)F)nn1-c1ncccc1Cl] |
| M5 | 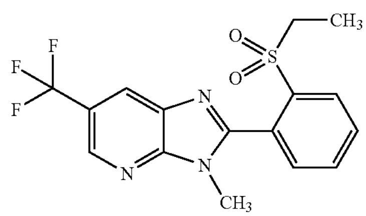 [SMILES: CCS(=O)(=O)c1ccccc1-c1nc2cc(C(F)(F)F)cnc2n1C] |
| M6 | 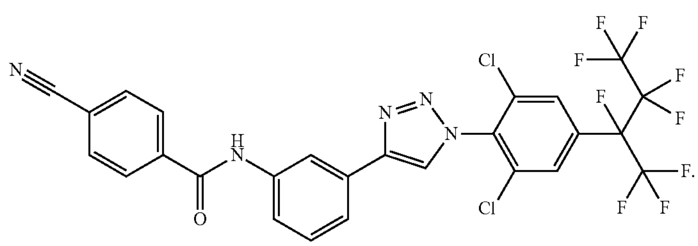 [SMILES: N#Cc1ccc(C(=O)Nc2cccc(-c3cn(-c4c(Cl)cc(C(F)(C(F)(F)F)C(F)(F)C(F)(F)F)cc4Cl)nn3)c2)cc1] |

As used in this disclosure, each of the above is an active ingredient. For more information consult the "Compendium of Pesticide Common Names" located at Alanwood.net and various editions, including the on-line edition, of "The Pesticide Manual" located at bcpcdata.com.

A particularly preferred selection of active ingredients are 1,3 dichloropropene, chlorpyrifos, hexaflumuron, methoxyfenozide, noviflumuron, spinetoram, spinosad, and sulfoxaflor (hereafter "AIGA-2").

Additionally, another particularly preferred selection of active ingredients are acequinocyl, acetamiprid, acetoprole, avermectin, azinphos-methyl, bifenazate, bifenthrin, carbaryl, carbofuran, chlorfenapyr, chlorfluazuron, chromafenozide, clothianidin, cyfluthrin, cypermethrin, deltamethrin, diafenthiuron, emamectin benzoate, endosulfan, esfenvalerate, ethiprole, etoxazole, fipronil, flonicamid, fluacrypyrim, gamma-cyhalothrin, halofenozide, indoxacarb, lambda-cyhalothrin, lufenuron, malathion, methomyl, novaluron, permethrin, pyridalyl, pyrimidifen, spirodiclofen, tebufenozide, thiacloprid, thiamethoxam, thiodicarb, tolfenpyrad, and zeta-cypermethrin (hereafter "AIGA-3").

The term "alkenyl" means an acyclic, unsaturated (at least one carbon-carbon double bond), branched or unbranched, substituent consisting of carbon and hydrogen, for example, vinyl, allyl, butenyl, pentenyl, and hexenyl.

The term "alkenyloxy" means an alkenyl further consisting of a carbon-oxygen single bond, for example, allyloxy, butenyloxy, pentenyloxy, hexenyloxy.

The term "alkoxy" means an alkyl further consisting of a carbon-oxygen single bond, for example, methoxy, ethoxy, propoxy, isopropoxy, butoxy, isobutoxy, and tertbutoxy.

The term "alkyl" means an acyclic, saturated, branched or unbranched, substituent consisting of carbon and hydrogen, for example, methyl, ethyl, propyl, isopropyl, butyl, and tertbutyl.

The term "alkynyl" means an acyclic, unsaturated (at least one carbon-carbon triple bond), branched or unbranched, substituent consisting of carbon and hydrogen, for example, ethynyl, propargyl, butynyl, and pentynyl.

The term "alkynyloxy" means an alkynyl further consisting of a carbon-oxygen single bond, for example, pentynyloxy, hexynyloxy, heptynyloxy, and octynyloxy.

The term "aryl" means a cyclic, aromatic substituent consisting of hydrogen and carbon, for example, phenyl, naphthyl, and biphenyl.

The term "biopesticide" means a microbial biological pest control agent that, in general, is applied in a similar manner to chemical pesticides. Commonly they are bacterial, but there are also examples of fungal control agents, including *Trichoderma* spp. and *Ampelomyces quisqualis*. One well-known biopesticide example is *Bacillus* species, a bacterial disease of Lepidoptera, Coleoptera, and Diptera. Biopesticides include products based on entomopathogenic fungi (e.g. *Metarhizium anisopliae*), entomopathogenic nematodes (e.g. *Steinernema feltiae*), and entomopathogenic viruses (e.g. *Cydia pomonella* granulovirus). Other examples of entomopathogenic organisms include, but are not limited to, baculoviruses, protozoa, and Microsporidia. For the avoidance of doubt, biopesticides are active ingredients.

The term "cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

The term "cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

The term "cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

The term "cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

The term "halo" means fluoro, chloro, bromo, and iodo.

The term "haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

The term "haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

The term "heterocyclyl" means a cyclic substituent that may be aromatic, fully saturated, or partially or fully unsaturated, where the cyclic structure contains at least one carbon and at least one heteroatom, where said heteroatom is nitrogen, sulfur, or oxygen. Examples are:

(1) aromatic heterocyclyl substituents include, but are not limited to, benzofuranyl, benzoisothiazolyl, benzoisoxazolyl, benzothienyl, benzothiazolyl, benzoxazolyl, cinnolinyl, furanyl, imidazolyl, indazolyl, indolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl;

(2) fully saturated heterocyclyl substituents include, but are not limited to, piperazinyl, piperidinyl, morpholinyl, pyrrolidinyl, tetrahydrofuranyl, tetrahydropyranyl, tetrahydrothiophenyl, tetrahydrothiophenyl-oxide, tetrahydrothiophenyl-dioxide;

(3) partially or fully unsaturated heterocyclyl substituents include, but are not limited to, 4,5-dihydro-isoxazolyl, 4,5-dihydro-oxazolyl, 4,5-dihydro-1H-pyrazolyl, 2,3-dihydro-[1,3,4]-oxadiazolyl, 2,5-dioxoimidazolidinyl, 2,4-dioxo-1,3-diazaspiro[4.4]nonanylisoxazolidinonyl, oxazolidinonyl, imidazolidinonyl, isoxazolidinonyl, pyrrolidinonyl, 1,2,3,4-tetrahydro-quinolinyl, and thioxothiazolidinonyl; and (4) Additional examples of heterocyclyls include the following:

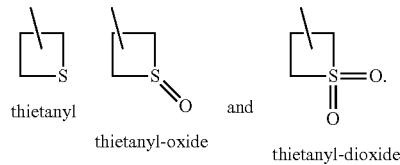

thietanyl   thietanyl-oxide   and   thietanyl-dioxide

The term "locus" means a habitat, breeding ground, plant, seed, soil, material, or environment, in which a pest is growing, may grow, or may traverse. For example, a locus may be: where crops, trees, fruits, cereals, fodder species, vines, turf, and/or ornamental plants, are growing; where domesticated animals are residing; the interior or exterior surfaces of buildings (such as places where grains are stored); the materials of construction used in buildings (such as impregnated wood); and the soil around buildings.

The phrase "MoA Material" means an active ingredient having a mode of action ("MoA") as indicated in IRAC MoA Classification v. 7.3, located at irac-online.org., which describes the following groups.

(1) Acetylcholinesterase (AChE) inhibitors, includes the following active ingredients alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC, xylylcarb, acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion.

(2) GABA-gated chloride channel antagonists, includes the following active ingredients chlordane, endosulfan, ethiprole, and fipronil.

(3) Sodium channel modulators, includes the following active ingredients acrinathrin, allethrin, d-cis-trans allethrin, d-trans allethrin, bifenthrin, bioallethrin, bioallethrin S-cyclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomers], deltamethrin, empenthrin [(EZ)-(1R)-isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomers], tralomethrin, and transfluthrin, and methoxychlor.

(4) Nicotinic acetylcholine receptor (nAChR) agonists, includes the following active ingredients
  (4A) acetamiprid, clothianidin, dinotefuran, imidacloprid, nitenpyram, thiacloprid, thiamethoxam,
  (4B) nicotine,
  (4C) sulfoxaflor,
  (4D) flupyradifurone,
  (4E) triflumezopyrim and dicloromezotiaz.

(5) Nicotinic acetylcholine receptor (nAChR) allosteric activators, includes the following active ingredients spinetoram and spinosad.

(6) Chloride channel activators, includes the following active ingredients abamectin, emamectin benzoate, lepimectin, and milbemectin.

(7) Juvenile hormone mimics, includes the following active ingredients hydroprene, kinoprene, methoprene, fenoxycarb, and pyriproxyfen.

(8) Miscellaneous nonspecific (multi-site) inhibitors, includes the following active ingredients methyl bromide, chloropicrin, sulfuryl fluoride, borax, and tartar emetic.

(9) Modulators of Chordotonal Organs, includes the following active ingredients pymetrozine and flonicamid.

(10) Mite growth inhibitors, includes the following active ingredients clofentezine, hexythiazox, diflovidazin, and etoxazole.

(11) Microbial disruptors of insect midgut membranes, includes the following active ingredients *Bacillus thuringiensis* subsp. *Israelensis, Bacillus thuringiensis* subsp. *aizawai, Bacillus thuringiensis* subsp. *Kurstaki, Bacillus thuringiensis* subsp. *tenebrionenis*, Bt crop proteins (Cry1Ab, Cry1Ac, Cry1Fa, Cry1A.105, Cry2Ab, Vip3A, mCry3A, Cry3Ab, Cry3Bb, Cry34Ab1/Cry35Ab1), and *Bacillus sphaericus*.

(12) Inhibitors of mitochondrial ATP synthase, includes the following active ingredients tetradifon, propargite, azocyclotin, cyhexatin, fenbutatin oxide, and diafenthiuron.

(13) Uncouplers of oxidative phosphorylation via disruption of the proton gradient, includes the following active ingredients chlorfenapyr, DNOC, and sulfluramid.

(14) Nicotinic acetylcholine receptor (nAChR) channel blockers, includes the following active ingredients bensultap, cartap hydrochloride, thiocyclam, and thiosultap-sodium.

(15) Inhibitors of chitin biosynthesis, type 0, includes the following active ingredients bistrifluron, chlorfluazuron, diflubenzuron, flucycloxuron, flufenoxuron, hexaflumuron, lufenuron, novaluron, noviflumuron, teflubenzuron, and triflumuron.

(16) Inhibitors of chitin biosynthesis, type 1, includes the following active ingredient buprofezin.

(17) Moulting disruptor, Dipteran, includes the following active ingredient cyromazine.

(18) Ecdysone receptor agonists, includes the following active ingredients chromafenozide, halofenozide, methoxyfenozide, and tebufenozide.

(19) Octopamine receptor agonists, includes the following active ingredient amitraz.

(20) Mitochondrial complex III electron transport inhibitors, includes the following active ingredients hydramethylnon, acequinocyl, and fluacrypyrim.

(21) Mitochondrial complex I electron transport inhibitors, includes the following active ingredients fenazaquin, fenpyroximate, pyrimidifen, pyridaben, tebufenpyrad, tolfenpyrad, and rotenone.

(22) Voltage-dependent sodium channel blockers, includes the following active ingredients indoxacarb and metaflumizone.

(23) Inhibitors of acetyl CoA carboxylase, includes the following active ingredients spirodiclofen, spiromesifen, and spirotetramat.

(24) Mitochondrial complex IV electron transport inhibitors, includes the following active ingredients, aluminium phosphide, calcium phosphide, phosphine, zinc phosphide, and cyanide.

(25) Mitochondrial complex II electron transport inhibitors, includes the following active ingredients cyenopyrafen and cyflumetofen, and

(28) Ryanodine receptor modulators, includes the following active ingredients chlorantraniliprole, cyantraniliprole, and flubendiamide. Groups 26 and 27 are unassigned in this version of the classification scheme.

Additionally, there is a Group UN that contains active ingredients of unknown or uncertain mode of action. This group includes the following active ingredients, azadirachtin, benzoximate, bifenazate, bromopropylate, chinomethionat, cryolite, dicofol, pyridalyl, and pyrifluquinazon.

The term "pest" means an organism that is detrimental to humans, or human concerns (such as, crops, food, livestock, etc.), where said organism is from Phyla Arthropoda, Mollusca, or Nematoda. Particular examples are ants, aphids, bed bugs, beetles, bristletails, caterpillars, cockroaches, crickets, earwigs, fleas, flies, grasshoppers, grubs, hornets, killer bees, leafhoppers, lice, locusts, maggots, mites, moths, nematodes, planthoppers, psyllids, sawflies, scales, silverfish, slugs, snails, spiders, springtails, stink bugs, symphylans, termites, *thrips*, ticks, wasps, whiteflies, and wireworms.

Additional examples are pests in
(1) Subphyla Chelicerata, Myriapoda, and Hexapoda.
(2) Classes of Arachnida, Symphyla, and Insecta.
(3) Order Anoplura. A non-exhaustive list of particular genera includes, but is not limited to, *Haematopinus* spp., *Hoplopleura* spp., *Linognathus* spp., *Pediculus* spp., *Polyplax* spp., *Solenopotes* spp., and *Neohaematopinis* spp. A non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis*.
(4) Order Coleoptera. A non-exhaustive list of particular genera includes, but is not limited to, *Acanthoscelides* spp., *Agriotes* spp., *Anthonomus* spp., *Apion* spp., *Apogonia* spp., *Araecerus* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Dinoderus* spp., *Gnathocerus* spp., *Hemicoelus* spp., *Heterobostruchus* spp., *Hypera* spp., *Ips* spp., *Lyctus* spp., *Megascelis* spp., *Meligethes* spp., *Mezium* spp., *Niptus* spp., *Otiorhynchus* spp., *Pantomorus* spp., *Phyllophaga* spp., *Phyllotreta* spp., *Ptinus* spp., *Rhizotrogus* spp., *Rhynchites* spp., *Rhynchophorus* spp., *Scolytus* spp., *Sphenophorus* spp., *Sitophilus* spp., *Tenebrio* spp., and *Tribolium* spp. A non-exhaustive list of particular species includes, but is not limited to, *Acanthoscelides*

*obtectus, Agrilus planipennis, Ahasverus advena, Alphitobius diaperinus, Anoplophora glabripennis, Anthonomus grandis, Anthrenus verbasci, Anthrenus falvipes, Ataenius spretulus, Atomaria linearis, Attagenus unicolor, Bothynoderes punctiventris, Bruchus pisorum, Callosobruchus maculatus, Carpophilus hemipterus, Cassida vittata, Cathartus quadricollis, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Euvrilletta peltata, Faustinus cubae, Hylobius pales, Hylotrupes bajulus, Hypera postica, Hypothenemus hampei, Lasioderma serricome, Leptinotarsa decemlineata, Limonius canus, Liogenys fuscus, Liogenys suturalis, Lissorhoptrus oryzophilus, Lophocateres pusillus, Lyctus planicollis, Maecolaspis joliveti, Melanotus communis, Meligethes aeneus, Melolontha melolontha, Necrobia rufipes, Oberea brevis, Oberea linearis, Oryctes rhinoceros, Oryzaephilus mercator, Oryzaephilus surinamensis, Oulema melanopus, Oulema oryzae, Phyllophaga cuyabana, Polycaon stoutti, Popillia japonica, Prostephanus truncatus, Rhyzopertha dominica, Sitona lineatus, Sitophilus granarius, Sitophilus oryzae, Sitophilus zeamais, Stegobium paniceum, Tenebroides mauritanicus, Tribolium castaneum, Tribolium confusum, Trogoderma granarium, Trogoderma variabile, Xestobium rufovillosum,* and *Zabrus tenebrioides.*

(5) Order *Dermaptera.* A non-exhaustive list of particular species includes, but is not limited to, *Forficula auricularia.*

(6) Order *Blattaria.* A non-exhaustive list of particular species includes, but is not limited to, *Blattella germanica, Blattella asahinai, Blatta orientalis, Blatta lateralis, Parcoblatta pennsylvanica, Periplaneta americana, Periplaneta australasiae, Periplaneta brunnea, Periplaneta fuliginosa, Pycnoscelus surinamensis,* and *Supella longipalpa.*

(7) Order *Diptera.* A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Culicoides* spp., *Dasineura* spp., *Delia* spp., *Drosophila* spp., *Fannia* spp., *Hylemya* spp., *Liriomyza* spp., *Musca* spp., *Phorbia* spp., *Pollenia* spp., *Psychoda* spp., *Simulium* spp., *Tabanus* spp., and *Tipula* spp. A non-exhaustive list of particular species includes, but is not limited to, *Agromyza frontella, Anastrepha suspensa, Anastrepha ludens, Anastrepha obliqua, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Piophila casei, Psila rosae, Rhagoletis cerasi, Rhagoletis pomonella, Rhagoletis mendax, Sitodiplosis mosellana,* and *Stomoxys calcitrans.*

(8) Order *Hemiptera.* A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Euschistus* spp., *Lepidosaphes* spp., *Lagynotomus* spp., *Lygus* spp., *Macrosiphum* spp., *Nephotettix* spp., *Nezara* spp., *Nilaparvata* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp., and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bactericera cockerelli, Bagrada hilaris, Bemisia argentifolii, Bemisia tabaci, Blissus leucopterus, Boisea trivittata, Brachycorynella asparagi, Brevennia rehi, Brevicoryne brassicae, Cacopsylla pyri, Cacopsylla pyricola, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus conspersus, Euschistus heros, Euschistus servus, Halyomorpha halys, Helopeltis antonii, Helopeltis theivora, Icerya purchasi, Idioscopus nitidulus, Laodelphax striatellus, Leptocorisa oratorius, Leptocorisa varicomis, Lygus hesperus, Maconellicoccus hirsutus, Macrosiphum euphorbiae, Macrosiphum granarium, Macrosiphum rosae, Macrosteles quadrilineatus, Mahanarva frimbiolata, Megacopta cribraria, Metopolophium dirhodum, Mictis longicomis, Myzus persicae, Nephotettix cincticeps, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris califomicus, Phytocoris relativus, Piezodorus guildinii, Poecilocapsus lineatus, Psallus vaccinicola, Pseudacysta perseae, Pseudococcus brevipes, Quadraspidiotus pemiciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis,* and *Zulia entrerriana.*

(9) Order *Hymenoptera.* A non-exhaustive list of particular genera includes, but is not limited to, *Acromyrmex* spp., *Atta* spp., *Camponotus* spp., *Diprion* spp., *Dolichovespula* spp., *Formica* spp., *Monomorium* spp., *Neodiprion* spp., *Paratrechina* spp., *Pheidole* spp., *Pogonomyrmex* spp., *Polistes* spp., *Solenopsis* spp., *Technomyrmex,* spp., *Tetramorium* spp., *Vespula* spp., *Vespa* spp., and *Xylocopa* spp. A non-exhaustive list of particular species includes, but is not limited to, *Athalia rosae, Atta texana, Caliroa cerasi, Cimbex americana, Iridomyrmex humilis, Linepithema humile, Mellifera Scutellata, Monomorium minimum, Monomorium pharaonis, Neodiprion sertifer, Solenopsis invicta, Solenopsis geminata, Solenopsis molesta, Solenopsis richtery, Solenopsis xyloni, Tapinoma sessile,* and *Wasmannia auropunctata.*

(10) Order *Isoptera.* A non-exhaustive list of particular genera includes, but is not limited to, *Coptotermes* spp., *Comitermes* spp., *Cryptotermes* spp., *Heterotermes* spp., *Kalotermes* spp., *Incisitermes* spp., *Macrotermes* spp., *Marginitermes* spp., *Microcerotermes* spp., *Procomitermes* spp., *Reticulitermes* spp., *Schedorhinotermes* spp., and *Zootermopsis* spp. A non-exhaustive list of particular species includes, but is not limited to, *Coptotermes acinaciformis, Coptotermes curvignathus, Coptotermes frenchi, Coptotermes formosanus, Coptotermes gestroi, Cryptotermes brevis, Heterotermes aureus, Heterotermes tenuis, Incisitermes minor, Incisitermes snyderi, Microtermes obesi, Nasutitermes comiger, Odontotermes formosanus, Odontotermes obesus, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis,* and *Reticulitermes virginicus.*

(11) Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Nemapogon* spp., *Peridroma* spp., *Phyllonorycter* spp., *Pseudaletia* spp., *Plutella* spp., *Sesamia* spp., *Spodoptera* spp., *Synanthedon* spp., and *Yponomeuta* spp. A non-exhaustive list of particular species includes, but is not limited to, *Achaea Janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia trans versa, Choristoneura rosaceana, Cnaphalocrocis medinalis, Conopomorpha cramerella, Corcyra cephalonica, Cossus cossus, Cydia caryana, Cydia funebrana, Cydia molesta, Cydia nigricana, Cydia pomonella, Darna diducta, Diaphania nitidalis, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Estigmene acrea, Eupoecilia ambiguella, Euxoa auxiliaris, Galleria mellonella, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia derkella, Mahasena corbetti, Mamestra brassicae, Manduca sexta, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Phyllonorycter blancardella, Pieris rapae, Plathypena scabra, Platynota idaeusalis, Plodia interpunctella, Plutella xylostella, Polychrosis viteana, Prays endocarpa, Prays oleae, Pseudaletia unipuncta, Pseudoplusia indudens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tinea pellionella, Tineola bisselliella, Trichoplusia ni, Tuta absoluta, Zeuzera coffeae,* and *Zeuzera pyrina*.

(12) Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae,* and *Trichodectes canis*.

(13) Order Orthoptera. A non-exhaustive list of particular genera includes, but is not limited to, *Melanoplus* spp. and *Pterophylla* spp. A non-exhaustive list of particular species includes, but is not limited to, *Acheta domesticus, Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria,* and *Scudderia furcata*.

(14) Order Psocoptera. A non-exhaustive list of particular species includes, but is not limited to, *Liposcelis decolor, Liposcelis entomophila, Lachesilla quercus,* and *Trogium pulsatorium*.

(15) Order Siphonaptera. A non-exhaustive list of particular species includes, but is not limited to, *Ceratophyllus gallinae, Ceratophyllus niger, Ctenocephalides canis, Ctenocephalides felis,* and *Pulex irritans*.

(16) Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular species includes, but is not limited to, *Frankliniella bispinosa, Frankliniella fusca, Frankliniella occidentalis, Frankliniella schultzei, Frankliniella tritici, Frankliniella williamsi, Heliothrips haemorrhoidalis, Rhipiphorothrips cruentatus, Scirtothrips citri, Scirtothrips dorsalis, Taeniothrips rhopalantennalis, Thrips hawaiiensis, Thrips nigropilosus, Thrips orientalis, Thrips palmi,* and *Thrips tabaci*.

(17) Order Thysanura. A non-exhaustive list of particular genera includes, but is not limited to, *Lepisma* spp. and *Thermobia* spp.

(18) Order Acarina. A non-exhaustive list of particular genera includes, but is not limited to, *Acarus* spp., *Aculops* spp., *Argus* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Liponyssoides sanguineus, Notoedres cati, Oligonychus coffeae, Oligonychus ilicis, Ornithonyssus bacoti, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae, Tyrophagus longior,* and *Varroa destructor*.

(19) Order Araneae. A non-exhaustive list of particular genera includes, but is not limited to, *Loxosceles* spp., *Latrodectus* spp., and *Atrax* spp. A non-exhaustive list of particular species includes, but is not limited to, *Loxosceles recluse, Latrodectus mactans,* and *Atrax robustus*.

(20) Class Symphyla. A non-exhaustive list of particular species includes, but is not limited to, *Scutigerella immaculate*.

(21) Subclass Collembola. A non-exhaustive list of particular species includes, but is not limited to, *Bourletiella hortensis, Onychiurus armatus, Onychiurus fimetarius,* and *Sminthurus viridis*.

(22) Phylum Nematoda. A non-exhaustive list of particular genera includes, but is not limited to, *Aphelenchoides* spp., *Belonolaimus* spp., *Criconemella* spp., *Ditylenchus* spp., *Globodera* spp., *Heterodera* spp., *Hirschmanniella* spp., *Hoplolaimus* spp., *Meloidogyne* spp., *Pratylenchus* spp., and *Radopholus* spp. A non-exhaustive list of particular species includes, but is not limited to, *Dirofilaria immitis, Globodera pallida, Heterodera glycines, Heterodera zeae, Meloidogyne incognita, Meloidogyne javanica, Onchocerca volvulus, Pratylenchus penetrans, Radopholus similis,* and *Rotylenchulus reniformis*.

(23) Phylum Mollusca. A non-exhaustive list of particular species includes, but is not limited to, *Arion vulgaris, Cornu aspersum, Deroceras reticulatum, Limax flavus, Milax gagates,* and *Pomacea canaliculata*.

A particularly preferred pest group to control is sap-feeding pests. Sap-feeding pests, in general, have piercing and/or sucking mouthparts and feed on the sap and inner plant tissues of plants. Examples of sap-feeding pests of particular concern to agriculture include, but are not limited to, aphids, leafhoppers, moths, scales, thrips, psyllids, mealybugs, stinkbugs, and whiteflies. Specific examples of Orders that have sap-feeding pests of concern in agriculture include but are not limited to, Anoplura and Hemiptera. Specific examples of Hemiptera that are of concern in agriculture include, but are not limited to, *Aulacaspis* spp., *Aphrophora* spp., *Aphis* spp., *Bemisia* spp., *Coccus* spp., *Euschistus* spp., *Lygus* spp., *Macrosiphum* spp., *Nezara* spp., and *Rhopalosiphum* spp.

Another particularly preferred pest group to control is chewing pests. Chewing pests, in general, have mouthparts that allow them to chew on the plant tissue including roots, stems, leaves, buds, and reproductive tissues (including, but not limited to flowers, fruit, and seeds). Examples of chewing pests of particular concern to agricultural include, but are not limited to, caterpillars, beetles, grasshoppers, and locusts. Specific examples of Orders that have chewing pests of concern in agriculture include but are not limited to, Coleoptera and Lepidoptera. Specific examples of Coleoptera that are of concern in agriculture include, but are not limited to, *Anthonomus* spp., *Cerotoma* spp., *Chaetocnema* spp., *Colaspis* spp., *Cyclocephala* spp., *Diabrotica* spp., *Hypera* spp., *Phyllophaga* spp., *Phyllotreta* spp., *Sphenophorus* spp., *Sitophilus* spp.

The phrase "pesticidally effective amount" means the amount of a pesticide needed to achieve an observable effect on a pest, for example, the effects of necrosis, death, retardation, prevention, removal, destruction, or otherwise diminishing the occurrence and/or activity of a pest in a locus. This effect may come about when pest populations are repulsed from a locus, pests are incapacitated in, or around, a locus, and/or pests are exterminated in, or around, a locus. Of course, a combination of these effects can occur. Generally, pest populations, activity, or both are desirably reduced more than fifty percent, preferably more than 90 percent, and most preferably more than 99 percent. In general, a pesticidally effective amount, for agricultural purposes, is from about 0.0001 grams per hectare to about 5000 grams per hectare, preferably from about 0.0001 grams per hectare to about 500 grams per hectare, and it is even more preferably from about 0.0001 grams per hectare to about 50 grams per hectare.

DETAILED DESCRIPTION OF THIS DISCLOSURE

This document discloses molecules of Formula One

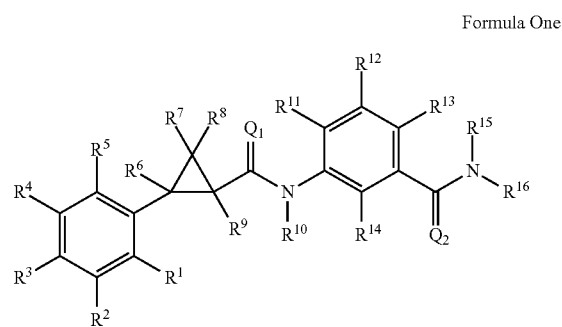

Formula One wherein:

(A) $R^1$ is selected from the group consisting of H, F, Cl, Br, I, CN, $NH_2$, $NO_2$, $(C_1$-$C_4)$alkyl, $(C_3$-$C_6)$cycloalkyl, $(C_2$-$C_4)$alkenyl, $(C_3$-$C_6)$cycloalkenyl, $(C_2$-$C_4)$alkynyl, $(C_1$-$C_4)$alkoxy, $(C_1$-$C_4)$haloalkyl, $(C_3$-$C_6)$halocycloalkyl, $(C_2$-$C_4)$haloalkenyl, $(C_3$-$C_6)$halocycloalkenyl, $(C_1$-$C_4)$haloalkoxy, $S(C_1$-$C_4)$alkyl, $S(O)(C_1$-$C_4)$alkyl, $S(O)_2(C_1$-$C_4)$alkyl, $S(C_1$-$C_4)$haloalkyl, $S(O)(C_1$-$C_4)$haloalkyl, $S(O)_2(C_1$-$C_4)$haloalkyl, $(C_1$-$C_4)$alkyl-$S(O)_2NH_2$, and $(C_1$-$C_4)$haloalkyl-$S(O)_2NH_2$;

(B) $R^2$ is selected from the group consisting of H, F, Cl, Br, I, CN, $NH_2$, $NO_2$, $(C_1$-$C_4)$alkyl, $(C_3$-$C_6)$cycloalkyl, $(C_2$-$C_4)$alkenyl, $(C_3$-$C_6)$cycloalkenyl, $(C_2$-$C_4)$alkynyl, $(C_1$-$C_4)$alkoxy, $(C_1$-$C_4)$haloalkyl, $(C_3$-$C_6)$halocycloalkyl, $(C_2$-$C_4)$haloalkenyl, $(C_3$-$C_6)$halocycloalkenyl, $(C_1$-$C_4)$haloalkoxy, $S(C_1$-$C_4)$alkyl, $S(O)(C_1$-$C_4)$alkyl, $S(O)_2(C_1$-$C_4)$alkyl, $S(C_1$-$C_4)$haloalkyl, $S(O)(C_1$-$C_4)$haloalkyl, $S(O)_2(C_1$-$C_4)$haloalkyl, $(C_1$-$C_4)$alkyl-$S(O)_2NH_2$, and $(C_1$-$C_4)$haloalkyl-$S(O)_2NH_2$;

(C) $R^3$ is selected from the group consisting of H, F, Cl, Br, I, CN, $NH_2$, $NO_2$, $(C_1$-$C_4)$alkyl, $(C_3$-$C_6)$cycloalkyl, $(C_2$-$C_4)$alkenyl, $(C_3$-$C_6)$cycloalkenyl, $(C_2$-$C_4)$alkynyl, $(C_1$-$C_4)$alkoxy, $(C_1$-$C_4)$haloalkyl, $(C_3$-$C_6)$halocycloalkyl, $(C_2$-$C_4)$haloalkenyl, $(C_3$-$C_6)$halocycloalkenyl, $(C_1$-$C_4)$haloalkoxy, $S(C_1$-$C_4)$alkyl, $S(O)(C_1$-$C_4)$alkyl, $S(O)_2(C_1$-$C_4)$alkyl, $S(C_1$-$C_4)$haloalkyl, $S(O)(C_1$-$C_4)$haloalkyl, $S(O)_2(C_1$-$C_4)$haloalkyl, $(C_1$-$C_4)$alkyl-$S(O)_2NH_2$, and $(C_1$-$C_4)$haloalkyl-$S(O)_2NH_2$;

(D) $R^4$ is selected from the group consisting of H, F, Cl, Br, I, CN, $NH_2$, $NO_2$, $(C_1$-$C_4)$alkyl, $(C_3$-$C_6)$cycloalkyl, $(C_2$-$C_4)$alkenyl, $(C_3$-$C_6)$cycloalkenyl, $(C_2$-$C_4)$alkynyl, $(C_1$-$C_4)$alkoxy, $(C_1$-$C_4)$haloalkyl, $(C_3$-$C_6)$halocycloalkyl, $(C_2$-$C_4)$haloalkenyl, $(C_3$-$C_6)$halocycloalkenyl, $(C_1$-$C_4)$haloalkoxy, $S(C_1$-$C_4)$alkyl, $S(O)(C_1$-$C_4)$alkyl, $S(O)_2(C_1$-$C_4)$alkyl, $S(C_1$-$C_4)$haloalkyl, $S(O)(C_1$-$C_4)$haloalkyl, $S(O)_2(C_1$-$C_4)$haloalkyl, $(C_1$-$C_4)$alkyl-$S(O)_2NH_2$, and $(C_1$-$C_4)$haloalkyl-$S(O)_2NH_2$;

(E) $R^5$ is selected from the group consisting of H, F, Cl, Br, I, CN, $NH_2$, $NO_2$, $(C_1$-$C_4)$alkyl, $(C_3$-$C_6)$cycloalkyl, $(C_2$-$C_4)$alkenyl, $(C_3$-$C_6)$cycloalkenyl, $(C_2$-$C_4)$alkynyl, $(C_1$-$C_4)$alkoxy, $(C_1$-$C_4)$haloalkyl, $(C_3$-$C_6)$halocycloalkyl, $(C_2$-$C_4)$haloalkenyl, $(C_3$-$C_6)$halocycloalkenyl, $(C_1$-$C_4)$haloalkoxy, $S(C_1$-$C_4)$alkyl, $S(O)(C_1$-$C_4)$alkyl, $S(O)_2(C_1$-$C_4)$alkyl, $S(C_1$-$C_4)$haloalkyl, $S(O)(C_1$-$C_4)$haloalkyl, $S(O)_2(C_1$-$C_4)$haloalkyl, $(C_1$-$C_4)$alkyl-$S(O)_2NH_2$, and $(C_1$-$C_4)$haloalkyl-$S(O)_2NH_2$;

(F) $R^6$ is selected from the group consisting of H and $(C_1$-$C_4)$alkyl;

(G) $R^7$ is selected from the group consisting of H, F, Cl, Br, and I;

(H) $R^8$ is selected from the group consisting of F, Cl, Br, and I;

(I) $R^9$ is selected from the group consisting of H and $(C_1$-$C_4)$alkyl;

(J) $R^{16}$ is selected from the group consisting of H, $(C_1$-$C_4)$alkyl, $(C_2$-$C_4)$alkenyl, $(C_1$-$C_4)$haloalkyl, $(C_1$-$C_4)$alkyl$(C_1$-$C_4)$alkoxy, $C(=O)(C_1$-$C_4)$alkyl, and $(C_1$-$C_4)$alkoxyC$(=O)(C_1$-$C_4)$alkyl;

(K) $R^{11}$ is selected from the group consisting of H, F, Cl, Br, I, CN, $NH_2$, $NO_2$, $(C_1$-$C_4)$alkyl, $(C_3$-$C_6)$cycloalkyl, $(C_2$-$C_4)$alkenyl, $(C_3$-$C_6)$cycloalkenyl, $(C_2$-$C_4)$alkynyl, $(C_1$-$C_4)$alkoxy, $(C_1$-$C_4)$haloalkyl, $(C_3$-$C_6)$halocycloalkyl, $(C_2$-$C_4)$haloalkenyl, $(C_3$-$C_6)$halocycloalkenyl, $(C_1$-$C_4)$haloalkoxy, $S(C_1$-$C_4)$alkyl, $S(O)(C_1$-$C_4)$alkyl, $S(O)_2(C_1$-$C_4)$alkyl, $S(C_1$-$C_4)$haloalkyl, $S(O)(C_1$-$C_4)$haloalkyl, $S(O)_2(C_1$-$C_4)$haloalkyl, $(C_1$-$C_4)$alkyl-$S(O)_2NH_2$, and $(C_1$-$C_4)$haloalkyl-$S(O)_2NH_2$;

(L) Ru is selected from the group consisting of H, F, Cl, Br, I, CN, $NH_2$, $NO_2$, $(C_1-C_4)$alkyl, $(C_3-C_6)$cycloalkyl, $(C_2-C_4)$alkenyl, $(C_3-C_6)$cycloalkenyl, $(C_2-C_4)$alkynyl, $(C_1-C_4)$alkoxy, $(C_1-C_4)$haloalkyl, $(C_3-C_6)$halocycloalkyl, $(C_2-C_4)$haloalkenyl, $(C_3-C_6)$halocycloalkenyl, $(C_1-C_4)$haloalkoxy, $S(C_1-C_4)$alkyl, $S(O)(C_1-C_4)$alkyl, $S(O)_2(C_1-C_4)$alkyl, $S(C_1-C_4)$haloalkyl, $S(O)(C_1-C_4)$haloalkyl, $S(O)_2(C_1-C_4)$haloalkyl, $(C_1-C_4)$alkyl-$S(O)_2NH_2$, and $(C_1-C_4)$haloalkyl-$S(O)_2NH_2$;

(M) $R^{13}$ is selected from the group consisting of H, F, Cl, Br, I, CN, $NH_2$, $NO_2$, $(C_1-C_4)$alkyl, $(C_3-C_6)$cycloalkyl, $(C_2-C_4)$alkenyl, $(C_3-C_6)$cycloalkenyl, $(C_2-C_4)$alkynyl, $(C_1-C_4)$alkoxy, $(C_1-C_4)$haloalkyl, $(C_3-C_6)$halocycloalkyl, $(C_2-C_4)$haloalkenyl, $(C_3-C_6)$halocycloalkenyl, $(C_1-C_4)$haloalkoxy, $S(C_1-C_4)$alkyl, $S(O)(C_1-C_4)$alkyl, $S(O)_2(C_1-C_4)$alkyl, $S(C_1-C_4)$haloalkyl, $S(O)(C_1-C_4)$haloalkyl, $S(O)_2(C_1-C_4)$haloalkyl, $(C_1-C_4)$alkyl-$S(O)_2NH_2$, and $(C_1-C_4)$haloalkyl-$S(O)_2NH_2$;

(N) $R^{14}$ is selected from the group consisting of H, F, Cl, Br, I, CN, $NH_2$, $NO_2$, $(C_1-C_4)$alkyl, $(C_3-C_6)$cycloalkyl, $(C_2-C_4)$alkenyl, $(C_3-C_6)$cycloalkenyl, $(C_2-C_4)$alkynyl, $(C_1-C_4)$alkoxy, $(C_1-C_4)$haloalkyl, $(C_3-C_6)$halocycloalkyl, $(C_2-C_4)$haloalkenyl, $(C_3-C_6)$halocycloalkenyl, $(C_1-C_4)$haloalkoxy, $S(C_1-C_4)$alkyl, $S(O)(C_1-C_4)$alkyl, $S(O)_2(C_1-C_4)$alkyl, $S(C_1-C_4)$haloalkyl, $S(O)(C_1-C_4)$haloalkyl, $S(O)_2(C_1-C_4)$haloalkyl, $(C_1-C_4)$alkyl-$S(O)_2NH_2$, and $(C_1-C_4)$haloalkyl-$S(O)_2NH_2$;

(O) $R^{15}$ is selected from the group consisting of (Q), H, $(C_1-C_4)$alkyl, $(C_2-C_4)$alkenyl, $(C_1-C_4)$haloalkyl, $(C_1-C_4)$alkyl$(C_1-C_4)$alkoxy, $C(=O)(C_1-C_4)$alkyl, and $(C_1-C_4)$alkoxyC$(=O)(C_1-C_4)$alkyl;

(P) $R^{16}$ is selected from the group consisting of (Q), $(C_1-C_8)$alkyl, $(C_1-C_8)$alkyl-O—$(C_1-C_8)$alkyl, $(C_1-C_8)$alkyl$(C_3-C_8)$cycloalkyl, $(C_1-C_8)$alkylphenyl, $(C_2-C_8)$alkenyl, $(C_2-C_8)$alkynyl, $(C_1-C_8)$haloalkyl, $(C_1-C_8)$alkyl-S—$(C_1-C_8)$alkyl, $(C_1-C_8)$alkyl-S(O)—$(C_1-C_8)$alkyl, $(C_1-C_8)$alkyl-$S(O)_2$—$(C_1-C_8)$alkyl, O-phenyl, O—$(C_2-C_8)$alkenyl, O—$(C_1-C_8)$alkyl$(C_3-C_8)$cycloalkyl, O—$(C_1-C_8)$alkylphenyl, $(C_1-C_8)$alkyl-O—$(C_1-C_8)$alkyl$(C_3-C_8)$cycloalkyl, $(C_1-C_8)$alkyl-O—$(C_1-C_8)$haloalkyl, $(C_1-C_8)$alkyl-$C(=O)$NH—$(C_1-C_8)$haloalkyl, $(C_1-C_8)$alkyl-NHC(O)—$(C_1-C_8)$alkyl, $(C_1-C_8)$alkyl-S—$(C_1-C_8)$haloalkyl, $(C_1-C_8)$alkyl-S(O)—$(C_1-C_8)$haloalkyl, $(C_1-C_8)$alkyl-$S(O)_2$—$(C_1-C_8)$haloalkyl, and $(C_1-C_8)$alkyl-$S(O)_2$—$NH_2$, wherein each alkyl, alkenyl, alkynyl, cycloalkyl, haloalkyl, and phenyl, may be optionally substituted with one or more substituents selected from the group consisting of F, Cl, Br, I, CN, OH, $NH_2$, $NO_2$, $(C_1-C_8)$alkyl, $(C_1-C_8)$alkoxy, $(C_1-C_8)$haloalkyl, $N((C_1-C_8)$alkyl$)_2$, $C(O)O(C_1-C_8)$alkyl, benzothioenyl, 2,3-dihydro-1H-imidazolonyl, furanyl, pyrazolyl, pyridinyl, thiazolyl, and triazolyl;

(Q) $R^{15}$ and $R^{16}$ together can optionally form a 2- to 5-membered saturated or unsaturated, hydrocarbyl link, which may contain one or more heteroatoms selected from the group consisting of nitrogen, sulfur, and oxygen, wherein said hydrocarbyl link may be optionally substituted with one or more substituents selected from the group consisting of F, Cl, Br, I, CN, $NH_2$, and $NO_2$;

(R) $Q^1$ and $Q^2$ are each independently selected from the group consisting of O and S; and N-oxides, agriculturally acceptable acid addition salts, salt derivatives, solvates, ester derivatives, crystal polymorphs, isotopes, resolved stereoisomers, and tautomers, of the molecules of Formula One.

The molecules of Formula One may exist in different geometric or optical isomeric or different tautomeric forms. One or more centers of chirality may be present in which case molecules of Formula One may be present as pure enantiomers, mixtures of enantiomers, pure diastereomers or mixtures of diastereomers. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. There may be double bonds present in the molecule, in which case compounds of Formula One may exist as single geometric isomers (cis or trans, E or Z) or mixtures of geometric isomers (cis and trans, E and Z). Centers of tautomerisation may be present. This disclosure covers all such isomers, tautomers, and mixtures thereof, in all proportions.

In another embodiment the molecules of Formula One, the carboxamido, and the phenyl, which are bonded to the cyclopropane, are in the R,R configuration. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $Q^1$, and $Q^2$.

In another embodiment $R^1$ is H or F. This embodiment may be used in combination with the other embodiments of $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $Q^1$, and $Q^2$.

In another embodiment $R^2$ is selected from the group consisting of H, F, and Cl. This embodiment may be used in combination with the other embodiments of $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $Q^1$, and $Q^2$.

In another embodiment $R^3$ is selected from the group consisting of H, F, and Cl. This embodiment may be used in combination with the other embodiments of $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $Q^1$, and $Q^2$.

In another embodiment $R^4$ is F or Cl. This embodiment may be used in combination with the other embodiments of $R^1$, $R^2$, $R^3$, $R^5$, $R^6$, $R^7$, $R^8$, $R^9$, $R^{10}$, $R^{11}$, $R^{12}$, $R^{13}$, $R^{14}$, $R^{15}$, $R^{16}$, $Q^1$, and $Q^2$.

In another embodiment $R^5$ is H or F. This embodiment may be used in combination with the other embodiments of $R^1$, $R^2$, $R^3$, $R^4$, $R^6$, $R^7$, $R^8$, $R^9$, $R^{10}$, $R^{11}$, $R^{12}$, $R^{13}$, $R^{14}$, $R^{15}$, $R^{16}$, $Q^1$, and $Q^2$.

In another embodiment $R^6$ is H. This embodiment may be used in combination with the other embodiments of $R^1$, $R^2$, $R^3$, $R^4$, $R^5$, $R^7$, $R^8$, $R^9$, $R^{10}$, $R^{11}$, $R^{12}$, $R^{13}$, $R^{14}$, $R^{15}$, $R^{16}$, $Q^1$, and $Q^2$.

In another embodiment $R^7$ is selected from the group consisting of Br and Cl. This embodiment may be used in combination with the other embodiments of $R^1$, $R^2$, $R^3$, $R^4$, $R^5$, $R^6$, $R^8$, $R^9$, $R^{10}$, $R^{11}$, $R^{12}$, $R^{13}$, $R^{14}$, $R^{15}$, $R^{16}$, $Q^1$, and $Q^2$.

In another embodiment $R^8$ is selected from the group consisting of Br and Cl. This embodiment may be used in combination with the other embodiments of $R^1$, $R^2$, $R^3$, $R^4$, $R^5$, $R^6$, $R^7$, $R^9$, $R^{10}$, $R^{11}$, $R^{12}$, $R^{13}$, $R^{14}$, $R^{15}$, $R^{16}$, $Q^1$, and $Q^2$.

In another embodiment $R^9$ is H. This embodiment may be used in combination with the other embodiments of $R^1$, $R^2$, $R^3$, $R^4$, $R^5$, $R^6$, $R^7$, $R^8$, $R^{10}$, $R^{11}$, $R^{12}$, $R^{13}$, $R^{14}$, $R^{15}$, $R^{16}$, $Q^1$, and $Q^2$.

In another embodiment $R^{10}$ is H. This embodiment may be used in combination with the other embodiments of $R^1$, $R^2$, $R^3$, $R^4$, $R^5$, $R^6$, $R^7$, $R^8$, $R^9$, $R^{11}$, $R^{12}$, $R^{13}$, $R^{14}$, $R^{15}$, $R^{16}$, $Q^1$, and $Q^2$.

In another embodiment $R^{11}$ is H. This embodiment may be used in combination with the other embodiments of $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $Q^1$, and $Q^2$.

In another embodiment $R^{12}$ is H. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $Q^1$, and $Q^2$.

In another embodiment $R^{13}$ is selected from the group consisting of H, Cl, and $(C_1-C_4)$haloalkyl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{14}$, $R^{15}$, $R^{16}$, $Q^1$, and $Q^2$.

In another embodiment $R^{13}$ is selected from the group consisting of H, Cl, and $CF_3$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{14}$, $R^{15}$, $R^{16}$, $Q^1$, and $Q^2$.

In another embodiment $R^{14}$ is H. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{15}$, $R^{16}$, $Q^1$, and $Q^2$.

In another embodiment $R^{15}$ is selected from the group consisting of H and $(C_1-C_4)$alkyl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{16}$, $Q^1$, and $Q^2$.

In another embodiment $R^{15}$ is selected from the group consisting of H and $CH_3$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{11}$, $R^{13}$, $R^{16}$, $Q^1$, and $Q^2$.

In another embodiment $R^{16}$ is selected from the group consisting of $(C_1-C_8)$alkyl, $(C_1-C_8)$alkyl-O—$(C_1-C_8)$alkyl, $(C_1-C_8)$alkyl$(C_3-C_8)$cycloalkyl, $(C_1-C_8)$alkylphenyl, $(C_2-C_8)$alkenyl, $(C_2-C_8)$alkynyl, $(C_1-C_8)$haloalkyl, $(C_1-C_8)$alkyl-S—$(C_1-C_8)$alkyl, $(C_1-C_8)$alkyl-S(O)—$(C_1-C_8)$alkyl, $(C_1-C_8)$alkyl-S(O)$_2$—$(C_1-C_8)$alkyl, O-phenyl, O—$(C_2-C_8)$alkenyl, O—$(C_1-C_8)$alkyl$(C_3-C_8)$cycloalkyl, O—$(C_1-C_8)$alkylphenyl, $(C_1-C_8)$alkyl-O—$(C_1-C_8)$alkyl$(C_3-C_8)$cycloalkyl, $(C_1-C_8)$alkyl-O—$(C_1-C_8)$haloalkyl, $(C_1-C_8)$alkyl-C(=O)NH—$(C_1-C_8)$haloalkyl, and $(C_1-C_8)$alkyl-NHC(O)—$(C_1-C_8)$alkyl, wherein each alkyl, alkenyl, alkynyl, cycloalkyl, haloalkyl, and phenyl, may be optionally substituted with one or more substituents selected from the group consisting of F, Cl, I, CN, $(C_1-C_8)$alkyl, $(C_1-C_8)$alkoxy, $(C_1-C_8)$haloalkyl, $N((C_1-C_8)$alkyl$)_2$, and pyridinyl. This embodiment may be used in combination with the other embodiments of $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, $Q^2$, and $R^{15}$.

In another embodiment $R^{16}$ is selected from the group consisting of $CH_2$, $CH_2CH_2$, $CH_2CH_2CH_2$, $CH_2CH_2CH_2CH_2$, $CH_2CH_2CH_2OCH_2CH_2$, $CH_3$, $CH_2CH_3$, $CH_2CH_2CH_3$, $CH_2CH_2CH_2CH_3$, $CH_2CH_2CH_2CH_2CH_3$, $CH_2CH_2CH_2CH_2CH_2CH_3$, $CH_2CH(CH_3)_2$, $CH_2$cyclopropyl, $CH_2CH_2$cyclopropyl, $CH_2$cyclobutyl, $CH_2$phenyl, $CH_2CH_2$phenyl, $CH_2C\equiv CH$, $CH_2C\equiv CH$, $CH_2CF_3$, $CH_2CHF_2$, $CH_2CH_2CF_3$, $CH_2CF_2CF_3$, $CH_2CH_2CH_2CF_3$, $CH_2CH_2CF_2CF_3$, $CH_2CF_2CF_2CF_3$, $CH_2CH_2CH_2CH_2F$, $CH_2CH_2SCH_3$, $CH_2CH_2S(O)CH_3$, $CH_2CH_2S(O)_2CH_3$, $C(CH_3)_2CH_2S(O)_2CH_3$, Ophenyl, $OCH_2CH=CH_2$, $OCH_2$cyclopropyl, $OCH_2$phenyl, $CH_2CH_2OCH_2$cyclopropyl, $CH_2CH_2CH_2OCH_2CF_3$, $CH_2C(=O)NHCH_2CF_3$, and $CH_2CH_2NHC(=O)CH_3$, wherein each $CH_2$, $CH_2CH_2$, $CH_2CH_2CH_2$, $CH_2CH_2CH_2CH_2$, cyclopropyl, cyclobutyl, and phenyl, may be optionally substituted with one or more substituents selected from the group consisting of F, Cl, CN, $C(CH_3)_3$, $CF_3$, $OCH_3$, $OCH_2CH_3$, $N(CH_3)_2$, and pyridinyl. This embodiment may be used in combination with the other embodiments of $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, $Q^2$, and $R^{15}$.

In another embodiment $R^{15}$ and $R^{16}$ together are a 4-membered saturated, hydrocarbyl link,
wherein said hydrocarbyl link is substituted with one or more F. This embodiment may be used in combination with the other embodiments of $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $Q^2$.

In another embodiment $R^{15}$ and $R^{16}$ together are —$CH_2CH_2CF_2CH_2$—. This embodiment may be used in combination with the other embodiments of $R^1$, $R^2$, $R^3$, $R_4$, $R^5$, $R^6$, $R^7$, $R^8$, $R^9$, $Q^1$, $R^{10}$, $R^{11}$, $R^{12}$, $R^{13}$, $R^{14}$, and $Q^2$.

In another embodiment $Q^1$ is O. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $Q^2$.

In another embodiment $Q^2$ is O. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $Q^1$.

In another embodiment:
(A) $R^1$ is H;
(B) $R^2$ is selected from the group consisting of H and Cl;
(C) $R^3$ is selected from the group consisting of H and Cl;
(D) $R^4$ is Cl;
(E) $R^5$ is H;
(F) $R^6$ is H;
(G) $R^7$ is selected from the group consisting of Cl and Br;
(H) $R^8$ is selected from the group consisting of Cl and Br;
(I) $R^9$ is H;
(J) $R^{10}$ is H;
(K) $R^{11}$ is H;
(L) $R^{12}$ is H;
(M) $R^{13}$ is selected from the group consisting of H, Cl, and $CF_3$;
(N) $R^{14}$ is H;
(O) $R^{15}$ is selected from the group consisting of H and $CH_3$;
(P) $R^{16}$ is selected from the group consisting of $CH_2$, $CH_2CH_2$, $CH_2CH_2CH_2$, $CH_2CH_2CH_2CH_2$, $CH_2CH_2CH_2OCH_2CH_2$, $CH_3$, $CH_2CH_3$, $CH_2CH_2CH_3$, $CH_2CH_2CH_2CH_3$, $CH_2CH_2CH_2CH_2CH_3$, $CH_2CH_2CH_2CH_2CH_2CH_3$, $CH_2CH(CH_3)_2$, $CH_2$cyclopropyl, $CH_2CH_2$cyclopropyl, $CH_2$cyclobutyl, $CH_2$phenyl, $CH_2CH_2$phenyl, $CH_2C\equiv CH$, $CH_2C\equiv CH$, $CH_2CF_3$, $CH_2CHF_2$, $CH_2CH_2CF_3$, $CH_2CF_2CF_3$, $CH_2CH_2CH_2CF_3$, $CH_2CH_2CF_2CF_3$, $CH_2CF_2CF_2CF_3$, $CH_2CH_2CH_2CH_2F$, $CH_2CH_2SCH_3$, $CH_2CH_2S(O)CH_3$, $CH_2CH_2S(O)_2CH_3$, $C(CH_3)_2CH_2S(O)_2CH_3$, Ophenyl, $OCH_2CH=CH_2$, $OCH_2$cyclopropyl, $OCH_2$phenyl, $CH_2CH_2OCH_2$cyclopropyl, $CH_2CH_2CH_2OCH_2CF_3$, $CH_2C(=O)NHCH_2CF_3$, and $CH_2CH_2NHC(=O)CH_3$,
wherein each $CH_2$, $CH_2CH_2$, $CH_2CH_2CH_2$, $CH_2CH_2CH_2CH_2$, cyclopropyl, cyclobutyl, and phenyl, may be optionally substituted with one or more substituents selected from the group consisting of F, Cl, CN, $C(CH_3)_3$, $CF_3$, $OCH_3$, $OCH_2CH_3$, $N(CH_3)_2$, and pyridinyl; and
(Q) $R^{15}$ and $R^{16}$ together are a 4-membered saturated, hydrocarbyl link,
wherein said hydrocarbyl link is substituted with one or more F.
(R) $Q^1$ and $Q^2$ are O.

In another embodiment:
(A) $R^1$, $R^2$, $R^3$, $R^4$, $R^5$, $R^{11}$, $R^{12}$, $R^{13}$, and $R^{14}$ are each independently selected from the group consisting of H, Cl, and $(C_1-C_4)$haloalkyl;

(B) $R^6$ and $R^9$ are H;
(C) $R^7$ is Cl;
(D) $R^8$ is Cl;
(E) $Q^1$ and $Q^2$ are O;
(F) $R^{10}$ is H;
(G) $R^{15}$ is selected from the group consisting of (I), H, and $(C_1-C_4)$alkyl;
(H) $R^{16}$ is selected from the group consisting of (I), $(C_1-C_8)$alkyl, $(C_1-C_8)$alkyl-O—$(C_1-C_8)$alkyl, $(C_1-C_8)$alkyl $(C_3-C_8)$cycloalkyl, $(C_1-C_8)$alkylphenyl, $(C_2-C_8)$alkenyl, $(C_2-C_8)$alkynyl, $(C_1-C_8)$haloalkyl, $(C_1-C_8)$alkyl-S—$(C_1-C_8)$alkyl, $(C_1-C_8)$alkyl-S(O)—$(C_1-C_8)$alkyl, $(C_1-C_8)$alkyl-S(O)$_2$—$(C_1-C_8)$alkyl, Ophenyl, O—$(C_2-C_8)$alkenyl, O—$(C_1-C_8)$alkyl$(C_3-C_8)$cycloalkyl, O—$(C_1-C_8)$alkylphenyl, $(C_1-C_8)$alkyl-O—$(C_1-C_8)$alkyl$(C_3-C_8)$cycloalkyl, $(C_1-C_8)$alkyl-O—$(C_1-C_8)$haloalkyl, $(C_1-C_8)$alkyl-C(=O)NH—$(C_1-C_8)$haloalkyl, and $(C_1-C_8)$alkyl-NHC(O)—$(C_1-C_8)$alkyl,
wherein each alkyl, alkenyl, alkynyl, cycloalkyl, haloalkyl, and phenyl, may be optionally substituted with one or more substituents selected from the group consisting of F, Cl, CN, $(C_1-C_8)$alkyl, $(C_1-C_8)$alkoxy, $(C_1-C_8)$haloalkyl, and $N((C_1-C_8)$alkyl$)_2$; and
(I) $R^{15}$ and $R^{16}$ together can optionally form a 2- to 5-membered saturated, hydrocarbyl link, wherein said hydrocarbyl link may be optionally substituted with one or more substituent selected from the group consisting of F, Cl, Br, and I.

In another embodiment:
(A) $R^1$, $R^2$, $R^3$, $R^4$, $R^5$, $R^{11}$, $R^{12}$, $R^{13}$, and $R^{14}$ are each independently selected from the group consisting of H, Cl, and $(C_1-C_4)$haloalkyl;
(B) $R^6$ and $R^9$ are H;
(C) $R^7$ is Cl;
(D) $R^8$ is Cl;
(E) $Q^1$ and $Q^2$ are O;
(F) $R^{10}$ is H;
(G) $R^{15}$ is selected from the group consisting of (I), H, and $(C_1-C_4)$alkyl;
(H) $R^{16}$ is selected from the group consisting of (I), $(C_1-C_8)$alkyl, $(C_1-C_8)$alkyl-O—$(C_1-C_8)$alkyl, $(C_1-C_8)$alkyl $(C_3-C_8)$cycloalkyl, $(C_1-C_8)$alkylphenyl, $(C_2-C_8)$alkenyl, $(C_2-C_8)$alkynyl, $(C_1-C_8)$haloalkyl, $(C_1-C_8)$alkyl-S—$(C_1-C_8)$alkyl, $(C_1-C_8)$alkyl-S(O)—$(C_1-C_8)$alkyl, $(C_1-C_8)$alkyl-S(O)$_2$—$(C_1-C_8)$alkyl, O—$(C_2-C_8)$alkenyl, O—$(C_1-C_8)$alkyl$(C_3-C_8)$cycloalkyl, O—$(C_1-C_8)$alkylphenyl, $(C_1-C_8)$alkyl-O—$(C_1-C_8)$alkyl$(C_3-C_8)$cycloalkyl, $(C_1-C_8)$alkyl-O—$(C_1-C_8)$haloalkyl, $(C_1-C_8)$alkyl-C(=O)NH—$(C_1-C_8)$haloalkyl, and $(C_1-C_8)$alkyl-NHC(O)—$(C_1-C_8)$alkyl,
wherein each alkyl, alkenyl, alkynyl, cycloalkyl, haloalkyl, and phenyl, may be optionally substituted with one or more substituents selected from the group consisting of F, Cl, CN, $(C_1-C_8)$alkoxy, and $(C_1-C_8)$haloalkyl; and
(I) $R^{15}$ and $R^{16}$ together can optionally form a 2- to 5-membered saturated, hydrocarbyl link,
wherein said hydrocarbyl link may be optionally substituted with one or more substituent selected from the group consisting of F, Cl, Br, and I.

Preparation of Cyclopropyl Carboxylic Acids

Stilbenes 1-1, wherein $R^1$, $R^2$, $R^3$, $R^4$, $R^5$, $R^6$, and $R^9$ are as previously disclosed, may be treated with a base such as sodium hydroxide in the presence of a carbene source such as chloroform or bromoform and a phase transfer catalyst such as N-benzyl-N,N-diethylethanaminium chloride in a polar protic solvent such as water at temperatures from about 0° C. to about 40° C. to provide diaryl cyclopropanes 1-2, wherein $R^1$, $R^2$, $R^3$, $R^4$, $R^5$, $R^6$, $R^7$, $R^8$, and $R^9$ are as previously disclosed (Scheme 1, step a). Treatment of diaryl cyclopropanes 1-2 with a transition metal such as ruthenium (III) chloride in the presence of a stoichiometric oxidant such as sodium periodate in a solvent mixture preferably water, ethyl acetate, and acetonitrile at temperatures from about 0° C. to about 40° C. may provide cyclopropyl carboxylic acids 1-3, wherein $R^1$, $R^2$, $R^3$, $R^4$, $R^5$, $R^6$, $R^7$, $R^8$, and $R^9$ are as previously disclosed (Scheme 1, step b).

Scheme 1

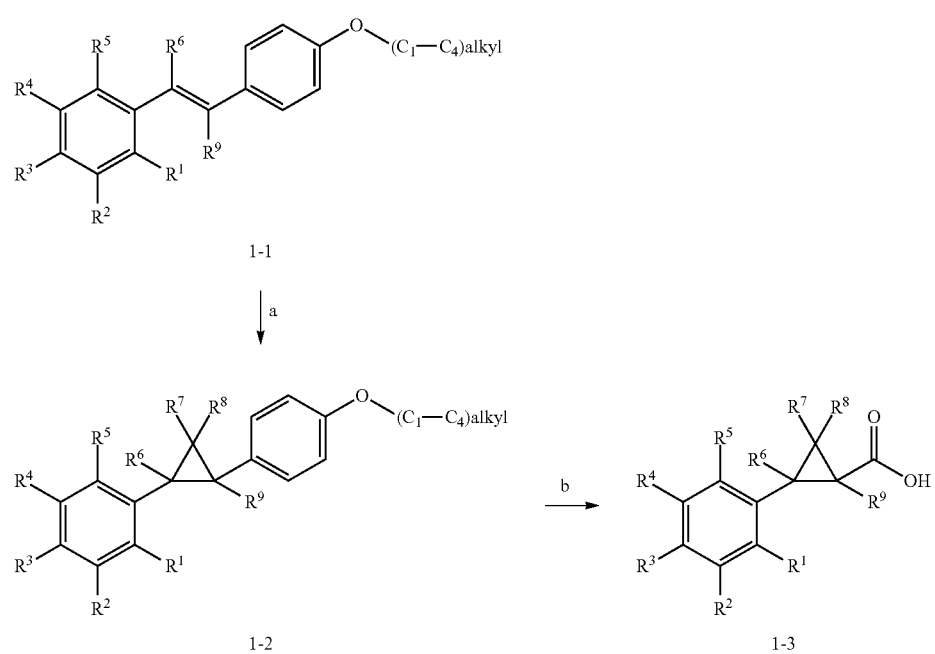

In yet other embodiments, 1-3 may be prepared from the aryl ketone 1.5-1, wherein $R^1$, $R^2$, $R^3$, $R^4$, and $R^5$ are as previously disclosed, and $R^6$ is methyl. The acetophenone 1.5-1 may be reacted in a first step with a stabilized phosphonate carbanion, generated by treating a phosphonate, such as ethyl 2-(diethoxyphosphoryl)-acetate with a strong base like sodium hydride or potassium tert-butoxide in a polar aprotic solvent, such as tetrahydrofuran at a temperature from about 0° C. to about 5° C. (Scheme 1.5, step a). This reaction, like many others involving the treatment of aldehydes or ketones with stabilized phosphonate carbanions to give olefins, will be readily recognized by one skilled in the art as the Horner-Wadsworth-Emmons olefination. In a second step, the α,β-unsaturated ester 1.5-2, wherein $R^1$, $R^2$, $R^3$, $R^4$, $R^5$, and $R^6$ are as defined above, may be treated with a reducing agent, for example a metal hydride like diisobutylaluminum hydride, in an aromatic hydrocarbon solvent like toluene at a temperature from about −78° C. to about 22° C. to give the intermediate primary alcohol 1.5-3 (Scheme 1.5, step b), wherein $R^1$, $R^2$, $R^3$, $R^4$, $R^5$, and $R^6$ are as defined above and $R^9$ is as previously disclosed. Protection of the primary alcohol 1.5-3 is required for the successful completion of subsequent chemical transformations, and a wide variety of protecting group strategies could be utilized. For example, treating the alcohol 1.5-3 with 3,4-dihydro-2-H-pyran in the presence of a catalytic amount of an organic acid, such as para-toluenesulfonic acid monohydrate, in an aprotic solvent like diethyl ether from a temperature of about 0° C. to about ambient temperature affords the tetrahydro-2-H-pyran (THP) protected alcohol 1.5-4 (Scheme 1.5, step c), wherein $R^1$, $R^2$, $R^3$, $R^4$, $R^5$, $R^6$ and $R^9$ are as defined above. The THP-protected styryl intermediate may be converted to the THP-protected cyclopropane intermediate 1.5-5, wherein $R^1$, $R^2$, $R^3$, $R^4$, $R^5$, $R^6$ and $R^9$ are as defined above and $R^7$ and $R^8$ are as previously disclosed, by treatment with carbene source such as chloroform in the presence of a base, such as sodium or potassium hydroxide, and a catalyst such as tetrabutylammonium hexafluorophosphate at a temperature from about 25 to about 45° C. (Scheme 1.5, step d). Deprotection of the THP-protected cyclopropane intermediate 1.5-5, wherein $R^1$, $R^2$, $R^3$, $R^4$, $R^5$, $R^6$, $R^7$, $R^8$, and $R^9$ are as defined above, can be achieved by treatment with a catalytic amount of an organic acid, such as para-toluenesulfonic acid monohydrate, in polar, protic solvent, such as methanol, at a temperature of about 22° C. to give the cyclopropyl methanol intermediate 1.5-6 (Scheme 1.5, step e). Oxidation of the primary alcohol intermediate 1.5-6, wherein $R^1$, $R^2$, $R^3$, $R^4$, $R^5$, $R^6$, $R^7$, $R^8$, and $R^9$ are as defined above, can be achieved using a wide range of reagents and conditions known in the art (Figadere, B. and Franck, X., "Carboxylic Acids: Synthesis from Alcohols" Science of Synthesis 2006, (20a) pp 173-204), many of which offer differential functional group compatibility and selectivity. For example, treating the alcohol intermediate 1.5-6 with solutions of chromium trioxide in solutions of dilute sulfuric acid and acetone, Jones reagent, affords the cyclopropyl carboxylic acid 1-3, wherein $R^1$, $R^2$, $R^3$, $R^4$, $R^5$, $R^6$, $R^7$, $R^8$, and $R^9$ are as defined above (Scheme 1.5, step f).

Scheme 1.5

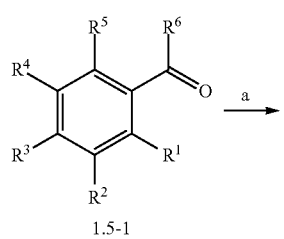

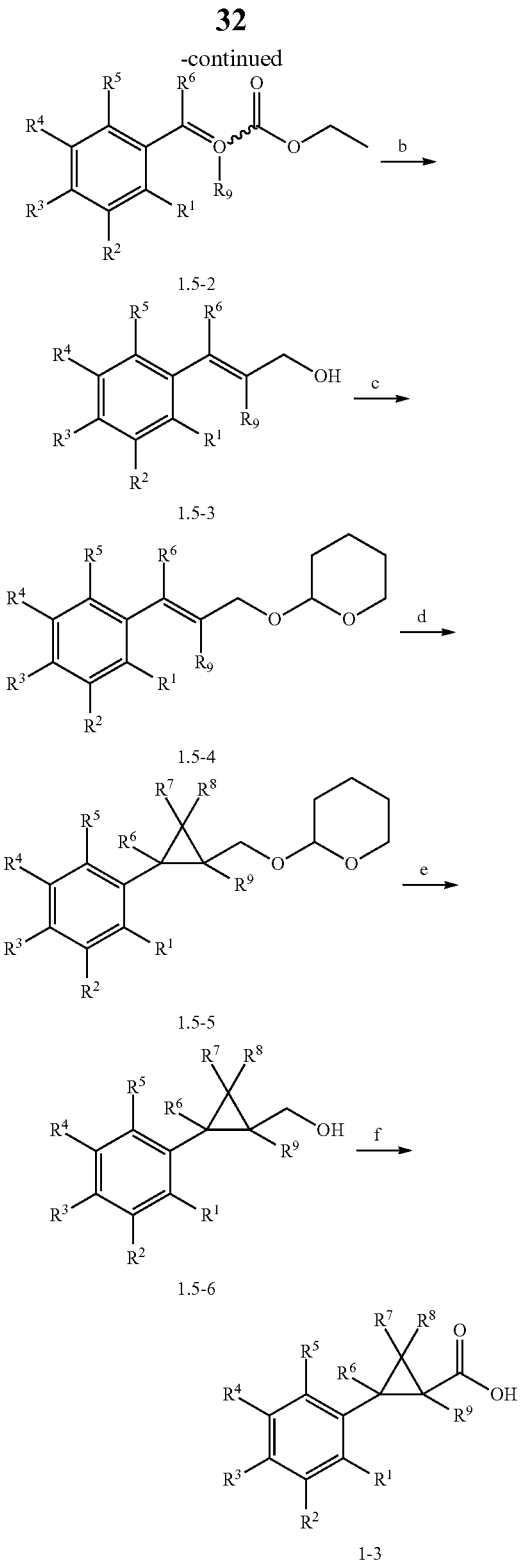

Preparation of Stilbenes

Stilbenes 1-1 may be prepared by several different methods as outlined in Scheme 2. Phenyl carbonyls 2-1, wherein $R^1$, $R^2$, $R^3$, $R^4$, $R^5$, and $R^6$ are as previously disclosed, may be treated with alkoxy benzyl phosphonates 2-2 in the presence of a base such as sodium methoxide in a polar aprotic solvent such as N,N-dimethylformamide at temperatures from about −10° C. to about 30° C. and subsequently heated to 40° C. to about 80° C. to provide stilbenes 1-1 (Scheme 2, step a).

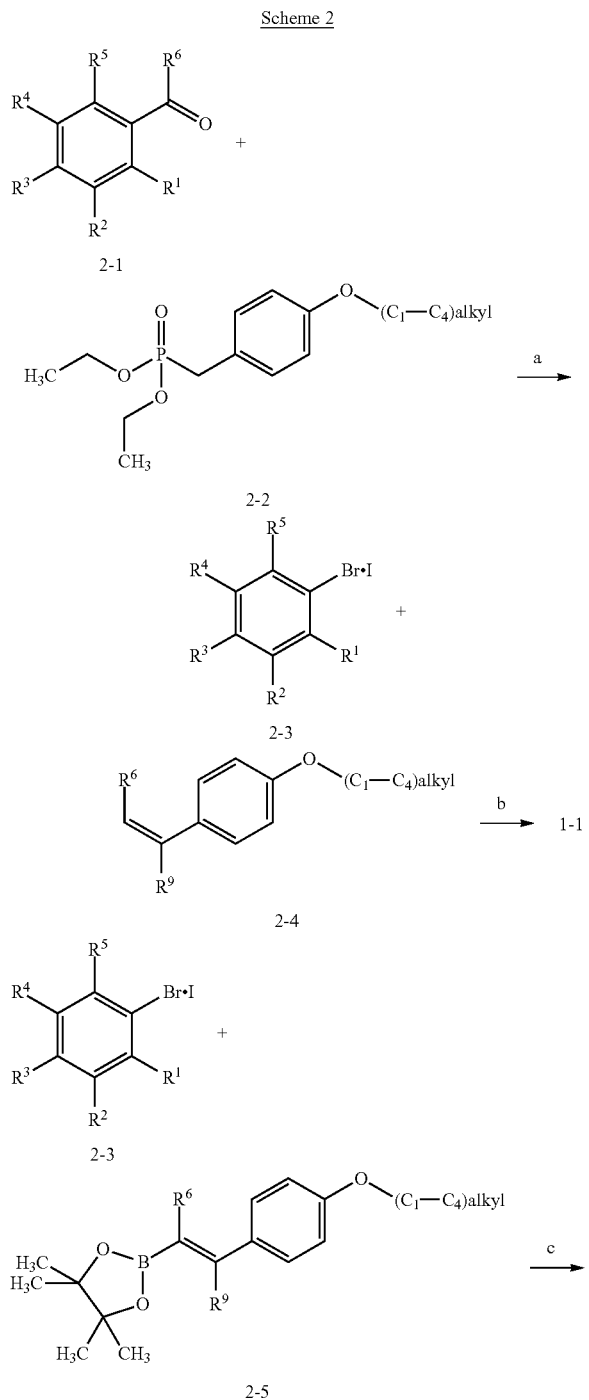

Aryl halides 2-3, wherein $R^1$, $R^2$, $R^3$, $R^4$, and $R^5$ are as previously disclosed, may be treated with vinylbenzenes 2-4, wherein $R^6$ and $R^9$ are as previously disclosed, in the presence of a transition metal catalyst such as palladium(II) acetate and a bisphosphine ligand such as 1,1'-bis(diphenylphosphino)ferrocene in a basic solvent such as triethylamine at temperatures from about 60° C. to about 100° C. to provide stilbenes 1-1 (Scheme 2, step b). Alternatively, aryl halides 2-3 may be treated with vinylboronates 2-5, wherein $R^6$ and $R^9$ are as previously disclosed, in the presence of a transition metal catalyst such as tetrakis(triphenylphosphine)palladium(0) and a base such as potassium carbonate in a solvent mixture such as 1,2-dimethoxyethane and water at temperatures from about 60° C. to about 100° C. to provide stilbenes 1-1 (Scheme 2, step c).

In yet another embodiment, stilbenes 1-1 may also be prepared by the Wittig olefination method (Chalal, M.; Vervandier-Fasseur, D.; Meunier, P.; Cattey, H.; Hierso, J.-C. *Tetrahedron* 2012, 68, 3899-3907) as outlined in Scheme 2.5. Phenyl carbonyls 2-1, wherein $R^1$, $R^2$, $R^3$, $R^4$, and $R^5$ are as previously disclosed and $R^6$ is H, may be treated with alkoxy benzyl triphenylphosphonium chlorides 2.5-2 in the presence of a base such as n-butyl lithium in a polar aprotic solvent such as tetrahydrofuran at temperatures from about −78° C. to ambient temperature to provide stilbenes 1-1 (Scheme 2.5, step a).

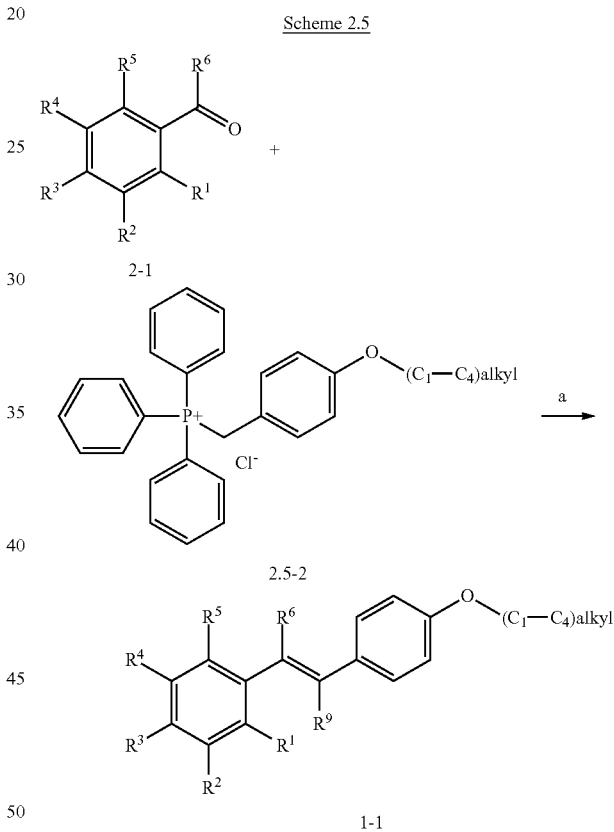

Preparation of Cyclopropyl Amides

Cyclopropyl amides 3-3, wherein $Q^1$ is O, and $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $Q^2$, $R^{15}$, and $R^{16}$ are as previously disclosed, may be prepared by treatment with amines or amine salts 3-2, wherein $R^{10}$, $R^{11}$, $R^{12}$, $R^{13}$, $R^{14}$, $Q^2$, and $R^{15}$, and $R^{16}$ are as previously disclosed, and activated carboxylic acids 3-1, wherein A is an activating group, and $R^1$, $R^2$, $R^3$, $R^4$, $R^5$, $R^6$, $R^7$, $R^8$, and $R^9$ are as previously disclosed, with a base, such as triethylamine, diisopropyl)ethylamine, 4-methylmorpholine, or 4-dimethylaminopyridine in an anhydrous aprotic solvent such as dichloromethane, tetrahydrofuran, 1,2-dichloroethane, dimethylformamide, or any combination thereof, at temperatures between about 0° C. and about 120° C. (Scheme 3, step a).

Activated carboxylic acids 3-1 may be an acid halide, such as an acid chloride, an acid bromide, or an acid fluoride; a carboxylic ester, such as a para-nitrophenyl ester, a pentafluorophenyl ester, an ethyl (hydroxyiminio)cyanoacetate ester, a methyl ester, an ethyl ester, a benzyl ester, an N-hydroxysuccinimidyl ester, a hydroxybenzotriazol-1-yl ester, or a hydroxypyridyltriazol-1-yl ester; an O-acylisourea; an acid anhydride; or a thioester. Acid chlorides may be prepared from the corresponding carboxylic acids by treatment with a dehydrating chlorinating reagent, such as oxalyl chloride or thionyl chloride. Activated carboxylic esters 3-1 may be prepared from carboxylic acids in situ with a uronium salt, such as 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium hexafluorophosphate (HBTU), or (1-cyano-2-ethoxy-2-oxoethylidenaminooxy)dimethylamino-morpholino-carbenium hexafluorophosphate (COMU). Activated carboxylic esters 3-1 may also be prepared from carboxylic acids in situ with a phosphonium salt such as benzotriazol-1-yl-oxytripyrrolidinophosphonium hexafluorophosphate (PyBop). Activated carboxylic esters 3-1 may also be prepared from carboxylic acids in situ with a coupling reagent such as 1-(3-dimethylamino propyl)-3-ethylcarbodiimide, or dicyclohexylcarbodiimide in the presence of a triazole such as hydroxybenzotriazole.monohydrate (HOBt) or 1-hydroxy-7-azabenzotriazole (HOAt). O-Acylisoureas may be prepared with a dehydrating carbodimide such as 1-(3-dimethylamino propyl)-3-ethylcarbodiimide or dicyclohexylcarbodiimide. Activated carboxylic esters 3-1 may also be prepared from carboxylic acids in situ with a coupling reagent such as 2-chloro-1,3-dimethylimidazolidinium hexafluorophosphate (CIP) in the presence of a triazole such as 1-hydroxy-7-azabenzotriazole (HOAt). Activated carboxylic esters 3-1 may also be prepared from carboxylic acids in situ with a coupling reagent such as 2,4,6-tripropyl-1,3,5,2,4,6-trioxatriphosphinane 2,4,6-trioxide (T3P®) in the presence of a base such as pyridine.

Cyclopropyl amides 3-3, wherein $R^{16}$ contains a sulfide and $R^{15}$ is as previously disclosed, may be oxidized to the corresponding sulfoxide or sulfone by treatment with about one equivalent of meta-chloroperoxybenzoic acid in a polar aprotic solvent such as dichloromethane (sulfoxide) or about two equivalents of meta-chloroperoxybenzoic acid (sulfone) at temperatures between about 0° C. to about 40° C. Alternatively, cyclopropyl amides 3-3, wherein $R^{16}$ contains a sulfide may be oxidized to the corresponding sulfoxide or sulfone by treatment with one equivalent of sodium perborate in a protic solvent such as acetic acid (sulfoxide) or two equivalents of sodium perborate (sulfone). Preferably, the oxidation will be performed at temperatures between about 40° C. to about 100° C. using about 1.5 equivalents of sodium perborate to provide chromatographically separable mixtures of sulfoxide and sulfone cyclopropyl amides 3-3.

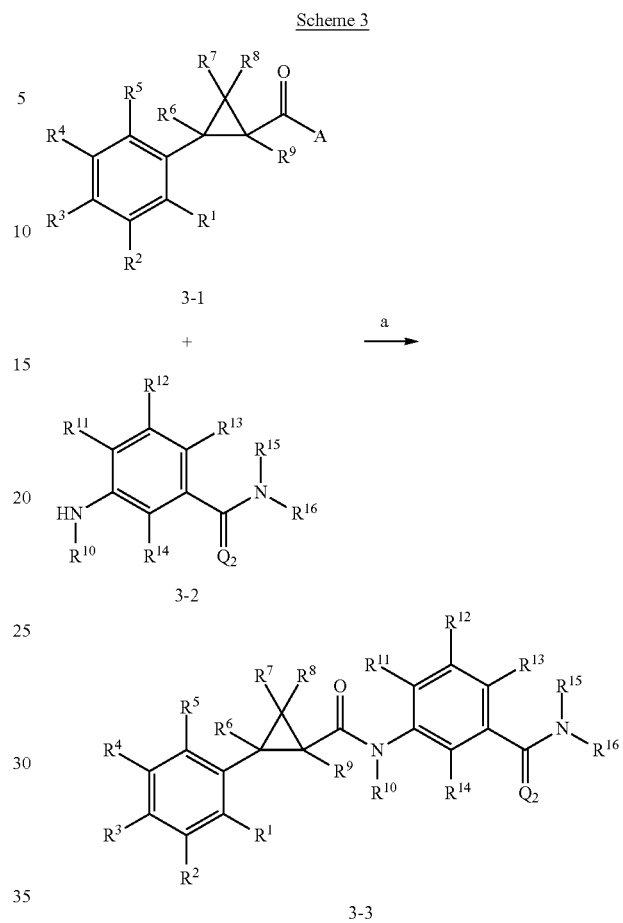

Scheme 3

Cyclopropyl amides 4-3, wherein $Q^2$ is O, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, $R^{15}$, and $R^{16}$ are as previously disclosed, may be prepared by treatment with amines or amine salts 4-2, wherein $R^{15}$ and $R^{16}$ are as previously disclosed, and activated carboxylic acids 4-1, wherein A is an activating group, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, and $R^{14}$ are as previously disclosed, with a base, such as triethylamine, diisopropylethylamine, 4-methylmorpholine, or 4-dimethylaminopyridine in an anhydrous aprotic solvent such as dichloromethane, tetrahydrofuran, 1,2-dichloroethane, dimethylformamide, or any combination thereof, at temperatures between about 0° C. and about 120° C. (Scheme 4, step a).

Activated carboxylic acids 4-1 may be an acid halide, such as an acid chloride, an acid bromide, or an acid fluoride; a carboxylic ester, such as a para-nitrophenyl ester, a pentafluorophenyl ester, an ethyl (hydroxyiminio)cyanoacetate ester, a methyl ester, an ethyl ester, a benzyl ester, an N-hydroxysuccinimidyl ester, a hydroxybenzotriazol-1-yl ester, or a hydroxypyridyltriazol-1-yl ester; an O-acylisourea; an acid anhydride; or a thioester. Acid chlorides may be prepared from the corresponding carboxylic acids by treatment with a dehydrating chlorinating reagent, such as oxalyl chloride or thionyl chloride. Activated carboxylic esters 4-1 may be prepared from carboxylic acids in situ with a uronium salt, such as 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium hexafluorophosphate (HBTU), or (1-cyano-2-ethoxy-2-oxoethylidenaminooxy)dimethylamino-morpholino-carbenium hexafluorophosphate (COMU). Activated carboxylic esters 4-1 may also be prepared from carboxylic acids in situ with a phosphonium salt such as benzotriazol-1-yl-oxytripyrrolidinophosphonium hexafluorophosphate (PyBop). Activated carboxylic esters 4-1 may also be prepared from carboxylic acids in situ with a coupling reagent such as 1-(3-dimethylamino propyl)-3-ethylcarbodiimide, or dicyclohexylcarbodiimide in the presence of a triazole such as hydroxybenzotriazole.monohydrate (HOBt) or 1-hydroxy-7-azabenzotriazole (HOAt). O-Acylisoureas may be prepared with a dehydrating carbodimide such as 1-(3-dimethylamino propyl)-3-ethylcarbodiimide or dicyclohexylcarbodiimide. Activated carboxylic esters 4-1 may also be prepared from carboxylic acids in situ with a coupling reagent such as 2-chloro-1,3-dimethylimidazolidinium hexafluorophosphate (CIP) in the presence of a triazole such as 1-hydroxy-7-azabenzotriazole (HOAt). Activated carboxylic esters 4-1 may also be prepared from carboxylic acids in situ with a coupling reagent such as 2,4,6-tripropyl-1,3,5,2,4,6-trioxatriphosphinane 2,4,6-trioxide (T3P®) in the presence of a base such as pyridine.

ence of an acid whose pH is 0-5 such as hydrobromic acid, N-bromosuccinimide, hydrochloric acid, N-chlorosuccinimide, and pyridinium p-toluenesulfonate (PPTS), in a $(C_1-C_6)$ alkanol solvent, at a temperature from 0° C. to ambient and under ambient pressure provides the acetal 5-2, wherein $R^1$, $R^2$, $R^3$, $R^4$, $R^5$, $R^6$, and $R^9$ are as previously disclosed and $R^a$ is a $(C_1-C_6)$alkyl or $R^a$ and $R^a$ taken together can form a cyclic acetal (Scheme 5, step a). The acetal 5-2 may be converted to the cyclopropyl acetal 5-3, wherein $R^1$, $R^2$, $R^3$, $R^4$, $R^5$, $R^6$, $R^7$, $R^8$, $R^9$, and $R^a$ are as previously disclosed, by treatment with a carbene source such as a haloform, for example, bromoform or chloroform, in the presence of an inorganic base, such as sodium or potassium hydroxide or sodium or potassium carbonate, and a phase-transfer catalyst such as benzyl triethylammonium chloride, (−)-N-dodecyl-N-methylephedrinium bromide, tetramethylammonium bromide, tetrapropylammonium bromide, tetrabutylammonium tetrafluoroborate, tetramethylammonium chloride or tetrabutylammonium hexafluorophosphate at a temperature from about ambient temperature up to below the boiling point of the haloform (Scheme 5, step b). Caution: Step B is an exothermic reaction and careful control of the exotherm should be exercised when conducting this reaction. The cyclopropyl acetal 5-3 may be transformed into the aldehyde 5-4, wherein $R^1$, $R^2$, $R^3$, $R^4$, $R^5$, $R^6$, $R^7$, $R^8$, and $R^9$ are as previously disclosed, in a polar solvent selected from the group consisting of acetone, acetonitrile, methanol, ethanol, nitromethane, N,N-dimethylformamide, dimethyl sulfoxide, ethyl acetate, tetrahydrofuran and 1,4-dioxane, in the presence of an aqueous mineral acid selected from the group consisting of nitric acid, hydrochloric acid, hydrobromic acid, and sulfuric acid (Scheme 5, step c) at ambient temperature. The cyclopropyl acid 1-3, wherein $R^1$, $R^2$, $R^3$, $R^4$, $R^5$, $R^6$, $R^7$, $R^8$, and $R^9$ are as previously disclosed, may be obtained by oxidation of the aldehyde 5-4 with oxidants such sodium permanganate or potassium permanganate, or under Pinnick oxidation conditions in a polar aprotic solvent selected from the group consisting of acetone, acetonitrile, N,N-dimethylformamide, dimethyl sulfoxide, ethyl acetate, tetrahydrofuran and 1,4-dioxane at a temperature from about 0° C. to about ambient temperature (Scheme 5, step d). Standard safety precautions should be exercised because an exotherm may occur when conducting this reaction.

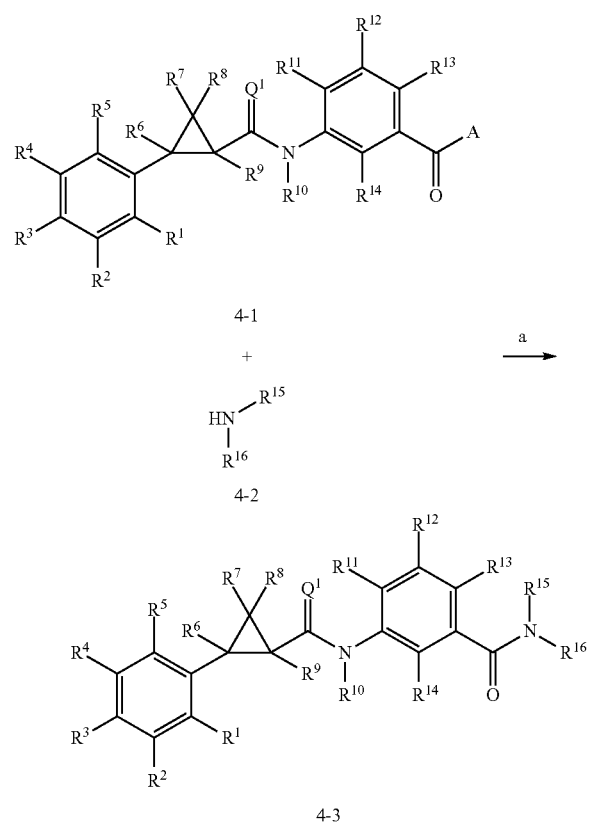

Scheme 4

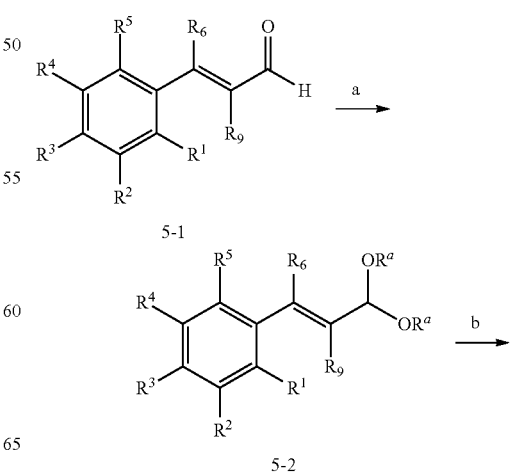

Scheme 5

In some embodiments, 1-3 may be prepared from the α,β-unsaturated aldehyde 5-1, wherein $R^1$, $R^2$, $R^3$, $R^4$, $R^5$, $R^6$, and $R^9$ are as previously. It will be understood by one skilled in the art that compound 5-1 may be synthesized via Aldol condensation (see Yoshikawa, M.; Kamei, T. PCT Int. Appl. 2010123006, 2010) of an appropriately substituted, commercially available aldehyde and acetaldehyde. Treatment of 5-1 with a $(C_1-C_6)$alkyl orthoformate, in the pres-

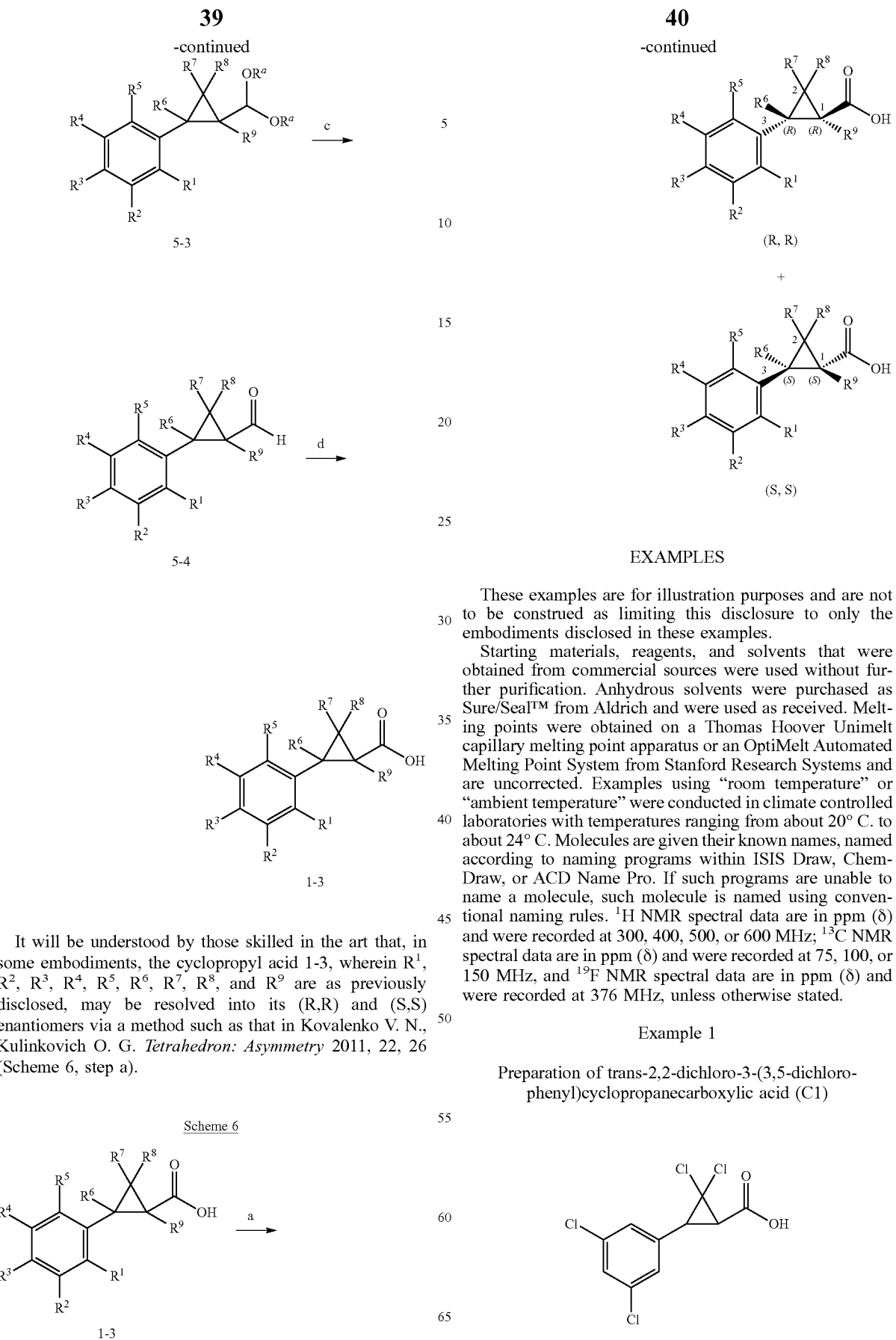

It will be understood by those skilled in the art that, in some embodiments, the cyclopropyl acid 1-3, wherein $R^1$, $R^2$, $R^3$, $R^4$, $R^5$, $R^6$, $R^7$, $R^8$, and $R^9$ are as previously disclosed, may be resolved into its (R,R) and (S,S) enantiomers via a method such as that in Kovalenko V. N., Kulinkovich O. G. *Tetrahedron: Asymmetry* 2011, 22, 26 (Scheme 6, step a).

EXAMPLES

These examples are for illustration purposes and are not to be construed as limiting this disclosure to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" or "ambient temperature" were conducted in climate controlled laboratories with temperatures ranging from about 20° C. to about 24° C. Molecules are given their known names, named according to naming programs within ISIS Draw, ChemDraw, or ACD Name Pro. If such programs are unable to name a molecule, such molecule is named using conventional naming rules. $^1$H NMR spectral data are in ppm ($\delta$) and were recorded at 300, 400, 500, or 600 MHz; $^{13}$C NMR spectral data are in ppm ($\delta$) and were recorded at 75, 100, or 150 MHz, and $^{19}$F NMR spectral data are in ppm ($\delta$) and were recorded at 376 MHz, unless otherwise stated.

Example 1

Preparation of trans-2,2-dichloro-3-(3,5-dichlorophenyl)cyclopropanecarboxylic acid (C1)

Ruthenium(III) chloride (0.080 g, 0.39 mmol) was added to a stirred mixture of trans-1,3-dichloro-5-(-2,2-dichloro-3-(4-methoxyphenyl)cyclopropyl)benzene (C22) (2.8 g, 7.7 mmol) and sodium periodate (33 g, 160 mmol) in water:ethyl acetate:acetonitrile (8:1:1, 155 mL) at 23° C. The resulting biphasic brown mixture was vigorously stirred at 23° C. for 5 hours. The reaction mixture was diluted with water (1000 mL) and extracted with dichloromethane (4×200 mL). The combined organic layers were dried over magnesium sulfate, filtered, and concentrated. The residue was diluted with a sodium hydroxide solution (1 M, 100 mL) and washed with diethyl ether (4×50 mL). The aqueous layer was adjusted to pH 2, using concentrated hydrochloric acid, and extracted with dichloromethane (3×50 mL). The combined organic layers were dried over magnesium sulfate, filtered, and concentrated to afford the title product as a light brown powder (0.78 g, 34%): mp 117-120° C.; $^1$H NMR (400 MHz, DMSO-$d_6$) δ 13.38 (br s, 1H), 7.52-7.65 (m, 3H), 3.57 (d, J=8.5 Hz, 1H), 3.50 (d, J=8.5 Hz, 1H); IR (thin film) 3083 (s), 3011 (s), 1731 (s), 1590 (w), 1566 (s), 1448 (w), 1431 (m), 1416 (m) cm$^{-1}$.

The following compounds were prepared in like manner to the procedure outlined in Example 1:

trans-2,2-Dichloro-3-(3,4,5-trichlorophenyl)cyclopropanecarboxylic acid (C2)

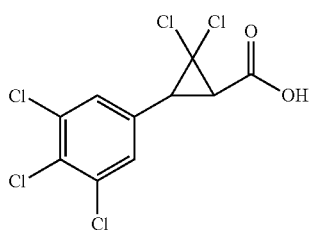 [SMILES: O=C(O)C1C(c2cc(Cl)c(Cl)c(Cl)c2)C1(Cl)Cl]

Isolated as a yellow powder (1.5 g, 39%): $^1$H NMR (400 MHz, CDCl$_3$) δ 7.31 (d, J=0.7 Hz, 2H), 3.40 (d, J=8.2 Hz, 1H), 2.86 (d, J=8.3 Hz, 1H); $^{13}$C NMR (101 MHz, CDCl$_3$) δ 171.05, 134.55, 132.44, 131.75, 128.89, 61.18, 39.26, 37.14; ESIMS m/z 333 ([M−H]$^-$).

trans-2,2-Dichloro-3-(3,4-dichlorophenyl)cyclopropanecarboxylic acid (C3)

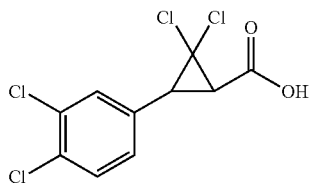

Isolated as a pale yellow solid (3.2 g, 51%): $^1$H NMR (400 MHz, CDCl$_3$) δ 7.47 (d, J=8.3 Hz, 1H), 7.37 (d, J=1.6 Hz, 1H), 7.12 (ddd, J=8.3, 2.1, 0.6 Hz, 1H), 3.43 (d, J=8.3 Hz, 1H), 2.86 (d, J=8.3 Hz, 1H); $^{13}$C NMR (101 MHz, CDCl$_3$) δ 171.52, 132.91, 132.76, 132.29, 130.66, 130.62, 128.02, 61.48, 39.65, 37.13; ESIMS m/z 298 ([M−H]$^-$).

Example 2

Preparation of trans-2,2-dichloro-3-(4-(trifluoromethyl)phenyl)cyclopropanecarboxylic acid (C4)

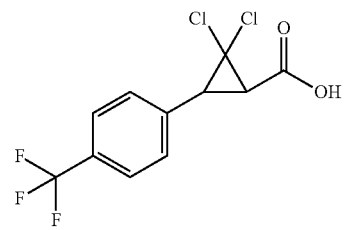 [SMILES: O=C(O)C1C(c2ccc(C(F)(F)F)cc2)C1(Cl)Cl]

To a stirred mixture of trans-1-(2,2-dichloro-3-(4-(trifluoromethyl)phenyl)cyclopropyl)-4-methoxybenzene (C25) (3.50 g, 9.60 mmol) and sodium periodate (30.8 g, 144 mmol) in water:ethyl acetate:acetonitrile (8:1:1, 200 mL) was added ruthenium(III) chloride (0.100 g, 0.400 mmol) at 23° C. The resulting mixture was vigorously stirred at 23° C. for about 5 hours. The reaction mixture was diluted with dichloromethane and washed with water. The combined organic layers were dried over sodium sulfate, filtered, and concentrated. Purification by flash column chromatography provided the title compound as an off-white solid (0.630 g, 38%): mp 100-102° C.; $^1$H NMR (400 MHz, DMSO-$d_6$) δ 13.43 (brs, 1H), 7.77-7.73 (m, 2H), 7.67-7.64 (m, 2H), 3.55 (d, J=8.8 Hz, 1H), 3.44 (d, J=8.8 Hz, 1H); ESIMS m/z 347 ([M−H]$^-$).

The following compounds were prepared in like manner to the procedure outlined in Example 2:

trans-2,2-Dichloro-3-(3-(trifluoromethyl)phenyl)cyclopropane carboxylic acid (C5)

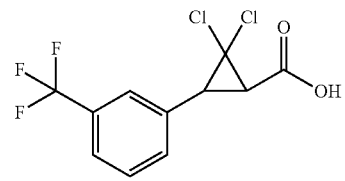 [SMILES: O=C(O)C1C(c2cccc(C(F)(F)F)c2)C1(Cl)Cl]

Isolated as an off-white solid (0.81 g, 33%): mp 86-88° C.; $^1$H NMR (400 MHz, DMSO-$d_6$) δ 13.37 (brs, 1H), 7.83 (s, 1H), 7.76-7.69 (m, 2H), 7.65-7.59 (m, 1H), 3.59-3.51 (m, 2H); ESIMS m/z 297 ([M−H]$^-$).

trans-2,2-Dichloro-3-(3-chloro-4-(trifluoromethoxy)phenyl)cyclopropanecarboxylic acid (C6)

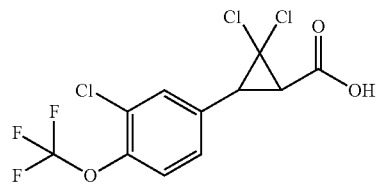 [SMILES: O=C(O)C1C(c2ccc(OC(F)(F)F)c(Cl)c2)C1(Cl)Cl]

Isolated as an off-white solid (0.3 g, 19%): mp 134-136° C.; $^1$H NMR (400 MHz, DMSO-d$_6$) δ 13.45 (brs, 1H), 7.82 (d, J=1.6 Hz, 1H), 7.60-7.53 (m, 2H), 3.53-3.47 (m, 2H); ESIMS m/z 347 ([M−H]$^-$).

trans-2,2-Dichloro-3-(2,4,5-trichlorophenyl)cyclopropanecarboxylic acid (C7)

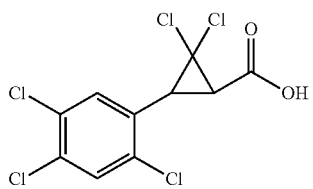 [SMILES: O=C(O)C1C(c2cc(Cl)c(Cl)cc2Cl)C1(Cl)Cl]

Isolated as an off-white solid (0.267 g, 18%): mp 189-192° C.; $^1$H NMR (400 MHz, DMSO-d$_6$) δ 13.44 (brs, 1H), 8.01 (s, 1H), 7.82 (s, 1H), 3.52 (d, J=8.2 Hz, 1H), 3.29 (d, J=8.2 Hz, 1H); ESIMS m/z 333 ([M−H]$^-$).

trans-3-(3,5-bis(trifluoromethyl)phenyl)-2,2-dichlorocyclopropanecarboxylic acid (C8)

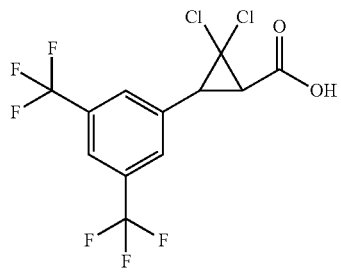 [SMILES: O=C(O)C1C(c2cc(C(F)(F)F)cc(C(F)(F)F)c2)C1(Cl)Cl]

Isolated as an off-white solid (0.5 g, 31%): mp 112-114° C.; $^1$H NMR (400 MHz, DMSO-d$_6$) δ 13.43 (brs, 1H), 8.22 (s, 2H), 8.08 (s, 1H), 3.80-3.71 (m, 2H); ESIMS m/z 365 ([M−H]$^-$).

trans-2,2-dichloro-3-(3,5-dibromophenyl)cyclopropanecarboxylic acid (C9)

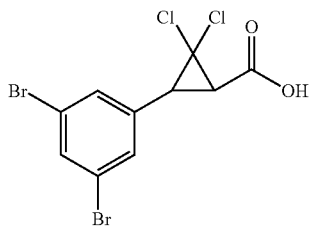

Isolated as an off-white solid (0.5 g, 24%): mp 157-159° C.; $^1$H NMR (400 MHz, DMSO-d$_6$) δ 13.36 (brs, 1H), 7.81 (d, J=1.5 Hz, 2H), 7.72 (d, J=1.5 Hz, 2H), 3.57-3.53 (m, 1H), 3.51-3.47 (m, 1H); ESIMS m/z 387 ([M−H]$^-$).

trans-2,2-Dichloro-3-(3-chloro-5-(trifluoromethyl)phenyl)cyclopropanecarboxylic acid (C10)

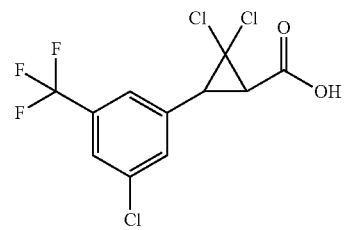 [SMILES: O=C(O)C1C(c2cc(Cl)cc(C(F)(F)F)c2)C1(Cl)Cl]

Isolated as an off-white solid (0.73 g, 28%): mp 113-115° C.; $^1$H NMR (400 MHz, DMSO-d$_6$) δ 13.39 (brs, 1H), 7.91 (s, 1H), 7.86 (s, 1H), 7.84 (s, 1H), 3.69-3.60 (m, 2H); ESIMS m/z 333 ([M−H]$^-$).

trans-2,2-Dichloro-3-(3,5-dichloro-4-fluorophenyl)cyclopropanecarboxylic acid (C11)

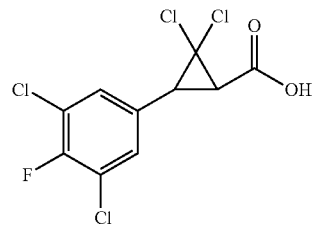

Isolated as an off-white solid (0.539 g, 34%): $^1$H NMR (400 MHz, DMSO-d$_6$): δ 13.37 (brs, 1H), 7.71 (d, J=6.4 Hz, 2H), 3.42 (s, 2H); ESIMS m/z 317 ([M−H]$^-$).

trans-3-(4-Bromo-3,5-dichlorophenyl)-2,2-dichlorocyclopropanecarboxylic acid (C12)

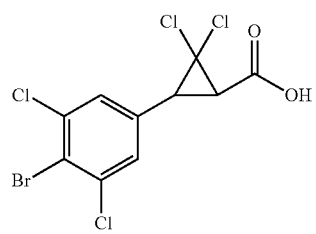

Isolated as an off-white solid (0.100 g, 10%): $^1$H NMR (400 MHz, DMSO-d$_6$) δ 13.37 (brs, 1H), 7.76 (s, 3H), 3.57 (d, J=8.8 Hz, 1H), 3.48 (d, J=8.8 Hz, 1H); ESIMS m/z 377 ([M−H]$^-$).

trans-3-(3-Bromo-5-chlorophenyl)-2,2-dichlorocyclopropanecarboxylic acid (C13)

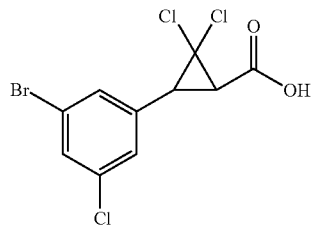

Isolated as an off-white solid (0.4 g, 25%): mp 161-163° C.; $^1$H NMR (400 MHz, DMSO-d$_6$) δ 13.38 (br s, 1H), 7.70 (d, J=5.3 Hz, 2H), 7.66-7.52 (m, 1H), 3.59-3.43 (m, 2H); ESIMS m/z 341 ([M–H]$^-$).

trans-2,2-Dichloro-3-(3-chloro-5-fluorophenyl)cyclopropanecarboxylic acid (C14)

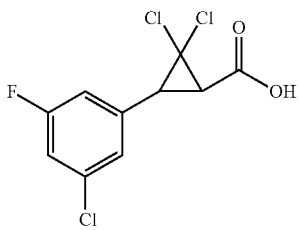 [SMILES: O=C(O)C1C(c2cc(F)cc(Cl)c2)C1(Cl)Cl]

Isolated as an off-white solid (0.700 g, 25%): mp 138-140° C.; $^1$H NMR (400 MHz, DMSO-d$_6$) δ 13.38 (brs, 1H), 7.46 (s, 1H), 7.42 (td, J=2.0, 8.7 Hz, 1H), 7.37 (d, J=9.8 Hz, 1H), 3.52 (q, J=8.5 Hz, 2H); ESIMS m/z 281 ([M–H]$^-$).

trans-2,2-Dichloro-3-(4-chloro-3-fluorophenyl)cyclopropanecarboxylic acid (C15)

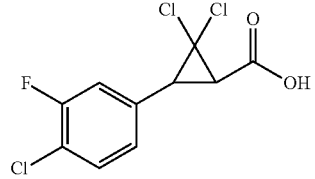 [SMILES: O=C(O)C1C(c2ccc(Cl)c(F)c2)C1(Cl)Cl]

Isolated as an off-white solid (0.500 g, 20%): mp 140-142° C.; $^1$H NMR (400 MHz, DMSO-d$_6$) δ 13.40 (brs, 1H), 7.59 (m, 1H), 7.55 (d, J=8.4 Hz, 1H), 7.33 (dd, J=2.0, 8.4 Hz, 1H), 3.55-3.38 (m, 2H); ESIMS m/z 281 ([M–H]$^-$).

trans-2,2-Dichloro-3-(3-chloro-4-fluorophenyl)cyclopropanecarboxylic acid (C16)

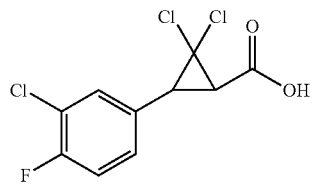

Isolated as an off-white solid (1.0 g, 53%): mp 121-123° C.; $^1$H NMR (400 MHz, DMSO-d$_6$) δ 13.35 (brs, 1H), 7.71 (dd, J=2.0, 7.2 Hz, 1H), 7.53-7.35 (m, 2H), 3.50-3.41 (m, 2H); ESIMS m/z 281 ([M–H]$^-$).

trans-2,2-Dichloro-3-(3-chloro-5-methylphenyl)cyclopropanecarboxylic acid (C17)

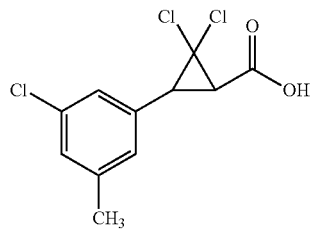 [SMILES: Cc1cc(Cl)cc(C2C(C(=O)O)C2(Cl)Cl)c1]

Isolated as an off-white solid (1.0 g, 42%): mp 124-126° C.; $^1$H NMR (400 MHz, DMSO-d$_6$) δ 13.33 (brs, 1H), 7.30 (s, 1H), 7.23 (s, 1H), 7.21 (s, 1H), 3.38 (s, 2H), 2.31 (s, 3H); ESIMS m/z 277 ([M–H]$^-$).

trans-2,2-Dichloro-3-(3,5-dichloro-4-methylphenyl)cyclopropanecarboxylic acid (C18)

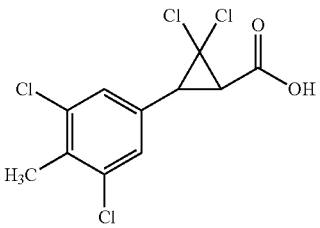 [SMILES: Cc1c(Cl)cc(C2C(C(=O)O)C2(Cl)Cl)cc1Cl]

Isolated as an off-white solid (0.8 g, 40%): mp 181-183° C.; $^1$H NMR (400 MHz, DMSO-d$_6$) δ 13.40 (s, 1H), 7.56 (s, 2H), 3.53-3.50 (m, 1H), 3.46-3.43 (m, 2H), 2.40 (s, 3H); ESIMS m/z 311 ([M–H]$^-$).

trans-2,2-Dichloro-3-(3,4-dichloro-5-methylphenyl)cyclopropanecarboxylic acid (C19)

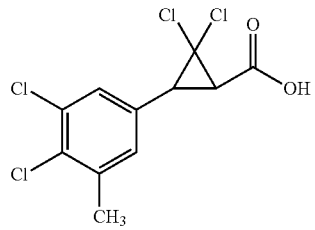 [SMILES: Cc1cc(C2C(C(=O)O)C2(Cl)Cl)cc(Cl)c1Cl]

Isolated as an off-white solid (0.73 g, 45%): mp 157-159° C.; $^1$H NMR (400 MHz, DMSO-d$_6$) δ 13.40 (s, 1H), 7.59 (d, J=2.0 Hz, 1H), 7.44 (d, J=1.6 Hz, 1H), 3.43 (q, J=8.5 Hz, 2H), 2.39 (s, 3H); ESIMS m/z 311 ([M−H]$^−$).

trans-2,2-Dichloro-3-(4-(perfluoroethyl)phenyl)cyclopropanecarboxylic acid (C20)

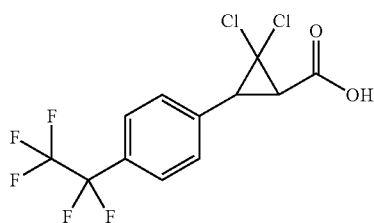 [SMILES: O=C(O)C1C(c2ccc(C(F)(F)C(F)(F)F)cc2)C1(Cl)Cl]

Isolated as an off-white solid (0.020 g, 10%): mp 116-118° C.; $^1$H NMR (300 MHz, CDCl$_3$) δ 7.63 (d, J=8.1 Hz, 2H), 7.42 (d, J=8.1 Hz, 2H), 3.53 (d, J=8.4 Hz, 1H), 2.94 (d, J=8.4 Hz, 1H); ESIMS m/z 347 ([M−H]$^−$).

trans-2,2-dichloro-3-(4-ethoxyphenyl)cyclopropanecarboxylic acid (C21)

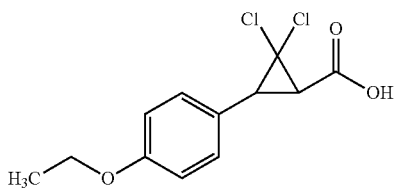 [SMILES: CCOc1ccc(C2C(C(=O)O)C2(Cl)Cl)cc1]

Isolated as an off-white solid (0.025 g, 5%): mp 129-130° C.; $^1$H NMR (400 MHz, CDCl$_3$) δ 7.16 (d, J=8.4 Hz, 2H), 6.88 (d, J=8.31 Hz, 2H), 4.03 (q, J=6.8 Hz, 2H), 3.41 (d, J=8.0 Hz, 1H), 2.81 (d, J=8.0 Hz, 1H), 1.41 (t, J=6.8 Hz, 3H); ESIMS m/z 273 ([M−H]$^−$).

Example 3

Preparation of trans-1,3-dichloro-5-(2,2-dichloro-3-(4-methoxyphenyl)cyclopropyl)benzene (C22)

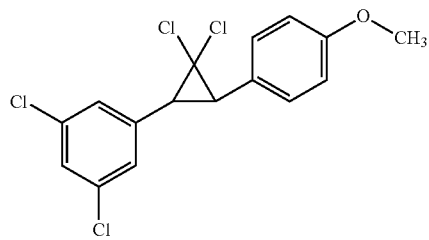

Aqueous sodium hydroxide (50%, 6.8 mL, 130 mmol) was added to a stirred solution of (E)-1,3-dichloro-5-(4-methoxystyryl)benzene (C43) (2.4 g, 8.6 mmol) and N-benzyl-N,N-diethylethanaminium chloride (0.20 g, 0.86 mmol) in chloroform (14 mL, 170 mmol) at 23° C. The resulting biphasic, dark brown mixture was vigorously stirred at 23° C. for 24 hours. The reaction mixture was diluted with water (200 mL) and extracted with dichloromethane (2×100 mL). The combined organic layers were dried over magnesium sulfate, filtered, and concentrated to afford the title product as a brown oil (2.8 g, 90%): $^1$H NMR (400 MHz, CDCl$_3$) δ 7.34 (t, J=1.8 Hz, 1H), 7.21-7.30 (m, 4H), 6.93 (m, 2H), 3.83 (s, 3H), 3.14 (d, J=8.5 Hz, 1H), 3.08 (d, J=8.5 Hz, 1H); IR (thin film) 3075 (w), 2934 (w), 2836 (w), 1724 (w), 1640 (w), 1609 (m), 1584 (m), 1568 (s), 1513 (s) cm$^{−1}$.

The following compounds were prepared in like manner to the procedure outlined in Example 3:

trans-1,2,3-Trichloro-5-(2,2-dichloro-3-(4-methoxyphenyl)cyclopropyl)benzene (C23)

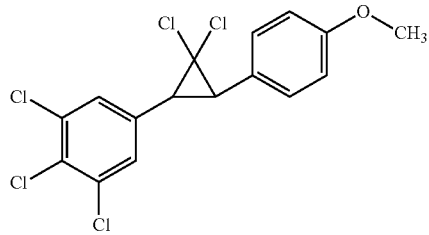 [SMILES: COc1ccc(C2C(c3cc(Cl)c(Cl)c(Cl)c3)C2(Cl)Cl)cc1]

Isolated as a dark foam (4.7 g, 100%): $^1$H NMR (400 MHz, CDCl$_3$) δ 7.40 (d, J=0.6 Hz, 2H), 7.29-7.22 (m, 2H), 6.96-6.89 (m, 2H), 3.83 (s, 3H), 3.12 (d, J=8.8 Hz, 1H), 3.06 (d, J=8.7 Hz, 1H); $^{13}$C NMR (101 MHz, CDCl$_3$) δ 159.46, 135.08, 134.23, 130.91, 129.85, 129.16, 125.42, 114.02, 64.67, 55.32, 39.62, 38.48.

trans-1,2-Dichloro-4-(2,2-dichloro-3-(4-methoxyphenyl)cyclopropyl)benzene (C24)

Isolated as an orange-red oil (7.6 g, 99%): $^1$H NMR (400 MHz, CDCl$_3$) δ 7.47 (d, J=4.9 Hz, 1H), 7.45 (bs, 1H), 7.30-7.23 (m, 2H), 7.21 (dd, J=8.2, 1.9 Hz, 1H), 6.96-6.90 (m, 2H), 3.83 (s, 3H), 3.11 (app. q, J=8.8 Hz, 2H); $^{13}$C NMR (101 MHz, CDCl$_3$) δ 159.39, 134.90, 132.62, 131.99, 130.90, 130.40, 129.90, 128.33, 125.81, 113.98, 64.94, 55.33, 39.52, 38.75.

Example 4

Preparation of trans-1-(2,2-dichloro-3-(4-(trifluoromethyl)phenyl)cyclopropyl)-4-methoxybenzene (C25)

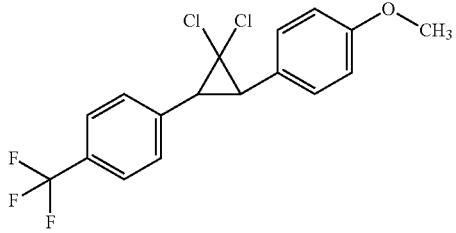 [SMILES: COc1ccc(C2C(c3ccc(C(F)(F)F)cc3)C2(Cl)Cl)cc1]

To a stirred solution of (E)-1-methoxy-4-(4-(trifluoromethyl)styryl)benzene (C46) (4.00 g, 14.0 mmol) and N-benzyl-N,N-diethylethanaminium chloride (0.320 g, 14.0 mmol) in chloroform (23.1 g, 288 mmol), was added aqueous sodium hydroxide (50%, 8.64 g, 216 mmol) in water (17 mL) at 23° C., and the resulting mixture was vigorously stirred at 23° C. for 16 hours. The reaction mixture was diluted with water and extracted with dichloromethane. The combined organic layers were dried over sodium sulfate, filtered, and concentrated. Purification by flash column chromatography provided the title compound as an off-white solid (3.70 g, 68%): $^1$H NMR (300 MHz, CDCl$_3$) δ 7.65 (d, J=8.4 Hz, 2H), 7.49 (d, J=8.4 Hz, 2H), 7.29 (d, J=8.4 Hz, 2H), 6.94 (d, J=8.4 Hz, 2H), 3.83 (s, 3H), 3.19 (s, 2H); ESIMS m/z 361 ([M+H]$^+$).

The following compounds were prepared in like manner to the procedure outlined in Example 4:

trans-1-(2,2-Dichloro-3-(4-methoxyphenyl)cyclopropyl)-3-(trifluoromethyl)benzene (C26)

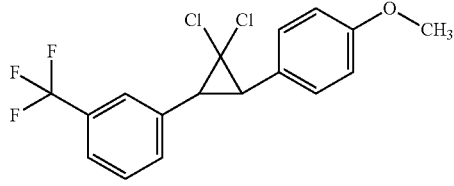 [SMILES: COc1ccc(C2C(c3cccc(C(F)(F)F)c3)C2(Cl)Cl)cc1]

Isolated as a brown liquid (3.5 g, 67%): $^1$H NMR (300 MHz, CDCl$_3$) δ 7.62-7.50 (m, 4H), 7.29 (d, J=9.0 Hz, 2H), 6.94 (d, J=9.0 Hz, 2H), 7.35-7.25 (m, 3H), 7.97-6.88 (m, 1H), 3.83 (s, 3H), 3.19 (m, 2H); ESIMS m/z 361 ([M+H]$^+$).

trans-2-Chloro-4-(2,2-dichloro-3-(4-methoxyphenyl)cyclopropyl)-1-(trifluoromethoxy)benzene (C27)

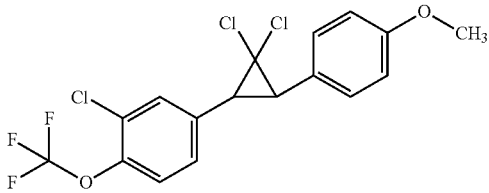

Isolated as an off-white solid (2.5 g, 65%): $^1$H NMR (400 MHz, CDCl$_3$) δ 7.57 (d, J=2.0 Hz, 1H), 7.44 (d, J=8.8 Hz, 1H), 7.35-7.25 (m, 3H), 7.97-6.88 (m, 1H), 3.84 (s, 3H), 3.15-3.05 (m, 2H); ESIMS m/z 411 ([M+H]$^+$).

trans-1,2,4-Trichloro-5-(2,2-dichloro-3-(4-methoxyphenyl)cyclopropyl)benzene (C28)

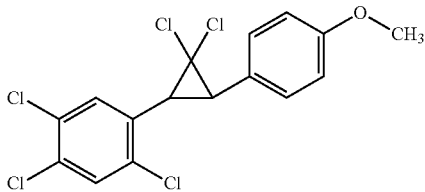 [SMILES: COc1ccc(C2C(c3cc(Cl)c(Cl)cc3Cl)C2(Cl)Cl)cc1]

Isolated as a brown liquid (2.0 g, 58%): EIMS m/z 394 ([M]$^+$).

51 trans-1-(2,2-Dichloro-3-(4-methoxyphenyl)cyclopropyl)-3,5-bis(trifluoromethyl)benzene (C29)

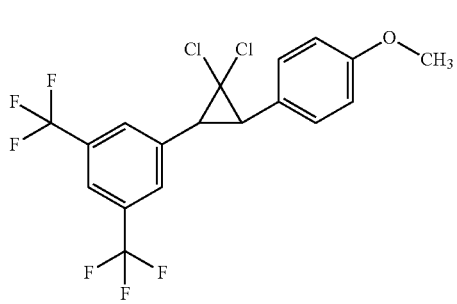 [SMILES: COc1ccc(C2C(c3cc(C(F)(F)F)cc(C(F)(F)F)c3)C2(Cl)Cl)cc1]

Isolated as a brown liquid (3.0 g, 61%): EIMS m/z 428 ([M]⁺).

trans-1,3-Dibromo-5-(2,2-dichloro-3-(4-methoxyphenyl)cyclopropyl)benzene (C30)

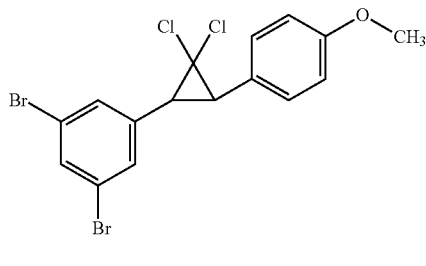

Isolated as a brown liquid (3.0 g, 57%): $^1$H NMR (300 MHz, CDCl$_3$) δ 7.64 (s, 1H), 7.45 (s, 2H), 7.25 (d, J=9.0 Hz, 2H), 6.92 (d, J=9.0 Hz, 1H), 3.83 (s, 3H), 3.15-3.05 (m, 2H); ESIMS m/z 453 ([M+H]⁺).

trans-1-Chloro-3-(2,2-dichloro-3-(4-methoxyphenyl)cyclopropyl)-5-(trifluoromethyl)benzene (C31)

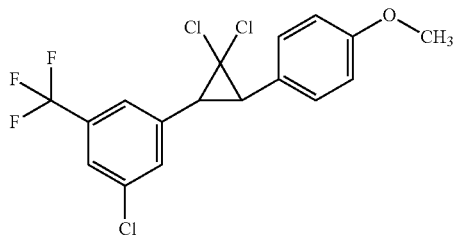 [SMILES: COc1ccc(C2C(c3cc(Cl)cc(C(F)(F)F)c3)C2(Cl)Cl)cc1]

Isolated as a brown solid (4.0 g, 74%): $^1$H NMR (300 MHz, CDCl$_3$) δ 7.64 (s, 1H), 7.45 (s, 1H), 7.42 (s, 1H), 7.26 (d, J=9.0 Hz, 2H), 6.93 (d, J=9.0 Hz, 1H), 3.83 (s, 3H), 3.15-3.05 (m, 2H); ESIMS m/z 395 ([M+H]⁺).

52 trans-1,3-Dichloro-5-(2,2-dichloro-3-(4-methoxyphenyl)cyclopropyl)-2-fluorobenzene (C32)

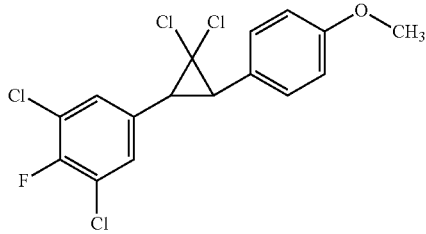 [SMILES: COc1ccc(C2C(c3cc(Cl)c(F)c(Cl)c3)C2(Cl)Cl)cc1]

Isolated as a brown solid (1.6 g, 54%): $^1$H NMR (300 MHz, CDCl$_3$) δ 7.32 (d, J=6.0 Hz, 2H), 7.30 (d, J=9.0 Hz, 1H), 6.93 (d, J=9.0 Hz, 1H), 3.83 (s, 3H), 3.12-3.05 (m, 2H); ESIMS m/z 297 ([M+H]⁺).

trans-2-Bromo-1,3-dichloro-5-(2,2-dichloro-3-(4-methoxyphenyl)cyclopropyl)benzene (C33)

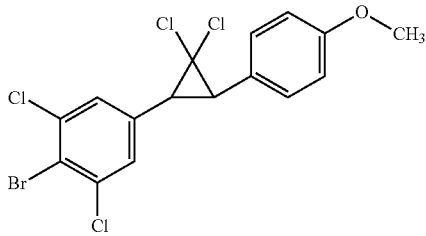

Isolated as an off-white solid (1.5 g, 44%): $^1$H NMR (300 MHz, CDCl$_3$) δ 7.36 (d, J=9.0 Hz, 2H), 7.20 (s, 2H), 6.93 (d, J=9.0 Hz, 2H), 3.83 (s, 3H), 3.15-3.05 (m, 2H); ESIMS m/z 439 ([M+H]⁺).

trans-1-Bromo-3-chloro-5-(2,2-dichloro-3-(4-methoxyphenyl)cyclopropyl)benzene (C34)

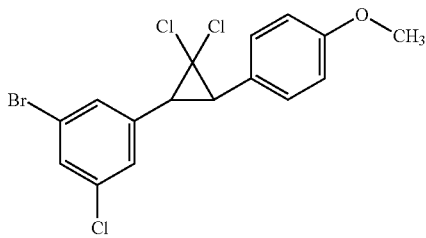 [SMILES: COc1ccc(C2C(c3cc(Cl)cc(Br)c3)C2(Cl)Cl)cc1]

Isolated as an off-white solid (2.5 g, 50%): $^1$H NMR (400 MHz, CDCl$_3$) δ 7.49 (s, 1H), 7.30 (s, 1H), 7.28-7.24 (m, 3H), 6.92 (d, J=8.0 Hz, 2H), 3.92 (s, 3H), 3.01 (q, J=8.8 Hz, 2H); ESIMS m/z 405 ([M+H]⁺).

trans-1-Chloro-3-(2,2-dichloro-3-(4-methoxyphenyl)
cyclopropyl)-5-fluorobenzene (C35)

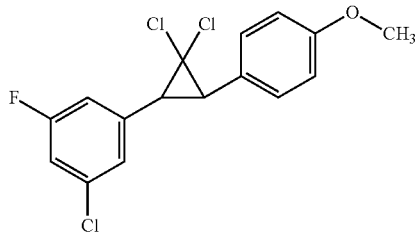

Isolated as a brown liquid (3.5 g, 67%): ESIMS m/z 345 ([M+H]$^+$).

trans-1-Chloro-4-(2,2-dichloro-3-(4-methoxyphenyl)
cyclopropyl)-2-fluorobenzene (C36)

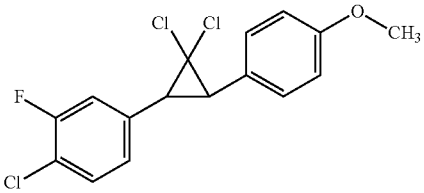 [SMILES: COc1ccc(C2C(c3ccc(Cl)c(F)c3)C2(Cl)Cl)cc1]

Isolated as an off-white solid (2.5 g, 65%): ESIMS m/z 345 ([M+H]$^+$).

trans-2-Chloro-4-(2,2-dichloro-3-(4-methoxyphenyl)
cyclopropyl)-1-fluorobenzene (C37)

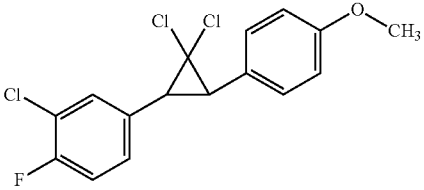 [SMILES: COc1ccc(C2C(c3ccc(F)c(Cl)c3)C2(Cl)Cl)cc1]

Isolated as a brown liquid (2.0 g, 58%): ESIMS m/z 345 ([M+H]$^+$).

trans-1-Chloro-3-(2,2-dichloro-3-(4-methoxyphenyl)
cyclopropyl)-5-methylbenzene (C38)

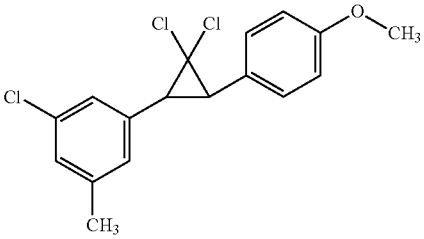 [SMILES: COc1ccc(C2C(c3cc(C)cc(Cl)c3)C2(Cl)Cl)cc1]

Isolated as an off-white solid (3.0 g, 47%): $^1$H NMR (400 MHz, CDCl$_3$) δ 7.27 (d, J=8.8 Hz, 2H), 7.14 (s, 2H), 7.06 (s, 1H), 6.92 (d, J=8.8 Hz, 2H), 3.82 (s, 3H), 3.10 (q, J=8.8 Hz, 2H), 2.36 (s, 3H); ESIMS m/z 341 ([M+H]$^+$).

trans-1,3-Dichloro-5-(2,2-dichloro-3-(4-methoxy-
phenyl)cyclopropyl)-2-methylbenzene (C39)

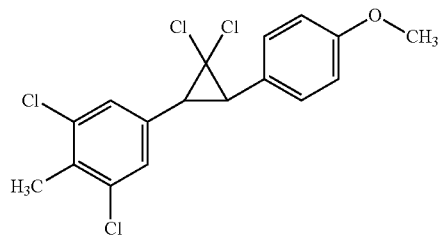 [SMILES: COc1ccc(C2C(c3cc(Cl)c(C)c(Cl)c3)C2(Cl)Cl)cc1]

Isolated as a brown liquid (2.5 g, 80%): $^1$H NMR (400 MHz, CDCl$_3$) δ 7.25 (d, J=8.0 Hz, 2H), 7.17 (d, J=8.8 Hz, 1H), 6.92 (d, J=8.0 Hz, 2H), 6.88 (d, J=8.8 Hz, 1H), 3.82 (s, 3H), 3.12-3.03 (m, 2H), 2.47 (s, 3H); ESIMS m/z 375 ([M+H]$^+$).

trans-1,2-Dichloro-5-(2,2-dichloro-3-(4-methoxy-
phenyl)cyclopropyl)-3-methylbenzene (C40)

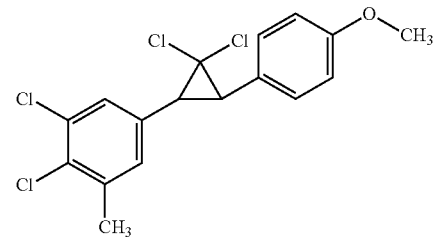 [SMILES: COc1ccc(C2C(c3cc(C)c(Cl)c(Cl)c3)C2(Cl)Cl)cc1]

Isolated as a Brown liquid (4.0 g, 90%): ESIMS m/z 375 ([M+H]$^+$).

trans-1-(2,2-Dichloro-3-(4-(perfluoroethyl)phenyl)
cyclopropyl)-4-methoxybenzene (C41)

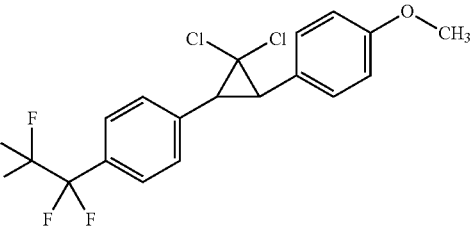

Isolated as an off-white solid (0.5 g, 46%): $^1$H NMR (400 MHz, CDCl$_3$) δ 7.60-7.50 (m, 4H), 7.47 (d, J=8.0 Hz, 2H), 6.92 (d, J=8.0 Hz, 2H), 3.82 (s, 3H), 3.20 (s, 2H); ESIMS m/z 411 ([M+H]$^+$).

trans-4,4'-(3,3-Dichlorocyclopropane-1,2-diyl)bis(ethoxybenzene) (C42)

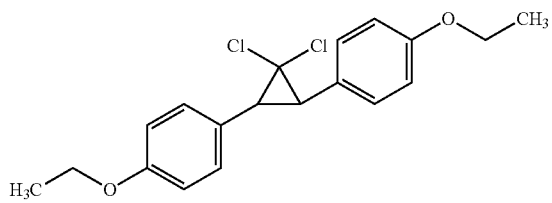 [SMILES: CCOc1ccc(C2C(c3ccc(OCC)cc3)C2(Cl)Cl)cc1]

Isolated as an off-white solid (1.5 g, 45%): $^1$H NMR (400 MHz, CDCl$_3$) δ 7.27 (d, J=8.0 Hz, 4H), 6.90 (d, J=8.0 Hz, 4H), 4.04 (q, J=6.8 Hz, 4H), 3.09 (s, 2H), 1.42 (t, J=6.8 Hz, 6H); ESIMS m/z 351 ([M+H]$^+$).

Example 5

Preparation of (E)-1,3-dichloro-5-(4-methoxystyryl)benzene (C43)

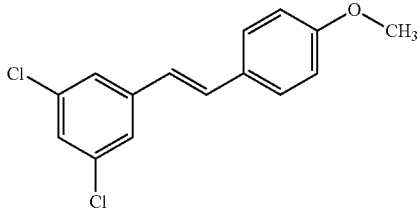 [SMILES: COc1ccc(/C=C/c2cc(Cl)cc(Cl)c2)cc1]

Sodium methoxide powder (98%, 0.63 g, 11 mmol) was added to a stirred solution of 3,5-dichlorobenzaldehyde (2.0 g, 11 mmol) and diethyl 4-methoxybenzylphosphonate (2.0 mL, 11 mmol) in dry N,N-dimethylformamide (38 mL) at 23° C. The resulting heterogeneous dark blue mixture was heated to 80° C., resulting in a dark brown mixture, and stirred for 24 hours. The cooled reaction mixture was diluted with water (500 mL) and extracted with diethyl ether (3×100 mL). The combined organic layers were diluted with hexane (150 mL) and washed with water (300 mL). The organic layer was dried over magnesium sulfate, filtered, and concentrated to afford the title product as a light brown oil (2.4 g, 75%): $^1$H NMR (400 MHz, CDCl$_3$) δ 7.44 (m, 2H), 7.34 (d, J=2 Hz, 2H), 7.20 (t, J=2 Hz, 1H), 7.06 (d, J=16.5 Hz, 1H), 6.91 (m, 2H), 6.82 (d, J=16.5 Hz, 1H), 3.84 (s, 3H); IR (thin film) 2934 (w), 2835 (w), 1724 (w), 1637 (w), 1605 (m), 1581 (m), 1558 (m), 1511 (s) cm$^{-1}$.

The following compounds were prepared in like manner to the procedure outlined in Example 5:

(E)-1,2,3-Trichloro-5-(4-methoxystyryl)benzene (C44)

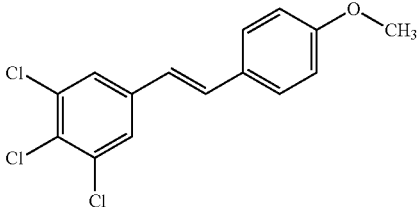 [SMILES: COc1ccc(/C=C/c2cc(Cl)c(Cl)c(Cl)c2)cc1]

Isolated as an off-white solid (3.7 g, 31%): $^1$H NMR (400 MHz, CDCl$_3$) δ 7.49-7.46 (m, 2H), 7.47-7.39 (m, 2H), 7.04 (d, J=16.3 Hz, 1H), 6.93-6.89 (m, 2H), 6.78 (d, J=16.3 Hz, 1H), 3.84 (s, 3H); $^{13}$C NMR (101 MHz, CDCl$_3$) δ 159.46, 135.08, 134.23, 130.91, 129.85, 129.16, 125.42, 114.02, 64.67, 55.32, 39.62, 38.48; EIMS m/z 313 ([M]$^+$).

(E)-1,2-Dichloro-4-(4-methoxystyryl)benzene (C45)

Isolated as an off-white solid (6.0 g, 53%): mp 91-94° C.; $^1$H NMR (400 MHz, CDCl$_3$) δ 7.56 (d, J=2.0 Hz, 1H), 7.46-7.42 (m, 2H), 7.39 (d, J=8.4 Hz, 1H), 7.29 (dd, J=8.4, 2.1 Hz, 1H), 7.04 (d, J=16.2 Hz, 1H), 6.93-6.88 (m, 2H), 6.85 (d, J=16.3 Hz, 1H), 3.84 (s, 3H); $^{13}$C NMR (101 MHz, CDCl$_3$) δ 159.75, 137.86, 132.72, 130.58, 130.49, 130.12, 129.33, 127.96, 127.77, 125.37, 123.98, 114.24, 55.35; EIMS m/z 279 ([M]$^+$).

Example 6

Preparation of (E)-1-methoxy-4-(4-(trifluoromethyl)styryl)benzene (C46)

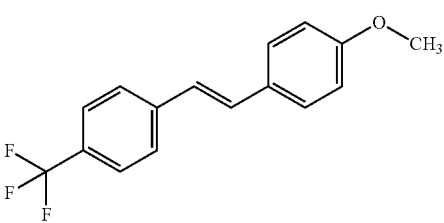 [SMILES: COc1ccc(/C=C/c2ccc(C(F)(F)F)cc2)cc1]

To a stirred solution of diethyl 4-methoxybenzyl phosphonate (8.89 g, 34.0 mmol) in N,N-dimethylformamide (30 mL) was added sodium methoxide powder (1.86 g, 34.0 mmol). The reaction mixture was stirred at room temperature for 1 hour. The reaction mixture was cooled to 0° C. and 4-(trifluoromethyl)benzaldehyde (5.00 g, 28.0 mmol) in N,N-dimethylformamide (30 mL) was added dropwise. The reaction mixture was stirred at 60° C. for 2 hours. The reaction mixture was poured in ice cold water, filtered, and dried to afford the title compound as an off-white solid (3.60 g, 80%): $^1$H NMR (300 MHz, CDCl$_3$) δ 7.61-7.52 (m, 4H), 7.47 (d, J=9.0 Hz, 2H), 7.14 (d, J=16.5 Hz, 1H), 6.97 (d, J=16.5 Hz, 1H), 6.91 (d, J=9.0 Hz, 2H), 3.84 (s, 3H); ESIMS m/z 279 ([M+H]$^+$).

The following compounds were prepared in like manner to the procedure outlined in Example 6:

(E)-1-(4-Methoxystyryl)-3-(trifluoromethyl)benzene (C47)

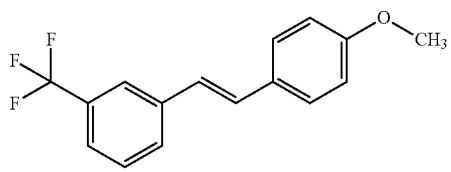 [SMILES: COc1ccc(/C=C/c2cccc(C(F)(F)F)c2)cc1]

Isolated as an off-white solid (4.0 g, 85%): $^1$H NMR (400 MHz, CDCl$_3$) δ 7.72 (s, 1H), 7.64 (d, J=6.8 Hz, 1H), 7.50-7.44 (m, 4H), 7.12 (d, J=16.0 Hz, 1H), 6.98 (d, J=16.0 Hz, 1H), 6.91 (d, J=8.8 Hz, 2H), 3.84 (s, 3H); ESIMS m/z 279 ([M+H]$^+$).

(E)-2-Chloro-4-(4-methoxystyryl)-1-(trifluoromethoxy)benzene (C48)

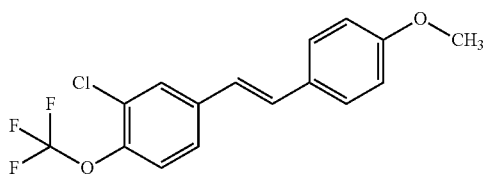 [SMILES: COc1ccc(/C=C/c2ccc(OC(F)(F)F)c(Cl)c2)cc1]

Isolated: ESIMS m/z 329 ([M+H]$^+$).

(E)-1-(4-Methoxystyryl)-3,5-bis(trifluoromethyl)benzene (C49)

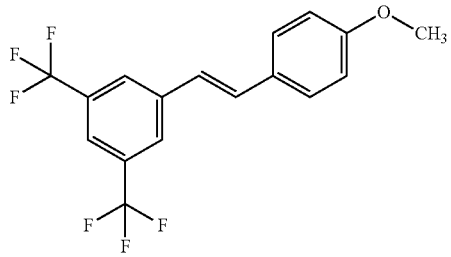 [SMILES: COc1ccc(/C=C/c2cc(C(F)(F)F)cc(C(F)(F)F)c2)cc1]

Isolated as an off-white solid (4.0 g, 56%): $^1$H NMR (300 MHz, CDCl$_3$) δ 7.88 (s, 2H), 7.70 (s, 1H), 7.49 (d, J=8.4 Hz, 2H), 7.19 (d, J=16.5 Hz, 1H), 6.99 (d, J=16.5 Hz, 1H), 6.92 (d, J=8.4 Hz, 2H), 3.84 (m, 3H); ESIMS m/z 347 ([M+H]$^+$).

(E)-1,3-Dibromo-5-(4-methoxystyryl)benzene (C50)

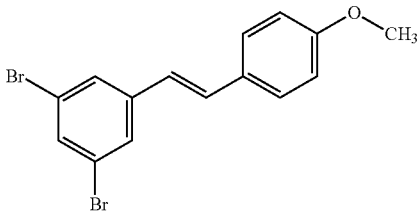 [SMILES: COc1ccc(/C=C/c2cc(Br)cc(Br)c2)cc1]

Isolated as an off-white solid (2.2 g, 54%): $^1$H NMR (300 MHz, CDCl$_3$) δ 7.53 (s, 1H), 7.50 (s, 2H), 7.43 (d, J=9.0 Hz, 2H), 7.05 (d, J=16.2 Hz, 1H), 6.90 (d, J=9.0 Hz, 2H), 6.79 (d, J=16.2 Hz, 1H), 3.80 (s, 3H); ESIMS m/z 367 ([M+H]$^+$).

(E)-1-Chloro-3-(4-methoxystyryl)-5-(trifluoromethyl)benzene (C51)

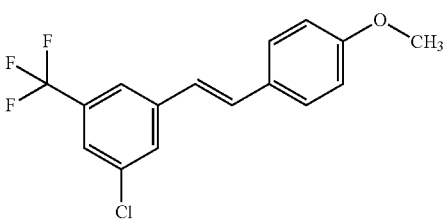 [SMILES: COc1ccc(/C=C/c2cc(Cl)cc(C(F)(F)F)c2)cc1]

Isolated as an off-white solid (4.3 g, 58%): $^1$H NMR (300 MHz, CDCl$_3$) δ 7.62 (s, 1H), 7.58 (s, 1H), 7.48-7.42 (m, 3H), 7.12 (d, J=16.2 Hz, 1H), 6.95-6.85(m, 3H), 3.84 (s, 3H); ESIMS m/z 313 ([M+H]$^+$).

(E)-2-Bromo-1,3-dichloro-5-(4-methoxystyryl)benzene (C52)

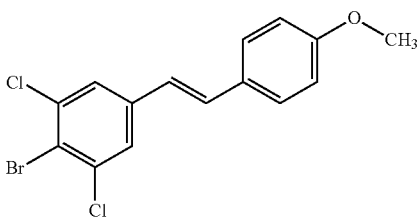 [SMILES: COc1ccc(/C=C/c2cc(Cl)c(Br)c(Cl)c2)cc1]

Isolated as an off-white solid (2.8 g, 40%): $^1$H NMR (300 MHz, CDCl$_3$) δ 7.46 (s, 2H), 7.43 (d, J=9.0 Hz, 2H), 7.07 (d, J=13.5 Hz, 1H), 6.90 (d, J=9.0 Hz, 1H), 6.73 (d, J=13.5 Hz, 1H), 3.84 (s, 3H); ESIMS m/z 358 ([M+H]$^+$).

(E)-1-Bromo-3-chloro-5-(4-methoxystyryl)benzene (C53)

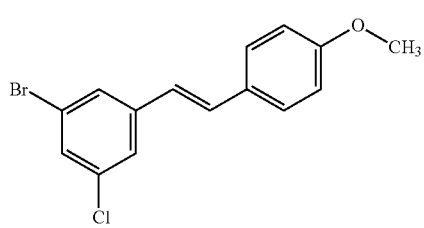 [SMILES: COc1ccc(/C=C/c2cc(Cl)cc(Br)c2)cc1]

Isolated as an off-white solid (4.0 g, 63%): $^1$H NMR (300 MHz, CDCl$_3$) δ 7.49 (s, 1H), 7.43 (d, J=8.4 Hz, 2H), 7.38 (s, 1H), 7.35 (s, 1H), 7.05 (d, J=16.5 Hz, 1H), 6.91 (d, J=8.4 Hz, 2H), 6.80 (d, J=16.5 Hz, 1H), 3.82 (s, 3H); ESIMS m/z 323 ([M+H]$^+$).

(E)-1-Chloro-3-fluoro-5-(4-methoxystyryl)benzene (C54)

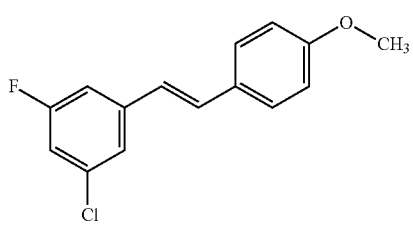 [SMILES: COc1ccc(/C=C/c2cc(F)cc(Cl)c2)cc1]

Isolated as an off-white solid (5.0 g, 60%): $^1$H NMR (400 MHz, CDCl$_3$) δ 7.45 (d, J=8.4 Hz, 2H), 7.10-7.0 (m, 3H), 6.96-6.80 (m, 4H), 3.80 (s, 3H); ESIMS m/z 263 ([M+H]$^+$).

(E)-1-Chloro-2-fluoro-4-(4-methoxystyryl)benzene (C55)

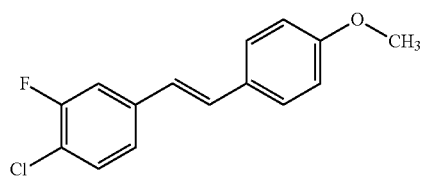

Isolated as an off-white solid (7.0 g, 84%): $^1$H NMR (400 MHz, CDCl$_3$) δ 7.44 (d, J=8.0 Hz, 2H), 7.35-7.31 (m, 1H), 7.28-7.24 (m, 1H), 7.17 (dd, J=1.6, 8.0 Hz, 1H), 7.03 (d, J=16.0 Hz, 1H), 6.90 (d, J=8.0 Hz, 1H), 7.49 (d, J=8.0 Hz, 1H), 6.86 (d, J=16.0 Hz, 1H), 3.82 (s, 3H); ESIMS m/z 263 ([M+H]$^+$).

(E)-2-Chloro-1-fluoro-4-(4-methoxystyryl)benzene (C56)

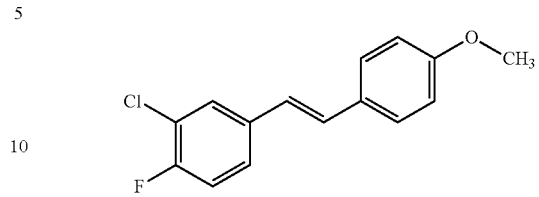

Isolated as an off-white solid (6.0 g, 72%): ESIMS m/z 263 ([M+H]$^+$).

(E)-1-Chloro-3-(4-methoxystyryl)-5-methylbenzene (C57)

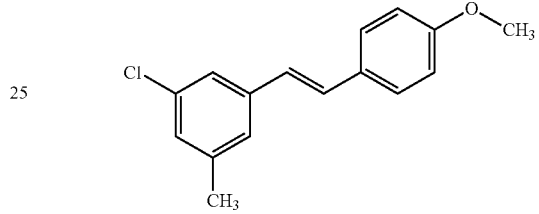

Isolated as an off-white solid (5.0 g, 60%): $^1$H NMR (300 MHz, CDCl$_3$) δ 7.44 (d, J=8.4 Hz, 2H), 7.28 (s, 1H), 7.15 (s, 1H), 7.05-7.00 (m, 2H), 6.91-6.83 (m, 3H), 3.83 (s, 3H), 2.24 (s, 3H); ESIMS m/z 259 ([M+H]$^+$).

(E)-1-Methoxy-4-(4-(perfluoroethyl)styryl)benzene (C58)

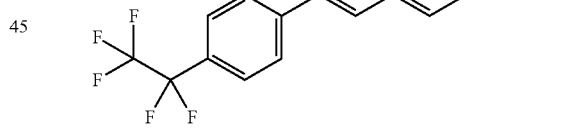

Isolated as an off-white solid (0.5 g, 42%): $^1$H NMR (400 MHz, CDCl$_3$) δ 7.60-7.50 (m, 4H), 7.47 (d, J=8.8 Hz, 2H), 7.15 (d, J=16.8 Hz, 1H), 6.98 (d, J=16.8 Hz, 1H), 6.92 (d, J=8.8 Hz, 2H), 3.82 (s, 3H); ESIMS m/z 329 ([M+H]$^+$).

(E)-1,2-bis(4-ethoxyphenyl)ethene (C59)

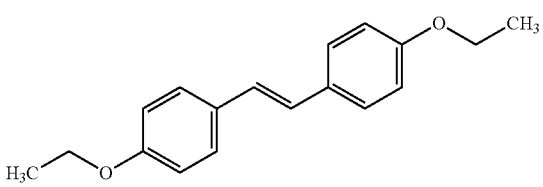 [SMILES: CCOc1ccc(/C=C/c2ccc(OCC)cc2)cc1]

Isolated as an off-white solid (1.7 g, 34%): $^1$H NMR (300 MHz, CDCl$_3$) δ 7.40 (d, J=9.0 Hz, 4H), 6.91 (s, 2H), 6.87 (d, J=9.0 Hz, 4H), 4.05 (q, J=6.9 Hz, 4H), 1.42 (t, J=6.9 Hz, 6H); ESIMS m/z 269 ([M+H]$^+$).

Example 7

Preparation of (E)-1,3-dichloro-2-fluoro-5-(4-methoxystyryl)benzene (C60)

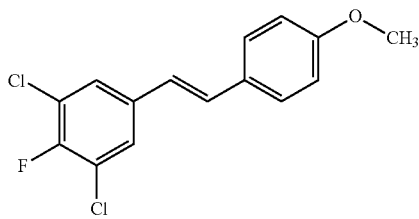 [SMILES: COc1ccc(/C=C/c2cc(Cl)c(F)c(Cl)c2)cc1]

A stirred mixture of 5-bromo-1,3-dichloro-2-fluorobenzene (2.00 g, 8.20 mmol), 1-methoxy-4-vinylbenzene (1.32 g, 9.80 mmol), and triethylamine (20 mL) under argon was degassed for 5 minutes. Palladium(II) acetate (0.0368 g, 0.164 mmol) and 1,1'-bis(diphenylphosphino)ferrocene (0.181 g, 0.328 mmol) were added and the reaction was heated to 90° C. for 16 hours. The reaction mixture was poured into water and extracted with ethyl acetate. The combined organic layers were dried over sodium sulfate, filtered, and concentrated. Purification by flash column chromatography provided the title compound as an off-white solid (1.60 g, 67%): $^1$H NMR (300 MHz, CDCl$_3$) δ 7.41 (d, J=8.8 Hz, 2H), 7.31 (s, 1H), 7.37 (s, 1H), 6.96 (d, J=16.0 Hz, 1H), 6.89 (d, J=8.8 Hz, 2H), 6.76 (d, J=16.0 Hz, 1H), 3.84 (s, 3H); ESIMS m/z 297 ([M+H]$^+$).

The following compounds were prepared in like manner to the procedure outlined in Example 7:

(E)-1,3-Dichloro-5-(4-methoxystyryl)-2-methylbenzene (C61)

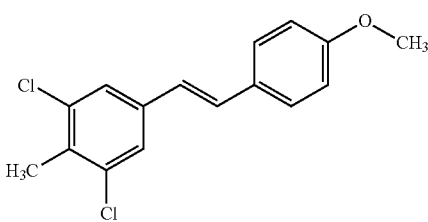 [SMILES: COc1ccc(/C=C/c2cc(Cl)c(C)c(Cl)c2)cc1]

Isolated as an off-white solid (2.5 g, 67%): $^1$H NMR (300 MHz, CDCl$_3$) δ 7.43 (d, J=8.7 Hz, 2H), 7.38 (s, 2H), 7.02 (d, J=16.5 Hz, 1H), 6.90 (d, J=8.7 Hz, 2H), 6.79 (d, J=16.5 Hz, 1H), 3.82 (s, 3H), 2.42 (s, 3H); ESIMS m/z 293 ([M+H]$^+$).

(E)-1,2-Dichloro-5-(4-methoxystyryl)-3-methyl benzene (C62)

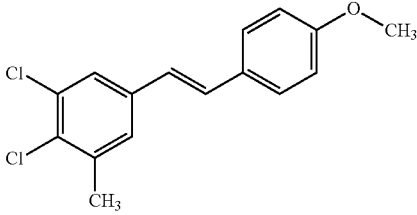 [SMILES: COc1ccc(/C=C/c2cc(C)c(Cl)c(Cl)c2)cc1]

Isolated as an off-white solid (3.0 g, 55%): $^1$H NMR (300 MHz, CDCl$_3$) δ 7.50-7.40 (m, 3H), 7.24 (s, 1H), 7.02 (d, J=15.9 Hz, 1H), 6.90 (d, J=9.0 Hz, 2H), 6.81 (d, J=15.9 Hz, 1H), 3.83 (s, 3H), 2.42 (s, 3H); ESIMS m/z 293 ([M+H]$^+$).

Example 8

Preparation of (E)-1,2,4-trichloro-5-(4-methoxystyryl)benzene (C63)

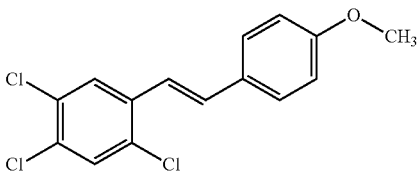 [SMILES: COc1ccc(/C=C/c2cc(Cl)c(Cl)cc2Cl)cc1]

To a sealed tube were added 1-bromo-2,4,5-trichlorobenzene (3.0 g, 12 mmol), 1,2-dimethoxyethane:water (10:1, 30 mL), (E)-2-(4-methoxystyryl)-4,4,5,5-tetramethyl-1,3,2-dioxaborolane (C64) (3.7 g, 14 mmol), and potassium carbonate (3.2 g, 24 mmol). The reaction mixture was degassed for 10 minutes with argon, followed by addition of tetrakis (triphenylphosphine)palladium(0) (0.55 g, 0.48 mmol). The reaction mixture was degassed for 10 minutes then heated at 90° C. for 16 hours. The reaction mixture was poured in to water and extracted with ethyl acetate. The combined organic layers were dried over sodium sulfate, filtered, and concentrated. Purification by flash column chromatography provided the title compound as an off-white solid (3.0 g, 80%): $^1$H NMR (400 MHz, CDCl$_3$) δ 7.73 (s, 1H), 7.50-7.45 (m, 3H), 7.20 (d, J=16.0 Hz, 1H), 7.02 (d, J=16 Hz, 1H), 6.92 (d, J=8.0 Hz, 2H), 3.84 (m, 3H); ESIMS m/z 313 ([M+H]$^+$).

Example 9

Preparation of (E)-2-(4-methoxystyryl)-4,4,5,5-tetramethyl-1,3,2-dioxaborolane (C64)

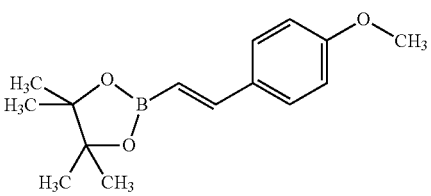

To a 50 mL round-bottomed flask were added 1-ethynyl-4-methoxybenzene (4.0 g, 30 mmol), 4,4,5,5-tetramethyl-1,3,2-dioxaborolane (3.3 g, 36 mmol), zirconocene hydrochloride (1.2 g, 4.0 mmol), and triethylamine (2.8 mL, 15 mmol) at 0° C. The reaction mixture was then stirred at 65° C. for 16 hours. The reaction mixture was poured in water and extracted with ethyl acetate. The combined organic layers were dried over sodium sulfate, filtered, and concentrated. Purification by flash column chromatography provided the title compound as an off-white semi solid (3.0 g, 38%): $^1$H NMR (400 MHz, CDCl$_3$) δ 7.43 (d, J=8.8 Hz, 2H), 7.35 (d, J=18.0 Hz, 1H), 6.86 (d, J=8.8 Hz, 2H), 6.01 (d, J=18.0 Hz, 1H), 3.81 (s, 3H), 1.30 (s, 12H).

Example 10

Preparation of 3,4,5-trichlorobenzaldehyde (C65)

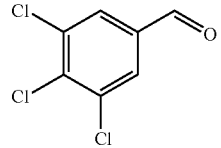 [SMILES: O=Cc1cc(Cl)c(Cl)c(Cl)c1]

In an oven dried, nitrogen flushed, 500 mL round-bottomed flask equipped with a pressure equalizing addition funnel, 5-bromo-1,2,3-trichlorobenzene (10.0 g, 38.4 mmol) was dissolved in tetrahydrofuran (100 mL), and the resulting solution was cooled in an ice bath under nitrogen. Isopropyl magnesium chloride (2 M solution tetrahydrofuran, 21.1 mL, 42.3 mmol) was added dropwise with good stirring over 15 minutes via the addition funnel. After 0.5 hours, N,N-dimethylformamide (3.72 mL, 48.0 mmol) was added to the dark solution with stirring. After an additional 0.5 hours, hydrochloric acid (1 N, 100 mL) was added with stirring. The layers were separated, and the organic layer was washed with brine. The combined aqueous layers were extracted with ether, and the combined organics were dried over sodium sulfate, filtered, and concentrated to afford the title compound as a white solid (10:1 mixture of title compound to 1,2,3-trichlorobenzene, 7.96 g, 99%): $^1$H NMR (CDCl$_3$) δ 9.91 (s, 1H), 7.88 (s, 2H); EIMS m/z 209 ([M]$^+$).

Example 11

Preparation of 1-bromo-4-(perfluoroethyl)benzene (C66)

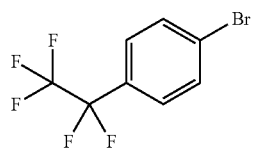 [SMILES: FC(F)(F)C(F)(F)c1ccc(Br)cc1]

To a stirred solution of 1-(4-bromophenyl)-2,2,2-trifluoroethanone (5.00 g, 19.7 mmol) in dichloromethane under argon were added 4-tert-butyl-2,6-dimethylphenylsulfur trifluoride (2.90 g, 11.8 mmol) and hydrogen fluoride pyridine complex (0.190 g, 9.80 mmol) at 0° C. The reaction mixture was allowed to warm to room temperature and stirred for 16 hours. The reaction mixture was poured into water and extracted with ethyl acetate. The combined organic extracts were dried over sodium sulfate, filtered, and concentrated. Purification by flash column chromatograph provided the title compound as colorless liquid (1.00 g, 20%): $^1$H NMR (300 MHz, CDCl$_3$) δ 7.65 (d, J=9.0 Hz, 2H), 7.47 (d, J=9.0 Hz, 2H); EIMS m/z 274 ([M]$^+$).

Example 12

Preparation of trans-2-chloro-5-(2,2-dichloro-3-(3,5-dichlorophenyl)cyclopropanecarboxamido)benzoic acid (C67)

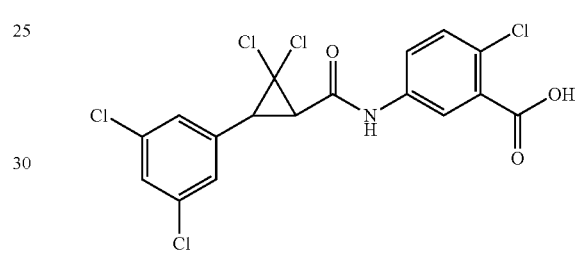

To a solution of trans-2,2-dichloro-3-(3,5-dichlorophenyl)cyclopropanecarboxylic acid (C1) (0.300 g, 1.00 mmol) in dichloromethane (5.00 mL) stirred at 0° C., were added N,N-dimethylformamide (1 drop) followed by oxalyl chloride (0.131 mL, 1.50 mmol) over 2 minutes. The ice batch was removed and the reaction allowed to warm to room temperature over 90 minutes. The reaction was then concentrated to yield a yellow-orange semi-solid. The semi-solid was dissolved in dichloromethane (3.5 mL), and the solution was added slowly to a cooled solution of 5-amino-2-chlorobenzoic acid (0.206 g, 1.20 mmol) and triethylamine (0.209 mL, 1.50 mmol) in dichloromethane (7 mL). The ice bath was removed and the reaction was allowed to warm to room temperature over 90 minutes. The reaction was diluted with dichloromethane (10 mL) and washed with hydrochloric acid (0.1 N). The resulting slurry was filtered and the solid washed with water. The precipitated solid was dried in a vacuum oven at 40° C. to provide the title compound as a light brown solid (0.421 g, 93%): mp 234-236° C.; $^1$H NMR (400 MHz, DMSO-d$_6$) δ 13.47 (s, 1H), 10.90 (s, 1H), 8.16 (d, J=2.3 Hz, 1H), 7.78 (dd, J=8.7, 2.4 Hz, 1H), 7.59 (m, 4H), 3.56 (dd, J=49.8, 8.5 Hz, 2H), 1.09 (m, 1H); $^{13}$C NMR (101 MHz, DMSO-d$_6$) δ 166.26, 165.77, 162.61, 137.57, 137.27, 134.04, 132.18, 131.44, 131.22, 127.88, 127.66, 126.40, 125.92, 122.88, 121.17, 102.37, 62.11, 38.41, 36.83; ESIMS m/z 454 ([M+H]$^+$).

Example 13

Preparation of trans-2-chloro-5-(2,2-dichloro-3-(3,5-dichlorophenyl)cyclopropane-1-carboxamido)-N-methylbenzamide (F1)

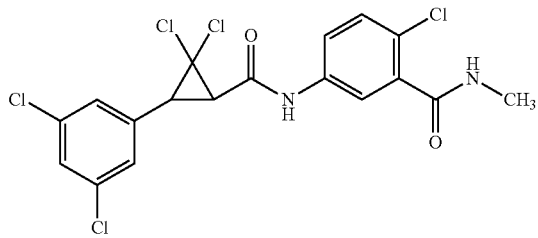 [SMILES: CNC(=O)c1cc(NC(=O)C2C(c3cc(Cl)cc(Cl)c3)C2(Cl)Cl)ccc1Cl]

5-Amino-2-chloro-N-methylbenzamide (C68) (0.072 g, 0.39 mmol) and 4-dimethylaminopyridine (0.052 g, 0.42 mmol) were sequentially added to a stirred mixture of trans-2,2-dichloro-3-(3,5-dichlorophenyl)cyclopropanecarboxylic acid (C1) (0.097 g, 0.33 mmol) and 1-ethyl-3-(3-dimethylaminopropyl)carbodiimide (0.093 g, 0.49 mmol) in 1,2-dichloroethane (3.3 mL) at room temperature. The reaction was stirred at room temperature for 20 hours. Dichloromethane was added and the mixture was washed with saturated aqueous sodium bicarbonate and hydrochloric acid (1 N). The organic phase was dried over magnesium sulfate, filtered, and concentrated. Purification by flash column chromatography using 0-100% ethyl acetate/hexanes as eluent provided the title compound as a yellow oil (0.047 g, 30%).

The following compounds were prepared in like manner to the procedure outlined in Example 13:

trans-5-(2,2-Dichloro-3-(3,5-dichlorophenyl)cyclopropane-1-carboxamido)-N-methyl-2-(trifluoromethyl)benzamide (F2)

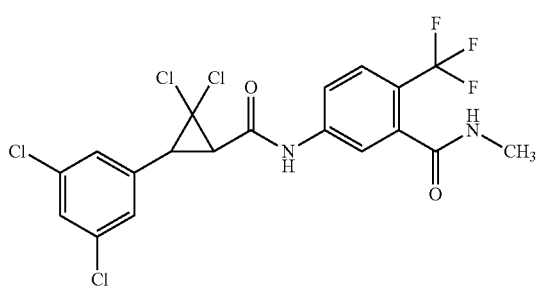 [SMILES: CNC(=O)c1cc(NC(=O)C2C(c3cc(Cl)cc(Cl)c3)C2(Cl)Cl)ccc1C(F)(F)F]

Isolated as a yellow solid (0.051 g, 32%).

trans-3-(2,2-Dichloro-3-(3,5-dichlorophenyl)cyclopropane-1-carboxamido)-N-(2,2,2-trifluoroethyl)benzamide (F3)

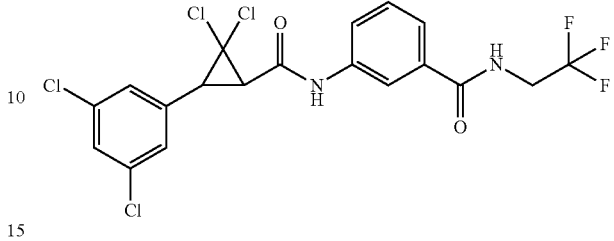

Isolated as a white solid (0.155 g, 62%).

trans-2-Chloro-5-(2,2-dichloro-3-(3,5-dichlorophenyl)cyclopropane-1-carboxamido)-N-(2,2,2-trifluoroethyl)benzamide (F4)

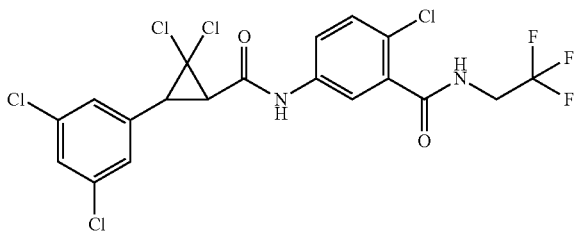

Isolated as a yellow solid (0.081 g, 44%).

trans-2-Chloro-5-(2,2-dichloro-3-(3,5-dichlorophenyl)cyclopropane-1-carboxamido)-N-(2-oxo-2-((2,2,2-trifluoroethyl)amino)ethyl)benzamide (F5)

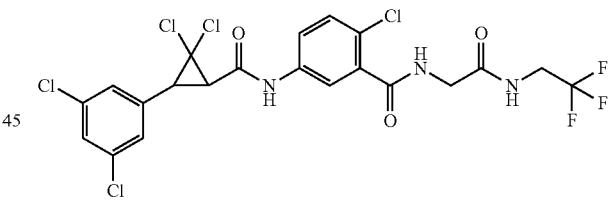

Isolated as a yellow solid (0.065 g, 39%).

trans-2-Chloro-5-(2,2-dichloro-3-(3,5-dichlorophenyl)cyclopropane-1-carboxamido)-N-(pyridin-3-ylmethyl)benzamide (F6)

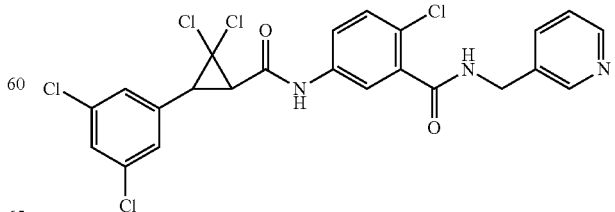

Isolated as a tan powder (0.091 g, 67%).

67 trans-2-Chloro-5-(2,2-dichloro-3-(3,4,5-trichloro-phenyl)cyclopropane-1-carboxamido)-N-(pyridin-3-ylmethyl)benzamide (F7)

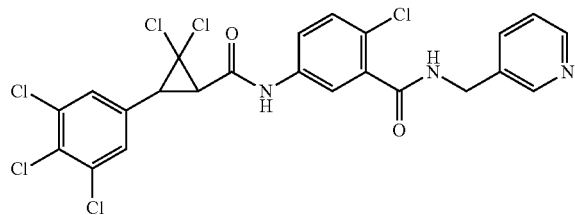 [SMILES: O=C(NCc1cccnc1)c1cc(NC(=O)C2C(c3cc(Cl)cc(Cl)c3)C2(Cl)Cl)ccc1Cl]

Isolated as a tan powder (0.051 g, 59%).

trans-2-Chloro-5-(2,2-dichloro-3-(3,5-dichlorophenyl)cyclopropane-1-carboxamido)-N-(pyridin-2-ylmethyl)benzamide (F8)

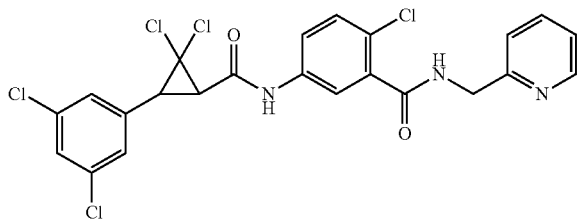

Isolated as an off-white powder (0.036 g, 26%).

trans-2-Chloro-5-(2,2-dichloro-3-(3,4,5-trichloro-phenyl)cyclopropane-1-carboxamido)-N-(pyridin-2-ylmethyl)benzamide (F9)

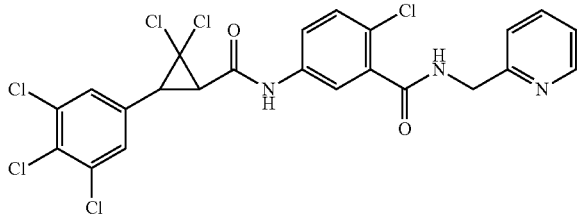 [SMILES: O=C(NCc1ccccn1)c1cc(NC(=O)C2C(c3cc(Cl)c(Cl)c(Cl)c3)C2(Cl)Cl)ccc1Cl]

Isolated as an off-white powder (0.017 g, 20%).

trans-N-(Allyloxy)-2-chloro-5-(2,2-dichloro-3-(3,5-dichlorophenyl)cyclopropane-1-carboxamido)benzamide (F10)

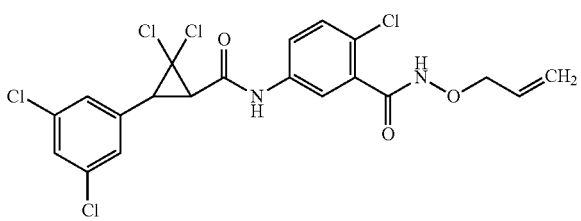 [SMILES: C=CCONC(=O)c1cc(NC(=O)C2C(c3cc(Cl)cc(Cl)c3)C2(Cl)Cl)ccc1Cl]

Isolated as an off-white semi-solid (0.034 g, 27%).

68 trans-N-(Allyloxy)-2-chloro-5-(2,2-dichloro-3-(3,4,5-trichlorophenyl)cyclopropane-1-carboxamido)benzamide (F11)

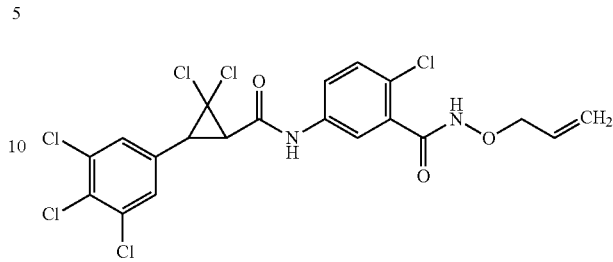

Isolated as a tan semi-solid (0.021 g, 26%).

trans-2-Chloro-5-(2,2-dichloro-3-(3,5-dichlorophenyl)cyclopropane-1-carboxamido)-N-(pyridin-4-ylmethyl)benzamide (F12)

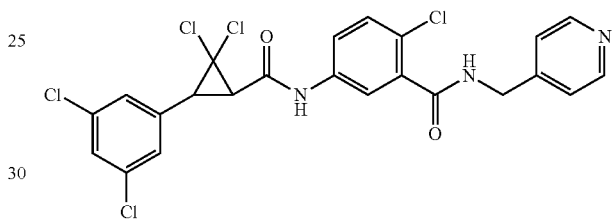

Isolated as a tan powder (0.100 g, 74%).

trans-2-Chloro-5-(2,2-dichloro-3-(3,4,5-trichloro-phenyl)cyclopropane-1-carboxamido)-N-(pyridin-4-ylmethyl)benzamide (F13)

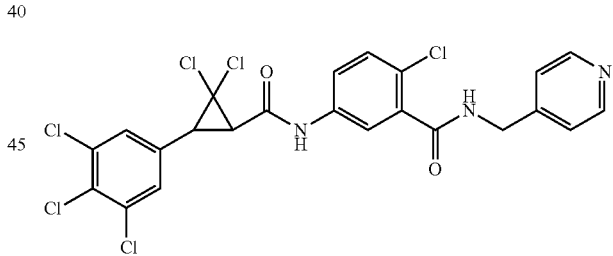

Isolated as an off-white powder (0.062 g, 72%).

trans-N-(Allyloxy)-2-chloro-5-(2,2-dichloro-3-(3,4-dichlorophenyl)cyclopropane-1-carboxamido)benzamide (F14)

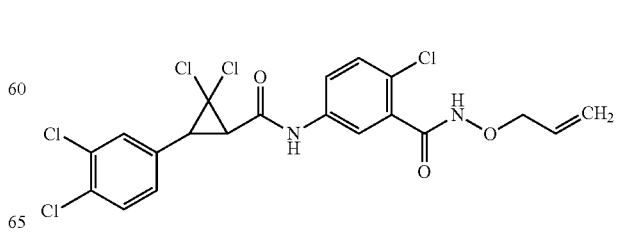

Isolated as a white powder (0.062 g, 49%).

trans-N-2-Chloro-N-(cyclopropylmethoxy)-5-(2,2-dichloro-3-(3,4,5-trichlorophenyl)cyclopropane-1-carboxamido)benzamide (F15)

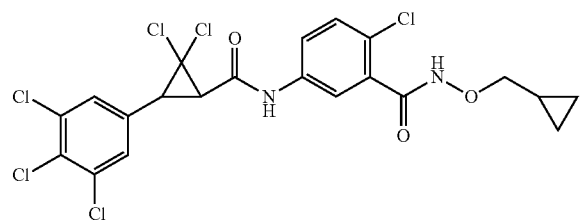 [SMILES: O=C(NOCC1CC1)c1cc(NC(=O)C2C(c3cc(Cl)c(Cl)c(Cl)c3)C2(Cl)Cl)ccc1Cl]

Isolated as a white foam (0.056 g, 56%).

trans-N-2-Chloro-N-(cyclopropylmethoxy)-5-(2,2-dichloro-3-(3,5-dichlorophenyl)cyclopropane-1-carboxamido)benzamide (F16)

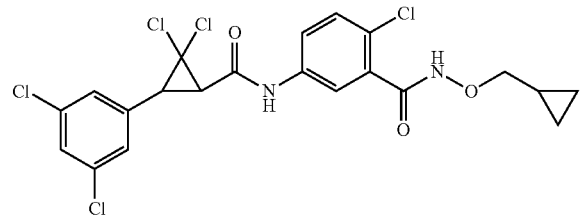

Isolated as a white powder (0.066 g, 50%).

trans-N-2-Chloro-5-(2,2-dichloro-3-(3,5-dichlorophenyl)cyclopropane-1-carboxamido)-N-((4-fluorobenzyl)oxy)benzamide (F17)

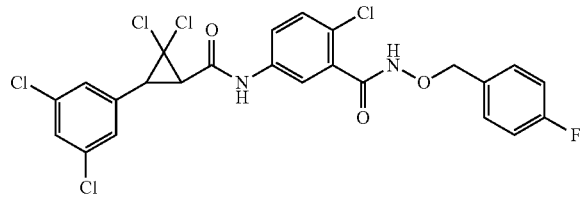 [SMILES: O=C(NOCc1ccc(F)cc1)c1cc(NC(=O)C2C(c3cc(Cl)cc(Cl)c3)C2(Cl)Cl)ccc1Cl]

Isolated as a tan foam (0.063 g, 44%).

trans-N-2-Chloro-5-(2,2-dichloro-3-(3,4,5-trichlorophenyl)cyclopropane-1-carboxamido)-N-((4-fluorobenzyl)oxy)benzamide (F18)

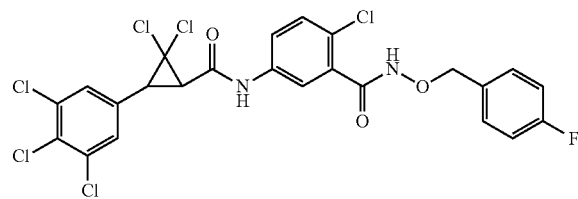 [SMILES: O=C(NOCc1ccc(F)cc1)c1cc(NC(=O)C2C(c3cc(Cl)c(Cl)c(Cl)c3)C2(Cl)Cl)ccc1Cl]

Isolated as a tan foam (0.048 g, 35%).

trans-N-2-Chloro-5-(2,2-dichloro-3-(3,5-dichlorophenyl)cyclopropane-1-carboxamido)-N-(4-fluorophenethyl)benzamide (F19)

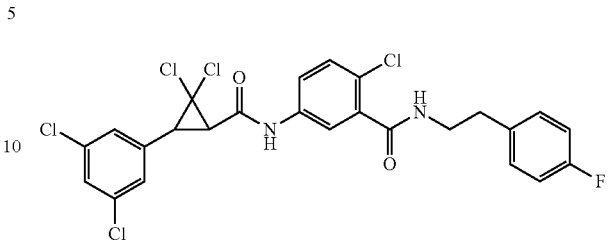

Isolated as an off-white powder (0.119 g, 83%).

trans-N-2-Chloro-5-(2,2-dichloro-3-(3,4,5-trichlorophenyl)cyclopropane-1-carboxamido)-N-(4-fluorophenethyl)benzamide (F20)

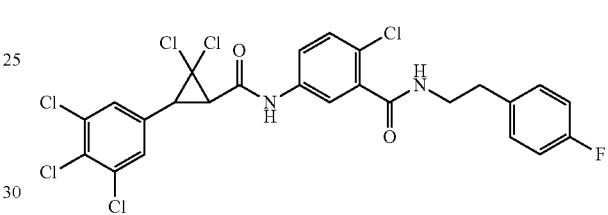

Isolated as a tan powder (0.097 g, 71%).

trans-N-2-Chloro-5-(2,2-dichloro-3-(3,5-dichlorophenyl)cyclopropane-1-carboxamido)-N-((2,2-difluorocyclopropyl)methoxy)benzamide (F21)

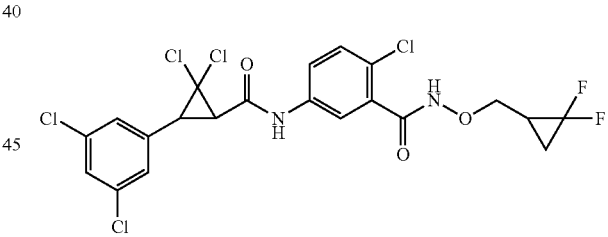

Isolated as a brown glass (0.130 g, 70%).

trans-N-2-Chloro-5-(2,2-dichloro-3-(3,4-dichlorophenyl)cyclopropane-1-carboxamido)-N-((2,2-difluorocyclopropyl)methoxy)benzamide (F22)

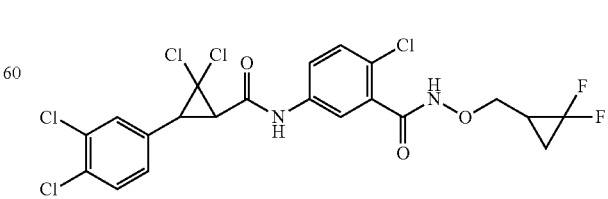

Isolated as a brown glass (0.150 g, 81%).

trans-N-2-Chloro-5-(2,2-dichloro-3-(3,4,5-trichlorophenyl)cyclopropane-1-carboxamido)-N-((2,2-difluorocyclopropyl)methoxy)benzamide (F23)

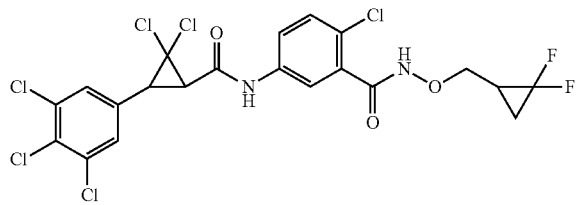 [SMILES: O=C(NOCC1CC1(F)F)c1cc(NC(=O)C2C(c3cc(Cl)c(Cl)c(Cl)c3)C2(Cl)Cl)ccc1Cl]

Isolated as a tan foam (0.130 g, 73%).

trans-N-2-Chloro-N-(2-cyclopropylethyl)-5-(2,2-dichloro-3-(3,5-dichlorophenyl)cyclopropane-1-carboxamido)benzamide (F24)

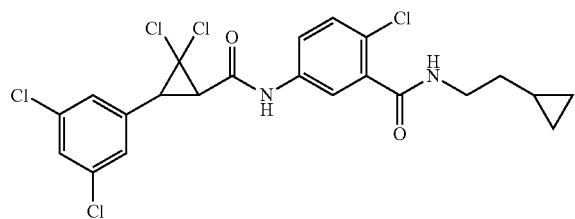 [SMILES: O=C(NCCC1CC1)c1cc(NC(=O)C2C(c3cc(Cl)cc(Cl)c3)C2(Cl)Cl)ccc1Cl]

Isolated as a tan powder (0.136 g, 78%).

trans-N-2-Chloro-N-(2-cyclopropylethyl)-5-(2,2-dichloro-3-(3,4-dichlorophenyl)cyclopropane-1-carboxamido)benzamide (F25)

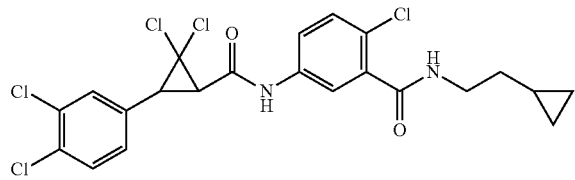 [SMILES: O=C(NCCC1CC1)c1cc(NC(=O)C2C(c3ccc(Cl)c(Cl)c3)C2(Cl)Cl)ccc1Cl]

Isolated as a tan powder (0.134 g, 77%).

trans-N-2-Chloro-N-(2-cyclopropylethyl)-5-(2,2-dichloro-3-(3,4,5-trichlorophenyl)cyclopropane-1-carboxamido)benzamide (F26)

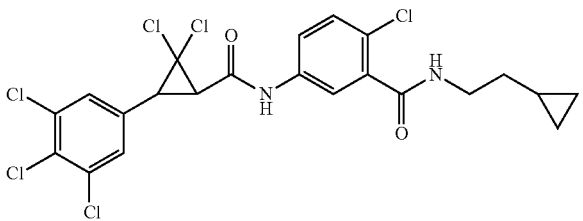 [SMILES: O=C(NCCC1CC1)c1cc(NC(=O)C2C(c3cc(Cl)c(Cl)c(Cl)c3)C2(Cl)Cl)ccc1Cl]

Isolated as a white powder (0.128 g, 77%).

Example 14

Preparation of trans-N-benzyl-2-chloro-5-(2,2-dichloro-3-(3,5-dichlorophenyl)cyclopropane-1-carboxamido)benzamide (F27)

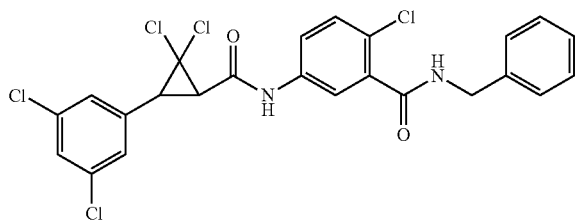 [SMILES: O=C(NCc1ccccc1)c1cc(NC(=O)C2C(c3cc(Cl)cc(Cl)c3)C2(Cl)Cl)ccc1Cl]

To a solution of phenylmethanamine (0.024 g, 0.23 mmol) in dichloromethane (2 mL) were added in sequence 1-ethyl-3-(3-dimethylaminopropyl)carbodiimide (0.054 g, 0.28 mmol), 4-dimethylaminopyridine (0.027 g, 0.23 mmol), and trans-2-chloro-5-(2,2-dichloro-3-(3,5-dichlorophenyl)cyclopropanecarboxamido)benzoic acid (C67) (0.085 g, 0.19 mmol). The reaction mixture was stirred at room temperature for 16 hours. Purification by flash column chromatography using 0-20% ethyl acetate/hexanes as eluent provided the title compound as a white solid (0.075 g, 74%).

The following compounds were prepared in like manner to the procedure outlined in Example 14:

trans-2-Chloro-5-(2,2-dichloro-3-(3,5-dichlorophenyl)cyclopropane-1-carboxamido)-N-(4-fluorobenzyl)benzamide (F28)

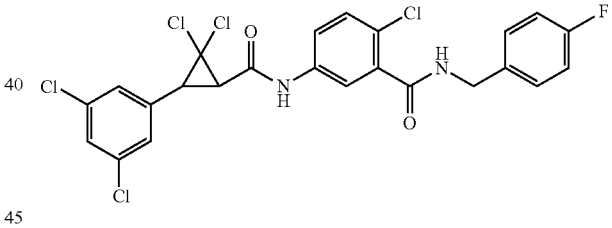

Isolated as a white solid (0.072 g, 68%).

Example 15

Preparation of trans-2-chloro-5-(2,2-dichloro-3-(3,5-dichlorophenyl)cyclopropane-1-carboxamido)-N-phenoxybenzamide (F29)

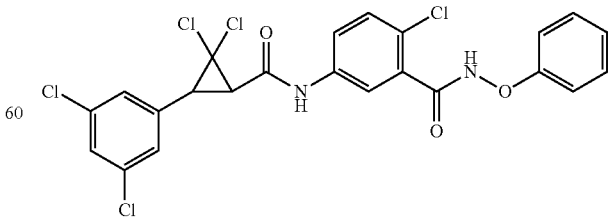

To a solution of trans-2-chloro-5-(2,2-dichloro-3-(3,5-dichlorophenyl)cyclopropanecarboxamido)benzoic acid (C67) (0.300 g, 0.661 mmol) in dichloromethane (5 mL) stirred at 0° C., were added N,N-dimethylformamide (1 drop) followed by oxalyl chloride (0.0870 mL, 0.992 mmol). The ice batch was removed and the reaction was allowed to warm to room temperature over 90 minutes. The reaction was concentrated and the resultant acid chloride was dissolved in dichloromethane (5 mL) and cooled in an ice bath. A solution of O-phenylhydroxylamine (0.108 g, 0.992 mmol) and triethylamine (0.230 mL, 1.65 mmol) in dichloromethane (3 mL) was added dropwise. The mixture was removed from the ice bath and warmed to room temperature over 1 hour. The reaction mixture was allowed to stir at room temperature for 16 hours. Purification by flash column chromatography using 0-35% ethyl acetate/hexanes as eluent followed by trituration with dichloromethane, filtration, and drying in a vacuum oven at 40° C. overnight provided the title compound as a white solid (0.0981 g, 27%).

Example 16

Preparation of trans-2-chloro-5-(2,2-dichloro-3-(3,5-dichlorophenyl)cyclopropane-1-carboxamido)-N-isobutylbenzamide (F30)

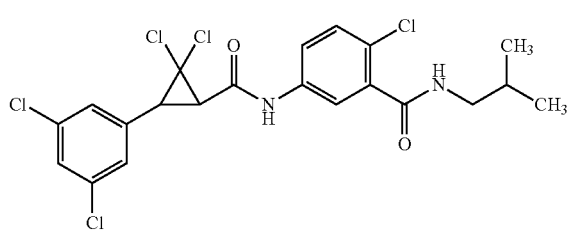 [SMILES: CC(C)CNC(=O)c1cc(NC(=O)C2C(c3cc(Cl)cc(Cl)c3)C2(Cl)Cl)ccc1Cl]

To a solution of trans-2-chloro-5-(2,2-dichloro-3-(3,5-dichlorophenyl)cyclopropanecarboxamido)benzoic acid (C67) (0.0750 g, 0.165 mmol) in dichloromethane (1 mL) were added 1-[bis(dimethylamino)methylene]-1H-1,2,3-triazolo[4,5-b]pyridinium 3-oxid hexafluorophosphate (0.0690 g, 0.182 mmol) followed by diisopropylethylamine (0.0280 g, 0.215 mmol), and the resulting pale-yellow solution was stirred for 15 minutes, treated with 2-methylpropan-1-amine (0.0150 g, 0.198 mmol), and stirred at room temperature for approximately 18 hours. The solution was washed with hydrochloric acid (1 N), and the phases were separated and dried by passing them through a phase separator cartridge. The organic phase was concentrated, purified by flash column chromatography, and dried under vacuum to provide the title compound as a sticky, viscous, oil that slowly solidifies upon scratching (0.0810 g, 100%).

The following compounds were prepared in like manner to the procedure outlined in Example 16:

trans-2-Chloro-5-(2,2-dichloro-3-(3,5-dichlorophenyl)cyclopropane-1-carboxamido)-N-hexylbenzamide (F31)

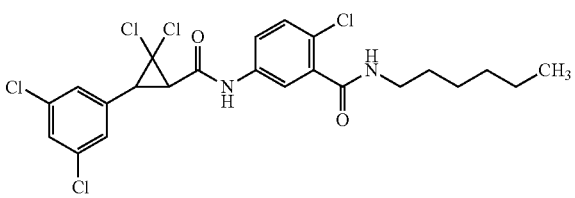 [SMILES: CCCCCCNC(=O)c1cc(NC(=O)C2C(c3cc(Cl)cc(Cl)c3)C2(Cl)Cl)ccc1Cl]

Isolated as a white solid (0.067 g, 75%).

trans-2-Chloro-5-(2,2-dichloro-3-(3,5-dichlorophenyl)cyclopropane-1-carboxamido)-N-(3,4-difluorobenzyl)benzamide (F32)

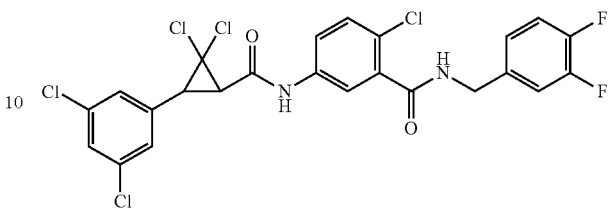

Isolated as a white solid (0.085 g, 85%).

trans-2-Chloro-5-(2,2-dichloro-3-(3,5-dichlorophenyl)cyclopropane-1-carboxamido)-N-pentylbenzamide (F33)

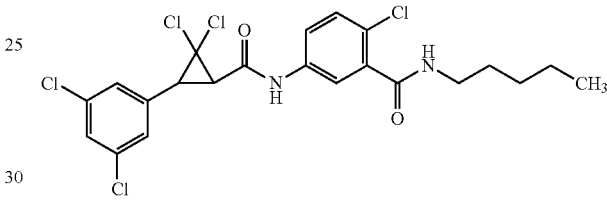

Isolated as a white solid (0.072 g, 79%).

trans-2-Chloro-5-(2,2-dichloro-3-(3,5-dichlorophenyl)cyclopropane-1-carboxamido)-N-(2,4-dimethoxybenzyl)benzamide (F34)

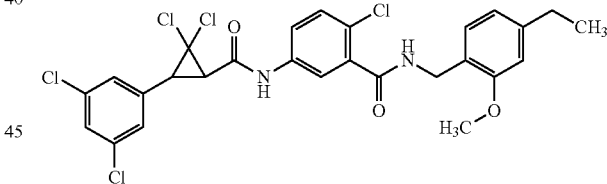

Isolated as a pale-yellow solid (0.084 g, 84%).

trans-2-Chloro-N-(cyclopropylmethyl)-5-(2,2-dichloro-3-(3,5-dichlorophenyl)cyclopropane-1-carboxamido)benzamide (F35)

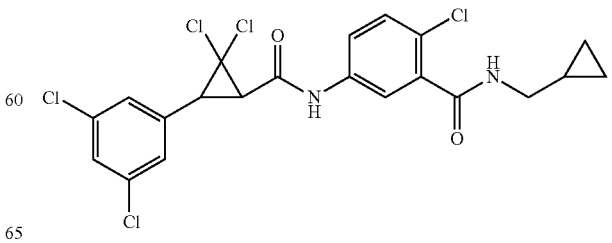

Isolated as a white solid (0.074 g, 84%).

75 trans-N-(4-(tert-Butylbenzyl)-2-chloro-5-(2,2-di-chloro-3-(3,5-dichlorophenyl)cyclopropane-1-car-boxamido)benzamide (F36)

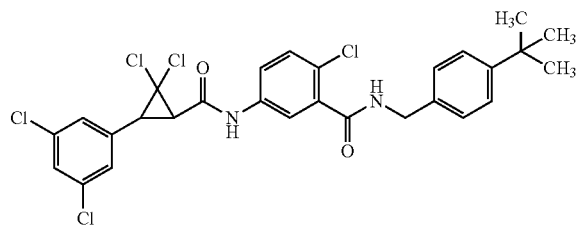 [SMILES: CC(C)(C)c1ccc(CNC(=O)c2cc(NC(=O)C3C(c4cc(Cl)cc(Cl)c4)C3(Cl)Cl)ccc2Cl)cc1]

Isolated as a white solid (0.061 g, 51%).

trans-2-Chloro-N-(2-cyanoethyl)-5-(2,2-dichloro-3-(3,5-dichlorophenyl)cyclopropane-1-carboxamido)benzamide (F37)

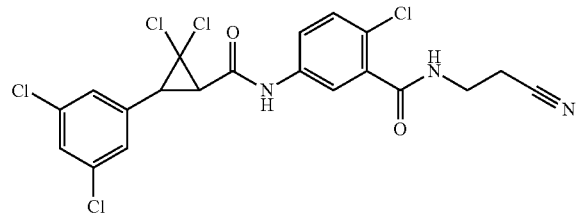 [SMILES: N#CCCNC(=O)c1cc(NC(=O)C2C(c3cc(Cl)cc(Cl)c3)C2(Cl)Cl)ccc1Cl]

Isolated as a white solid (0.072 g, 82%).

trans-2-Chloro-N-(3-cyanopropyl)-5-(2,2-dichloro-3-(3,5-dichlorophenyl)cyclopropane-1-carboxamido)benzamide (F38)

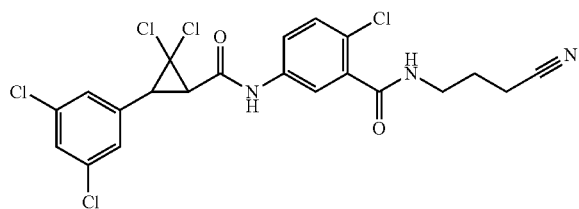 [SMILES: N#CCCCNC(=O)c1cc(NC(=O)C2C(c3cc(Cl)cc(Cl)c3)C2(Cl)Cl)ccc1Cl]

Isolated as a white solid (0.081 g, 90%).

trans-2-Chloro-5-(2,2-dichloro-3-(3,5-dichlorophenyl)cyclopropane-1-carboxamido)-N-(3-(2,2,2-trifluoroethoxy)propyl)benzamide (F39)

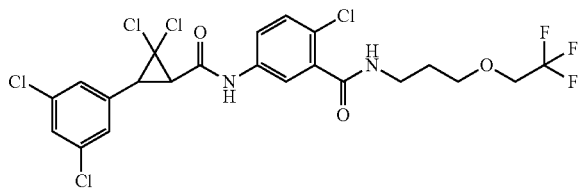 [SMILES: O=C(NCCCOCC(F)(F)F)c1cc(NC(=O)C2C(c3cc(Cl)cc(Cl)c3)C2(Cl)Cl)ccc1Cl]

Isolated as a white solid (0.082 g, 79%).

76 trans-2-Chloro-5-(2,2-dichloro-3-(3,5-dichlorophenyl)cyclopropane-1-carboxamido)-N-(3,3,3-trifluoropropyl)benzamide (F40)

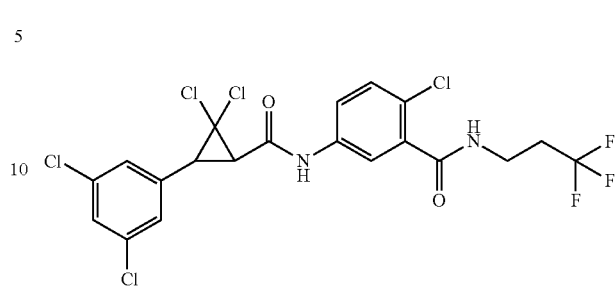

Isolated as a white solid (0.077 g, 81%).

trans-2-Chloro-5-(2,2-dichloro-3-(3,5-dichlorophenyl)cyclopropane-1-carboxamido)-N-(4-(trifluoromethyl)benzyl)benzamide (F41)

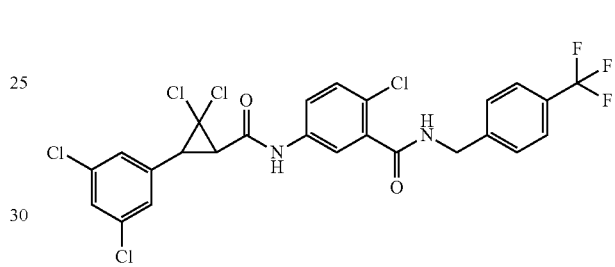

Isolated as a white solid (0.087 g, 82%).

trans-2-Chloro-5-(2,2-dichloro-3-(3,5-dichlorophenyl)cyclopropane-1-carboxamido)-N-(2-methyl-1-(methylsulfonyl)propan-2-yl)benzamide (F42)

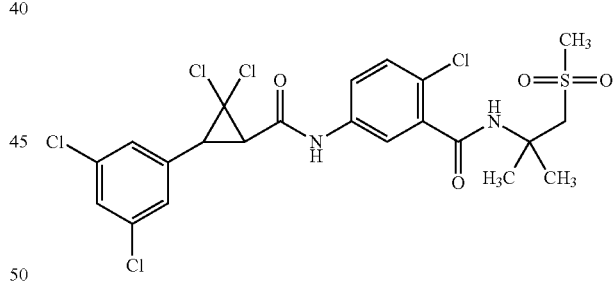

Isolated as a white solid (0.090 g, 88%).

trans-2-Chloro-N-(2-(cyclopropylmethoxy)ethyl)-5-(2,2-dichloro-3-(3,5-dichlorophenyl)cyclopropane-1-carboxamido)benzamide (F43)

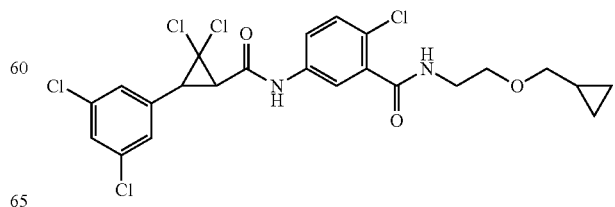

Isolated as a white solid (0.042 g, 44%).

trans-2-Chloro-5-(2,2-dichloro-3-(3,5-dichlorophenyl)cyclopropane-1-carboxamido)-N-(3-fluoropropyl)benzamide (F44)

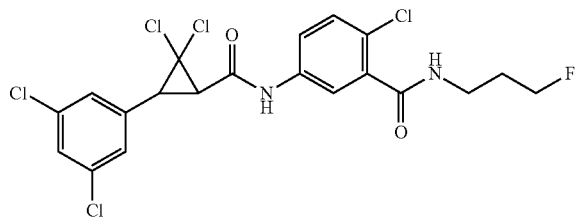 [SMILES: O=C(NCCCF)c1cc(NC(=O)C2C(c3cc(Cl)cc(Cl)c3)C2(Cl)Cl)ccc1Cl]

Isolated as a white solid (0.053 g, 59%).

trans-N-Butyl-2-chloro-5-(2,2-dichloro-3-(3,5-dichlorophenyl)cyclopropane-1-carboxamido)benzamide (F45)

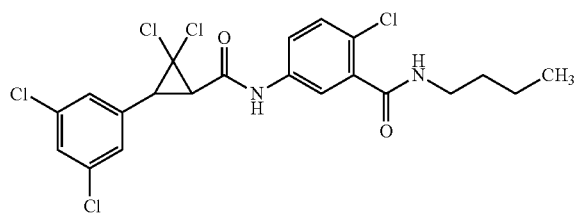

Isolated as a white solid (0.067 g, 76%).

trans-2-Chloro-5-(2,2-dichloro-3-(3,5-dichlorophenyl)cyclopropane-1-carboxamido)-N-ethylbenzamide (F46)

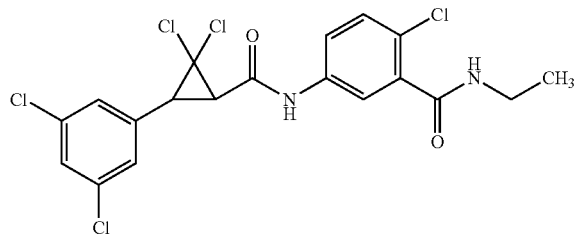 [SMILES: CCNC(=O)c1cc(NC(=O)C2C(c3cc(Cl)cc(Cl)c3)C2(Cl)Cl)ccc1Cl]

Isolated as a white solid (0.065 g, 82%).

trans-2-Chloro-5-(2,2-dichloro-3-(3,5-dichlorophenyl)cyclopropane-1-carboxamido)-N-(prop-2-yn-1-yl)benzamide (F47)

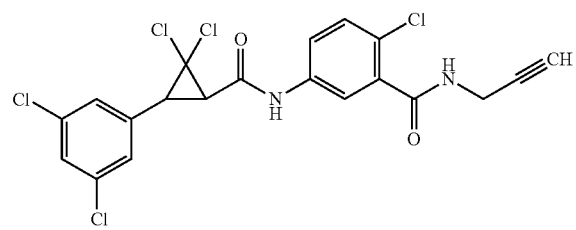 [SMILES: C#CCNC(=O)c1cc(NC(=O)C2C(c3cc(Cl)cc(Cl)c3)C2(Cl)Cl)ccc1Cl]

Isolated as a white solid (0.043 g, 53%).

trans-2-Chloro-5-(2,2-dichloro-3-(3,5-dichlorophenyl)cyclopropane-1-carboxamido)-N-(2,2-difluoroethyl)benzamide (F48)

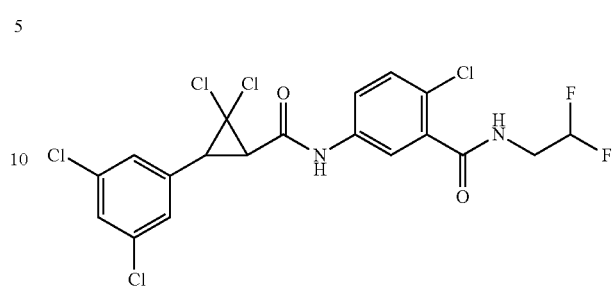

Isolated as a white solid (0.065 g, 76%).

trans-2-Chloro-5-(2,2-dichloro-3-(3,5-dichlorophenyl)cyclopropane-1-carboxamido)-N-(2,2,3,3,3-pentafluoropropyl)benzamide (F49)

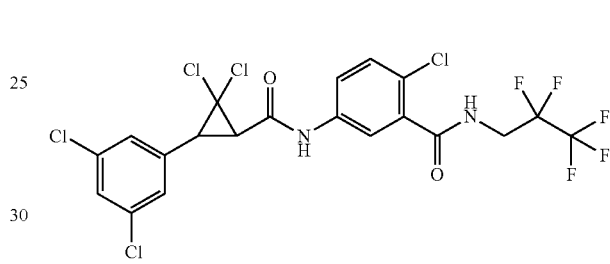

Isolated as a white solid (0.070 g, 72%).

trans-2-Chloro-5-(2,2-dichloro-3-(3,5-dichlorophenyl)cyclopropane-1-carboxamido)-N-(4-(dimethylamino)butyl)benzamide (F50)

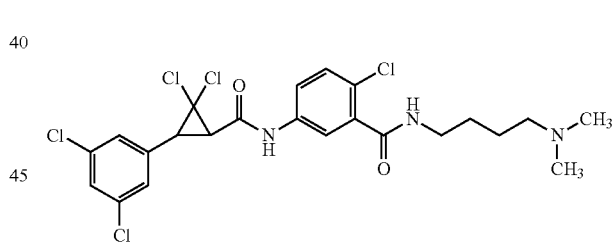

Isolated as a white solid (0.031 g, 34%).

trans-2-Chloro-N-(2-chloroethyl)-5-(2,2-dichloro-3-(3,5-dichlorophenyl)cyclopropane-1-carboxamido)benzamide (F51)

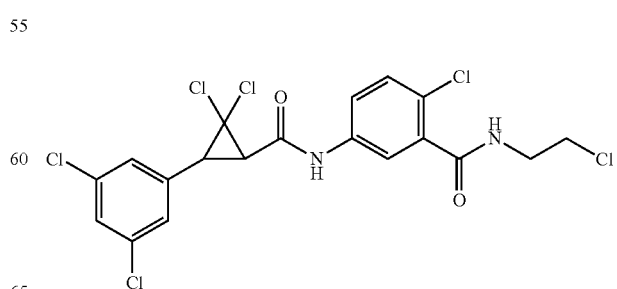

Isolated as a white solid (0.073 g, 86%).

trans-2-Chloro-5-(2,2-dichloro-3-(3,5-dichlorophenyl)cyclopropane-1-carboxamido)-N-(2-(methylthio)ethyl)benzamide (F52)

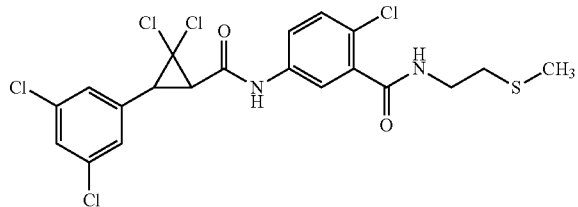

Isolated as a white solid (0.255 g, 88%).

trans-2-Chloro-5-(2,2-dichloro-3-(3,5-dichlorophenyl)cyclopropane-1-carboxamido)-N-(2-methoxyethyl)benzamide (F53)

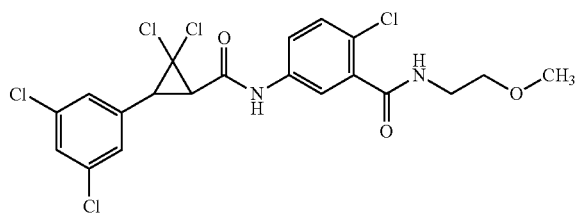 [SMILES: COCCNC(=O)c1cc(NC(=O)C2C(c3cc(Cl)cc(Cl)c3)C2(Cl)Cl)ccc1Cl]

Isolated as a white solid (0.064 g, 76%).

trans-2-Chloro-5-(2,2-dichloro-3-(3,5-dichlorophenyl)cyclopropane-1-carboxamido)-N-(2-ethoxyethyl)benzamide (F54)

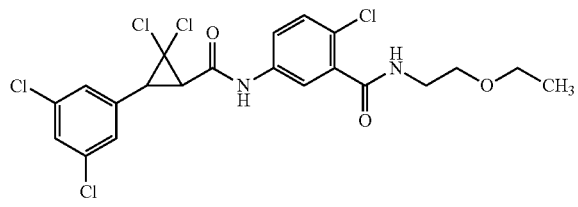

Isolated as a white solid (0.066 g, 76%).

trans-N-(2-Acetamidoethyl)-2-chloro-5-(2,2-dichloro-3-(3,5-dichlorophenyl)cyclopropane-1-carboxamido)benzamide (F55)

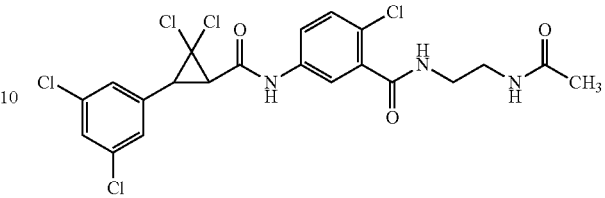

Isolated as a tan solid (0.063 g, 71%).

trans-2-Chloro-5-(2,2-dichloro-3-(3,5-dichlorophenyl)cyclopropane-1-carboxamido)-N-propylbenzamide (F56)

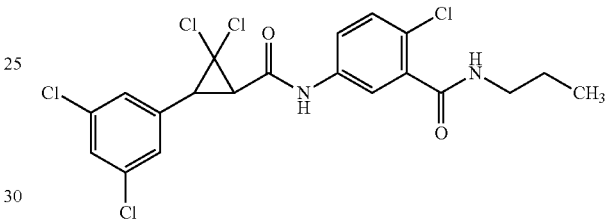

Isolated as a white solid (0.074 g, 90%).

trans-2-Chloro-N-(3-chloropropyl)-5-(2,2-dichloro-3-(3,5-dichlorophenyl)cyclopropane-1-carboxamido)benzamide (F57)

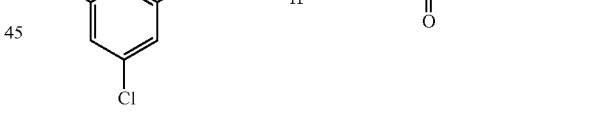

Isolated as a white solid (0.084 g, 96%).

trans-2-Chloro-5-(2,2-dichloro-3-(3,5-dichlorophenyl)cyclopropane-1-carboxamido)-N-(3-(2-methoxyethoxy)propyl)benzamide (F58)

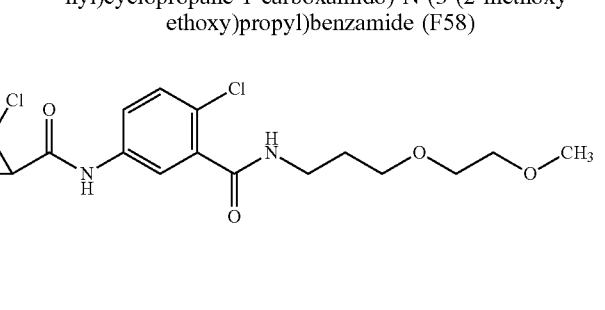

Isolated as a white solid (0.071 g, 75%).

81 trans-2-Chloro-5-(2,2-dichloro-3-(3,5-dichlorophenyl)cyclopropane-1-carboxamido)-N-methyl-N-(2,2,2-trifluoroethyl)benzamide (F59)

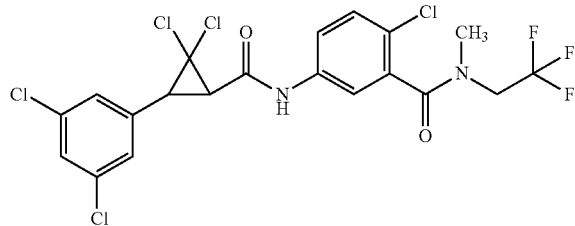 [SMILES: CN(CC(F)(F)F)C(=O)c1cc(NC(=O)C2C(c3cc(Cl)cc(Cl)c3)C2(Cl)Cl)ccc1Cl]

Isolated as a white solid (0.056 g, 62%).

trans-2-Chloro-5-(2,2-dichloro-3-(3,5-dichlorophenyl)cyclopropane-1-carboxamido)-N-(3,3,4,4,4-pentafluorobutyl)benzamide (F60)

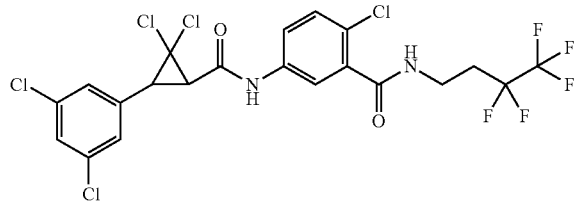 [SMILES: O=C(NCCC(F)(F)C(F)(F)F)c1cc(NC(=O)C2C(c3cc(Cl)cc(Cl)c3)C2(Cl)Cl)ccc1Cl]

Isolated as a white solid (0.093 g, 94%).

trans-2-Chloro-5-(2,2-dichloro-3-(3,5-dichlorophenyl)cyclopropane-1-carboxamido)-N-(2,2,3,3,4,4,4-heptafluorobutyl)benzamide (F61)

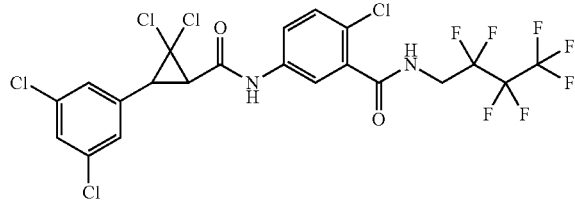 [SMILES: O=C(NCC(F)(F)C(F)(F)C(F)(F)F)c1cc(NC(=O)C2C(c3cc(Cl)cc(Cl)c3)C2(Cl)Cl)ccc1Cl]

Isolated as a white solid (0.054 g, 52%).

trans-2-Chloro-5-(2,2-dichloro-3-(3,5-dichlorophenyl)cyclopropane-1-carboxamido)-N-methyl-N-propylbenzamide (F62)

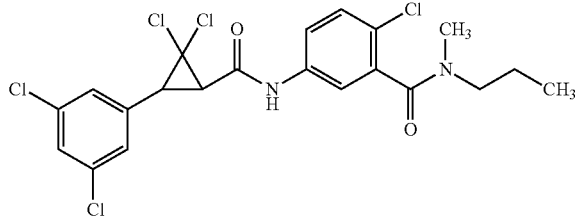 [SMILES: CCCN(C)C(=O)c1cc(NC(=O)C2C(c3cc(Cl)cc(Cl)c3)C2(Cl)Cl)ccc1Cl]

Isolated as a white solid (0.071 g, 84%).

82 trans-2-Chloro-5-(2,2-dichloro-3-(3,5-dichlorophenyl)cyclopropane-1-carboxamido)-N-ethyl-N-methylbenzamide (F63)

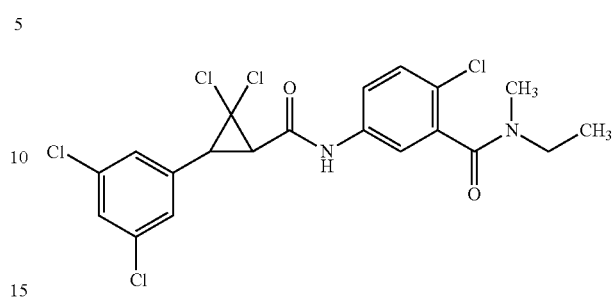

Isolated as a white solid (0.077 g, 94%).

trans-2-Chloro-5-(2,2-dichloro-3-(3,5-dichlorophenyl)cyclopropane-1-carboxamido)-N-methyl-N-(3,3,3-trifluoropropyl)benzamide (F64)

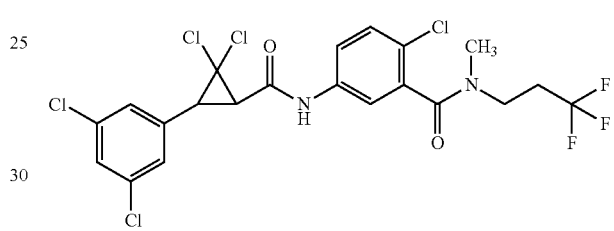

Isolated as a white solid (0.083 g, 89%).

trans-2-Chloro-5-(2,2-dichloro-3-(3,5-dichlorophenyl)cyclopropane-1-carboxamido)-N-methyl-N-(prop-2-yn-1-yl)benzamide (F65)

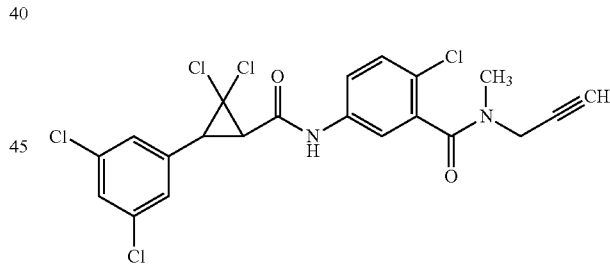

Isolated as a tan solid (0.035 g, 42%).

trans-2-Chloro-N-(cyanomethyl)-5-(2,2-dichloro-3-(3,5-dichlorophenyl)cyclopropane-1-carboxamido)-N-methylbenzamide (F66)

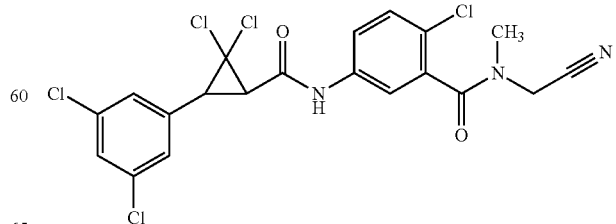

Isolated as a light yellow solid (0.023 g, 28%).

trans-2-Chloro-5-(2,2-dichloro-3-(3,5-dichlorophenyl)cyclopropane-1-carboxamido)-N-(2-methoxyethyl)-N-methylbenzamide (F67)

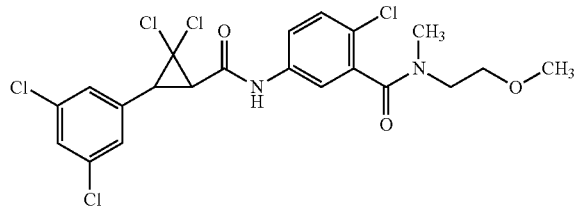 [SMILES: COCCN(C)C(=O)c1cc(NC(=O)C2C(c3cc(Cl)cc(Cl)c3)C2(Cl)Cl)ccc1Cl]

Isolated as a light yellow solid (0.064 g, 74%).

trans-2-Chloro-5-(2,2-dichloro-3-(3,5-dichlorophenyl)cyclopropane-1-carboxamido)-N-methyl-N-(2-(methylthio)ethyl)benzamide (F68)

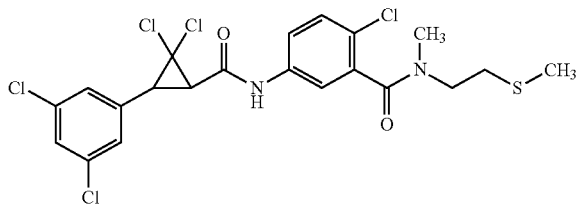 [SMILES: CSCCN(C)C(=O)c1cc(NC(=O)C2C(c3cc(Cl)cc(Cl)c3)C2(Cl)Cl)ccc1Cl]

Isolated as a white solid (0.069 g, 77%).

trans-2-Chloro-N-(cyclopropylmethyl)-5-(2,2-dichloro-3-(3,5-dichlorophenyl)cyclopropane-1-carboxamido)-N-methylbenzamide (F69)

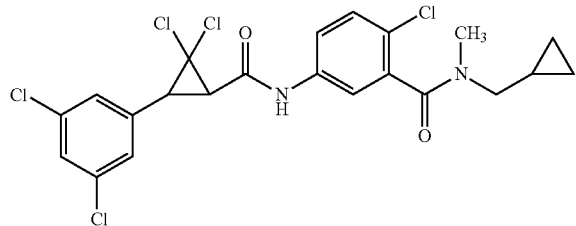 [SMILES: CN(CC1CC1)C(=O)c1cc(NC(=O)C2C(c3cc(Cl)cc(Cl)c3)C2(Cl)Cl)ccc1Cl]

Isolated as a colorless oil (0.066 g, 77%).

trans-2-Chloro-5-(2,2-dichloro-3-(3,5-dichlorophenyl)cyclopropane-1-carboxamido)-N-((3,3-difluorocyclobutyl)methyl)benzamide (F70)

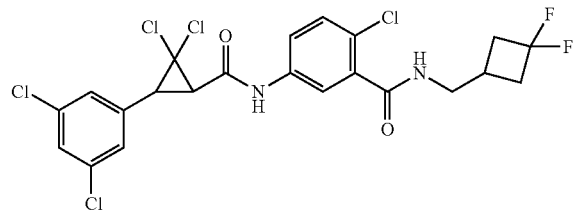 [SMILES: O=C(NCC1CC(F)(F)C1)c1cc(NC(=O)C2C(c3cc(Cl)cc(Cl)c3)C2(Cl)Cl)ccc1Cl]

Isolated as a white solid (0.074 g, 80%).

trans-2,2-Dichloro-N-(4-chloro-3-(3,3-difluoropyrrolidine-1-carbonyl)phenyl)-3-(3,5-dichlorophenyl)cyclopropane-1-carboxamide (F71)

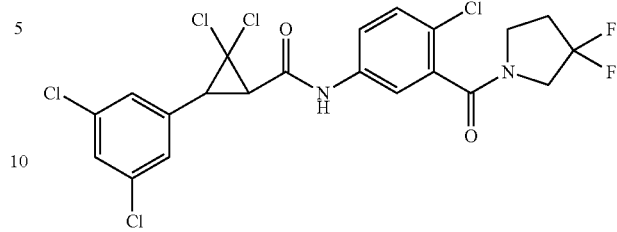

Isolated as a white solid (0.079 g, 88%).

trans-2-Chloro-5-(2,2-dichloro-3-(3,5-dichlorophenyl)cyclopropane-1-carboxamido)-N-(4,4,4-trifluorobutyl)benzamide (F72)

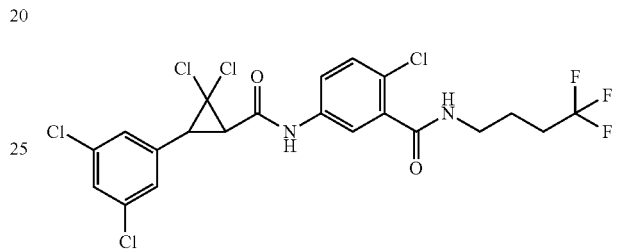

Isolated as a white solid (0.090 g, 97%).

trans-2-Chloro-5-(2,2-dichloro-3-(3,5-dichlorophenyl)cyclopropane-1-carboxamido)-N-((3,3-difluorocyclobutyl)methyl)-N-methylbenzamide (F73)

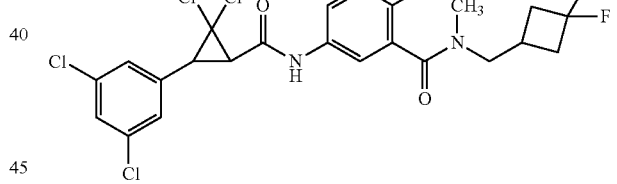

Isolated as a white solid (0.087 g, 92%).

Example 17a

Preparation of trans-2-chloro-5-(2,2-dichloro-3-(3,5-dichlorophenyl)cyclopropane-1-carboxamido)-N-(2-(methylsulfinyl)ethyl)benzamide (F74) and trans-2-chloro-5-(2,2-dichloro-3-(3,5-dichlorophenyl)cyclopropane-1-carboxamido)-N-(2-(methylsulfonyl)ethyl)benzamide (F75)

F74

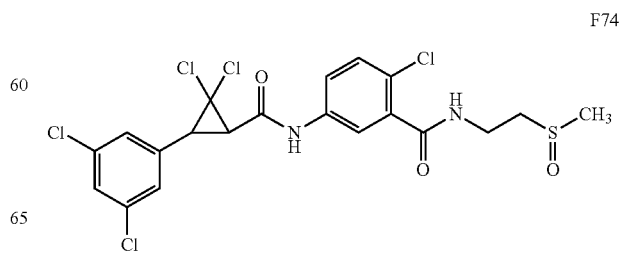

-continued

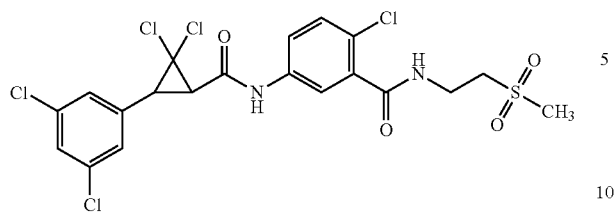
F75

To a solution of trans-2-Chloro-5-(2,2-dichloro-3-(3,5-dichlorophenyl)cyclopropane-1-carboxamido)-N-(2-(methylthio)ethyl)benzamide (F52) (0.179 g, 0.340 mmol) in acetic acid (4 mL) was added sodium perborate tetrahydrate (0.0840 g, 0.540 mmol), and the colorless mixture was warmed to 55° C. and stirred for about 3 hours. The reaction mixture was diluted with dichloromethane (50 mL) and neutralized by the slow addition of saturated aqueous sodium bicarbonate. The phases were separated and the aqueous phase was extracted with dichloromethane, and the combined organic layers were washed with brine, dried by passing through a phase separator cartridge, and concentrated. Purification by flash column chromatography using 0-100% ethyl acetate/hexanes followed by 1:1 dichloromethane/methanol as eluent and drying in a vacuum oven (house vacuum) at 47° C. overnight provided (F74) as a white solid (0.048 g, 26%) and (F75) as a white solid (0.135 g, 71%).

Example 17b

Preparation of
5-amino-2-chloro-N-methylbenzamide (C68)

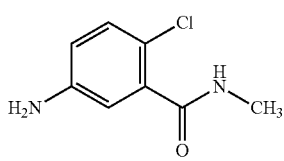

To a solution of 2-chloro-N-methyl-5-nitrobenzamide (C81) (0.280 g, 1.31 mmol) in methanol (8.70 mL) and water (4.35 mL) were added iron powder (0.364 g, 6.52 mmol) and ammonium chloride (0.209 g, 3.91 mmol). The reaction was heated at 60° C. for 2 hours. The reaction was filtered through Celite®. The filtrate was diluted with dichloromethane and extracted with hydrochloric acid (1 N). The combined aqueous phases were neutralized with saturated aqueous sodium bicarbonate and extracted with dichloromethane. The combined organic phases were dried over magnesium sulfate, filtered, and concentrated to give the title compound as a yellow solid (0.0720 g, 22%): $^1$H NMR (400 MHz, CDCl$_3$) δ 7.09 (d, J=8.5 Hz, 1H), 6.89 (d, J=2.9 Hz, 1H), 6.61 (dd, J=8.6, 2.9 Hz, 1H), 6.53 (s, 1H), 3.92 (s, 2H), 2.96 (d, J=4.9 Hz, 3H); EIMS m/z 185 ([M]$^+$).

The following compounds were prepared in like manner to the procedure outlined in Example 17b:

5-Amino-N-methyl-2-(trifluoromethyl)benzamide
(C69)

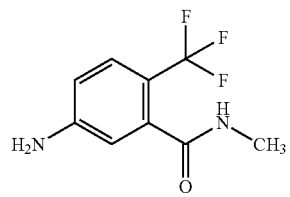

Isolated as a white solid (0.067 g, 75%): $^1$H NMR (400 MHz, CDCl$_3$) δ 7.43 (d, J=8.5 Hz, 1H), 6.74 (d, J=2.4 Hz, 1H), 6.71 6.66 (m, 1H), 5.76 (s, 1H), 4.07 (s, 2H), 2.98 (d, J=4.9 Hz, 3H); IR (thin film) 3465, 3350, 1612 cm$^{-1}$; EIMS m/z 218 ([M]$^+$).

5-Amino-2-chloro-N-(2,2,2-trifluoroethyl)benzamide
(C70)

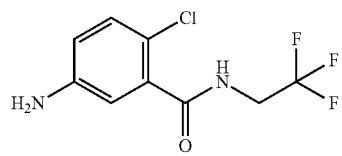 [SMILES: Nc1ccc(Cl)c(C(=O)NCC(F)(F)F)c1]

Isolated as a white solid (0.067 g, 75%): $^1$H NMR (400 MHz, DMSO-d$_6$) δ 8.98 (t, J=6.3 Hz, 1H), 7.08 (d, J=8.5 Hz, 1H), 6.64 6.52 (m, 2H), 5.46 (s, 2H), 4.01 (qd, J=9.7, 6.5 Hz, 2H); IR (thin film) 3428, 3281, 1656 cm$^{-1}$; ESIMS m/z 254 ([M+H]$^+$).

5-Amino-2-chloro-N-(2-oxo-2-((2,2,2-trifluoroethyl)amino)ethyl)benzamide (C71)

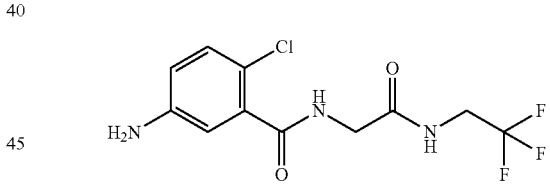

Isolated as a white solid (0.067 g, 75%): $^1$H NMR (400 MHz, CDCl$_3$) δ 8.03 (t, J=6.3 Hz, 1H), 7.69 (t, J=5.2 Hz, 1H), 6.68 6.58 (m, 2H), 6.51 (d, J=6.4 Hz, 1H), 4.27 (s, 2H), 3.96 3.70 (m, 4H); IR (thin film) 3307, 2941, 1693, 1647 cm$^{-1}$; ESIMS m/z 311 ([M+H]$^+$).

Example 18

Preparation of 5-amino-2-chloro-N-(pyridin-3-ylmethyl)benzamide (C72)

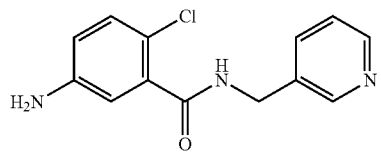 [SMILES: Nc1ccc(Cl)c(C(=O)NCc2cccnc2)c1]

1-Ethyl-3-(3-dimethylaminopropyl)-carbodiimide hydrochloride (0.840 g, 4.40 mmol) and 4-dimethylaminopyridine (0.460 g, 3.80 mmol) were sequentially added to a stirred mixture of 5-amino-2-chlorobenzoic acid (0.500 g, 2.90 mmol) and pyridin-3-ylmethanamine (0.360 mL, 3.50 mmol) in dichloromethane (12 mL) at 23° C. The resulting heterogeneous pink reaction mixture was stirred at 23° C. for 2 hours. N,N-Dimethylformamide (6 mL) was added to improve solubility and the resulting homogeneous orange solution was stirred at 23° C. for 70 hours. The reaction mixture was concentrated, and the residue was purified by reverse phase column chromatography using 5-100% acetonitrile/water as eluent to provide the title compound as a light brown powder (0.650 g, 86%): mp 133-136° C.; $^1$H NMR (400 MHz, DMSO-$d_6$) δ 8.89 (br t, J=6 Hz, 1H), 8.55 (d, J=1.5 Hz, 1H), 8.47 (dd, J=5, 1.5 Hz, 1H), 7.73 (dt, J=8, 1.5 Hz, 1H), 7.37 (ddd, J=8, 5, 0.8 Hz, 1H), 7.07 (d, J=8 Hz, 1H), 6.55-6.62 (m, 2H), 5.41 (br s, 2H), 4.42 (d, J=6 Hz, 2H); IR (thin film) 3432 (m), 3340 (m), 3195 (m), 3025 (m), 1654 (s), 1626 (s), 1602 (s), 1559 (s), 1474 (s), 1439 (s), 1428 (s) cm$^{-1}$; ESIMS m/z 262 ([M+H]$^+$).

The following compounds were prepared in like manner to the procedure outlined in Example 18:

5-Amino-2-chloro-N-(pyridin-2-ylmethyl)benzamide (C73)

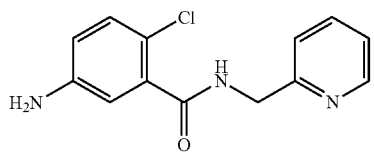 [SMILES: Nc1ccc(Cl)c(C(=O)NCc2ccccn2)c1]

Isolated as a white solid (0.067 g, 75%): $^1$H NMR (400 MHz, CDCl$_3$) δ 8.55 (br d, J=5 Hz, 1H), 7.69 (td, J=7.5, 2 Hz, 1H), 7.52 (br s, 1H), 7.35 (d, J=7.5 Hz, 1H), 7.21 (dd, J=7.5, 5 Hz, 1H), 7.16 (d, J=8.5 Hz, 1H), 7.04 (d, J=3 Hz, 1H), 6.67 (dd, J=8.5, 3 Hz, 1H), 4.78 (d, J=5 Hz, 2H), 3.77 (br s, 2H); IR (thin film) 3340 (m), 3223 (m), 3055 (w), 1640 (s), 1594 (s), 1571 (s), 1520 (s), 1474 (s), 1435 (s) cm$^{-1}$; ESIMS m/z 262 ([M+H]$^+$).

5-Amino-2-chloro-N-(pyridin-4-ylmethyl)benzamide (C74)

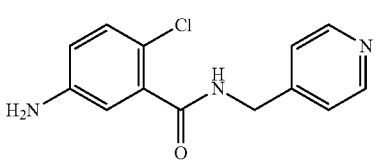 [SMILES: Nc1ccc(Cl)c(C(=O)NCc2ccncc2)c1]

Isolated as a white solid (0.067 g, 75%): mp 122-125° C.; $^1$H NMR (400 MHz, CDCl$_3$) δ 8.56-8.60 (m, 2H), 7.28-7.31 (m, 2H), 7.17 (d, J=8.5 Hz, 1H), 7.08 (d, J=3 Hz, 1H), 6.79 (br s, 1H), 6.69 (dd, J=8.5, 3 Hz, 1H), 4.67 (d, J=6 Hz, 2H), 3.81 (br s, 2H); IR (thin film) 3428 (w), 3240 (m), 3056 (w), 1651 (s), 1596 (s), 1543 (s), 1478 (s), 1416 (s) cm$^{-1}$; ESIMS m/z 262 ([M+H]$^+$).

5-Amino-2-chloro-N-(4-fluorophenethyl)benzamide (C75)

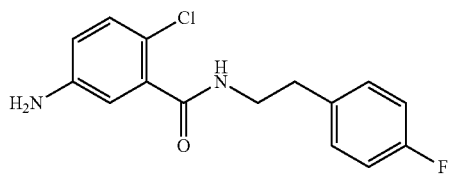 [SMILES: Nc1ccc(Cl)c(C(=O)NCCc2ccc(F)cc2)c1]

Isolated as a white solid (0.067 g, 75%): $^1$H NMR (400 MHz, CDCl$_3$) δ 8.32 (br t, J=5.5 Hz, 1H), 7.28 (m, 2H), 7.12 (m, 2H), 7.03 (d, J=8.5 Hz, 1H), 6.56 (dd, J=8.5, 3 Hz, 1H), 6.51 (d, J=3 Hz, 1H), 5.37 (br s, 2H), 3.39 (m, 2H), 2.79 (t, J=7.2 Hz, 2H); IR (thin film) 3482 (w), 3366 (w), 3302 (m), 3070 (w), 2946 (w), 1637 (s), 1596 (m), 1544 (m), 1508 (m), 1474 (m), 1436 (m) cm$^{-1}$; ESIMS m/z 293 ([M+H]$^+$).

5-Amino-2-chloro-N-(2-cyclopropylethyl)benzamide (C76)

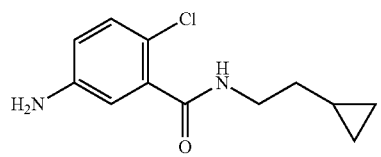 [SMILES: Nc1ccc(Cl)c(C(=O)NCCC2CC2)c1]

Isolated as a white solid (0.067 g, 75%): $^1$H NMR (400 MHz, DMSO-$d_6$) δ 8.23 (br t, J=6 Hz, 1H), 7.04 (d, J=9 Hz, 1H), 6.53-6.59 (m, 2H), 5.36 (br s, 2H), 3.23 (td, J=7, 6 Hz, 2H), 1.38 (q, J=7 Hz, 2H), 0.74 (m, 1H), 0.38-0.44 (m, 2H), 0.03-0.08 (m, 2H); IR (thin film) 3281 (m), 3076 (w), 3000 (w), 2914 (w), 1634 (s), 1595 (m), 1579 (m), 1552 (m), 1476 (m), 1433 (m) cm$^{-1}$; ESIMS m/z 239 ([M+H]$^+$).

Example 19

Preparation of N-(allyloxy)-5-amino-2-chlorobenzamide (C77)

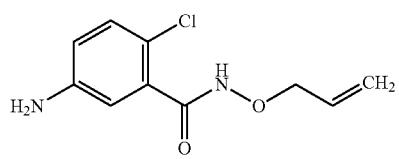

1-Ethyl-3-(3-dimethylaminopropyl)-carbodiimide hydrochloride (0.840 g, 4.40 mmol) and 4-dimethylaminopyridine (0.460 g, 3.80 mmol) were sequentially added to a stirred mixture of 5-amino-2-chlorobenzoic acid (0.500 g, 2.90 mmol), 0-allylhydroxylamine hydrochloride (0.380 g, 3.50 mmol), and triethylamine (0.490 mL, 3.50 mmol) in dichloromethane (15 mL) at 23° C. The resulting homogeneous gray solution was stirred at 23° C. for 48 hours. The reaction mixture was concentrated, and the residue was purified by reverse phase flash column chromatography using 5-100% acetonitrile/water as eluent to provide the title compound as a light brown oil (0.440 g, 67%): $^1$H NMR (400 MHz, CDCl$_3$) δ 7.13 (d, J=9 Hz, 1H), 6.95 (d, J=2.5 Hz, 1H), 6.66 (dd, J=9, 2.5 Hz, 1H), 6.05 (m, 1H), 5.32-5.45 (m, 2H), 4.53 (d, J=6 Hz, 2H), 3.79 (br s, 2H); IR (thin film) 3346 (w), 3214 (w), 2935 (w), 1629 (s), 1598 (s), 1575 (s), 1474 (s), 1433 (m), 1330 (m), 1271 (m) cm$^{-1}$; ESIMS m/z 227 ([M+H]$^+$).

The following compounds were prepared in like manner to the procedure outlined in Example 19:

5-Amino-2-chloro-N-(cyclopropylmethoxy)benzamide (C78)

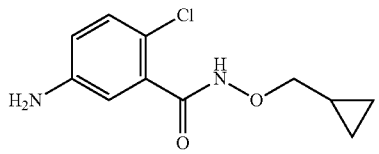 [SMILES: Nc1ccc(Cl)c(C(=O)NOCC2CC2)c1]

Isolated as a white solid (0.067 g, 75%): $^1$H NMR (400 MHz, CDCl$_3$) δ 7.13 (d, J=8.5 Hz, 1H), 6.95 (d, J=2.5 Hz, 1H), 6.67 (dd, J=8.5, 2.5 Hz, 1H), 3.88 (br d, J=7 Hz, 2H), 3.81 (br s, 2H), 1.21 (m, 1H), 0.57-0.66 (m, 2H), 0.32-0.39 (m, 2H); IR (thin film) 3344 (w), 3215 (w), 2936 (w), 1644 (s), 1599 (s), 1526 (m), 1474 (s), 1431 (m) cm$^{-1}$; ESIMS m/z 241 ([M+H]$^+$).

5-Amino-2-chloro-N-((4-fluorobenzyl)oxy)benzamide (C79)

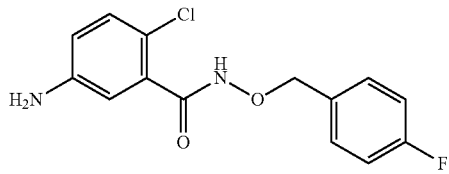

Isolated as a white solid (0.067 g, 75%).

Example 20

Preparation of 5-amino-2-chloro-N-((2,2-difluorocyclopropyl)methoxy)benzamide (C80)

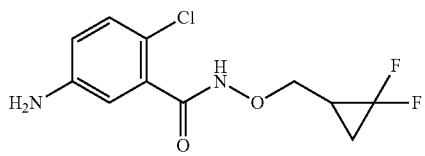 [SMILES: Nc1ccc(Cl)c(C(=O)NOCC2CC2(F)F)c1]

1-Ethyl-3-(3-dimethylaminopropyl)-carbodiimide hydrochloride (0.900 g, 4.70 mmol) and 4-dimethylaminopyridine (0.500 g, 4.10 mmol) were sequentially added to a stirred mixture of 5-amino-2-chlorobenzoic acid (0.535 g, 3.10 mmol), O-((2,2-difluorocyclopropyl)methyl)hydroxylamine hydrochloride (0.500 g, 3.10 mmol), and triethylamine (0.520 mL, 3.70 mmol) in dichloromethane (16 mL) at 23° C. The resulting homogeneous light pink solution was stirred at 23° C. for 24 hours. The reaction mixture was concentrated, and the residue was purified by reverse phase flash column chromatography using 5-100% acetonitrile/water as eluent to provide the title compound as a brown semi-solid (0.560 g, 65%): $^1$H NMR (400 MHz, DMSO-d$_6$) δ 11.51 (br s, 1H), 7.06 (d, J=8.3 Hz, 1H), 6.55-6.61 (m, 2H), 5.41 (br s, 2H), 3.96 (m, 1H), 3.85 (m, 1H), 2.08 (m, 1H), 1.67 (m, 1H), 1.39 (m, 1H); IR (thin film) 3343 (w), 3211 (w), 2937 (w), 1645 (m), 1600 (s), 1527 (m), 1472 (s), 1437 (m) cm$^{-1}$; ESIMS m/z 277 ([M+H]$^+$).

Example 21

Preparation of 2-chloro-N-methyl-5-nitrobenzamide (C81)

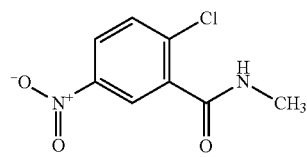

2-Chloro-5-nitrobenzoic acid (0.500 g, 2.48 mmol), diisopropylethylamine (0.650 mL, 3.72 mmol), and 4-dimethylaminopyridine (0.545 g, 4.47 mmol) were sequentially added to a stirred mixture of methanamine hydrochloride (0.251 g, 3.72 mmol) and 1-ethyl-3-(3-dimethylaminopropyl)-carbodiimide hydrochloride (0.951 g, 4.96 mmol) in 1,2-dichloroethane (25 mL) at room temperature. The reaction mixture was diluted with dichloromethane and washed with saturated aqueous sodium bicarbonate and hydrochloric acid (1 N). The organic phase was dried over magnesium sulfate, filtered, and concentrated to give the title compound as a white solid (0.283 g, 50%): $^1$H NMR (400 MHz, CDCl$_3$) δ 8.53 (d, J=2.7 Hz, 1H), 8.22 (dd, J=8.8, 2.8 Hz, 1H), 7.60 (d, J=8.8 Hz, 1H), 6.21 (s, 1H), 3.08 (d, J=4.9 Hz, 3H); EIMS m/z 215 ([M]$^+$).

The following compounds were prepared in like manner to the procedure outlined in Example 21:

N-Methyl-5-nitro-2-(trifluoromethyl)benzamide
(C82)

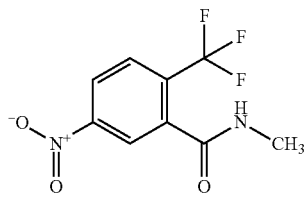

Isolated as a white solid (0.067 g, 75%): ¹H NMR (400 MHz, CDCl₃) δ 8.41-8.34 (m, 2H), 7.92 (d, J=8.4 Hz, 1H), 5.87 (s, 1H), 3.06 (d, J=4.9 Hz, 3H); EIMS m/z 248 ([M]⁺).

2-Chloro-5-nitro-N-(2-oxo-2-((2,2,2-trifluoroethyl)amino)ethyl)benzamide (C83)

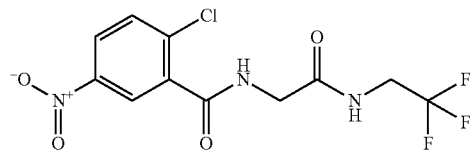

Isolated as a white solid (0.067 g, 75%): ¹H NMR (400 MHz, DMSO-d₆) δ 9.04 (t, J=5.9 Hz, 1H), 8.70 (t, J=6.3 Hz, 1H), 8.34 8.28 (m, 2H), 7.83 (d, J=8.6 Hz, 1H), 4.03 3.92 (m, 4H); IR (thin film) 3293, 3089, 1694, 1654 cm⁻¹; ESIMS m/z 341 ([M+H]⁺).

Example 22

Preparation of
2-chloro-5-nitro-N-(2,2,2-trifluoroethyl)benzamide
(C84)

2-Chloro-5-nitrobenzoic acid (0.500 g, 2.48 mmol) and 4-dimethylaminopyridine (0.394 g, 3.22 mmol) were sequentially added to a stirred mixture of 2,2,2-trifluoroethanamine (0.295 g, 2.98 mmol) and 1-ethyl-3-(3-dimethylaminopropyl)-carbodiimide hydrochloride (0.713 g, 3.72 mmol) in 1,2-dichloroethane (12 mL) at room temperature, and the mixture was stirred at room temperature for 1 day. The reaction mixture was diluted with dichloromethane and washed with saturated aqueous sodium bicarbonate followed by hydrochloric acid (1 N) to provide the title compound as a white solid (0.379 g, 51%): ¹H NMR (400 MHz, DMSO-d₆) δ 9.42 (t, J=6.2 Hz, 1H), 8.32 (dd, J=8.8, 2.8 Hz, 1H), 8.25 (d, J=2.7 Hz, 1H), 7.86 (d, J=8.8 Hz, 1H), 4.13 (qd, J=9.7, 6.4 Hz, 2H); IR (thin film) 3378, 2964, 1739, 1675 cm⁻¹; ESIMS m/z 284 ([M+H]⁺).

The following molecules in Table 1 may be prepared according to the procedures disclosed in

TABLE P1

Structure and preparation method for prophetic molecules

| No. | Structure | Prep* |
|---|---|---|
| P1 | 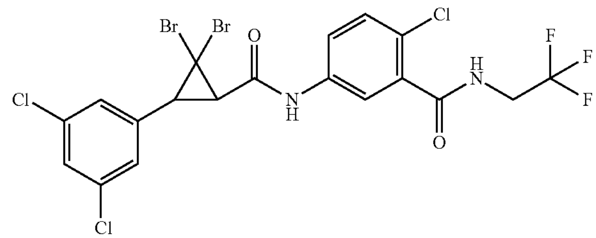 | 13, 16 |
| P2 | 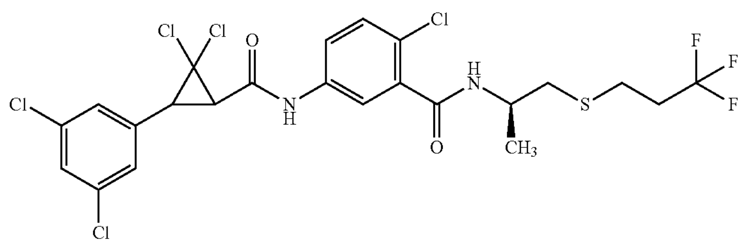 [SMILES: C[C@H](CSCCC(F)(F)F)NC(=O)c1cc(NC(=O)C2C(c3cc(Cl)cc(Cl)c3)C2(Cl)Cl)ccc1Cl] | 13, 16 |

TABLE P1-continued

Structure and preparation method for prophetic molecules

| No. | Structure | Prep* |
|---|---|---|
| P3 | 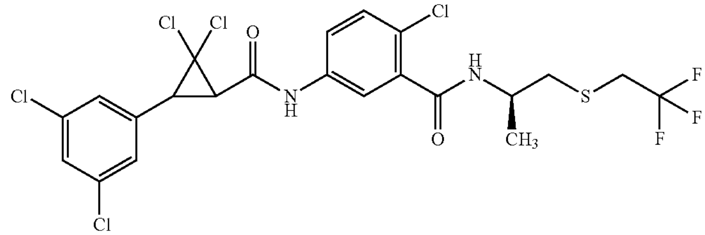 [SMILES: C[C@H](CSCC(F)(F)F)NC(=O)c1cc(NC(=O)C2C(c3cc(Cl)cc(Cl)c3)C2(Cl)Cl)ccc1Cl] | 13, 16 |
| P4 | 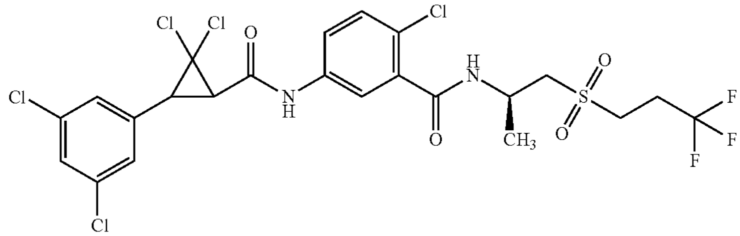 [SMILES: C[C@H](CS(=O)(=O)CCC(F)(F)F)NC(=O)c1cc(NC(=O)C2C(c3cc(Cl)cc(Cl)c3)C2(Cl)Cl)ccc1Cl] | 13, 16, 17a |
| P5 | 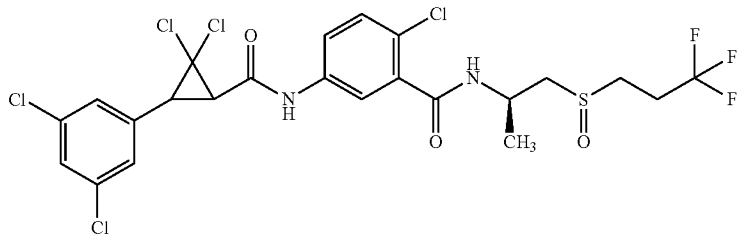 [SMILES: C[C@H](CS(=O)CCC(F)(F)F)NC(=O)c1cc(NC(=O)C2C(c3cc(Cl)cc(Cl)c3)C2(Cl)Cl)ccc1Cl] | 13, 16, 17a |
| P6 | 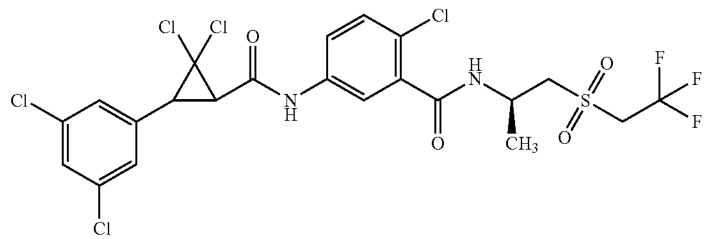 [SMILES: C[C@H](CS(=O)(=O)CC(F)(F)F)NC(=O)c1cc(NC(=O)C2C(c3cc(Cl)cc(Cl)c3)C2(Cl)Cl)ccc1Cl] | 13, 16, 17a |
| P7 | 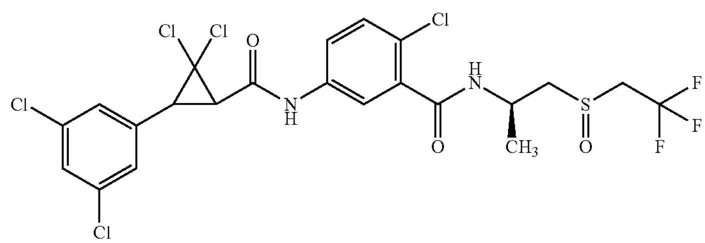 [SMILES: C[C@H](CS(=O)CC(F)(F)F)NC(=O)c1cc(NC(=O)C2C(c3cc(Cl)cc(Cl)c3)C2(Cl)Cl)ccc1Cl] | 13, 16, 17a |
| P8 | 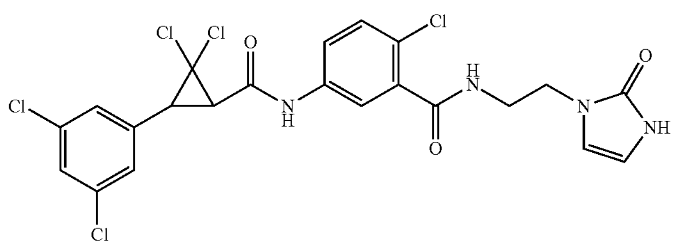 [SMILES: O=C(NCCn1cc[nH]c1=O)c1cc(NC(=O)C2C(c3cc(Cl)cc(Cl)c3)C2(Cl)Cl)ccc1Cl] | 13, 16 |

TABLE P1-continued

Structure and preparation method for prophetic molecules

| No. | Structure | Prep* |
|-----|-----------|-------|
| P9 | 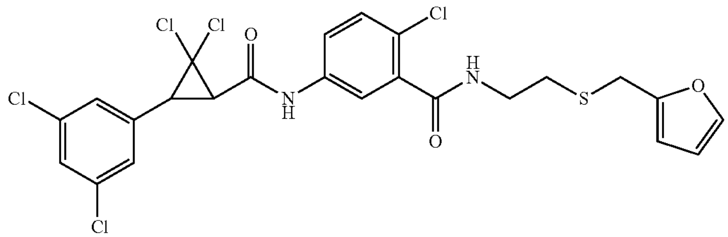 [SMILES: O=C(NCCSCc1ccco1)c1cc(NC(=O)C2C(c3cc(Cl)cc(Cl)c3)C2(Cl)Cl)ccc1Cl] | 13, 16 |
| P10 | 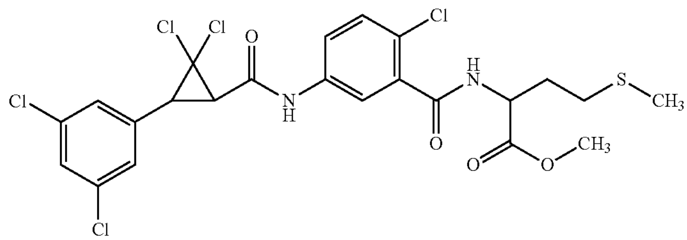 [SMILES: COC(=O)C(CCSC)NC(=O)c1cc(NC(=O)C2C(c3cc(Cl)cc(Cl)c3)C2(Cl)Cl)ccc1Cl] | 13, 16 |
| P11 | 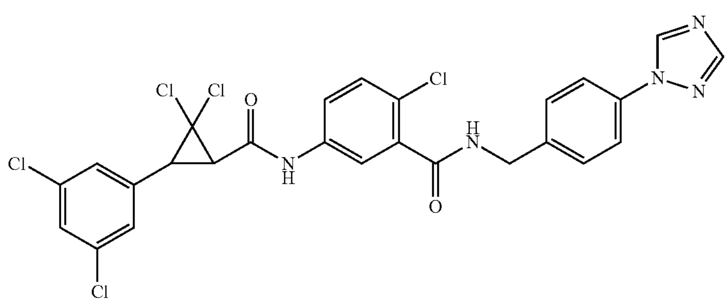 [SMILES: O=C(NCc1ccc(-n2cncn2)cc1)c1cc(NC(=O)C2C(c3cc(Cl)cc(Cl)c3)C2(Cl)Cl)ccc1Cl] | 13, 16 |
| P12 | 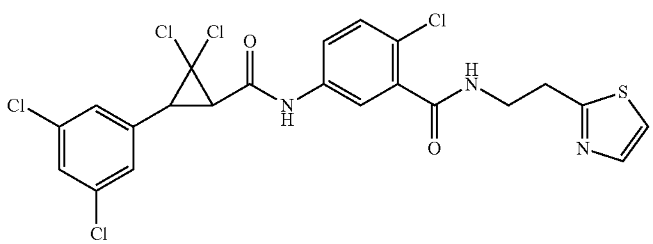 [SMILES: O=C(NCCc1nccs1)c1cc(NC(=O)C2C(c3cc(Cl)cc(Cl)c3)C2(Cl)Cl)ccc1Cl] | 13, 16 |
| P13 | 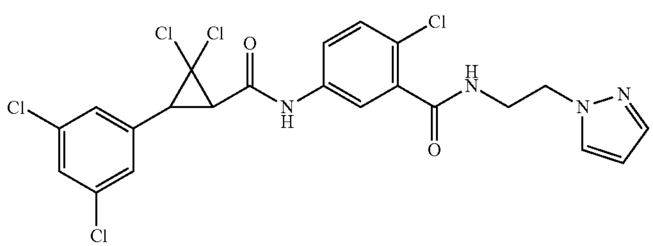 [SMILES: O=C(NCCn1cccn1)c1cc(NC(=O)C2C(c3cc(Cl)cc(Cl)c3)C2(Cl)Cl)ccc1Cl] | 13, 16 |
| P14 | 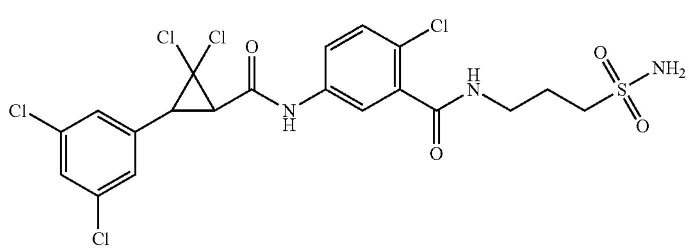 [SMILES: NS(=O)(=O)CCCNC(=O)c1cc(NC(=O)C2C(c3cc(Cl)cc(Cl)c3)C2(Cl)Cl)ccc1Cl] | 13, 16 |

TABLE P1-continued

Structure and preparation method for prophetic molecules

| No. | Structure | Prep* |
|---|---|---|
| P15 | 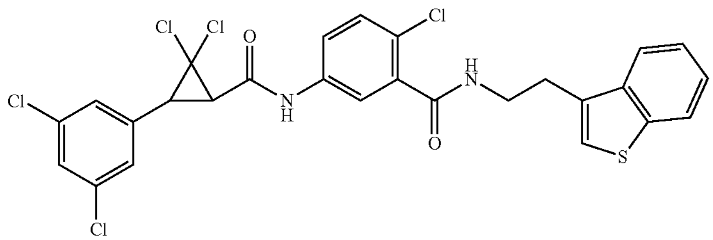 [SMILES: O=C(NCCc1csc2ccccc12)c1cc(NC(=O)C2C(c3cc(Cl)cc(Cl)c3)C2(Cl)Cl)ccc1Cl] | 13, 16 |
| P16 | 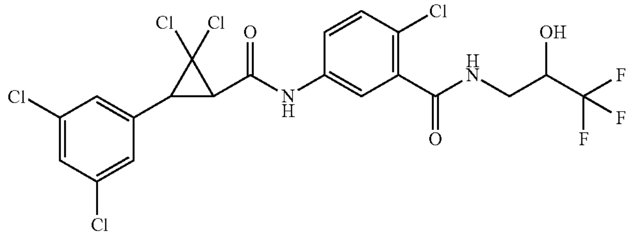 [SMILES: O=C(NCC(O)C(F)(F)F)c1cc(NC(=O)C2C(c3cc(Cl)cc(Cl)c3)C2(Cl)Cl)ccc1Cl] | 13, 16 |

Prep* means prepare according to Example or Scheme

The following compounds were prepared in like manner to the procedure outlined in Example 2:

trans-2,2-Dichloro-3-(3-chloro-5-(difluoromethyl)phenyl)cyclopropane-1-carboxylic acid (C85)

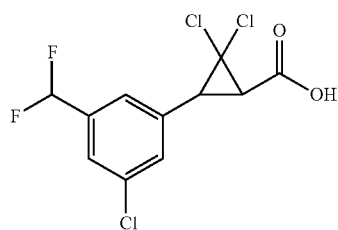

Isolated as an off-white solid (2.6 g, 63%): $^1$H NMR (300 MHz, CDCl$_3$) missing COOH signal δ 7.49 (s, 1H), 7.38 (s, 1H), 7.30 (s, 1H), 6.63 (t, J=56.0 Hz, 1H), 3.50 (d, J=8.4 Hz, 1H), 2.91 (d, J=8.0 Hz, 1H); $^{19}$F NMR (282 MHz, CDCl$_3$) δ −112.04; ESIMS m/z 313 ([M−H]$^-$).

trans-2,2-Dichloro-3-(4-chloro-3-(difluoromethyl)phenyl)cyclopropane-1-carboxylic acid (C86)

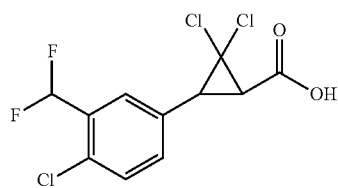

Isolated as an off-white solid (6.2 g, 69%): $^1$H NMR (400 MHz, CDCl$_3$) δ 10.5 (br s, 1H), 7.55 (s, 1H), 7.46 (d, J=8.0 Hz, 1H), 7.34 (d, J=8.4 Hz, 1H), 6.95 (t, J=54.8 Hz, 1H), 3.50 (d, J=8.4 Hz, 1H), 2.91 (d, J=8.4 Hz, 1H); $^{19}$F NMR (376 MHz, CDCl$_3$) δ −115.52; ESIMS m/z 313 ([M−H]$^-$).

trans-2,2-Dichloro-3-(3-(difluoromethyl)-5-fluorophenyl)cyclopropane-1-carboxylic acid (C87)

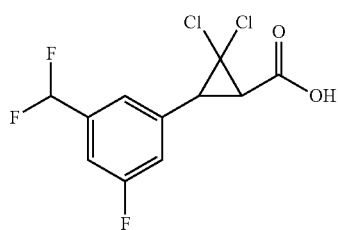 [SMILES: O=C(O)C1C(c2cc(F)cc(C(F)F)c2)C1(Cl)Cl]

Isolated as an off-white solid (5 g, 38%): $^1$H NMR (400 MHz, CDCl$_3$) missing COOH signal δ 7.23-7.21 (m, 2H), 7.11 (d, J=8.8 Hz, 1H), 6.64 (t, J=55.6 Hz, 1H), 3.51 (d, J=8.4 Hz, 1H), 2.91 (d, J=8.0 Hz, 1H); $^{19}$F NMR (376 MHz, CDCl$_3$) δ −110.37; ESIMS m/z 297.19 ([M−H]$^-$).

trans-2,2-Dichloro-3-(3-(difluoromethyl)-4-fluorophenyl)cyclopropane-1-carboxylic acid (C88)

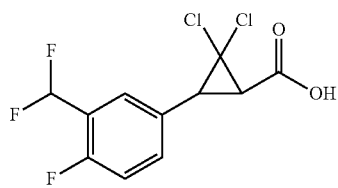 [SMILES: O=C(O)C1C(c2ccc(F)c(C(F)F)c2)C1(Cl)Cl]

Isolated as an off-white solid (6.0 g, 77%): $^1$H NMR (400 MHz, CDCl$_3$) missing COOH signal δ 7.49 (d, J=6.0 Hz, 1H), 7.40 (br s, 1H), 7.17 (t, J=9.2 Hz, 1H), 6.90 (t, J=54.8

Hz, 1H), 3.49 (d, J=8.0 Hz, 1H), 2.89 (d, J=8.4 Hz, 1H); $^{19}$F NMR (376 MHz, CDCl$_3$) δ −114.47, −119.69; ESIMS m/z 297 ([M−H]$^-$).

trans-2,2-Dichloro-3-(3-chloro-4-(difluoromethyl) phenyl)cyclopropane-1-carboxylic acid (C89)

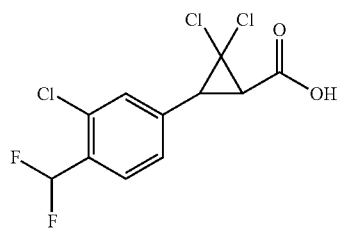 [SMILES: O=C(O)C1C(c2ccc(C(F)F)c(Cl)c2)C1(Cl)Cl]

Isolated as an off-white solid (3.5 g, 42%): $^1$H NMR (400 MHz, CDCl$_3$) missing COOH signal δ 7.68 (d, J=7.6 Hz, 1H), 7.35 (s, 1H), 7.29 (d, J=8.4 Hz, 1H), 6.94 (t, J=54.8 Hz, 1H), 3.48 (d, J=8.4 Hz, 1H), 2.91 (d, J=8.4 Hz, 1H); $^{19}$F NMR (376 MHz, CDCl$_3$) δ −115.46; ESIMS m/z 313 ([M−H]$^-$).

trans-2,2-Dichloro-3-(4-(difluoromethyl)-3-fluorophenyl)cyclopropane-1-carboxylic acid (C90)

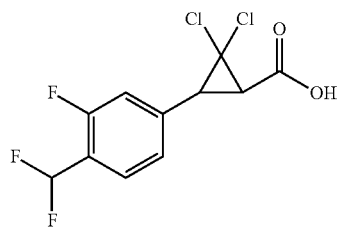

Isolated as an off-white solid (4.4 g, 77%): $^1$H NMR (400 MHz, CDCl$_3$) δ 7.62 (t, J=7.6 Hz, 1H), 7.18 (d, J=7.6 Hz, 1H), 7.06 (d, J=10.0 Hz, 1H), 6.89 (t, J=54.8 Hz, 1H), 3.50 (d, J=8.4 Hz, 1H), 2.90 (d, J=8.4 Hz, 1H); $^{19}$F NMR (376 MHz, CDCl$_3$) δ −114.42, −118.63; ESIMS m/z 297.15 ([M−H]$^-$).

trans-2,2-Dichloro-3-(3-(difluoromethyl)phenyl) cyclopropane-1-carboxylic acid (C91)

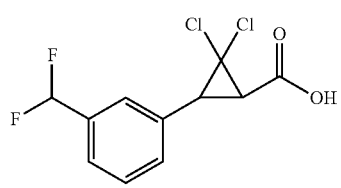

Isolated as an off-white solid (6.2 g, 53%): $^1$H NMR (300 MHz, CDCl$_3$) δ 7.49 (br s, 2H), 7.41 (br s, 2H), 6.66 (t, J=56.0 Hz, 1H), 3.53 (d, J=8.4 Hz, 1H), 2.92 (d, J=8.0 Hz, 1H); $^{19}$F NMR (282 MHz, CDCl$_3$) δ −111.20; ESIMS m/z 279.20 ([M−H]$^-$).

trans-2,2-Dichloro-3-(4-(difluoromethyl)phenyl) cyclopropane-1-carboxylic acid (C92)

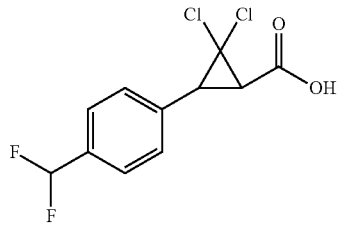 [SMILES: O=C(O)C1C(c2ccc(C(F)F)cc2)C1(Cl)Cl]

Isolated as an off-white solid (7 g, 61%): $^1$H NMR (300 MHz, CDCl$_3$) δ 7.53 (d, J=8.0 Hz, 2H), 7.37 (d, J=8.0 Hz, 2H), 6.66 (t, J=56.4 Hz, 1H), 3.52 (d, J=8.4 Hz, 1H), 2.92 (d, J=8.0 Hz, 1H); $^{19}$F NMR (282 MHz, CDCl$_3$) δ −112.20; ESIMS m/z 279.30 ([M−H]$^-$).

trans-2,2-Dichloro-3-(3,5-difluoro-4-methoxyphenyl)cyclopropane-1-carboxylic acid (C93)

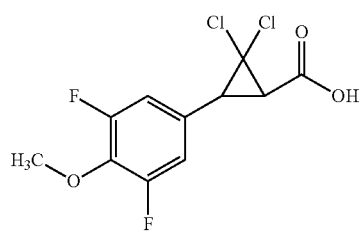 [SMILES: COc1c(F)cc(C2C(C(=O)O)C2(Cl)Cl)cc1F]

Isolated as a tan solid (0.440 g, 53%): $^1$H NMR (400 MHz, CDCl$_3$) δ 10.72 (s, 1H), 6.89-6.77 (m, 2H), 4.02 (t, J=1.2 Hz, 3H), 3.39 (d, J=8.3 Hz, 1H), 2.80 (d, J=8.3 Hz, 1H); $^{19}$F NMR (376 MHz, CDCl$_3$) δ −127.43, −127.43, −127.44; ESIMS m/z 296 ([M−H]$^-$).

cis/trans-2,2-Dichloro-3-(3,4,5-trifluorophenyl)cyclopropane-1-carboxylic acid (C94)

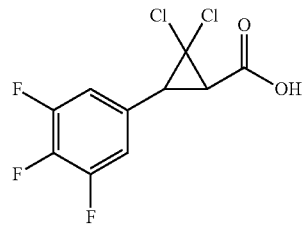 [SMILES: O=C(O)C1C(c2cc(F)c(F)c(F)c2)C1(Cl)Cl]

Isolated as a white solid (0.411 g, 53%): $^1$H NMR (400 MHz, CDCl$_3$) δ 7.72 (s, 1H), 7.06-6.74 (m, 2H), 3.46-3.23 (m, 1H), 3.01-2.74 (m, 1H); $^{19}$F NMR (376 MHz, CDCl$_3$) δ −132.88, −132.94, −133.81, −133.87, −159.60, −159.65, −159.71, −160.34, −160.39, −160.45; ESIMS m/z 284 ([M−H]$^-$).

The following compounds were prepared in like manner to the procedure outlined in Example 4:

101 trans-1-Chloro-3-(2,2-dichloro-3-(4-methoxyphenyl)cyclopropyl)-5-(difluoromethyl)benzene (C95)

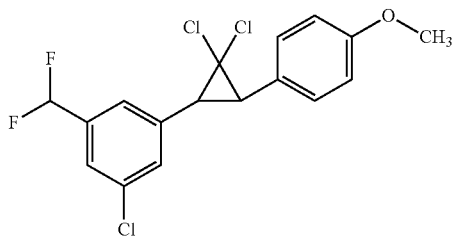 [SMILES: COc1ccc(C2C(c3cc(Cl)cc(C(F)F)c3)C2(Cl)Cl)cc1]

Isolated as a yellow liquid (11.5 g, 69%): $^1$H NMR (300 MHz, CDCl$_3$): δ 7.47 (s, 2H), 7.39 (s, 1H), 7.28 (d, J=8.7 Hz, 2H), 6.93 (d, J=8.7 Hz, 2H), 6.64 (t, J=56.1 Hz, 1H), 3.83 (s, 3H), 3.16 (q, J=8.7 Hz, 2H).

trans-1-Chloro-4-(2,2-dichloro-3-(4-methoxyphenyl)cyclopropyl)-2-(difluoromethyl)benzene (C96)

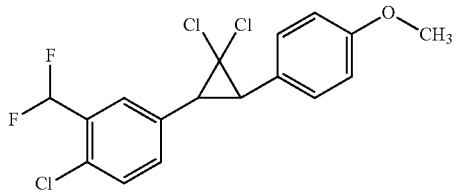 [SMILES: COc1ccc(C2C(c3ccc(Cl)c(C(F)F)c3)C2(Cl)Cl)cc1]

Isolated as a pale yellow solid (10.7 g, 83%): $^1$H NMR (400 MHz, CDCl$_3$) δ 7.65 (s, 1H), 7.46-7.41 (m, 2H), 7.28 (d, J=8.4 Hz, 2H), 7.10-6.83 (m, 3H), 3.83 (s, 3H), 3.18-3.13 (m, 2H).

trans-1-(2,2-Dichloro-3-(4-methoxyphenyl)cyclopropyl)-3-(difluoromethyl)-5-fluorobenzene (C97)

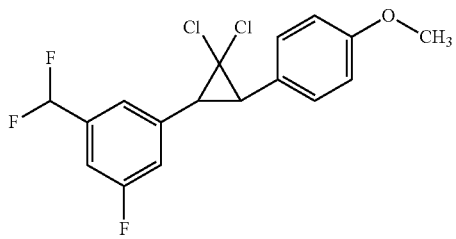 [SMILES: COc1ccc(C2C(c3cc(F)cc(C(F)F)c3)C2(Cl)Cl)cc1]

Isolated as an off-white solid (16.5 g, 64%): $^1$H NMR (400 MHz, CDCl$_3$) δ 7.29 (d, J=8.8 Hz, 2H), 7.20 (d, J=8.8 Hz, 2H), 6.93 (d, J=8.8 Hz, 2H), 6.65 (t, J=56.0 Hz, 2H), 3.83 (s, 3H), 3.16 (s, 2H).

102 trans-4-(2,2-Dichloro-3-(4-methoxyphenyl)cyclopropyl)-2-(difluoromethyl)-1-fluorobenzene (C98)

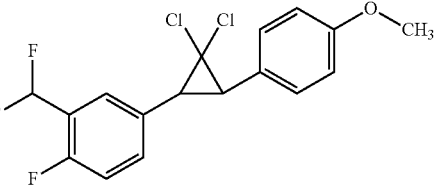

Isolated as an off-white solid (10.0 g, 55%): ESIMS m/z 374 ([M+H]$^+$).

trans-2-Chloro-4-(2,2-dichloro-3-(4-methoxyphenyl)cyclopropyl)-1-(difluoromethyl)benzene (C99)

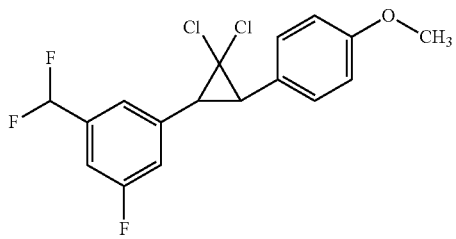 [SMILES: COc1ccc(C2C(c3cc(F)cc(C(F)F)c3)C2(Cl)Cl)cc1]

Isolated as an off-white solid (10.0 g, 34%): $^1$H NMR (400 MHz, CDCl$_3$) δ 7.68 (d, J=8.0 Hz, 1H), 7.43 (s, 1H), 7.38 (d, J=8.4 Hz, 1H), 7.28-7.25 (m, 2H), 7.09-6.92 (m, 3H), 3.83 (s, 3H), 3.15 (q, J=12.0 Hz, 2H); ESIMS m/z 376 ([M+H]$^+$).

trans-2-Fluoro-4-(2,2-dichloro-3-(4-methoxyphenyl)cyclopropyl)-1-(difluoromethyl) benzene (C100)

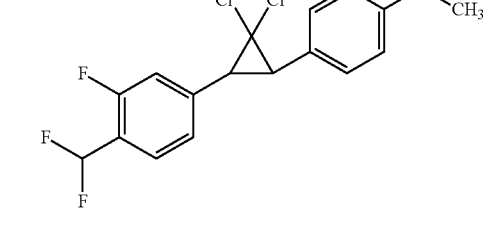

Isolated as a pale yellow liquid (6.9 g, 58%): $^1$H NMR (400 MHz, CDCl$_3$) δ 7.31 (t, J=7.6 Hz, 1H), 7.27 (d, J=9.2 Hz, 2H), 7.14 (d, J=10.8 Hz, 1H), 7.04-6.76 (m, 4H), 3.83 (s, 3H), 3.16 (t, J=8.8 Hz, 2H); $^{19}$F NMR (376 MHz, CDCl$_3$) δ −114.14, −114.32, −119.30.

trans-1-(2,2-Dichloro-3-(4-methoxyphenyl)cyclopropyl)-3-(difluoromethyl) benzene (C101)

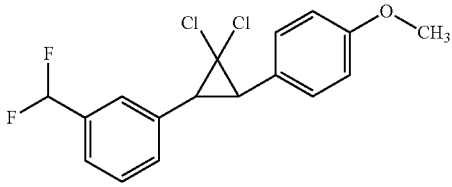 [SMILES: COc1ccc(C2C(c3cccc(C(F)F)c3)C2(Cl)Cl)cc1]

Isolated as a pale yellow solid (6.3 g, 95%): $^1$H NMR (400 MHz, CDCl$_3$) δ 7.50 (br s, 4H), 7.29 (d, J=8.8 Hz, 2H), 6.93 (d, J=8.0 Hz, 2H), 6.67 (t, 1H), 3.83 (s, 3H), 3.19 (s, 2H); $^{19}$F NMR (376 MHz, CDCl$_3$) δ −110.87, −111.02.

trans-1-(2,2-Dichloro-3-(4-(difluoromethyl)phenyl) cyclopropyl)-4-methoxybenzene (C102)

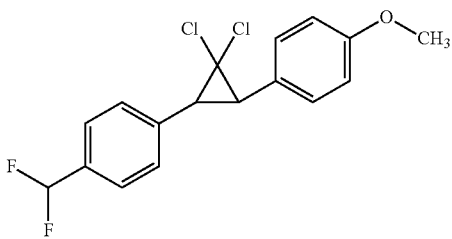 [SMILES: COc1ccc(C2C(c3ccc(C(F)F)cc3)C2(Cl)Cl)cc1]

Isolated as a white solid (14 g, 69%): $^1$H NMR (400 MHz, CDCl$_3$) δ 7.54 (d, J=8.0 Hz, 2H), 7.46 (d, J=8.0 Hz, 2H), 7.28 (t, J=8.4 Hz, 2H), 6.93 (d, J=8.0 Hz, 2H), 6.67 (t, J=56.8 Hz, 1H), 3.83 (s, 3H), 3.18 (s, 2H).

The following compounds were prepared in like manner to the procedure outlined in Example 12:

trans-2-Chloro-5-(2,2-dichloro-3-(3,5-dichloro-4-methoxyphenyl)cyclopropane-1-carboxamido)benzoic acid (C103)

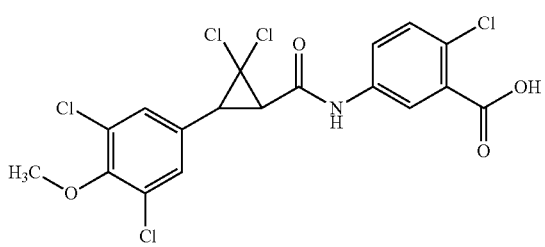 [SMILES: COc1c(Cl)cc(C2C(C(=O)Nc3ccc(Cl)c(C(=O)O)c3)C2(Cl)Cl)cc1Cl]

Isolated as a cream-colored solid (1.565 g, 90%): mp 227-231° C.; $^1$H NMR (400 MHz, DMSO-d$_6$) δ 13.48 (s, 1H), 10.89 (s, 1H), 8.16 (d, J=2.4 Hz, 1H), 7.78 (dd, J=8.7, 2.4 Hz, 1H), 7.61 (s, 2H), 7.53 (d, J=8.7 Hz, 1H), 3.84 (s, 3H), 3.57 (d, J=8.4 Hz, 1H), 3.45 (d, J=8.5 Hz, 1H); $^{13}$C NMR (101 MHz, DMSO-d$_6$) δ 166.27, 162.66, 151.18, 137.58, 131.44, 131.42, 131.22, 129.72, 128.18, 125.90, 122.87, 121.16, 62.19, 60.64, 38.51, 36.44; HRMS-ESI (m/z) [M+]$^+$calcd for C$_{18}$H$_{12}$Cl$_5$NO$_4$, 480.9209; found, 480.9216.

trans-2-Chloro-5-(2,2-dichloro-3-(3-chloro-4-fluorophenyl)cyclopropane-1-carboxamido)benzoic acid (C104)

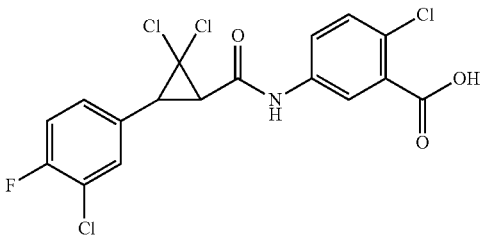 [SMILES: O=C(O)c1cc(NC(=O)C2C(c3ccc(F)c(Cl)c3)C2(Cl)Cl)ccc1Cl]

Isolated as a white solid (6.589 g, 93%): mp 207-210° C.; $^1$H NMR (400 MHz, DMSO-d$_6$) δ 13.50 (s, 1H), 10.95 (s, 1H), 8.18 (d, J=2.5 Hz, 1H), 7.80 (dd, J=8.7, 2.5 Hz, 1H), 7.71 (d, J=7.2 Hz, 1H), 7.51 (dd, J=28.2, 8.8 Hz, 3H), 3.59 (d, J=8.4 Hz, 1H), 3.43 (d, J=8.5 Hz, 1H); $^{13}$C NMR (101 MHz, DMSO-d$_6$) δ 166.22, 162.68, 158.01, 155.55, 137.53, 131.37, 131.17, 131.00, 130.95, 130.91, 129.74, 129.67, 125.86, 122.82, 121.12, 119.49, 119.32, 116.91, 116.70, 62.21, 38.49, 36.58; $^{19}$F NMR (376 MHz, DMSO-d$_6$) δ −117.26; ESIMS m/z 438 ([M+H]$^+$).

trans-2,3-Dichloro-5-(2,2-dichloro-3-(3,5-dichlorophenyl)cyclopropane-1-carboxamido)benzoic acid (C105)

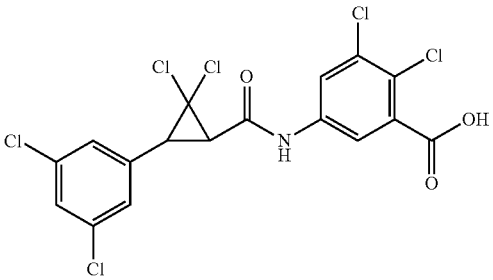 [SMILES: O=C(O)c1cc(NC(=O)C2C(c3cc(Cl)cc(Cl)c3)C2(Cl)Cl)cc(Cl)c1Cl]

Isolated as a tan solid (1.685 g, 79%): mp 231-235° C.; $^1$H NMR (400 MHz, DMSO-d$_6$) 13.82 (s, 1H), 11.05 (s, 1H), 8.13 (d, J=2.4 Hz, 1H), 7.97 (d, J=2.4 Hz, 1H), 7.63 (s, 1H), 7.56 (s, 2H), 3.63 (d, J=8.5 Hz, 1H), 3.50 (d, J=8.5 Hz, 1H); $^{13}$C NMR (101 MHz, DMSO-d$_6$) δ 165.84, 162.96, 138.00, 137.09, 134.14, 133.98, 133.01, 127.83, 127.64, 123.41, 122.15, 119.27, 61.94, 38.37, 36.78; HRMS-ESI (m/z) [M+]$^+$ calcd for C$_{17}$H$_9$Cl$_6$NO$_3$, 484.8714; found, 484.8711.

trans-2,4-Dichloro-5-(2,2-dichloro-3-(3,5-dichlorophenyl)cyclopropane-1-carboxamido)benzoic acid (C106)

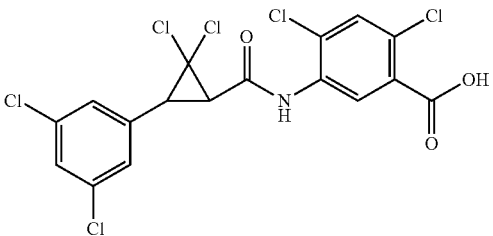 [SMILES: O=C(O)c1cc(NC(=O)C2C(c3cc(Cl)cc(Cl)c3)C2(Cl)Cl)c(Cl)cc1Cl]

Isolated as a light-yellow solid (0.855 g, 42%): mp 263-266° C.; $^1$H NMR (500 MHz, DMSO-$d_6$) δ 13.67 (s, 1H), 10.37 (s, 1H), 8.37 (s, 1H), 7.85 (s, 1H), 7.63 (s, 1H), 7.53 (d, J=1.6 Hz, 2H), 3.82 (d, J=8.6 Hz, 1H), 3.63 (d, J=8.5 Hz, 1H); $^{13}$C NMR (126 MHz, DMSO-$d_6$) δ 165.41, 163.35, 137.17, 133.95, 133.66, 131.17, 129.96, 128.80, 128.24, 127.74, 127.60, 126.63, 62.37, 37.24, 37.09; HRMS-ESI (m/z) [M+]$^+$ calcd for $C_{17}H_9Cl_6NO_3$, 484.8714; found, 484.8715.

The following compounds were prepared in like manner to the procedure outlined in Example 13:

trans-2-Chloro-5-(2,2-dibromo-3-(3,5-dichlorophenyl)cyclopropane-1-carboxamido)-N-(2,2,2-trifluoroethyl)benzamide (PF1)

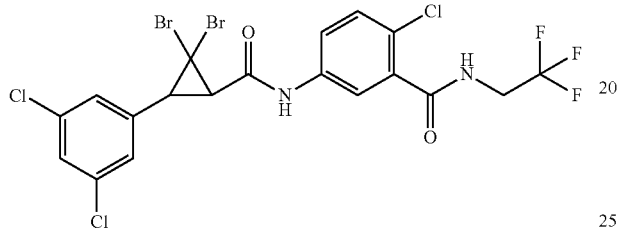

Isolated as a white solid (0.100 g, 32%) The following compounds were prepared in like manner to the procedure outlined in Example 15:

2-Chloro-5-(trans-2,2-dichloro-3-(3,5-dichlorophenyl)cyclopropane-1-carboxamido)-N-(2-(4-fluorophenyl)propan-2-yl)benzamide (F97)

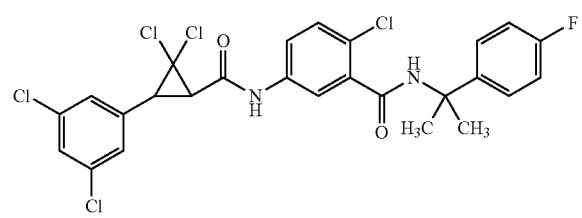 [SMILES: CC(C)(NC(=O)c1cc(NC(=O)C2C(c3cc(Cl)cc(Cl)c3)C2(Cl)Cl)ccc1Cl)c1ccc(F)cc1]

Isolated as a white foam (0.086 g, 63%).

The following compounds were prepared in like manner to the procedure outlined in Example 16:

trans-2-Chloro-5-(2,2-dichloro-3-(3,5-dichlorophenyl)cyclopropane-1-carboxamido)-N—((R)-1-((3,3,3-trifluoropropyl)thio)propan-2-yl)benzamide (PF2)

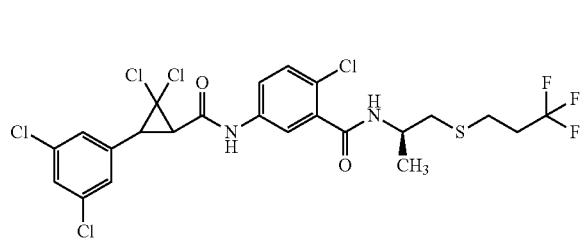 [SMILES: C[C@H](CSCCC(F)(F)F)NC(=O)c1cc(NC(=O)C2C(c3cc(Cl)cc(Cl)c3)C2(Cl)Cl)ccc1Cl]

Isolated as a white solid (0.311 mg, 91%).

trans-2-Chloro-5-(2,2-dichloro-3-(3,5-dichlorophenyl)cyclopropane-1-carboxamido)-N—((R)-1-((2,2,2-trifluoroethyl)thio)propan-2-yl)benzamide (PF3)

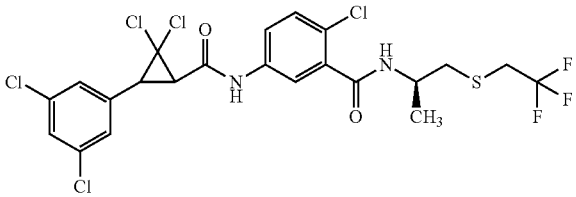 [SMILES: C[C@H](CSCC(F)(F)F)NC(=O)c1cc(NC(=O)C2C(c3cc(Cl)cc(Cl)c3)C2(Cl)Cl)ccc1Cl]

Isolated as a white solid (0.306 g, 91%).

trans-2-Chloro-5-(2,2-dichloro-3-(3,5-dichlorophenyl)cyclopropane-1-carboxamido)-N-(2-((furan-2-ylmethyl)thio)ethyl)benzamide (PF9)

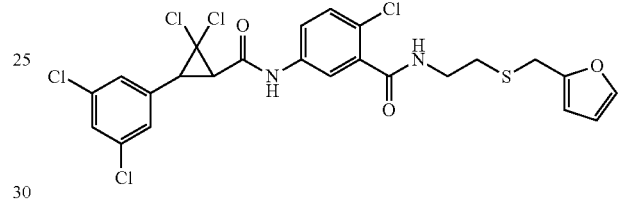

Isolated as a tan solid (0.064 g, 65%).

trans-Methyl-2-(2-chloro-5-(2,2-dichloro-3-(3,5-dichlorophenyl)cyclopropane-1-carboxamido)benzamido)-4-(methylthio)butanoate (PF10)

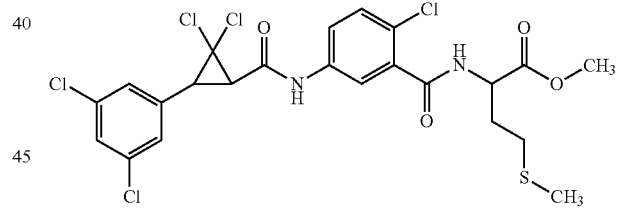

Isolated as a light green solid (0.052 g, 52%).

trans-N-(4-(1H-1,2,4-Triazol-1-yl)benzyl)-2-chloro-5-(2,2-dichloro-3-(3,5-dichlorophenyl)cyclopropane-1-carboxamido)benzamide (PF11)

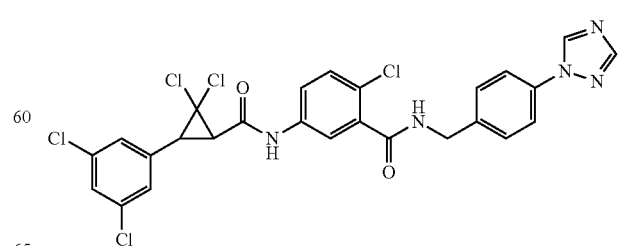

Isolated as a tan solid (0.077 g, 76%).

107 trans-2-Chloro-5-(2,2-dichloro-3-(3,5-dichlorophenyl)cyclopropane-1-carboxamido)-N-(2-(thiazol-2-yl)ethyl)benzamide (PF12)

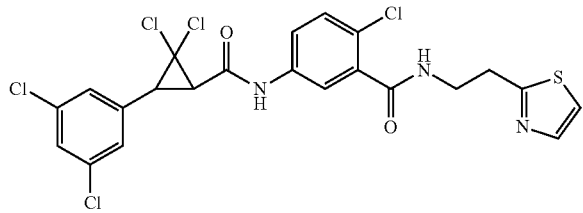 [SMILES: O=C(NCCc1nccs1)c1cc(NC(=O)C2C(c3cc(Cl)cc(Cl)c3)C2(Cl)Cl)ccc1Cl]

Isolated as a white solid (0.032 g, 34%).

trans-N-(2-(1H-Pyrazol-1-yl)ethyl)-2-chloro-5-(2,2-dichloro-3-(3,5-dichlorophenyl)cyclopropane-1-carboxamido)benzamide (PF13)

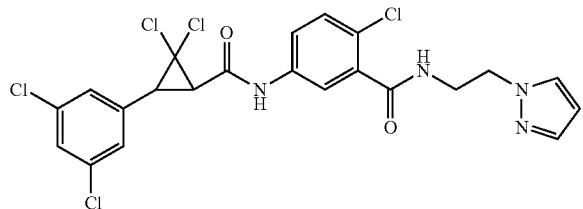 [SMILES: O=C(NCCn1cccn1)c1cc(NC(=O)C2C(c3cc(Cl)cc(Cl)c3)C2(Cl)Cl)ccc1Cl]

Isolated as a white solid (0.061 g, 68%).

trans-2-Chloro-5-(2,2-dichloro-3-(3,5-dichlorophenyl)cyclopropane-1-carboxamido)-N-(3-sulfamoylpropyl)benzamide (PF14)

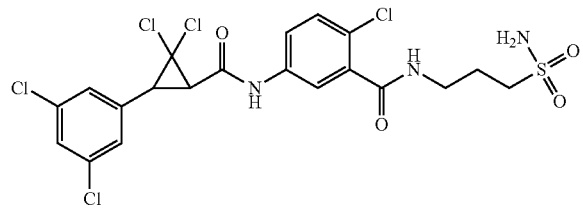 [SMILES: NS(=O)(=O)CCCNC(=O)c1cc(NC(=O)C2C(c3cc(Cl)cc(Cl)c3)C2(Cl)Cl)ccc1Cl]

Isolated as a white solid (0.023 g, 24%).

trans-N-(2-(Benzo[b]thiophen-3-yl)ethyl)-2-chloro-5-(2,2-dichloro-3-(3,5-dichlorophenyl)cyclopropane-1-carboxamido)benzamide (PF15)

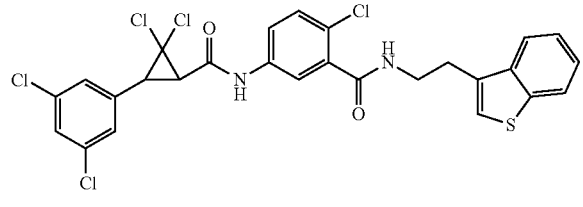 [SMILES: O=C(NCCc1csc2ccccc12)c1cc(NC(=O)C2C(c3cc(Cl)cc(Cl)c3)C2(Cl)Cl)ccc1Cl]

Isolated as a tan solid (0.064 g, 63%).

108 trans-2-Chloro-5-(2,2-dichloro-3-(3,5-dichlorophenyl)cyclopropane-1-carboxamido)-N-(3,3,3-trifluoro-2-hydroxypropyl)benzamide (PF16)

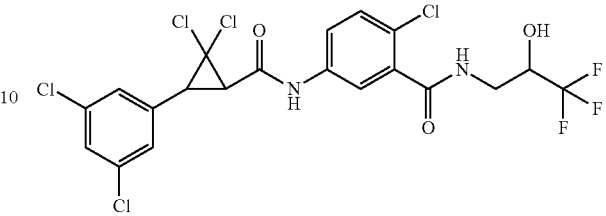

Isolated as a white solid (0.055 g, 59%).

trans-2-Chloro-5-(2,2-dichloro-3-(3,5-dichlorophenyl)cyclopropane-1-carboxamido)-N-(2-hydroxypropyl)benzamide (F78)

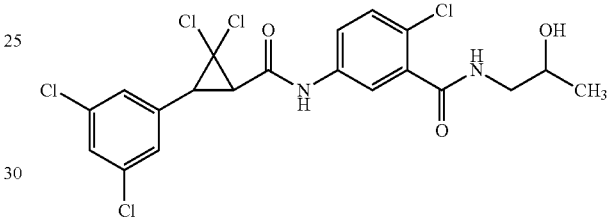

Isolated as a white solid (0.036 g, 43%).

trans-2-Chloro-5-(2,2-dichloro-3-(3,5-dichlorophenyl)cyclopropane-1-carboxamido)-N-(2-(2-oxoimidazolidin-1-yl)ethyl)benzamide (F79)

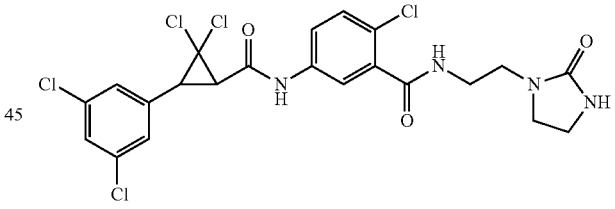

Isolated as a white solid (0.038 g, 41%).

trans-2-Chloro-5-(2,2-dichloro-3-(3,5-dichloro-4-methoxyphenyl)cyclopropane-1-carboxamido)-N-propylbenzamide (F84)

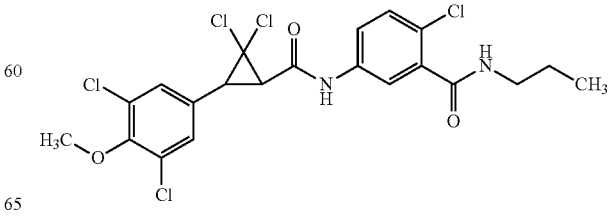

Isolated as a white solid (0.125 g, 92%).

trans-2-Chloro-5-(2,2-dichloro-3-(3,5-dichloro-4-methoxyphenyl)cyclopropane-1-carboxamido)-N-ethylbenzamide (F85)

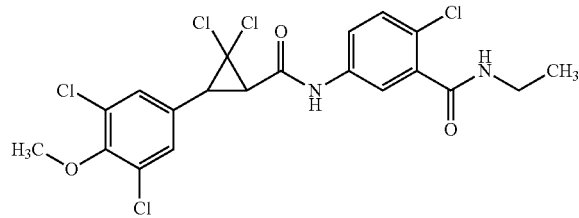 [SMILES: CCNC(=O)c1cc(NC(=O)C2C(c3cc(Cl)c(OC)c(Cl)c3)C2(Cl)Cl)ccc1Cl]

Isolated as a white solid (0.126 g, 95%).

trans-2-Chloro-5-(2,2-dichloro-3-(3,5-dichloro-4-methoxyphenyl)cyclopropane-1-carboxamido)-N-(2-fluoroethyl)benzamide (F86)

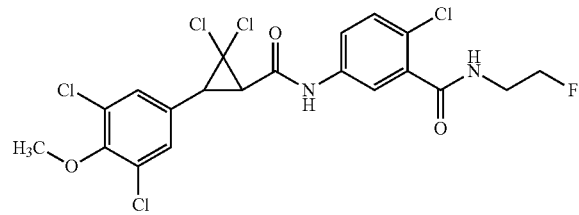 [SMILES: COc1c(Cl)cc(C2C(C(=O)Nc3ccc(Cl)c(C(=O)NCCF)c3)C2(Cl)Cl)cc1Cl]

Isolated as a white solid (0.119 g, 87%).

trans-2-Chloro-5-(2,2-dichloro-3-(3,5-dichloro-4-methoxyphenyl)cyclopropane-1-carboxamido)-N-(2,2,2-trifluoroethyl)benzamide (F87)

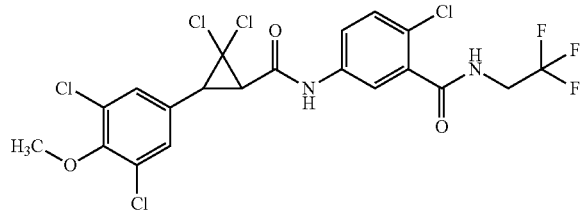 [SMILES: COc1c(Cl)cc(C2C(C(=O)Nc3ccc(Cl)c(C(=O)NCC(F)(F)F)c3)C2(Cl)Cl)cc1Cl]

Isolated as a white solid (0.128 g, 88%).

trans-2-Chloro-5-(2,2-dichloro-3-(3,5-dichloro-4-methoxyphenyl)cyclopropane-1-carboxamido)-N-(3,3,3-trifluoropropyl)benzamide (F88)

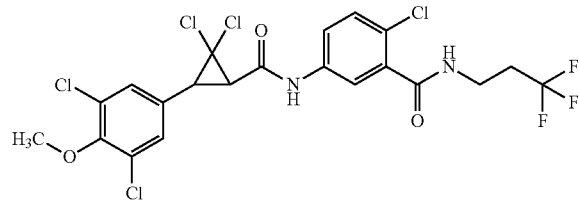 [SMILES: COc1c(Cl)cc(C2C(C(=O)Nc3ccc(Cl)c(C(=O)NCCC(F)(F)F)c3)C2(Cl)Cl)cc1Cl]

Isolated as a white solid (0.138 g, 92%).

trans-2,3-Dichloro-5-(2,2-dichloro-3-(3,5-dichlorophenyl)cyclopropane-1-carboxamido)-N-ethylbenzamide (F91)

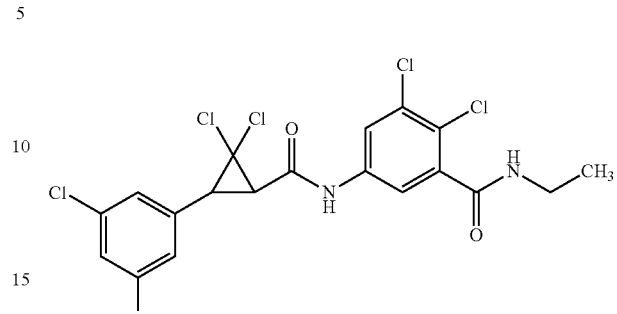

Isolated as a white solid (0.038 g, 43%).

trans-2,3-Dichloro-5-(2,2-dichloro-3-(3,5-dichlorophenyl)cyclopropane-1-carboxamido)-N-(2-fluoroethyl)benzamide (F92)

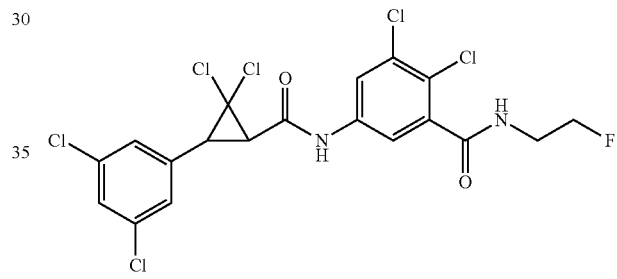

Isolated as a white solid (0.037 g, 40%).

trans-2,3-Dichloro-5-(2,2-dichloro-3-(3,5-dichlorophenyl)cyclopropane-1-carboxamido)-N-(2,2,2-trifluoroethyl)benzamide (F93)

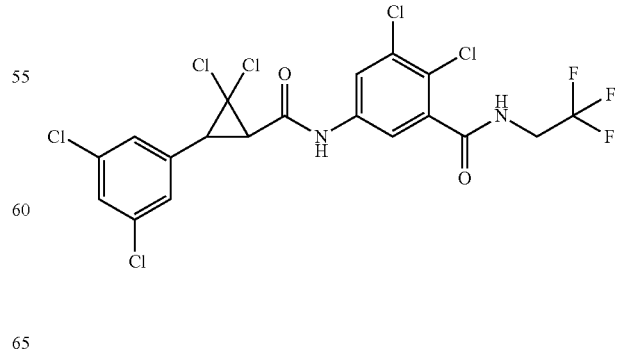

Isolated as a white solid (0.013 g, 13%).

111 trans-2,3-Dichloro-5-(2,2-dichloro-3-(3,5-dichlorophenyl)cyclopropane-1-carboxamido)-N-(3,3,3-trifluoropropyl)benzamide (F94)

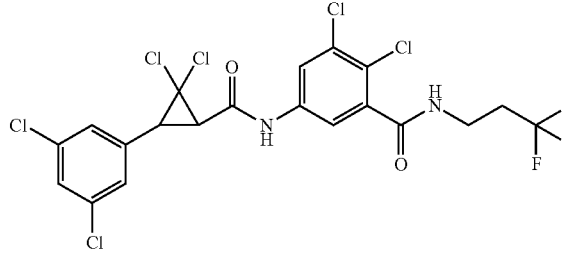 [SMILES: CCCNC(=O)c1cc(NC(=O)C2C(c3cc(Cl)cc(Cl)c3)C2(Cl)Cl)cc(Cl)c1Cl]

Isolated as a white solid (0.046 g, 46%).

trans-2,3-Dichloro-5-(2,2-dichloro-3-(3,5-dichlorophenyl)cyclopropane-1-carboxamido)-N-propylbenzamide (F95)

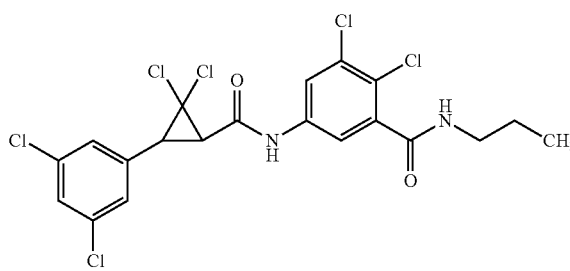

Isolated as a white solid (0.061 g, 68%).

trans-2,4-Dichloro-5-(2,2-dichloro-3-(3,5-dichlorophenyl)cyclopropane-1-carboxamido)-N-ethylbenzamide (F98)

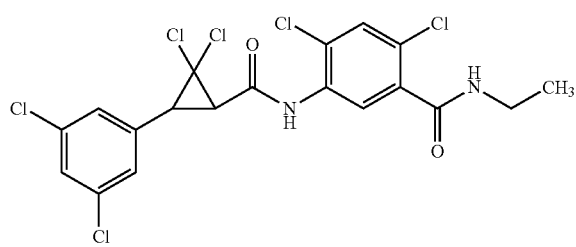 [SMILES: CCNC(=O)c1cc(NC(=O)C2C(c3cc(Cl)cc(Cl)c3)C2(Cl)Cl)c(Cl)cc1Cl]

Isolated as a white solid (0.052 g, 57%).

112 trans-2,4-Dichloro-5-(2,2-dichloro-3-(3,5-dichlorophenyl)cyclopropane-1-carboxamido)-N-(2-fluoroethyl)benzamide (F99)

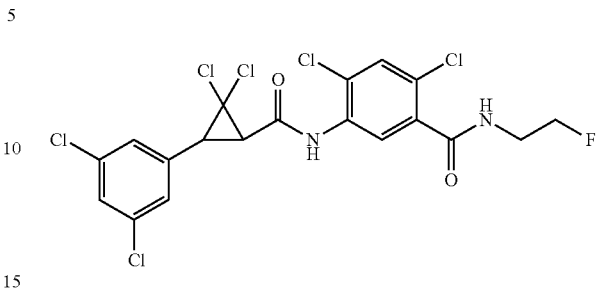

Isolated as a white solid (0.047 g, 51%).

trans-2,4-Dichloro-5-(2,2-dichloro-3-(3,5-dichlorophenyl)cyclopropane-1-carboxamido)-N-(2,2,2-trifluoroethyl)benzamide (F100)

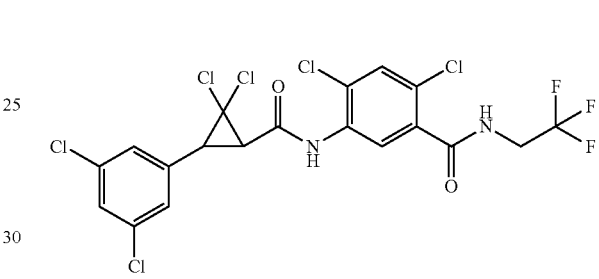

Isolated as a white solid (0.041 g, 43%).

trans-2,4-Dichloro-5-(2,2-dichloro-3-(3,5-dichlorophenyl)cyclopropane-1-carboxamido)-N-propylbenzamide (F101)

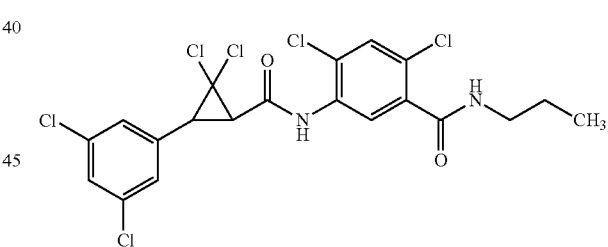

Isolated as a white solid (0.037 g, 40%).

trans-2,4-Dichloro-5-(2,2-dichloro-3-(3,5-dichlorophenyl)cyclopropane-1-carboxamido)-N-(3,3,3-trifluoropropyl)benzamide (F102)

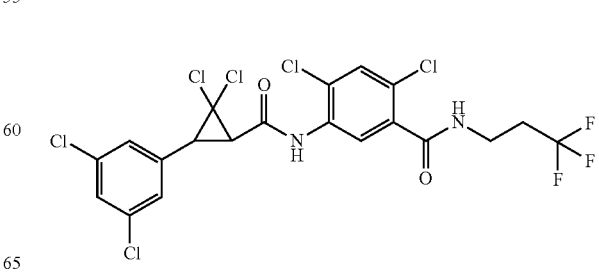

Isolated as a white solid (0.046 g, 48%).

113 trans-2-Chloro-5-(2,2-dichloro-3-(3-chloro-4-fluoro-phenyl)cyclopropane-1-carboxamido)-N-ethylbenzamide (F103)

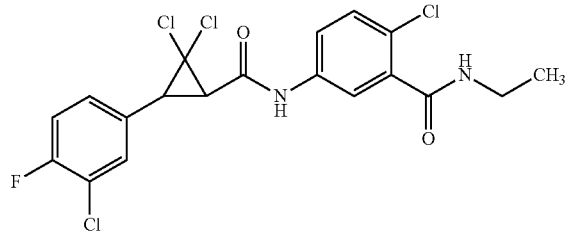 [SMILES: CCNC(=O)c1cc(NC(=O)C2C(c3ccc(F)c(Cl)c3)C2(Cl)Cl)ccc1Cl]

Isolated as a white solid (0.061 g, 68%).

trans-2-Chloro-5-(2,2-dichloro-3-(3-chloro-4-fluoro-phenyl)cyclopropane-1-carboxamido)-N-(2-fluoroethyl)benzamide (F104)

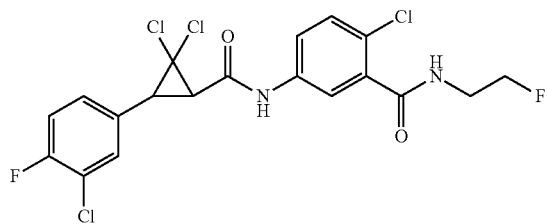 [SMILES: O=C(NCCF)c1cc(NC(=O)C2C(c3ccc(F)c(Cl)c3)C2(Cl)Cl)ccc1Cl]

Isolated as a white solid (0.063 g, 69%).

trans-2-Chloro-5-(2,2-dichloro-3-(3-chloro-4-fluoro-phenyl)cyclopropane-1-carboxamido)-N-(2,2,2-trifluoroethyl)benzamide (F105)

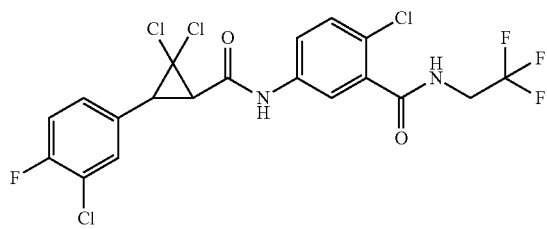 [SMILES: O=C(NCC(F)(F)F)c1cc(NC(=O)C2C(c3ccc(F)c(Cl)c3)C2(Cl)Cl)ccc1Cl]

Isolated as a white solid (0.069 g, 71%).

114 trans-2-Chloro-5-(2,2-dichloro-3-(3-chloro-4-fluoro-phenyl)cyclopropane-1-carboxamido)-N-propylbenzamide (F106)

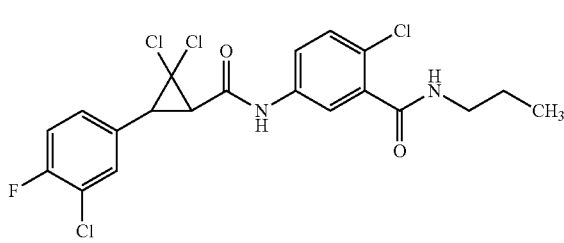 [SMILES: CCCNC(=O)c1cc(NC(=O)C2C(c3ccc(F)c(Cl)c3)C2(Cl)Cl)ccc1Cl]

Isolated as a white solid (0.077 g, 85%).

trans-2-Chloro-5-(2,2-dichloro-3-(3-chloro-4-fluoro-phenyl)cyclopropane-1-carboxamido)-N-(3,3,3-trifluoropropyl)benzamide (F107)

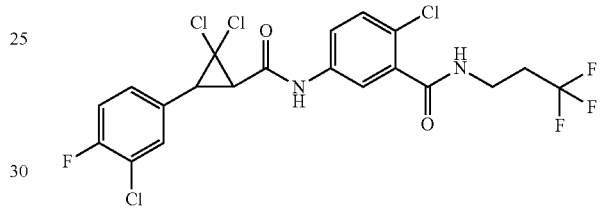

Isolated as a white solid (0.068 mg, 65%).

The following compounds were prepared in like manner to the procedure outlined in Example 17a:

trans-2-Chloro-5-(2,2-dichloro-3-(3,5-dichlorophenyl)cyclopropane-1-carboxamido)-N—((R)-1-((3,3,3-trifluoropropyl)sulfonyl)propan-2-yl)benzamide (PF4)

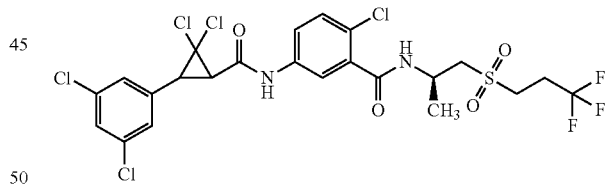

Isolated as a white solid (0.0137 g, 54%).

trans-2-Chloro-5-(2,2-dichloro-3-(3,5-dichlorophenyl)cyclopropane-1-carboxamido)-N-((2R)-1-((3,3,3-trifluoropropyl)sulfinyl)propan-2-yl)benzamide (PF5)

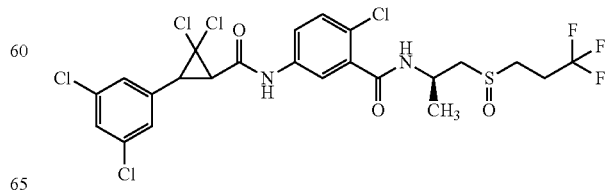

Isolated as a white solid (0.109 g, 44%).

115 trans-2-Chloro-5-(2,2-dichloro-3-(3,5-dichlorophenyl)cyclopropane-1-carboxamido)-N—((R)-1-((2,2,2-trifluoroethyl)sulfonyl)propan-2-yl)benzamide (PF6)

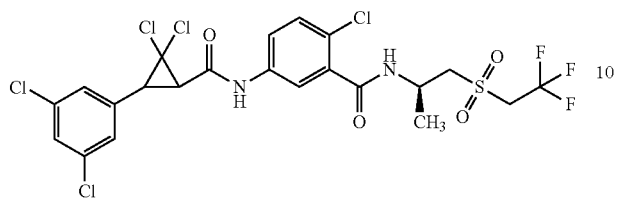

Isolated as a white solid (0.107 g, 45%).

trans-2-Chloro-5-(2,2-dichloro-3-(3,5-dichlorophenyl)cyclopropane-1-carboxamido)-N-((2R)-1-((2,2,2-trifluoroethyl)sulfinyl)propan-2-yl)benzamide (PF7)

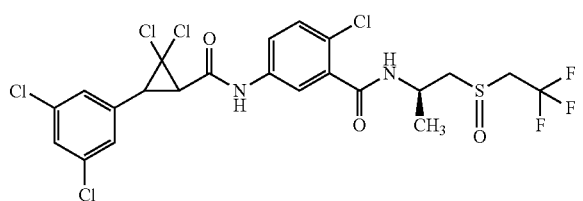 [SMILES: C[C@H](CS(=O)CC(F)(F)F)NC(=O)c1cc(NC(=O)C2C(c3cc(Cl)cc(Cl)c3)C2(Cl)Cl)ccc1Cl]

Isolated as a white solid (0.120 g, 52%).

Example 23

Preparation of 2-chloro-5-(trans-2,2-dichloro-3-(3,5-dichlorophenyl)cyclopropane-1-carboxamido)-N-(1-(4-fluorophenyl)ethyl)benzamide (F96)

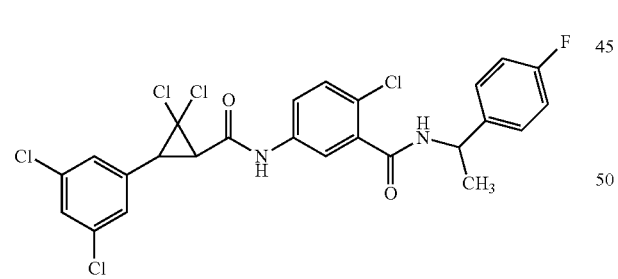

To a solution of trans-2-chloro-5-(2,2-dichloro-3-(3,5-dichlorophenyl)cyclopropane carboxamido)benzoic acid (C67) (0.100 g, 0.220 mmol) and 1-(4-fluorophenyl)ethan-1-amine (0.037 g, 0.220 mmol) in ethyl acetate (3 mL) were added sequentially pyridine (0.054 mL, 0.661 mmol) and 2,4,6-tripropyl-1,3,5,2,4,6-trioxatriphosphorinane-2,4,6-trioxide (50% solution in ethyl acetate, 0.281 g 0.441 mmol), and the resulting pale-yellow solution was stirred at room temperature for approximately 12 hours. The solution was concentrated under a stream of nitrogen, and purified by silica gel flash column chromatography with a mobile phase of hexanes/ethyl acetate. The pure fractions were combined and concentrated under vacuum on a rotary evaporator to provide the title compound as a clear, colorless oil (0.058 g, 44%).

Example 24

Preparation of 2-chloro-5-(trans-2,2-dichloro-3-(3,4-difluorophenyl)cyclopropane-1-carboxamido)-N-(2,2,2-trifluoroethyl)benzamide (F108)

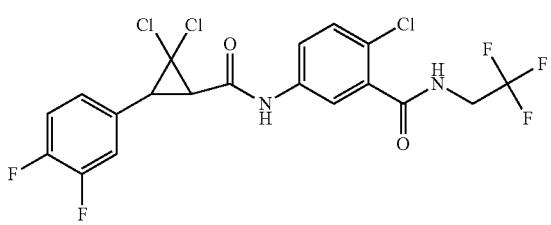 [SMILES: O=C(NCC(F)(F)F)c1cc(NC(=O)C2C(c3ccc(F)c(F)c3)C2(Cl)Cl)ccc1Cl]

To a solution of 5-amino-2-chloro-N-(2,2,2-trifluoroethyl)benzamide (C70) (0.071 g, 0.281 mmol) and trans-2,2-dichloro-3-(3,4-difluorophenyl)cyclopropanecarboxylic acid (C124) (0.075 g, 0.281 mmol) in ethyl acetate (3 mL) were added sequentially pyridine (0.068 mL, 0.843 mmol) and 2,4,6-tripropyl-1,3,5,2,4,6-trioxatriphosphorinane-2,4,6-trioxide (50% solution in ethyl acetate, 0.357 g, 0.562 mmol), and the resulting pale-yellow solution was stirred at room temperature for approximately 14 hours. The solution was concentrated under a stream of nitrogen, and purified by silica gel flash column chromatography with a mobile phase of hexanes/ethyl acetate. The pure fractions were combined and concentrated under vacuum on a rotary evaporator to provide the title compound as a white foam (0.083 g, 56%).

The following compounds were prepared in like manner to the procedure outlined in Example 24:

5-(trans-3-(3-Bromo-4-chlorophenyl)-2,2-dichlorocyclopropane-1-carboxamido)-2-chloro-N-(2,2,2-trifluoroethyl)benzamide (F109)

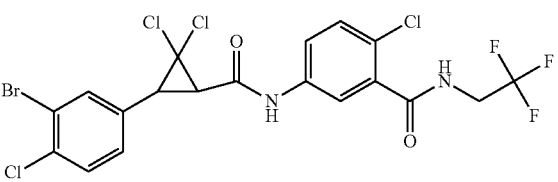

Isolated as a white foam (0.100 g, 75%).

2-Chloro-5-(trans-2,2-dichloro-3-(3,4-dibromophenyl)cyclopropane-1-carboxamido)-N-(2,2,2-trifluoroethyl)benzamide (F111)

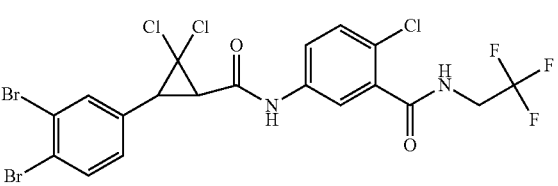 [SMILES: O=C(NCC(F)(F)F)c1cc(NC(=O)C2C(c3ccc(Cl)c(Br)c3)C2(Cl)Cl)ccc1Cl]

Isolated as a white solid (0.090 g, 71%).

117

2-Chloro-5-(trans-2,2-dichloro-3-(3-fluoro-4-(trifluoromethyl)phenyl)cyclopropane-1-carboxamido)-N-(2,2,2-trifluoroethyl)benzamide (F112)

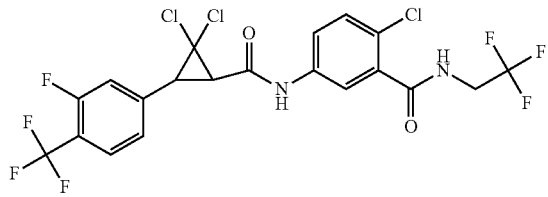 [SMILES: O=C(NCC(F)(F)F)c1cc(NC(=O)C2C(c3ccc(C(F)(F)F)c(F)c3)C2(Cl)Cl)ccc1Cl]

Isolated as a white foam (0.073 g, 53%).

5-(trans-3-(4-Bromo-3-fluorophenyl)-2,2-dichlorocyclopropane-1-carboxamido)-2-chloro-N-(2,2,2-trifluoroethyl)benzamide (F113)

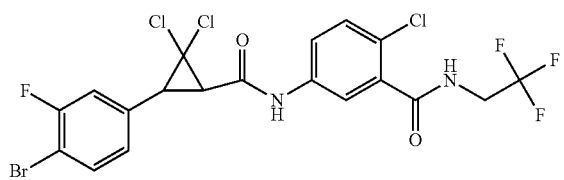

Isolated as a white foam (0.086 g, 64%).

5-(trans-3-(3-Bromo-4-(trifluoromethyl)phenyl)-2,2-dichlorocyclopropane-1-carboxamido)-2-chloro-N-(2,2,2-trifluoroethyl)benzamide (F114)

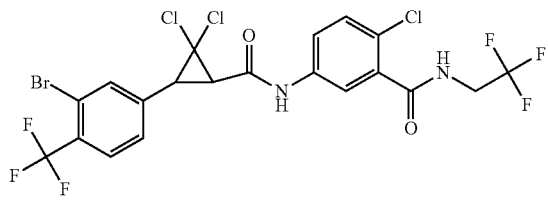

Isolated as a white foam (0.085 g, 66%).

5-(trans-3-(4-Bromo-3-(trifluoromethyl)phenyl)-2,2-dichlorocyclopropane-1-carboxamido)-2-chloro-N-(2,2,2-trifluoroethyl)benzamide (F115)

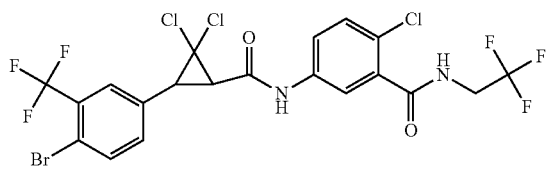 [SMILES: O=C(NCC(F)(F)F)c1cc(NC(=O)C2C(c3ccc(Br)c(C(F)(F)F)c3)C2(Cl)Cl)ccc1Cl]

Isolated as a white foam (0.095 g, 74%).

118

2-Chloro-5-(trans-2,2-dichloro-3-(3-chloro-4-(trifluoromethyl)phenyl)cyclopropane-1-carboxamido)-N-(2,2,2-trifluoroethyl)benzamide (F116)

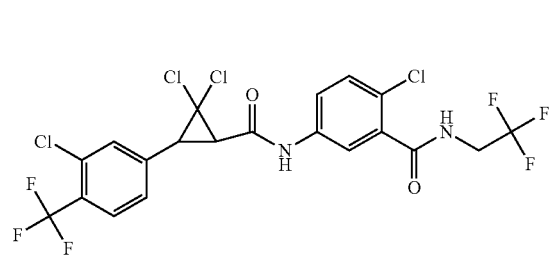 [SMILES: O=C(NCC(F)(F)F)c1cc(NC(=O)C2C(c3ccc(C(F)(F)F)c(Cl)c3)C2(Cl)Cl)ccc1Cl]

Isolated as a white foam (0.081 g, 60%).

2-Chloro-5-(trans-2,2-dichloro-3-(4-chloro-3-(trifluoromethyl)phenyl)cyclopropane-1-carboxamido)-N-(2,2,2-trifluoroethyl)benzamide (F117)

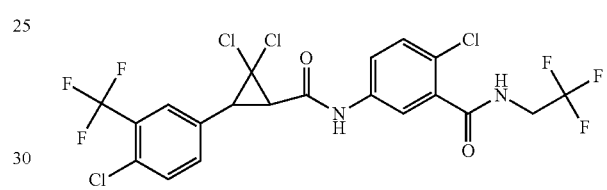

Isolated as a white foam (0.097 g, 72%).

5-(trans-3-(3-Bromo-4-fluorophenyl)-2,2-dichlorocyclopropane-1-carboxamido)-2-chloro-N-(2,2,2-trifluoroethyl)benzamide (F118)

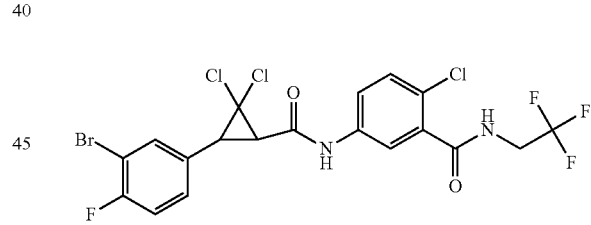

Isolated as a white foam (0.113 g, 83%).

2-Chloro-5-(trans-2,2-dichloro-3-(4-fluoro-3-(trifluoromethyl)phenyl)cyclopropane-1-carboxamido)-N-(2,2,2-trifluoroethyl)benzamide (F119)

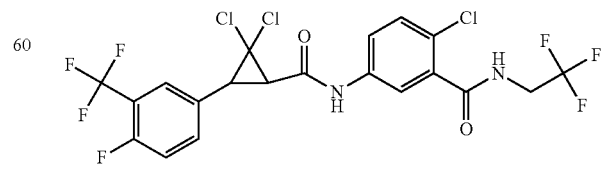

Isolated as a gold foam (0.111 g, 81%).

2-Chloro-5-(trans-2,2-dichloro-3-(4-chloro-3-fluorophenyl)cyclopropane-1-carboxamido)-N-(2,2,2-trifluoroethyl)benzamide (F120)

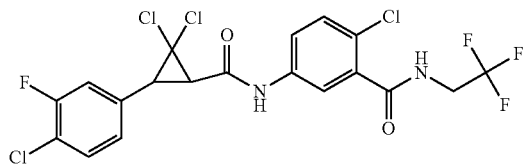 [SMILES: O=C(NCC(F)(F)F)c1cc(NC(=O)C2C(c3ccc(Cl)c(F)c3)C2(Cl)Cl)ccc1Cl]

Isolated as a white foam (0.120 g, 83%).

2-Chloro-5-(trans-2,2-dichloro-3-(3,5-difluorophenyl)cyclopropane-1-carboxamido)-N-(2,2,2-trifluoroethyl)benzamide (F121)

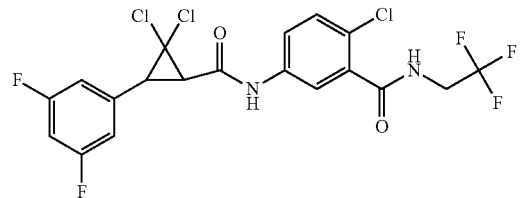 [SMILES: O=C(NCC(F)(F)F)c1cc(NC(=O)C2C(c3cc(F)cc(F)c3)C2(Cl)Cl)ccc1Cl]

Isolated as a white foam (0.058 g, 39%).

2-Chloro-5-(trans-2,2-dichloro-3-(3-fluoro-5-(trifluoromethyl)phenyl)cyclopropane-1-carboxamido)-N-(2,2,2-trifluoroethyl)benzamide (F122)

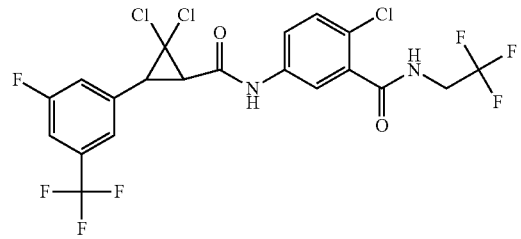 [SMILES: O=C(NCC(F)(F)F)c1cc(NC(=O)C2C(c3cc(F)cc(C(F)(F)F)c3)C2(Cl)Cl)ccc1Cl]

Isolated as a white foam (0.112 g, 82%).

5-(trans-3-(3-Bromo-5-fluorophenyl)-2,2-dichlorocyclopropane-1-carboxamido)-2-chloro-N-(2,2,2-trifluoroethyl)benzamide (F123)

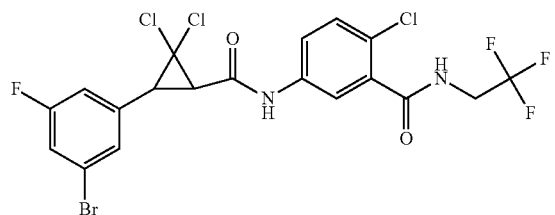 [SMILES: O=C(NCC(F)(F)F)c1cc(NC(=O)C2C(c3cc(F)cc(Br)c3)C2(Cl)Cl)ccc1Cl]

Isolated as a white solid (0.097 g, 72%).

5-(trans-3-(3-Bromo-5-(trifluoromethyl)phenyl)-2,2-dichlorocyclopropane-1-carboxamido)-2-chloro-N-(2,2,2-trifluoroethyl)benzamide (F124)

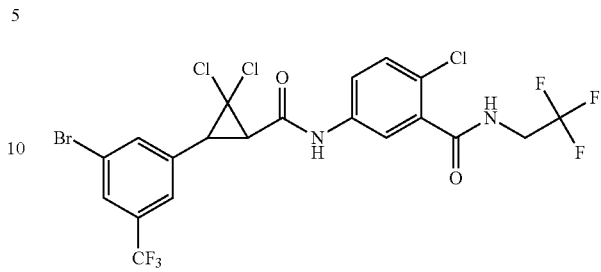

Isolated as a clear colorless oil (0.102 g, 80%).

2-Chloro-5-trans-(2,2-dichloro-3-(3,5-difluoro-4-methoxyphenyl)cyclopropane-1-carboxamido)-N-(2,2,2-trifluoroethyl)benzamide (F125)

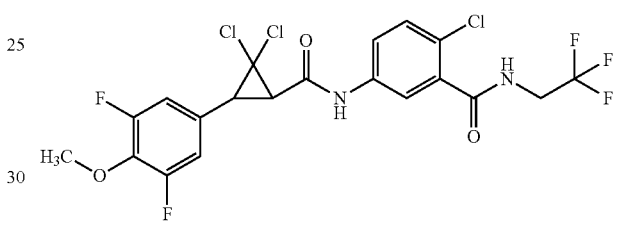

Isolated as a white foam (0.075 g, 80%).

2-Chloro-5-trans-(2,2-dichloro-3-(3,4,5-trifluorophenyl)cyclopropane-1-carboxamido)-N-(2,2,2-trifluoroethyl)benzamide (F126)

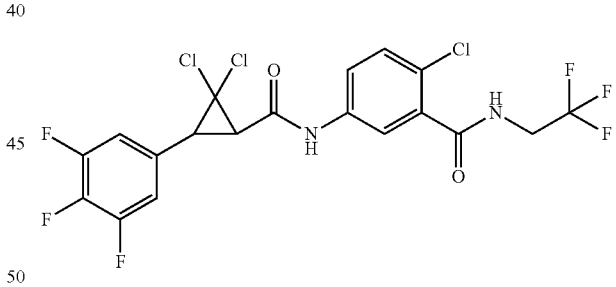

Isolated as a clear colorless oil (0.052 g, 54%).

2-Chloro-5-cis-(2,2-dichloro-3-(3,4,5-trifluorophenyl)cyclopropane-1-carboxamido)-N-(2,2,2-trifluoroethyl)benzamide (F127)

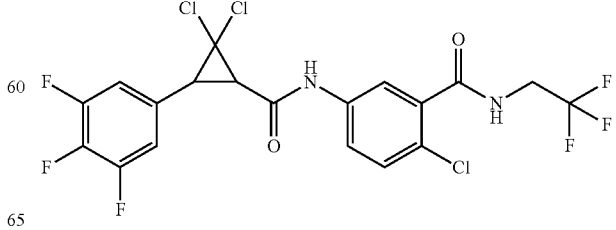

Isolated as a clear colorless oil (0.017 g, 18%).

121
2-Chloro-5-(trans-2,2-dichloro-3-(3-chloro-5-(difluoromethyl)phenyl)cyclopropane-1-carboxamido)-N-(2,2,2-trifluoroethyl)benzamide (F128)

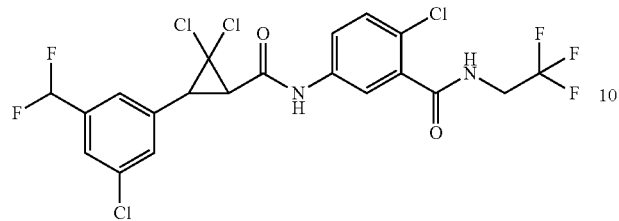

Isolated as a yellow oil (0.063 g, 73%).

2-Chloro-5-(trans-2,2-dichloro-3-(4-chloro-3-(difluoromethyl)phenyl)cyclopropane-1-carboxamido)-N-(2,2,2-trifluoroethyl)benzamide (F129)

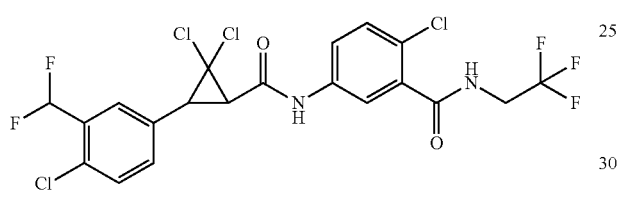

Isolated as a pale yellow oil (0.063 g, 73%).

2-Chloro-5-(trans-2,2-dichloro-3-(3-(difluoromethyl)-5-fluorophenyl)cyclopropane-1-carboxamido)-N-(2,2,2-trifluoroethyl)benzamide (F130)

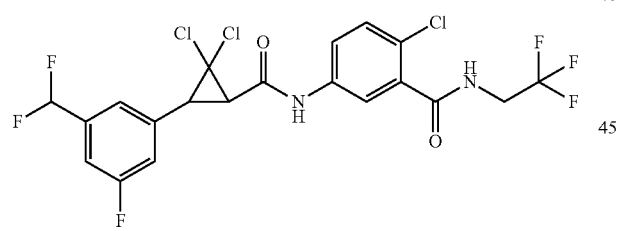

Isolated as a yellow foam (0.051 g, 61%).

2-Chloro-5-(trans-2,2-dichloro-3-(3-(difluoromethyl)-4-fluorophenyl)cyclopropane-1-carboxamido)-N-(2,2,2-trifluoroethyl)benzamide (F131)

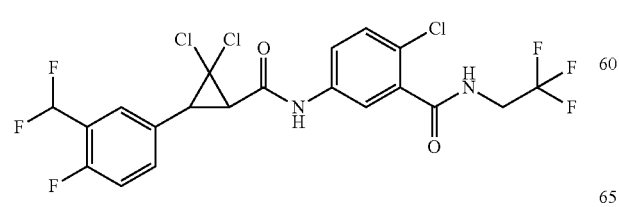

Isolated as a white foam (0.059 g, 70%).

122
2-Chloro-5-(trans-2,2-dichloro-3-(3-chloro-4-(difluoromethyl)phenyl)cyclopropane-1-carboxamido)-N-(2,2,2-trifluoroethyl)benzamide (F132)

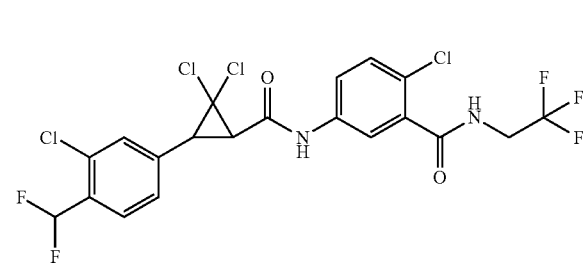 [SMILES: O=C(NCC(F)(F)F)c1cc(NC(=O)C2C(c3ccc(C(F)F)c(F)c3)C2(Cl)Cl)ccc1Cl]

Isolated as a yellow foam (0.068 g, 78%).

2-Chloro-5-(trans-2,2-dichloro-3-(4-(difluoromethyl)-3-fluorophenyl)cyclopropane-1-carboxamido)-N-(2,2,2-trifluoroethyl)benzamide (F133)

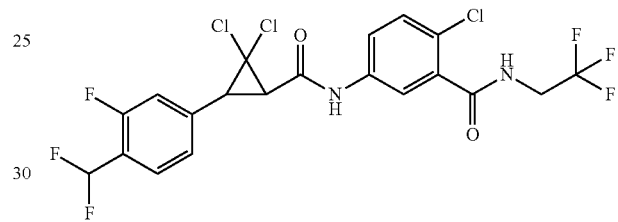

Isolated as a yellow foam (0.059 g, 70%).

2-Chloro-5-(trans-2,2-dichloro-3-(3-(difluoromethyl)phenyl)cyclopropane-1-carboxamido)-N-(2,2,2-trifluoroethyl)benzamide (F134)

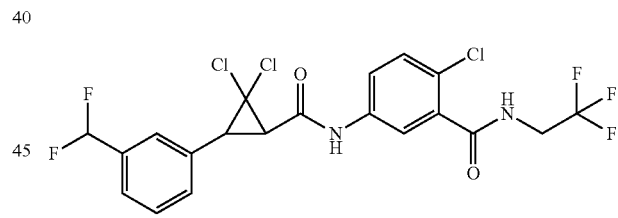

Isolated as a white foam (0.058 g, 71%).

2-Chloro-5-(trans-2,2-dichloro-3-(4-(difluoromethyl)phenyl)cyclopropane-1-carboxamido)-N-(2,2,2-trifluoroethyl)benzamide (F135)

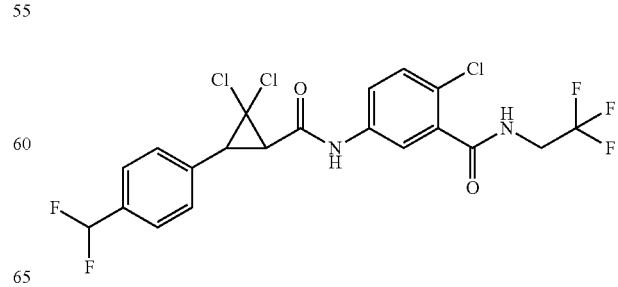

Isolated as a white foam (0.057 g, 70%).

Example 25

Preparation of (E)-1-chloro-3-(difluoromethyl)-5-(4-methoxystyryl)benzene (C107)

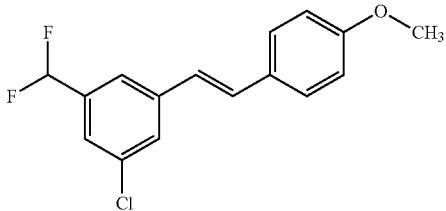 [SMILES: COc1ccc(/C=C/c2cc(Cl)cc(C(F)F)c2)cc1]

To a stirred solution of (E)-3-chloro-5-(4-methoxystyryl)benzaldehyde (C115) (13 g, 47.79 mmol) in dichloromethane (130 mL) was added diethylaminosulfur trifluoride (31.5 mL, 238.97 mmol) at −78° C. The resulting solution was stirred for 20 hours at room temperature. The reaction mixture was cooled to 0° C., and a solution of saturated aqueous sodium bicarbonate was added dropwise. The layers were separated and the aqueous layer was extracted with dichloromethane (3×75 mL). The combined organic layer was washed with water and brine, dried over sodium sulfate, and concentrated. The crude material was purified by flash column chromatography using 10-20% ethyl acetate in hexanes as the eluent to afford the title compound as a pale yellow oil (13.1 g, 94%): $^1$H NMR (400 MHz, CDCl$_3$) δ 7.55 (s, 1H), 7.45 (d, J=8.8 Hz, 3H), 7.34 (s, 1H), 7.10 (d, J=16 Hz, 1H), 6.90 (t, J=8.4 Hz, 3H), 6.61 (t, J=56.4 Hz, 1H), 3.80 (s, 3H); $^{19}$F NMR (376 MHz, CDCl$_3$) δ −111.72.

The following compounds were prepared in like manner to the procedure outlined in Example 25:

(E)-1-Chloro-2-(difluoromethyl)-4-(4-methoxystyryl) benzene (C108)

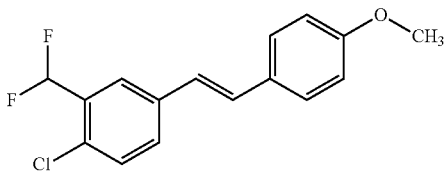 [SMILES: COc1ccc(/C=C/c2ccc(Cl)c(C(F)F)c2)cc1]

Isolated as an off-white solid (12 g, 94%): $^1$H NMR (300 MHz, CDCl$_3$) δ 7.75 (s, 1H), 7.51-7.44 (m, 3H), 7.37 (d, J=8.4 Hz, 1H), 7.13 (d, J=6.6 Hz, 1H), 7.06 (s, 1H), 6.95-6.89 (m, 3H), 3.95 (s, 3H); $^{19}$F NMR (282 MHz, CDCl$_3$) δ −115.31; ESIMS m/z 295 ([M+H]$^+$).

(E)-1-(Difluoromethyl)-3-fluoro-5-(4-methoxystyryl) benzene (C109)

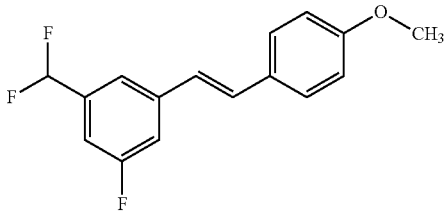

Isolated as an off-white solid (20 g, 75%); $^1$H NMR (300 MHz, CDCl$_3$) δ 7.46 (d, J=8.0 Hz, 2H), 7.38 (s, 1H), 7.28 (s, 1H), 7.08 (t, J=16.2 Hz, 2H), 6.92 (t, J=15.6 Hz, 3H), 6.63 (t, J=56.0 Hz, 1H), 3.84 (s, 3H); ESIMS m/z 279 ([M+H]$^+$).

(E)-2-(Difluoromethyl)-1-fluoro-5-(4-methoxystyryl) benzene (C110)

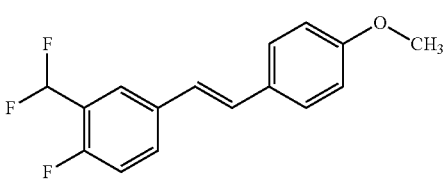 [SMILES: COc1ccc(/C=C/c2ccc(F)c(C(F)F)c2)cc1]

Isolated as an off-white solid (14.0 g, 70%): $^1$H NMR (300 MHz, CDCl$_3$) δ 7.69 (d, J=9.0 Hz, 1H), 7.57-7.53 (m, 1H), 7.45 (d, J=9.9 Hz, 2H), 7.13-7.06 (m, 2H), 7.00-6.89 (m, 4H), 3.85 (s, 3H); ESIMS m/z 279 ([M+H]$^+$).

(E)-2-Chloro-1-(Difluoromethyl)-4-(4-methoxystyryl) benzene (C111)

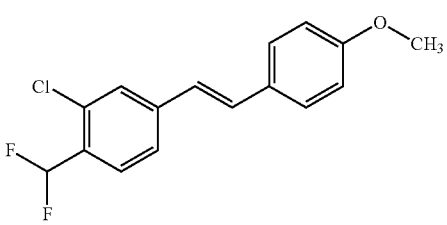 [SMILES: COc1ccc(/C=C/c2ccc(C(F)F)c(Cl)c2)cc1]

Isolated as an off-white solid (18.0 g, 90%): $^1$H NMR (400 MHz, CDCl$_3$) δ 7.61 (d, J=8.0 Hz, 1H), 7.51 (s, 1H), 7.47-7.43 (m, 3H), 7.14-7.07 (m, 1H), 6.94-6.80 (m, 4H), 3.85 (s, 3H); ESIMS m/z 294 ([M+H]$^+$).

(E)-1-(Difluoromethyl)-2-fluoro-4-(4-methoxystyryl) benzene (C112)

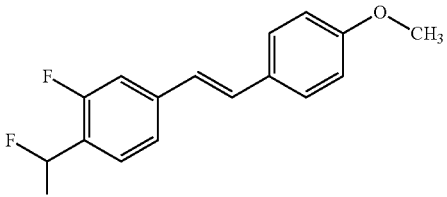

Isolated as a pale yellow solid (9 g, 55%): $^1$H NMR (400 MHz, CDCl$_3$) δ 7.54 (t, J=8.0 Hz, 1H), 7.46 (d, J=8.8 Hz, 2H), 7.32 (d, J=8.0 Hz, 1H), 7.22 (d, J=11.6 Hz, 1H), 7.11 (d, J=16.4 Hz, 1H), 7.01-6.83 (m, 4H), 3.95 (s, 3H); $^{19}$F NMR (376 MHz, CDCl$_3$) δ −113.57, −114.25, −120.33; ESIMS m/z 279 ([M+H]$^+$).

(E)-1-(Difluoromethyl)-3-(4-methoxystyryl) benzene (C113)

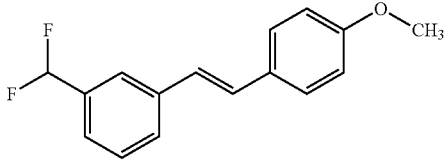 [SMILES: COc1ccc(/C=C/c2cccc(C(F)F)c2)cc1]

Isolated as a pale yellow solid (6 g, 68%): $^1$H NMR (300 MHz, CDCl$_3$) δ 7.62-7.56 (m, 2H), 7.48-7.34 (m, 4H), 7.11 (d, J=16.5 Hz, 1H), 7.00 (s, 1H), 6.95-6.89 (t, 2H), 6.66 (t, 1H), 3.95 (s, 3H); $^{19}$F NMR (282 MHz, CDCl$_3$) δ −110.84; ESIMS m/z 261 ([M+H]$^+$).

(E)-1-(Difluoromethyl)-4-(4-methoxystyryl) benzene (C114)

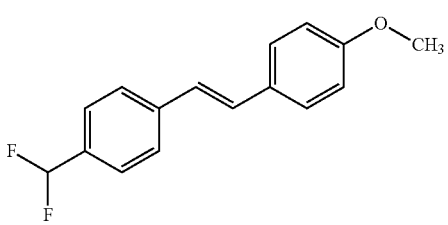 [SMILES: COc1ccc(/C=C/c2ccc(C(F)F)cc2)cc1]

Isolated as an off-white solid (15.4 g, 75%); $^1$H NMR (300 MHz, CDCl$_3$) δ 7.57-7.45 (m, 6H), 7.12 (d, J=15.9 Hz, 1H), 7.00-6.89 (m, 3H), 6.64 (t, J=57 Hz, 1H), 3.92 (s, 3H); ESIMS m/z 260.17 ([M+H]$^+$).

Example 26

Preparation of (E)-3-chloro-5-(4-methoxystyryl) benzaldehyde (C115)

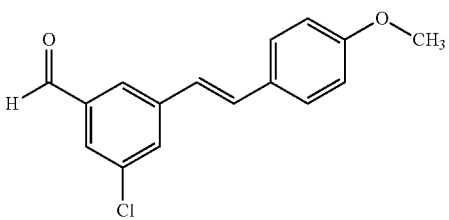

To a stirred solution of 3-bromo-5-chlorobenzaldehyde (20.0 g, 91.32 mmol) in dimethylacetamide, 1-methoxy-4-vinylbenzene (18.3 g, 136.9 mmol) and triethylamine (50.5 mL, 273.96 mmol) were added, and the reaction mixture was degassed with argon for 5 minutes. Palladium(II) acetate (410 mg, 1.83 mmol) and tri-o-tolylphosphine (1.11 g, 3.65 mmol) were added, and the resulting reaction mixture was heated to 100° C. for 16 hours. The reaction mixture was poured into water and extracted with ethyl acetate. The combined organic layer was dried over sodium sulfate and concentrated under reduced pressure. The resulting crude material was purified by flash column chromatography using 5-10% ethyl acetate in petroleum ether as the eluent to afford the title compound as a yellow solid (13.5 g, 54%): $^1$H NMR (300 MHz, CDCl$_3$) δ 9.99 (s, 1H), 7.85 (s, 1H), 7.69 (s, 2H), 7.47 (d, J=8.4 Hz, 2H), 7.16 (d, J=16.2 Hz, 1H), 6.94 (t, J=8.4 Hz, 3H), 3.84 (s, 3H); ESIMS m/z 273 ([M+H]$^+$).

The following compounds were prepared in like manner to the procedure outlined in Example 26:

(E)-2-Chloro-5-(4-methoxystyryl)benzaldehyde (C116)

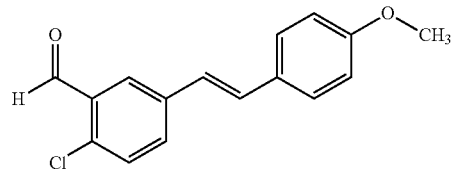 [SMILES: COc1ccc(/C=C/c2ccc(Cl)c(C=O)c2)cc1]

Isolated as a pale yellow solid (11.8 g, 27%): $^1$H NMR (300 MHz, CDCl$_3$) δ 10.45 (s, 1H), 8.02 (s, 1H), 7.62 (d, J=6.4 Hz, 1H), 7.46-7.40 (m, 3H), 7.12 (d, J=16.4 Hz, 1H), 6.95-6.90 (m, 3H), 3.95 (s, 3H); ESIMS m/z 273 ([M+H]$^+$).

(E)-3-Fluoro-5-(4-methoxystyryl)benzaldehyde (C117)

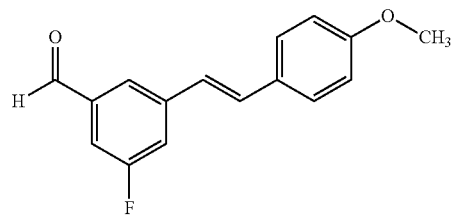

Isolated as a pale yellow solid (25 g, 57%): $^1$H NMR (300 MHz, CDCl$_3$) δ 10 (s, 1H), 7.77 (s, 1H), 7.48-7.40 (m, 4H), 7.16 (d, J=16.2 Hz, 1H), 6.94 (t, J=15.6 Hz, 3H), 3.84 (s, 3H); ESIMS m/z 275 ([M+H]$^+$).

(E)-2-Fluoro-5-(4-methoxystyryl)benzaldehyde (C118)

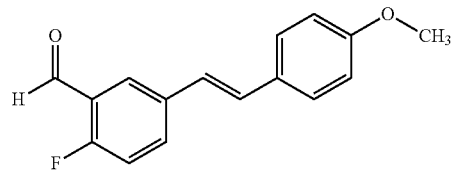 [SMILES: COc1ccc(/C=C/c2ccc(F)c(C=O)c2)cc1]

Isolated as an off-white solid (0.25 g, 20%): $^1$H NMR (400 MHz, CDCl$_3$) δ 10.43 (s, 1H), 7.90 (d, J=8.4 Hz, 1H), 7.54-7.46 (m, 4H), 7.20 (d, J=16.0 Hz, 1H), 6.94-6.90 (m, 3H), 3.85 (s, 3H); ESIMS m/z 274 ([M+H]$^+$).

127

(E)-2-Chloro-4-(4-methoxystyryl)benzaldehyde (C119)

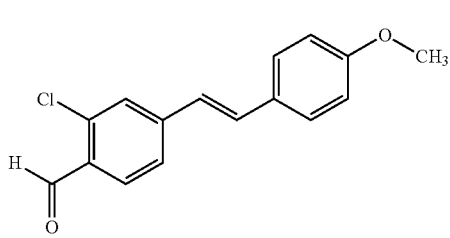

Isolated as an off-white solid (8.0 g, 57%): $^1$H NMR (400 MHz, CDCl$_3$) δ 10.41 (s, 1H), 7.97 (dd, J=2.4, 6.8 Hz, 1H), 7.71-7.67 (m, 1H), 7.44 (d, J=8.0 Hz, 2H), 7.18-7.13 (m, 1H), 7.08-7.04 (m, 1H), 6.95-6.90 (m, 3H), 3.85 (s, 3H); ESIMS m/z 257 ([M+H]$^+$).

(E)-2-Fluoro-4-(4-methoxystyryl)benzaldehyde (C120)

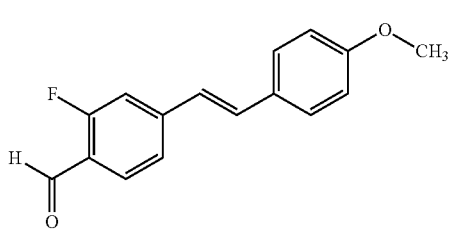

Isolated as a brown solid (15 g, 78%): $^1$H NMR (400 MHz, CDCl$_3$) δ 10.35 (s, 1H), 7.83 (t, J=7.6 Hz, 1H), 7.48 (d, J=8.8 Hz, 2H), 7.35 (d, J=8.4 Hz, 1H), 7.23-7.18 (m, 2H), 6.96-6.91 (m, 3H), 3.95 (s, 3H); $^{19}$F NMR (376 MHz, CDCl$_3$) δ −122.26;

ESIMS m/z 257 ([M+H]$^+$).

(E)-3-(4-Methoxystyryl)benzaldehyde (C121)

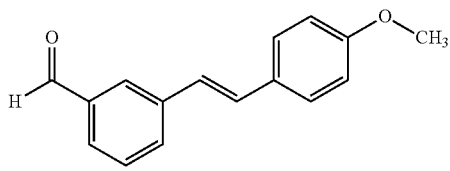

Isolated as a brown solid (18 g, 46%): $^1$H NMR (400 MHz, CDCl$_3$) δ 10.15 (s, 1H), 8.00 (s, 1H), 7.73 (d, J=7.2 Hz, 2H), 7.53-7.46 (m, 3H), 7.17 (d, J=16.8 Hz, 1H), 7.01 (d, J=16.0 Hz, 1H), 6.92 (d, J=8.8 Hz, 2H), 3.84 (s, 3H); ESIMS m/z 239 ([M+H]$^+$).

128

(E)-4-(4-Methoxystyryl) benzaldehyde (C122)

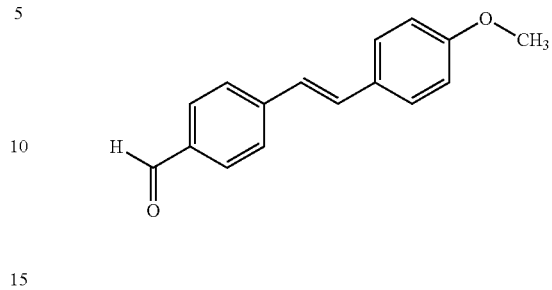

Isolated as a light brown solid (9 g, 47%): $^1$H NMR (400 MHz, CDCl$_3$) δ 10 (s, 1H), 7.84 (d, J=8.0 Hz, 2H), 7.61 (d, J=7.6 Hz, 2H), 7.48 (d, J=8.0 Hz, 2H), 7.23 (t, J=7.6 Hz, 1H), 7.00 (d, J=16.0 Hz, 1H), 6.92 (d, J=8.8 Hz, 2H), 3.84 (s, 3H).

Example 27

Preparation of trans-2,2-dichloro-3-(3,5-dichlorophenyl)cyclopropane-1carboxylic acid (C1)

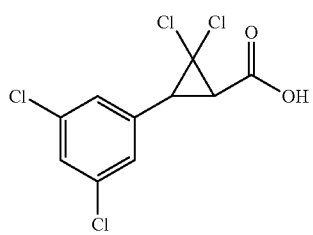

Sodium permanganate (40% aqueous) (84 g, 236 mmol) was added dropwise to a stirred mixture of trans-2,2-dichloro-3-(3,5-dichlorophenyl)cyclopropane-1-carbaldehyde (C115) (58.7 g, 196 mmol) in acetone (982 mL) at 15° C. The resulting mixture was stirred at 20° C. for 2 hours. The reaction mixture was diluted with isopropyl alcohol (20 mL) and concentrated to remove the acetone. Celite® and aqueous hydrochloric acid (1 N, 295 mL, 295 mmol) were added to the brown residue. The resulting mixture was diluted with ethyl acetate (500 mL) and filtered through Celite®. The filtrate was washed with brine (200 mL). The organic layer was dried over sodium sulfate, filtered and concentrated. The resulting slurry was diluted with heptane (~200 mL) and allowed to solidify at 20° C. The solid was collected, washed with heptane and dried to afford the title product as a white solid (54.68 g, 91%): $^1$H NMR (300 MHz, CDCl$_3$) δ 7.36 (t, J=1.9 Hz, 1H), 7.17 (dd, J=1.9, 0.7 Hz, 2H), 3.48-3.37 (m, 1H), 2.87 (d, J=8.3 Hz, 1H); $^{13}$C NMR (400 MHz, CDCl$_3$) δ 135.44, 135.28, 128.66, 127.30, 39.68, 36.88; ESIMS m/z=298.9 ([M−H])$^-$.

The following compounds were prepared in like manner to the procedure outlined in Example 27:

trans-2,2-Dichloro-3-(3,4,5-trichlorophenyl)cyclopropane-1-carboxylic acid (C2)

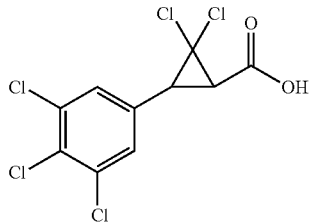

Isolated as a white solid (2.78 g, 95%): $^1$H NMR (400 MHz, DMSO-$d_6$) δ 13.41 (s, 1H), 7.81 (d, J=0.6 Hz, 2H), 3.62 (d, J=8.6 Hz, 1H), 3.52 (d, J=8.6 Hz, 1H); ESIMS m/z 332 ([M−H]$^-$).

trans-2,2-Dichloro-3-(3,4-dichlorophenyl)cyclopropane-1-carboxylic acid (C3)

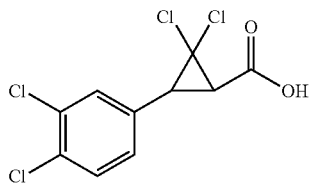

Isolated as a white solid (124 g, 82%): mp 133-135° C.: $^1$H NMR (500 MHz, DMSO-$d_6$) δ 13.39 (s, 1H), 7.76 (d, J=2.0 Hz, 1H), 7.64 (d, J=8.3 Hz, 1H), 7.44 (dd, J=8.4, 2.1 Hz, 1H), 3.49 (s, 2H). $^{13}$C NMR (126 MHz, DMSO-$d_6$) δ 166.34, 133.35, 130.47, 130.33, 130.09, 129.77, 128.81, 61.43, 37.00, 36.06.

trans-2,2-Dichloro-3-(3-chloro-4-fluorophenyl)cyclopropane-1-carboxylic acid (C16)

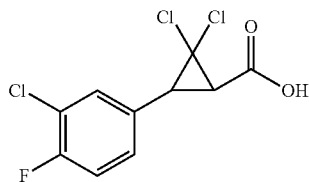 [SMILES: O=C(O)C1C(c2ccc(F)c(Cl)c2)C1(Cl)Cl]

Isolated as a white solid (165 g, 71%): $^1$H NMR (400 MHz, CDCl$_3$) δ 11.57 (s, 1H), 7.42 (dd, J=8.2, 7.6 Hz, 1H), 7.11-6.98 (m, 2H), 3.46 (d, J=8.2 Hz, 1H), 2.85 (d, J=8.3 Hz, 1H); $^{19}$F NMR (376 MHz, CDCl$_3$) δ −114.07; ESIMS m/z 282 ([M−H]$^-$).

In another preparation, isolated as a white powder (10.385 g, 77%): 119-121° C.; $^1$H NMR (400 MHz, CDCl$_3$) δ 11.83 (s, 1H), 7.32 (d, J=6.9 Hz, 1H), 7.16 (d, J=6.7 Hz, 2H), 3.45 (d, J=8.3 Hz, 1H), 2.85 (d, J=8.3 Hz, 1H); $^{13}$C NMR (101 MHz, CDCl$_3$) δ 172.18, 159.26, 156.77, 130.95, 129.26, 129.22, 128.57, 128.50, 121.52, 121.34, 116.94, 116.73, 61.59, 39.64, 37.30; $^{19}$F NMR (376 MHz, CDCl$_3$) δ −115.16; ESIMS m/z 281 [(M−H)$^-$].

trans-2,2-Dichloro-3-(3,5-dichloro-4-methoxyphenyl)cyclopropanecarboxylic acid (C123)

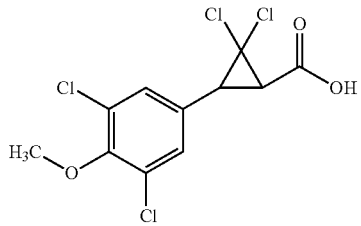 [SMILES: COc1c(Cl)cc(C2C(C(=O)O)C2(Cl)Cl)cc1Cl]

Isolated as an off-white solid (1.33 g, 96%): mp 161-164° C.; $^1$H NMR (400 MHz, DMSO-$d_6$) δ 13.35 (s, 1H), 7.63 (s, 2H), 3.83 (s, 3H), 3.52 (d, J=8.6 Hz, 1H), 3.45 (d, J=8.6 Hz, 1H); $^{13}$C NMR (126 MHz, DMSO-$d_6$) δ 166.81, 151.02, 131.07, 129.63, 128.03, 61.93, 60.52, 37.22, 36.54; ESIMS m/z 329 [(M−H)$^-$].

Example 28

Preparation of trans-2,2-dichloro-3-(3,5-dichlorophenyl)cyclopropane-1-carbaldehyde (C140)

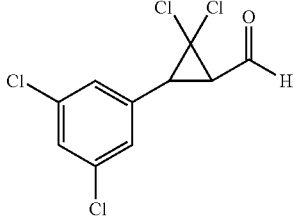 [SMILES: O=CC1C(c2cc(Cl)cc(Cl)c2)C1(Cl)Cl]

Aqueous hydrochloric acid (2 N, 237 mL) was added to a stirred solution of 1,3-dichloro-5-((trans-2,2-dichloro-3-(diethoxymethyl)cyclopropyl)benzene (C145) (85.7 g, 227 mmol) in acetonitrile (1184 mL). The mixture was stirred at 20° C. for 16 hours. The resulting mixture was diluted with water (200 mL) and concentrated to remove the acetonitrile. The resulting aqueous mixture was extracted with hexanes (600 mL). The organic layer was washed water (300 mL), dried over anhydrous sodium sulfate, filtered and concentrated. The crude product was purified by chromatography to afford the title product as a yellow oil (58.7 g, 86%, purity 95%): $^1$H NMR (400 MHz, CDCl$_3$) δ 9.54 (d, J=4.0 Hz, 1H), 7.46-7.09 (m, 3H), 3.51 (d, J=8.0 Hz, 1H), 2.92 (dd, J=8.0, 4.0 Hz, 1H); $^{13}$C NMR (126 MHz, CDCl$_3$) δ 193.41, 135.33, 135.09, 128.78, 127.34, 42.89, 39.31; IR (thin film) 3077.79, 2847.30, 1713.57, 1590.66, 1566.39, 1416.76, 1387.06. IR: 3078, 2847, 1714, 1590, 1566, 1417, 1387.

The following compounds were prepared in like manner to the procedure outlined in Example 28:

131
trans-2,2-Dichloro-3-(3,4-dichlorophenyl)cyclopropane-1-carbaldehyde (C141)

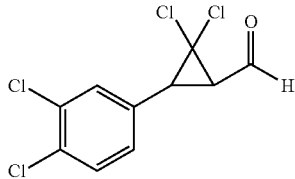 [SMILES: O=CC1C(c2ccc(Cl)c(Cl)c2)C1(Cl)Cl]

Isolated as orange oil (143 g, 98%): $^1$H NMR (400 MHz, CDCl$_3$) δ 9.53 (d, J=4.1 Hz, 1H), 7.47 (d, J=8.3 Hz, 1H), 7.37 (dd, J=2.2, 0.7 Hz, 1H), 7.12 (ddd, J=8.3, 2.2, 0.7 Hz, 1H), 3.51 (dd, J=7.9, 0.8 Hz, 1H), 2.90 (dd, J=8.0, 4.1 Hz, 1H).

trans-2,2-Dichloro-3-(3,4,5-trichlorophenyl)cyclopropane-1-carbaldehyde (C142)

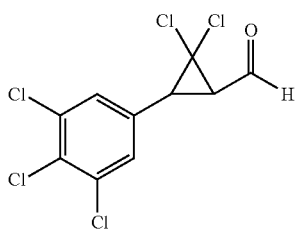 [SMILES: O=CC1C(c2cc(Cl)c(Cl)c(Cl)c2)C1(Cl)Cl]

Isolated as a yellow solid (2.8 g, 69%): $^1$H NMR (400 MHz, CDCl$_3$) δ 9.55 (d, J=3.9 Hz, 1H), 7.30 (d, J=0.7 Hz, 2H), 3.48 (dt, J=8.0, 0.8 Hz, 1H), 2.92 (dd, J=7.9, 3.9 Hz, 1H).

trans-2,2-Dichloro-3-(3,5-dichloro-4-methoxyphenyl)cyclopropane-1-carbaldehyde (C143)

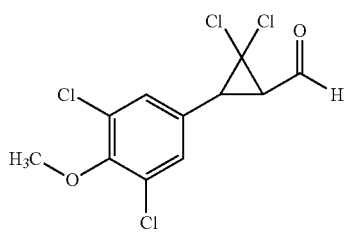 [SMILES: COc1c(Cl)cc(C2C(C=O)C2(Cl)Cl)cc1Cl]

Isolated as a light-yellow oil (1.346 g, 74%): $^1$H NMR (400 MHz, CDCl$_3$) δ 9.52 (d, J=4.0 Hz, 1H), 7.22 (s, 2H), 3.90 (s, 3H), 3.48 (d, J=8.0 Hz, 1H), 2.91 (dd, J=8.0, 4.0 Hz, 1H); $^{13}$C NMR (101 MHz, CDCl$_3$) δ 191.67, 150.58, 127.74, 127.54, 127.35, 59.76, 58.94, 41.14, 37.13; EIMS m/z 314.

132
trans-2,2-Dichloro-3-(3-chloro-4-fluorophenyl)cyclopropane-1-carbaldehyde (C144)

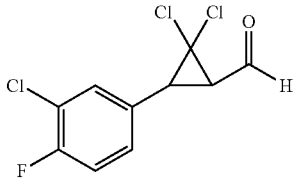 [SMILES: O=CC1C(c2ccc(F)c(Cl)c2)C1(Cl)Cl]

Isolated as a yellow oil (12.496 g, 71%): $^1$H NMR (400 MHz, CDCl$_3$) δ 9.52 (d, J=4.1 Hz, 1H), 7.33 (d, J=7.2 Hz, 1H), 7.16 (dd, J=6.8, 1.0 Hz, 2H), 3.53 (d, J=7.9 Hz, 1H), 2.90 (dd, J=7.9, 4.1 Hz, 1H); $^{13}$C NMR (101 MHz, CDCl$_3$) δ 193.77, 159.27, 156.78, 131.03, 129.04, 129.00, 128.66, 128.59, 121.49, 121.31, 116.95, 116.74, 61.68, 43.10, 39.25; $^{19}$F NMR (376 MHz, CDCl$_3$) δ −115.01; EIMS m/z 266.

Example 29

Preparation of 1,3-dichloro-5-(trans-2,2-dichloro-3-(diethoxymethyl)cyclopropyl)benzene (C145)

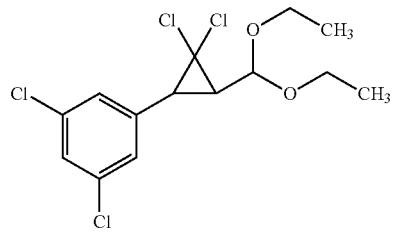 [SMILES: CCOC(OCC)C1C(c2cc(Cl)cc(Cl)c2)C1(Cl)Cl]

A 1 L 4-neck flask equipped with a mechanical stirrer, condenser, temperature probe and nitrogen inlet was charged with (E)-1,3-dichloro-5-(3,3-diethoxyprop-1-en-1-yl)benzene (C150) (40 g, 138 mmol) and CHCl$_3$ (447 mL). Tetrabutylammonium hexafluorophosphate(V) (1.081 g, 2.76 mmol) was added. The light yellow solution was heated to 45° C. With vigorous stirring (~400 rpm), aqueous sodium hydroxide (50%, 182 mL) was added dropwise via addition funnel (over 1 hour). After 20 hours, the mixture was allowed to cool. The mixture was diluted with hexane (200 mL). The organic top layer was decanted (off the aqueous lower suspension) through Celite®, washing the filtercake with hexane (200 mL). The filtrate was washed with brine (~200 mL), dried over sodium sulfate, filtered and concentrated to provide the title compound as a brown oil (50.2 g, 97%, purity 95%): $^1$H NMR (300 MHz, CDCl$_3$) δ 7.31 (t, J=1.9 Hz, 1H), 7.15 (dd, J=1.9, 0.7 Hz, 2H), 4.59 (d, J=6.2 Hz, 1H), 3.80-3.57 (m, 4H), 2.77 (d, J=8.5 Hz, 1H), 2.25 (dd, J=8.5, 6.2 Hz, 1H), 1.30 (t, J=7.0 Hz, 3H), 1.20 (t, J=7.1 Hz, 3H).

The following compounds were prepared in like manner to the procedure outlined in Example 29:

1,2-Dichloro-4-(trans-2,2-dichloro-3-(diethoxymethyl)cyclopropyl)benzene (C146)

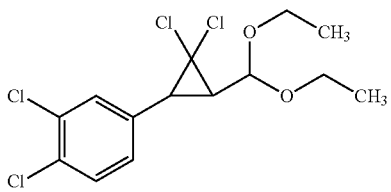 [SMILES: CCOC(OCC)C1C(c2ccc(Cl)c(Cl)c2)C1(Cl)Cl]

Isolated as a brown oil (184 g, 99%): ¹H NMR (400 MHz, CDCl₃) δ 7.43 (d, J=8.2 Hz, 1H), 7.36 (dd, J=2.2, 0.7 Hz, 1H), 7.10 (ddd, J=8.3, 2.1, 0.7 Hz, 1H), 4.59 (d, J=6.2 Hz, 1H), 3.82-3.55 (m, 4H), 2.77 (d, J=8.5 Hz, 1H), 2.24 (dd, J=8.5, 6.3 Hz, 1H), 1.30 (t, J=7.0 Hz, 3H), 1.20 (t, J=7.1 Hz, 3H).

1,2,3-Trichloro-5-(trans-2,2-dichloro-3-(diethoxymethyl)cyclopropyl)benzene (C147)

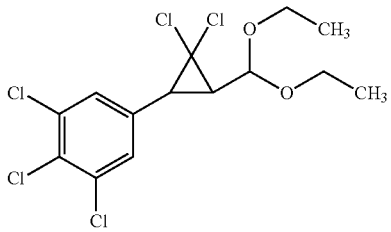 [SMILES: CCOC(OCC)C1C(c2cc(Cl)c(Cl)c(Cl)c2)C1(Cl)Cl]

Isolated as a brown oil (146 g, 93%): ¹H NMR (400 MHz, CDCl₃) δ 7.29 (d, J=0.7 Hz, 2H), 4.59 (d, J=6.1 Hz, 1H), 3.82-3.54 (m, 4H), 2.75 (d, J=8.5 Hz, 1H), 2.23 (dd, J=8.5, 6.1 Hz, 1H), 1.30 (t, J=7.0 Hz, 3H), 1.20 (t, J=7.0 Hz, 3H).

trans-1,3-Dichloro-5-(2,2-dichloro-3-(diethoxymethyl)cyclopropyl)-2-methoxybenzene (C148)

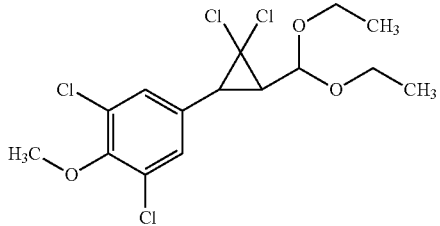 [SMILES: CCOC(OCC)C1C(c2cc(Cl)c(OC)c(Cl)c2)C1(Cl)Cl]

Isolated as an orange oil (2.254 g, 80%): ¹H NMR (400 MHz, CDCl₃) δ 7.20 (d, J=0.5 Hz, 2H), 4.58 (d, J=6.2 Hz, 1H), 3.90 (s, 3H), 3.67 (m, 4H), 2.74 (d, J=8.5 Hz, 1H), 2.22 (dd, J=8.5, 6.2 Hz, 1H), 1.31 (m, 3H), 1.21 (m, 3H); ¹³C NMR (101 MHz, CDCl₃) δ 151.87, 131.55, 129.27, 129.20, 127.21, 101.21, 62.39, 61.88, 61.68, 60.70, 37.67, 36.96, 15.34, 15.25; EIMS m/z 387.

2-Chloro-4-(trans-2,2-dichloro-3-(diethoxymethyl)cyclopropyl)-1-fluorobenzene (C149)

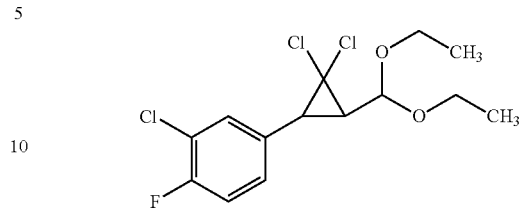

Isolated as a brown oil (63 g, 96%): ¹H NMR (400 MHz, CDCl₃) δ 7.44 (dd, J=7.0, 2.2 Hz, 1H), 7.29-7.22 (m, 1H), 7.09 (t, J=8.7 Hz, 1H), 6.62 (dd, J=16.1, 1.2 Hz, 1H), 6.14 (dd, J=16.1, 5.0 Hz, 1H), 5.05 (dd, J=4.9, 1.2 Hz, 1H), 3.70 (dq, J=9.3, 7.0 Hz, 2H), 3.56 (dq, J=9.4, 7.1 Hz, 2H), 1.25 (t, J=7.1 Hz, 6H); ¹³C NMR (101 MHz, CDCl₃) δ 158.91, 156.42, 133.65, 133.62, 130.47, 128.65, 128.07, 128.05, 126.39, 126.32, 121.26, 121.08, 116.72, 116.51, 100.93, 61.17, 15.24; ¹⁹F NMR (376 MHz, CDCl₃) δ -116.36.

In another preparation, isolated as an amber oil (22.38 g, 88%): ¹H NMR (400 MHz, CDCl₃) δ 7.31 (m, 1H), 7.13 (m, 2H), 4.59 (d, J=6.3 Hz, 1H), 3.69 (m, 4H), 2.78 (d, J=8.5 Hz, 1H), 2.23 (dd, J=8.5, 6.3 Hz, 1H), 1.30 (t, J=7.1 Hz, 3H), 1.20 (t, J=7.1 Hz, 3H); ¹⁹F NMR (376 MHz, CDCl₃) δ -116.48; EIMS m/z 295 [M-OEt].

Example 30

Preparation of (E)-1,3-dichloro-5-(3,3-diethoxyprop-1-en-1-yl)benzene (C150)

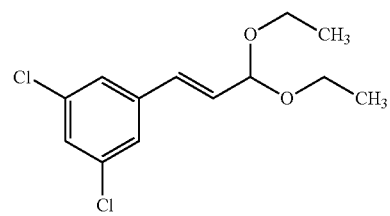 [SMILES: CCOC(/C=C/c1cc(Cl)cc(Cl)c1)OCC]

Step 1a: Acetaldehyde (120 g, 2688 mmol) was added to a stirred mixture of 3,5-dichlorobenzaldehyde (96 g, 538 mmol) in toluene (400 mL) at 0° C. A solution of potassium hydroxide (3.35 g, 53.8 mmol) in methyl alcohol (10 mL) was added dropwise via addition funnel. The resulting mixture was stirred at 0° C. for 4 hours until all of the 3,5-dichlorobenzaldehyde was consumed by thin layer chromatography. Step 1b: Ethyl acetate (500 mL) and concentrated hydrochloric acid (37% aqueous, 44.1 mL, 538 mmol) were added to the reaction mixture. The resulting mixture was heated at 80° C., and a colorless liquid was allowed to distill (200 mL). The reaction mixture was diluted with water (500 mL) and extracted with ethyl acetate. The organic layer was washed with brine, dried over sodium sulfate, filtered, and concentrated to afford (E)-3-(3,5-dichlorophenyl) acrylaldehyde as a light yellow solid (115 g) which was used directly without further purification: ¹H NMR (300 MHz, CDCl₃) δ 9.72 (dd, J=7.4, 0.5 Hz, 1H), 7.43 (q, J=1.8 Hz, 3H), 7.35 (d, J=16.0 Hz, 1H), 6.69 (dd, J=16.0, 7.4 Hz, 1H).

Step 2: Triethoxymethane (31.4 g, 208 mmol) and pyridin-1-ium 4-methylbenzenesulfonate (0.528 g, 2.079 mmol) were added to a stirred solution of (E)-3-(3,5-dichlorophenyl) acrylaldehyde (44 g, 208 mmol) in ethanol (416 mL). The resulting mixture was stirred at 20° C. for 20 hours. A solution of saturated aqueous sodium carbonate (50 mL) was added to the reaction mixture. The resulting mixture was concentrated at 45° C. to remove the ethanol. The concentrate was diluted with water and extracted with hexane. The organic layer was washed with brine, dried over sodium sulfate, filtered and concentrated to afford the title product as a light yellow oil (56.13 g, 93%): $^1$H NMR (400 MHz, CDCl$_3$) δ 7.25 (dt, J=10.6, 1.9 Hz, 3H), 6.61 (dd, J=16.1, 1.1 Hz, 1H), 6.22 (dd, J=16.1, 4.7 Hz, 1H), 5.17 (s, 1H), 5.14-5.00 (m, 1H), 3.78-3.49 (m, 4H), 1.24 (q, J=7.2 Hz, 6H); $^{13}$C NMR (101 MHz, CDCl$_3$) δ 139.34, 135.14, 130.27, 129.88, 127.71, 125.08, 100.60, 61.20, 15.25.

The following compounds were prepared in like manner to the procedure outlined in Example 30:

(E)-1,2-Dichloro-4-(3,3-diethoxyprop-1-en-1-yl)benzene (C151)

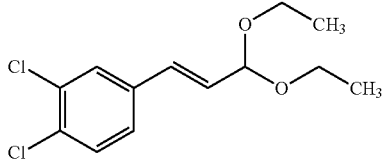 [SMILES: CCOC(/C=C/c1ccc(Cl)c(Cl)c1)OCC]

Isolated as an orange oil (142 g, 91%): $^1$H NMR (300 MHz, CDCl$_3$) δ 7.48 (d, J=2.0 Hz, 1H), 7.39 (dd, J=8.3, 0.8 Hz, 1H), 6.62 (d, J=16.1 Hz, 1H), 6.20 (ddd, J=16.1, 4.9, 0.8 Hz, 1H), 5.06 (dt, J=4.9, 1.0 Hz, 1H), 3.78-3.48 (m, 4H), 1.25 (td, J=7.1, 0.8 Hz, 6H).

(E)-1,2,3-Trichloro-5-(3,3-diethoxyprop-1-en-1-yl)benzene (C152)

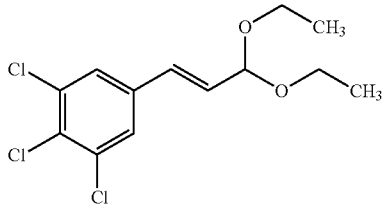 [SMILES: CCOC(/C=C/c1cc(Cl)c(Cl)c(Cl)c1)OCC]

Isolated as an orange oil (40 g, 91%): $^1$H NMR (400 MHz, CDCl$_3$) δ 7.41 (s, 2H), 6.58 (dd, J=16.1, 1.2 Hz, 1H), 6.21 (dd, J=16.1, 4.6 Hz, 1H), 5.06 (dd, J=4.7, 1.2 Hz, 1H), 3.69 (dq, J=9.3, 7.1 Hz, 2H), 3.55 (dq, J=9.5, 7.0 Hz, 2H), 1.25 (t, J=7.1 Hz, 6H).

(E)-1,3-Dichloro-5-(3,3-diethoxyprop-1-en-1-yl)-2-methoxybenzene (C153)

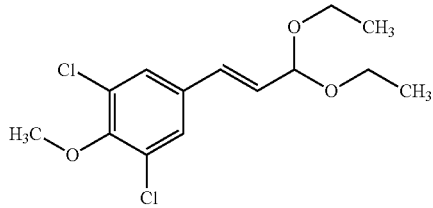 [SMILES: CCOC(/C=C/c1cc(Cl)c(OC)c(Cl)c1)OCC]

Isolated as a yellow oil (2.305 g, 56%): $^1$H NMR (400 MHz, CDCl$_3$) δ 7.32 (s, 2H), 6.56 (d, J=16.0 Hz, 1H), 6.14 (dd, J=16.1, 4.8 Hz, 1H), 5.05 (dd, J=4.8, 1.0 Hz, 1H), 3.89 (s, 3H), 3.69 (m, 2H), 3.55 (m, 2H), 1.25 (t, J=7.1 Hz, 6H); $^{13}$C NMR (101 MHz, CDCl$_3$) δ 151.75, 133.87, 129.87, 129.45, 128.85, 126.91, 100.68, 61.14, 60.73, 15.24; EIMS m/z 304.

(E)-2-Chloro-4-(3,3-diethoxyprop-1-en-1-yl)-1-fluorobenzene (C154)

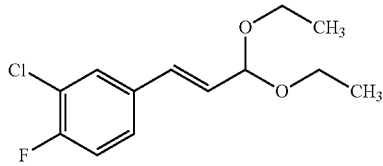

Isolated as an orange oil (283 g, 84%): $^1$H NMR (400 MHz, CDCl$_3$) δ 7.44 (dd, J=7.0, 2.2 Hz, 1H), 7.29-7.22 (m, 1H), 7.09 (t, J=8.7 Hz, 1H), 6.62 (dd, J=16.1, 1.2 Hz, 1H), 6.14 (dd, J=16.1, 5.0 Hz, 1H), 5.05 (dd, J=4.9, 1.2 Hz, 1H), 3.70 (dq, J=9.3, 7.0 Hz, 2H), 3.56 (dq, J=9.4, 7.1 Hz, 2H), 1.25 (t, J=7.1 Hz, 6H); $^{13}$C NMR (101 MHz, CDCl$_3$) δ 158.91, 156.42, 133.65, 133.62, 130.47, 128.65, 128.07, 128.05, 126.39, 126.32, 121.26, 121.08, 116.72, 116.51, 100.93, 61.17, 15.24; $^{19}$F NMR (376 MHz, CDCl$_3$) δ −116.36.

In another preparation, isolated as a colorless oil (16.75 g, 64%): $^1$H NMR (400 MHz, CDCl$_3$) δ 7.43 (dd, J=7.0, 2.2 Hz, 1H), 7.25 (m, 1H), 7.07 (t, J=8.7 Hz, 1H), 6.62 (d, J=16.1 Hz, 1H), 6.13 (dd, J=16.1, 4.9 Hz, 1H), 5.05 (dd, J=4.9, 1.0 Hz, 1H), 3.70 (dq, J=9.4, 7.1 Hz, 2H), 3.56 (dq, J=9.4, 7.0 Hz, 2H), 1.25 (t, J=7.1 Hz, 5H); $^{13}$C NMR (101 MHz, CDCl$_3$) δ 158.91, 156.42, 133.65, 133.62, 130.47, 128.65, 128.07, 128.05, 126.39, 126.32, 121.26, 121.08, 116.72, 116.51, 100.93, 61.17, 15.24; $^{19}$F NMR (376 MHz, CDCl$_3$) δ −116.36; EIMS m/z 258.

The following compounds were prepared in like manner to the procedures outlined in Examples 27 through 30:

trans-2,2-dichloro-3-(3,4-difluorophenyl)cyclopropane-1-carboxylic acid (C124)

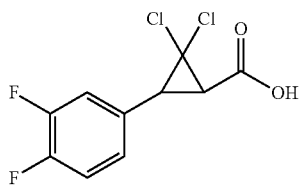 [SMILES: O=C(O)C1C(c2ccc(F)c(F)c2)C1(Cl)Cl]

Isolated as a white solid (1.44 g, 67%): $^1$H NMR (400 MHz, CDCl$_3$) δ 8.69 (s, 1H), 7.18 (dt, J=9.9, 8.3 Hz, 1H), 7.10 (ddd, J=10.8, 7.3, 2.3 Hz, 1H), 7.01 (ddt, J=8.1, 3.8, 1.7 Hz, 1H), 3.44 (dd, J=8.4, 1.0 Hz, 1H), 2.83 (d, J=8.3 Hz, 1H); $^{19}$F NMR (376 MHz, CDCl$_3$) δ −136.40, −136.46, −137.42, −137.48; ESIMS m/z 266 ([M−H]$^-$).

trans-3-(3-Bromo-4-chlorophenyl)-2,2-dichlorocyclopropane-1-carboxylic acid (C125)

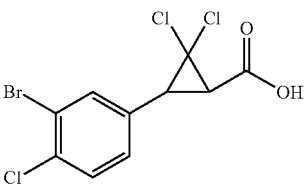

Isolated as a white solid (1.05 g, 63%): $^1$H NMR (400 MHz, CDCl$_3$) δ 8.07-7.63 (m, 1H), 7.58-7.42 (m, 2H), 7.17 (dd, J=8.3, 2.1 Hz, 1H), 3.43 (d, J=8.3 Hz, 1H), 2.86 (d, J=8.3 Hz, 1H); $^{13}$C NMR (101 MHz, CDCl$_3$) δ 171.46, 134.71, 133.88, 132.43, 130.42, 128.70, 122.73, 77.33, 77.22, 77.01, 76.69, 61.51, 39.50, 37.21; ESIMS m/z 343 ([M−H]$^-$).

trans-2,2-Dichloro-3-(3,4-dibromophenyl)cyclopropane-1-carboxylic acid (C126)

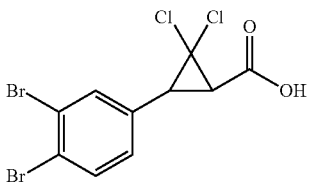

Isolated as a white solid (0.488 g, 57%): $^1$H NMR (400 MHz, CDCl$_3$) δ 8.85 (s, 1H), 7.77-7.47 (m, 2H), 7.08 (ddd, J=8.3, 2.1, 0.7 Hz, 1H), 3.57-3.25 (m, 1H), 2.86 (d, J=8.3 Hz, 1H); $^{13}$C NMR (101 MHz, CDCl$_3$) δ 171.54, 133.82, 133.78, 133.08, 128.78, 125.13, 124.98, 77.33, 77.22, 77.01, 76.70, 61.41, 39.59, 37.14, 0.01; ESIMS m/z 387 ([M−H]$^-$).

trans-2,2-Dichloro-3-(3-fluoro-4-(trifluoromethyl)phenyl)cyclopropane-1-carboxylic acid (C127)

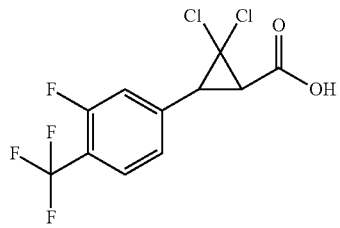 [SMILES: O=C(O)C1C(c2ccc(C(F)(F)F)c(F)c2)C1(Cl)Cl]

Isolated as a waxy tan solid (4.09 g, 69%): $^1$H NMR (400 MHz, CDCl$_3$) δ 7.83 (s, 1H), 7.63 (t, J=7.7 Hz, 1H), 7.23-7.04 (m, 2H), 3.51 (d, J=8.3 Hz, 1H), 2.92 (d, J=8.3 Hz, 1H); $^{19}$F NMR (376 MHz, CDCl$_3$) δ −61.40, −61.43, −113.24, −113.27; ESIMS m/z 316 ([M−H]$^-$).

trans-3-(4-Bromo-3-fluorophenyl)-2,2-dichlorocyclopropane-1-carboxylic acid (C128)

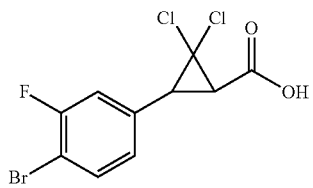

Isolated as a white solid (0.41 g, 42%): $^1$H NMR (400 MHz, CDCl$_3$) δ 8.04 (s, 1H), 7.57 (dd, J=8.2, 7.1 Hz, 1H), 7.00 (ddd, J=33.6, 8.7, 2.1 Hz, 2H), 3.43 (d, J=8.3 Hz, 1H), 2.85 (d, J=8.3 Hz, 1H); $^{19}$F NMR (376 MHz, CDCl$_3$) δ −106.06; ESIMS m/z 327 ([M−H]$^-$).

trans-3-(3-Bromo-4-(trifluoromethyl)phenyl)-2,2-dichlorocyclopropane-1-carboxylic acid (C129)

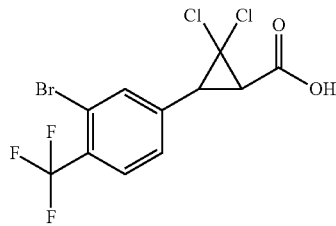 [SMILES: O=C(O)C1C(c2ccc(C(F)(F)F)c(Br)c2)C1(Cl)Cl]

Isolated as a white solid (0.55 g, 54%): $^1$H NMR (400 MHz, CDCl$_3$) δ 7.78-7.57 (m, 2H), 7.42-7.29 (m, 1H), 3.50 (d, J=8.3 Hz, 1H), 2.93 (d, J=8.3 Hz, 1H); $^{19}$F NMR (376 MHz, CDCl$_3$) δ −62.66, −62.67, −62.81; ESIMS m/z 377 ([M−H]$^-$).

trans-3-(4-Bromo-3-(trifluoromethyl)phenyl)-2,2-dichlorocyclopropane-1-carboxylic acid (C130)

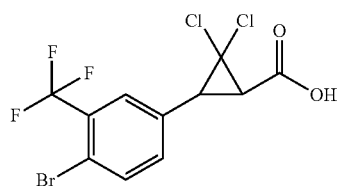 [SMILES: O=C(O)C1C(c2ccc(Br)c(C(F)(F)F)c2)C1(Cl)Cl]

Isolated as a white solid (1.21 g, 51%): $^1$H NMR (400 MHz, CDCl$_3$) δ 10.87 (s, 1H), 7.74 (d, J=8.3 Hz, 1H), 7.58 (d, J=2.2 Hz, 1H), 7.30 (dd, J=8.3, 2.2 Hz, 1H), 3.49 (d, J=8.3 Hz, 1H), 2.91 (d, J=8.3 Hz, 1H); $^{19}$F NMR (376 MHz, CDCl$_3$) δ −62.77, −62.78; ESIMS m/z 377 ([M−H]$^-$).

trans-2,2-Dichloro-3-(3-chloro-4-(trifluoromethyl)phenyl)cyclopropane-1-carboxylic acid (C131)

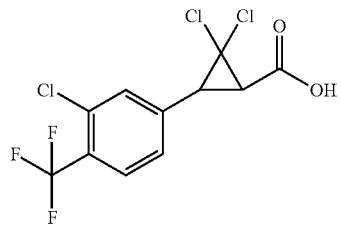

Isolated as a white solid (0.778 g, 43%): $^1$H NMR (400 MHz, CDCl$_3$) δ 9.72 (s, 1H), 7.71 (d, J=8.2 Hz, 1H), 7.53-7.39 (m, 1H), 7.35-7.19 (m, 1H), 3.50 (d, J=8.3 Hz, 1H), 2.93 (d, J=8.3 Hz, 1H); $^{19}$F NMR (376 MHz, CDCl$_3$) δ −62.63; ESIMS m/z 332 ([M−H]$^-$).

trans-2,2-Dichloro-3-(4-chloro-3-(trifluoromethyl)phenyl)cyclopropane-1-carboxylic acid (C132)

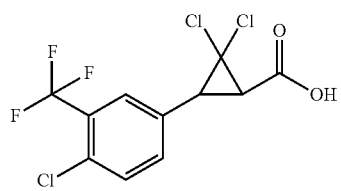

Isolated as a white solid (2.02 g, 43%): $^1$H NMR (400 MHz, CDCl$_3$) δ 7.96-7.51 (m, 3H), 7.39 (dd, J=8.3, 2.2 Hz, 1H), 3.50 (d, J=8.3 Hz, 1H), 2.90 (d, J=8.3 Hz, 1H); $^{19}$F NMR (376 MHz, CDCl$_3$) δ −62.75, −62.75; ESIMS m/z 332 ([M−H]$^-$).

trans-3-(3-Bromo-4-fluorophenyl)-2,2-dichlorocyclopropane-1-carboxylic acid (C133)

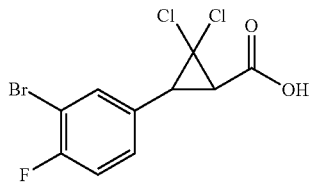

Isolated as a white solid (0.850 g, 44%): $^1$H NMR (400 MHz, CDCl$_3$) δ 8.47 (s, 1H), 7.47 (ddd, J=6.3, 2.3, 0.7 Hz, 1H), 7.32-7.08 (m, 2H), 3.44 (dd, J=8.3, 1.0 Hz, 1H), 2.84 (d, J=8.3 Hz, 1H); $^{19}$F NMR (376 MHz, CDCl$_3$) δ −107.16; ESIMS m/z 327 ([M−H]$^-$).

trans-2,2-Dichloro-3-(4-fluoro-3-(trifluoromethyl)phenyl)cyclopropane-1-carboxylic acid (C134)

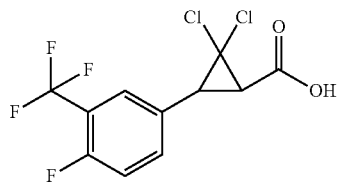 [SMILES: O=C(O)C1C(c2ccc(F)c(C(F)(F)F)c2)C1(Cl)Cl]

Isolated as a white solid (3.08 g, 67%): $^1$H NMR (400 MHz, CDCl$_3$) δ 8.18 (s, 1H), 7.64-7.39 (m, 2H), 7.24 (t, J=9.3 Hz, 1H), 3.50 (dd, J=8.4, 1.0 Hz, 1H), 2.89 (d, J=8.3 Hz, 1H); $^{19}$F NMR (376 MHz, CDCl$_3$) δ −61.48, −61.51, −114.23, −114.26, −114.29; ESIMS m/z 316 ([M−H]$^-$).

trans-2,2-Dichloro-3-(4-chloro-3-fluorophenyl)cyclopropane-1-carboxylic acid (C135)

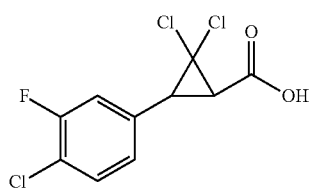

Isolated as a white solid (0.96 g, 36%): $^1$H NMR (400 MHz, CDCl$_3$) δ 11.57 (s, 1H), 7.42 (dd, J=8.2, 7.6 Hz, 1H), 7.11-6.98 (m, 2H), 3.46 (d, J=8.2 Hz, 1H), 2.85 (d, J=8.3 Hz, 1H); $^{19}$F NMR (376 MHz, CDCl$_3$) δ −114.07; ESIMS m/z 282 ([M−H]$^-$).

141 trans-2,2-Dichloro-3-(3,5-difluorophenyl)cyclopropane-1-carboxylic acid (C136)

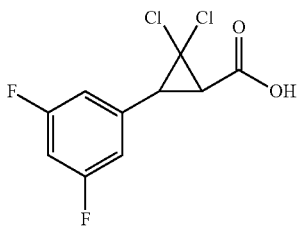 [SMILES: O=C(O)C1C(c2cc(F)cc(F)c2)C1(Cl)Cl]

Isolated as a clear colorless oil (1.55 g, 29%): $^1$H NMR (400 MHz, CDCl$_3$) δ 10.44 (s, 1H), 6.82 (qd, J=6.4, 2.3 Hz, 3H), 3.44 (d, J=8.3 Hz, 1H), 2.86 (d, J=8.3 Hz, 1H); $^{19}$F NMR (376 MHz, CDCl$_3$) δ −108.49, −108.69, −108.82, −109.85; ESIMS m/z 266 ([M−H]$^−$).

trans-2,2-Dichloro-3-(3-fluoro-5-(trifluoromethyl)phenyl)cyclopropane-1-carboxylic acid (C137)

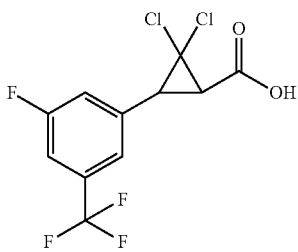 [SMILES: O=C(O)C1C(c2cc(F)cc(C(F)(F)F)c2)C1(Cl)Cl]

Isolated as a white solid (3.7 g, 55%): $^1$H NMR (400 MHz, CDCl$_3$) δ 11.40 (s, 1H), 7.42-7.27 (m, 2H), 7.20 (dt, J=8.9, 2.0 Hz, 1H), 3.53 (d, J=8.3 Hz, 1H), 2.93 (d, J=8.3 Hz, 1H); $^{19}$F NMR (376 MHz, CDCl$_3$) δ −62.86, −109.49; ESIMS m/z 316 ([M−H]$^−$).

trans-3-(3-Bromo-5-fluorophenyl)-2,2-dichlorocyclopropane-1-carboxylic acid (C138)

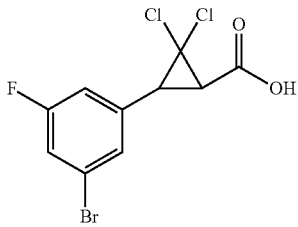

Isolated as a white solid (0.76 g, 47%): $^1$H NMR (400 MHz, CDCl$_3$) δ 11.06 (s, 1H), 7.36-7.14 (m, 2H), 7.03-6.87 (m, 1H), 3.45 (d, J=8.3 Hz, 1H), 2.87 (d, J=8.3 Hz, 1H); $^{19}$F NMR (376 MHz, CDCl$_3$) δ −109.73, −109.73; ESIMS m/z 327 ([M−H]$^−$).

142 trans-3-(3-Bromo-5-(trifluoromethyl)phenyl)-2,2-dichlorocyclopropane-1-carboxylic acid (C139)

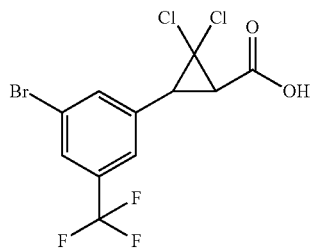 [SMILES: O=C(O)C1C(c2cc(Br)cc(C(F)(F)F)c2)C1(Cl)Cl]

Isolated as a tan solid (0.375 g, 31%): $^1$H NMR (400 MHz, CDCl$_3$) δ 10.52 (s, 1H), 7.77 (s, 1H), 7.62 (d, J=1.8 Hz, 1H), 7.46 (s, 1H), 3.52 (d, J=8.2 Hz, 1H), 2.93 (d, J=8.3 Hz, 1H); $^{19}$F NMR (376 MHz, CDCl$_3$) δ −62.84; ESIMS m/z 377 ([M−H]$^−$).

Example 31

Preparation of trans-2,2-dibromo-3-(3,5-dichlorophenyl) cyclopropane-1-carboxylic acid (C155)

To a solution of trans-2,2-dibromo-3-(3,5-dichlorophenyl)cyclopropane-1-carbaldehyde (C156) (1.67 g, 4.48 mmol) in acetonitrile (15.36 mL) and water (2.5 mL) was added sodium hydrogen sulfite (3.26 g, 31.36 mmol). The resultant solution was cooled to 0° C., sodium chlorite (3.54 g, 17.92 mmol) was added slowly, and the solution was stirred for overnight while slowly warming to room temperature. The mixture was then diluted with aqueous hydrochloric acid solution (1 N) until the pH was equal to or less than 3. The mixture was then repeatedly extracted with ethyl acetate. The combined organic extracts were dried over sodium sulfate, filtered and concentrated under vacuum. Purification of the crude solid by flash column chromatography with 0-100% ethyl acetate/hexanes as eluent provided the title compound as a light brown solid (0.91 g, 52%): $^1$H NMR (400 MHz, CDCl$_3$) δ 7.36 (t, J=1.9 Hz, 1H), 7.17 (dd, J=1.9, 0.8 Hz, 2H), 3.39 (d, J=8.2 Hz, 1H), 2.91 (d, J=8.2 Hz, 1H); $^{13}$C NMR (101 MHz, CDCl$^3$) δ 172.15, 136.91, 135.25, 128.64, 127.29, 40.29, 37.32, 26.57; ESIMS m/z 386 ([M−H]$^−$).

Example 32

Preparation of trans-2,2-dibromo-3-(3,5-dichlorophenyl) cyclopropane-1-carbaldehyde (C156)

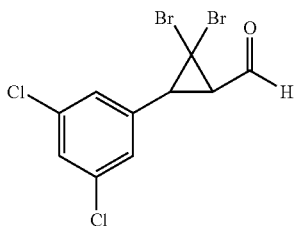 [SMILES: O=CC1C(c2cc(Cl)cc(Cl)c2)C1(Br)Br]

To a solution of (E)-1,3-dichloro-5-(3,3-diethoxyprop-1-en-1-yl)benzene (C150) (0.500 g, 1.817 mmol) in bromoform (12.1 mL) were added tetrabutylammonium hexafluorophosphate(V) (70.4 mg, 0.182 mmol) followed by the careful addition of solid sodium hydroxide (1454 mg, 36.3 mmol). The mixture was heated to 90° C. while stirring overnight. The mixture was diluted with dichloromethane and water and was extracted with additional dichloromethane. The organic layer was then dried over sodium sulfate, filtered, and concentrated. Purification by flash column chromatography using 0-100% ethyl acetate/hexanes as eluent provided an elutant which was then dissolved in acetone (4 mL) and aqueous hydrochloric acid (2 N)(1 mL, 2 mmol). The mixture was stirred overnight. The mixture was diluted with saturated sodium bicarbonate solution until the pH was greater than 7. The mixture was then extracted with diethyl ether and ethyl acetate, and the combined organic layers were dried over sodium sulfate and concentrated providing the dark brown product (0.03 g, 4%): $^1$H NMR (400 MHz, CDCl$_3$) δ 9.48 (d, J=4.0 Hz, 1H), 7.37 (t, J=1.9 Hz, 1H), 7.17 (dd, J=1.9, 0.7 Hz, 2H), 3.60-3.36 (m, 1H), 2.90 (dd, J=7.9, 4.0 Hz, 1H); $^{13}$C NMR (101 MHz, CDCl$_3$) δ 194.74, 136.55, 135.31, 128.76, 127.34, 42.34, 39.84, 26.05; ESIMS m/z 343 ([M−CHO]$^−$).

Example 33

Preparation of (1R,3R)-2,2-dichloro-3-(3,5-dichlorophenyl)-cyclopropane-1-carboxylic acid (C157)

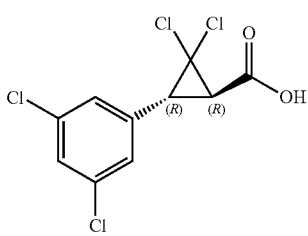

1$^{st}$ resolution: (R)-1-Phenylethanamine (6.49 g, 53.0 mmol) was slowly added to a stirred solution of rac-2,2-dichloro-3-(3,5-dichlorophenyl)cyclopropane-carboxylic acid) (32.45 g, 106 mmol) in acetone (106 mL). The resulting solution was stirred at 45° C. After a solid began to deposit, the mixture was placed at 5° C. for 4 hours. The solid was collected, washed with minimal cold acetone and dried. The white solid salt was diluted with ethyl acetate (100 mL) and washed with aqueous hydrochloric acid (1 N, 10 mL) and brine (30 mL). The organic layer was dried over sodium sulfate, filtered and concentrated to afford the title product as a white solid (10.33 g, 88% enantiomeric excess "ee").

2$^{nd}$ resolution: (R)-1-Phenylethanamine (3.4 g, 28 mmol) was slowly added to a stirred solution of rac-2,2-dichloro-3-(3,5-dichlorophenyl)cyclopropane-carboxylic acid) (10.33 g, 88% ee) in acetone (100 mL). After 2 hours, a solid was collected, washed with minimal cold acetone and dried. The solid was treated with aqueous hydrochloric acid to afford the title compound as a white solid (7.84 g, 97% ee, 24.2%): Specific Rotation: +47.4 (10 mg/mL in acetonitrile, 589 nm, 25.2° C.); $^1$H NMR (300 MHz, CDCl$_3$) δ 7.36 (t, J=1.9 Hz, 1H), 7.17 (dd, J=1.9, 0.7 Hz, 2H), 3.48-3.37 (m, 1H), 2.87 (d, J=8.3 Hz, 1H); $^{13}$C NMR (400 MHz, DMSO-d$_6$) δ 166.28, 136.40, 133.39, 127.27, 127.04, 61.36, 37.10, 35.98; ESIMS m/z 298.9 ([M−H]$^−$).

ee was determined by Chiral HPLC method as follows: Column: CHIRALPAK© ZWIX(+), particle size 3 μm, dimension 3 mm×150 mm, DAIC 511584; Mobile phase: 49% acetonitrile/49% methanol/water with 50 mM formic acid and diethylamine; Flow rate: 0.5 mL/min; Time: 9 min; Temperature: 25° C.

The following compounds were prepared in like manner to the procedure outlined in Example 33:

(1R,3R)-2,2-Dichloro-3-(3,4-dichlorophenyl)cyclopropane-1-carboxylic acid (C158)

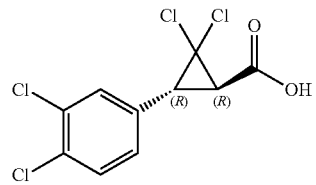

Isolated as a white solid (6.7 g, 30%, 96% ee). Analytical data are consistent with racemic acid C3.

(1R,3R)-2,2-Dichloro-3-(3-chloro-4-fluorophenyl) cyclopropane-1-carboxylic acid (C159)

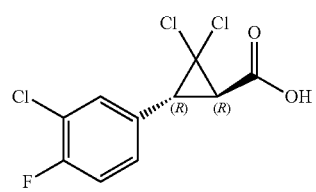

Isolated as a white solid (0.5 g, 13%, 99% ee). Analytical data are consistent with racemic acid C16.

145

(1R,3R)-2,2-Dichloro-3-(3,4,5-trichlorophenyl)cyclopropane-1-carboxylic acid (C160)

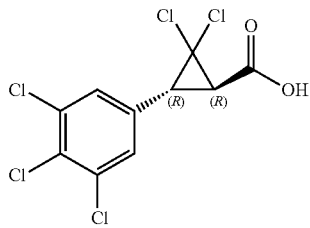

Isolated as a white solid (2 g, 29%, 99% ee). Analytical data are consistent with racemic acid C2.

Example 34

(1S,3S)-2,2-Dichloro-3-(3,5-dichlorophenyl)-cyclopropane-1-carboxylic acid (C161)

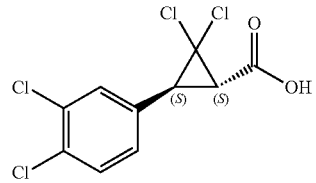

The mother liquor from the 1$^{st}$ R,R-acid resolution (from Example 33) was concentrated and dissolved in acetone (~100 mL) and warmed to 45° C. With swirling, (S)-1-phenylethanamine (5.0 g, 41.2 mmol, 0.8 eq) was added. The resulting solution was stirred at 45° C. After a solid began to deposit, the mixture was placed at 5° C. for 2 hours. A solid was collected, washed with minimal cold acetone and vacuum-dried at 35° C. The solid was treated with aqueous hydrochloric acid to provide the free 5,5-acid as a white solid (9.87 g, 59%, 85% ee). A second resolution of the 85% ee combined 5,5-acid (13.45 g, 41.7 mmol, 85% ee) using the same procedure with (S)-1-phenylethanamine (3.8 g, 31.3 mmol, 0.75 eq) provided the 5,5-acid as a white solid (8.53 g, 26%, 99% ee). Specific Rotation: −51.9 (10 mg/mL in acetonitrile, 589 nm, 25.2° C.). Analytical data are consistent with racemic acid C1 ee was determined by Chiral HPLC method as follows: Column: CHIRALPAK© ZWIX(+), particle size 3 μm, dimension 3 mm×150 mm, DAIC 511584; Mobile phase: 49% acetonitrile/49% methanol/water with 50 mM formic acid and diethylamine; Flow rate: 0.5 mL/min; Time: 9 min; Temperature: 25° C.

The following compounds were prepared in like manner to the procedure outlined in Example 34:

146

(1S,3S)-2,2-Dichloro-3-(3,4-dichlorophenyl)cyclopropane-1-carboxylic acid (C162)

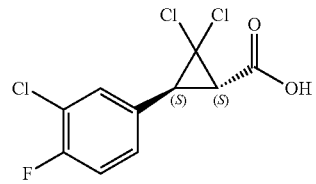

Isolated as a as a white solid (7 g, 35%, 98% ee). Analytical data are consistent with racemic acid C3.

(1S,3S)-2,2-Dichloro-3-(3-chloro-4-fluorophenyl)cyclopropane-1-carboxylic acid (C163)

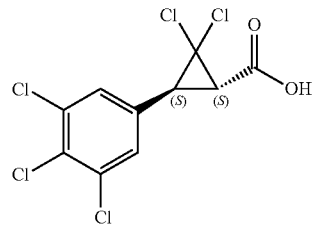

Isolated as a white solid (0.64 g, 27%, 98% ee). Analytical data are consistent with racemic acid C16.

(1S,3S)-2,2-Dichloro-3-(3,4,5-trichlorophenyl)cyclopropane-1-carboxylic acid (C164)

Isolated as a white solid (0.75 g, 41%, 99% ee). Analytical data are consistent with racemic acid C2.

It is recognized that some reagents and reaction conditions may not be compatible with certain functionalities that may be present in certain molecules of Formula One or certain molecules used in the preparation of certain molecules of Formula One. In such cases, it may be necessary to employ standard protection and deprotection protocols comprehensively reported in the literature and well known to a person skilled in the art. In addition, in some cases it may be necessary to perform further routine synthetic steps not described herein to complete the synthesis of desired molecules. A person skilled in the art will also recognize that it may be possible to achieve the synthesis of desired molecules by performing some of the steps of the synthetic routes in a different order to that described. A person skilled in the art will also recognize that it may be possible to perform standard functional group interconversions or substitution reactions on desired molecules to introduce or modify substituents.

Biological Assays

The following bioassays against Beet Armyworm (*Spodoptera exigua*), Cabbage Looper (*Trichoplusia ni*), Green Peach Aphid (*Myzus persicae*), and Yellow Fever Mosquito (*Aedes aegypti*), are included herein due to the damage they inflict. Furthermore, the Beet Armyworm and Cabbage Looper are two good indicator species for a broad range of chewing pests. Additionally, the Green Peach Aphid is a good indicator species for a broad range of sap-feeding pests. The results with these three indicator species along with the Yellow Fever Mosquito show the broad usefulness of the molecules of Formula One in controlling pests in Phyla Arthropoda, Mollusca, and Nematoda (Drewes et al.)

Example A

Bioassays on Beet Armyworm (*Spodoptera exigua*, LAPHEG) ("BAW"), and Cabbage Looper (*Trichoplusia ni*, TRIPNI) ("CL")

Beet armyworm is a serious pest of economic concern for alfalfa, asparagus, beets, citrus, corn, cotton, onions, peas, peppers, potatoes, soybeans, sugar beets, sunflowers, tobacco, and tomatoes, among other crops. It is native to Southeast Asia but is now found in Africa, Australia, Japan, North America, and Southern Europe. The larvae may feed in large swarms causing devastating crop losses. It is known to be resistant to several pesticides.

Cabbage looper is a serious pest found throughout the world. It attacks alfalfa, beans, beets, broccoli, Brussel sprouts, cabbage, cantaloupe, cauliflower, celery, collards, cotton, cucumbers, eggplant, kale, lettuce, melons, mustard, parsley, peas, peppers, potatoes, soybeans, spinach, squash, tomatoes, turnips, and watermelons, among other crops. This species is very destructive to plants due to its voracious appetite. The larvae consume three times their weight in food daily. The feeding sites are marked by large accumulations of sticky, wet, fecal material, which may contribute to higher disease pressure thereby causing secondary problems on the plants in the site. It is known to be resistant to several pesticides.

Consequently, because of the above factors control of these pests is important. Furthermore, molecules that control these pests (BAW and CL), which are known as chewing pests, will be useful in controlling other pests that chew on plants.

Certain molecules disclosed in this document were tested against BAW and CL using procedures described in the following examples. In the reporting of the results, the "BAW & CL Rating Table" was used (See Table Section).

Bioassays on BAW

Bioassays on BAW were conducted using a 128-well diet tray assay. One to five second instar BAW larvae were placed in each well (3 mL) of the diet tray that had been previously filled with approximately 1.5 mL of artificial diet to which 50 μg/cm² of the test molecule (dissolved in 50 μL of 90:10 acetone-water mixture) had been applied (to each of eight wells) and then allowed to dry. Trays were covered with a clear self-adhesive cover, vented to allow gas exchange, and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Bioassays on CL

Bioassays on CL were conducted using a 128-well diet tray assay, one to five second instar CL larvae were placed in each well (3 mL) of the diet tray that had been previously filled with 1 mL of artificial diet to which 50 μg/cm² of the test molecule (dissolved in 50 μL of 90:10 acetone-water mixture) had been applied (to each of eight wells) and then allowed to dry. Trays were covered with a clear self-adhesive cover, vented to allow gas exchange, and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Example B

Bioassays on Green Peach Aphid (*Myzus persicae*, MYZUPE) ("GPA")

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the night-shade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other crops. GPA also attacks many ornamental crops such as carnation, chrysanthemum, flowering white cabbage, poinsettia, and roses. GPA has developed resistance to many pesticides. Currently, it is a pest that has the third largest number of reported cases of insect resistance (Sparks et al.). Consequently, because of the above factors control of this pest is important. Furthermore, molecules that control this pest (GPA), which is known as a sap-feeding pest, are useful in controlling other pests that feed on the sap from plants.

Certain molecules disclosed in this document were tested against GPA using procedures described in the following example. In the reporting of the results, the "GPA & YFM Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test molecules (2 mg) were dissolved in 2 mL of acetone/methanol (1:1) solvent, forming stock solutions of 1000 ppm test molecule. The stock solutions were diluted 5× with 0.025% Tween 20 in water to obtain the solution at 200 ppm test molecule. A hand-held aspirator-type sprayer was used for spraying a solution to both sides of cabbage leaves until runoff. Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent control was measured using Abbott's correction formula (W. S. Abbott, "A Method of Computing the Effectiveness of an Insecticide" J. Econ. Entomol. 18 (1925), pp. 265-267) as follows. Corrected % Control=100*(X−Y)/X where X=No. of live aphids on solvent check plants and Y=No. of live aphids on treated plants. The results are indicated in the table entitled "Table ABC: Biological Results" (See Table Section).

Example C

Bioassays on Yellow Fever Mosquito (*Aedes aegypti*, AEDSAE) ("YFM")

YFM prefers to feed on humans during the daytime and is most frequently found in or near human habitations. YFM is a vector for transmitting several diseases. It is a mosquito that can spread the dengue fever and yellow fever viruses. Yellow fever is the second most dangerous mosquito-borne disease after malaria. Yellow fever is an acute viral hemorrhagic disease and up to 50% of severely affected persons without treatment will die from yellow fever. There are an estimated 200,000 cases of yellow fever, causing 30,000 deaths worldwide each year. Dengue fever is a nasty, viral disease; it is sometimes called "breakbone fever" or "breakheart fever" because of the intense pain it can produce. Dengue fever kills about 20,000 people annually. Consequently, because of the above factors control of this pest is important. Furthermore, molecules that control this pest (YFM), which is known as a sucking pest, are useful in controlling other pests that cause human and animal suffering.

Certain molecules disclosed in this document were tested against YFM using procedures described in the following paragraph. In the reporting of the results, the "GPA & YFM Rating Table" was used (See Table Section).

Master plates containing 400 µg of a molecule dissolved in 100 µL of dimethyl sulfoxide (DMSO) (equivalent to a 4000 ppm solution) are used. A master plate of assembled molecules contains 15 µL per well. To this plate, 135 µL of a 90:10 water/acetone mixture is added to each well. A robot is programmed to dispense 15 µL aspirations from the master plate into an empty 96-well shallow plate ("daughter" plate). There are 6 reps ("daughter" plates) created per master. The created "daughter" plates are then immediately infested with YFM larvae.

The day before plates are to be treated, mosquito eggs are placed in Millipore water containing liver powder to begin hatching (4 g. into 400 mL). After the "daughter" plates are created using the robot, they are infested with 220 µL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality. The results are indicated in the table entitled "Table ABC: Biological Results" (See Table Section).

Agriculturally Acceptable Acid Addition Salts, Salt Derivatives, Solvates, Ester Derivatives, Polymorphs, Isotopes, and Radionuclides Molecules of Formula One may be formulated into agriculturally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxyl-methanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative may be prepared by contacting a free base with a sufficient amount of the desired acid to produce a salt. A free base may be regenerated by treating the salt with a suitable dilute aqueous base solution such as dilute aqueous sodium hydroxide, potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One containing an acid functionality may be made into ester derivatives. These ester derivatives can then be applied in the same manner as the molecules disclosed in this document are applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2$H (also known as deuterium) or $^3$H (also known as tritium) in place of $^1$H. Molecules of Formula One may be made with different radionuclides. Of particular importance are molecules having $^{14}$C (also known as radiocarbon). Molecules of Formula One having deuterium, tritium, or $^{14}$C may be used in biological studies allowing tracing in chemical and physiological processes and half-life studies, as well as, MoA studies.

Combinations

In another embodiment of this invention, molecules of Formula One may be used in combination (such as, in a compositional mixture, or a simultaneous or sequential application) with one or more active ingredients.

In another embodiment of this invention, molecules of Formula One may be used in combination (such as, in a compositional mixture, or a simultaneous or sequential application) with one or more active ingredients each having a MoA that is the same as, similar to, but more likely—different from, the MoA of the molecules of Formula One.

In another embodiment, molecules of Formula One may be used in combination (such as, in a compositional mixture, or a simultaneous or sequential application) with one or more molecules having acaricidal, algicidal, avicidal, bactericidal, fungicidal, herbicidal, insecticidal, molluscicidal, nematicidal, rodenticidal, and/or virucidal properties.

In another embodiment, the molecules of Formula One may be used in combination (such as, in a compositional mixture, or a simultaneous or sequential application) with one or more molecules that are antifeedants, bird repellents, chemosterilants, herbicide safeners, insect attractants, insect repellents, mammal repellents, mating disrupters, plant activators, plant growth regulators, and/or synergists.

In another embodiment, molecules of Formula One may also be used in combination (such as in a compositional mixture, or a simultaneous or sequential application) with one or more biopesticides.

In another embodiment, in a pesticidal composition combinations of a molecule of Formula One and an active ingredient may be used in a wide variety of weight ratios. For example, in a two-component mixture, the weight ratio of a molecule of Formula One to an active ingredient, the weight ratios in Table B may be used. However, in general, weight ratios less than about 10:1 to about 1:10 are preferred. It is also preferred sometimes to use a three, four, five, six, seven, or more, component mixture comprising a molecule of Formula One and an additional two or more active ingredients.

Weight ratios of a molecule of Formula One to an active ingredient may also be depicted as X:Y; wherein X is the parts by weight of a molecule of Formula One and Y is the parts by weight of active ingredient. The numerical range of the parts by weight for X is $0<X\leq100$ and the parts by weight for Y is $0<Y\leq100$ and is shown graphically in TABLE C. By way of non-limiting example, the weight ratio of a molecule of Formula One to an active ingredient may be 20:1.

Ranges of weight ratios of a molecule of Formula One to an active ingredient may be depicted as $X_1:Y_1$ to $X_2:Y_2$, wherein X and Y are defined as above.

In one embodiment, the range of weight ratios may be $X_1:Y_1$ to $X_2:Y_2$, wherein $X_1>Y_1$ and $X_2<Y_2$. By way of non-limiting example, the range of a weight ratio of a molecule of Formula One to an active ingredient may be between 3:1 and 1:3, inclusive of the endpoints.

In another embodiment, the range of weight ratios may be $X_1:Y_1$ to $X_2:Y_2$, wherein $X_1>Y_1$ and $X_2>Y_2$. By way of non-limiting example, the range of weight ratio of a molecule of Formula One to an active ingredient may be between 15:1 and 3:1, inclusive of the endpoints.

In another embodiment, the range of weight ratios may be $X_1:Y_1$ to $X_2:Y_2$, wherein $X_1<Y_1$ and $X_2<Y_2$. By way of non-limiting example, the range of weight ratios of a molecule of Formula One to an active ingredient may be between about 1:3 and about 1:20, inclusive of the endpoints.

Formulations

A pesticide is many times not suitable for application in its pure form. It is usually necessary to add other substances so that the pesticide may be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions.

Pesticides are applied most often as aqueous suspensions or emulsions prepared from concentrated formulations of such pesticides. Such water-soluble, water-suspendable, or emulsifiable formulations are either solids, usually known as wettable powders, water dispersible granules, liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may, also be added to increase the density and viscosity of the aqueous carrier. It is often most effective to grind and mix the pesticide at the same time by preparing the aqueous mixture and homogenizing it in an implement such as a sand mill, ball mill, or piston-type homogenizer. The pesticide in suspension might be microencapsulated in plastic polymer.

Oil dispersions (OD) comprise suspensions of organic solvent-insoluble pesticides finely dispersed in a mixture of organic solvent and emulsifiers at a concentration in the range from about 2% to about 50% by weight. One or more pesticide might be dissolved in the organic solvent. Useful organic solvents include aromatics, especially xylenes and petroleum fractions, especially the high-boiling naphthalenic and olefinic portions of petroleum such as heavy aromatic naphtha. Other solvents may include vegetable oils, seed oils, and esters of vegetable and seed oils. Suitable emulsifiers for oil dispersions are selected from conventional anionic and non-ionic surfactants. Thickeners or gelling agents are added in the formulation of oil dispersions to modify the rheology or flow properties of the liquid and to prevent separation and settling of the dispersed particles or droplets.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier, which has been pre-formed to the appropriate particle size, in the range of from about 0.5 mm to about 3 mm. Such compositions may also be formulated by making a dough or paste of the carrier and molecule, and then crushing and drying to obtain the desired granular particle size. Another form of granules is a water emulsifiable granule (EG). It is a formulation consisting of granules to be applied as a conventional oil-in-water emulsion of the active ingredient(s), either solubilized or diluted in an organic solvent, after disintegration and dissolution in water. Water emulsifiable granules comprise one or several active ingredient(s), either solubilized or diluted in a suitable organic solvent that is (are) absorbed in a water soluble polymeric shell or some other type of soluble or insoluble matrix.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. Dusts may be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions, the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait, they also consume the pesticide. Baits may take the form of granules, gels, flowable powders, liquids, or solids. Baits may be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings, or in special chambers.

Pesticides may be microencapsulated by suspending the pesticide particles or droplets in plastic polymers of various types. By altering, the chemistry of the polymer or by changing factors in the processing, microcapsules may be formed of various sizes, solubility, wall thicknesses, and degrees of penetrability. These factors govern the speed with which the active ingredient within is released, which in turn, affects the residual performance, speed of action, and odor of the product. The microcapsules might be formulated as suspension concentrates or water dispersible granules.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one molecule which is agriculturally active, and is individually coated with a monolamellar or oligolamellar layer comprising: (1) at least one non-ionic lipophilic surface-active agent, (2) at least one non-ionic hydrophilic surface-active agent, and (3) at least one ionic surface-active agent, wherein the globules having a mean particle diameter of less than 800 nanometers.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance that adsorbs onto the surface of particles, helps to preserve the state of dispersion of the particles, and prevents them from reaggregating. Dispersing agents are added to agrochemical formulations to facilitate dispersion and suspension during manufacture, and to ensure the particles redisperse into water in a spray tank. They are widely used in wettable powders, suspension concentrates, and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium-naphthalene-sulfonate-formaldehyde-condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol-ethoxylate-phosphate-esters; aliphatic alcohol ethoxylates; alkyl ethoxylates; EO-PO block copolymers; and graft copolymers.

An emulsifying agent is a substance that stabilizes a suspension of droplets of one liquid phase in another liquid phase. Without the emulsifying agent, the two liquids would separate into two immiscible liquid phases. The most commonly used emulsifier blends contain an alkylphenol or an aliphatic alcohol with twelve or more ethylene oxide units and the oil-soluble calcium salt of dodecylbenzenesulfonic acid. A range of hydrophile-lipophile balance ("HLB") values from about 8 to about 18 will normally provide good stable emulsions. Emulsion stability can sometimes be improved by the addition of a small amount of an EO-PO block copolymer surfactant.

A solubilizing agent is a surfactant that will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; and aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules, and water-dispersible granules.

Organic solvents are used mainly in the formulation of emulsifiable concentrates, oil-in-water emulsions, suspoemulsions, oil dispersions, and ultra-low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, oil dispersions, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate and oil dispersion formulations using clays and silicas. Examples of these types of materials, include, but are not limited to, montmorillonite, bentonite, magnesium aluminum silicate, and attapulgite. Water-soluble polysaccharides in water based suspension concentrates have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); and hydroxyethyl cellulose (HEC). Other types of anti-settling agents are based on modified starches, polyacrylates, polyvinyl alcohol, and polyethylene oxide. Another good anti-settling agent is xanthan gum.

Microorganisms can cause spoilage of formulated products. Therefore, preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

Applications

Molecules of Formula One may be applied to any locus. Particular loci to apply such molecules include loci where alfalfa, almonds, apples, barley, beans, canola, corn, cotton, crucifers, flowers, fodder species (Rye Grass, Sudan Grass, Tall Fescue, Kentucky Blue Grass, and Clover), fruits, lettuce, oats, oil seed crops, oranges, peanuts, pears, peppers, potatoes, rice, sorghum, soybeans, strawberries, sugarcane, sugarbeets, sunflowers, tobacco, tomatoes, wheat (for example, Hard Red Winter Wheat, Soft Red Winter Wheat, White Winter Wheat, Hard Red Spring Wheat, and Durum Spring Wheat), and other valuable crops are growing or the seeds thereof are going to be planted.

Molecules of Formula One may also be applied where plants, such as crops, are growing and where there are low levels (even no actual presence) of pests that can commercially damage such plants. Applying such molecules in such locus is to benefit the plants being grown in such locus. Such benefits, may include, but are not limited to: helping the plant grow a better root system; helping the plant better withstand stressful growing conditions; improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

Molecules of Formula One may be applied with ammonium sulfate when growing various plants as this may provide additional benefits.

Molecules of Formula One may be applied on, in, or around plants genetically modified to express specialized traits, such as *Bacillus thuringiensis* (for example, Cry1Ab, Cry1Ac, Cry1Fa, Cry1A.105, Cry2Ab, Vip3A, mCry3A, Cry3Ab, Cry3Bb, Cry34Ab1/Cry35Ab1), other insecticidal toxins, or those expressing herbicide tolerance, or those with "stacked" foreign genes expressing insecticidal toxins, herbicide tolerance, nutrition-enhancement, or any other beneficial traits.

Molecules of Formula One may be applied to the foliar and/or fruiting portions of plants to control pests. Either such molecules will come in direct contact with the pest, or the pest will consume such molecules when eating the plant or while extracting sap or other nutrients from the plant.

Molecules of Formula One may also be applied to the soil, and when applied in this manner, root and stem feeding pests may be controlled. The roots may absorb such molecules thereby taking it up into the foliar portions of the plant to control above ground chewing and sap feeding pests.

Systemic movement of pesticides in plants may be utilized to control pests on one portion of the plant by applying (for example by spraying a locus) a molecule of Formula One to a different portion of the plant. For example, control of foliar-feeding insects may be achieved by drip irrigation or furrow application, by treating the soil with for example pre- or post-planting soil drench, or by treating the seeds of a plant before planting.

Molecules of Formula One may be used with baits. Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait.

Molecules of Formula One may be encapsulated inside, or placed on the surface of a capsule. The size of the capsules can range from nanometer size (about 100-900 nanometers in diameter) to micrometer size (about 10-900 microns in diameter).

Molecules of Formula One may be applied to eggs of pests. Because of the unique ability of the eggs of some pests to resist certain pesticides, repeated applications of such molecules may be desirable to control newly emerged larvae.

Molecules of Formula One may be applied as seed treatments. Seed treatment may be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide tolerance, such as "Roundup Ready" seed, or those with "stacked" foreign genes expressing insecticidal toxins, herbicide tolerance, nutrition-enhancement, drought tolerance, or any other beneficial traits. Furthermore, such seed treatments with molecules of Formula One may further enhance the ability of a plant to withstand stressful growing conditions better. This results in a healthier, more vigorous plant, which can lead to higher yields at harvest time. Generally, about 1 gram of such molecules to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits. Molecules of Formula One may be applied with one or more active ingredients in a soil amendment.

Molecules of Formula One may be used for controlling endoparasites and ectoparasites in the veterinary medicine sector or in the field of non-human-animal keeping. Such molecules may be applied by oral administration in the form of, for example, tablets, capsules, drinks, granules, by dermal application in the form of, for example, dipping, spraying, pouring on, spotting on, and dusting, and by parenteral administration in the form of, for example, an injection.

Molecules of Formula One may also be employed advantageously in livestock keeping, for example, cattle, chickens, geese, goats, pigs, sheep, and turkeys. They may also be employed advantageously in pets such as, horses, dogs, and cats. Particular pests to control would be flies, fleas, and ticks that are bothersome to such animals. Suitable formulations are administered orally to the animals with the drinking water or feed. The dosages and formulations that are suitable depend on the species.

Molecules of Formula One may also be used for controlling parasitic worms, especially of the intestine, in the animals listed above.

Molecules of Formula One may also be employed in therapeutic methods for human health care. Such methods include, but are limited to, oral administration in the form of, for example, tablets, capsules, drinks, granules, and by dermal application.

Molecules of Formula One may also be applied to invasive pests. Pests around the world have been migrating to new environments (for such pest) and thereafter becoming a new invasive species in such new environment. Such molecules may also be used on such new invasive species to control them in such new environments.

Before a pesticide may be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

Molecules according to Formula One may be tested to determine its efficacy against pests. Furthermore, mode of action studies may be conducted to determine if said molecule has a different mode of action than other pesticides. Thereafter, such acquired data may be disseminated, such as by the internet, to third parties.

The Headings in this Document are for Convenience Only and Must not be Used to Interpret any Portion Hereof.

Tables

TABLE B

Weight Ratios
Molecule of the Formula One:active ingredient

100:1 to 1:100
50:1 to 1:50
20:1 to 1:20
10:1 to 1:10
5:1 to 1:5
3:1 to 1:3
2:1 to 1:2
1:1

TABLE C

| active ingredient (Y) Parts by weight | 1 | 2 | 3 | 5 | 10 | 15 | 20 | 50 | 100 |
|---|---|---|---|---|---|---|---|---|---|
| 100 | X, Y | | X, Y | | X, Y | | | | |
| 50 | X, Y | X, Y | X, Y | | | X, Y | X, Y | | |
| 20 | X, Y | | X, Y | X, Y | | X, Y | | X, Y | |
| 15 | X, Y | X, Y | | | | | X, Y | X, Y | X, Y |
| 10 | X, Y | | X, Y | | | | | | |
| 5 | X, Y | X, Y | X, Y | | | X, Y | | | |
| 3 | X, Y | X, Y | | X, Y | X, Y | | X, Y | X, Y | X, Y |
| 2 | X, Y | | X, Y | X, Y | | X, Y | | X, Y | |
| 1 | X, Y | X, Y | X, Y | X, Y | X, Y | X, Y | X, Y | X, Y | X, Y | molecule of Formula One (X) Parts by weight

TABLE 2

Structure and preparation method for F and PF Series molecules

| No. | Structure | Prep.* |
|---|---|---|
| F1 | 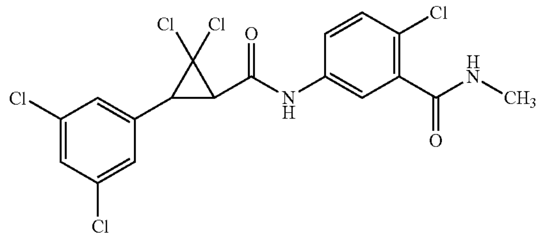 [SMILES: CNC(=O)c1cc(NC(=O)C2C(c3cc(Cl)cc(Cl)c3)C2(Cl)Cl)ccc1Cl] | 13 |
| F2 | 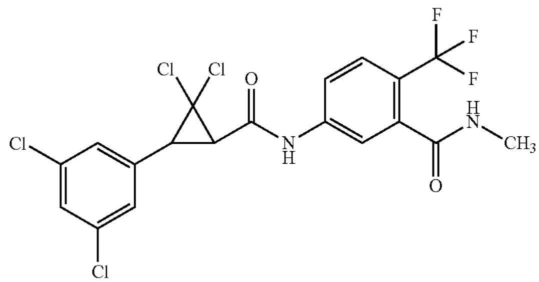 [SMILES: CNC(=O)c1cc(NC(=O)C2C(c3cc(Cl)cc(Cl)c3)C2(Cl)Cl)ccc1C(F)(F)F] | 13 |
| F3 | 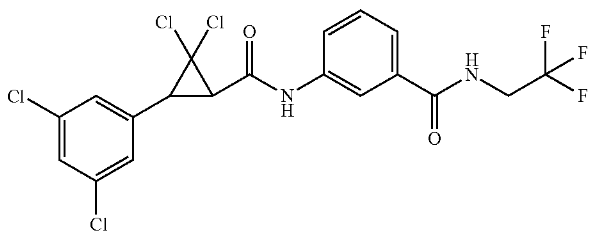 [SMILES: O=C(NCC(F)(F)F)c1cccc(NC(=O)C2C(c3cc(Cl)cc(Cl)c3)C2(Cl)Cl)c1] | 13 |
| F4 | 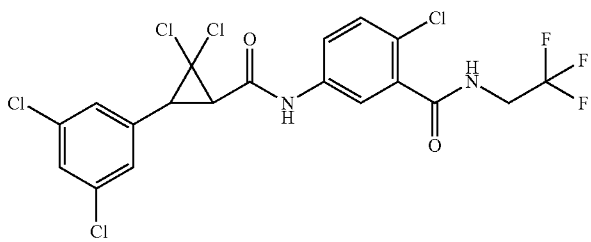 | 13 |
| F5 | 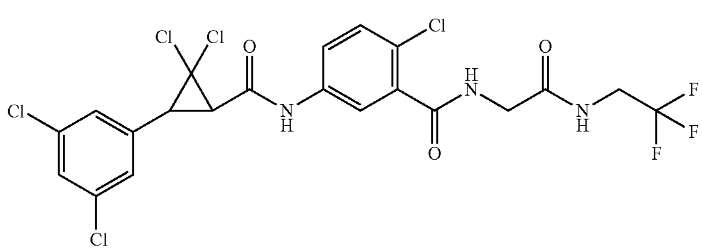 [SMILES: O=C(CNC(=O)c1cc(NC(=O)C2C(c3cc(Cl)cc(Cl)c3)C2(Cl)Cl)ccc1Cl)NCC(F)(F)F] | 13 |
| F6 | 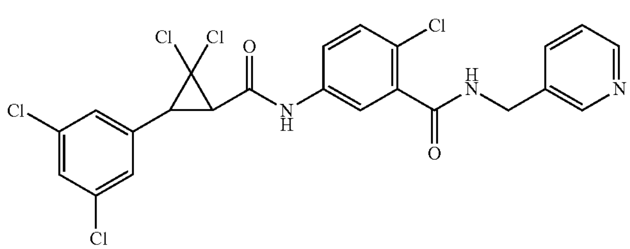 | 13 |

TABLE 2-continued

Structure and preparation method for F and PF Series molecules

| No. | Structure | Prep.* |
|---|---|---|
| F7 | 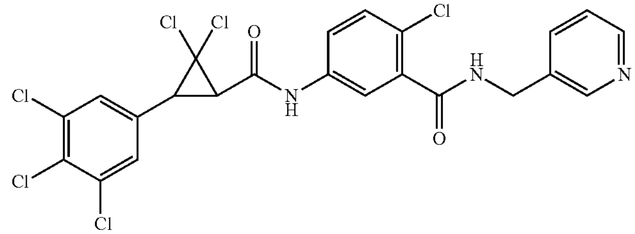 [SMILES: O=C(NCc1cccnc1)c1cc(NC(=O)C2C(c3cc(Cl)c(Cl)c(Cl)c3)C2(Cl)Cl)ccc1Cl] | 13 |
| F8 | 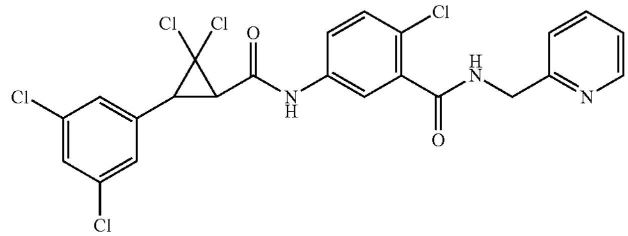 | 13 |
| F9 | 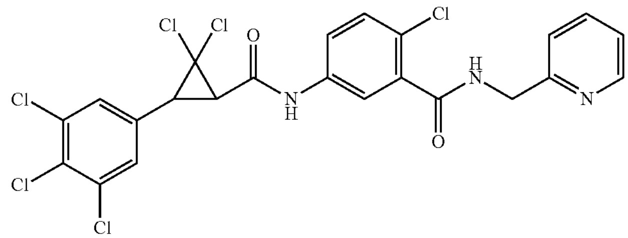 [SMILES: O=C(NCc1ccccn1)c1cc(NC(=O)C2C(c3cc(Cl)c(Cl)c(Cl)c3)C2(Cl)Cl)ccc1Cl] | 13 |
| F10 | 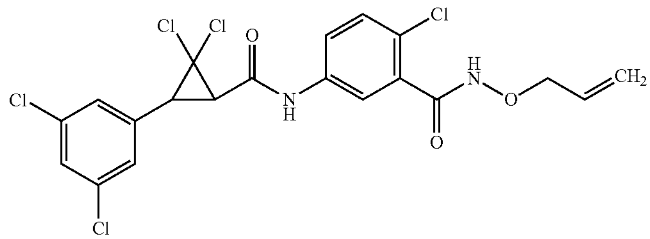 [SMILES: C=CCONC(=O)c1cc(NC(=O)C2C(c3cc(Cl)cc(Cl)c3)C2(Cl)Cl)ccc1Cl] | 13 |
| F11 | 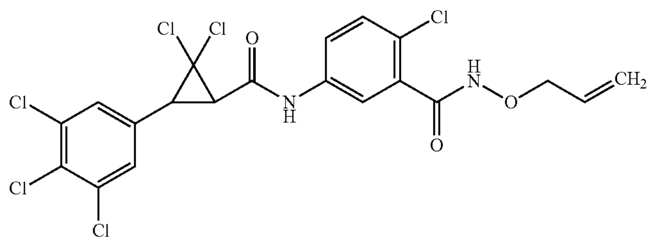 [SMILES: C=CCONC(=O)c1cc(NC(=O)C2C(c3cc(Cl)c(Cl)c(Cl)c3)C2(Cl)Cl)ccc1Cl] | 13 |
| F12 | 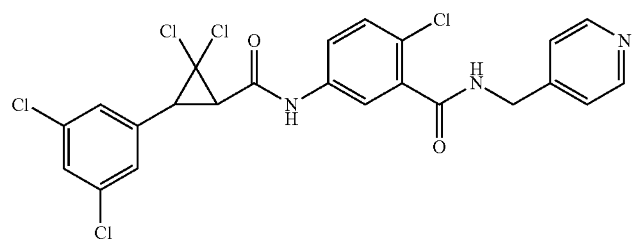 [SMILES: O=C(NCc1ccncc1)c1cc(NC(=O)C2C(c3cc(Cl)cc(Cl)c3)C2(Cl)Cl)ccc1Cl] | 13 |

TABLE 2-continued

Structure and preparation method for F and PF Series molecules

| No. | Structure | Prep.* |
|---|---|---|
| F13 | 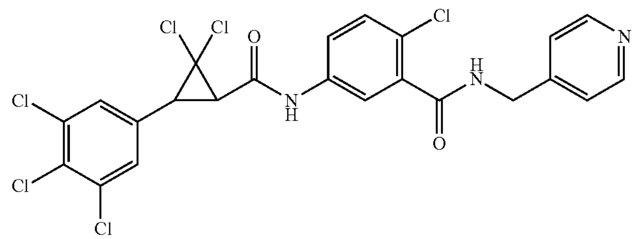 | 13 |
| F14 | 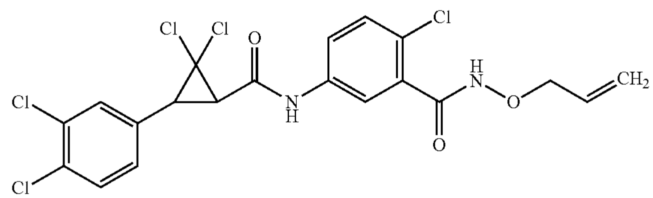 [SMILES: C=CCONC(=O)c1cc(NC(=O)C2C(c3ccc(Cl)c(Cl)c3)C2(Cl)Cl)ccc1Cl] | 13 |
| F15 | 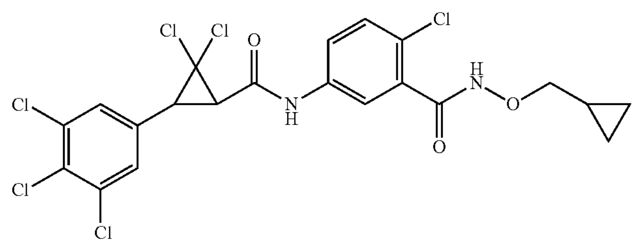 | 13 |
| F16 | 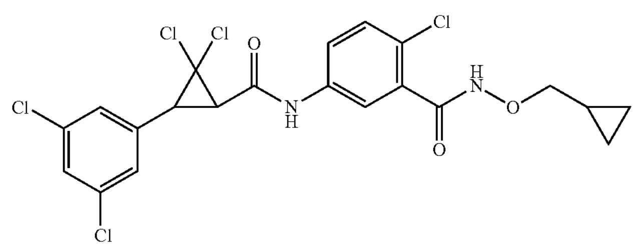 | 13 |
| F17 | 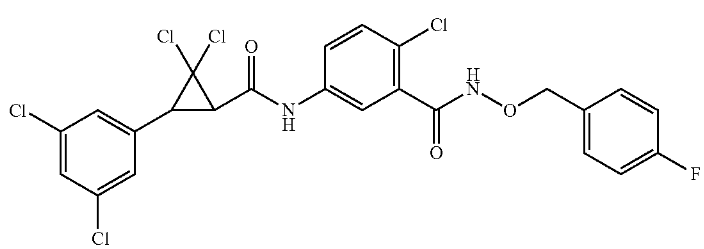 [SMILES: O=C(NOCc1ccc(F)cc1)c1cc(NC(=O)C2C(c3cc(Cl)cc(Cl)c3)C2(Cl)Cl)ccc1Cl] | 13 |
| F18 | 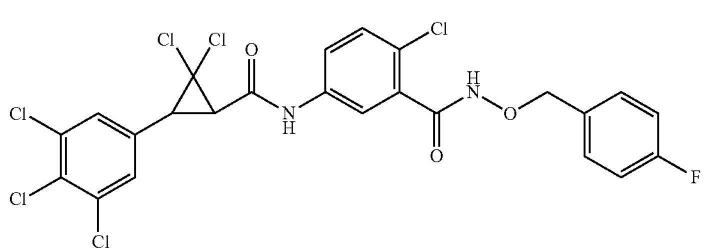 | 13 |

TABLE 2-continued

Structure and preparation method for F and PF Series molecules

| No. | Structure | Prep.* |
|---|---|---|
| F19 | 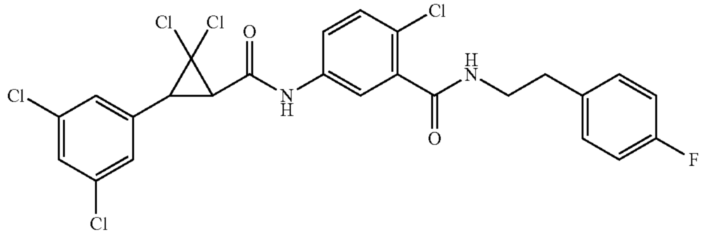 [SMILES: O=C(NCCc1ccc(F)cc1)c1cc(NC(=O)C2C(c3cc(Cl)cc(Cl)c3)C2(Cl)Cl)ccc1Cl] | 13 |
| F20 | 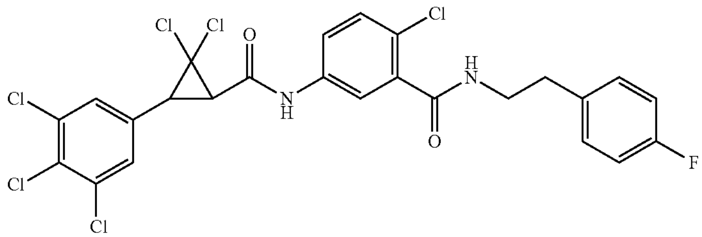 | 13 |
| F21 | 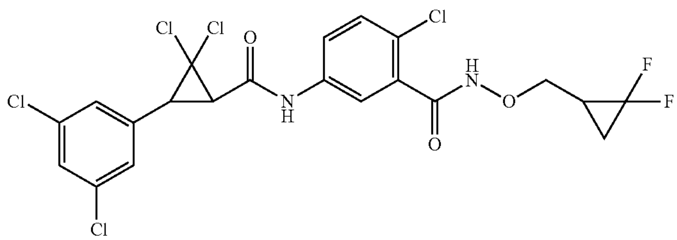 [SMILES: O=C(NOCC1CC1(F)F)c1cc(NC(=O)C2C(c3cc(Cl)cc(Cl)c3)C2(Cl)Cl)ccc1Cl] | 13 |
| F22 | 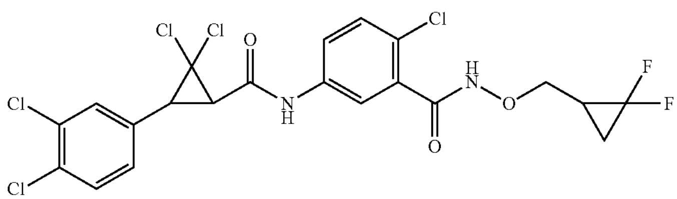 [SMILES: O=C(NOCC1CC1(F)F)c1cc(NC(=O)C2C(c3ccc(Cl)c(Cl)c3)C2(Cl)Cl)ccc1Cl] | 13 |
| F23 | 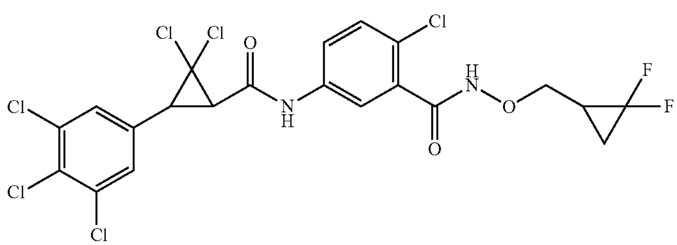 [SMILES: O=C(NOCC1CC1(F)F)c1cc(NC(=O)C2C(c3cc(Cl)c(Cl)c(Cl)c3)C2(Cl)Cl)ccc1Cl] | 13 |
| F24 | 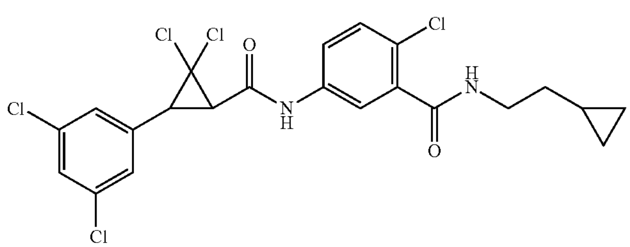 | 13 |

TABLE 2-continued
Structure and preparation method for F and PF Series molecules
| No. | Structure | Prep.* |
|---|---|---|
| F25 | 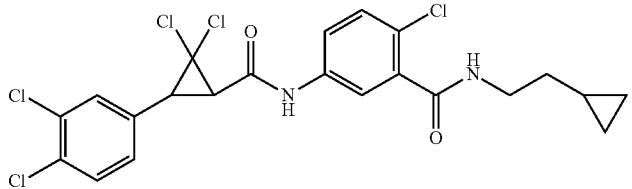 [SMILES: O=C(NCCC1CC1)c1cc(NC(=O)C2C(c3ccc(Cl)c(Cl)c3)C2(Cl)Cl)ccc1Cl] | 13 |
| F26 | 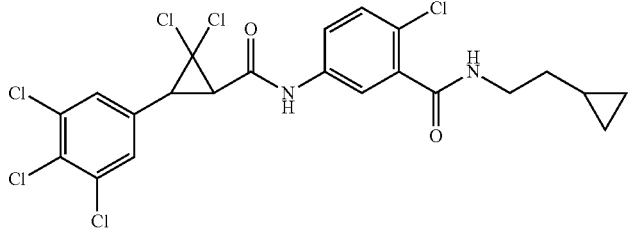 | 13 |
| F27 | 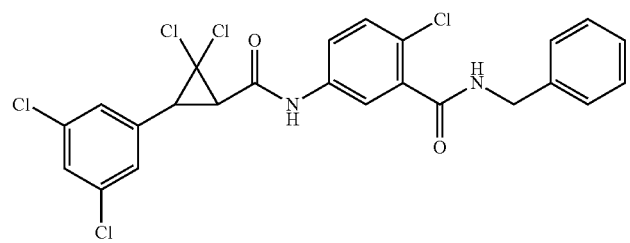 | 14 |
| F28 | 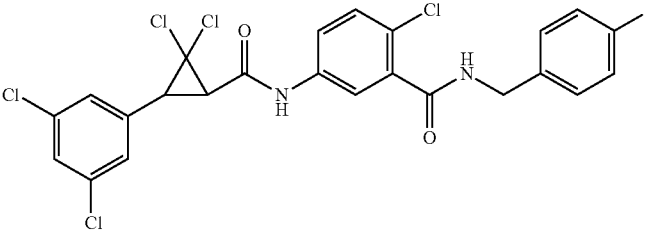 | 14 |
| F29 | 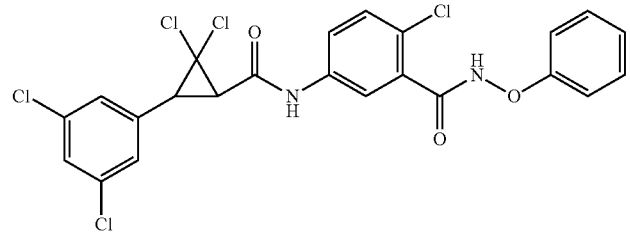 | 15 |
| F30 | 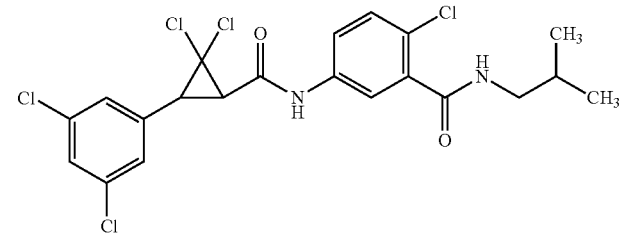 [SMILES: CC(C)CNC(=O)c1cc(NC(=O)C2C(c3cc(Cl)cc(Cl)c3)C2(Cl)Cl)ccc1Cl] | 16 |

TABLE 2-continued

Structure and preparation method for F and PF Series molecules

| No. | Structure | Prep.* |
|---|---|---|
| F31 | 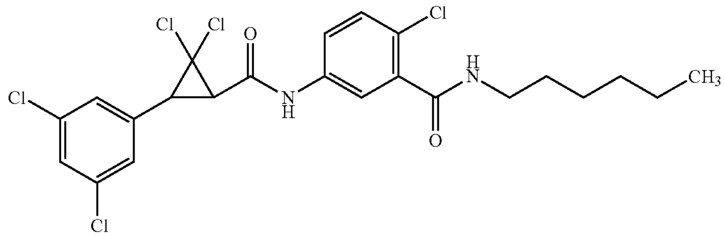 [SMILES: CCCCCCNC(=O)c1cc(NC(=O)C2C(c3cc(Cl)cc(Cl)c3)C2(Cl)Cl)ccc1Cl] | 16 |
| F32 | 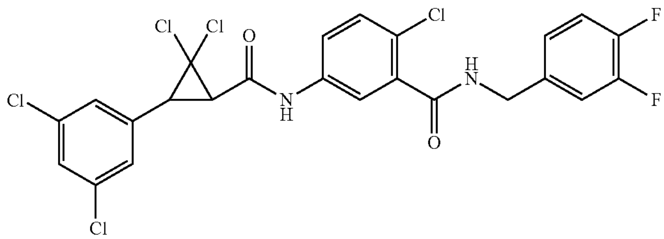 [SMILES: O=C(NCc1ccc(F)c(F)c1)c1cc(NC(=O)C2C(c3cc(Cl)cc(Cl)c3)C2(Cl)Cl)ccc1Cl] | 16 |
| F33 | 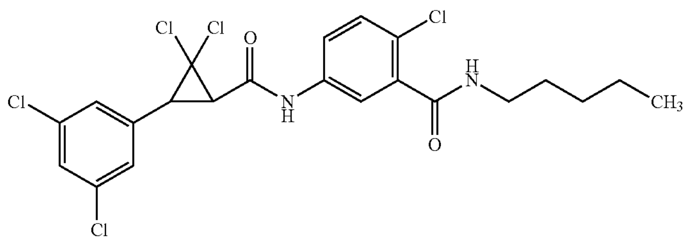 | 16 |
| F34 | 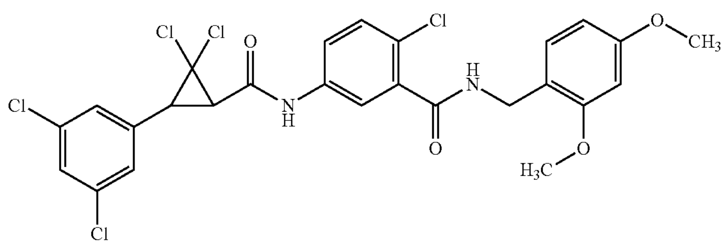 [SMILES: COc1ccc(CNC(=O)c2cc(NC(=O)C3C(c4cc(Cl)cc(Cl)c4)C3(Cl)Cl)ccc2Cl)c(OC)c1] | 16 |
| F35 | 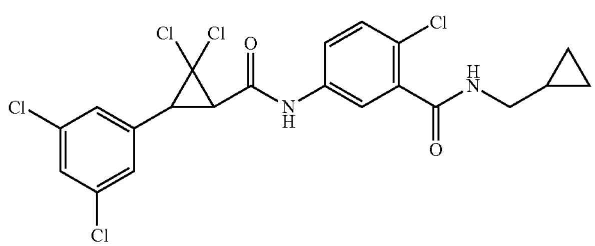 [SMILES: O=C(NCC1CC1)c1cc(NC(=O)C2C(c3cc(Cl)cc(Cl)c3)C2(Cl)Cl)ccc1Cl] | 16 |
| F36 | 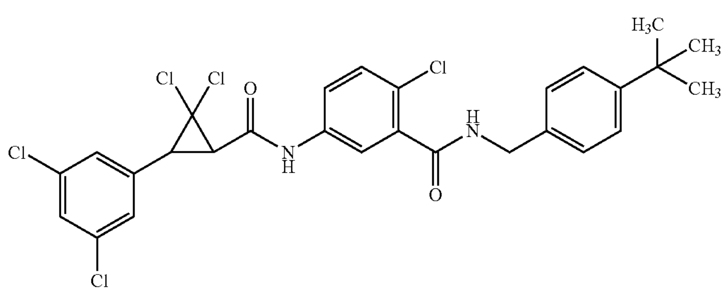 [SMILES: CC(C)(C)c1ccc(CNC(=O)c2cc(NC(=O)C3C(c4cc(Cl)cc(Cl)c4)C3(Cl)Cl)ccc2Cl)cc1] | 16 |

TABLE 2-continued

Structure and preparation method for F and PF Series molecules

| No. | Structure | Prep.* |
|---|---|---|
| F37 | 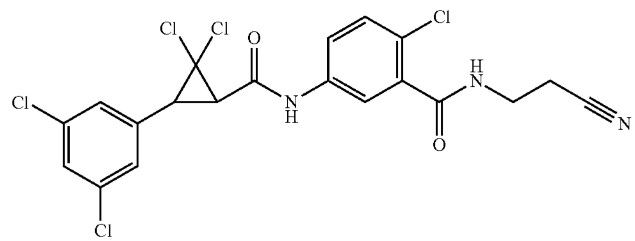 [SMILES: N#CCCNC(=O)c1cc(NC(=O)C2C(c3cc(Cl)cc(Cl)c3)C2(Cl)Cl)ccc1Cl] | 16 |
| F38 | 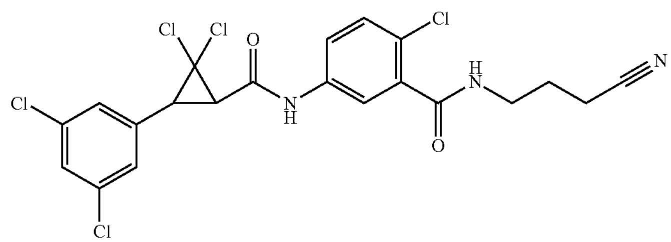 [SMILES: N#CCCCNC(=O)c1cc(NC(=O)C2C(c3cc(Cl)cc(Cl)c3)C2(Cl)Cl)ccc1Cl] | 16 |
| F39 | 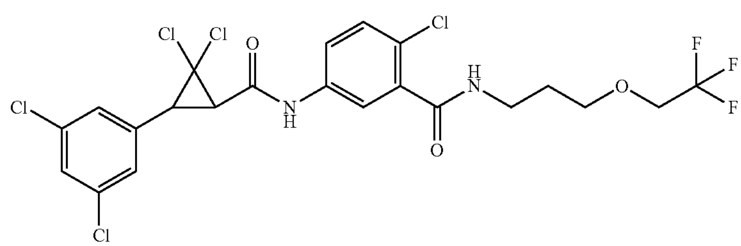 [SMILES: O=C(NCCCOCC(F)(F)F)c1cc(NC(=O)C2C(c3cc(Cl)cc(Cl)c3)C2(Cl)Cl)ccc1Cl] | 16 |
| F40 | 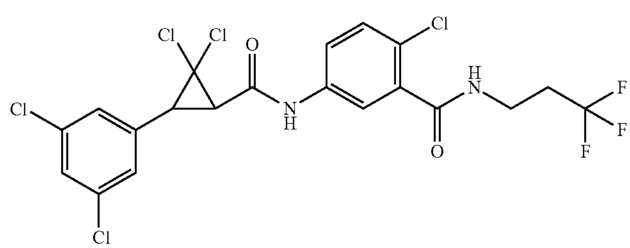 [SMILES: O=C(NCCC(F)(F)F)c1cc(NC(=O)C2C(c3cc(Cl)cc(Cl)c3)C2(Cl)Cl)ccc1Cl] | 16 |
| F41 | 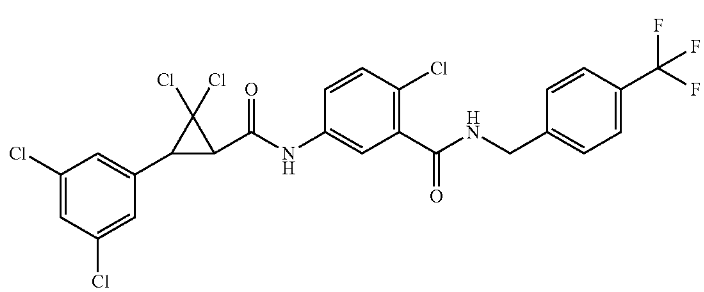 [SMILES: O=C(NCc1ccc(C(F)(F)F)cc1)c1cc(NC(=O)C2C(c3cc(Cl)cc(Cl)c3)C2(Cl)Cl)ccc1Cl] | 16 |
| F42 | 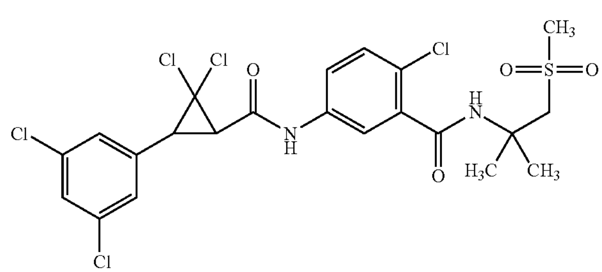 [SMILES: CC(C)(CS(C)(=O)=O)NC(=O)c1cc(NC(=O)C2C(c3cc(Cl)cc(Cl)c3)C2(Cl)Cl)ccc1Cl] | 16 |

TABLE 2-continued

Structure and preparation method for F and PF Series molecules

| No. | Structure | Prep.* |
|---|---|---|
| F43 | 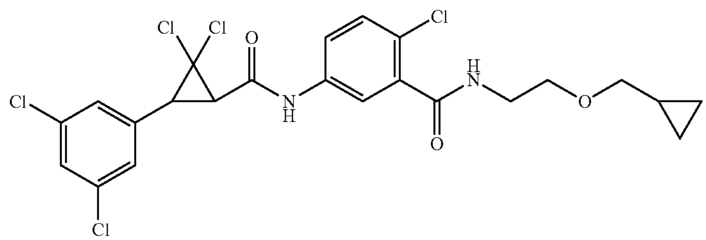 [SMILES: O=C(NCCOCC1CC1)c1cc(NC(=O)C2C(c3cc(Cl)cc(Cl)c3)C2(Cl)Cl)ccc1Cl] | 16 |
| F44 | 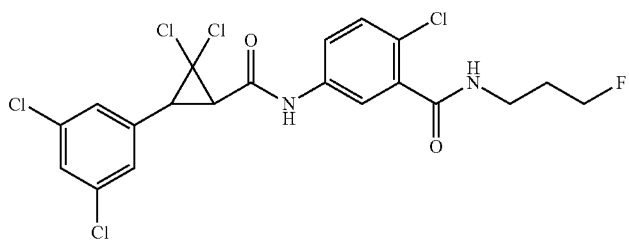 [SMILES: O=C(NCCCF)c1cc(NC(=O)C2C(c3cc(Cl)cc(Cl)c3)C2(Cl)Cl)ccc1Cl] | 16 |
| F45 | 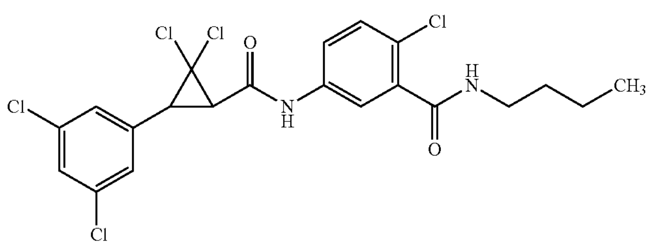 | 16 |
| F46 | 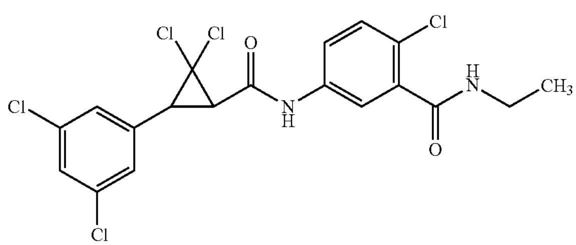 [SMILES: CCNC(=O)c1cc(NC(=O)C2C(c3cc(Cl)cc(Cl)c3)C2(Cl)Cl)ccc1Cl] | 16 |
| F47 | 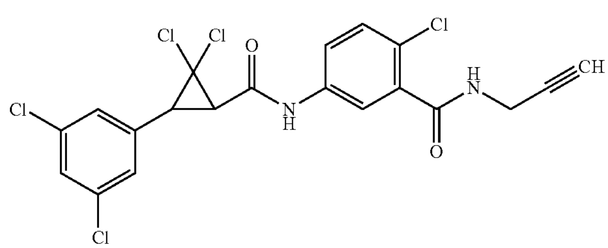 [SMILES: C#CCNC(=O)c1cc(NC(=O)C2C(c3cc(Cl)cc(Cl)c3)C2(Cl)Cl)ccc1Cl] | 16 |
| F48 | 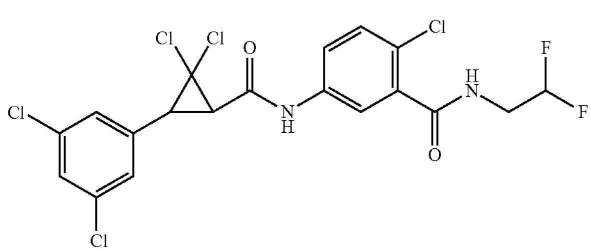 [SMILES: O=C(NCC(F)F)c1cc(NC(=O)C2C(c3cc(Cl)cc(Cl)c3)C2(Cl)Cl)ccc1Cl] | 16 |

TABLE 2-continued

Structure and preparation method for F and PF Series molecules

| No. | Structure | Prep.* |
|---|---|---|
| F49 | 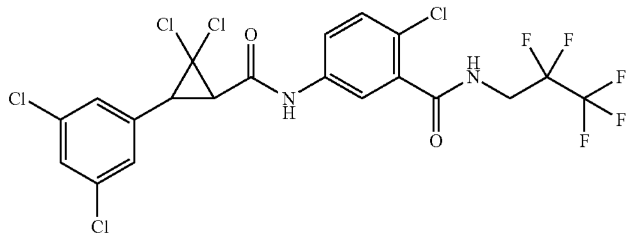 [SMILES: O=C(NCC(F)(F)C(F)(F)F)c1cc(NC(=O)C2C(c3cc(Cl)cc(Cl)c3)C2(Cl)Cl)ccc1Cl] | 16 |
| F50 | 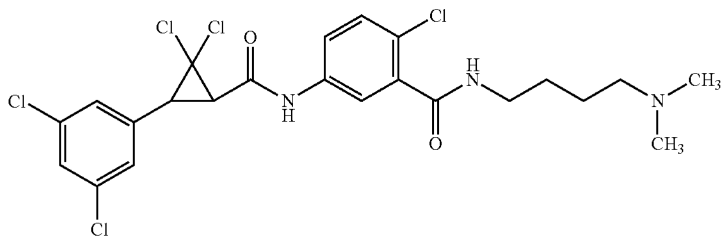 [SMILES: CN(C)CCCCNC(=O)c1cc(NC(=O)C2C(c3cc(Cl)cc(Cl)c3)C2(Cl)Cl)ccc1Cl] | 16 |
| F51 | 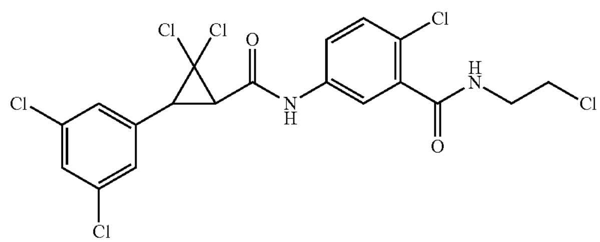 [SMILES: O=C(NCCCl)c1cc(NC(=O)C2C(c3cc(Cl)cc(Cl)c3)C2(Cl)Cl)ccc1Cl] | 16 |
| F52 | 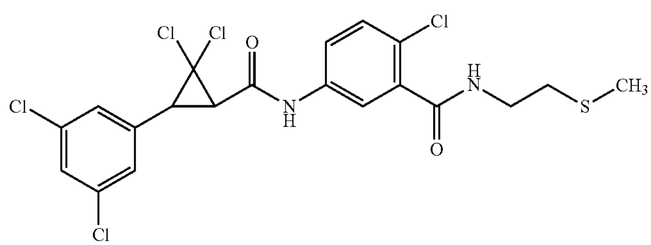 [SMILES: CSCCNC(=O)c1cc(NC(=O)C2C(c3cc(Cl)cc(Cl)c3)C2(Cl)Cl)ccc1Cl] | 16 |
| F53 | 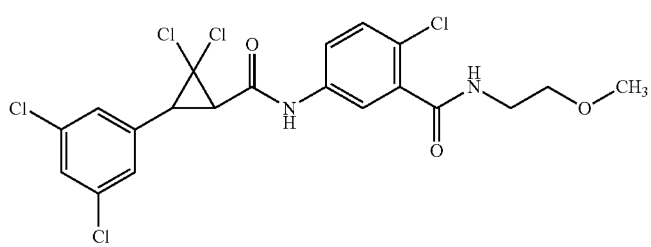 | 16 |
| F54 | 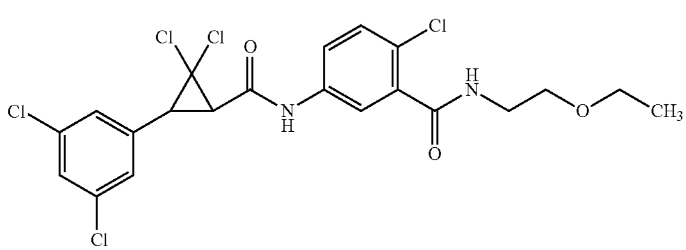 | 16 |

TABLE 2-continued

Structure and preparation method for F and PF Series molecules

| No. | Structure | Prep.* |
|---|---|---|
| F55 | 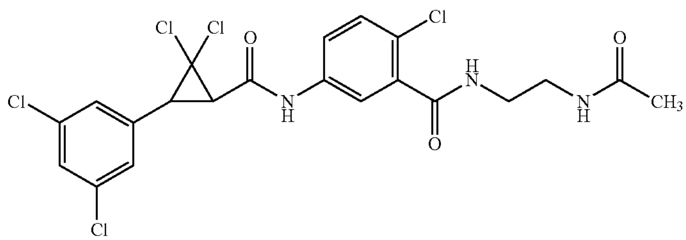 [SMILES: CC(=O)NCCNC(=O)c1cc(NC(=O)C2C(c3cc(Cl)cc(Cl)c3)C2(Cl)Cl)ccc1Cl] | 16 |
| F56 | 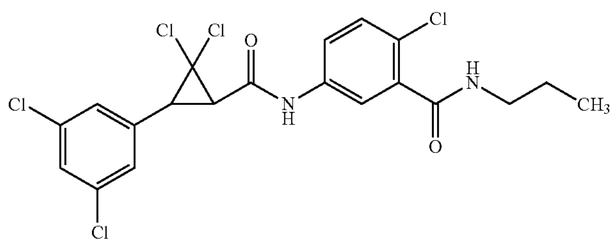 [SMILES: CCCNC(=O)c1cc(NC(=O)C2C(c3cc(Cl)cc(Cl)c3)C2(Cl)Cl)ccc1Cl] | 16 |
| F57 | 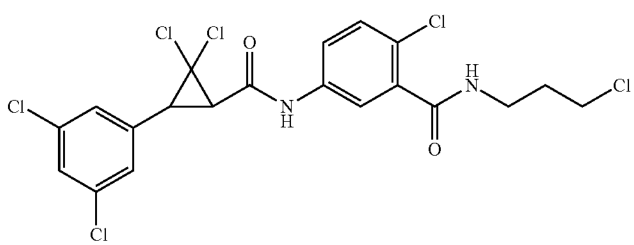 [SMILES: O=C(NCCCCl)c1cc(NC(=O)C2C(c3cc(Cl)cc(Cl)c3)C2(Cl)Cl)ccc1Cl] | 16 |
| F58 | 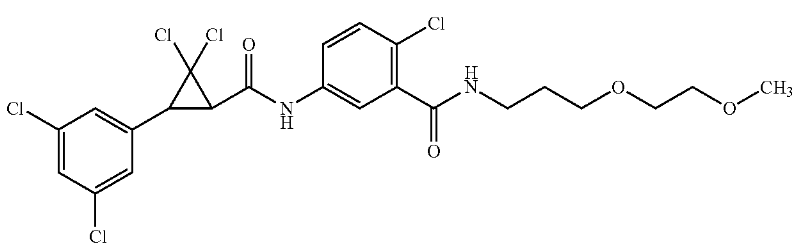 [SMILES: COCCOCCCNC(=O)c1cc(NC(=O)C2C(c3cc(Cl)cc(Cl)c3)C2(Cl)Cl)ccc1Cl] | 16 |
| F59 | 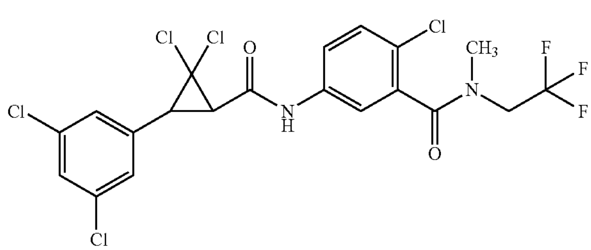 [SMILES: CN(CC(F)(F)F)C(=O)c1cc(NC(=O)C2C(c3cc(Cl)cc(Cl)c3)C2(Cl)Cl)ccc1Cl] | 16 |
| F60 | 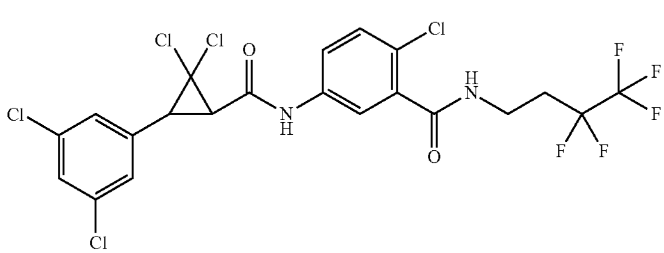 [SMILES: O=C(NCCC(F)(F)C(F)(F)F)c1cc(NC(=O)C2C(c3cc(Cl)cc(Cl)c3)C2(Cl)Cl)ccc1Cl] | 16 |

TABLE 2-continued

Structure and preparation method for F and PF Series molecules

| No. | Structure | Prep.* |
|---|---|---|
| F61 | 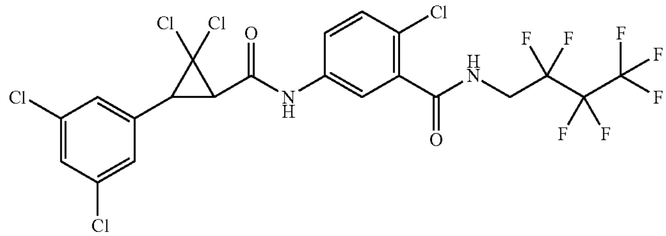 [SMILES: O=C(NCC(F)(F)C(F)(F)C(F)(F)F)c1cc(NC(=O)C2C(c3cc(Cl)cc(Cl)c3)C2(Cl)Cl)ccc1Cl] | 16 |
| F62 | 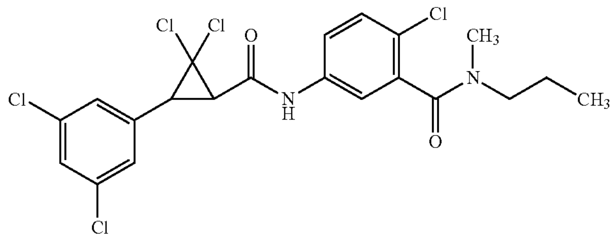 [SMILES: CCCN(C)C(=O)c1cc(NC(=O)C2C(c3cc(Cl)cc(Cl)c3)C2(Cl)Cl)ccc1Cl] | 16 |
| F63 | 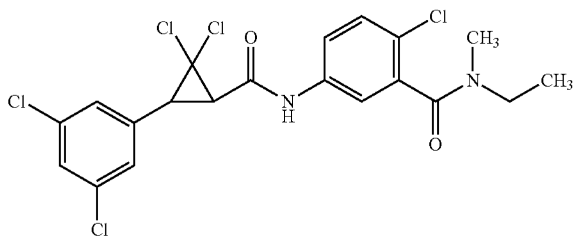 [SMILES: CCN(C)C(=O)c1cc(NC(=O)C2C(c3cc(Cl)cc(Cl)c3)C2(Cl)Cl)ccc1Cl] | 16 |
| F64 | 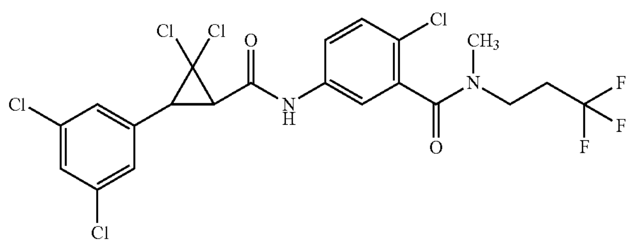 [SMILES: CN(CCC(F)(F)F)C(=O)c1cc(NC(=O)C2C(c3cc(Cl)cc(Cl)c3)C2(Cl)Cl)ccc1Cl] | 16 |
| F65 | 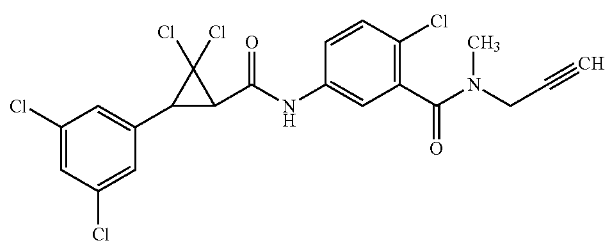 [SMILES: C#CCN(C)C(=O)c1cc(NC(=O)C2C(c3cc(Cl)cc(Cl)c3)C2(Cl)Cl)ccc1Cl] | 16 |
| F66 | 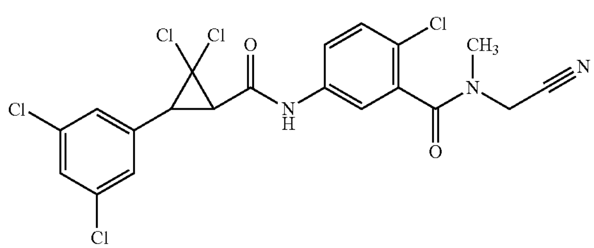 [SMILES: CN(CC#N)C(=O)c1cc(NC(=O)C2C(c3cc(Cl)cc(Cl)c3)C2(Cl)Cl)ccc1Cl] | 16 |

TABLE 2-continued

Structure and preparation method for F and PF Series molecules

| No. | Structure | Prep.* |
|---|---|---|
| F67 | 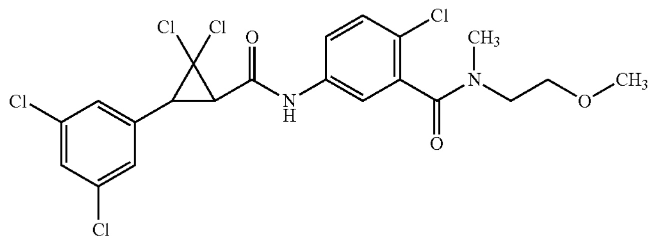 | 16 |
| F68 | 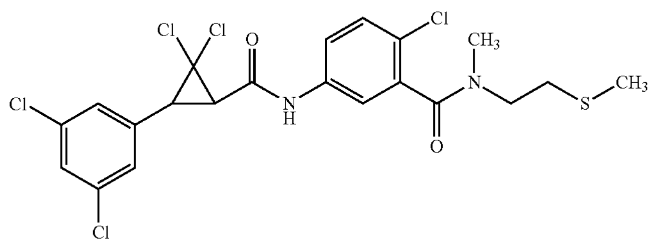 | 16 |
| F69 | 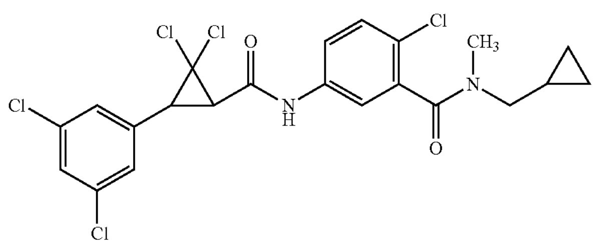 [SMILES: CN(CC1CC1)C(=O)c1cc(NC(=O)C2C(c3cc(Cl)cc(Cl)c3)C2(Cl)Cl)ccc1Cl] | 16 |
| F70 | 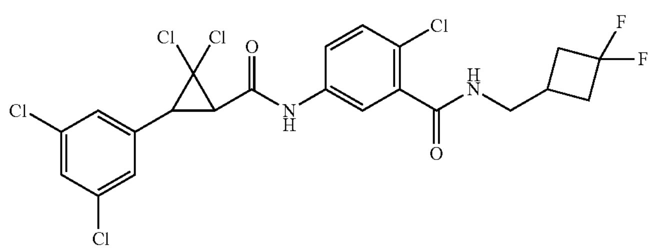 [SMILES: O=C(NCC1CC(F)(F)C1)c1cc(NC(=O)C2C(c3cc(Cl)cc(Cl)c3)C2(Cl)Cl)ccc1Cl] | 16 |
| F71 | 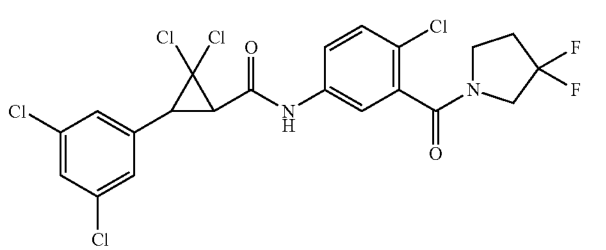 [SMILES: O=C(Nc1ccc(Cl)c(C(=O)N2CCC(F)(F)C2)c1)C1C(c2cc(Cl)cc(Cl)c2)C1(Cl)Cl] | 16 |
| F72 | 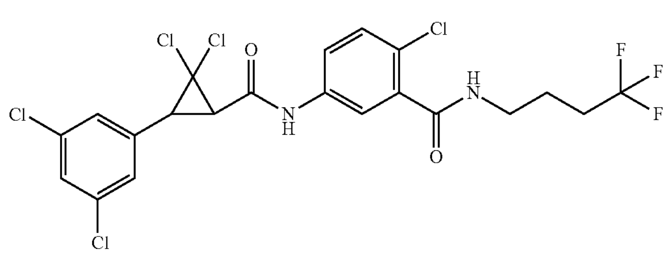 [SMILES: O=C(NCCCC(F)(F)F)c1cc(NC(=O)C2C(c3cc(Cl)cc(Cl)c3)C2(Cl)Cl)ccc1Cl] | 16 |

TABLE 2-continued

Structure and preparation method for F and PF Series molecules

| No. | Structure | Prep.* |
|---|---|---|
| F73 | 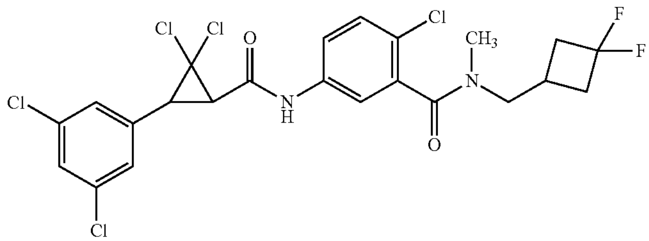 [SMILES: CN(CC1CC(F)(F)C1)C(=O)c1cc(NC(=O)C2C(c3cc(Cl)cc(Cl)c3)C2(Cl)Cl)ccc1Cl] | 16 |
| F74 | 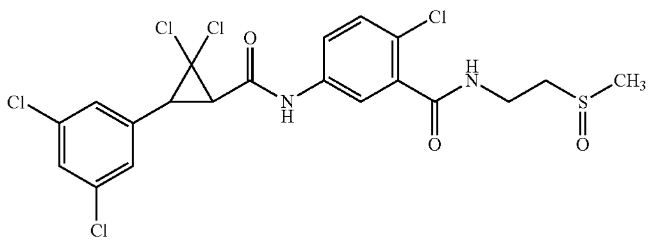 [SMILES: CS(=O)CCNC(=O)c1cc(NC(=O)C2C(c3cc(Cl)cc(Cl)c3)C2(Cl)Cl)ccc1Cl] | 17 |
| F75 | 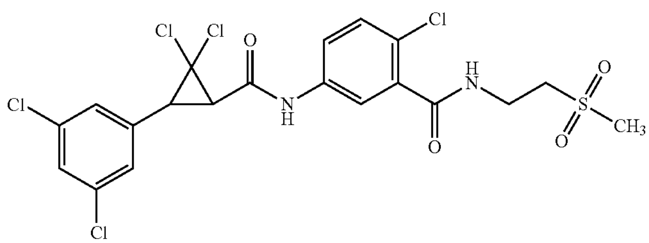 [SMILES: CS(=O)(=O)CCNC(=O)c1cc(NC(=O)C2C(c3cc(Cl)cc(Cl)c3)C2(Cl)Cl)ccc1Cl] | 17 |
| F78 | 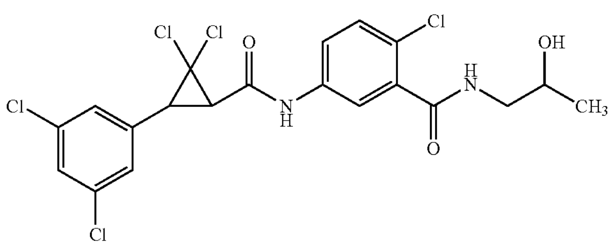 [SMILES: CC(O)CNC(=O)c1cc(NC(=O)C2C(c3cc(Cl)cc(Cl)c3)C2(Cl)Cl)ccc1Cl] | 16 |
| F79 | 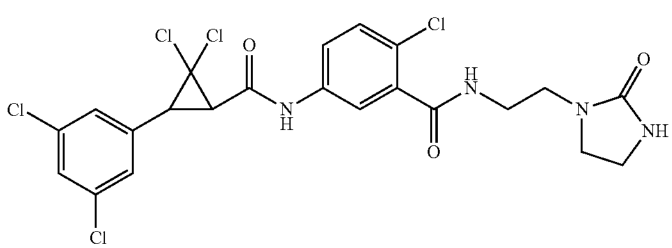 [SMILES: O=C(NCCN1CCNC1=O)c1cc(NC(=O)C2C(c3cc(Cl)cc(Cl)c3)C2(Cl)Cl)ccc1Cl] | 16 |
| F84 | 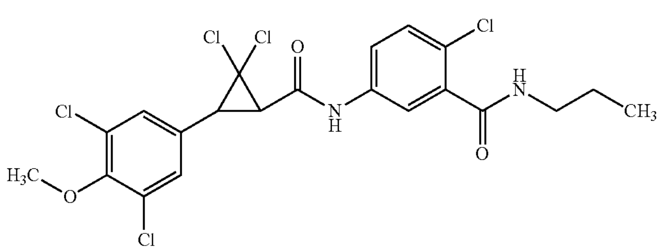 [SMILES: CCCNC(=O)c1cc(NC(=O)C2C(c3cc(Cl)c(OC)c(Cl)c3)C2(Cl)Cl)ccc1Cl] | 16 |

TABLE 2-continued

Structure and preparation method for F and PF Series molecules

| No. | Structure | Prep.* |
|---|---|---|
| F85 | 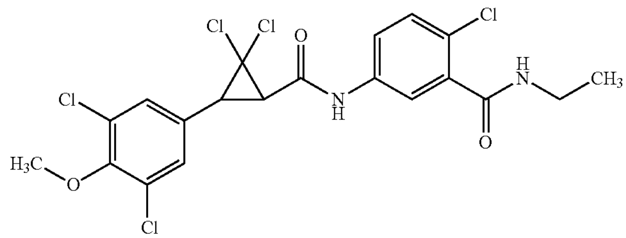 [SMILES: CCNC(=O)c1cc(NC(=O)C2C(c3cc(Cl)c(OC)c(Cl)c3)C2(Cl)Cl)ccc1Cl] | 16 |
| F86 | 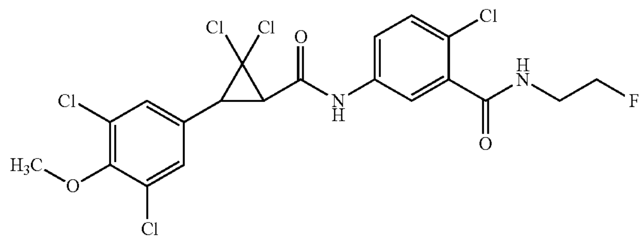 [SMILES: COc1c(Cl)cc(C2C(C(=O)Nc3ccc(Cl)c(C(=O)NCCF)c3)C2(Cl)Cl)cc1Cl] | 16 |
| F87 | 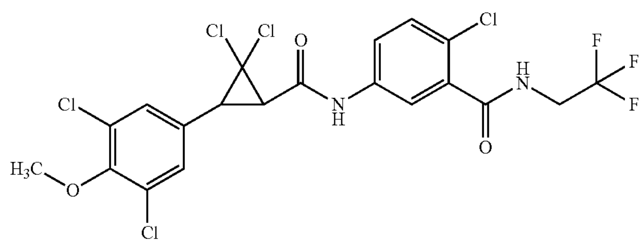 [SMILES: COc1c(Cl)cc(C2C(C(=O)Nc3ccc(Cl)c(C(=O)NCC(F)(F)F)c3)C2(Cl)Cl)cc1Cl] | 16 |
| F88 | 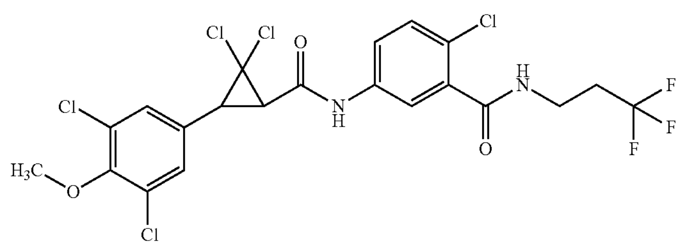 [SMILES: COc1c(Cl)cc(C2C(C(=O)Nc3ccc(Cl)c(C(=O)NCCC(F)(F)F)c3)C2(Cl)Cl)cc1Cl] | 16 |
| F91 | 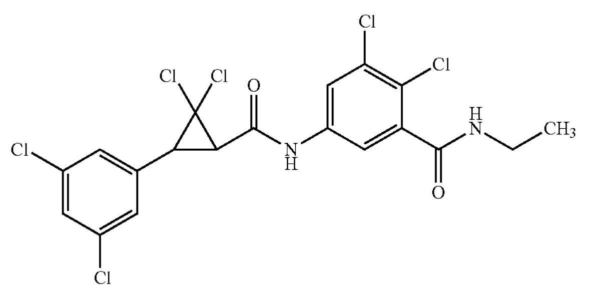 [SMILES: CCNC(=O)c1cc(NC(=O)C2C(c3cc(Cl)cc(Cl)c3)C2(Cl)Cl)cc(Cl)c1Cl] | 16 |
| F92 | 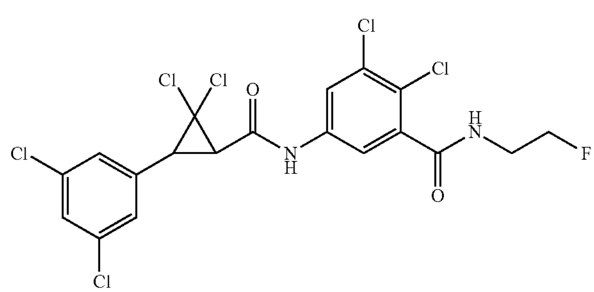 [SMILES: O=C(NCCF)c1cc(NC(=O)C2C(c3cc(Cl)cc(Cl)c3)C2(Cl)Cl)cc(Cl)c1Cl] | 16 |

TABLE 2-continued

Structure and preparation method for F and PF Series molecules

| No. | Structure | Prep.* |
|---|---|---|
| F93 | 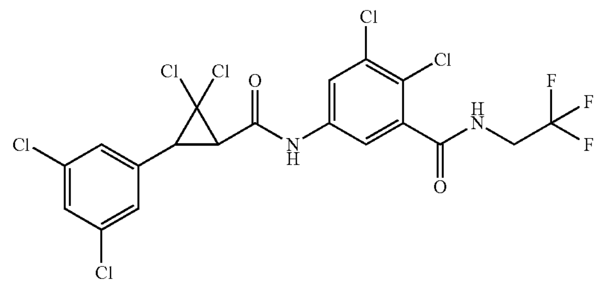 [SMILES: O=C(NCC(F)(F)F)c1cc(NC(=O)C2C(c3cc(Cl)cc(Cl)c3)C2(Cl)Cl)cc(Cl)c1Cl] | 16 |
| F94 | 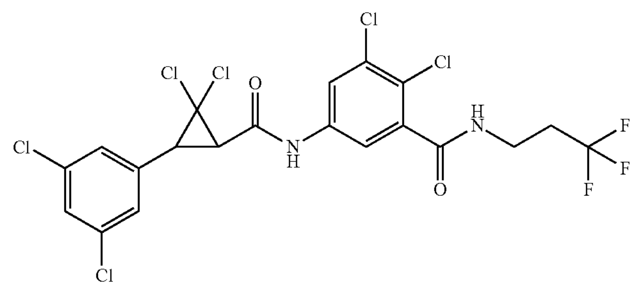 [SMILES: O=C(NCCC(F)(F)F)c1cc(NC(=O)C2C(c3cc(Cl)cc(Cl)c3)C2(Cl)Cl)cc(Cl)c1Cl] | 16 |
| F95 | 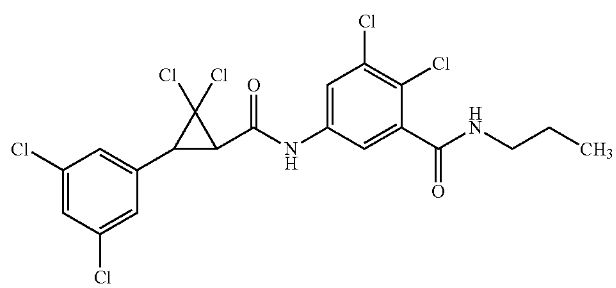 [SMILES: CCCNC(=O)c1cc(NC(=O)C2C(c3cc(Cl)cc(Cl)c3)C2(Cl)Cl)cc(Cl)c1Cl] | 16 |
| F96 | 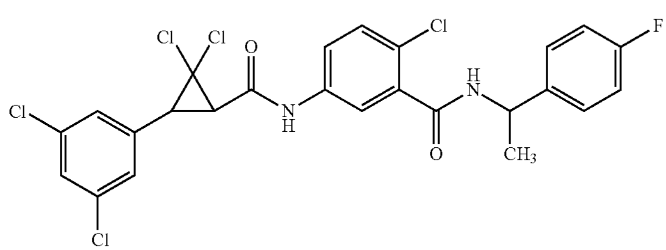 [SMILES: CC(NC(=O)c1cc(NC(=O)C2C(c3cc(Cl)cc(Cl)c3)C2(Cl)Cl)ccc1Cl)c1ccc(F)cc1] | 23 |
| F97 | 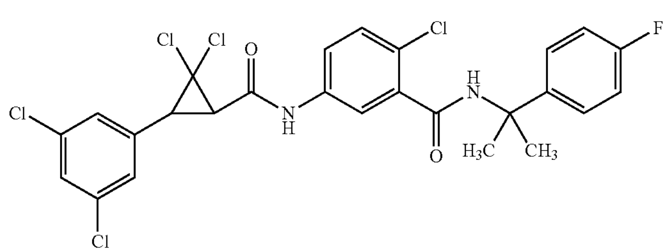 [SMILES: CC(C)(NC(=O)c1cc(NC(=O)C2C(c3cc(Cl)cc(Cl)c3)C2(Cl)Cl)ccc1Cl)c1ccc(F)cc1] | 15 |

TABLE 2-continued

Structure and preparation method for F and PF Series molecules

| No. | Structure | Prep.* |
|---|---|---|
| F98 | 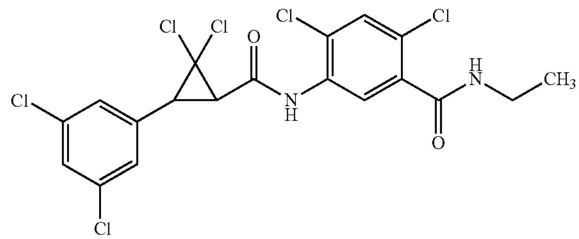 [SMILES: CCNC(=O)c1cc(NC(=O)C2C(c3cc(Cl)cc(Cl)c3)C2(Cl)Cl)c(Cl)cc1Cl] | 16 |
| F99 | 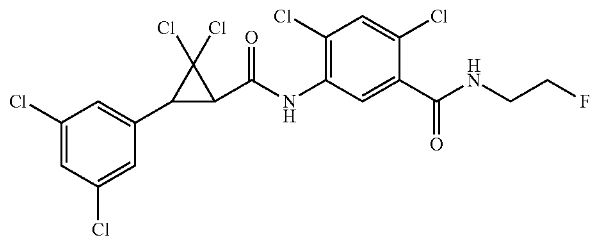 [SMILES: O=C(NCCF)c1cc(NC(=O)C2C(c3cc(Cl)cc(Cl)c3)C2(Cl)Cl)c(Cl)cc1Cl] | 16 |
| F100 | 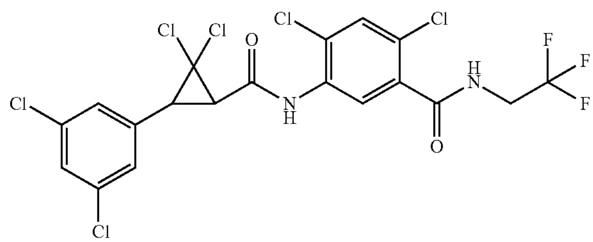 [SMILES: O=C(NCC(F)(F)F)c1cc(NC(=O)C2C(c3cc(Cl)cc(Cl)c3)C2(Cl)Cl)c(Cl)cc1Cl] | 16 |
| F101 | 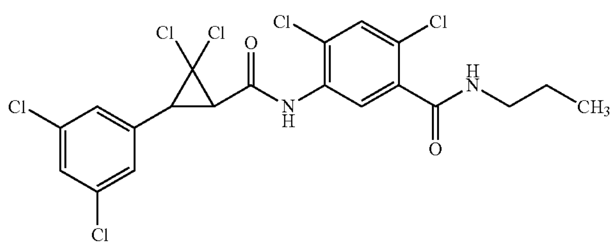 [SMILES: CCCNC(=O)c1cc(NC(=O)C2C(c3cc(Cl)cc(Cl)c3)C2(Cl)Cl)c(Cl)cc1Cl] | 16 |
| F102 | 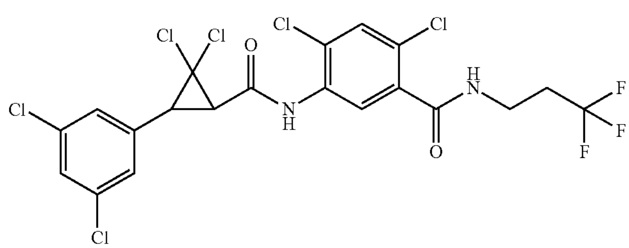 [SMILES: O=C(NCCC(F)(F)F)c1cc(NC(=O)C2C(c3cc(Cl)cc(Cl)c3)C2(Cl)Cl)c(Cl)cc1Cl] | 16 |
| F103 | 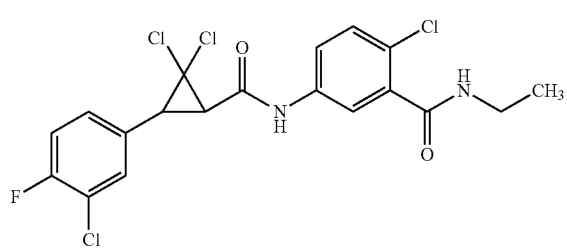 [SMILES: CCNC(=O)c1cc(NC(=O)C2C(c3ccc(F)c(Cl)c3)C2(Cl)Cl)ccc1Cl] | 16 |

TABLE 2-continued
Structure and preparation method for F and PF Series molecules
| No. | Structure | Prep.* |
|---|---|---|
| F104 | 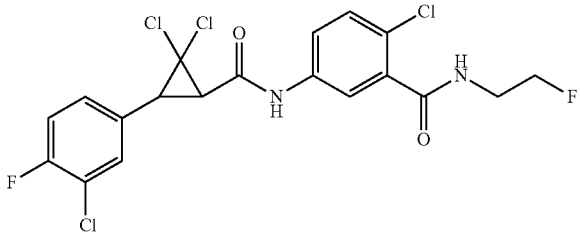 [SMILES: O=C(NCCF)c1cc(NC(=O)C2C(c3ccc(F)c(Cl)c3)C2(Cl)Cl)ccc1Cl] | 16 |
| F105 | 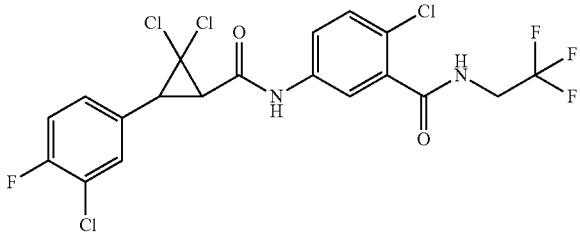 [SMILES: O=C(NCC(F)(F)F)c1cc(NC(=O)C2C(c3ccc(F)c(Cl)c3)C2(Cl)Cl)ccc1Cl] | 16 |
| F106 | 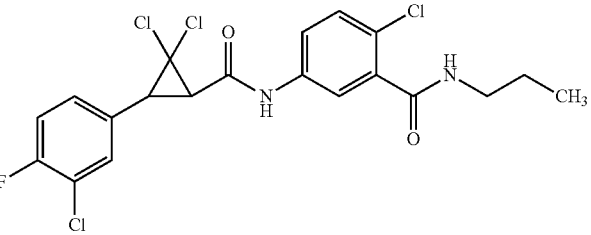 | 16 |
| F107 | 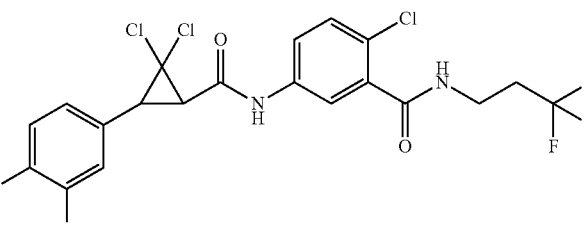 | 16 |
| F108 | 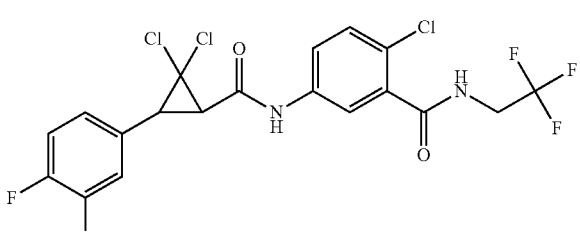 | 24 |
| F109 | 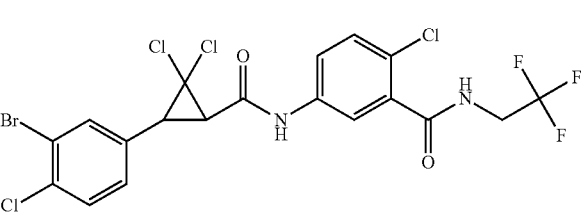 | 24 |

TABLE 2-continued

Structure and preparation method for F and PF Series molecules

| No. | Structure | Prep.* |
|---|---|---|
| F111 | 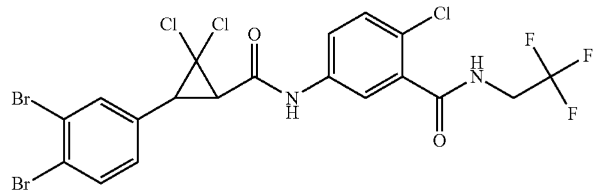 [SMILES: O=C(NCC(F)(F)F)c1cc(NC(=O)C2C(c3ccc(Cl)c(Br)c3)C2(Cl)Cl)ccc1Cl] | 24 |
| F112 | 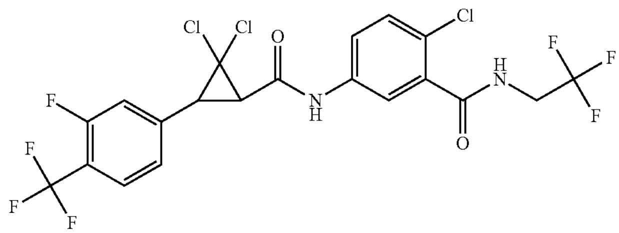 [SMILES: O=C(NCC(F)(F)F)c1cc(NC(=O)C2C(c3ccc(C(F)(F)F)c(F)c3)C2(Cl)Cl)ccc1Cl] | 24 |
| F113 | 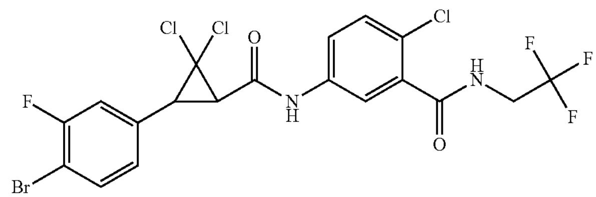 [SMILES: O=C(NCC(F)(F)F)c1cc(NC(=O)C2C(c3ccc(Br)c(F)c3)C2(Cl)Cl)ccc1Cl] | 24 |
| F114 | 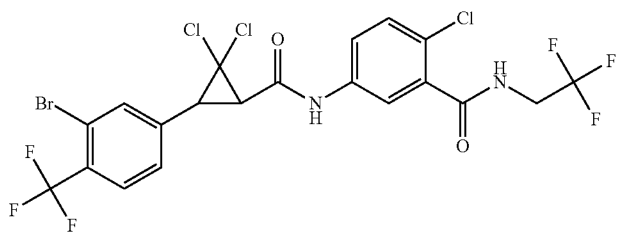 | 24 |
| F115 | 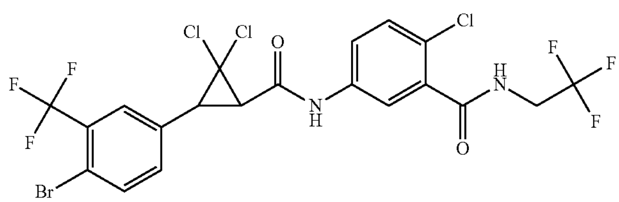 | 24 |
| F116 | 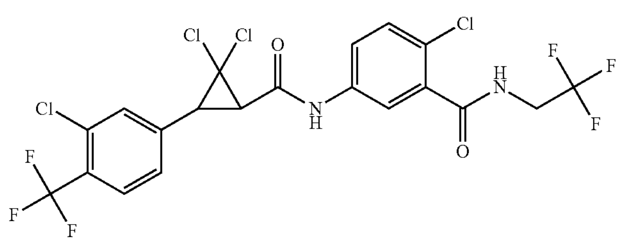 | 24 |
| F117 | 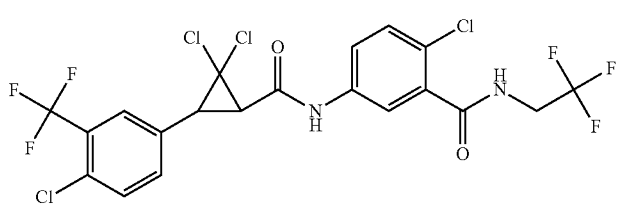 | 24 |

TABLE 2-continued

Structure and preparation method for F and PF Series molecules

| No. | Structure | Prep.* |
|---|---|---|
| F118 | 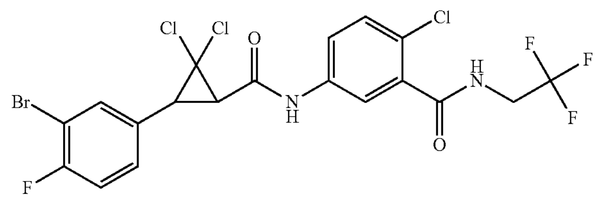 [SMILES: O=C(NCC(F)(F)F)c1cc(NC(=O)C2C(c3ccc(F)c(Br)c3)C2(Cl)Cl)ccc1Cl] | 24 |
| F119 | 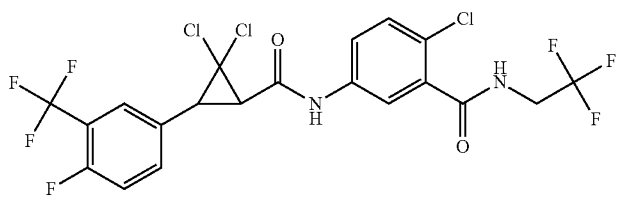 [SMILES: O=C(NCC(F)(F)F)c1cc(NC(=O)C2C(c3ccc(F)c(C(F)(F)F)c3)C2(Cl)Cl)ccc1Cl] | 24 |
| F120 | 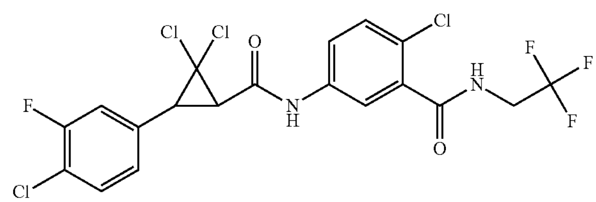 [SMILES: O=C(NCC(F)(F)F)c1cc(NC(=O)C2C(c3ccc(Cl)c(F)c3)C2(Cl)Cl)ccc1Cl] | 24 |
| F121 | 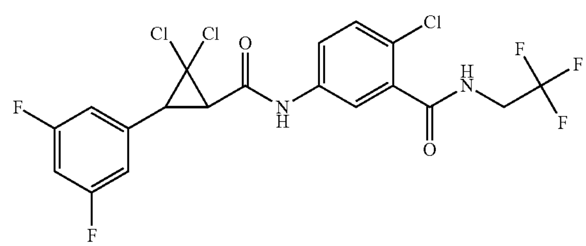 [SMILES: O=C(NCC(F)(F)F)c1cc(NC(=O)C2C(c3cc(F)cc(F)c3)C2(Cl)Cl)ccc1Cl] | 24 |
| F122 | 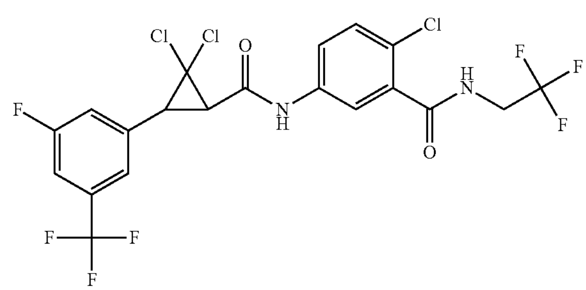 [SMILES: O=C(NCC(F)(F)F)c1cc(NC(=O)C2C(c3cc(F)cc(C(F)(F)F)c3)C2(Cl)Cl)ccc1Cl] | 24 |
| F123 | 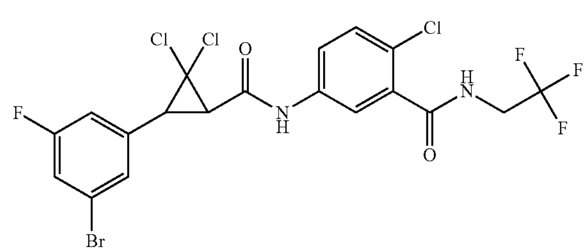 | 24 |

TABLE 2-continued

Structure and preparation method for F and PF Series molecules

| No. | Structure | Prep.* |
|---|---|---|
| F124 | 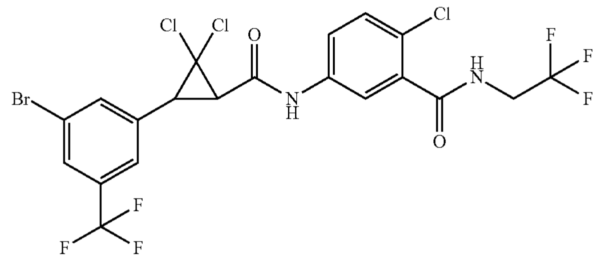 [SMILES: O=C(NCC(F)(F)F)c1cc(NC(=O)C2C(c3cc(Br)cc(C(F)(F)F)c3)C2(Cl)Cl)ccc1Cl] | 24 |
| F125 | 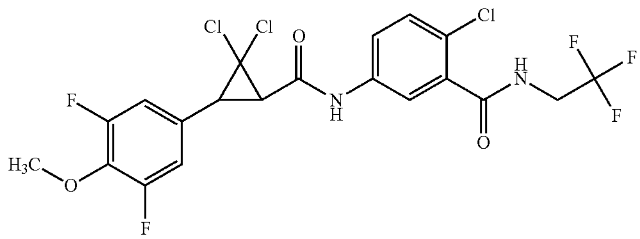 | 24 |
| F126 | 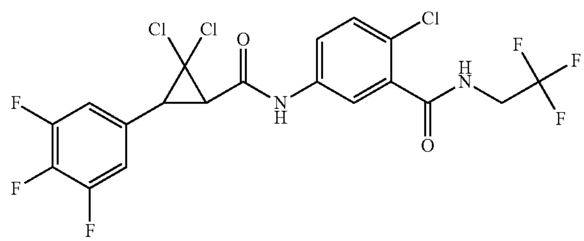 [SMILES: O=C(NCC(F)(F)F)c1cc(NC(=O)C2C(c3cc(F)c(F)c(F)c3)C2(Cl)Cl)ccc1Cl] | 24 |
| F127 | 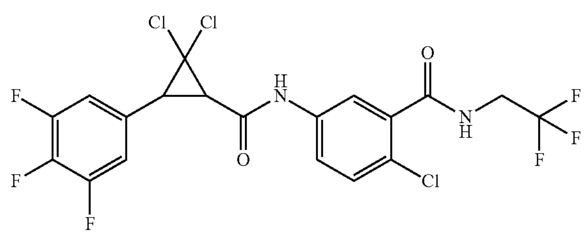 [SMILES: O=C(NCC(F)(F)F)c1cc(NC(=O)C2C(c3cc(F)c(F)c(F)c3)C2(Cl)Cl)ccc1Cl] | 24 |
| F128 | 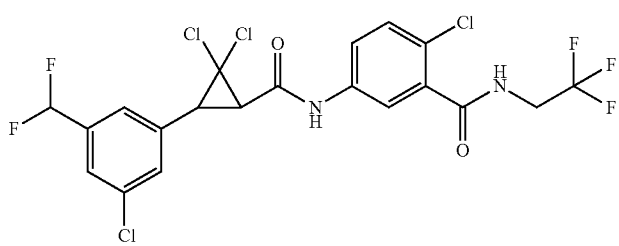 | 24 |
| F129 | 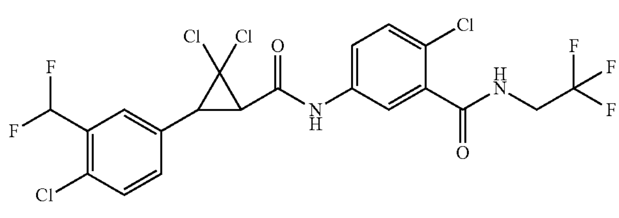 | 24 |

TABLE 2-continued

Structure and preparation method for F and PF Series molecules

| No. | Structure | Prep.* |
|---|---|---|
| F130 | 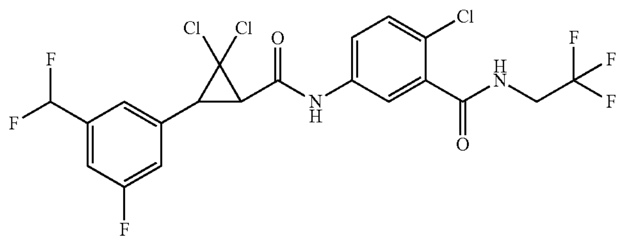 [SMILES: O=C(NCC(F)(F)F)c1cc(NC(=O)C2C(c3cc(F)cc(C(F)F)c3)C2(Cl)Cl)ccc1Cl] | 24 |
| F131 | 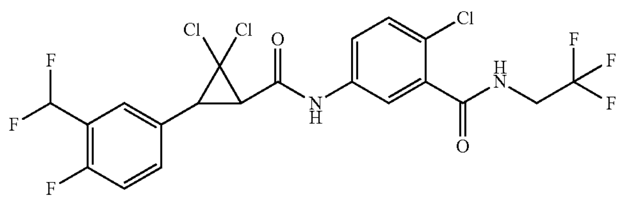 | 24 |
| F132 | 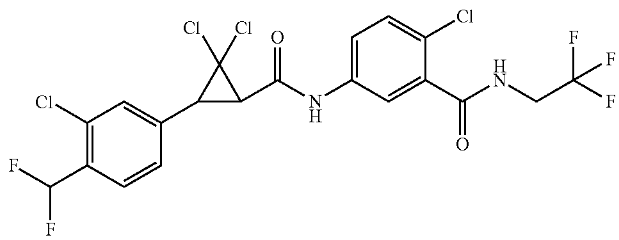 | 24 |
| F133 | 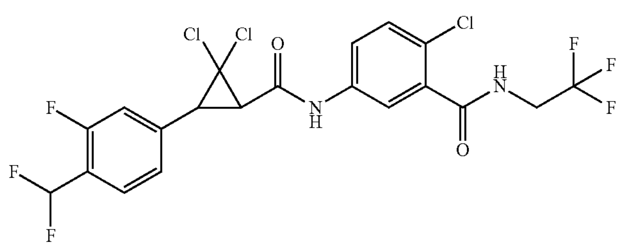 | 24 |
| F134 | 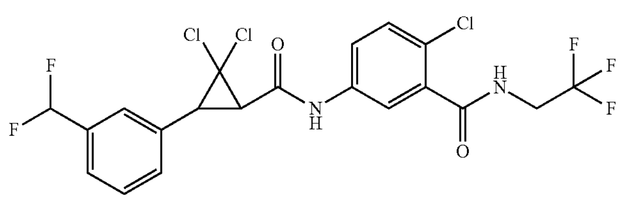 [SMILES: O=C(NCC(F)(F)F)c1cc(NC(=O)C2C(c3cccc(C(F)F)c3)C2(Cl)Cl)ccc1Cl] | 24 |
| F135 | 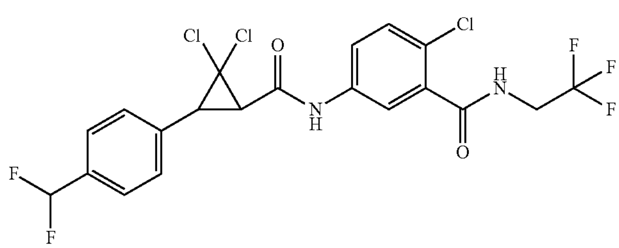 [SMILES: O=C(NCC(F)(F)F)c1cc(NC(=O)C2C(c3ccc(C(F)F)cc3)C2(Cl)Cl)ccc1Cl] | 24 |

TABLE 2-continued
Structure and preparation method for F and PF Series molecules
| No. | Structure | Prep.* |
|---|---|---|
| PF1 | 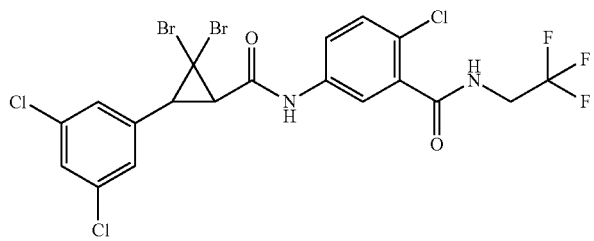 [SMILES: O=C(NCC(F)(F)F)c1cc(NC(=O)C2C(c3cc(Cl)cc(Cl)c3)C2(Br)Br)ccc1Cl] | 13 |
| PF2 | 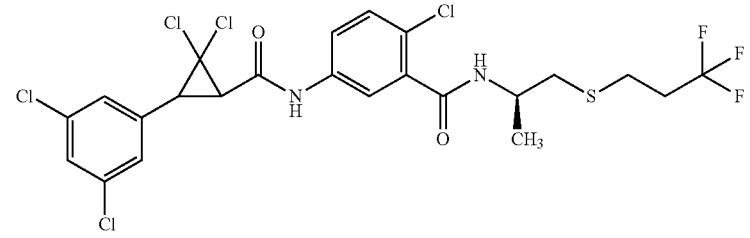 [SMILES: C[C@H](CSCCC(F)(F)F)NC(=O)c1cc(NC(=O)C2C(c3cc(Cl)cc(Cl)c3)C2(Cl)Cl)ccc1Cl] | 16 |
| PF3 | 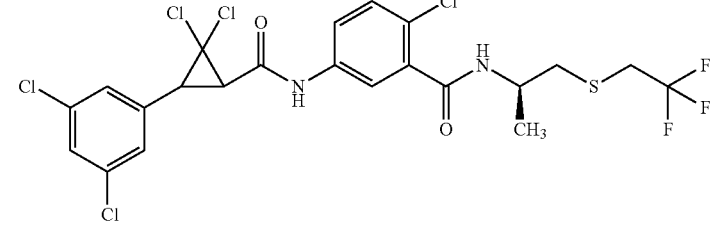 | 16 |
| PF4 | 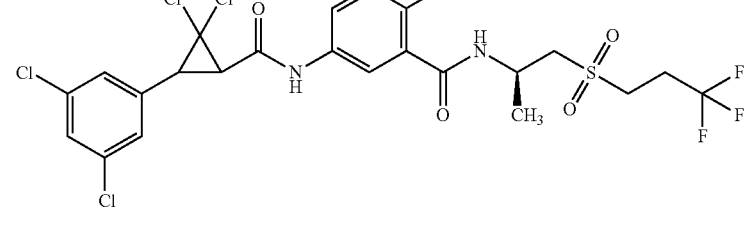 | 17a |
| PF5 | 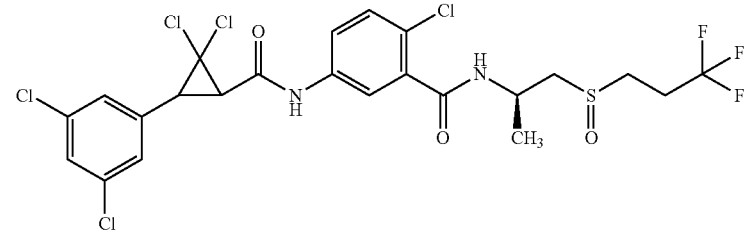 [SMILES: C[C@H](CS(=O)CCC(F)(F)F)NC(=O)c1cc(NC(=O)C2C(c3cc(Cl)cc(Cl)c3)C2(Cl)Cl)ccc1Cl] | 17a |
| PF6 | 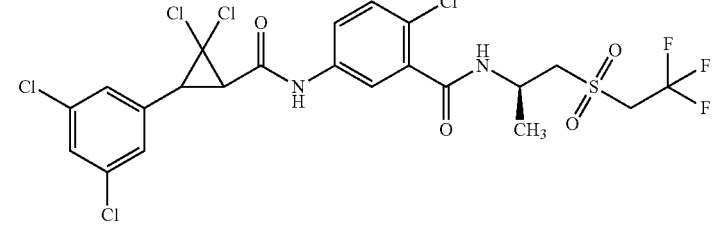 | 17a |

TABLE 2-continued

Structure and preparation method for F and PF Series molecules

| No. | Structure | Prep.* |
|---|---|---|
| PF7 | 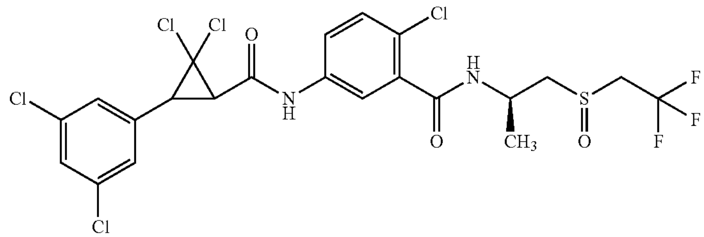 [SMILES: C[C@H](CS(=O)CC(F)(F)F)NC(=O)c1cc(NC(=O)C2C(c3cc(Cl)cc(Cl)c3)C2(Cl)Cl)ccc1Cl] | 17a |
| PF9 | 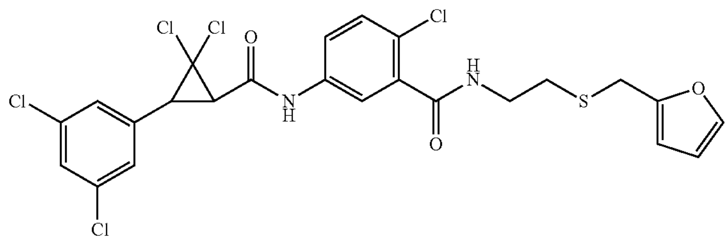 [SMILES: O=C(NCCSCc1ccco1)c1cc(NC(=O)C2C(c3cc(Cl)cc(Cl)c3)C2(Cl)Cl)ccc1Cl] | 16 |
| PF10 | 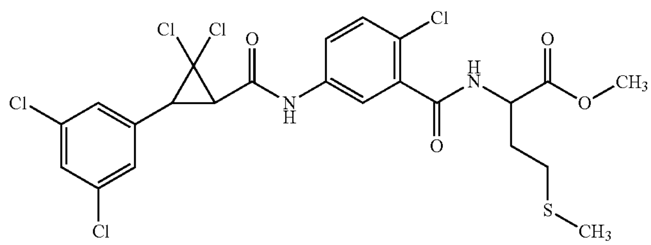 [SMILES: COC(=O)C(CCSC)NC(=O)c1cc(NC(=O)C2C(c3cc(Cl)cc(Cl)c3)C2(Cl)Cl)ccc1Cl] | 16 |
| PF11 | 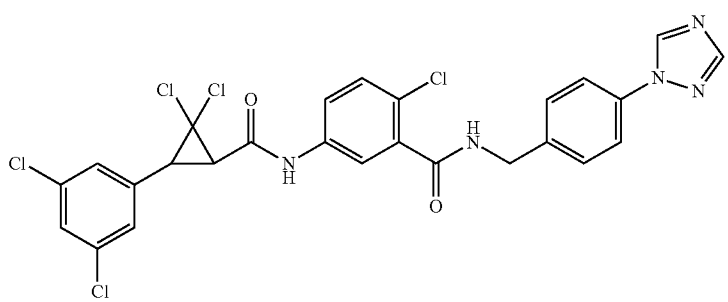 [SMILES: O=C(NCc1ccc(-n2cncn2)cc1)c1cc(NC(=O)C2C(c3cc(Cl)cc(Cl)c3)C2(Cl)Cl)ccc1Cl] | 16 |
| PF12 | 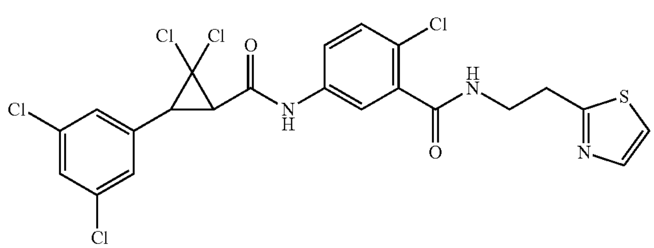 [SMILES: O=C(NCCc1nccs1)c1cc(NC(=O)C2C(c3cc(Cl)cc(Cl)c3)C2(Cl)Cl)ccc1Cl] | 16 |
| PF13 | 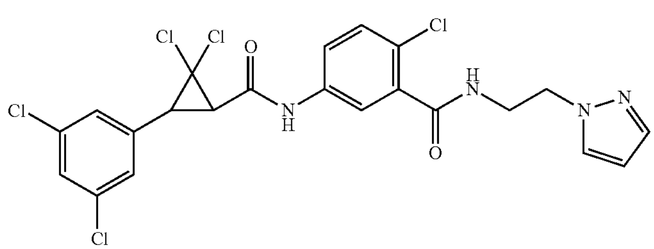 [SMILES: O=C(NCCn1cccn1)c1cc(NC(=O)C2C(c3cc(Cl)cc(Cl)c3)C2(Cl)Cl)ccc1Cl] | 16 |

TABLE 2-continued

Structure and preparation method for F and PF Series molecules

| No. | Structure | Prep.* |
|---|---|---|
| PF14 | 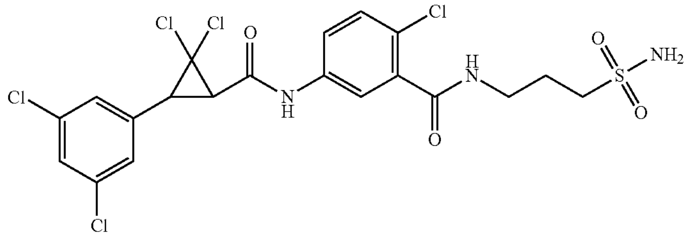 [SMILES: NS(=O)(=O)CCCNC(=O)c1cc(NC(=O)C2C(c3cc(Cl)cc(Cl)c3)C2(Cl)Cl)ccc1Cl] | 16 |
| PF15 | 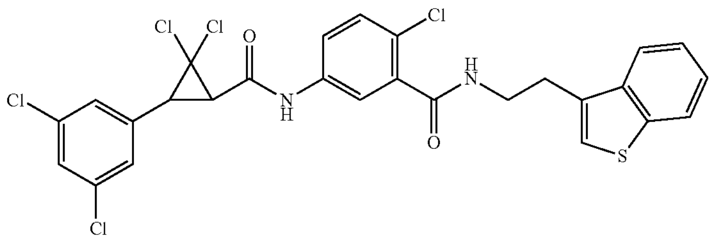 [SMILES: O=C(NCCc1csc2ccccc12)c1cc(NC(=O)C2C(c3cc(Cl)cc(Cl)c3)C2(Cl)Cl)ccc1Cl] | 16 |
| PF16 | 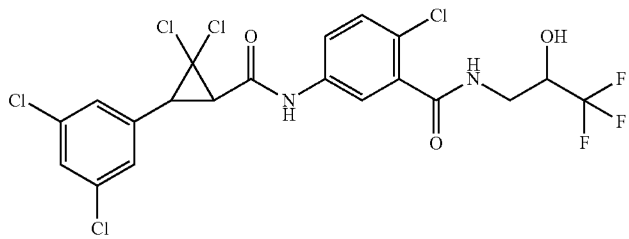 [SMILES: O=C(NCC(O)C(F)(F)F)c1cc(NC(=O)C2C(c3cc(Cl)cc(Cl)c3)C2(Cl)Cl)ccc1Cl] | 16 |

*prepared according to example number

TABLE 3

Structure and preparation method for C series molecules

| No. | Structure | Prep* |
|---|---|---|
| C1 | 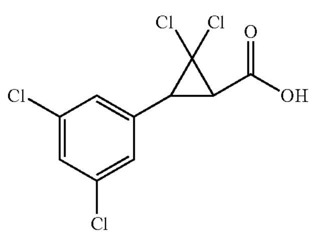 [SMILES: O=C(O)C1C(c2cc(Cl)cc(Cl)c2)C1(Cl)Cl] | 1 |
| C2 | 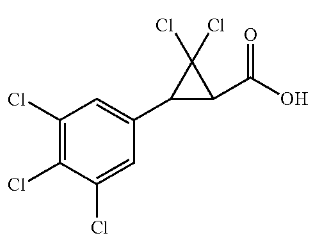 [SMILES: O=C(O)C1C(c2cc(Cl)c(Cl)c(Cl)c2)C1(Cl)Cl] | 1 |

TABLE 3-continued

Structure and preparation method for C series molecules

| No. | Structure | Prep* |
|---|---|---|
| C3 | 2-(3,4-dichlorophenyl)-3,3-dichlorocyclopropane-1-carboxylic acid | 1 |
| C4 | 3,3-dichloro-2-(4-(trifluoromethyl)phenyl)cyclopropane-1-carboxylic acid | 2 |
| C5 | 3,3-dichloro-2-(3-(trifluoromethyl)phenyl)cyclopropane-1-carboxylic acid | 2 |
| C6 | 3,3-dichloro-2-(3-chloro-4-(trifluoromethoxy)phenyl)cyclopropane-1-carboxylic acid | 2 |
| C7 | 3,3-dichloro-2-(2,4,5-trichlorophenyl)cyclopropane-1-carboxylic acid | 2 |
| C8 | 3,3-dichloro-2-(3,5-bis(trifluoromethyl)phenyl)cyclopropane-1-carboxylic acid | 2 |

TABLE 3-continued

Structure and preparation method for C series molecules

| No. | Structure | Prep* |
|-----|-----------|-------|
| C9  | 3,5-dibromophenyl-2,2-dichlorocyclopropanecarboxylic acid | 2 |
| C10 | 3-chloro-5-(trifluoromethyl)phenyl-2,2-dichlorocyclopropanecarboxylic acid | 2 |
| C11 | 3,5-dichloro-4-fluorophenyl-2,2-dichlorocyclopropanecarboxylic acid | 2 |
| C12 | 3,5-dichloro-4-bromophenyl-2,2-dichlorocyclopropanecarboxylic acid | 2 |
| C13 | 3-bromo-5-chlorophenyl-2,2-dichlorocyclopropanecarboxylic acid | 2 |
| C14 | 3-chloro-5-fluorophenyl-2,2-dichlorocyclopropanecarboxylic acid | 2 |

TABLE 3-continued

Structure and preparation method for C series molecules

| No. | Structure | Prep* |
|---|---|---|
| C15 | (structure) | 2 |
| C16 | (structure) | 2 |
| C17 | (structure) | 2 |
| C18 | (structure) | 2 |
| C19 | (structure) | 2 |
| C20 | (structure) | 2 |
| C21 | (structure) | 2 |

TABLE 3-continued

Structure and preparation method for C series molecules

| No. | Structure | Prep* |
|-----|-----------|-------|
| C22 | 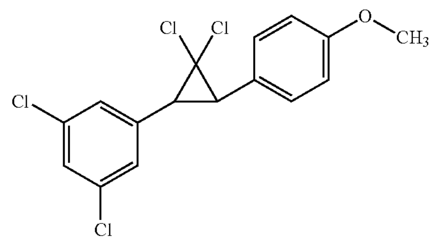 [SMILES: COc1ccc(C2C(c3cc(Cl)cc(Cl)c3)C2(Cl)Cl)cc1] | 3 |
| C23 | 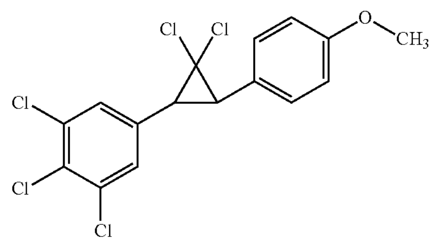 [SMILES: COc1ccc(C2C(c3cc(Cl)c(Cl)c(Cl)c3)C2(Cl)Cl)cc1] | 3 |
| C24 | 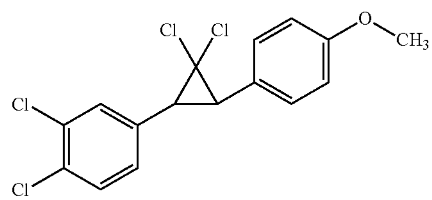 [SMILES: COc1ccc(C2C(c3ccc(Cl)c(Cl)c3)C2(Cl)Cl)cc1] | 3 |
| C25 | 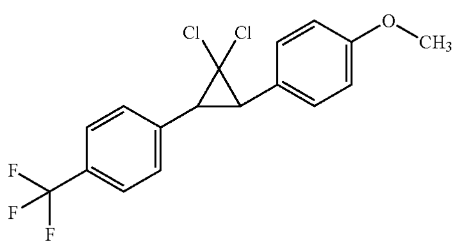 [SMILES: COc1ccc(C2C(c3ccc(C(F)(F)F)cc3)C2(Cl)Cl)cc1] | 4 |
| C26 | 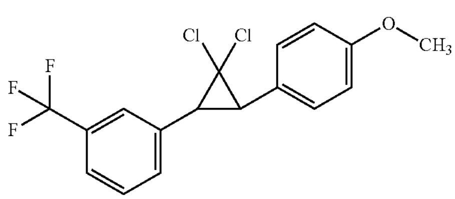 [SMILES: COc1ccc(C2C(c3cccc(C(F)(F)F)c3)C2(Cl)Cl)cc1] | 4 |
| C27 | 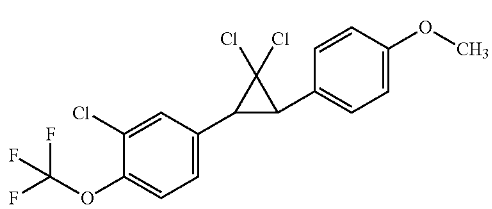 [SMILES: COc1ccc(C2C(c3ccc(OC(F)(F)F)c(Cl)c3)C2(Cl)Cl)cc1] | 4 |
| C28 | 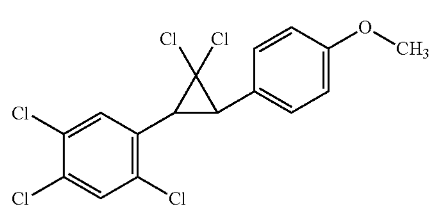 [SMILES: COc1ccc(C2C(c3cc(Cl)c(Cl)cc3Cl)C2(Cl)Cl)cc1] | 4 |

TABLE 3-continued

Structure and preparation method for C series molecules

| No. | Structure | Prep* |
|-----|-----------|-------|
| C29 | 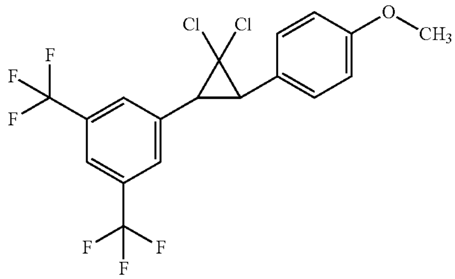 [SMILES: COc1ccc(C2C(c3cc(C(F)(F)F)cc(C(F)(F)F)c3)C2(Cl)Cl)cc1] | 4 |
| C30 | 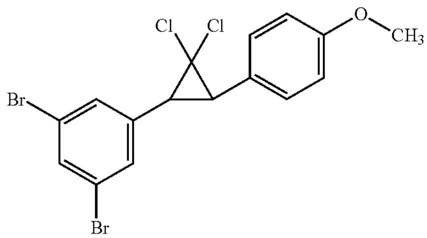 | 4 |
| C31 | 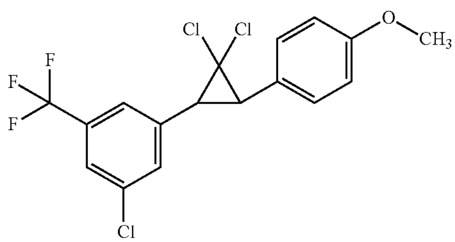 [SMILES: COc1ccc(C2C(c3cc(Cl)cc(C(F)(F)F)c3)C2(Cl)Cl)cc1] | 4 |
| C32 | 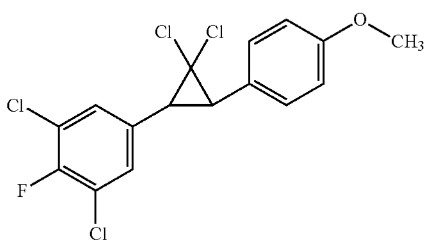 | 4 |
| C33 | 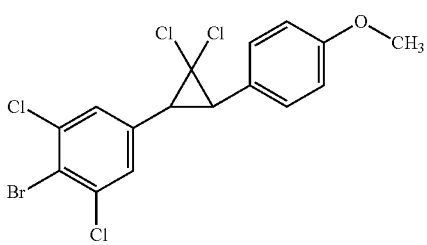 [SMILES: COc1ccc(C2C(c3cc(Cl)c(F)c(Cl)c3)C2(Cl)Cl)cc1] | 4 |
| C34 | 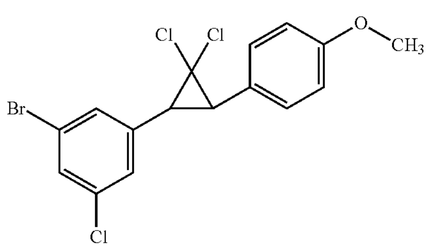 | 4 |

TABLE 3-continued
Structure and preparation method for C series molecules
| No. | Structure | Prep* |
|---|---|---|
| C35 | 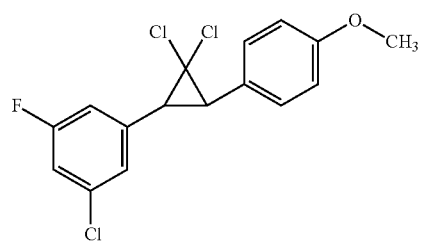 [SMILES: COc1ccc(C2C(c3cc(F)cc(Cl)c3)C2(Cl)Cl)cc1] | 4 |
| C36 | 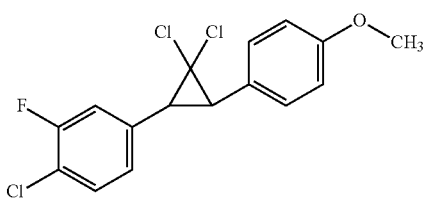 | 4 |
| C37 | 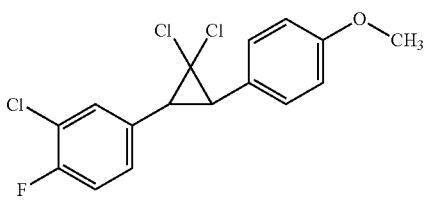 | 4 |
| C38 | 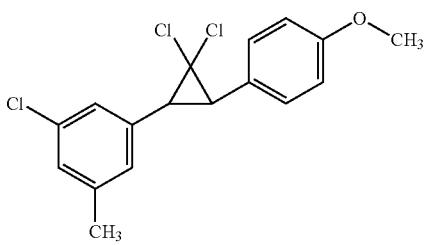 [SMILES: COc1ccc(C2C(c3cc(C)cc(Cl)c3)C2(Cl)Cl)cc1] | 4 |
| C39 | 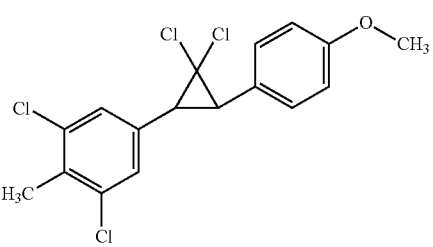 [SMILES: COc1ccc(C2C(c3cc(Cl)c(C)c(Cl)c3)C2(Cl)Cl)cc1] | 4 |
| C40 | 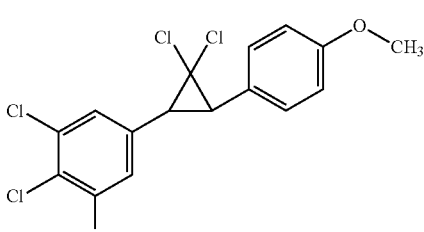 | 4 |

TABLE 3-continued

Structure and preparation method for C series molecules

| No. | Structure | Prep* |
|-----|-----------|-------|
| C41 | 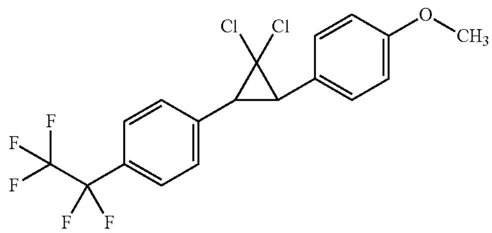 [SMILES: COc1ccc(C2C(c3ccc(C(F)(F)C(F)(F)F)cc3)C2(Cl)Cl)cc1] | 4 |
| C42 | 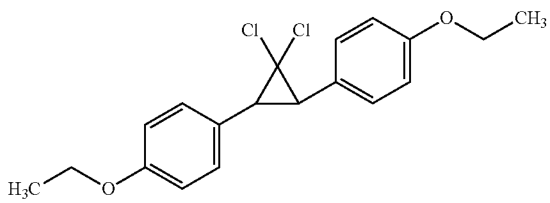 [SMILES: CCOc1ccc(C2C(c3ccc(OCC)cc3)C2(Cl)Cl)cc1] | 4 |
| C43 | 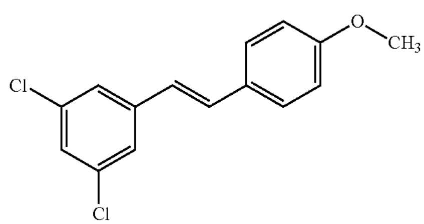 [SMILES: COc1ccc(/C=C/c2cc(Cl)cc(Cl)c2)cc1] | 5 |
| C44 | 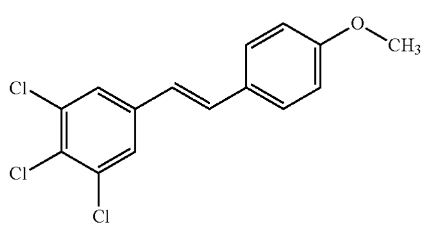 [SMILES: COc1ccc(/C=C/c2cc(Cl)c(Cl)c(Cl)c2)cc1] | 5 |
| C45 | 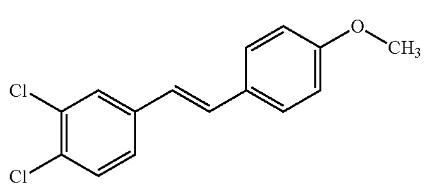 [SMILES: COc1ccc(/C=C/c2ccc(Cl)c(Cl)c2)cc1] | 5 |
| C46 | 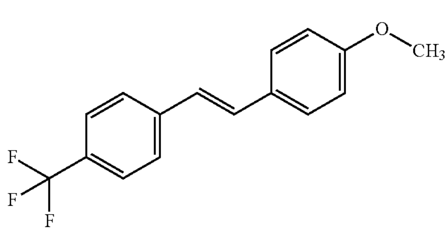 [SMILES: COc1ccc(/C=C/c2ccc(C(F)(F)F)cc2)cc1] | 6 |
| C47 | 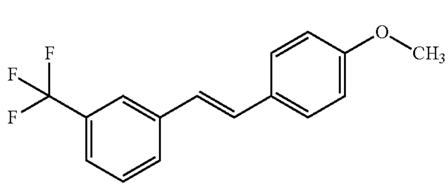 [SMILES: COc1ccc(/C=C/c2cccc(C(F)(F)F)c2)cc1] | 6 |

TABLE 3-continued

Structure and preparation method for C series molecules

| No. | Structure | Prep* |
|-----|-----------|-------|
| C48 | 3-chloro-4-(trifluoromethoxy)-4'-methoxystilbene | 6 |
| C49 | 3,5-bis(trifluoromethyl)-4'-methoxystilbene | 6 |
| C50 | 3,5-dibromo-4'-methoxystilbene | 6 |
| C51 | 3-chloro-5-(trifluoromethyl)-4'-methoxystilbene | 6 |
| C52 | 3,5-dichloro-4-bromo-4'-methoxystilbene | 6 |
| C53 | 3-bromo-5-chloro-4'-methoxystilbene | 6 |
| C54 | 3-chloro-5-fluoro-4'-methoxystilbene | 6 |

TABLE 3-continued
Structure and preparation method for C series molecules
| No. | Structure | Prep* |
|---|---|---|
| C55 | 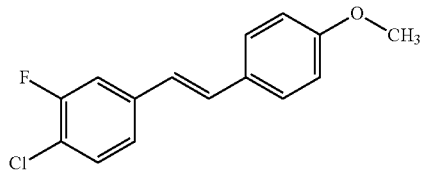 | 6 |
| C56 | 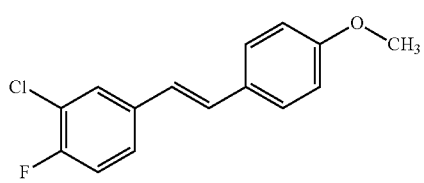 | 6 |
| C57 | 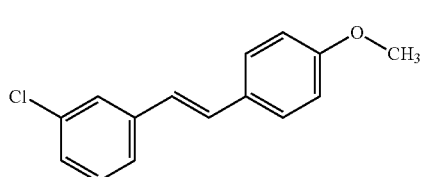 | 6 |
| C58 | 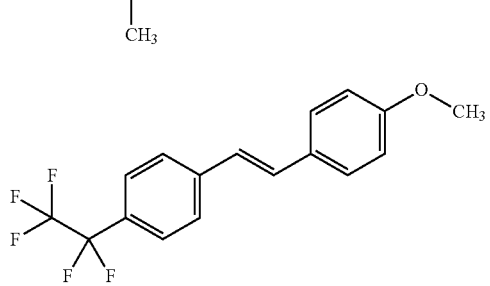 | 6 |
| C59 | 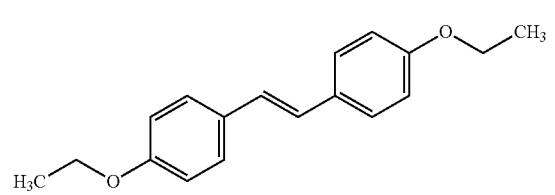 [SMILES: CCOc1ccc(/C=C/c2ccc(OCC)cc2)cc1] | 6 |
| C60 | 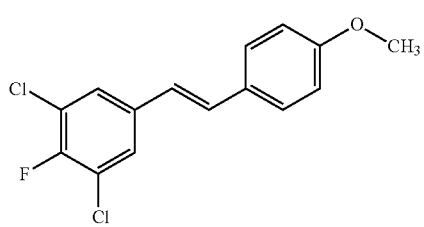 | 7 |
| C61 | 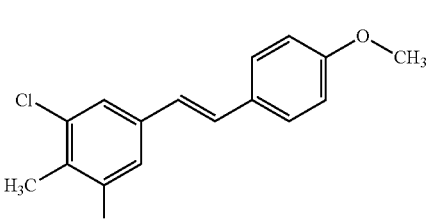 | 7 |

TABLE 3-continued

Structure and preparation method for C series molecules

| No. | Structure | Prep* |
|---|---|---|
| C62 | (structure) | 7 |
| C63 | (structure) | 8 |
| C64 | (structure) | 9 |
| C65 | (structure) | 10 |
| C66 | (structure) | 11 |
| C67 | (structure) | 12 |
| C68 | (structure) | 17b |
| C69 | (structure) | 17b |

TABLE 3-continued

Structure and preparation method for C series molecules

| No. | Structure | Prep* |
|---|---|---|
| C70 | 5-amino-2-chloro-N-(2,2,2-trifluoroethyl)benzamide | 17b |
| C71 | 5-amino-2-chloro-N-(2-oxo-2-((2,2,2-trifluoroethyl)amino)ethyl)benzamide | 17b |
| C72 | 5-amino-2-chloro-N-(pyridin-3-ylmethyl)benzamide | 18 |
| C73 | 5-amino-2-chloro-N-(pyridin-2-ylmethyl)benzamide | 18 |
| C74 | 5-amino-2-chloro-N-(pyridin-4-ylmethyl)benzamide | 18 |
| C75 | 5-amino-2-chloro-N-(4-fluorophenethyl)benzamide | 18 |
| C76 | 5-amino-2-chloro-N-(2-cyclopropylethyl)benzamide | 18 |
| C77 | 5-amino-N-(allyloxy)-2-chlorobenzamide | 19 |
| C78 | 5-amino-2-chloro-N-(cyclopropylmethoxy)benzamide | 19 |

TABLE 3-continued

Structure and preparation method for C series molecules

| No. | Structure | Prep* |
|---|---|---|
| C79 | 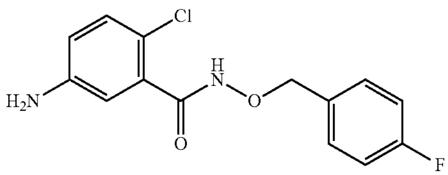 | 19 |
| C80 | 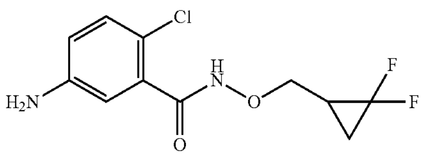 [SMILES: Nc1ccc(Cl)c(C(=O)NOCC2CC2(F)F)c1] | 20 |
| C81 | 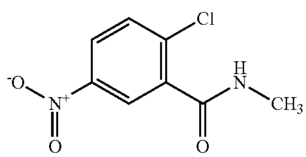 | 21 |
| C82 | 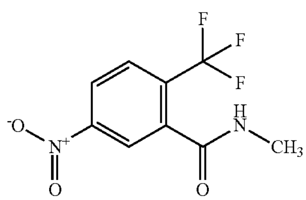 | 21 |
| C83 | 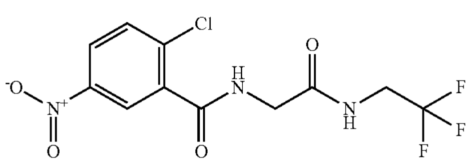 | 21 |
| C84 | 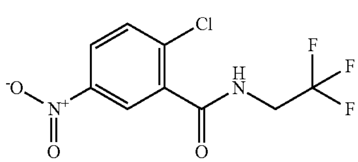 | 22 |
| C85 | 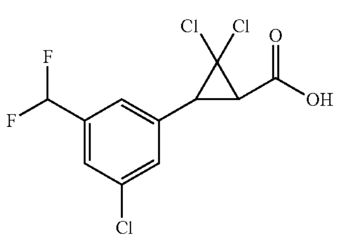 [SMILES: O=C(O)C1C(c2cc(Cl)cc(C(F)F)c2)C1(Cl)Cl] | 2 |
| C86 | 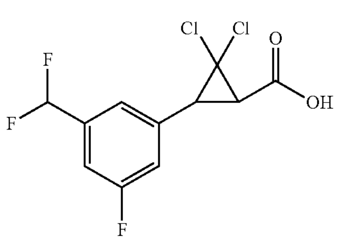 [SMILES: O=C(O)C1C(c2cc(F)cc(C(F)F)c2)C1(Cl)Cl] | 2 |

TABLE 3-continued

Structure and preparation method for C series molecules

| No. | Structure | Prep* |
|---|---|---|
| C87 | 3-(difluoromethyl)-5-fluorophenyl 2,2-dichlorocyclopropanecarboxylic acid | 2 |
| C88 | 3-(difluoromethyl)-4-fluorophenyl 2,2-dichlorocyclopropanecarboxylic acid | 2 |
| C89 | 3-chloro-4-(difluoromethyl)phenyl 2,2-dichlorocyclopropanecarboxylic acid | 2 |
| C90 | 3-fluoro-4-(difluoromethyl)phenyl 2,2-dichlorocyclopropanecarboxylic acid | 2 |
| C91 | 3-(difluoromethyl)phenyl 2,2-dichlorocyclopropanecarboxylic acid | 2 |
| C92 | 4-(difluoromethyl)phenyl 2,2-dichlorocyclopropanecarboxylic acid | 2 |
| C93 | 3,5-difluoro-4-methoxyphenyl 2,2-dichlorocyclopropanecarboxylic acid | 2 |

TABLE 3-continued

Structure and preparation method for C series molecules

| No. | Structure | Prep* |
|---|---|---|
| C94 | (structure: 2,2-dichloro-3-(3,4,5-trifluorophenyl)cyclopropanecarboxylic acid) | 2 |
| C95 | (structure: 1-[3-chloro-5-(difluoromethyl)phenyl]-2,2-dichloro-3-(4-methoxyphenyl)cyclopropane) | 4 |
| C96 | (structure: 1-[4-chloro-3-(difluoromethyl)phenyl]-2,2-dichloro-3-(4-methoxyphenyl)cyclopropane) | 4 |
| C97 | (structure: 1-[3-(difluoromethyl)-5-fluorophenyl]-2,2-dichloro-3-(4-methoxyphenyl)cyclopropane) | 4 |
| C98 | (structure: 1-[2-fluoro-5-(difluoromethyl)phenyl]-2,2-dichloro-3-(4-methoxyphenyl)cyclopropane) | 4 |
| C99 | (structure: 1-[3-chloro-4-(difluoromethyl)phenyl]-2,2-dichloro-3-(4-methoxyphenyl)cyclopropane) | 4 |

TABLE 3-continued

Structure and preparation method for C series molecules

| No. | Structure | Prep* |
|---|---|---|
| C100 | 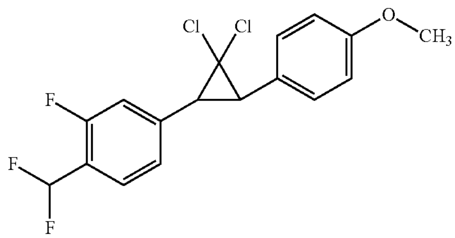 [SMILES: COc1ccc(C2C(c3ccc(C(F)F)c(F)c3)C2(Cl)Cl)cc1] | 4 |
| C101 | 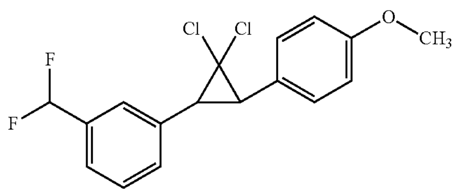 [SMILES: COc1ccc(C2C(c3cccc(C(F)F)c3)C2(Cl)Cl)cc1] | 4 |
| C102 | 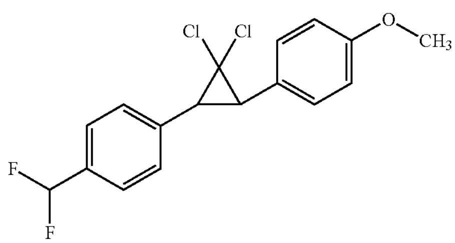 [SMILES: COc1ccc(C2C(c3ccc(C(F)F)cc3)C2(Cl)Cl)cc1] | 4 |
| C103 | 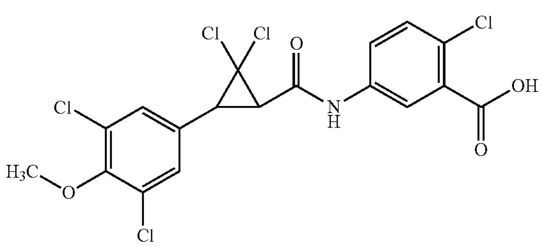 [SMILES: COc1c(Cl)cc(C2C(C(=O)Nc3ccc(Cl)c(C(=O)O)c3)C2(Cl)Cl)cc1Cl] | 12 |
| C104 | 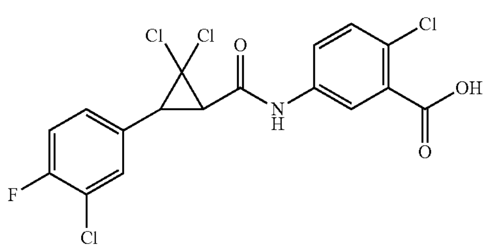 [SMILES: O=C(O)c1cc(NC(=O)C2C(c3ccc(F)c(Cl)c3)C2(Cl)Cl)ccc1Cl] | 12 |
| C105 | 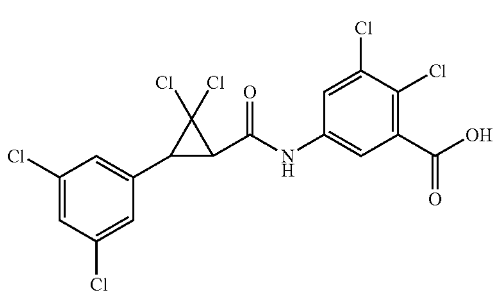 [SMILES: O=C(O)c1cc(NC(=O)C2C(c3cc(Cl)cc(Cl)c3)C2(Cl)Cl)cc(Cl)c1Cl] | 12 |

TABLE 3-continued

Structure and preparation method for C series molecules

| No. | Structure | Prep* |
|---|---|---|
| C106 | 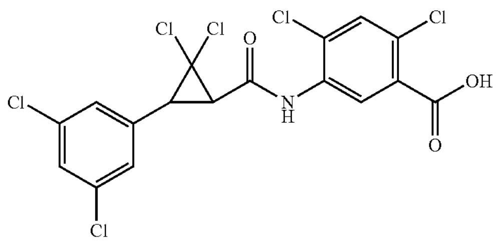 [SMILES: O=C(O)c1cc(NC(=O)C2C(c3cc(Cl)cc(Cl)c3)C2(Cl)Cl)c(Cl)cc1Cl] | 12 |
| C107 | 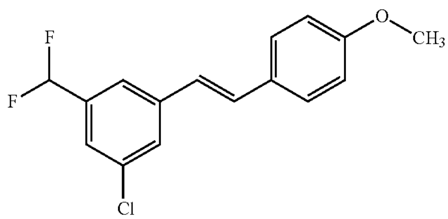 [SMILES: COc1ccc(/C=C/c2cc(Cl)cc(C(F)F)c2)cc1] | 25 |
| C108 | 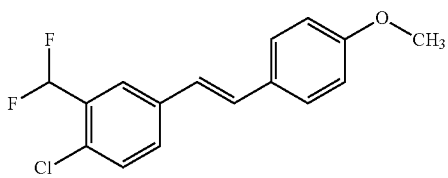 [SMILES: COc1ccc(/C=C/c2ccc(Cl)c(C(F)F)c2)cc1] | 25 |
| C109 | 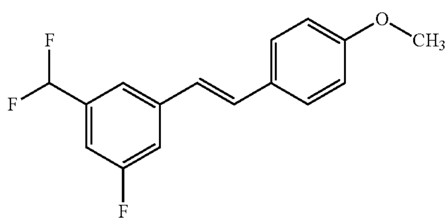 [SMILES: COc1ccc(/C=C/c2cc(F)cc(C(F)F)c2)cc1] | 25 |
| C110 | 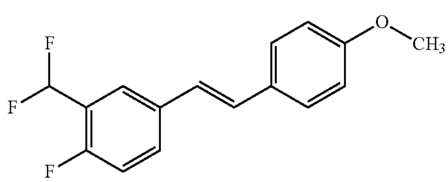 [SMILES: COc1ccc(/C=C/c2ccc(F)c(C(F)F)c2)cc1] | 25 |
| C111 | 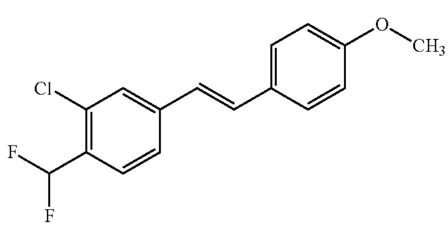 | 25 |
| C112 | 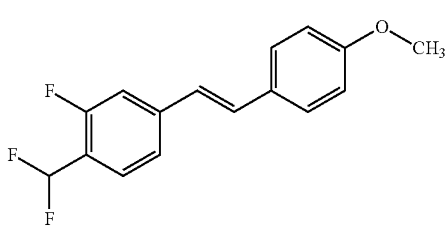 [SMILES: COc1ccc(/C=C/c2ccc(C(F)F)c(F)c2)cc1] | 25 |

TABLE 3-continued

Structure and preparation method for C series molecules

| No. | Structure | Prep* |
|---|---|---|
| C113 | 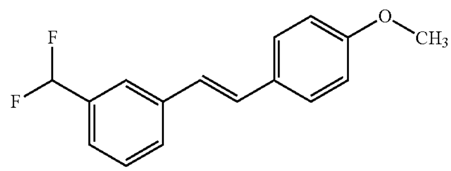 [SMILES: COc1ccc(/C=C/c2cccc(C(F)F)c2)cc1] | 25 |
| C114 | 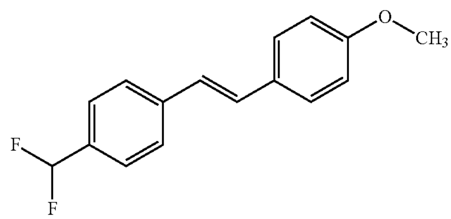 [SMILES: COc1ccc(/C=C/c2ccc(C(F)F)cc2)cc1] | 25 |
| C115 | 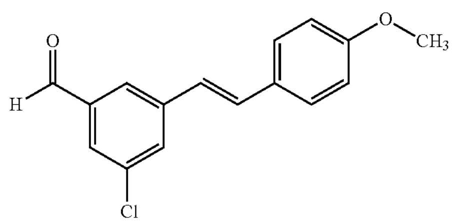 [SMILES: COc1ccc(/C=C/c2cc(Cl)cc(C=O)c2)cc1] | 26 |
| C116 | 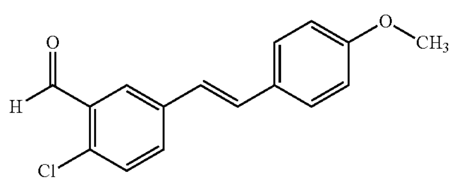 [SMILES: COc1ccc(/C=C/c2ccc(Cl)c(C=O)c2)cc1] | 26 |
| C117 | 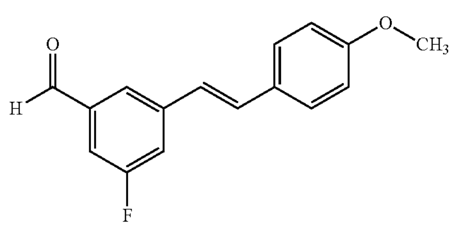 | 26 |
| C118 | 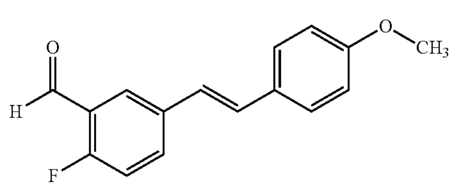 | 26 |
| C119 | 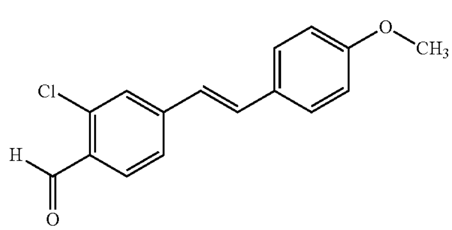 | 26 |

TABLE 3-continued

Structure and preparation method for C series molecules

| No. | Structure | Prep* |
|---|---|---|
| C120 | 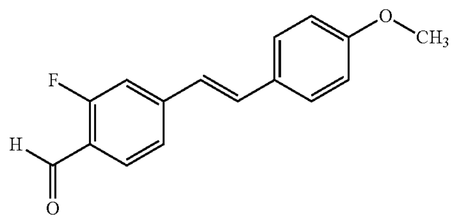 [SMILES: COc1ccc(/C=C/c2ccc(C=O)c(F)c2)cc1] | 26 |
| C121 | 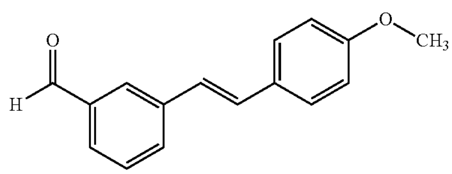 | 26 |
| C122 | 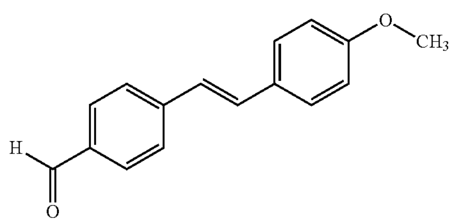 [SMILES: COc1ccc(/C=C/c2ccc(C=O)cc2)cc1] | 26 |
| C123 | 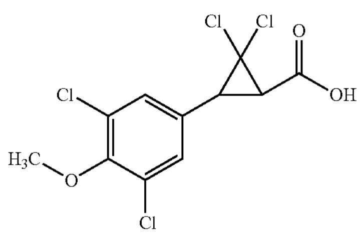 | 27 |
| C124 | 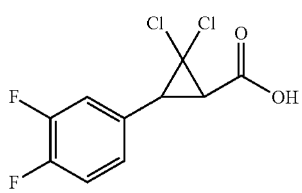 [SMILES: O=C(O)C1C(c2ccc(F)c(F)c2)C1(Cl)Cl] | 27 |
| C125 | 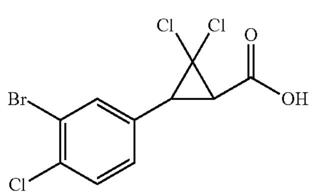 | 27 |
| C126 | 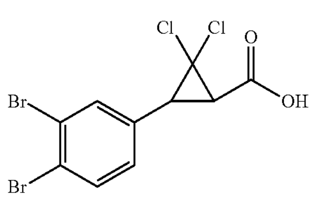 | 27 |

TABLE 3-continued
Structure and preparation method for C series molecules
| No. | Structure | Prep* |
|---|---|---|
| C127 | 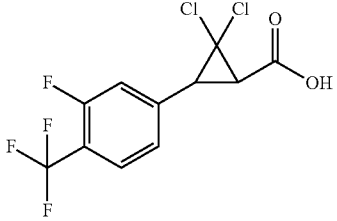 | 27 |
| C128 | 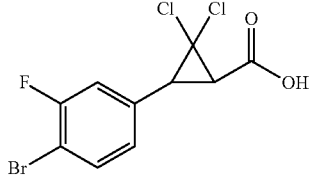 | 27 |
| C129 | 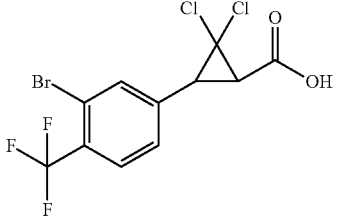 | 27 |
| C130 | 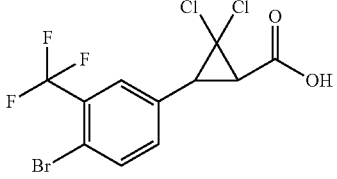 | 27 |
| C131 | 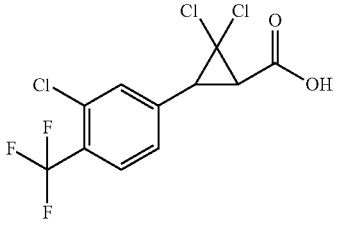 | 27 |
| C132 | 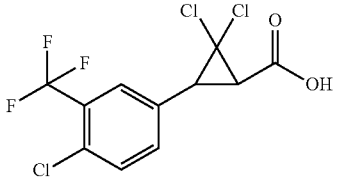 | 27 |
| C133 | 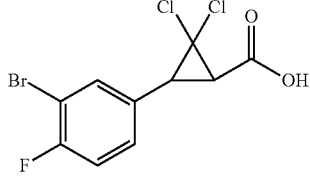 | 27 |

TABLE 3-continued
Structure and preparation method for C series molecules
| No. | Structure | Prep* |
|---|---|---|
| C134 | 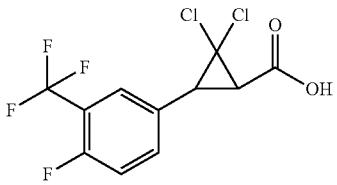 | 27 |
| C135 | 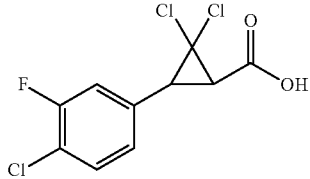 [SMILES: O=C(O)C1C(c2ccc(Cl)c(F)c2)C1(Cl)Cl] | 27 |
| C136 | 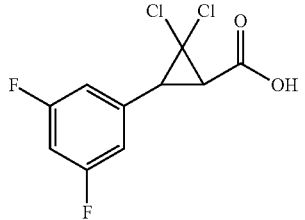 [SMILES: O=C(O)C1C(c2cc(F)cc(F)c2)C1(Cl)Cl] | 27 |
| C137 | 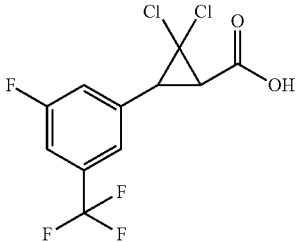 [SMILES: O=C(O)C1C(c2cc(F)cc(C(F)(F)F)c2)C1(Cl)Cl] | 27 |
| C138 | 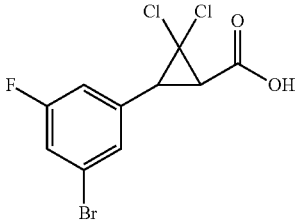 | 27 |
| C139 | 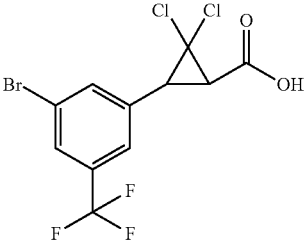 [SMILES: O=C(O)C1C(c2cc(Br)cc(C(F)(F)F)c2)C1(Cl)Cl] | 27 |

TABLE 3-continued

Structure and preparation method for C series molecules

| No. | Structure | Prep* |
|---|---|---|
| C140 | 3,5-dichlorophenyl-2,2-dichlorocyclopropanecarboxylic acid | 28 |
| C141 | 3,4-dichlorophenyl-2,2-dichlorocyclopropanecarboxylic acid | 28 |
| C142 | 3,4,5-trichlorophenyl-2,2-dichlorocyclopropanecarboxylic acid | 28 |
| C143 | 3,5-dichloro-4-methoxyphenyl-2,2-dichlorocyclopropanecarboxylic acid | 28 |
| C144 | 3-chloro-4-fluorophenyl-2,2-dichlorocyclopropanecarboxylic acid | 28 |
| C145 | 3,5-dichlorophenyl-2,2-dichloro-cyclopropyl diethyl acetal | 29 |
| C146 | 3,4-dichlorophenyl-2,2-dichloro-cyclopropyl diethyl acetal | 29 |

TABLE 3-continued
Structure and preparation method for C series molecules
| No. | Structure | Prep* |
|-----|-----------|-------|
| C147 | 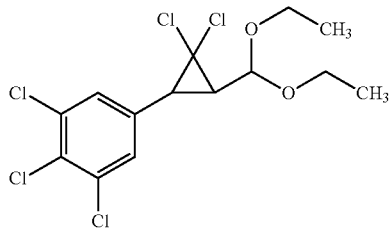 [SMILES: CCOC(OCC)C1C(c2cc(Cl)c(Cl)c(Cl)c2)C1(Cl)Cl] | 29 |
| C148 | 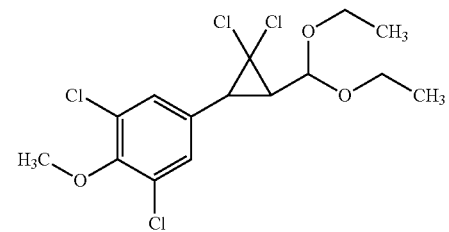 [SMILES: CCOC(OCC)C1C(c2cc(Cl)c(OC)c(Cl)c2)C1(Cl)Cl] | 29 |
| C149 | 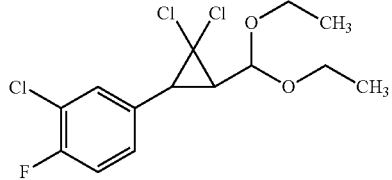 [SMILES: CCOC(OCC)C1C(c2ccc(F)c(Cl)c2)C1(Cl)Cl] | 29 |
| C150 | 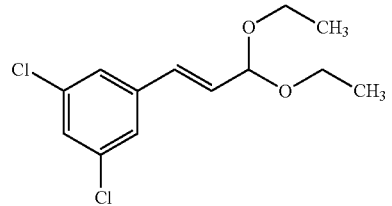 [SMILES: CCOC(/C=C/c1cc(Cl)cc(Cl)c1)OCC] | 30 |
| C151 | 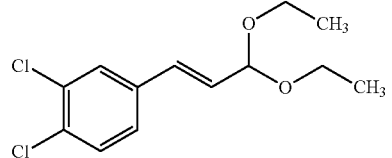 [SMILES: CCOC(/C=C/c1ccc(Cl)c(Cl)c1)OCC] | 30 |
| C152 | 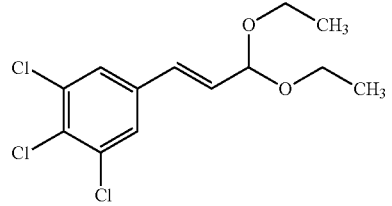 [SMILES: CCOC(/C=C/c1cc(Cl)c(Cl)c(Cl)c1)OCC] | 30 |
| C153 | 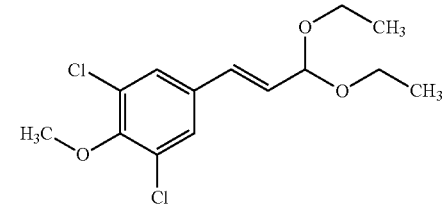 [SMILES: CCOC(/C=C/c1cc(Cl)c(OC)c(Cl)c1)OCC] | 30 |

TABLE 3-continued

Structure and preparation method for C series molecules

| No. | Structure | Prep* |
|---|---|---|
| C154 | 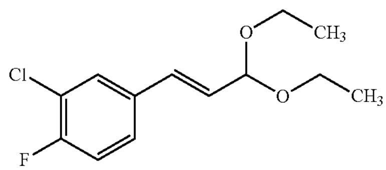 [SMILES: CCOC(/C=C/c1ccc(F)c(Cl)c1)OCC] | 30 |
| C155 | 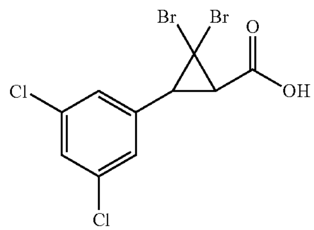 [SMILES: O=C(O)C1C(c2cc(Cl)cc(Cl)c2)C1(Br)Br] | 31 |
| C156 | 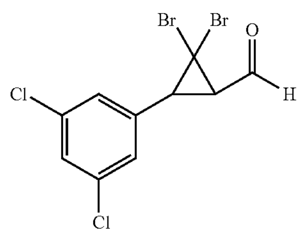 [SMILES: O=CC1C(c2cc(Cl)cc(Cl)c2)C1(Br)Br] | 32 |
| C157 | 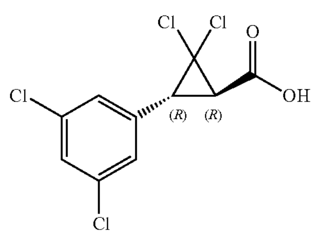 | 33 |
| C158 | 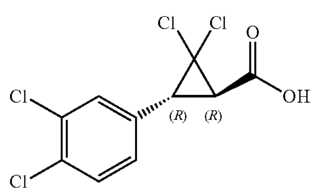 | 33 |
| C159 | 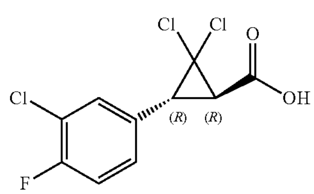 | 33 |
| C160 | 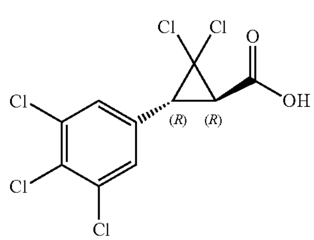 | 33 |

TABLE 3-continued

Structure and preparation method for C series molecules

| No. | Structure | Prep* |
|---|---|---|
| C161 | 3,5-dichlorophenyl-2,2-dichlorocyclopropanecarboxylic acid (S,S) | 33 |
| C162 | 3,4-dichlorophenyl-2,2-dichlorocyclopropanecarboxylic acid (S,S) | 33 |
| C163 | 3-chloro-4-fluorophenyl-2,2-dichlorocyclopropanecarboxylic acid (S,S) | 33 |
| C164 | 3,4,5-trichlorophenyl-2,2-dichlorocyclopropanecarboxylic acid (S,S) | 33 |

*prepared according to example number

TABLE 4

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| F1 | 185-187 | | HRMS-ESI [M]$^+$ calcd for C$_{18}$H$_{14}$Cl$_5$N$_2$O$_2$, 466.9464; found, 466.9472. | $^1$H NMR (400 MHz, CDCl$_3$) δ 10.14 (s, 1H), 7.93 (dd, J = 8.8, 2.6 Hz, 1H), 7.43 (d, J = 2.6 Hz, 1H), 7.33 (t, J = 1.7 Hz, 1H), 7.27 (d, J = 8.8 Hz, 1H), 7.18 (dd, J = 1.8, 0.6 Hz, 2H), 6.70 (q, J = 4.6 Hz, 1H), 3.50 (d, J = 8.2 Hz, 1H), 3.10 (d, J = 8.2 Hz, 1H), 3.05 (d, J = 4.9 Hz, 3H); $^{13}$C NMR (126 MHz, DMSO-d$_6$) δ 166.32, 162.44, 137.45, 137.32, 137.18, 133.96, 130.01, 127.80, 127.59, 123.87, 120.85, 118.98, 62.04, 38.28, 36.67, 25.85 |
| F2 | (thin film) | 3274, 3069, 1641 | ESIMS 501 ([M + H]$^+$) | $^1$H NMR (400 MHz, DMSO-d$_6$) δ 11.09 (s, 1H), 8.45 (q, J = 4.5 Hz, 1H), 7.89-7.73 (m, 3H), 7.64 (t, J = 1.8 Hz, 1H), 7.57 (dd, J = 1.9, 0.5 Hz, 2H), |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | | 3.64 (d, J = 8.5 Hz, 1H), 3.55 (d, J = 8.5 Hz, 1H), 2.76 (d, J = 4.6 Hz, 3H) |
| F3 | 244-245 | | ESIMS 499 ([M − H]$^−$) | $^1$H NMR (400 MHz, DMSO-d$_6$) δ 10.90 (s, 1H), 9.15 (t, J = 6.3 Hz, 1H), 8.16 (br s, 1H), 7.86 (br d, J = 8 Hz, 1H), 7.66-7.60 (m, 2H), 7.57 (d, J = 2 Hz, 2H), 7.50 (t, J = 8 Hz, 1H), 4.16-4.04 (m, 2H), 3.62 (d, J = 8.5 Hz, 1H), 3.55 (d, J = 8.5 Hz, 1H) |
| F4 | | (thin film) 3249, 3085, 1654 | ESIMS 536 ([M + H]$^+$) | $^1$H NMR (400 MHz, DMSO-d$_6$) δ 10.90 (s, 1H), 9.22 (t, J = 6.3 Hz, 1H), 7.77 (d, J = 2.5 Hz, 1H), 7.73 (dd, J = 8.7, 2.6 Hz, 1H), 7.65-7.61 (m, 1H), 7.59-7.53 (m, 2H), 7.52 (d, J = 8.7 Hz, 1H), 4.16-4.00 (m, 2H), 3.62 (d, J = 8.5 Hz, 1H), 3.50 (d, J = 8.5 Hz, 1H) |
| F5 | | (thin film) 3299, 3076, 1657 | ESIMS 593 ([M + H]$^+$) | $^1$H NMR (400 MHz, DMSO-d$_6$) δ 10.90 (s, 1H), 8.73 (t, J = 6.0 Hz, 1H), 8.63 (t, J = 6.3 Hz, 1H), 7.81 (d, J = 2.6 Hz, 1H), 7.74 (dd, J = 8.8, 2.6 Hz, 1H), 7.63 (t, J = 1.8 Hz, 1H), 7.57-7.54 (m, 2H), 7.48 (d, J = 8.7 Hz, 1H), 4.02-3.94 (m, 2H), 3.93 (d, J = 6.2 Hz, 2H), 3.61 (d, J = 8.5 Hz, 1H), 3.50 (d, J = 8.5 Hz, 1H) |
| F6 | 220-223 | (thin film) 3270 (w), 3061 (w), 1674 (s), 1591 (m), 1538 (m), 1414 (m), 1367 (m) | ESIMS 543 ([M + H]$^+$) | $^1$H NMR (400 MHz, DMSO-d$_6$) δ 10.86 (br s, 1H), 9.11 (br t, J = 6 Hz, 1H), 8.58 (d, J = 1.7 Hz, 1H), 8.48 (dd, J = 4.8, 1.4 Hz, 1H), 7.69-7.79 (m, 3H), 7.63 (t, J = 1.8 Hz, 1H), 7.53-7.56 (m, 2H), 7.49 (d, J = 8.6 Hz, 1H), 7.39 (ddd, J = 8.1, 4.8, 1 Hz, 1H), 4.48 (br d, J = 6.7 Hz, 2H), 3.62 (d, J = 8.5 Hz, 1H), 3.50 (d, J = 8.5 Hz, 1H) |
| F7 | 230-232 | (thin film) 3280 (w), 3054 (w), 1672 (s), 1593 (m), 1535 (m), 1472 (m), 1414 (m) | ESIMS 578 ([M + H]$^+$) | $^1$H NMR (400 MHz, DMSO-d$_6$) δ 10.87 (br s, 1H), 9.11 (br t, J = 6 Hz, 1H), 8.58 (d, J = 1.7 Hz, 1H), 8.48 (dd, J = 5, 1.5 Hz, 1H), 7.79 (s, 2H), 7.78-7.69 (m, 3H), 7.50 (d, J = 8.7 Hz, 1H), 7.39 (ddd, J = 7.8, 4.8, 0.6 Hz, 1H), 4.48 (br d, J = 6 Hz, 2H), 3.62 (d, J = 8.6 Hz, 1H), 3.52 (d, J = 8.6 Hz, 1H) |
| F8 | | (thin film) 3269 (w), 3058 (w), 1703 (w), 1642 (s), 1591 (s), 1554 (s), 1475 (s) | ESIMS 544 ([M + H]$^+$) | $^1$H NMR (400 MHz, DMSO-d$_6$) δ 10.88 (br s, 1H), 9.11 (br t, J = 6 Hz, 1H), 8.53 (m, 1H), 7.84-7.78 (m, 2H), 7.72 (dd, J = 9, 2.5 Hz, 1H), 7.63 (t, J = 1.8 Hz, 1H), 7.57-7.54 (m, 2H), 7.50 (d, J = 9 Hz, 1H), 7.41 (d, J = 8 Hz, 1H), 7.29 (m, 1H), 4.54 (br d, J = 6 Hz, 2H), 3.62 (d, J = 8.5 Hz, 1H), 3.50 (d, J = 8.5 Hz, 1H) |
| F9 | | (thin film) 3188 (w), 3053 (w), 1695 (w), 1637 (s), 1609 (w), 1589 (m), 1548 (s), 1473 (s), 1405 (s), 1320 (s) | ESIMS 578 ([M + H]$^+$) | $^1$H NMR (400 MHz, DMSO-d$_6$) δ 10.89 (br s, 1H), 9.11 (br t, J = 6 Hz, 1H), 8.53 (m, 1H), 7.84-7.78 (m, 4H), 7.73 (dd, J = 9, 2.5 Hz, 1H), 7.51 (d, J = 8.5 Hz, 1H), 7.41 (d, J = 8 Hz, 1H), 7.29 (m, 1H), 4.54 (br d, J = 6 Hz, 2H), 3.63 (d, J = 8.5 Hz, 1H), 3.53 (d, J = 8.5 Hz, 1H) |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| F10 | | (thin film) 3189 (w), 1659 (s), 1588 (s), 1567 (m), 1544 (s), 1473 (s), 1404 (m), 1323 (m) | ESIMS 511 ([M + H]$^+$) | $^1$H NMR (400 MHz, CDCl$_3$) δ 9.16-9.04 (m, 2H), 8.02 (m, 1H), 7.68 (d, J = 2.2 Hz, 1H), 7.38 (d, J = 9 Hz, 1H), 7.35 (t, J = 1.5 Hz, 1H), 7.22 (d, J = 1.5 Hz, 2H), 6.03 (m, 1H), 5.47-5.35 (m, 2H), 4.54 (br d, J = 6.7 Hz, 2H), 3.54 (d, J = 8 Hz, 1H), 3.04 (d, J = 8 Hz, 1H) |
| F11 | | (thin film) 3195 (w), 1657 (s), 1609 (m), 1587 (m), 1547 (s), 1472 (s), 1404 (s), 1323 (m) | ESIMS 544 ([M + H]$^+$) | $^1$H NMR (400 MHz, CDCl$_3$) δ 9.12 (br s, 2H), 8.03 (m, 1H), 7.70 (d, J = 2.2 Hz, 1H), 7.38 (d, J = 9 Hz, 1H), 7.35 (s, 2H), 6.03 (m, 1H), 5.46-5.36 (m, 2H), 4.54 (br d, J = 6.5 Hz, 2H), 3.52 (d, J = 8 Hz, 1H), 3.04 (d, J = 8 Hz, 1H) |
| F12 | 57-62 | (thin film) 3267 (w), 3062 (w), 1648 (s), 1607 (s), 1588 (s), 1566 (s), 1544 (s), 1473 (s), 1406 (s), 1323 (s) | ESIMS 544 ([M + H]$^+$) | $^1$H NMR (400 MHz, DMSO-d$_6$) δ 10.90 (br s, 1H), 9.14 (br t, J = 6 Hz, 1H), 8.58-8.51 (m, 2H), 7.81 (d, J = 2.6 Hz, 1H), 7.73 (dd, J = 8.7, 2.6 Hz, 1H), 7.63 (t, J = 2 Hz, 1H), 7.58-7.48 (m, 3H), 7.39-7.32 (m, 2H), 4.48 (d, J = 6 Hz, 2H), 3.62 (d, J = 8.5 Hz, 1H), 3.51 (d, J = 8.5 Hz, 1H) |
| F13 | 136-139 | (thin film) 3268 (w), 3032 (w), 1658 (s), 1606 (m), 1590 (s), 1547 (s), 1472 (s), 1413 (s) | ESIMS 578 ([M + H]$^+$) | $^1$H NMR (400 MHz, DMSO-d$_6$) δ 10.90 (br s, 1H), 9.14 (t, J = 6 Hz, 1H), 8.58-8.51 (m, 2H), 7.83-7.77 (m, 3H), 7.73 (dd, J = 8.8, 2.6 Hz, 1H), 7.52 (d, J = 8.8 Hz, 1H), 7.39-7.32 (m, 2H), 4.48 (d, J = 6 Hz, 2H), 3.63 (d, J = 8.5 Hz, 1H), 3.54 (d, J = 8.5 Hz, 1H) |
| F14 | | (thin film) 3237 (w), 3002 (w), 1650 (s), 1532 (m), 1473 (m) | ESIMS 509 ([M + H]$^+$) | $^1$H NMR (400 MHz, DMSO-d$_6$) δ 11.60 (br s, 1H), 10.91 (br s, 1H), 7.77-7.66 (m, 4H), 7.51 (d, J = 9 Hz, 1H), 7.43 (dd, J = 9, 2 Hz, 1H), 5.99 (m, 1H), 5.38 (m, 1H), 5.30 (d, J = 10.4 Hz, 1H), 4.42 (br d, J = 6 Hz, 2H), 3.60 (d, J = 8.2 Hz, 1H), 3.45 (d, J = 8.2 Hz, 1H) |
| F15 | | (thin film) 3256 (w), 3004 (w), 1660 (s), 1609 (m), 1588 (s), 1548 (s), 1473 (m), 1404 (m), 1325 (m) | ESIMS 557 ([M + H]$^+$) | $^1$H NMR (400 MHz, CDCl$_3$) δ 11.57 (br s, 1H), 10.89 (br s, 1H), 7.80 (s, 2H), 7.77 (d, J = 2.2 Hz, 1H), 7.70 (dd, J = 9, 2.2 Hz, 1H), 7.51 (d, J = 9 Hz, 1H), 3.72 (d, J = 7 Hz, 2H), 3.63 (d, J = 8.5 Hz, 1H), 3.53 (d, J = 8.5 Hz, 1H), 1.11 (m, 1H), 0.58-0.52 (m, 2H), 0.32-0.26 (m, 2H) |
| F16 | | (thin film) 3252 (w), 3077 (w), 1654 (s), 1609 (m), 1588 (s), 1542 (s), 1473 (s), 1404 (s) | ESIMS 523 ([M + H]$^+$) | $^1$H NMR (400 MHz, DMSO-d$_6$) δ 11.57 (br s, 1H), 10.89 (br s, 1H), 7.77 (d, J = 2.5 Hz, 1H), 7.70 (dd, J = 9, 2.5 Hz, 1H), 7.63 (t, J = 1.5 Hz, 1H), 7.55 (d, J = 1.5 Hz, 2H), 7.50 (d, J = 9 Hz, 1H), 3.72 (d, J = 7 Hz, 2H), 3.62 (d, J = 8.6 Hz, 1H), 3.50 (d, J = 8.6 Hz, 1H), 1.10 (m, 1H), 0.58-0.52 (m, 2H), 0.31-0.27 (m, 2H) |
| F17 | | (thin film) 3190 (w), 1661 (s), 1605 (m), 1588 (s), 1567 (m), 1544 (s), | ESIMS 577 ([M + H]$^+$) | $^1$H NMR (400 MHz, DMSO-d$_6$) δ 11.68 (br s, 1H), 10.90 (s, 1H), 7.77 (d, J = 2.3 Hz, 1H), 7.68 (dd, J = 9, 2.3 Hz, 1H), 7.63 (t, J = 1 Hz, 1H), 7.55 (d, J = 1 Hz, 2H), 7.53-7.48 (m, 3H), 7.26-7.19 (m, 2H), 4.92 (s, |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | 1510 (s), 1472 (s), 1403 (s) | | 2H), 3.62 (d, J = 8.6 Hz, 1H), 3.51 (d, J = 8.6 Hz, 1H) |
| F18 | | (thin film) 3186 (w), 1659 (s), 1606 (m), 1587 (m), 1547 (s), 1510 (s), 1472 (m), 1403 (m) | ESIMS 611 ([M + H]$^+$) | $^1$H NMR (400 MHz, DMSO-d$_6$) δ 11.68 (s, 1H), 10.89 (s, 1H), 7.80 (s, 2H), 7.77 (d, J = 2.4 Hz, 1H), 7.68 (dd, J = 9, 2.4 Hz, 1H), 7.54-7.48 (m, 3H), 7.26-7.20 (m, 2H), 4.92 (s, 2H), 3.63 (d, J = 8.5 Hz, 1H), 3.53 (d, J = 8.5 Hz, 1H) |
| F19 | | (thin film) 3268 (w), 3070 (w), 1639 (m), 1587 (m), 1540 (s), 1509 (s), 1472 (s), 1404 (m), 1320 (m), 1220 (m), 1184 (m) | ESIMS 575 ([M + H]$^+$) | $^1$H NMR (400 MHz, DMSO-d$_6$) δ 10.84 (br s, 1H), 8.55 (t, J = 5.5 Hz, 1H), 7.76 (d, J = 2.4 Hz, 1H), 7.65-7.59 (m, 2H), 7.56 (d, J = 1.3 Hz, 2H), 7.46 (d, J = 8.8 Hz, 1H), 7.30 (m, 2H), 7.12 (m, 2H), 3.62 (d, J = 8.6 Hz, 1H), 3.50 (d, J = 8.6 Hz, 1H), 3.44 (m, 2H), 2.81 (t, J = 7 Hz, 2H) |
| F20 | | (thin film) 3424 (w), 3275 (w), 3065 (w), 1644 (m), 1588 (m), 1548 (s), 1509 (s), 1472 (m), 1407 (m), 1322 (m), 1222 (m) | ESIMS 609 ([M + H]$^+$) | $^1$H NMR (400 MHz, DMSO-d$_6$) δ 10.85 (br s, 1H), 8.55 (t, J = 5.7 Hz, 1H), 7.80 (s, 2H), 7.76 (d, J = 2.6 Hz, 1H), 7.62 (dd, J = 8.8, 2.6 Hz, 1H), 7.46 (d, J = 8.8 Hz, 1H), 7.30 (m, 2H), 7.12 (m, 2H), 3.63 (d, J = 8.5 Hz, 1H), 3.53 (d, J = 8.5 Hz, 1H), 3.45 (m, 2H), 2.82 (t, J = 7.2 Hz, 2H) |
| F21 | | (thin film) 3186 (w), 1658 (m), 1588 (m), 1544 (m), 1473 (s), 1402 (m) | HRMS-ESI (TOF) [M + H]$^+$ calcd for C$_{21}$H$_{16}$Cl$_5$F$_2$N$_2$O$_3$ 558.9538; found 558.9538. | $^1$H NMR (400 MHz, DMSO-d$_6$) δ 11.77 (br s, 1H), 10.99 (s, 1H), 7.80-7.69 (m, 2H), 7.62 (t, J = 1.8 Hz, 1H), 7.55 (d, J = 1.8 Hz, 2H), 7.50 (d, J = 9 Hz, 1H), 4.03 (m, 1H), 3.89 (m, 1H), 3.62 (d, J = 8.5 Hz, 1H), 3.54 (d, J = 8.5 Hz, 1H), 2.10 (m, 1H), 1.69 (m, 1H), 1.41 (m, 1H) |
| F22 | | (thin film) 3016 (w), 1651 (m), 1588 (m), 1545 (m), 1473 (s), 1401 (m) | HRMS-ESI (TOF) [M + H]$^+$ calcd for C$_{21}$H$_{16}$Cl$_5$F$_2$N$_2$O$_3$ 558.9538; found 558.9540. | $^1$H NMR (400 MHz, DMSO-d$_6$) δ 11.74 (br s, 1H), 11.04 (s, 1H), 7.80-7.73 (m, 3H), 7.68 (d, J = 8.5 Hz, 1H), 7.49 (d, J = 8.8 Hz, 1H), 7.42 (dd, J = 8.8, 2 Hz, 1H), 4.02 (m, 1H), 3.88 (m, 1H), 3.59 (d, J = 8.5 Hz, 1H), 3.50 (d, J = 8.5 Hz, 1H), 2.09 (m, 1H), 1.68 (m, 1H), 1.40 (m, 1H) |
| F23 | 131-133 | (thin film) 3016 (w), 1642 (m), 1587 (m), 1548 (m), 1472 (s), 1403 (m) | HRMS-ESI (TOF) [M + H]$^+$ calcd for C$_{21}$H$_{15}$Cl$_6$F$_2$N$_2$O$_3$ 592.9148; found 592.9151. | $^1$H NMR (400 MHz, DMSO-d$_6$) δ 11.64 (br s, 1H), 11.00 (s, 1H), 7.83-7.67 (m, 4H), 7.49 (d, J = 8.8 Hz, 1H), 4.01 (m, 1H), 3.88 (m, 1H), 3.63 (d, J = 8.5 Hz, 1H), 3.57 (d, J = 8.5 Hz, 1H), 2.09 (m, 1H), 1.68 (m, 1H), 1.40 (m, 1H) |
| F24 | 166-168 | (thin film) 3247 (w), 3077 (w), 1636 (s), 1588 (s), 1536 (s), 1472 (s), 1404 (s), 1320 (s) | HRMS-ESI (TOF) [M + H]$^+$ calcd for C$_{22}$H$_{20}$Cl$_5$N$_2$O$_2$ 520.9934; found 520.9936. | $^1$H NMR (400 MHz, DMSO-d$_6$) δ 10.85 (br s, 1H), 8.47 (br t, J = 5.6 Hz, 1H), 7.75 (d, J = 2.6 Hz, 1H), 7.66 (dd, J = 8.7, 2.6 Hz, 1H), 7.62 (t, J = 1.8 Hz, 1H), 7.55 (d, J = 1.8 Hz, 2H), 7.46 (d, J = 8.7 Hz, 1H), 3.61 (d, J = 8.6 Hz, 1H), 3.50 (d, J = 8.6 Hz, 1H), 3.29 (m, 2H), |

TABLE 4-continued

Analytical data for molecules in Table 2

| No. | Mp (° C.) | IR (cm⁻¹) | Mass (m/z) | NMR (¹H, ¹³C, or ¹⁹F) |
|---|---|---|---|---|
| | | | | 1.41 (q, J = 7 Hz, 2H), 0.76 (m, 1H), 0.45-0.39 (m, 2H), 0.10-0.05 (m, 2H) |
| F25 | 163-165 | (thin film) 3248 (m), 3080 (w), 2914 (w), 1648 (s), 1524 (s), 1471 (s) | HRMS-ESI (TOF) [M + H]⁺ calcd for C₂₂H₂₀Cl₅N₂O₂ 520.9934; found 520.9941. | ¹H NMR (400 MHz, DMSO-d₆) δ 10.88 (br s, 1H), 8.47 (br t, J = 5.6 Hz, 1H), 7.77-7.64 (m, 4H), 7.46 (d, J = 9 Hz, 1H), 7.42 (dd, J = 9, 2 Hz, 1H), 3.59 (d, J = 8.6 Hz, 1H), 3.45 (d, J = 8.6 Hz, 1H), 3.29 (m, 2H), 1.41 (q, J = 7 Hz, 2H), 0.76 (m, 1H), 0.45-0.39 (m, 2H), 0.10-0.05 (m, 2H) |
| F26 | 122-125 | (thin film) 3427 (w), 3259 (w), 3069 (w), 3003 (w), 1682 (s), 1659 (s), 1612 (m), 1592 (s), 1549 (s), 1526 (s), 1471 (s), 1412 (s) | HRMS-ESI (TOF) [M + H]⁺ calcd for C₂₂H₁₉Cl₆N₂O₂ 554.9544; found 554.9553. | ¹H NMR (400 MHz, DMSO-d₆) δ 10.84 (br s, 1H), 8.47 (br t, J = 5.6 Hz, 1H), 7.79 (s, 2H), 7.74 (d, J = 2.8 Hz, 1H), 7.66 (dd, J = 8.7, 2.8 Hz, 1H), 7.47 (d, J = 8.7 Hz, 1H), 3.62 (d, J = 8.6 Hz, 1H), 3.53 (d, J = 8.6 Hz, 1H), 3.29 (m, 2H), 1.41 (q, J = 7 Hz, 2H), 0.75 (m, 1H), 0.45-0.39 (m, 2H), 0.10-0.05 (m, 2H) |
| F27 | 189-190 | | ESIMS 543 ([M + H]⁺) | ¹H NMR (400 MHz, Acetone-d₆) δ 10.07 (s, 1H), 8.01 (t, J = 6.2 Hz, 1H), 7.88 (d, J = 2.6 Hz, 1H), 7.76 (dd, J = 8.7, 2.6 Hz, 1H), 7.48 (s, 3H), 7.42 (t, J = 8.0 Hz, 3H), 7.34 (t, J = 7.5 Hz, 2H), 7.29-7.23 (m, 1H), 4.61 (d, J = 6.0 Hz, 2H), 3.64 (d, J = 8.4 Hz, 1H), 3.40 (d, J = 8.3 Hz, 1H); ¹³C NMR (101 MHz, Acetone-d₆) δ 166.95, 163.27, 140.11, 138.68, 138.59, 138.31, 135.60, 131.13, 129.22, 128.73, 128.48, 127.85, 125.82, 122.25, 122.17, 120.62, 120.54, 62.81, 44.01, 40.10, 38.39 |
| F28 | 126-127 | | | ¹H NMR (400 MHz, Acetone-d₆) δ 10.07 (s, 1H), 8.05 (t, J = 6.1 Hz, 1H), 7.88 (d, J = 2.5 Hz, 1H), 7.74 (dd, J = 8.8, 2.6 Hz, 1H), 7.52-7.44 (m, 5H), 7.41 (d, J = 8.7 Hz, 1H), 7.10 (t, J = 8.7 Hz, 2H), 4.60 (d, J = 6.0 Hz, 2H), 3.64 (d, J = 8.3 Hz, 1H), 3.40 (d, J = 8.3 Hz, 1H); ¹⁹F NMR (376 MHz, DMSO-d₆) δ −117.46 |
| F29 | 197 | | ESIMS 545 ([M + H]⁺) | ¹H NMR (400 MHz, DMSO-d₆) δ 12.51 (s, 1H), 10.95 (s, 1H), 7.92 (dd, J = 4.1, 2.5 Hz, 1H), 7.81 (dd, J = 8.8, 2.6 Hz, 1H), 7.66-7.53 (m, 4H), 7.43-7.35 (m, 2H), 7.17-7.12 (m, 2H), 7.08 (t, J = 7.3 Hz, 1H), 3.65 (d, J = 8.5 Hz, 1H), 3.53 (d, J = 8.5 Hz, 1H); ¹³C NMR (101 MHz, DMSO-d₆) δ 163.43, 162.70, 159.33, 137.79, 137.25, 134.05, 133.53, 130.52, 129.56, 127.88, 127.68, 124.57, 122.66, 122.05, 119.53, 112.87, 62.12, 38.44, 36.81 |
| F30 | 185-187 | | HRMS-ESI [M + H]⁺ calcd for C₂₁H₂₀Cl₅N₂O₂, | ¹H NMR (400 MHz, DMSO-d₆) δ 10.84 (s, 1H), 8.48 (t, J = 5.9 Hz, 1H), 7.74 (d, J = 2.6 Hz, |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | 508.9934; found, 508.9935. | 1H), 7.68 (dd, J = 8.7, 2.6 Hz, 1H), 7.62 (t, J = 1.8 Hz, 1H), 7.55 (d, J = 1.6 Hz, 2H), 7.47 (d, J = 8.7 Hz, 1H), 3.62 (d, J = 8.5 Hz, 1H), 3.50 (d, J = 8.5 Hz, 1H), 3.05 (t, J = 6.6 Hz, 2H), 1.82 (dp, J = 13.2, 6.6 Hz, 1H), 0.92 (d, J = 6.7 Hz, 6H) |
| F31 | 158-160 | | HRMS-ESI [M + H]$^+$ calcd for C$_{23}$H$_{24}$Cl$_5$N$_2$O$_2$, 537.0247; found, 537.0249. | $^1$H NMR (400 MHz, DMSO-d$_6$) δ 10.83 (s, 1H), 8.44 (t, J = 5.6 Hz, 1H), 7.72 (d, J = 2.6 Hz, 1H), 7.67 (dd, J = 8.7, 2.6 Hz, 1H), 7.63 (t, J = 1.8 Hz, 1H), 7.55 (d, J = 1.6 Hz, 2H), 7.46 (d, J = 8.7 Hz, 1H), 3.61 (d, J = 8.5 Hz, 1H), 3.50 (d, J = 8.5 Hz, 1H), 3.21 (q, J = 6.7 Hz, 2H), 1.49 (q, J = 7.0 Hz, 2H), 1.30 (m, 6H), 0.87 (m, 3H) |
| F32 | 159-162 | | HRMS-ESI [M + H]$^+$ calcd for C$_{24}$H$_{16}$Cl$_5$F$_2$N$_2$O$_2$, 578.9590; found, 578.9596. | $^1$H NMR (400 MHz, DMSO-d$_6$) δ 10.86 (s, 1H), 9.08 (t, J = 6.0 Hz, 1H), 7.77 (d, J = 2.5 Hz, 1H), 7.71 (dd, J = 8.8, 2.6 Hz, 1H), 7.62 (d, J = 1.7 Hz, 1H), 7.55 (d, J = 1.5 Hz, 2H), 7.50 (d, J = 8.7 Hz, 1H), 7.41 (m, 2H), 7.21 (s, 1H), 4.44 (d, J = 6.0 Hz, 2H), 3.61 (d, J = 8.5 Hz, 1H), 3.50 (d, J = 8.5 Hz, 1H) |
| F33 | 158-160 | | HRMS-ESI [M + H]$^+$ calcd for C$_{22}$H$_{22}$Cl$_5$N$_2$O$_2$, 523.0091; found, 523.0092. | $^1$H NMR (400 MHz, DMSO-d$_6$) δ 10.83 (s, 1H), 8.44 (t, J = 5.6 Hz, 1H), 7.72 (d, J = 2.5 Hz, 1H), 7.67 (dd, J = 8.7, 2.5 Hz, 1H), 7.63 (s, 1H), 7.55 (d, J = 1.4 Hz, 2H), 7.47 (d, J = 8.7 Hz, 1H), 3.61 (d, J = 8.5 Hz, 1H), 3.50 (d, J = 8.5 Hz, 1H), 3.21 (q, J = 6.6 Hz, 2H), 1.50 (m, 2H), 1.31 (m, 4H), 0.89 (m, 3H) |
| F34 | 167-170 | | HRMS-ESI [M + H]$^+$ calcd for C$_{26}$H$_{22}$Cl$_5$N$_2$O$_4$, 602.9990; found, 602.9958. | $^1$H NMR (400 MHz, DMSO-d$_6$) δ 10.84 (s, 1H), 8.75 (t, J = 5.7 Hz, 1H), 7.75 (d, J = 2.5 Hz, 1H), 7.69 (dd, J = 8.7, 2.5 Hz, 1H), 7.63 (s, 1H), 7.55 (d, J = 1.5 Hz, 2H), 7.47 (d, J = 8.7 Hz, 1H), 7.20 (d, J = 8.3 Hz, 1H), 6.56 (d, J = 2.2 Hz, 1H), 6.51 (dd, J = 8.3, 2.2 Hz, 1H), 4.33 (d, J = 5.8 Hz, 2H), 3.80 (s, 3H), 3.75 (s, 3H), 3.61 (d, J = 8.5 Hz, 1H), 3.50 (d, J = 8.5 Hz, 1H) |
| F35 | 188-191 | | HRMS-ESI [M + H]$^+$ calcd for C$_{21}$H$_{18}$Cl$_5$N$_2$O$_2$, 506.9778; found, 506.9780. | $^1$H NMR (400 MHz, DMSO-d$_6$) δ 10.85 (s, 1H), 8.55 (t, J = 5.7 Hz, 1H), 7.73 (d, J = 2.5 Hz, 1H), 7.68 (dd, J = 8.7, 2.6 Hz, 1H), 7.63 (t, J = 1.8 Hz, 1H), 7.55 (d, J = 1.7 Hz, 2H), 7.47 (d, J = 8.7 Hz, 1H), 3.62 (d, J = 8.5 Hz, 1H), 3.50 (d, J = 8.5 Hz, 1H), 3.14 (t, J = 6.2 Hz, 2H), 1.01 (m, 1H), 0.44 (m, 2H), 0.24 (m, 2H) |
| F36 | 222-225 | | HRMS-ESI [M + H]$^+$ calcd for C$_{28}$H$_{26}$Cl$_5$N$_2$O$_2$, 599.0405; found, 599.0416. | $^1$H NMR (400 MHz, DMSO-d$_6$) δ 10.85 (s, 1H), 8.98 (t, J = 6.0 Hz, 1H), 7.73 (m, 2H), 7.63 (s, 1H), 7.55 (d, J = 1.5 Hz, 2H), 7.49 (d, J = 8.7 Hz, 1H), 7.37 (d, J = 8.3 Hz, 2H), 7.28 (d, J = 8.3 Hz, 2H), 4.41 (d, J = 4.4 Hz, 2H), 3.61 (d, J = 8.5 Hz, 1H), 3.49 (d, J = 8.5 Hz, 1H), 1.28 (s, 9H) |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| F37 | 192-194 | | HRMS-ESI [M + H]$^+$ calcd for C$_{20}$H$_{15}$Cl$_5$N$_3$O$_2$, 503.9601; found, 503.9606. | $^1$H NMR (400 MHz, DMSO-d$_6$) δ 10.88 (s, 1H), 8.86 (t, J = 5.7 Hz, 1H), 7.76 (d, J = 2.5 Hz, 1H), 7.71 (dd, J = 8.7, 2.6 Hz, 1H), 7.63 (t, J = 1.8 Hz, 1H), 7.55 (d, J = 1.7 Hz, 2H), 7.50 (d, J = 8.7 Hz, 1H), 3.62 (d, J = 8.5 Hz, 1H), 3.48 (m, 3H), 2.77 (t, J = 6.4 Hz, 2H) |
| F38 | 114-118 | | HRMS-ESI [M + NH$_4$]$^+$ calcd for C$_{21}$H$_{20}$Cl$_5$N$_3$O$_2$, 536.9996; found, 536.9997. | $^1$H NMR (400 MHz, DMSO-d$_6$) δ 10.84 (s, 1H), 8.58 (t, J = 5.6 Hz, 1H), 7.76 (d, J = 2.6 Hz, 1H), 7.68 (dd, J = 8.8, 2.6 Hz, 1H), 7.63 (t, J = 1.8 Hz, 1H), 7.55 (d, J = 1.5 Hz, 2H), 7.49 (d, J = 8.7 Hz, 1H), 3.61 (d, J = 8.5 Hz, 1H), 3.50 (d, J = 8.5 Hz, 1H), 3.30 (m, 2H), 2.57 (t, J = 7.2 Hz, 2H), 1.81 (p, J = 7.0 Hz, 2H), |
| F39 | 72-78 | | HRMS-ESI [M + H]$^+$ calcd for C$_{22}$H$_{19}$Cl$_5$F$_3$N$_2$O$_3$, 592.9757; found, 592.9766. | $^1$H NMR (400 MHz, DMSO-d$_6$) δ 10.84 (s, 1H), 8.50 (t, J = 5.6 Hz, 1H), 7.75 (d, J = 2.6 Hz, 1H), 7.67 (dd, J = 8.8, 2.6 Hz, 1H), 7.63 (t, J = 1.8 Hz, 1H), 7.55 (d, J = 1.5 Hz, 2H), 7.48 (d, J = 8.7 Hz, 1H), 4.04 (q, J = 9.4 Hz, 2H), 3.66 (t, J = 6.3 Hz, 2H), 3.61 (d, J = 8.5 Hz, 1H), 3.50 (d, J = 8.5 Hz, 1H), 3.29 (m, 2H), 1.78 (p, J = 6.5 Hz, 2H) |
| F40 | 170-172 | | HRMS-ESI [M + H]$^+$ calcd for C$_{20}$H$_{15}$Cl$_5$F$_3$N$_2$O$_2$, 548.9495; found, 548.9501. | $^1$H NMR (400 MHz, DMSO-d$_6$) δ 10.86 (s, 1H), 8.71 (t, J = 5.7 Hz, 1H), 7.76 (d, J = 2.6 Hz, 1H), 7.69 (dd, J = 8.8, 2.6 Hz, 1H), 7.63 (t, J = 1.8 Hz, 1H), 7.55 (d, J = 1.5 Hz, 2H), 7.49 (d, J = 8.7 Hz, 1H), 3.62 (d, J = 8.5 Hz, 1H), 3.48 (m, 3H), 2.54 (m, 2H) |
| F41 | 199-202 | | HRMS-ESI [M + H]$^+$ calcd for C$_{25}$H$_{17}$Cl$_5$F$_3$N$_2$O$_2$, 610.9652; found, 610.9654. | $^1$H NMR (400 MHz, DMSO-d$_6$) δ 10.86 (s, 1H), 9.14 (t, J = 6.0 Hz, 1H), 7.78 (d, J = 2.6 Hz, 1H), 7.72 (m, 3H), 7.63 (t, J = 1.8 Hz, 1H), 7.59 (d, J = 8.1 Hz, 2H), 7.55 (d, J = 1.6 Hz, 2H), 7.51 (d, J = 8.7 Hz, 1H), 4.54 (d, J = 5.9 Hz, 2H), 3.62 (d, J = 8.5 Hz, 1H), 3.50 (d, J = 8.5 Hz, 1H) |
| F42 | 120-128 | | HRMS-ESI [M + H]$^+$ calcd for C$_{22}$H$_{22}$Cl$_5$N$_2$O$_4$S, 586.9710; found, 586.9713. | $^1$H NMR (400 MHz, DMSO-d$_6$) δ 10.85 (s, 1H), 8.46 (s, 1H), 7.76 (dd, J = 8.8, 2.6 Hz, 1H), 7.66 (d, J = 2.6 Hz, 1H), 7.63 (t, J = 1.8 Hz, 1H), 7.54 (d, J = 1.5 Hz, 2H), 7.45 (d, J = 8.8 Hz, 1H), 3.82 (s, 2H), 3.61 (d, J = 8.5 Hz, 1H), 3.51 (d, J = 8.5 Hz, 1H), 3.01 (s, 3H), 1.52 (s, 6H) |
| F43 | 201-203 | | HRMS-ESI [M + H]$^+$ calcd for C$_{23}$H$_{22}$Cl$_5$N$_2$O$_3$, 551.0040; found, 551.0043. | $^1$H NMR (400 MHz, DMSO-d$_6$) δ 10.84 (s, 1H), 8.53 (t, J = 5.6 Hz, 1H), 7.74 (d, J = 2.5 Hz, 1H), 7.66 (dd, J = 8.8, 2.6 Hz, 1H), 7.63 (t, J = 1.8 Hz, 1H), 7.55 (d, J = 1.6 Hz, 2H), 7.47 (d, J = 8.7 Hz, 1H), 3.61 (d, J = 8.5 Hz, 1H), 3.50 (m, 3H), 3.38 (q, J = 5.8 Hz, 2H), 3.26 (d, J = 6.8 Hz, 2H), 0.99 (m, 1H), 0.45 (m, 2H), 0.18 (m, 2H) |
| F44 | 180-183 | | HRMS-ESI [M + H]$^+$ calcd for | $^1$H NMR (400 MHz, DMSO-d$_6$) δ 10.84 (s, 1H), 8.56 (t, J = 5.7 Hz, |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | C$_{20}$H$_{17}$Cl$_5$FN$_2$O$_2$, 512.9683; found, 512.9686. | 1H), 7.75 (d, J = 2.6 Hz, 1H), 7.68 (dd, J = 8.8, 2.6 Hz, 1H), 7.63 (t, J = 1.8 Hz, 1H), 7.55 (d, J = 1.5 Hz, 2H), 7.48 (d, J = 8.7 Hz, 1H), 4.59 (t, J = 5.9 Hz, 1H), 4.47 (t, J = 5.9 Hz, 1H), 3.61 (d, J = 8.5 Hz, 1H), 3.50 (d, J = 8.5 Hz, 1H), 3.34 (d, J = 6.1 Hz, 2H), 1.89 (dt, J = 26.0, 6.3 Hz, 2H) |
| F45 | 163-165 | | HRMS-ESI [M + H]$^+$ calcd for C$_{21}$H$_{20}$Cl$_5$N$_2$O$_2$, 508.9934; found, 508.9936. | $^1$H NMR (400 MHz, DMSO-d$_6$) δ 10.83 (s, 1H), 8.44 (t, J = 5.7 Hz, 1H), 7.72 (d, J = 2.6 Hz, 1H), 7.67 (dd, J = 8.7, 2.6 Hz, 1H), 7.62 (t, J = 1.8 Hz, 1H), 7.55 (d, J = 1.4 Hz, 2H), 7.47 (d, J = 8.7 Hz, 1H), 3.61 (d, J = 8.5 Hz, 1H), 3.50 (d, J = 8.5 Hz, 1H), 3.22 (q, J = 6.5 Hz, 2H), 1.49 (p, J = 7.0 Hz, 2H), 1.37 (dt, J = 14.7, 7.1 Hz, 2H), 0.91 (t, J = 7.3 Hz, 3H) |
| F46 | 194-196 | | HRMS-ESI [M + H]$^+$ calcd for C$_{19}$H$_{16}$Cl$_5$N$_2$O$_2$, 480.9621; found, 480.9628. | $^1$H NMR (500 MHz, DMSO-d$_6$) δ 10.84 (s, 1H), 8.46 (t, J = 5.5 Hz, 1H), 7.74 (d, J = 2.3 Hz, 1H), 7.66 (dd, J = 8.8, 2.4 Hz, 1H), 7.63 (s, 1H), 7.55 (s, 2H), 7.47 (d, J = 8.7 Hz, 1H), 3.61 (d, J = 8.5 Hz, 1H), 3.50 (d, J = 8.5 Hz, 1H), 3.25 (p, J = 7.0 Hz, 2H), 1.11 (t, J = 7.2 Hz, 3H); $^{13}$C NMR (126 MHz, DMSO-d$_6$) δ 165.59, 162.43, 137.47, 137.45, 137.19, 133.95, 129.97, 127.80, 127.59, 123.86, 120.75, 118.88, 62.04, 38.29, 36.67, 33.74, 14.45 |
| F47 | 194-196 | | HRMS-ESI [M]$^+$ calcd for C$_{20}$H$_{14}$Cl$_5$N$_2$O$_2$, 490.9464; found, 490.9469. | $^1$H NMR (500 MHz, DMSO-d$_6$) δ10.86 (s, 1H), 8.95 (t, J = 5.5 Hz, 1H), 7.76 (d, J = 2.2 Hz, 1H), 7.69 (dd, J = 8.8, 2.3 Hz, 1H), 7.63 (s, 1H), 7.55 (s, 2H), 7.49 (d, J = 8.7 Hz, 1H), 4.03 (m, 2H), 3.61 (d, J = 8.5 Hz, 1H), 3.50 (d, J = 8.5 Hz, 1H), 3.16 (s, 1H); $^{13}$C NMR (126 MHz, DMSO-d$_6$) δ 165.62, 162.47, 137.48, 137.19, 136.53, 133.95, 130.10, 127.80, 127.59, 123.91, 121.05, 118.93, 80.59, 73.04, 62.03, 38.31, 36.67, 28.19 |
| F48 | 208-210 | | HRMS-ESI [M + H]$^+$ calcd for C$_{19}$H$_{14}$Cl$_5$F$_2$N$_2$O$_2$, 516.9432; found, 516.9438. | $^1$H NMR (500 MHz, DMSO-d$_6$) δ10.88 (s, 1H), 8.91 (t, J = 5.9 Hz, 1H), 7.77 (d, J = 2.3 Hz, 1H), 7.71 (dd, J = 8.8, 2.4 Hz, 1H), 7.63 (s, 1H), 7.55 (s, 2H), 7.50 (d, J = 8.7 Hz, 1H), 6.13 (tt, J = 55.8, 3.7 Hz, 1H), 3.65 (m, 3H), 3.50 (d, J = 8.5 Hz, 1H); $^{13}$C NMR (126 MHz, DMSO-d$_6$) δ 166.61, 162.48, 137.49, 137.18, 136.52, 133.96, 130.11, 127.80, 127.60, 123.84, 121.14, 118.93, 116.10, 114.19, 112.28, 62.03, 41.30, 41.09, 40.89, 38.30, 36.67 |
| F49 | 96-102 | | HRMS-ESI [M + H]$^+$ calcd for C$_{20}$H$_{13}$Cl$_5$F$_5$N$_2$O$_2$, 584.9306; found, | $^1$H NMR (500 MHz, DMSO-d$_6$) δ10.89 (s, 1H), 9.22 (t, J = 6.3 Hz, 1H), 7.77 (d, J = 2.2 Hz, 1H), 7.73 (dd, J = 8.8, 2.4 Hz, |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | 584.9323. | 1H), 7.63 (s, 1H), 7.55 (s, 2H), 7.52 (d, J = 8.7 Hz, 1H), 4.13 (td, J = 15.5, 6.2 Hz, 2H), 3.63 (d, J = 8.5 Hz, 1H), 3.50 (d, J = 8.5 Hz, 1H) |
| F50 | 154-159 | | HRMS-ESI [M + H]$^+$ calcd for C$_{23}$H$_{25}$Cl$_5$N$_3$O$_2$, 550.0384; found, 550.0391. | $^1$H NMR (400 MHz, DMSO-d$_6$) δ 10.84 (s, 1H), 8.49 (t, J = 5.6 Hz, 1H), 7.74 (d, J = 2.5 Hz, 1H), 7.66 (dd, J = 8.8, 2.6 Hz, 1H), 7.63 (t, J = 1.7 Hz, 1H), 7.55 (d, J = 1.6 Hz, 2H), 7.47 (d, J = 8.7 Hz, 1H), 3.61 (d, J = 8.5 Hz, 1H), 3.50 (d, J = 8.5 Hz, 1H), 3.22 (q, J = 6.2 Hz, 2H), 2.21 (t, J = 6.7 Hz, 2H), 2.10 (s, 6H), 1.47 (m, 4H); $^{13}$C NMR (126 MHz, DMSO-d$_6$) δ 166.35, 163.01, 138.17, 138.04, 137.77, 134.54, 130.53, 128.39, 128.18, 124.38, 121.31, 119.46, 62.63, 59.21, 45.60, 39.29, 38.87, 37.24, 27.32, 24.87 |
| F51 | 179-182 | | HRMS-ESI [M]$^+$ calcd for C$_{19}$H$_{15}$Cl$_6$N$_2$O$_2$, 514.9231; found, 514.9228. | $^1$H NMR (500 MHz, DMSO-d$_6$) δ10.87 (s, 1H), 8.75 (t, J = 5.6 Hz, 1H), 7.77 (d, J = 2.6 Hz, 1H), 7.70 (dd, J = 8.8, 2.6 Hz, 1H), 7.63 (t, J = 1.8 Hz, 1H), 7.55 (d, J = 1.6 Hz, 2H), 7.49 (d, J = 8.7 Hz, 1H), 3.73 (t, J = 6.1 Hz, 2H), 3.62 (d, J = 8.5 Hz, 1H), 3.56 (m, 2H), 3.50 (d, J = 8.5 Hz, 1H); $^{13}$C NMR (126 MHz, DMSO-d$_6$) δ 166.21, 162.46, 137.48, 137.19, 136.92, 133.95, 130.06, 127.80, 127.59, 123.85, 121.01, 118.93, 62.05, 42.98, 40.97, 38.29, 36.66 |
| F52 | 147-150 | | HRMS-ESI [M + H]$^+$ calcd for C$_{20}$H$_{18}$Cl$_5$N$_2$O$_2$S, 526.9498; found, 526.9498. | $^1$H NMR (500 MHz, DMSO-d$_6$) δ 10.85 (s, 1H), 8.60 (t, J = 5.7 Hz, 1H), 7.76 (d, J = 2.6 Hz, 1H), 7.69 (dd, J = 8.8, 2.6 Hz, 1H), 7.62 (t, J = 1.8 Hz, 1H), 7.55 (d, J = 1.6 Hz, 2H), 7.48 (d, J = 8.7 Hz, 1H), 3.61 (d, J = 8.5 Hz, 1H), 3.50 (d, J = 8.5 Hz, 1H), 3.42 (q, J = 6.3 Hz, 2H), 2.64 (t, J = 7.0 Hz, 2H), 2.11 (s, 3H); $^{13}$C NMR (126 MHz, DMSO-d$_6$) δ 165.91, 162.44, 137.45, 137.19, 133.95, 130.02, 127.80, 127.59, 123.86, 120.90, 118.93, 62.05, 38.29, 38.20, 36.66, 32.41, 14.45 |
| F53 | 165-167 | | HRMS-ESI [M]$^+$ calcd for C$_{20}$H$_{18}$Cl$_5$N$_2$O$_3$, 510.9727; found, 510.9729. | $^1$H NMR (500 MHz, DMSO-d$_6$) δ10.85 (s, 1H), 8.53 (t, J = 5.5 Hz, 1H), 7.73 (d, J = 2.6 Hz, 1H), 7.68 (dd, J = 8.7, 2.6 Hz, 1H), 7.63 (t, J = 1.8 Hz, 1H), 7.55 (d, J = 1.6 Hz, 2H), 7.47 (d, J = 8.7 Hz, 1H), 3.61 (d, J = 8.5 Hz, 1H), 3.50 (d, J = 8.5 Hz, 1H), 3.45 (t, J = 5.8 Hz, 2H), 3.38 (q, J = 5.4 Hz, 2H), 3.28 (s, 3H); $^{13}$C NMR (126 MHz, DMSO-d$_6$) δ 166.01, 162.43, 137.42, 137.25, 137.19, 133.95, 129.97, 127.80, 127.59, 123.86, 120.81, 118.91, 70.15, 62.04, 57.83, 38.69, 38.29, 36.66 |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| F54 | 77-85 | | HRMS-ESI [M + H]$^+$ calcd for C$_{21}$H$_{20}$Cl$_5$N$_2$O$_3$, 524.9883; found, 524.9890. | $^1$H NMR (500 MHz, DMSO-d$_6$) δ 10.84 (s, 1H), 8.52 (t, J = 5.6 Hz, 1H), 7.74 (d, J = 2.6 Hz, 1H), 7.67 (dd, J = 8.8, 2.6 Hz, 1H), 7.62 (t, J = 1.8 Hz, 1H), 7.55 (d, J = 1.6 Hz, 2H), 7.47 (d, J = 8.7 Hz, 1H), 3.61 (d, J = 8.5 Hz, 1H), 3.48 (m, 5H), 3.38 (q, J = 5.9 Hz, 2H), 1.12 (t, J = 7.0 Hz, 3H); $^{13}$C NMR (126 MHz, DMSO-d$_6$) δ 166.01, 162.42, 137.42, 137.27, 137.19, 133.95, 129.97, 127.80, 127.59, 123.86, 120.83, 118.94, 67.99, 65.27, 62.05, 38.29, 36.66, 15.02 |
| F55 | 156-160 | | ESIMS 538 ([M + H]$^+$) | $^1$H NMR (500 MHz, DMSO-d$_6$) δ10.85 (s, 1H), 8.48 (t, J = 5.6 Hz, 1H), 7.90 (t, J = 5.6 Hz, 1H), 7.76 (d, J = 2.6 Hz, 1H), 7.67 (dd, J = 8.8, 2.6 Hz, 1H), 7.63 (t, J = 1.8 Hz, 1H), 7.55 (d, J = 1.7 Hz, 2H), 7.48 (d, J = 8.7 Hz, 1H), 3.61 (d, J = 8.5 Hz, 1H), 3.50 (d, J = 8.5 Hz, 1H), 3.28 (m, 2H), 3.19 (q, J = 6.3 Hz, 2H), 1.81 (s, 3H); $^{13}$C NMR (126 MHz, DMSO-d$_6$) δ 169.26, 165.99, 162.45, 137.43, 137.18, 137.16, 133.96, 130.00, 127.80, 127.59, 123.89, 120.99, 119.04, 62.05, 38.72, 38.25, 38.05, 36.67, 22.55 |
| F56 | 187-190 | | HRMS-ESI [M + H]$^+$ calcd for C$_{20}$H$_{18}$Cl$_5$N$_2$O$_2$, 494.9778; found, 494.9779. | $^1$H NMR (500 MHz, DMSO-d$_6$) δ10.84 (s, 1H), 8.45 (t, J = 5.7 Hz, 1H), 7.74 (d, J = 2.6 Hz, 1H), 7.67 (dd, J = 8.7, 2.6 Hz, 1H), 7.62 (t, J = 1.8 Hz, 1H), 7.55 (d, J = 1.5 Hz, 2H), 7.47 (d, J = 8.7 Hz, 1H), 3.62 (d, J = 8.5 Hz, 1H), 3.50 (d, J = 8.5 Hz, 1H), 3.19 (q, J = 6.7 Hz, 2H), 1.52 (h, J = 7.2 Hz, 2H), 0.92 (t, J = 7.4 Hz, 3H); $^{13}$C NMR (126 MHz, DMSO-d$_6$) δ 165.83, 162.43, 137.59, 137.45, 137.19, 133.95, 129.95, 127.80, 127.59, 123.81, 120.70, 118.88, 62.04, 40.56, 38.30, 36.65, 22.13, 11.31 |
| F57 | 94-99 | | HRMS-ESI [M + H]$^+$ calcd for C$_{20}$H$_{17}$Cl$_6$N$_2$O$_2$, 528.9388; found, 528.9388. | $^1$H NMR (500 MHz, DMSO-d$_6$) δ 10.85 (s, 1H), 8.57 (t, J = 5.6 Hz, 1H), 7.75 (d, J = 2.6 Hz, 1H), 7.68 (dd, J = 8.8, 2.6 Hz, 1H), 7.63 (t, J = 1.8 Hz, 1H), 7.55 (d, J = 1.6 Hz, 2H), 7.48 (d, J = 8.7 Hz, 1H), 3.72 (t, J = 6.6 Hz, 2H), 3.61 (d, J = 8.5 Hz, 1H), 3.50 (d, J = 8.5 Hz, 1H), 3.36 (d, J = 6.9 Hz, 2H), 1.97 (m, 2H); $^{13}$C NMR (126 MHz, DMSO-d$_6$) δ 166.02, 162.46, 137.48, 137.28, 137.18, 133.95, 129.99, 127.80, 127.59, 123.79, 120.87, 118.88, 62.04, 42.76, 38.29, 36.66, 36.31, 31.85 |
| F58 | 64-69 | | HRMS-ESI [M + H]$^+$ calcd for C$_{23}$H$_{24}$Cl$_5$N$_2$O$_4$, 569.0146; found, | $^1$H NMR (500 MHz, DMSO-d$_6$) δ10.84 (s, 1H), 8.45 (t, J = 5.6 Hz, 1H), 7.74 (d, J = 2.6 Hz, 1H), 7.67 (dd, J = 8.8, 2.6 Hz, |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | 569.0155. | 1H), 7.62 (t, J = 1.8 Hz, 1H), 7.55 (d, J = 1.7 Hz, 2H), 7.47 (d, J = 8.7 Hz, 1H), 3.61 (d, J = 8.5 Hz, 1H), 3.47 (m, 7H), 3.28 (q, J = 6.5 Hz, 2H), 3.24 (s, 3H), 1.73 (p, J = 6.6 Hz, 2H); $^{13}$C NMR (126 MHz, DMSO-d$_6$) δ 165.83, 162.44, 137.46, 137.45, 137.19, 133.96, 129.97, 127.80, 127.59, 123.83, 120.79, 118.90, 71.15, 69.29, 67.90, 62.05, 57.95, 38.29, 36.66, 36.17, 29.11 |
| F59 | 205-208 | | HRMS-ESI [M + H]$^+$ calcd for C$_{20}$H$_{15}$Cl$_5$F$_3$N$_2$O$_2$, 548.9504; found, 548.9495. | $^1$H NMR (500 MHz, DMSO-d$_6$) δ10.90 (s, 1H), 7.73 (d, J = 2.4 Hz, 1H), 7.68 (dd, J = 8.8, 2.2 Hz, 1H), 7.63 (s, 1H), 7.56 (d, J = 10.7 Hz, 3H), 4.40 (d, J = 44.7 Hz, 2H), 3.62 (d, J = 8.5 Hz, 1H), 3.49 (d, J = 8.5 Hz, 1H), 2.92 (s, 3H) |
| F60 | 97-103 | | HRMS-ESI [M + H]$^+$ calcd for C$_{21}$H$_{15}$Cl$_5$F$_5$N$_2$O$_2$, 598.9463; found, 598.9469. | $^1$H NMR (500 MHz, DMSO-d$_6$) δ10.86 (s, 1H), 8.73 (t, J = 5.6 Hz, 1H), 7.76 (d, J = 2.6 Hz, 1H), 7.69 (dd, J = 8.8, 2.6 Hz, 1H), 7.62 (t, J = 1.8 Hz, 1H), 7.55 (d, J = 1.5 Hz, 2H), 7.49 (d, J = 8.7 Hz, 1H), 3.62 (d, J = 8.5 Hz, 1H), 3.54 (q, J = 6.6 Hz, 2H), 3.50 (d, J = 8.5 Hz, 1H), 2.50 (dd, J = 3.7, 1.8 Hz, 2H); $^{13}$C NMR (126 MHz, DMSO-d$_6$) δ 166.60, 163.05, 138.09, 137.76, 137.36, 134.54, 130.67, 128.38, 128.17, 124.44, 121.67, 119.43, 62.62, 38.87, 37.24, 31.99, 29.73, 29.57, 29.41 |
| F61 | 109-112 | | HRMS-ESI [M + H]$^+$ calcd for C$_{21}$H$_{13}$Cl$_5$F$_7$N$_2$O$_2$, 634.9275; found, 634.9278. | $^1$H NMR (500 MHz, DMSO-d$_6$) δ10.89 (s, 1H), 9.23 (t, J = 6.3 Hz, 1H), 7.77 (d, J = 2.6 Hz, 1H), 7.74 (dd, J = 8.7, 2.6 Hz, 1H), 7.63 (t, J = 1.8 Hz, 1H), 7.55 (d, J = 1.5 Hz, 2H), 7.52 (d, J = 8.7 Hz, 1H), 4.17 (td, J = 16.4, 6.1 Hz, 2H), 3.62 (d, J = 8.5 Hz, 1H), 3.50 (d, J = 8.5 Hz, 1H); $^{13}$C NMR (126 MHz, DMSO-d$_6$) δ 166.81, 162.52, 137.57, 137.19, 136.11, 133.96, 130.22, 127.81, 127.60, 123.79, 121.33, 118.85, 62.04, 38.33, 36.66 |
| F62 | 108-112 | | HRMS-ESI [M + H]$^+$ calcd for C$_{21}$H$_{20}$Cl$_5$N$_2$O$_2$, 508.9934; found, 508.9939. | $^1$H NMR (500 MHz, DMSO-d$_6$) δ10.85 (s, 1H), 7.65 (m, 3H), 7.55 (t, J = 1.6 Hz, 2H), 7.51 (dd, J = 8.8, 2.9 Hz, 1H), 3.62 (dd, J = 8.5, 3.3 Hz, 1H), 3.48 (m, 2H), 3.05 (dt, J = 22.6, 7.0 Hz, 1H), 2.98 (s, 1.4H), 2.77 (s, 1.6H), 1.61 (h, J = 7.2 Hz, 1H), 1.48 (m, 1H), 0.92 (t, J = 7.4 Hz, 1.6H), 0.70 (t, J = 7.4 Hz, 1.4H); $^{13}$C NMR (126 MHz, DMSO-d$_6$) δ 166.54, 162.51, 137.96, 137.70, 137.19, 136.86, 136.52, 133.95, 129.89, 127.81, 127.59, 123.16, 122.89, 120.57, 118.11, 117.64, 62.03, 59.64, 51.19, 47.50, 39.91, 38.31, 36.71, |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | | 36.66, 35.39, 31.52, 20.66, 20.49, 19.53, 13.98, 11.05, 10.71 |
| F63 | 109-113 | | HRMS-ESI [M + H]$^+$ calcd for C$_{20}$H$_{18}$Cl$_5$N$_2$O$_2$, 494.9778; found, 494.9781. | $^1$H NMR (500 MHz, DMSO-d$_6$) δ10.85 (s, 1H), 7.68 (m, 1H), 7.62 (m, 2H), 7.55 (s, 2H), 7.51 (dd, J = 8.8, 2.5 Hz, 1H), 3.61 (dd, J = 8.5, 3.2 Hz, 1H), 3.48 (m, 2H), 3.11 (m, 1H), 2.98 (s, 1.6H), 2.77 (s, 1.4H), 1.14 (t, J = 7.1 Hz, 1.5H), 1.04 (t, J = 7.1 Hz, 1.5H); $^{13}$C NMR (126 MHz, DMSO-d$_6$) δ 166.27, 166.09, 162.53, 137.94, 137.75, 137.19, 136.70, 136.58, 133.95, 129.93, 129.87, 127.81, 127.59, 123.08, 123.00, 120.60, 117.63, 62.03, 59.64, 44.55, 40.91, 38.28, 36.71, 34.83, 31.07, 20.66, 13.98, 13.04, 11.65 |
| F64 | 95-99 | | HRMS-ESI [M + H]$^+$ calcd for C$_{21}$H$_{17}$Cl$_5$F$_3$N$_2$O$_2$, 562.9651; found, 562.9652. | $^1$H NMR (500 MHz, DMSO-d$_6$) δ10.87 (d, J = 2.7 Hz, 1H), 7.65 (m, 3H), 7.54 (m, 3H), 3.73 (s, 1.4H), 3.61 (d, J = 8.5 Hz, 1H), 3.49 (m, 1H), 3.36 (m, 0.6H), 3.02 (s, 0.9H), 2.82 (s, 2.1H), 2.64 (m, 2H); $^{13}$C NMR (126 MHz, DMSO-d$_6$) δ 166.79, 166.62, 162.52, 137.97, 137.83, 137.19, 136.16, 135.76, 133.96, 129.94, 127.80, 127.60, 125.58, 123.02, 122.96, 120.83, 118.19, 117.60, 62.03, 59.64, 38.29, 36.71, 35.61, 31.46, 29.98, 29.76, 20.66, 13.98 |
| F65 | 88-95 | | HRMS-ESI [M + H]$^+$ calcd for C$_{21}$H$_{16}$Cl$_5$N$_2$O$_2$, 504.9621; found, 504.9620. | $^1$H NMR (500 MHz, DMSO-d$_6$) δ10.88 (s, 1H), 7.70 (m, 1H), 7.65 (m, 1H), 7.62 (t, J = 1.8 Hz, 1H), 7.54 (m, 3H), 4.34 (s, 1.1H), 3.94 (m, 0.9H), 3.61 (d, J = 8.5 Hz, 1H), 3.49 (m, 1H), 3.34 (t, J = 2.3 Hz, 0.4H), 3.29 (t, J = 2.5 Hz, 0.6H), 3.05 (s, 1H), 2.84 (s, 2H); $^{13}$C NMR (126 MHz, DMSO-d$_6$) δ 166.39, 166.35, 162.56, 162.51, 137.98, 137.87, 137.18, 135.67, 135.47, 133.95, 130.06, 130.03, 127.81, 127.59, 123.19, 123.09, 120.95, 117.65, 78.63, 78.11, 75.69, 74.50, 62.02, 38.29, 36.71, 35.08, 34.87, 31.49 |
| F66 | 89-94 | | HRMS-ESI [M + H]$^+$ calcd for C$_{20}$H$_{15}$Cl$_5$N$_3$O$_2$, 505.9574; found, 505.9584. | $^1$H NMR (500 MHz, DMSO-d$_6$) δ10.91 (m, 1H), 7.76 (m, 1H), 7.68 (m, 1H), 7.63 (t, J = 1.8 Hz, 1H), 7.56 (m, 3H), 4.63 (s, 1.4H), 4.36 (dd, J = 22.2, 5.5 Hz, 0.6H), 3.61 (d, J = 8.5 Hz, 1H), 3.50 (m, J = 8.0 Hz, 1H), 3.09 (s, 0.7H), 2.90 (s, 2.3H); $^{13}$C NMR (126 MHz, DMSO-d$_6$) δ 167.24, 162.60, 138.04, 137.16, 134.71, 133.96, 130.12, 127.80, 127.60, 123.12, 121.33, 117.77, 116.08, 62.01, 38.28, 36.73, 35.97, 34.68 |
| F67 | 224-226 | | HRMS-ESI [M + H]$^+$ calcd for | $^1$H NMR (500 MHz, DMSO-d$_6$) δ10.84 (m, 1H), 7.57 (m, 6H), |

TABLE 4-continued

Analytical data for molecules in Table 2

| No. | Mp (° C.) | IR (cm$^{-1}$) | Mass (m/z) | NMR ($^{1}$H, $^{13}$C, or $^{19}$F) |
|---|---|---|---|---|
| | | | C$_{21}$H$_{20}$Cl$_5$N$_2$O$_3$, 524.9883; found, 524.9885. | 3.60 (m, 3H), 3.48 (m, 2H), 3.30 (s, 1.7H), 3.26 (m, 1H), 3.15 (s, 1.3H), 3.02 (s, 1.4H), 2.82 (s, 1.6H); $^{13}$C NMR (126 MHz, DMSO-d$_6$) δ 166.92, 166.66, 162.51, 162.45, 137.94, 137.65, 137.19, 136.59, 136.37, 133.95, 129.92, 129.69, 127.81, 127.59, 123.13, 122.95, 120.64, 120.59, 117.62, 69.27, 62.06, 62.03, 57.99, 57.96, 54.81, 49.02, 45.73, 38.29, 36.65, 36.61 |
| F68 | 94-99 | | HRMS-ESI [M + H]$^{+}$ calcd for C$_{21}$H$_{20}$Cl$_5$N$_2$O$_2$S, 540.9655; found, 540.9669. | $^{1}$H NMR (500 MHz, DMSO-d$_6$) δ10.86 (m, 1H), 7.76 (m, 0.5H), 7.65 (m, 2.5H), 7.55 (m, 2H), 7.51 (d, J = 8.7 Hz, 1H), 3.62 (m, 2H), 3.49 (m, 1H), 3.26 (m, 1H), 3.01 (s, 1.4H), 2.81 (s, 1.6H), 2.75 (t, J = 7.0 Hz, 1H), 2.63 (m, 1H), 2.14 (s, 1.5H), 1.75 (d, J = 6.4 Hz, 1.5H); $^{13}$C NMR (126 MHz, DMSO-d$_6$) δ 166.70, 162.51, 137.93, 137.76, 137.19, 136.53, 136.16, 133.95, 129.90, 129.81, 127.81, 127.59, 123.11, 122.94, 120.73, 120.68, 118.58, 117.70, 62.03, 44.98, 38.29, 36.70, 36.63, 35.74, 31.69, 30.89, 30.01, 14.44, 14.11 |
| F69 | | | HRMS-ESI [M + H]$^{+}$ calcd for C$_{22}$H$_{20}$Cl$_5$N$_2$O$_2$, 520.9934; found, 520.9936. | $^{1}$H NMR (500 MHz, DMSO-d$_6$) δ10.86 (s, 1H), 7.69 (m, 1H), 7.63 (m, 2H), 7.55 (m, 2H), 7.51 (m, 1H), 3.61 (d, J = 8.5 Hz, 1H), 3.48 (d, J = 8.5 Hz, 2H), 3.07 (s, 1.5H), 2.95 (m, 1H), 2.84 (s, 1.5H), 1.08 (m, 0.5H), 0.86 (m, 0.5H), 0.48 (m, 2H), 0.30 (m, 1H), 0.07 (m, 1H); $^{13}$C NMR (126 MHz, DMSO-d$_6$) δ 166.48, 166.27, 162.52, 137.95, 137.74, 137.19, 136.74, 136.49, 133.95, 129.91, 127.81, 127.59, 123.14, 122.95, 120.58, 117.62, 62.03, 54.10, 49.91, 38.30, 36.68, 35.51, 31.85, 9.44, 8.89, 3.40, 3.30, 2.97, 2.84 |
| F70 | 105-110 | | HRMS-ESI [M + H]$^{+}$ calcd for C$_{22}$H$_{18}$Cl$_5$F$_2$N$_2$O$_2$, 556.9746; found, 556.9754 | $^{1}$H NMR (500 MHz, DMSO-d$_6$) δ10.85 (s, 1H), 8.64 (t, J = 5.9 Hz, 1H), 7.75 (d, J = 2.6 Hz, 1H), 7.68 (dd, J = 8.8, 2.6 Hz, 1H), 7.62 (t, J = 1.8 Hz, 1H), 7.55 (d, J = 1.6 Hz, 2H), 7.49 (d, J = 8.7 Hz, 1H), 3.62 (d, J = 8.5 Hz, 1H), 3.50 (d, J = 8.5 Hz, 1H), 3.37 (t, J = 5.7 Hz, 2H), 2.63 (m, 2H), 2.40 (m, 3H); $^{13}$C NMR (126 MHz, DMSO-d$_6$) δ 166.29, 162.46, 137.50, 137.30, 137.18, 133.96, 130.01, 127.80, 127.59, 123.75, 120.91, 118.82, 62.04, 42.34, 38.29, 37.82, 37.65, 37.47, 36.66, 22.56, 22.50, 22.46, 22.41 |
| F71 | 114-121 | | HRMS-ESI [M + H]$^{+}$ calcd for | $^{1}$H NMR (500 MHz, DMSO-d$_6$) δ10.88 (m, 1H), 7.79 (m, 1H), |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | C$_{21}$H$_{16}$Cl$_5$F$_2$N$_2$O$_2$, 542.9589; found, 542.9591. | 7.63 (m, 2H), 7.55 (m, 3H), 3.93 (t, J = 13.1 Hz, 1H), 3.74 (t, J = 7.6 Hz, 1H), 3.61 (m, 2H), 3.49 (d, J = 8.5 Hz, 1H), 3.40 (t, J = 7.6 Hz, 1H), 2.50 (m, 2H); $^{13}$C NMR (126 MHz, DMSO-d$_6$) δ 170.22, 165.39, 165.23, 162.56, 137.96, 137.17, 135.96, 135.45, 133.96, 130.20, 130.12, 127.80, 127.61, 127.38, 123.01, 122.80, 121.30, 118.06, 117.91, 62.04, 59.64, 38.25, 36.73, 20.66, 13.98 |
| F72 | 115-118 | | HRMS-ESI [M + H]$^+$ calcd for C$_{21}$H$_{17}$Cl$_5$F$_3$N$_2$O$_2$, 562.9651; found, 562.9653. | $^1$H NMR (500 MHz, DMSO-d$_6$) δ10.85 (s, 1H), 8.59 (t, J = 5.7 Hz, 1H), 7.75 (d, J = 2.6 Hz, 1H), 7.68 (dd, J = 8.8, 2.6 Hz, 1H), 7.62 (t, J = 1.8 Hz, 1H), 7.55 (d, J = 1.6 Hz, 2H), 7.49 (d, J = 8.7 Hz, 1H), 3.61 (d, J = 8.5 Hz, 1H), 3.50 (d, J = 8.5 Hz, 1H), 3.30 (m, 2H), 2.34 (ddt, J = 14.8, 9.1, 3.3 Hz, 2H), 1.74 (dt, J = 14.7, 6.9 Hz, 2H); $^{13}$C NMR (126 MHz, DMSO-d$_6$) δ 166.05, 162.47, 137.52, 137.27, 137.18, 133.96, 130.02, 127.81, 127.60, 123.75, 120.90, 118.84, 62.04, 59.64, 38.30, 37.62, 36.66, 30.50, 30.28, 30.06, 29.84, 21.60, 20.66, 13.98 |
| F73 | 103-108 | | HRMS-ESI [M + H]$^+$ calcd for C$_{23}$H$_{20}$Cl$_5$F$_2$N$_2$O$_2$, 570.9903; found, 570.9908. | $^1$H NMR (500 MHz, DMSO-d$_6$) δ10.86 (m, 1H), 7.74 (d, J = 2.3 Hz, 0.3H), 7.68 (d, J = 2.5 Hz, 0.7H), 7.63 (m, 2H), 7.55 (m, 2H), 7.52 (d, J = 8.8 Hz, 1H), 3.83 (s, 0.6H), 3.62 (m, 1H), 3.49 (m, 1.6H), 3.25 (m, 0.7H), 2.99 (s, 0.9H), 2.79 (s, 2H), 2.69 (m, 1.6H), 2.55 (m, 1.3H), 2.45 (m, 1.4H), 2.17 (m, 0.9H) |
| F74 | 108-111 | | HRMS-ESI [M + H]$^+$ calcd for C$_{20}$H$_{18}$Cl$_5$N$_2$O$_3$S, 542.9447; found, 542.9444. | $^1$H NMR (500 MHz, DMSO-d$_6$) δ10.88 (s, 1H), 8.76 (t, J = 5.5 Hz, 1H), 7.76 (m, 1H), 7.69 (m, 1H), 7.63 (t, J = 1.7 Hz, 1H), 7.55 (d, J = 1.6 Hz, 2H), 7.48 (d, J = 8.7 Hz, 1H), 3.60 (m, 3H), 3.51 (d, J = 8.5 Hz, 1H), 3.04 (dt, J = 13.9, 7.2 Hz, 1H), 2.89 (dt, J = 12.7, 6.2 Hz, 1H), 2.62 (s, 3H); $^{13}$C NMR (126 MHz, DMSO-d$_6$) δ 166.08, 162.46, 137.48, 137.18, 136.88, 133.95, 130.05, 127.80, 127.59, 123.87, 121.04, 118.92, 62.05, 52.82, 38.26, 38.06, 36.66, 33.07 |
| F75 | 104-108 | | HRMS-ESI [M + H]$^+$ calcd for C$_{20}$H$_{18}$Cl$_5$N$_2$O$_4$S, 558.9396; found, 558.9402. | $^1$H NMR (500 MHz, DMSO-d$_6$) δ10.87 (s, 1H), 8.74 (t, J = 5.6 Hz, 1H), 7.78 (d, J = 2.5 Hz, 1H), 7.69 (dd, J = 8.8, 2.6 Hz, 1H), 7.63 (t, J = 1.7 Hz, 1H), 7.55 (d, J = 1.6 Hz, 2H), 7.49 (d, J = 8.7 Hz, 1H), 3.64 (m, 3H), 3.50 (d, J = 8.5 Hz, 1H), 3.37 (t, J = 6.9 Hz, 2H), 3.06 (s, 3H); $^{13}$C NMR (126 MHz, DMSO-d$_6$) δ 166.09, 162.47, 137.48, |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | | 137.18, 136.68, 133.96, 130.07, 127.80, 127.59, 123.89, 121.17, 118.99, 62.05, 52.60, 40.61, 38.25, 36.67, 33.05 |
| F78 | 107–112 | | HRMS-ESI [M+]$^+$ calcd for C$_{20}$H$_{17}$Cl$_5$N$_2$O$_3$, 507.9682; found, 507.9679. | $^1$H NMR (500 MHz, DMSO-d$_6$) δ 10.84 (s, 1H), 8.41 (t, J = 5.8 Hz, 1H), 7.75 (d, J = 2.6 Hz, 1H), 7.68 (dd, J = 8.8, 2.6 Hz, 1H), 7.63 (t, J = 1.8 Hz, 1H), 7.55 (d, J = 1.4 Hz, 2H), 7.47 (d, J = 8.7 Hz, 1H), 4.70 (d, J = 4.8 Hz, 1H), 3.76 (dt, J = 11.5, 6.0 Hz, 1H), 3.61 (d, J = 8.5 Hz, 1H), 3.50 (d, J = 8.5 Hz, 1H), 3.22 (m, 1H), 3.14 (m, 1H), 1.10 (d, J = 6.2 Hz, 3H); $^{13}$C NMR (126 MHz, DMSO-d$_6$) δ 165.96, 162.42, 137.42, 137.40, 137.19, 133.95, 129.95, 127.80, 127.59, 123.84, 120.78, 119.00, 64.97, 62.05, 46.63, 38.29, 36.66, 21.07 |
| F79 | 233–236 | | HRMS-ESI [M]$^+$ calcd for C$_{22}$H$_{19}$Cl$_5$N$_4$O$_3$, 561.9900; found, 561.9911. | $^1$H NMR (500 MHz, DMSO-d$_6$) δ 10.85 (s, 1H), 8.54 (t, J = 5.7 Hz, 1H), 7.73 (d, J = 2.5 Hz, 1H), 7.69 (dd, J = 8.7, 2.5 Hz, 1H), 7.62 (d, J = 1.7 Hz, 1H), 7.55 (d, J = 1.5 Hz, 2H), 7.47 (d, J = 8.7 Hz, 1H), 6.29 (s, 1H), 3.61 (d, J = 8.5 Hz, 1H), 3.50 (d, J = 8.5 Hz, 1H), 3.42 (m, 2H), 3.35 (d, J = 6.2 Hz, 2H), 3.22 (m, 4H); $^{13}$C NMR (126 MHz, DMSO-d$_6$) δ 165.95, 162.44, 162.11, 137.43, 137.25, 137.19, 133.95, 129.99, 127.80, 127.59, 123.88, 120.92, 118.95, 62.06, 44.69, 42.51, 38.26, 37.43, 36.67 |
| F84 | 187–190 | | HRMS-ESI [M+]$^+$ calcd for C$_{21}$H$_{19}$Cl$_5$N$_2$O$_3$, 521.9839; found, 521.9838. | $^1$H NMR (500 MHz, DMSO-d$_6$) δ 10.83 (s, 1H), 8.45 (t, J = 5.7 Hz, 1H), 7.74 (d, J = 2.5 Hz, 1H), 7.67 (dd, J = 8.7, 2.5 Hz, 1H), 7.61 (s, 2H), 7.47 (d, J = 8.7 Hz, 1H), 3.84 (s, 3H), 3.56 (d, J = 8.5 Hz, 1H), 3.45 (d, J = 8.5 Hz, 1H), 3.19 (q, J = 6.4 Hz, 2H), 1.52 (h, J = 7.3 Hz, 2H), 0.92 (t, J = 7.4 Hz, 3H); $^{13}$C NMR (126 MHz, DMSO-d$_6$) δ 165.83, 162.47, 151.07, 137.59, 137.47, 131.36, 129.95, 129.65, 128.10, 123.79, 120.70, 118.87, 62.13, 60.57, 40.57, 38.40, 36.28, 22.14, 11.32 |
| F85 | 206–208 | | HRMS-ESI [M+]$^+$ calcd for C$_{20}$H$_{17}$Cl$_5$N$_2$O$_3$, 507.9682; found, 507.9687. | $^1$H NMR (500 MHz, DMSO-d$_6$) δ 10.83 (s, 1H), 8.46 (t, J = 5.5 Hz, 1H), 7.74 (d, J = 2.5 Hz, 1H), 7.66 (dd, J = 8.8, 2.6 Hz, 1H), 7.61 (s, 2H), 7.47 (d, J = 8.7 Hz, 1H), 3.84 (s, 3H), 3.56 (d, J = 8.5 Hz, 1H), 3.45 (d, J = 8.5 Hz, 1H), 3.25 (p, J = 6.9 Hz, 2H), 1.11 (t, J = 7.2 Hz, 3H); $^{13}$C NMR (126 MHz, DMSO-d$_6$) δ 165.60, 162.48, 151.07, 137.47, 131.36, 129.97, |

TABLE 4-continued

Analytical data for molecules in Table 2

| No. | Mp (° C.) | IR (cm$^{-1}$) | Mass (m/z) | NMR ($^{1}$H, $^{13}$C, or $^{19}$F) |
|---|---|---|---|---|
| F86 | 185-188 | | HRMS-ESI [M+]$^{+}$ calcd for C$_{20}$H$_{16}$Cl$_{5}$FN$_{2}$O$_{3}$, 525.9588; found, 525.9602. | 129.65, 128.11, 123.85, 120.74, 118.88, 62.12, 60.57, 38.40, 36.29, 33.74, 14.45 $^{1}$H NMR (500 MHz, DMSO-d$_{6}$) δ 10.85 (s, 1H), 8.73 (t, J = 5.6 Hz, 1H), 7.76 (d, J = 2.5 Hz, 1H), 7.69 (dd, J = 8.7, 2.5 Hz, 1H), 7.61 (s, 2H), 7.48 (d, J = 8.7 Hz, 1H), 4.53 (dt, J = 47.5, 5.0 Hz, 2H), 3.84 (s, 3H), 3.56 (m, 2H), 3.52 (m, 1H), 3.45 (d, J = 8.5 Hz, 1H); $^{13}$C NMR (126 MHz, DMSO-d$_{6}$) δ 166.25, 162.50, 151.07, 137.47, 137.01, 131.36, 130.03, 129.65, 128.11, 123.85, 120.93, 118.92, 82.58, 81.26, 62.12, 60.57, 38.40, 36.29; $^{19}$F NMR (471 MHz, DMSO-d$_{6}$) δ 19.95, 19.89, 19.85, 19.83, 19.79, 19.75, 19.73, 19.69, 19.63 |
| F87 | 193-196 | | HRMS-ESI [M+]$^{+}$ calcd for C$_{20}$H$_{14}$Cl$_{5}$F$_{3}$N$_{2}$O$_{3}$, 561.9399; found, 561.9403. | $^{1}$H NMR (500 MHz, DMSO-d$_{6}$) δ 10.88 (s, 1H), 9.21 (t, J = 6.3 Hz, 1H), 7.77 (d, J = 2.1 Hz, 1H), 7.73 (dd, J = 8.8, 2.1 Hz, 1H), 7.61 (s, 2H), 7.51 (d, J = 8.7 Hz, 1H), 4.08 (dt, J = 17.4, 9.5 Hz, 2H), 3.84 (s, 3H), 3.57 (d, J = 8.5 Hz, 1H), 3.46 (d, J = 8.5 Hz, 1H); $^{13}$C NMR (126 MHz, DMSO-d$_{6}$) δ 166.62, 162.56, 151.07, 137.56, 136.15, 131.35, 130.19, 129.65, 128.11, 125.65, 123.77, 123.43, 121.28, 118.83, 62.11, 60.57, 38.42, 36.28; $^{19}$F NMR (471 MHz, DMSO-d$_{6}$) δ −70.42, −70.44, −70.46 |
| F88 | 181-185 | | HRMS-ESI [M+]$^{+}$ calcd for C$_{21}$H$_{16}$Cl$_{5}$F$_{3}$N$_{2}$O$_{3}$, 575.9556; found, 575.9562. | $^{1}$H NMR (500 MHz, DMSO-d$_{6}$) δ 10.85 (s, 1H), 8.71 (t, J = 5.6 Hz, 1H), 7.76 (d, J = 2.4 Hz, 1H), 7.68 (dd, J = 8.7, 2.4 Hz, 1H), 7.60 (s, 2H), 7.48 (d, J = 8.7 Hz, 1H), 3.84 (s, 3H), 3.56 (d, J = 8.5 Hz, 1H), 3.46 (t, J = 8.2 Hz, 3H), 2.54 (dd, J = 11.5, 6.5 Hz, 2H); $^{13}$C NMR (126 MHz, DMSO-d$_{6}$) δ 166.00, 162.50, 151.07, 137.51, 136.84, 131.36, 130.07, 129.99, 129.65, 128.11, 127.78, 125.58, 123.84, 123.37, 121.03, 118.83, 62.13, 60.57, 38.39, 36.28, 32.43, 32.30, 32.09, 31.87, 30.85, 28.37, 24.68, 21.96; $^{19}$F NMR (471 MHz, DMSO-d$_{6}$) δ −63.75, −63.77, −63.79 |
| F91 | 254-260 | | HRMS-ESI [M+]$^{+}$ calcd for C$_{19}$H$_{14}$Cl$_{6}$N$_{2}$O$_{2}$, 511.9186; found, 511.9189. | $^{1}$H NMR (500 MHz, DMSO-d$_{6}$) δ 10.99 (s, 1H), 8.57 (t, J = 5.6 Hz, 1H), 8.01 (d, J = 2.4 Hz, 1H), 7.63 (t, J = 1.8 Hz, 1H), 7.59 (d, J = 2.5 Hz, 1H), 7.56 (d, J = 1.5 Hz, 2H), 3.62 (d, J = 8.5 Hz, 1H), 3.51 (d, J = 8.5 Hz, 1H), 3.26 (p, J = 6.3 Hz, 2H), 1.11 (t, J = 7.2 Hz, 3); $^{13}$C NMR (126 MHz, DMSO-d$_{6}$) δ 164.90, 162.85, 139.55, 138.13, 137.08, 133.97, 132.00, 127.82, 127.63, |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| F92 | 235-237 | | HRMS-ESI [M+]$^+$ calcd for C$_{19}$H$_{13}$Cl$_6$FN$_2$O$_2$, 529.9092; found, 529.9093. | 122.06, 120.30, 117.36, 61.93, 38.36, 36.72, 33.81, 14.36 $^1$H NMR (500 MHz, DMSO-d$_6$) δ 11.01 (s, 1H), 8.86 (t, J = 5.6 Hz, 1H), 8.04 (d, J = 2.5 Hz, 1H), 7.62 (m, 2H), 7.56 (d, J = 1.4 Hz, 2H), 4.54 (dt, J = 47.5, 4.9 Hz, 2H), 3.62 (d, J = 8.5 Hz, 1H), 3.54 (m, 3H); $^{13}$C NMR (126 MHz, DMSO-d$_6$) δ 165.56, 162.87, 139.11, 138.15, 137.08, 133.97, 132.05, 127.82, 127.63, 122.05, 120.46, 117.41, 82.58, 81.26, 61.93, 54.80, 38.37, 36.72; $^{19}$F NMR (471 MHz, DMSO-d$_6$) δ −69.39, −70.90 |
| F93 | 210-213 | | HRMS-ESI [M+]$^+$ calcd for C$_{19}$H$_{11}$Cl$_6$F$_3$N$_2$O$_2$, 565.8904; found, 565.8902. | $^1$H NMR (500 MHz, DMSO) δ 11.04 (s, 1H), 9.33 (t, J = 6.3 Hz, 1H), 8.07 (d, J = 2.4 Hz, 1H), 7.63 (m, 2H), 7.56 (d, J = 1.5 Hz, 2H), 4.11 (dt, J = 16.4, 8.5 Hz, 2H), 3.63 (d, J = 8.5 Hz, 1H), 3.51 (d, J = 8.5 Hz, 1H); $^{19}$F NMR (471 MHz, DMSO-d$_6$) δ −70.42, −70.44, −70.46 |
| F94 | 185-189 | | HRMS-ESI [M+]$^+$ calcd for C$_{20}$H$_{13}$Cl$_6$F$_3$N$_2$O$_2$, 579.9060; found, 579.9043. | $^1$H NMR (500 MHz, DMSO-d$_6$) δ 11.01 (s, 1H), 8.83 (t, J = 5.7 Hz, 1H), 8.04 (d, J = 2.4 Hz, 1H), 7.63 (t, J = 1.8 Hz, 1H), 7.60 (d, J = 2.5 Hz, 1H), 7.56 (d, J = 1.5 Hz, 2H), 3.63 (d, J = 8.5 Hz, 1H), 3.50 (m, 3H), 2.56 (m, 2H); $^{13}$C NMR (126 MHz, DMSO-d$_6$) δ 165.31, 162.88, 138.95, 138.19, 137.08, 133.97, 132.11, 129.99, 127.82, 127.78, 127.63, 125.58, 123.38, 122.04, 120.56, 117.32, 61.95, 38.36, 36.71, 32.56, 32.53, 32.50, 32.47, 32.45, 32.24, 32.02, 31.81; $^{19}$F NMR (471 MHz, DMSO-d$_6$) δ −63.71, −63.74, −63.76 |
| F95 | 224-227 | | HRMS-ESI [M+]$^+$ calcd for C$_{20}$H$_{16}$Cl$_6$N$_2$O$_2$, 521.9343; found, 525.9348. | $^1$H NMR (500 MHz, DMSO-d$_6$) δ 11.00 (s, 1H), 8.57 (t, J = 5.6 Hz, 1H), 8.02 (d, J = 2.4 Hz, 1H), 7.63 (d, J = 1.7 Hz, 1H), 7.59 (d, J = 2.4 Hz, 1H), 7.56 (d, J = 1.6 Hz, 2H), 3.63 (d, J = 8.5 Hz, 1H), 3.51 (d, J = 8.5 Hz, 1H), 3.20 (q, J = 6.5 Hz, 2H), 1.52 (h, J = 7.2 Hz, 2H), 0.92 (t, J = 7.4 Hz, 3H); $^{13}$C NMR (126 MHz, DMSO-d$_6$) δ 165.15, 162.86, 139.66, 138.14, 137.08, 133.97, 131.99, 127.82, 127.63, 122.00, 120.26, 117.36, 61.94, 40.61, 38.36, 36.71, 22.07, 11.30 |
| F96 | | | ESIMS 575 ([M + H]$^+$) | $^1$H NMR (400 MHz, Acetone-d$_6$) δ 10.11 (s, 1H), 8.02 (d, J = 8.0 Hz, 1H), 7.80 (d, J = 2.5 Hz, 1H), 7.74 (dd, J = 8.7, 2.6 Hz, 1H), 7.56-7.45 (m, 5H), 7.39 (d, J = 8.7 Hz, 1H), 7.15-7.04 (m, 2H), 5.28 (p, J = 7.2 Hz, 1H), 3.64 (d, J = 8.3 Hz, 1H), 3.40 (d, J = 8.3 Hz, 1H), |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| F97 | | | ESIMS 589 ([M + H]$^+$) | 1.56 (d, J = 7.0 Hz, 3H); $^{19}$F NMR (376 MHz, Acetone) δ −117.60, −117.61, −117.63 $^1$H NMR (400 MHz, Acetone-d$_6$) δ 10.10 (s, 1H), 7.87 (s, 1H), 7.81-7.70 (m, 2H), 7.64-7.55 (m, 2H), 7.59-7.46 (m, 3H), 7.39 (d, J = 8.6 Hz, 1H), 7.08 (t, J = 8.8 Hz, 2H), 3.65 (d, J = 8.3 Hz, 1H), 3.41 (d, J = 8.4 Hz, 1H), 1.78 (d, J = 2.0 Hz, 6H); $^{19}$F NMR (376 MHz, Acetone-d$_6$) δ −119.11 |
| F98 | 158-163 | | HRMS-ESI [M+]$^+$ calcd for C$_{19}$H$_{14}$Cl$_6$N$_2$O$_2$, 511.9186; found, 511.9187. | $^1$H NMR (500 MHz, DMSO-d$_6$) δ 10.32 (s, 1H), 8.52 (t, J = 5.5 Hz, 1H), 7.93 (s, 1H), 7.79 (s, 1H), 7.63 (t, J = 1.8 Hz, 1H), 7.52 (d, J = 1.7 Hz, 2H), 3.81 (d, J = 8.6 Hz, 1H), 3.62 (d, J = 8.5 Hz, 1H), 3.24 (p, J = 7.0 Hz, 2H), 1.10 (t, J = 7.2 Hz, 3H); $^{13}$C NMR (126 MHz, DMSO-d$_6$) δ 164.72, 163.26, 137.15, 136.23, 133.96, 133.59, 129.95, 127.72, 127.61, 126.47, 126.20, 124.21, 62.38, 37.21, 37.07, 33.83, 14.36 |
| F99 | 140-145 | | HRMS-ESI [M+]$^+$ calcd for C$_{19}$H$_{13}$Cl$_6$FN$_2$O$_2$, 529.9092; found, 529.9092. | $^1$H NMR (500 MHz, DMSO-d$_6$) δ 10.33 (s, 1H), 8.81 (t, J = 5.6 Hz, 1H), 7.96 (s, 1H), 7.81 (s, 1H), 7.63 (t, J = 1.7 Hz, 1H), 7.52 (d, J = 1.6 Hz, 2H), 4.52 (dt, J = 47.4, 5.0 Hz, 2H), 3.81 (d, J = 8.6 Hz, 1H), 3.62 (d, J = 8.5 Hz, 1H), 3.53 (dq, J = 27.1, 5.3 Hz, 2H); $^{13}$C NMR (126 MHz, DMSO-d$_6$) δ 165.38, 163.27, 137.15, 135.78, 133.96, 133.61, 130.02, 127.72, 127.61, 126.69, 126.21, 124.25, 82.56, 81.24, 62.38, 37.21, 37.08; $^{19}$F NMR (471 MHz, DMSO-d$_6$) δ 20.05, 19.99, 19.95, 19.93, 19.89, 19.85, 19.83, 19.79, 19.73 |
| F100 | 175-179 | | HRMS-ESI [M+]$^+$ calcd for C$_{19}$H$_{11}$Cl$_6$F$_3$N$_2$O$_2$, 565.8904; found, 565.8905. | $^1$H NMR (500 MHz, DMSO-d$_6$) δ 10.36 (s, 1H), 9.27 (t, J = 6.3 Hz, 1H), 7.99 (s, 1H), 7.85 (s, 1H), 7.63 (t, J = 1.7 Hz, 1H), 7.52 (d, J = 1.6 Hz, 2H), 4.08 (m, 2H), 3.82 (d, J = 8.6 Hz, 1H), 3.63 (d, J = 8.5 Hz, 1H); $^{13}$C NMR (126 MHz, DMSO-d$_6$) δ 165.79, 163.34, 137.15, 134.92, 133.96, 133.74, 130.19, 127.81, 127.72, 127.61, 127.04, 126.12, 125.59, 124.09, 123.37, 121.15, 62.39, 37.23, 37.09; $^{19}$F NMR (471 MHz, DMSO-d$_6$) δ −70.38, −70.40, −70.43 |
| F101 | 186-190 | | HRMS-ESI [M+]$^+$ calcd for C$_{20}$H$_{16}$Cl$_6$N$_2$O$_2$, 525.9343; found, 525.9348. | $^1$H NMR (500 MHz, DMSO-d$_6$) δ 10.32 (s, 1H), 8.52 (t, J = 5.7 Hz, 1H), 7.93 (s, 1H), 7.79 (s, 1H), 7.63 (t, J = 1.8 Hz, 1H), 7.52 (d, J = 1.6 Hz, 2H), 3.81 (d, J = 8.6 Hz, 1H), 3.63 (d, J = 8.5 Hz, 1H), 3.18 (q, J = 6.4 Hz, 2H), 1.51 (h, J = 7.3 Hz, 2H), 0.90 (t, J = 7.4 Hz, 3H); $^{13}$C NMR (126 MHz, DMSO-d$_6$) δ164.95, 163.26, 137.16, |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | | 136.34, 133.95, 133.60, 129.93, 127.72, 127.60, 126.41, 126.13, 124.18, 62.39, 40.65, 37.21, 37.05, 22.06, 11.30 |
| F102 | 190-195 | | HRMS-ESI [M+]$^+$ calcd for C$_{20}$H$_{13}$Cl$_6$F$_3$N$_2$O$_2$, 579.9060; found, 579.9060. | $^1$H NMR (500 MHz, DMSO-d$_6$) δ 10.34 (s, 1H), 8.78 (t, J = 5.7 Hz, 1H), 7.95 (s, 1H), 7.81 (s, 1H), 7.63 (t, J = 1.6 Hz, 1H), 7.52 (d, J = 1.6 Hz, 2H), 3.82 (d, J = 8.6 Hz, 1H), 3.63 (d, J = 8.5 Hz, 1H), 3.46 (q, J = 6.6 Hz, 2H), 2.53 (m, 2H); $^{13}$C NMR (126 MHz, DMSO-d$_6$) δ 165.13, 163.27, 137.15, 135.58, 133.96, 133.65, 130.09, 129.95, 127.74, 127.72, 127.61, 126.84, 126.23, 125.54, 124.24, 123.34, 62.39, 37.20, 37.06, 32.54, 32.51, 32.47, 32.26, 32.04, 31.83; $^{19}$F NMR (471 MHz, DMSO-d$_6$) δ −63.79, −63.82, −63.84 |
| F103 | 162-165 | | HRMS-ESI [M+]$^+$ calcd for C$_{19}$H$_{15}$Cl$_4$FN$_2$O$_2$, 461.9872; found, 461.9873. | $^1$H NMR (500 MHz, DMSO-d$_6$) δ 10.87 (s, 1H), 8.46 (t, J = 5.6 Hz, 1H), 7.74 (d, J = 2.6 Hz, 1H), 7.70 (dd, J = 7.1, 1.9 Hz, 1H), 7.67 (dd, J = 8.8, 2.6 Hz, 1H), 7.46 (m, 3H), 3.57 (d, J = 8.5 Hz, 1H), 3.42 (d, J = 8.5 Hz, 1H), 3.25 (p, J = 6.6 Hz, 2H), 1.11 (t, J = 7.2 Hz, 3H); $^{13}$C NMR (126 MHz, DMSO-d$_6$) δ 165.60, 162.56, 157.73, 155.76, 137.46, 130.97, 130.93, 130.90, 129.97, 129.72, 129.66, 123.85, 120.75, 119.43, 119.29, 118.89, 116.89, 116.72, 62.20, 38.42, 36.48, 33.74, 14.45; $^{19}$F NMR (471 MHz, DMSO-d$_6$) δ −117.27, −117.28, −117.29, −117.30, −117.31 |
| F104 | 188-191 | | HRMS-ESI [M+]$^+$ calcd for C$_{19}$H$_{14}$Cl$_4$F$_2$N$_2$O$_2$, 479.9777; found, 479.9779. | $^1$H NMR (500 MHz, DMSO-d$_6$) δ 10.89 (s, 1H), 8.74 (t, J = 5.6 Hz, 1H), 7.76 (d, J = 2.6 Hz, 1H), 7.69 (m, 2H), 7.47 (m, 3H), 4.53 (dt, J = 47.5, 5.0 Hz, 2H), 3.54 (dd, J = 31.2, 6.4 Hz, 3H), 3.42 (d, J = 8.5 Hz, 1H); $^{13}$C NMR (126 MHz, DMSO-d$_6$) δ 166.26, 162.58, 157.73, 155.76, 137.48, 137.00, 130.97, 130.93, 130.90, 130.03, 129.73, 129.66, 123.86, 120.94, 119.44, 119.29, 118.93, 116.89, 116.72, 82.59, 81.27, 62.20, 38.43, 36.49; $^{19}$F NMR (471 MHz, DMSO-d$_6$) δ 19.95, 19.89, 19.85, 19.83, 19.79, 19.75, 19.73, 19.69, 19.63, −117.27, −117.28, −117.29, −117.30, −117.31 |
| F105 | 190-193 | | HRMS-ESI [M+]$^+$ calcd for C$_{19}$H$_{12}$Cl$_4$F$_4$N$_2$O$_2$, 515.9589; found, 515.9593. | $^1$H NMR (500 MHz, DMSO-d$_6$) δ 10.93 (s, 1H), 9.22 (t, J = 6.3 Hz, 1H), 7.78 (d, J = 2.6 Hz, 1H), 7.74 (dd, J = 8.8, 2.6 Hz, 1H), 7.70 (dd, J = 7.1, 1.8 Hz, 1H), 7.52 (d, J = 8.7 Hz, 1H), 7.46 (m, 2H), 4.09 (m, 2H), 3.58 (d, J = 8.5 Hz, 1H), 3.42 (d, J = 8.5 Hz, 1H); $^{13}$C NMR (126 MHz, DMSO-d$_6$) |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | | δ 166.63, 162.65, 157.74, 155.78, 137.58, 136.15, 130.98, 130.92, 130.90, 130.20, 129.73, 129.67, 127.89, 125.66, 123.80, 123.44, 121.31, 121.22, 119.45, 119.31, 118.85, 116.90, 116.73, 62.20, 38.46, 36.50; $^{19}$F NMR (471 MHz, DMSO-d$_6$) δ −70.43, −70.45, −70.47, −117.25, −117.27, −117.28, −117.30 |
| F106 | 171-174 | | HRMS-ESI [M+]$^+$ calcd for C$_{20}$H$_{17}$Cl$_4$FN$_2$O$_2$, 476.0028; found, 476.0026. | $^1$H NMR (500 MHz, DMSO-d$_6$) δ 10.87 (s, 1H), 8.45 (t, J = 5.7 Hz, 1H), 7.74 (d, J = 2.6 Hz, 1H), 7.69 (m, 2H), 7.46 (m, 3H), 3.58 (d, J = 8.4 Hz, 1H), 3.42 (d, J = 8.5 Hz, 1H), 3.19 (m, 2H), 1.52 (h, J = 7.2 Hz, 2H), 0.92 (t, J = 7.4 Hz, 3H); $^{13}$C NMR (126 MHz, DMSO-d$_6$) δ 165.84, 162.56, 157.73, 155.77, 137.59, 137.47, 130.97, 130.93, 130.90, 129.95, 129.73, 129.66, 123.81, 120.72, 119.44, 119.30, 118.89, 116.89, 116.72, 62.20, 40.57, 38.43, 36.48, 22.14, 11.32; $^{19}$F NMR (471 MHz, DMSO-d$_6$) δ −117.26, −117.28, −117.29, −117.31 |
| F107 | 86-92 | | HRMS-ESI [M+]$^+$ calcd for C$_{20}$H$_{14}$Cl$_4$F$_4$N$_2$O$_2$, 529.9749; found, 529.9746. | $^1$H NMR (500 MHz, DMSO-d$_6$) δ 10.89 (s, 1H), 8.71 (t, J = 5.7 Hz, 1H), 7.76 (d, J = 2.6 Hz, 1H), 7.69 (m, 2H), 7.47 (m, 3H), 3.58 (d, J = 8.5 Hz, 1H), 3.47 (q, J = 6.4 Hz, 2H), 3.42 (d, J = 8.5 Hz, 1H), 2.54 (m, 2H); $^{19}$F NMR (471 MHz, DMSO-d$_6$) δ −63.74, −63.77, −63.79, −117.27, −117.28, −117.30, −117.31 |
| F108 | | | ESIMS 503 ([M + H]$^+$) | $^1$H NMR (400 MHz, Acetone-d$_6$) δ 10.16 (s, 1H), 8.23 (t, J = 6.5 Hz, 1H), 7.92 (d, J = 2.6 Hz, 1H), 7.82-7.74 (m, 1H), 7.49-7.36 (m, 2H), 7.40-7.25 (m, 2H), 4.27-4.14 (m, 2H), 3.65-3.58 (m, 1H), 3.33 (d, J = 8.3 Hz, 1H); $^{19}$F NMR (376 MHz, Acetone-d$_6$) δ −72.58, −72.59, −139.57, −139.63, −140.84 |
| F109 | | | ESIMS 580 ([M + H]$^+$) | $^1$H NMR (400 MHz, Acetone-d$_6$) δ 10.14 (s, 1H), 8.24 (t, J = 6.5 Hz, 1H), 7.91 (d, J = 2.6 Hz, 1H), 7.84-7.73 (m, 2H), 7.61 (d, J = 8.3 Hz, 1H), 7.51-7.41 (m, 2H), 4.21 (qd, J = 9.4, 6.5 Hz, 2H), 3.63 (dt, J = 8.2, 0.7 Hz, 1H), 3.37 (d, J = 8.3 Hz, 1H); $^{19}$F NMR (376 MHz, Acetone-d$_6$) δ −72.54, −72.54, −72.55, −72.55, −72.56 |
| F111 | | | ESIMS 624 ([M + H]$^+$) | $^1$H NMR (400 MHz, Acetone-d$_6$) δ 10.14 (s, 1H), 8.24 (t, J = 6.5 Hz, 1H), 7.91 (d, J = 2.6 Hz, 1H), 7.83-7.72 (m, 3H), 7.50-7.35 (m, 2H), 4.20 (qd, J = 9.5, 6.5 Hz, 2H), 3.61 (dt, J = 8.3, 0.8 Hz, 1H), 3.36 (d, J = 8.3 Hz, 1H); $^{19}$F NMR (376 MHz, Acetone-d$_6$) δ −72.55 |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| F112 | | | ESIMS 552 ([M + H]$^+$) | $^1$H NMR (400 MHz, Acetone-d$_6$) δ 10.21 (s, 1H), 8.24 (t, J = 6.5 Hz, 1H), 7.92 (d, J = 2.6 Hz, 1H), 7.85-7.74 (m, 2H), 7.58-7.48 (m, 2H), 7.45 (d, J = 8.7 Hz, 1H), 4.21 (qd, J = 9.4, 6.5 Hz, 2H), 3.77-3.70 (m, 1H), 3.46 (d, J = 8.3 Hz, 1H); $^{19}$F NMR (376 MHz, Acetone-d$_6$) δ −61.78, −61.79, −61.81, −61.82, −61.82, −72.57, −72.58, −72.58, −72.59, −72.60, −116.26, −116.30, −116.33, −116.36 |
| F113 | | | ESIMS 563 ([M + H]$^+$) | $^1$H NMR (400 MHz, Acetone-d$_6$) δ 10.16 (s, 1H), 8.23 (t, J = 6.4 Hz, 1H), 7.92 (d, J = 2.6 Hz, 1H), 7.82-7.74 (m, 1H), 7.71 (dd, J = 8.3, 7.3 Hz, 1H), 7.51-7.35 (m, 2H), 7.30-7.22 (m, 1H), 4.20 (qd, J = 9.4, 6.5 Hz, 2H), 3.62 (dd, J = 8.3, 0.8 Hz, 1H), 3.36 (d, J = 8.3 Hz, 1H); $^{19}$F NMR (376 MHz, Acetone-d$_6$) δ −72.59, −72.60, −108.83 |
| F114 | | | ESIMS 613 ([M + H]$^+$) | $^1$H NMR (400 MHz, Acetone-d$_6$) δ 10.17 (s, 1H), 8.23 (s, 1H), 8.23 (d, J = 13.2 Hz, 0H), 8.01-7.84 (m, 3H), 7.78 (dd, J = 8.7, 2.7 Hz, 1H), 7.68 (ddt, J = 8.2, 1.7, 0.8 Hz, 1H), 7.46 (d, J = 8.7 Hz, 1H), 4.20 (qd, J = 9.5, 6.5 Hz, 2H), 3.73 (d, J = 8.3 Hz, 1H), 3.47 (d, J = 8.4 Hz, 1H); $^{19}$F NMR (376 MHz, Acetone-d$_6$) δ −62.89, −62.90, −72.60, −72.61 |
| F115 | | | ESIMS 613 ([M + H]$^+$) | $^1$H NMR (400 MHz, Acetone-d$_6$) δ 10.16 (s, 1H), 8.23 (t, J = 6.5 Hz, 1H), 7.95-7.85 (m, 3H), 7.82-7.72 (m, 1H), 7.67 (dd, J = 8.4, 2.2 Hz, 1H), 7.45 (d, J = 8.7 Hz, 1H), 4.27-4.13 (m, 2H), 3.71 (d, J = 8.3 Hz, 1H), 3.44 (d, J = 8.3 Hz, 1H); $^{19}$F NMR (376 MHz, Acetone-d$_6$) δ −63.00, −63.00, −63.00, −72.60, −72.61 |
| F116 | | | ESIMS 569 ([M + H]$^+$) | $^1$H NMR (400 MHz, Acetone-d$_6$) δ 10.18 (s, 1H), 8.24 (t, J = 6.4 Hz, 1H), 7.96-7.85 (m, 2H), 7.83-7.74 (m, 2H), 7.64 (ddt, J = 8.2, 1.7, 0.9 Hz, 1H), 7.46 (d, J = 8.8 Hz, 1H), 4.21 (qd, J = 9.5, 6.5 Hz, 2H), 3.73 (d, J = 8.4 Hz, 1H), 3.47 (d, J = 8.4 Hz, 1H); $^{19}$F NMR (376 MHz, Acetone-d$_6$) δ −62.87, −62.88, −62.88, −62.89, −62.89, −62.90, −62.90, −62.91, −72.60, −72.61, −72.61, −72.63 |
| F117 | | | ESIMS 568 ([M + H]$^+$) | $^1$H NMR (400 MHz, Acetone-d$_6$) δ 10.16 (s, 1H), 8.24 (t, J = 6.5 Hz, 1H), 7.91 (dd, J = 4.1, 2.2 Hz, 2H), 7.83-7.69 (m, 3H), 7.45 (d, J = 8.8 Hz, 1H), 4.21 (qd, J = 9.4, 6.5 Hz, 2H), 3.73 (d, J = 8.3 Hz, 1H), 3.44 (d, J = 8.3 Hz, 1H); $^{19}$F NMR (376 MHz, Acetone-d$_6$) δ −63.00, −72.59 |
| F118 | | | ESIMS 563 ([M + H]$^+$) | $^1$H NMR (400 MHz, Acetone-d$_6$) δ 10.13 (s, 1H), 8.24 (t, J = 6.5 Hz, |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | | 1H), 7.92 (d, J = 2.6 Hz, 1H), 7.81-7.71 (m, 2H), 7.55-7.41 (m, 2H), 7.33 (t, J = 8.6 Hz, 1H), 4.21 (qd, J = 9.5, 6.5 Hz, 2H), 3.62 (dd, J = 8.3, 0.9 Hz, 1H), 3.34 (d, J = 8.3 Hz, 1H); $^{19}$F NMR (376 MHz, Acetone-d$_6$) δ −72.55, −72.57, −110.10 |
| F119 | | | ESIMS 552 ([M + H]$^+$) | $^1$H NMR (400 MHz, Acetone-d$_6$) δ 10.17 (s, 1H), 8.25 (t, J = 6.5 Hz, 1H), 7.92 (d, J = 2.5 Hz, 1H), 7.87-7.74 (m, 3H), 7.53-7.41 (m, 2H), 4.28-4.14 (m, 2H), 3.75-3.68 (m, 1H), 3.43 (d, J = 8.3 Hz, 1H); $^{19}$F NMR (376 MHz, Acetone-d$_6$) δ −61.84, −61.87, −61.87, −72.58, −117.54, −117.58 |
| F120 | | | ESIMS 519 ([M + H]$^+$) | $^1$H NMR (400 MHz, Acetone-d$_6$) δ 10.15 (s, 1H), 8.23 (t, J = 6.5 Hz, 1H), 7.92 (d, J = 2.6 Hz, 1H), 7.81-7.73 (m, 1H), 7.57 (t, J = 8.0 Hz, 1H), 7.51-7.38 (m, 2H), 7.31 (ddt, J = 8.3, 1.9, 0.8 Hz, 1H), 4.20 (qd, J = 9.4, 6.5 Hz, 2H), 3.63 (dd, J = 8.3, 0.8 Hz, 1H), 3.35 (d, J = 8.3 Hz, 1H); $^{19}$F NMR (376 MHz, Acetone-d$_6$) δ −72.57, −72.57, −72.58, −72.58, −116.92, −116.93 |
| F121 | | | ESIMS 502 ([M + H]$^+$) | $^1$H NMR (400 MHz, Acetone-d$_6$) δ 10.16 (s, 1H), 8.23 (t, J = 6.5 Hz, 1H), 7.92 (d, J = 2.6 Hz, 1H), 7.78 (dd, J = 8.8, 2.6 Hz, 1H), 7.45 (d, J = 8.7 Hz, 1H), 7.20-7.09 (m, 2H), 7.05 (tt, J = 9.1, 2.4 Hz, 1H), 4.27-4.13 (m, 2H), 3.65 (d, J = 8.3 Hz, 1H), 3.38 (d, J = 8.4 Hz, 1H); $^{19}$F NMR (376 MHz, Acetone-d$_6$) δ −72.58, −72.59, −72.59, −72.60, −110.72, −110.98, −110.98, −110.99 |
| F122 | | | ESIMS 552 ([M + H]$^+$) | $^1$H NMR (400 MHz, Acetone-d$_6$) δ 10.15 (s, 1H), 8.24 (t, J = 6.4 Hz, 1H), 7.92 (d, J = 2.6 Hz, 1H), 7.78 (dd, J = 8.8, 2.7 Hz, 1H), 7.69 (dt, J = 1.8, 1.0 Hz, 1H), 7.58 (ddt, J = 24.9, 8.6, 2.0 Hz, 2H), 7.45 (d, J = 8.7 Hz, 1H), 4.21 (qd, J = 9.5, 6.5 Hz, 2H), 3.77 (d, J = 8.3 Hz, 1H), 3.49 (d, J = 8.3 Hz, 1H); $^{19}$F NMR (376 MHz, Acetone-d$_6$) δ −63.21, −72.60, −72.60, −111.80 |
| F123 | | | ESIMS 563 ([M + H]$^+$) | $^1$H NMR (400 MHz, Acetone-d$_6$) δ 10.13 (s, 1H), 8.24 (t, J = 6.5 Hz, 1H), 7.91 (d, J = 2.6 Hz, 1H), 7.77 (dd, J = 8.7, 2.6 Hz, 1H), 7.51 (s, 1H), 7.50-7.37 (m, 2H), 7.30 (dt, J = 9.5, 1.9 Hz, 1H), 4.21 (qd, J = 9.5, 6.5 Hz, 2H), 3.66 (d, J = 8.3 Hz, 1H), 3.40 (d, J = 8.4 Hz, 1H); $^{19}$F NMR (376 MHz, Acetone-d$_6$) δ −72.54, −72.56, −111.81 |
| F124 | | | ESIMS 613 ([M + H]$^+$) | $^1$H NMR (400 MHz, Acetone-d$_6$) δ 10.13 (s, 1H), 8.23 (t, J = 6.5 Hz, 1H), 8.01-7.88 (m, 3H), 7.84 (s, 1H), 7.78 (dd, J = 8.7, |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | | 2.6 Hz, 1H), 7.45 (d, J = 8.7 Hz, 1H), 4.21 (qd, J = 9.5, 6.5 Hz, 2H), 3.77 (d, J = 8.3 Hz, 1H), 3.51 (d, J = 8.3 Hz, 1H); $^{19}$F NMR (376 MHz, Acetone-d$_6$) δ −63.23, −63.24, −72.60, −72.61 |
| F125 | | | ESIMS 532 ([M + H]$^+$) | $^1$H NMR (400 MHz, Acetone-d$_6$) δ 10.13 (s, 1H), 8.22 (t, J = 6.5 Hz, 1H), 7.91 (d, J = 2.6 Hz, 1H), 7.77 (dd, J = 8.8, 2.6 Hz, 1H), 7.45 (d, J = 8.8 Hz, 1H), 7.30-7.02 (m, 2H), 4.20 (qd, J = 9.5, 6.5 Hz, 2H), 3.99 (d, J = 1.1 Hz, 3H), 3.58 (d, J = 8.3 Hz, 1H), 3.31 (d, J = 8.3 Hz, 1H); $^{19}$F NMR (376 MHz, Acetone-d$_6$) δ −72.61, −129.67 |
| F126 | | | ESIMS 520 ([M + H]$^+$) | $^1$H NMR (400 MHz, Acetone-d$_6$) δ 10.16 (s, 1H), 8.23 (t, J = 6.5 Hz, 1H), 7.91 (d, J = 2.6 Hz, 1H), 7.77 (dd, J = 8.8, 2.6 Hz, 1H), 7.45 (d, J = 8.7 Hz, 1H), 7.41-7.27 (m, 2H), 4.20 (qd, J = 9.5, 6.5 Hz, 2H), 3.74-3.48 (m, 1H), 3.37 (d, J = 8.3 Hz, 1H); $^{19}$F NMR (376 MHz, Acetone-d$_6$) δ −72.61, −136.27, −163.62 |
| F127 | | | ESIMS m/z 520 ([M + H]+) | $^1$H NMR (400 MHz, Acetone-d$_6$) δ 10.05 (s, 1H), 8.43-8.04 (m, 1H), 7.79 (d, J = 2.6 Hz, 1H), 7.68 (dd, J = 8.8, 2.7 Hz, 1H), 7.41 (d, J = 8.8 Hz, 1H), 7.36-7.22 (m, 2H), 4.35-4.11 (m, 2H), 3.54 (d, J = 11.3 Hz, 1H), 3.25 (d, J = 11.3 Hz, 1H); $^{19}$F NMR (376 MHz, Acetone-d$_6$) δ −72.51, −137.68, −164.86 |
| F128 | | | HRMS-ESI [M + H]$^+$ calcd for C$_{20}$H$_{14}$Cl$_4$F$_5$N$_2$O$_2$, 548.9724; found, 548.9720. | $^1$H NMR (500 MHz, Acetone-d$_6$) δ 10.15 (s, 1H), 8.23 (t, J = 6.5 Hz, 1H), 7.92 (dd, J = 2.6, 1.2 Hz, 1H), 7.77 (ddd, J = 8.8, 2.7, 1.2 Hz, 1H), 7.68 (tt, J = 1.9, 0.9 Hz, 1H), 7.63 (p, J = 1.4 Hz, 2H), 7.45 (d, J = 8.7 Hz, 1H), 6.96 (t, J = 55.8 Hz, 1H), 4.27-4.09 (m, 2H), 3.71 (d, J = 8.3 Hz, 1H), 3.45 (d, J = 8.3 Hz, 1H); $^{19}$F NMR (471 MHz, Acetone-d$_6$) δ −72.57 (t, J = 9.6 Hz), −112.20 (dd, J = 55.8, 14.2 Hz) |
| F129 | | | HRMS-ESI [M + H]$^+$ calcd for C$_{20}$H$_{14}$Cl$_4$F$_5$N$_2$O$_2$, 548.9724; found, 548.9719. | $^1$H NMR (500 MHz, Acetone-d$_6$) δ 10.15 (s, 1H), 8.22 (t, J = 6.4 Hz, 1H), 7.92 (dd, J = 2.7, 1.2 Hz, 1H), 7.77 (ddd, J = 8.7, 2.6, 1.1 Hz, 1H), 7.76-7.73 (m, 1H), 7.66-7.57 (m, 2H), 7.45 (d, J = 8.7 Hz, 1H), 7.14 (t, J = 54.5 Hz, 1H), 4.25-4.14 (m, 2H), 3.69 (d, J = 8.3 Hz, 1H), 3.41 (d, J = 8.3 Hz, 1H); $^{19}$F NMR (471 MHz, Acetone-d$_6$) δ −116.25 (d, J = 54.7 Hz) |
| F130 | | | HRMS-ESI [M + H]$^+$ calcd for C$_{20}$H$_{14}$Cl$_3$F$_6$N$_2$O$_2$, 533.0020; found, 533.0013. | $^1$H NMR (500 MHz, Acetone-d$_6$) δ 10.16 (s, 1H), 8.23 (t, J = 6.5 Hz, 1H), 7.92 (dd, J = 2.6, 1.2 Hz, 1H), 7.78 (ddd, J = 8.8, 2.7, 1.2 Hz, 1H), 7.53 (q, J = 1.1 Hz, 1H), 7.45 (d, J = 8.7 Hz, 1H), 7.47-7.41 (m, 1H), |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | | 7.38 (ddd, J = 8.9, 2.6, 1.3 Hz, 1H), 6.97 (t, J = 55.8 Hz, 1H), 4.25-4.14 (m, 2H), 3.71 (d, J = 8.3 Hz, 1H), 3.43 (d, J = 8.4 Hz, 1H); $^{19}$F NMR (471 MHz, Acetone-d$_6$) δ −72.59 (t, J = 9.4 Hz), −112.06 (dd, J = 55.8, 14.3 Hz), −112.93 (t, J = 9.1 Hz) |
| F131 | | | HRMS-ESI [M + H]$^+$ calcd for C$_{20}$H$_{14}$Cl$_3$F$_6$N$_2$O$_2$, 533.0020; found, 533.0016. | $^1$H NMR (500 MHz, Acetone-d$_6$) δ 10.15 (s, 1H), 8.23 (t, J = 6.5 Hz, 1H), 7.92 (dd, J = 2.6, 1.2 Hz, 1H), 7.78 (ddd, J = 8.8, 2.7, 1.1 Hz, 1H), 7.68 (ddt, J = 9.6, 6.1, 1.7 Hz, 2H), 7.45 (d, J = 8.7 Hz, 1H), 7.39-7.31 (m, 1H), 7.12 (t, J = 54.6 Hz, 1H), 4.28-4.14 (m, 2H), 3.67 (d, J = 8.3 Hz, 1H), 3.37 (d, J = 8.3 Hz, 1H); $^{19}$F NMR (471 MHz, Acetone-d$_6$) δ −72.58 (t, J = 9.5 Hz), −114.91 (dd, J = 54.7, 3.6 Hz), −119.78--122.55 (m) |
| F132 | | | HRMS-ESI [M + H]$^+$ calcd for C$_{20}$H$_{14}$Cl$_4$F$_5$N$_2$O$_2$, 548.9724; found, 548.9723. | $^1$H NMR (500 MHz, Acetone-d$_6$) δ 10.16 (s, 1H), 8.23 (t, J = 6.5 Hz, 1H), 7.92 (dd, J = 2.6, 1.2 Hz, 1H), 7.80-7.72 (m, 2H), 7.65 (dd, J = 1.9, 1.0 Hz, 1H), 7.58 (dd, J = 8.1, 1.6 Hz, 1H), 7.45 (d, J = 8.7 Hz, 1H), 7.13 (t, J = 54.6 Hz, 1H), 4.30-4.12 (m, 2H), 3.72-3.65 (m, 1H), 3.43 (d, J = 8.3 Hz, 1H); $^{19}$F NMR (471 MHz, Acetone-d$_6$) δ −72.56 (t, J = 9.5 Hz), −116.13 (d, J = 54.6 Hz) |
| F133 | | | HRMS-ESI [M + H]$^+$ calcd for C$_{20}$H$_{14}$Cl$_3$F$_6$N$_2$O$_2$, 533.0020; found, 533.0011. | $^1$H NMR (500 MHz, Acetone-d$_6$) δ 10.18 (s, 1H), 8.23 (t, J = 6.5 Hz, 1H), 7.92 (dd, J = 2.6, 1.1 Hz, 1H), 7.78 (ddd, J = 8.8, 2.7, 1.1 Hz, 1H), 7.70 (t, J = 7.7 Hz, 1H), 7.45 (d, J = 8.8 Hz, 1H), 7.44 (dd, J = 8.2, 1.5 Hz, 1H), 7.42-7.38 (m, 1H), 7.11 (t, J = 54.7 Hz, 1H), 4.29-4.11 (m, 2H), 3.69 (d, J = 8.3 Hz, 1H), 3.41 (d, J = 8.3 Hz, 1H); $^{19}$F NMR (471 MHz, Acetone-d$_6$) δ −72.58 (t, J = 9.4 Hz), −114.82 (dd, J = 54.7, 3.7 Hz), −119.99 (ddt, J = 11.4, 7.5, 3.6 Hz) |
| F134 | | | HRMS-ESI [M + H]$^+$ calcd for C$_{20}$H$_{15}$Cl$_3$F$_5$N$_2$O$_2$, 515.0114; found, 515.0108. | $^1$H NMR (500 MHz, Acetone-d$_6$) δ 10.16 (s, 1H), 8.23 (t, J = 6.6 Hz, 1H), 7.93 (d, J = 2.6 Hz, 1H), 7.78 (dd, J = 8.7, 2.6 Hz, 1H), 7.65-7.56 (m, 4H), 7.45 (d, J = 8.7 Hz, 1H), 6.93 (t, J = 56.1 Hz, 1H), 4.25-4.15 (m, 2H), 3.68 (d, J = 8.3 Hz, 1H), 3.38 (d, J = 8.4 Hz, 1H); $^{19}$F NMR (471 MHz, Acetone-d$_6$) δ −72.57 (t, J = 9.5 Hz), −111.22 (dd, J = 56.0, 14.1 Hz) |
| F135 | | | HRMS-ESI [M + H]$^+$ calcd for C$_{20}$H$_{15}$Cl$_3$F$_5$N$_2$O$_2$, 515.0114; found, 515.0108. | $^1$H NMR (500 MHz, Acetone-d$_6$) δ 10.17 (s, 1H), 8.23 (t, J = 6.4 Hz, 1H), 7.93 (dd, J = 2.6, 1.2 Hz, 1H), 7.78 (ddd, J = 8.7, 2.6, 1.1 Hz, 1H), 7.64 (dt, J = 8.3, 1.2 Hz, 2H), 7.57 (dt, J = 8.0, 0.9 Hz, 2H), 7.45 (d, J = 8.7 Hz, 1H), 6.93 (t, J = 56.1 Hz, |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | | 1H), 4.20 (ttd, J = 9.5, 6.5, 3.2 Hz, 2H), 3.66 (d, J = 8.4 Hz, 1H), 3.36 (d, J = 8.3 Hz, 1H); $^{19}$F NMR (471 MHz, Acetone-d$_6$) δ −72.57 (t, J = 9.4 Hz), −111.22 (d, J = 56.2 Hz) |
| PF1 | | | ESIMS 622 ([M − H]−) | $^1$H NMR (400 MHz, Acetone-d$_6$) δ 10.15 (s, 1H), 8.22 (t, J = 6.4 Hz, 1H), 7.92 (d, J = 2.6 Hz, 1H), 7.78 (dd, J = 8.8, 2.6 Hz, 1H), 7.53-7.42 (m, 4H), 4.20 (qd, J = 9.5, 6.5 Hz, 2H), 3.59 (d, J = 8.3 Hz, 1H), 3.41 (d, J = 8.2 Hz, 1H), 2.88 (d, J = 13.0 Hz, 1H); $^{19}$F NMR (376 MHz, Acetone-d$_6$) δ −72.58 |
| PF2 | 87-93 | | HRMS-ESI [M+]$^+$ calcd for C$_{23}$H$_{20}$Cl$_5$F$_3$N$_2$O$_2$S, 619.9640; found, 619.9644. | $^1$H NMR (500 MHz, DMSO-d$_6$) δ 10.86 (s, 1H), 8.48 (d, J = 8.1 Hz, 1H), 7.72 (m, 2H), 7.62 (s, 1H), 7.54 (m, 2H), 7.47 (d, J = 8.7 Hz, 1H), 4.08 (dt, J = 14.2, 6.9 Hz, 1H), 3.61 (d, J = 8.5 Hz, 1H), 3.50 (d, J = 8.5 Hz, 1H), 2.75 (dt, J = 10.0, 4.7 Hz, 2H), 2.70 (d, J = 6.9 Hz, 2H), 2.59 (m, 2H), 1.21 (d, J = 6.6 Hz, 3H); $^{13}$C NMR (126 MHz, DMSO-d$_6$) δ 165.97, 163.01, 138.01, 137.93, 137.77, 134.54, 130.54, 130.46, 128.37, 128.25, 128.17, 126.04, 124.48, 123.84, 121.40, 119.48, 62.62, 45.10, 38.88, 37.60, 37.25, 34.32, 34.11, 33.89, 33.67, 23.92, 20.00; $^{19}$F NMR (471 MHz, DMSO-d$_6$) δ −64.53, −64.56, −64.58 |
| PF3 | 90-95 | | HRMS-ESI (m/z) [M+]$^+$ calcd for C$_{22}$H$_{18}$Cl$_5$F$_3$N$_2$O$_2$S, 605.9484; found, 605.9485. | $^1$H NMR (500 MHz, DMSO-d$_6$) δ 10.86 (s, 1H), 8.51 (d, J = 8.2 Hz, 1H), 7.72 (m, 2H), 7.62 (d, J = 1.7 Hz, 1H), 7.55 (d, J = 1.5 Hz, 2H), 7.48 (d, J = 8.8 Hz, 1H), 4.12 (hept, J = 6.7 Hz, 1H), 3.62 (d, J = 8.5 Hz, 1H), 3.53 (m, 3H), 2.80 (m, 2H), 1.21 (d, J = 6.6 Hz, 3H); $^{13}$C NMR (126 MHz, DMSO-d$_6$) δ 165.41, 162.44, 137.46, 137.30, 137.20, 133.96, 129.98, 129.80, 127.80, 127.60, 125.41, 123.88, 123.22, 120.84, 118.85, 62.05, 44.73, 38.31, 38.09, 36.67, 33.33, 33.08, 32.83, 32.58, 19.40; $^{19}$F NMR (471 MHz, DMSO-d$_6$) δ −65.06, −65.08, −65.08, −65.10, −65.11, −65.12 |
| PF4 | 113-118 | | HRMS-ESI (m/z) [M + H]$^+$ calcd for C$_{23}$H$_{21}$Cl$_5$F$_3$N$_2$O$_4$S, 652.9611; found, 652.9620. | $^1$H NMR (500 MHz, DMSO-d$_6$) δ 10.87 (s, 1H), 8.69 (dd, J = 8.2, 2.7 Hz, 1H), 7.73 (dd, J = 5.5, 3.2 Hz, 2H), 7.62 (s, 1H), 7.54 (d, J = 1.4 Hz, 2H), 7.48 (d, J = 9.0 Hz, 1H), 4.52 (dt, J = 13.8, 6.9 Hz, 1H), 3.61 (d, J = 8.5 Hz, 1H), 3.48 (m, 5H), 2.78 (m, 2H), 1.31 (d, J = 6.1 Hz, 3H); $^{13}$C NMR (126 MHz, DMSO-d$_6$) δ 165.68, 163.03, 163.01, 138.04, 137.77, 137.51, 134.54, 130.55, 128.36, |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | | 128.17, 127.88, 125.68, 124.48, 121.66, 119.49, 62.63, 57.20, 46.16, 38.83, 37.25, 34.66, 26.89, 26.65, 26.41, 26.17, 25.25, 22.54, 21.09, 14.44, 11.73; $^{19}$F NMR (471 MHz, DMSO-d$_6$) δ −64.28, −64.30, −64.32 |
| PF5 | 121-126 | | HRMS-ESI [M + H]$^+$ calcd for C$_{23}$H$_{21}$Cl$_5$F$_3$N$_2$O$_3$S, 636.9662; found, 636.9665. | |
| PF6 | 102-107 | | HRMS-ESI [M + H]$^+$ calcd for C$_{22}$H$_{19}$Cl$_5$F$_3$N$_2$O$_4$S, 638.9455; found, 638.9465. | $^1$H NMR (500 MHz, DMSO-d$_6$) δ 10.88 (s, 1H), 8.75 (d, J = 8.1 Hz, 1H), 7.73 (m, 2H), 7.62 (s, 1H), 7.54 (d, J = 1.3 Hz, 2H), 7.49 (d, J = 8.6 Hz, 1H), 4.75 (q, J = 10.2 Hz, 2H), 4.55 (dq, J = 13.3, 6.6 Hz, 1H), 3.58 (m, 2H), 3.49 (m, 2H), 1.33 (d, J = 6.7 Hz, 3H); $^{13}$C NMR (126 MHz, DMSO-d$_6$) δ 165.08, 162.47, 137.50, 137.20, 136.85, 133.96, 130.01, 127.79, 127.59, 125.53, 123.89, 123.32, 121.11, 118.84, 62.06, 58.66, 54.73, 54.50, 54.27, 54.06, 38.27, 36.67, 34.09, 30.85, 24.68, 21.96, 20.40, 13.86; $^{19}$F NMR (471 MHz, DMSO-d$_6$) δ −59.40, −59.42, −59.44 |
| PF7 | 123-128 | | HRMS-ESI (m/z) [M + H]$^+$ calcd for C$_{22}$H$_{19}$Cl$_5$F$_3$N$_2$O$_3$S, 622.9506; found, 622.9508. | $^1$H NMR (500 MHz, DMSO-d$_6$) δ 10.87 (d, J = 2.5 Hz, 1H), 8.81 (dd, J = 8.2, 2.0 Hz, 0.5H), 8.69 (d, J = 8.1 Hz, 0.5H), 7.72 (td, J = 6.4, 2.4 Hz, 2H), 7.62 (s, 1H), 7.55 (s, 2H), 7.49 (d, J = 8.8 Hz, 1H), 4.39 (dt, J = 13.8, 6.7 Hz, 1H), 4.07 (m, 2H), 3.62 (d, J = 8.5 Hz, 1H), 3.50 (d, J = 8.5 Hz, 1H), 3.14 (m, 2H), 1.31 (m, 3H); $^{19}$F NMR (471 MHz, DMSO-d$_6$) δ −59.52, −59.53, −59.54, −59.55, −59.56, −59.58, −59.63, −59.65, −59.67, −59.69 |
| PF9 | 73-79 | | HRMS-ESI (m/z) [M+]$^+$ calcd for C$_{24}$H$_{19}$Cl$_5$N$_2$O$_3$S, 589.9559; found, 589.9564. | $^1$H NMR (500 MHz, DMSO-d$_6$) δ 10.88 (s, 1H), 8.62 (t, J = 5.7 Hz, 1H), 7.75 (d, J = 2.6 Hz, 1H), 7.70 (dd, J = 8.8, 2.6 Hz, 1H), 7.62 (t, J = 1.8 Hz, 1H), 7.59 (dd, J = 1.8, 0.8 Hz, 1H), 7.55 (d, J = 1.5 Hz, 2H), 7.48 (d, J = 8.7 Hz, 1H), 6.40 (dd, J = 3.1, 1.9 Hz, 1H), 6.32 (m, 1H), 3.84 (s, 2H), 3.61 (d, J = 8.5 Hz, 1H), 3.51 (d, J = 8.5 Hz, 1H), 3.40 (q, J = 6.3 Hz, 2H), 2.63 (t, J = 7.1 Hz, 2H); $^{13}$C NMR (126 MHz, DMSO-d$_6$) δ 166.52, 163.03, 151.84, 142.95, 138.04, 137.78, 137.71, 134.54, 130.60, 128.38, 128.17, 124.45, 121.50, 119.52, 111.05, 108.21, 62.64, 38.88, 38.85, 37.25, 30.63, 27.36 |
| PF10 | 93-99 | | HRMS-ESI [M]$^+$ calcd for C$_{23}$H$_{21}$Cl$_5$N$_2$O$_4$S, 595.9665; found, 595.9668. | $^1$H NMR (500 MHz, DMSO-d$_6$) δ 10.88 (d, J = 6.5 Hz, 1H), 8.95 (d, J = 7.6 Hz, 1H), 7.75 (ddd, J = 18.2, 8.1, 2.6 Hz, 2H), 7.63 (t, J = 1.8 Hz, 1H), 7.55 (m, 2H), 7.49 (d, J = 8.7 Hz, 1H), |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| | | | | 4.58 (ddt, J = 7.5, 5.2, 2.4 Hz, 1H), 3.69 (s, 3H), 3.63 (d, J = 8.5 Hz, 1H), 3.50 (dd, J = 8.5, 3.0 Hz, 1H), 2.59 (m, 2H), 2.07 (s, 3H), 2.00 (m, 2H); $^{13}$C NMR (126 MHz, DMSO-d$_6$) δ 171.82, 166.25, 162.46, 137.48, 137.19, 136.63, 136.61, 133.95, 130.04, 127.80, 127.59, 123.88, 121.03, 119.06, 62.04, 51.96, 51.16, 51.13, 38.32, 36.65, 30.05, 29.52, 14.46, 14.45 |
| PF11 | 129-135 | | HRMS-ESI [M+]$^+$ calcd for C$_{26}$H$_{18}$Cl$_5$N$_5$O$_2$, 606.9903; found, 606.9916. | $^1$H NMR (500 MHz, DMSO-d$_6$) δ 10.86 (s, 1H), 9.28 (s, 1H), 9.11 (t, J = 6.0 Hz, 1H), 8.24 (s, 1H), 7.85 (m, 2H), 7.80 (d, J = 2.6 Hz, 1H), 7.71 (dd, J = 8.8, 2.6 Hz, 1H), 7.62 (t, J = 1.8 Hz, 1H), 7.54 (m, 4H), 7.51 (d, J = 8.7 Hz, 1H), 4.51 (d, J = 6.4 Hz, 2H), 3.62 (d, J = 8.5 Hz, 1H), 3.50 (d, J = 8.5 Hz, 1H); $^{13}$C NMR (126 MHz, DMSO-d$_6$) δ 166.07, 162.47, 152.24, 142.12, 138.76, 137.53, 137.18, 137.03, 135.49, 133.95, 130.10, 128.45, 127.80, 127.59, 123.86, 120.98, 119.28, 118.91, 62.03, 41.86, 38.31, 36.66 |
| PF12 | 94-99 | | HRMS-ESI [M]$^+$ calcd for C$_{22}$H$_{16}$Cl$_5$N$_3$O$_2$S, 560.9406; found, 560.9399. | $^1$H NMR (500 MHz, DMSO-d$_6$) δ 10.85 (s, 1H), 8.66 (t, J = 5.7 Hz, 1H), 7.76 (dd, J = 11.8, 3.0 Hz, 2H), 7.67 (dd, J = 8.8, 2.6 Hz, 1H), 7.63 (t, J = 1.8 Hz, 1H), 7.61 (d, J = 3.3 Hz, 1H), 7.55 (d, J = 1.5 Hz, 2H), 7.47 (d, J = 8.7 Hz, 1H), 3.62 (m, 3H), 3.50 (d, J = 8.5 Hz, 1H), 3.24 (t, J = 7.1 Hz, 2H) $^{13}$C NMR (126 MHz, DMSO-d$_6$) δ 166.90, 165.95, 162.42, 142.21, 137.43, 137.19, 137.11, 133.95, 129.99, 127.80, 127.59, 123.89, 120.95, 119.49, 118.97, 62.06, 38.28, 36.66, 32.15 |
| PF13 | 187-189 | | HRMS-ESI [M]$^+$ calcd for C$_{22}$H$_{17}$Cl$_5$N$_4$O$_2$, 543.9794; found, 543.9800. | $^1$H NMR (500 MHz, DMSO-d$_6$) δ 10.84 (s, 1H), 8.60 (t, J = 5.6 Hz, 1H), 7.74 (dd, J = 8.8, 2.3 Hz, 2H), 7.66 (dd, J = 8.8, 2.6 Hz, 1H), 7.63 (t, J = 1.8 Hz, 1H), 7.55 (d, J = 1.6 Hz, 2H), 7.47 (m, 2H), 6.24 (t, J = 2.0 Hz, 1H), 4.29 (t, J = 6.3 Hz, 2H), 3.62 (q, J = 5.6 Hz, 3H), 3.50 (d, J = 8.5 Hz, 1H); $^{13}$C NMR (126 MHz, DMSO-d$_6$) δ 166.11, 162.43, 138.77, 137.42, 137.19, 137.00, 133.96, 130.04, 129.98, 127.81, 127.59, 123.87, 121.02, 119.01, 104.93, 62.06, 49.94, 38.26, 36.67 |
| PF14 | 150-155 | | ESIMS 596 ([M − H + Na]$^-$) | $^1$H NMR (500 MHz, DMSO-d$_6$) δ 10.72 (s, 1H), 7.74 (d, J = 2.6 Hz, 1H), 7.61 (m, 3H), 7.55 (d, J = 1.5 Hz, 2H), 7.30 (d, J = 8.7 Hz, 1H), 3.60 (d, J = 8.5 Hz, 1H), 3.46 (m, 3H), 3.12 (m, 2H), 1.90 (p, J = 7.1 Hz, 2H); $^{13}$C NMR (126 MHz, DMSO-d$_6$) |

TABLE 4-continued

Analytical data for molecules in Table 2

| No. | Mp (° C.) | IR (cm$^{-1}$) | Mass (m/z) | NMR ($^1$H, $^{13}$C, or $^{19}$F) |
|---|---|---|---|---|
| PF15 | 115-119 | | HRMS-ESI [M+]$^+$ calcd for C$_{27}$H$_{19}$Cl$_5$N$_2$O$_2$S, 609.9610; found, 609.9618. | δ 171.09, 162.70, 142.03, 137.90, 137.43, 134.50, 130.20, 128.39, 128.10, 124.76, 120.37, 119.81, 62.68, 50.22, 49.01, 38.90, 37.21, 24.24 <br> $^1$H NMR (500 MHz, DMSO-d$_6$) δ 10.84 (s, 1H), 8.68 (t, J = 5.7 Hz, 1H), 7.95 (dd, J = 37.3, 7.9 Hz, 2H), 7.78 (d, J = 2.6 Hz, 1H), 7.66 (dd, J = 8.8, 2.6 Hz, 1H), 7.63 (t, J = 1.8 Hz, 1H), 7.55 (d, J = 1.7 Hz, 2H), 7.53 (s, 1H), 7.48 (d, J = 8.7 Hz, 1H), 7.44 (m, 1H), 7.38 (t, J = 7.1 Hz, 1H), 3.61 (m, 3H), 3.50 (d, J = 8.5 Hz, 1H), 3.09 (t, J = 7.2 Hz, 2H); <br> $^{13}$C NMR (126 MHz, DMSO-d$_6$) δ 165.96, 162.44, 139.56, 138.61, 137.44, 137.25, 137.19, 133.96, 133.39, 130.02, 127.80, 127.59, 124.19, 124.00, 123.92, 122.82, 122.74, 121.55, 120.92, 119.00, 62.05, 38.62, 38.28, 36.67, 27.86 |
| PF16 | 108-112 | | HRMS-ESI [M+]$^+$ calcd for C$_{20}$H$_{14}$Cl$_5$F$_3$N$_2$O$_3$, 561.9399; found, 561.9402. | $^1$H NMR (500 MHz, DMSO-d$_6$) δ 10.86 (s, 1H), 8.73 (t, J = 5.6 Hz, 1H), 7.78 (m, 1H), 7.68 (m, 1H), 7.63 (t, J = 1.8 Hz, 1H), 7.55 (d, J = 1.7 Hz, 2H), 7.48 (d, J = 8.7 Hz, 1H), 6.53 (dd, J = 6.5, 2.2 Hz, 1H), 4.17 (m, 1H), 3.61 (d, J = 8.5 Hz, 1H), 3.57 (m, 1H), 3.50 (d, J = 8.5 Hz, 1H), 3.30 (m, 1H); <br> $^{19}$F NMR (471 MHz, DMSO-d$_6$) δ −76.93, −76.95 |

BAW & CL Rating Table

| % Control (or Mortality) | Rating |
|---|---|
| 50-100 | A |
| More than 0-Less than 50 | B |
| Not Tested | C |
| No activity noticed in this bioassay | D |

GPA & YFM Rating Table

| % Control (or Mortality) | Rating |
|---|---|
| 80-100 | A |
| More than 0-Less than 80 | B |
| Not Tested | C |
| No activity noticed in this bioassay | D |

TABLE ABC

Biological Results

| No. | BAW | CL | GPA | YFM |
|---|---|---|---|---|
| F1 | A | A | C | A |
| F2 | A | A | B | A |
| F3 | A | A | C | A |
| F4 | A | A | A | A |
| F5 | A | A | C | C |
| F6 | A | A | B | A |
| F7 | A | A | C | A |
| F8 | A | A | C | C |
| F9 | A | A | C | C |
| F10 | A | A | C | C |
| F11 | A | A | C | C |
| F12 | A | A | B | A |
| F13 | A | A | B | A |
| F14 | A | A | B | A |
| F15 | A | A | A | A |
| F16 | A | A | B | A |
| F17 | A | A | B | A |
| F18 | A | A | B | C |
| F19 | A | A | B | A |
| F20 | A | A | B | A |
| F21 | A | A | B | B |
| F22 | A | A | A | B |

TABLE ABC-continued

Biological Results

| No. | BAW | CL | GPA | YFM |
|---|---|---|---|---|
| F23 | A | A | A | B |
| F24 | A | A | C | A |
| F25 | A | A | C | A |
| F26 | A | A | C | A |
| F27 | A | A | B | A |
| F28 | A | A | A | A |
| F29 | D | D | B | A |
| F30 | A | A | A | A |
| F31 | A | A | B | B |
| F32 | A | A | B | A |
| F33 | A | A | B | A |
| F34 | A | A | D | A |
| F35 | A | A | A | A |
| F36 | D | D | D | B |
| F37 | A | A | B | A |
| F38 | A | A | A | A |
| F39 | A | A | A | A |
| F40 | A | A | A | A |
| F41 | A | A | D | A |
| F42 | A | A | B | A |
| F43 | A | A | A | C |
| F44 | A | A | A | A |
| F45 | A | A | A | A |
| F46 | A | A | A | A |
| F47 | A | A | A | A |
| F48 | A | A | A | B |
| F49 | A | A | A | A |
| F50 | D | A | C | C |
| F51 | A | A | C | B |
| F52 | A | A | C | B |
| F53 | A | A | C | B |
| F54 | A | A | C | B |
| F55 | A | A | A | B |
| F56 | A | A | A | A |
| F57 | A | A | C | D |
| F58 | A | A | C | A |
| F59 | A | A | B | A |
| F60 | A | A | C | D |
| F61 | A | A | C | D |
| F62 | A | A | C | D |
| F63 | A | A | C | D |
| F64 | A | A | C | D |
| F65 | A | A | C | C |
| F66 | A | A | C | C |
| F67 | A | A | C | D |
| F68 | A | A | C | D |
| F69 | A | A | C | D |
| F70 | A | A | C | D |
| F71 | A | A | C | D |
| F72 | A | A | C | A |
| F73 | A | A | C | A |
| F74 | A | A | C | C |
| F75 | A | A | A | A |
| F78 | A | A | C | A |
| F79 | A | A | C | A |
| F84 | A | A | C | D |
| F85 | A | A | C | B |
| F86 | A | A | C | B |
| F87 | A | A | C | B |
| F88 | A | A | C | B |
| F91 | A | A | C | A |
| F92 | A | A | C | A |
| F93 | A | A | C | C |
| F94 | A | A | C | A |
| F95 | A | A | C | A |
| F96 | A | A | C | A |
| F97 | A | A | C | A |
| F98 | B | D | C | A |
| F99 | A | A | C | A |
| F100 | A | D | C | A |
| F101 | D | D | C | D |
| F102 | B | D | C | A |
| F103 | A | A | C | A |
| F104 | A | A | C | A |
| F105 | A | A | C | A |
| F106 | A | A | C | A |
| F107 | A | A | C | B |
| F108 | A | A | C | A |
| F109 | A | A | C | A |
| F111 | A | A | C | A |
| F112 | A | A | C | A |
| F113 | A | A | C | A |
| F114 | A | A | C | A |
| F115 | A | A | C | A |
| F116 | A | A | C | A |
| F117 | A | A | C | A |
| F118 | A | A | C | A |
| F119 | A | A | C | A |
| F120 | A | A | C | A |
| F121 | A | A | C | A |
| F122 | A | A | C | A |
| F123 | A | A | C | A |
| F124 | A | A | C | A |
| F125 | A | A | C | A |
| F126 | A | A | C | A |
| F127 | A | A | C | A |
| F128 | A | A | C | A |
| F129 | A | A | C | A |
| F130 | A | A | C | A |
| F131 | A | A | C | A |
| F132 | A | A | C | A |
| F133 | A | A | C | A |
| F134 | A | A | C | A |
| F135 | D | A | C | A |
| PF1 | A | A | C | D |
| PF2 | A | A | C | A |
| PF3 | A | A | A | B |
| PF4 | A | A | C | A |
| PF5 | A | A | C | A |
| PF6 | A | A | B | A |
| PF7 | A | A | C | A |
| PF9 | A | A | C | A |
| PF10 | A | A | C | B |
| PF11 | A | A | C | A |
| PF12 | A | A | C | A |
| PF13 | A | A | C | A |
| PF14 | B | A | C | D |
| PF15 | A | A | C | A |
| PF16 | A | A | A | A |

The invention claimed is:
1. A molecule having the following formula

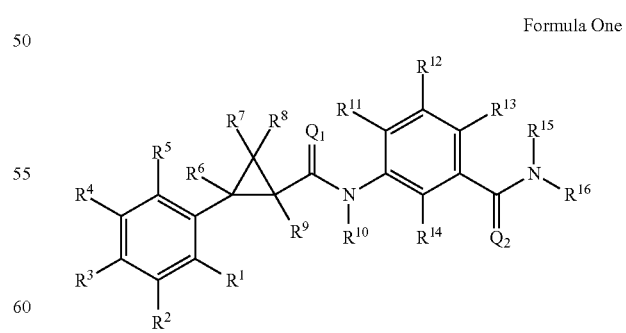

Formula One wherein:
(A) $R^1$ is selected from the group consisting of H, F, Cl, Br, I, CN, $NH_2$, $NO_2$, $(C_1-C_4)$alkyl, $(C_3-C_6)$cycloalkyl, $(C_2-C_4)$alkenyl, $(C_3-C_6)$cycloalkenyl, $(C_2-C_4)$alkynyl, $(C_1-C_4)$alkoxy, $(C_1-C_4)$haloalkyl, $(C_3-C_6)$halocycloalkyl, $(C_2-C_4)$haloalkenyl, $(C_3-C_6)$halocycloalkenyl, $(C_1-C_4)$haloalkoxy, $S(C_1-C_4)$alkyl, $S(O)(C_1-C_4)$alkyl, $S(O)_2(C_1-C_4)$alkyl, $S(C_1-C_4)$haloalkyl, $S(O)(C_1-C_4)$haloalkyl, $S(O)_2(C_1-C_4)$haloalkyl, $(C_1-C_4)$alkyl-S$(O)_2NH_2$, and $(C_1-C_4)$haloalkyl-S$(O)_2NH_2$;

(B) $R^2$ is selected from the group consisting of H, F, Cl, Br, I, CN, $NH_2$, $NO_2$, $(C_1-C_4)$alkyl, $(C_3-C_6)$cycloalkyl, $(C_2-C_4)$alkenyl, $(C_3-C_6)$cycloalkenyl, $(C_2-C_4)$alkynyl, $(C_1-C_4)$alkoxy, $(C_1-C_4)$haloalkyl, $(C_3-C_6)$halocycloalkyl, $(C_2-C_4)$haloalkenyl, $(C_3-C_6)$halocycloalkenyl, $(C_1-C_4)$haloalkoxy, $S(C_1-C_4)$alkyl, $S(O)(C_1-C_4)$alkyl, $S(O)_2(C_1-C_4)$alkyl, $S(C_1-C_4)$haloalkyl, $S(O)_2(C_1-C_4)$haloalkyl, $S(O)_2(C_1-C_4)$haloalkyl, $(C_1-C_4)$alkyl-S$(O)_2NH_2$, and $(C_1-C_4)$haloalkyl-S$(O)_2NH_2$;

(C) $R^3$ is selected from the group consisting of H, F, Cl, Br, I, CN, $NH_2$, $NO_2$, $(C_1-C_4)$alkyl, $(C_3-C_6)$cycloalkyl, $(C_2-C_4)$alkenyl, $(C_3-C_6)$cycloalkenyl, $(C_2-C_4)$alkynyl, $(C_1-C_4)$alkoxy, $(C_1-C_4)$haloalkyl, $(C_3-C_6)$halocycloalkyl, $(C_2-C_4)$haloalkenyl, $(C_3-C_6)$halocycloalkenyl, $(C_1-C_4)$haloalkoxy, $S(C_1-C_4)$alkyl, $S(O)(C_1-C_4)$alkyl, $S(O)_2(C_1-C_4)$alkyl, $S(C_1-C_4)$haloalkyl, $S(O)(C_1-C_4)$haloalkyl, $S(O)_2(C_1-C_4)$haloalkyl, $(C_1-C_4)$alkyl-S$(O)_2NH_2$, and $(C_1-C_4)$haloalkyl-S$(O)_2NH_2$;

(D) $R^4$ is selected from the group consisting of H, F, Cl, Br, I, CN, $NH_2$, $NO_2$, $(C_1-C_4)$alkyl, $(C_3-C_6)$cycloalkyl, $(C_2-C_4)$alkenyl, $(C_3-C_6)$cycloalkenyl, $(C_2-C_4)$alkynyl, $(C_1-C_4)$alkoxy, $(C_1-C_4)$haloalkyl, $(C_3-C_6)$halocycloalkyl, $(C_2-C_4)$haloalkenyl, $(C_3-C_6)$halocycloalkenyl, $(C_1-C_4)$haloalkoxy, $S(C_1-C_4)$alkyl, $S(O)(C_1-C_4)$alkyl, $S(O)_2(C_1-C_4)$alkyl, $S(C_1-C_4)$haloalkyl, $S(O)(C_1-C_4)$haloalkyl, $S(O)_2(C_1-C_4)$haloalkyl, $(C_1-C_4)$alkyl-S$(O)_2NH_2$, and $(C_1-C_4)$haloalkyl-S$(O)_2NH_2$;

(E) $R^5$ is selected from the group consisting of H, F, Cl, Br, I, CN, $NH_2$, $NO_2$, $(C_1-C_4)$alkyl, $(C_3-C_6)$cycloalkyl, $(C_2-C_4)$alkenyl, $(C_3-C_6)$cycloalkenyl, $(C_2-C_4)$alkynyl, $(C_1-C_4)$alkoxy, $(C_1-C_4)$haloalkyl, $(C_3-C_6)$halocycloalkyl, $(C_2-C_4)$haloalkenyl, $(C_3-C_6)$halocycloalkenyl, $(C_1-C_4)$haloalkoxy, $S(C_1-C_4)$alkyl, $S(O)(C_1-C_4)$alkyl, $S(O)_2(C_1-C_4)$alkyl, $S(C_1-C_4)$haloalkyl, $S(O)(C_1-C_4)$haloalkyl, $S(O)_2(C_1-C_4)$haloalkyl, $(C_1-C_4)$alkyl-S$(O)_2NH_2$, and $(C_1-C_4)$haloalkyl-S$(O)_2NH_2$;

(F) $R^6$ is selected from the group consisting of H and $(C_1-C_4)$alkyl;

(G) $R^7$ is selected from the group consisting of H, F, Cl, Br, and I;

(H) $R^8$ is selected from the group consisting of F, Cl, Br, and I;

(I) $R^9$ is selected from the group consisting of H and $(C_1-C_4)$alkyl;

(J) $R^{10}$ is selected from the group consisting of H, $(C_1-C_4)$alkyl, $(C_2-C_4)$alkenyl, $(C_1-C_4)$haloalkyl, $(C_1-C_4)$alkyl$(C_1-C_4)$alkoxy, C(=O)$(C_1-C_4)$alkyl, and $(C_1-C_4)$alkoxyC(=O)$(C_1-C_4)$alkyl;

(K) $R^{11}$ is selected from the group consisting of H, F, Cl, Br, I, CN, $NH_2$, $NO_2$, $(C_1-C_4)$alkyl, $(C_3-C_6)$cycloalkyl, $(C_2-C_4)$alkenyl, $(C_3-C_6)$cycloalkenyl, $(C_2-C_4)$alkynyl, $(C_1-C_4)$alkoxy, $(C_1-C_4)$haloalkyl, $(C_3-C_6)$halocycloalkyl, $(C_2-C_4)$haloalkenyl, $(C_3-C_6)$halocycloalkenyl, $(C_1-C_4)$haloalkoxy, $S(C_1-C_4)$alkyl, $S(O)(C_1-C_4)$alkyl, $S(O)_2(C_1-C_4)$alkyl, $S(C_1-C_4)$haloalkyl, $S(O)(C_1-C_4)$haloalkyl, $S(O)_2(C_1-C_4)$haloalkyl, $(C_1-C_4)$alkyl-S$(O)_2NH_2$, and $(C_1-C_4)$haloalkyl-S$(O)_2NH_2$;

(L) $R^{12}$ is selected from the group consisting of H, F, Cl, Br, I, CN, $NH_2$, $NO_2$, $(C_1-C_4)$alkyl, $(C_3-C_6)$cycloalkyl, $(C_2-C_4)$alkenyl, $(C_3-C_6)$cycloalkenyl, $(C_2-C_4)$alkynyl, $(C_1-C_4)$alkoxy, $(C_1-C_4)$haloalkyl, $(C_3-C_6)$halocycloalkyl, $(C_2-C_4)$haloalkenyl, $(C_3-C_6)$halocycloalkenyl, $(C_1-C_4)$haloalkoxy, $S(C_1-C_4)$alkyl, $S(O)(C_1-C_4)$alkyl, $S(O)_2(C_1-C_4)$alkyl, $S(C_1-C_4)$haloalkyl, $S(O)(C_1-C_4)$haloalkyl, $S(O)_2(C_1-C_4)$haloalkyl, $(C_1-C_4)$alkyl-S$(O)_2NH_2$, and $(C_1-C_4)$haloalkyl-S$(O)_2NH_2$;

(M) $R^{13}$ is selected from the group consisting of H, F, Cl, Br, I, CN, $NH_2$, $NO_2$, $(C_1-C_4)$alkyl, $(C_3-C_6)$cycloalkyl, $(C_2-C_4)$alkenyl, $(C_3-C_6)$cycloalkenyl, $(C_2-C_4)$alkynyl, $(C_1-C_4)$alkoxy, $(C_1-C_4)$haloalkyl, $(C_3-C_6)$halocycloalkyl, $(C_2-C_4)$haloalkenyl, $(C_3-C_6)$halocycloalkenyl, $(C_1-C_4)$haloalkoxy, $S(C_1-C_4)$alkyl, $S(O)(C_1-C_4)$alkyl, $S(O)_2(C_1-C_4)$alkyl, $S(C_1-C_4)$haloalkyl, $S(O)(C_1-C_4)$haloalkyl, $S(O)_2(C_1-C_4)$haloalkyl, $(C_1-C_4)$alkyl-S$(O)_2NH_2$, and $(C_1-C_4)$haloalkyl-S$(O)_2NH_2$;

(N) $R^{14}$ is selected from the group consisting of H, F, Cl, Br, I, CN, $NH_2$, $NO_2$, $(C_1-C_4)$alkyl, $(C_3-C_6)$cycloalkyl, $(C_2-C_4)$alkenyl, $(C_3-C_6)$cycloalkenyl, $(C_2-C_4)$alkynyl, $(C_1-C_4)$alkoxy, $(C_1-C_4)$haloalkyl, $(C_3-C_6)$halocycloalkyl, $(C_2-C_4)$haloalkenyl, $(C_3-C_6)$halocycloalkenyl, $(C_1-C_4)$haloalkoxy, $S(C_1-C_4)$alkyl, $S(O)(C_1-C_4)$alkyl, $S(O)_2(C_1-C_4)$alkyl, $S(C_1-C_4)$haloalkyl, $S(O)(C_1-C_4)$haloalkyl, $S(O)_2(C_1-C_4)$haloalkyl, $(C_1-C_4)$alkyl-S$(O)_2NH_2$, and $(C_1-C_4)$haloalkyl-S$(O)_2NH_2$;

(O) $R^{15}$ is selected from the group consisting of (Q), H, $(C_1-C_4)$alkyl, $(C_2-C_4)$alkenyl, $(C_1-C_4)$haloalkyl, $(C_1-C_4)$alkyl$(C_1-C_4)$alkoxy, C(=O)$(C_1-C_4)$alkyl, and $(C_1-C_4)$alkoxyC(=O)$(C_1-C_4)$alkyl;

(P) $R^{16}$ is selected from the group consisting of (Q), $(C_1-C_8)$alkyl, $(C_1-C_8)$alkyl-O-$(C_1-C_8)$alkyl, $(C_1-C_8)$alkyl$(C_3-C_8)$cycloalkyl, $(C_1-C_8)$alkylphenyl, $(C_2-C_8)$alkenyl, $(C_2-C_8)$alkynyl, $(C_1-C_8)$haloalkyl, $(C_1-C_8)$alkyl-S-$(C_1-C_8)$alkyl, $(C_1-C_8)$alkyl-S(O)-$(C_1-C_8)$alkyl, $(C_1-C_8)$alkyl-S$(O)_2$-$(C_1-C_8)$alkyl, O-phenyl, O-$(C_2-C_8)$alkenyl, O-$(C_1-C_8)$alkyl $(C_3-C_8)$cycloalkyl, O-$(C_1-C_8)$alkylphenyl, $(C_1-C_8)$alkyl-O-$(C_1-C_8)$alkyl$(C_3-C_8)$cycloalkyl, $(C_1-C_8)$alkyl-O-$(C_1-C_8)$haloalkyl, $(C_1-C_8)$alkyl-C(=O)NH-$(C_1-C_8)$haloalkyl, $(C_1-C_8)$alkyl-NHC(O)-$(C_1-C_8)$alkyl, $(C_1-C_8)$alkyl-S-$(C_1-C_8)$haloalkyl, $(C_1-C_8)$alkyl-S(O)-$(C_1-C_8)$haloalkyl, $(C_1-C_8)$alkyl-S$(O)_2$-$(C_1-C_8)$haloalkyl, and $(C_1-C_8)$alkyl-S$(O)_2$-$NH_2$, wherein each alkyl, alkenyl, alkynyl, cycloalkyl, haloalkyl, and phenyl, may be optionally substituted with one or more substituents selected from the group consisting of F, Cl, Br, I, CN, OH, $NH_2$, $NO_2$, $(C_1-C_8)$alkyl, $(C_1-C_8)$alkoxy, $(C_1-C_8)$haloalkyl, N(($C_1-C_8)$alkyl)$_2$, C(O)O$(C_1-C_8)$alkyl, benzothioenyl, 2,3-dihydro-1H-imidazolonyl, furanyl, pyrazolyl, pyridinyl, thiazolyl, and triazolyl;

(Q) $R^{15}$ and $R^{16}$ together can optionally form a 2- to 5-membered saturated or unsaturated, hydrocarbyl link, which may contain one or more heteroatoms selected from the group consisting of nitrogen, sulfur, and oxygen, wherein said hydrocarbyl link may be optionally substituted with one or more substituents selected from the group consisting of F, Cl, Br, I, CN, $NH_2$, and $NO_2$;

(R) $Q^1$ and $Q^2$ are each independently selected from the group consisting of O and S; and N-oxides, agriculturally acceptable acid addition salts, salt derivatives, solvates, ester derivatives, crystal polymorphs, isotopes, resolved stereoisomers, and tautomers, of the molecules of Formula One.

2. A molecule according to claim 1, wherein $R^2$ is selected from the group consisting of H, F, and Cl.

3. A molecule according to claim 1, wherein $R^3$ is selected from the group consisting of H, F, and Cl.

4. A molecule according to claim 1, wherein $R^4$ is F or Cl.

5. A molecule according to claim 1, wherein $R^1$, $R^5$, $R^6$, $R^9$, $R^{10}$, $R^{11}$, $R^{12}$, and $R^{14}$ are each independently H.

6. A molecule according to claim 1, wherein $R^7$ is selected from the group consisting of Cl and Br.

7. A molecule according to claim 1, wherein $R^8$ is selected from the group consisting of Cl and Br.

8. A molecule according to claim 1, wherein $R^{13}$ is selected from the group consisting of H, Cl, and $CF_3$.

9. A molecule according to claim 1, wherein $R^{15}$ is selected from the group consisting of H and $CH_3$.

10. A molecule according to claim 1, wherein $R^{16}$ is selected from the group consisting of $CH_2$, $CH_2CH_2$, $CH_2CH_2CH_2$, $CH_2CH_2CH_2CH_2$, $CH_2CH_2CH_2OCH_2CH_2$, $CH_3$, $CH_2CH_3$, $CH_2CH_2CH_3$, $CH_2CH_2CH_2CH_3$, $CH_2CH_2CH_2CH_2CH_3$, $CH_2CH_2CH_2CH_2CH_2CH_3$, $CH_2CH(CH_3)_2$, $CH_2$cyclopropyl, $CH_2CH_2$cyclopropyl, $CH_2$cyclobutyl, $CH_2$phenyl, $CH_2CH_2$phenyl, $CH_2C\!\!=\!\!CH$, $CH_2C\!\!=\!\!CH$, $CH_2CF_3$, $CH_2CHF_2$, $CH_2CH_2CF_3$, $CH_2CF_2CF_3$, $CH_2CH_2CH_2CF_3$, $CH_2CH_2CF_2CF_3$, $CH_2CF_2CF_2CF_3$, $CH_2CH_2CH_2CH_2F$, $CH_2CH_2SCH_3$, $CH_2CH_2S(O)CH_3$, $CH_2CH_2S(O)_2CH_3$, $C(CH_3)_2CH_2S(O)_2CH_3$, Ophenyl, $OCH_2CH\!\!=\!\!CH_2$, $OCH_2$cyclopropyl, $OCH_2$phenyl, $CH_2CH_2OCH_2$cyclopropyl, $CH_2CH_2CH_2OCH_2CF_3$, $CH_2C(\!\!=\!\!O)NHCH_2CF_3$, or $CH_2CH_2NHC(\!\!=\!\!O)CH_3$, wherein each $CH_2$, $CH_2CH_2$, $CH_2CH_2CH_2$, $CH_2CH_2CH_2CH_2$, cyclopropyl, cyclobutyl, and phenyl, may be optionally substituted with one or more substituents selected from the group consisting of F, Cl, CN, $C(CH_3)_3$, $CF_3$, $OCH_3$, $OCH_2CH_3$, $N(CH_3)_2$, and pyridinyl.

11. A molecule according to claim 1, wherein $R^{15}$ and $R^{16}$ together are —$CH_2CH_2CF_2CH_2$—.

12. A molecule according to claim 1, wherein $Q^1$ and $Q^2$ are O.

13. A molecule according to claim 1, wherein:

(A) $R^1$ is H;
(B) $R^2$ is selected from the group consisting of H and Cl;
(C) $R^3$ is selected from the group consisting of H and Cl;
(D) $R^4$ is Cl;
(E) $R^5$ is H;
(F) $R^6$ is H;
(G) $R^7$ is selected from the group consisting of Cl and Br;
(H) $R^8$ is selected from the group consisting of Cl and Br;
(I) $R^9$ is H;
(J) $R^{10}$ is H;
(K) $R^{11}$ is H;
(L) $R^{12}$ is H;
(M) $R^{13}$ is selected from the group consisting of H, Cl, and $CF_3$;
(N) $R^{14}$ is H;
(O) $R^{15}$ is selected from the group consisting of H and $CH_3$;
(P) $R^{16}$ is selected from the group consisting of $CH_2$, $CH_2CH_2$, $CH_2CH_2CH_2$, $CH_2CH_2CH_2CH_2$, $CH_2CH_2CH_2OCH_2CH_2$, $CH_3$, $CH_2CH_3$, $CH_2CH_2CH_3$, $CH_2CH_2CH_2CH_3$, $CH_2CH_2CH_2CH_2CH_3$, $CH_2CH_2CH_2CH_2CH_2CH_3$, $CH_2CH(CH_3)_2$, $CH_2$cyclopropyl, $CH_2CH_2$cyclopropyl, $CH_2$cyclobutyl, $CH_2$phenyl, $CH_2CH_2$phenyl, $CH_2C\!\!=\!\!CH$, $CH_2C\!\!=\!\!CH$, $CH_2CF_3$, $CH_2CHF_2$, $CH_2CH_2CF_3$, $CH_2CF_2CF_3$, $CH_2CH_2CH_2CF_3$, $CH_2CH_2CF_2CF_3$, $CH_2CF_2CF_2CF_3$, $CH_2CH_2CH_2CH_2F$, $CH_2CH_2SCH_3$, $CH_2CH_2S(O)CH_3$, $CH_2CH_2S(O)_2CH_3$, $C(CH_3)_2CH_2S(O)_2CH_3$, Ophenyl, $OCH_2CH\!\!=\!\!CH_2$, $OCH_2$cyclopropyl, $OCH_2$phenyl, $CH_2CH_2OCH_2$cyclopropyl, $CH_2CH_2CH_2OCH_2CF_3$, $CH_2C(\!\!=\!\!O)NHCH_2CF_3$, and $CH_2CH_2NHC(\!\!=\!\!O)CH_3$, wherein each $CH_2$, $CH_2CH_2$, $CH_2CH_2CH_2$, $CH_2CH_2CH_2CH_2$, cyclopropyl, cyclobutyl, and phenyl, may be optionally substituted with one or more substituents selected from the group consisting of F, Cl, CN, $C(CH_3)_3$, $CF_3$, $OCH_3$, $OCH_2CH_3$, $N(CH_3)_2$, and pyridinyl;

(Q) $R^{15}$ and $R^{16}$ together are a 4-membered saturated, hydrocarbyl link, wherein said hydrocarbyl link is substituted with one or more F; and (R) $Q^1$ and $Q^2$ are O.

14. A composition comprising
(a) a molecule according to claim 1 and
(b) an active ingredient.

15. A composition comprising
(a) a molecule according to claim 13 and
(b) an active ingredient.

16. A process comprising applying to a locus a pesticidally effective amount of a molecule according to claim 1.

17. A process according to claim 16 wherein said pest is a chewing pest.

18. A process according to claim 16 wherein said pest is a sap-feeding pest.

19. A molecule according to claim 1 wherein said molecule is selected from the following

| No. | Structure |
|---|---|
| F1 | ![structure] |

-continued
| No. | Structure |
|---|---|
| F2 | 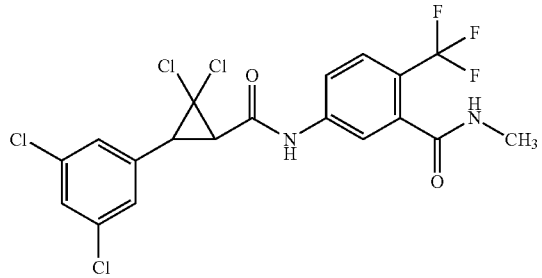 [SMILES: CNC(=O)c1cc(NC(=O)C2C(c3cc(Cl)cc(Cl)c3)C2(Cl)Cl)ccc1C(F)(F)F] |
| F3 | 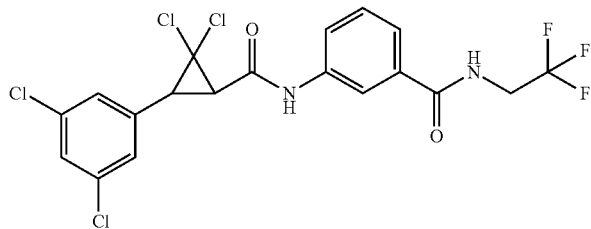 [SMILES: O=C(NCC(F)(F)F)c1cccc(NC(=O)C2C(c3cc(Cl)cc(Cl)c3)C2(Cl)Cl)c1] |
| F4 | 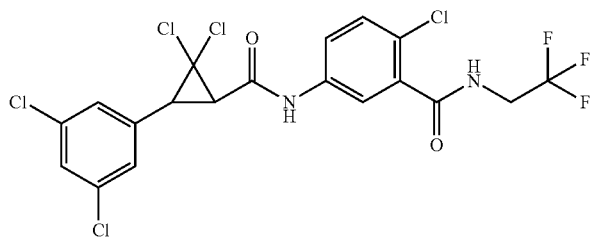 [SMILES: O=C(NCC(F)(F)F)c1cc(NC(=O)C2C(c3cc(Cl)cc(Cl)c3)C2(Cl)Cl)ccc1Cl] |
| F5 | 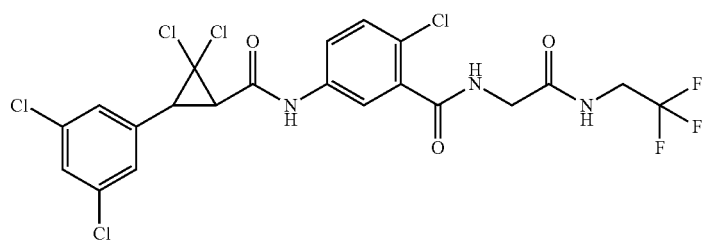 [SMILES: O=C(CNC(=O)c1cc(NC(=O)C2C(c3cc(Cl)cc(Cl)c3)C2(Cl)Cl)ccc1Cl)NCC(F)(F)F] |
| F6 | 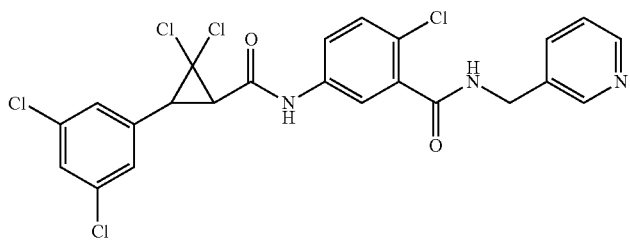 |
| F7 | 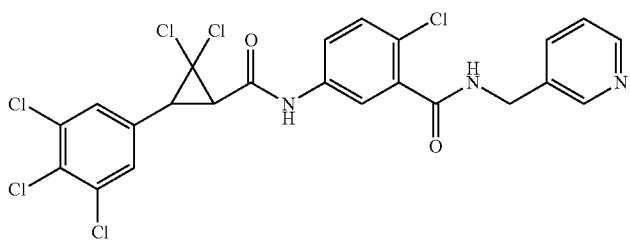 [SMILES: O=C(NCc1cccnc1)c1cc(NC(=O)C2C(c3cc(Cl)c(Cl)c(Cl)c3)C2(Cl)Cl)ccc1Cl] |

| No. | Structure |
|---|---|
| F8 | 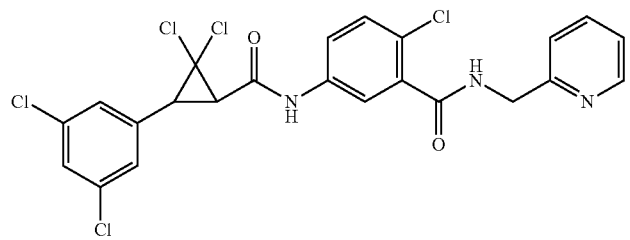 [SMILES: O=C(NCc1ccccn1)c1cc(NC(=O)C2C(c3cc(Cl)cc(Cl)c3)C2(Cl)Cl)ccc1Cl] |
| F9 | 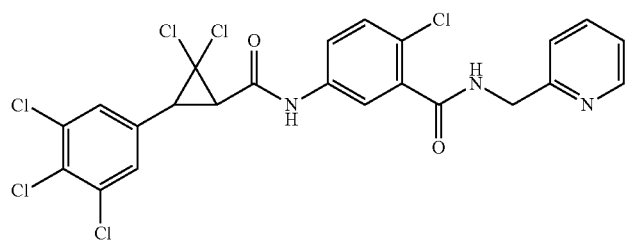 [SMILES: O=C(NCc1ccccn1)c1cc(NC(=O)C2C(c3cc(Cl)c(Cl)c(Cl)c3)C2(Cl)Cl)ccc1Cl] |
| F10 | 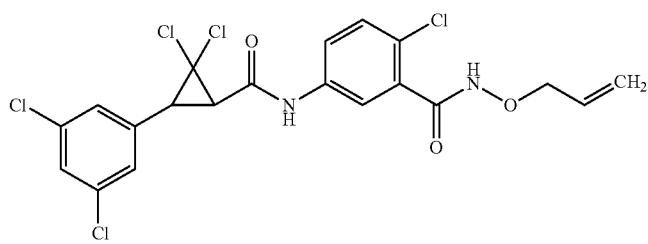 [SMILES: C=CCONC(=O)c1cc(NC(=O)C2C(c3cc(Cl)cc(Cl)c3)C2(Cl)Cl)ccc1Cl] |
| F11 | 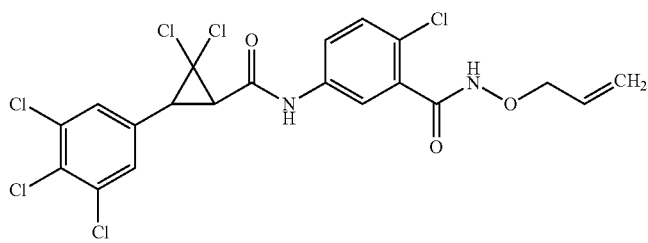 [SMILES: C=CCONC(=O)c1cc(NC(=O)C2C(c3cc(Cl)c(Cl)c(Cl)c3)C2(Cl)Cl)ccc1Cl] |
| F12 | 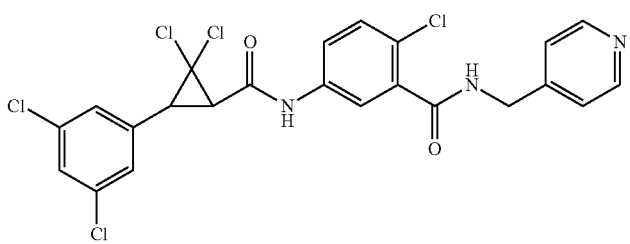 [SMILES: O=C(NCc1ccncc1)c1cc(NC(=O)C2C(c3cc(Cl)cc(Cl)c3)C2(Cl)Cl)ccc1Cl] |
| F13 | 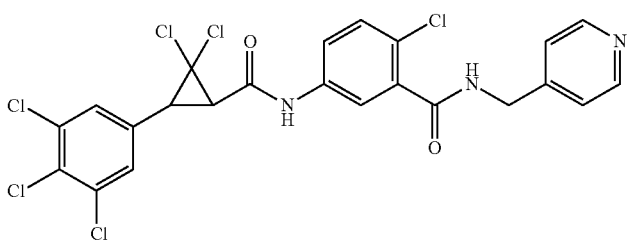 [SMILES: O=C(NCc1ccncc1)c1cc(NC(=O)C2C(c3cc(Cl)c(Cl)c(Cl)c3)C2(Cl)Cl)ccc1Cl] |

| No. | Structure |
|---|---|
| F14 | 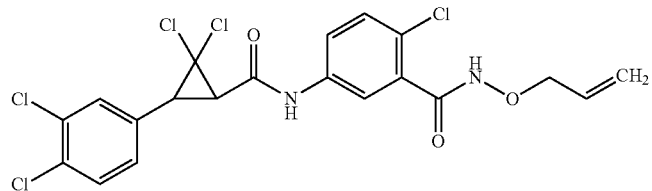 [SMILES: C=CCONC(=O)c1cc(NC(=O)C2C(c3ccc(Cl)c(Cl)c3)C2(Cl)Cl)ccc1Cl] |
| F15 | 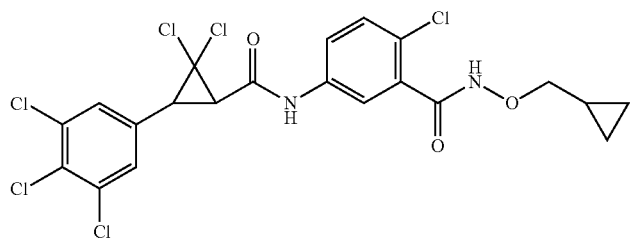 [SMILES: O=C(NOCC1CC1)c1cc(NC(=O)C2C(c3cc(Cl)c(Cl)c(Cl)c3)C2(Cl)Cl)ccc1Cl] |
| F16 | 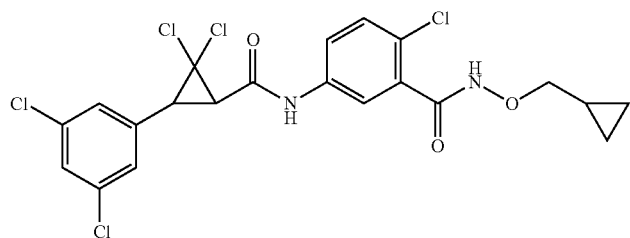 [SMILES: O=C(NOCC1CC1)c1cc(NC(=O)C2C(c3cc(Cl)cc(Cl)c3)C2(Cl)Cl)ccc1Cl] |
| F17 | 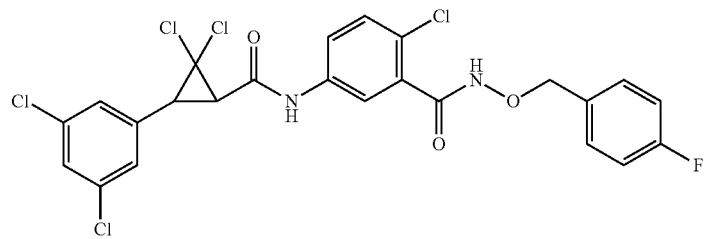 [SMILES: O=C(NOCc1ccc(F)cc1)c1cc(NC(=O)C2C(c3cc(Cl)cc(Cl)c3)C2(Cl)Cl)ccc1Cl] |
| F18 | 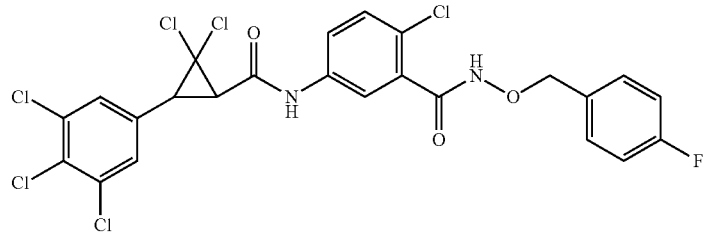 [SMILES: O=C(NOCc1ccc(F)cc1)c1cc(NC(=O)C2C(c3cc(Cl)c(Cl)c(Cl)c3)C2(Cl)Cl)ccc1Cl] |
| F19 | 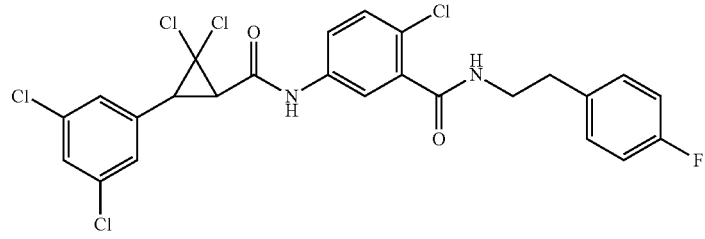 [SMILES: O=C(NCCc1ccc(F)cc1)c1cc(NC(=O)C2C(c3cc(Cl)cc(Cl)c3)C2(Cl)Cl)ccc1Cl] |

-continued
| No. | Structure |
|---|---|
| F20 | 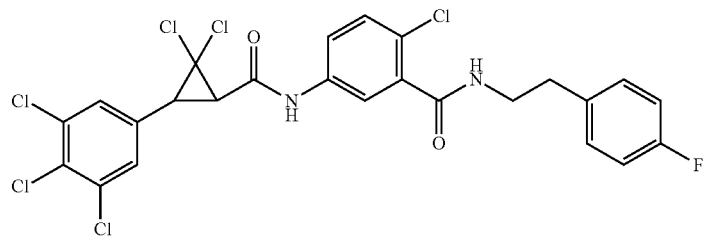 [SMILES: O=C(NCCc1ccc(F)cc1)c1cc(NC(=O)C2C(c3cc(Cl)c(Cl)c(Cl)c3)C2(Cl)Cl)ccc1Cl] |
| F21 | 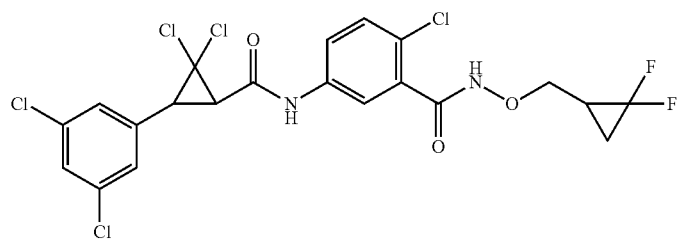 [SMILES: O=C(NOCC1CC1(F)F)c1cc(NC(=O)C2C(c3cc(Cl)cc(Cl)c3)C2(Cl)Cl)ccc1Cl] |
| F22 | 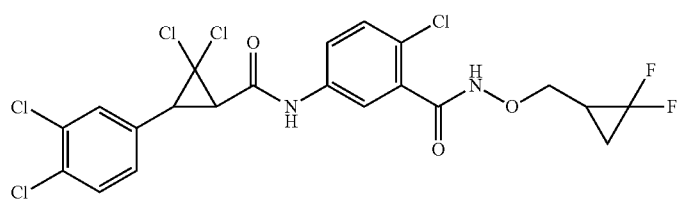 [SMILES: O=C(NOCC1CC1(F)F)c1cc(NC(=O)C2C(c3ccc(Cl)c(Cl)c3)C2(Cl)Cl)ccc1Cl] |
| F23 | 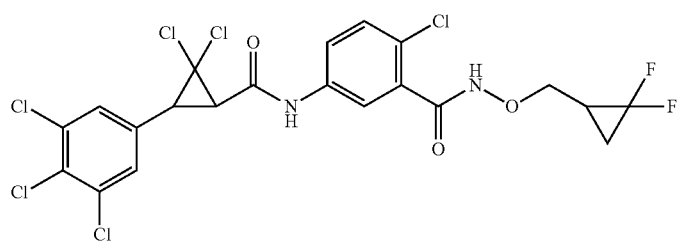 [SMILES: O=C(NOCC1CC1(F)F)c1cc(NC(=O)C2C(c3cc(Cl)c(Cl)c(Cl)c3)C2(Cl)Cl)ccc1Cl] |
| F24 | 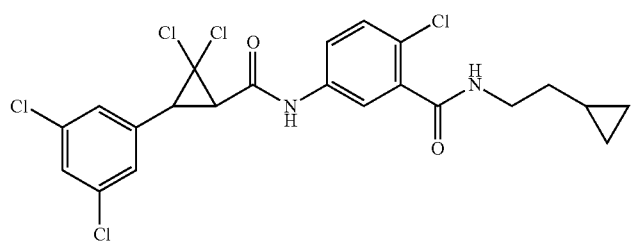 |
| F25 | 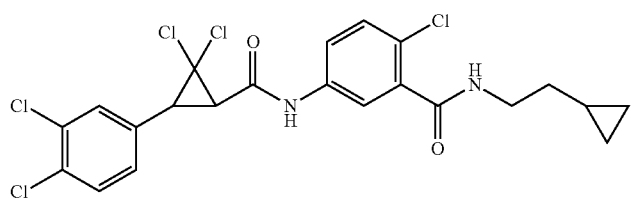 [SMILES: O=C(NCCC1CC1)c1cc(NC(=O)C2C(c3ccc(Cl)c(Cl)c3)C2(Cl)Cl)ccc1Cl] |

-continued
| No. | Structure |
|---|---|
| F26 | 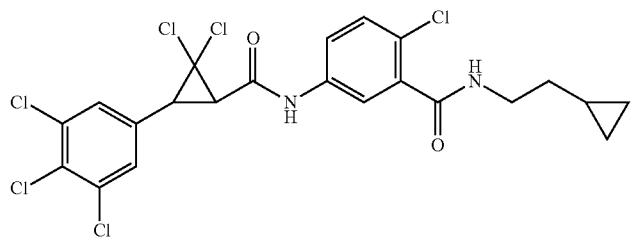 [SMILES: O=C(NCCC1CC1)c1cc(NC(=O)C2C(c3cc(Cl)c(Cl)c(Cl)c3)C2(Cl)Cl)ccc1Cl] |
| F27 | 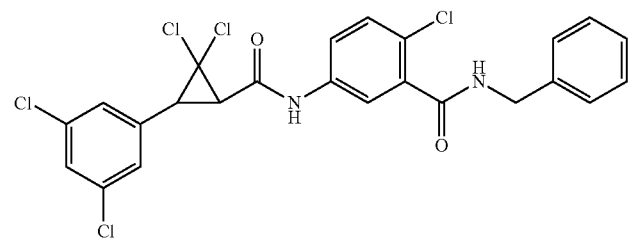 [SMILES: O=C(NCc1ccccc1)c1cc(NC(=O)C2C(c3cc(Cl)cc(Cl)c3)C2(Cl)Cl)ccc1Cl] |
| F28 | 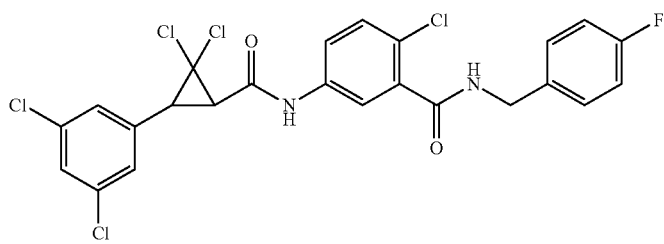 [SMILES: O=C(NCc1ccc(F)cc1)c1cc(NC(=O)C2C(c3cc(Cl)cc(Cl)c3)C2(Cl)Cl)ccc1Cl] |
| F29 | 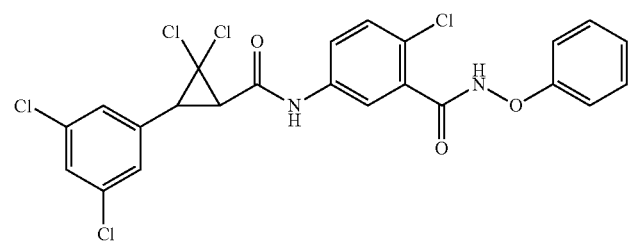 [SMILES: O=C(NOc1ccccc1)c1cc(NC(=O)C2C(c3cc(Cl)cc(Cl)c3)C2(Cl)Cl)ccc1Cl] |
| F30 | 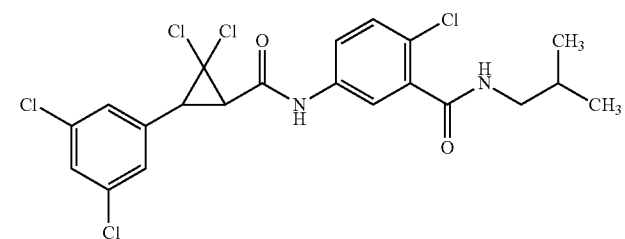 [SMILES: CC(C)CNC(=O)c1cc(NC(=O)C2C(c3cc(Cl)cc(Cl)c3)C2(Cl)Cl)ccc1Cl] |
| F31 | 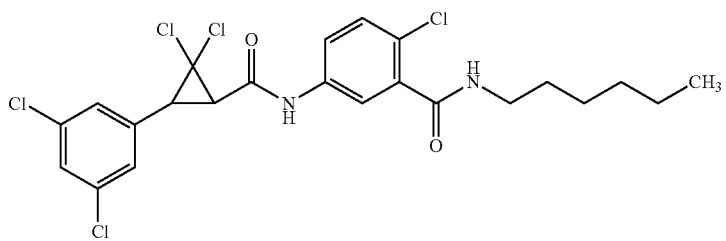 [SMILES: CCCCCCNC(=O)c1cc(NC(=O)C2C(c3cc(Cl)cc(Cl)c3)C2(Cl)Cl)ccc1Cl] |

-continued
| No. | Structure |
|---|---|
| F32 | 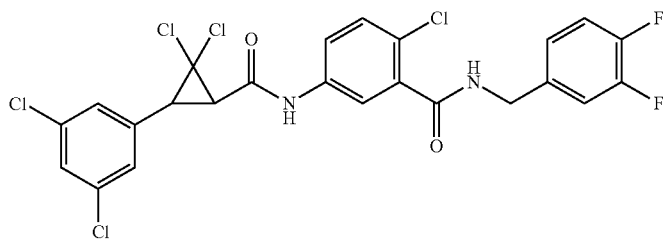 [SMILES: O=C(NCc1ccc(F)c(F)c1)c1cc(NC(=O)C2C(c3cc(Cl)cc(Cl)c3)C2(Cl)Cl)ccc1Cl] |
| F33 | 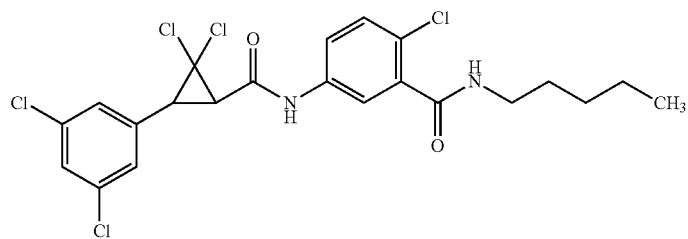 [SMILES: CCCCCNC(=O)c1cc(NC(=O)C2C(c3cc(Cl)cc(Cl)c3)C2(Cl)Cl)ccc1Cl] |
| F34 | 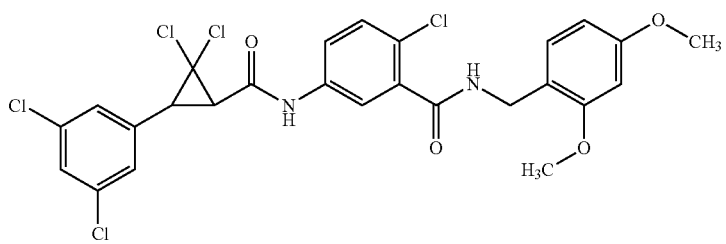 [SMILES: COc1ccc(CNC(=O)c2cc(NC(=O)C3C(c4cc(Cl)cc(Cl)c4)C3(Cl)Cl)ccc2Cl)c(OC)c1] |
| F35 | 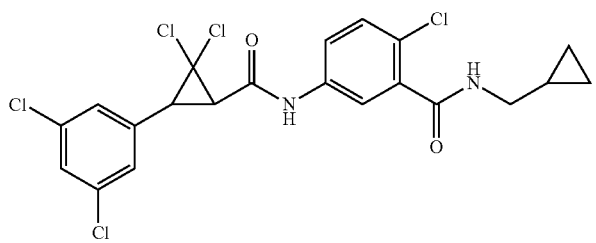 [SMILES: O=C(NCC1CC1)c1cc(NC(=O)C2C(c3cc(Cl)cc(Cl)c3)C2(Cl)Cl)ccc1Cl] |
| F36 | 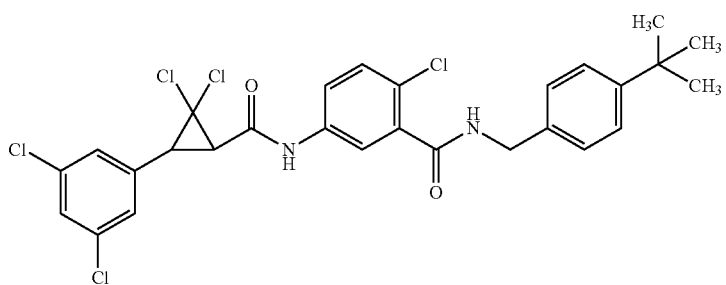 [SMILES: CC(C)(C)c1ccc(CNC(=O)c2cc(NC(=O)C3C(c4cc(Cl)cc(Cl)c4)C3(Cl)Cl)ccc2Cl)cc1] |
| F37 | 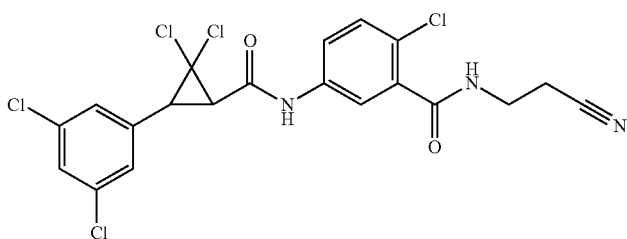 [SMILES: N#CCCNC(=O)c1cc(NC(=O)C2C(c3cc(Cl)cc(Cl)c3)C2(Cl)Cl)ccc1Cl] |

| No. | Structure |
|---|---|
| F38 | 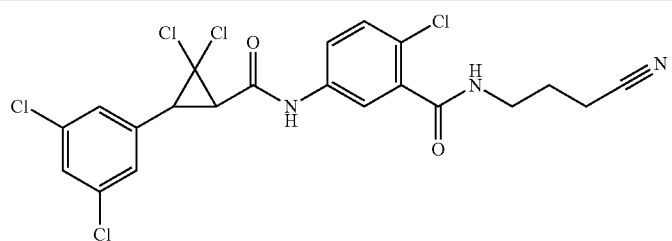 [SMILES: N#CCCCNC(=O)c1cc(NC(=O)C2C(c3cc(Cl)cc(Cl)c3)C2(Cl)Cl)ccc1Cl] |
| F39 | 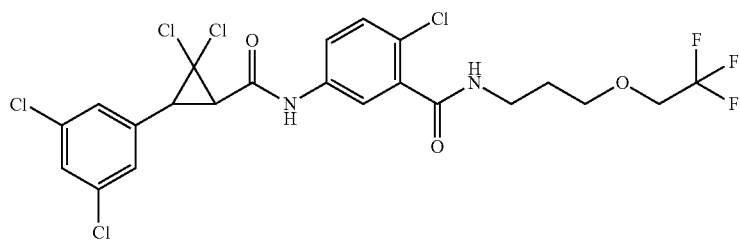 [SMILES: O=C(NCCCOCC(F)(F)F)c1cc(NC(=O)C2C(c3cc(Cl)cc(Cl)c3)C2(Cl)Cl)ccc1Cl] |
| F40 | 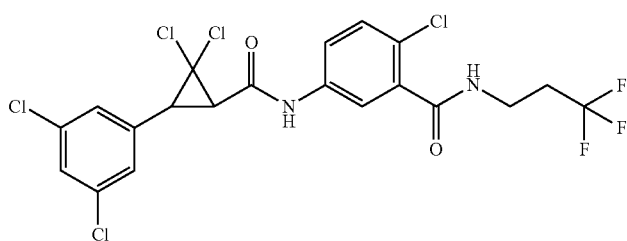 [SMILES: O=C(NCCC(F)(F)F)c1cc(NC(=O)C2C(c3cc(Cl)cc(Cl)c3)C2(Cl)Cl)ccc1Cl] |
| F41 | 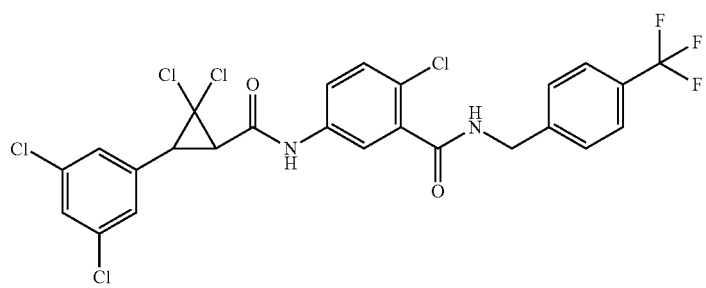 [SMILES: O=C(NCc1ccc(C(F)(F)F)cc1)c1cc(NC(=O)C2C(c3cc(Cl)cc(Cl)c3)C2(Cl)Cl)ccc1Cl] |
| F42 | 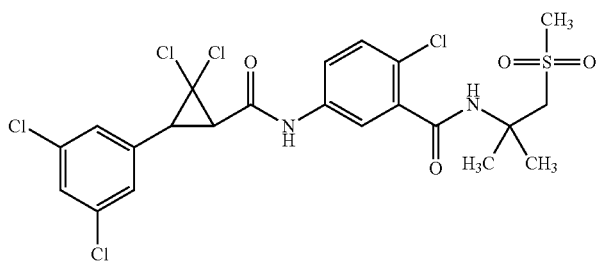 [SMILES: CC(C)(CS(C)(=O)=O)NC(=O)c1cc(NC(=O)C2C(c3cc(Cl)cc(Cl)c3)C2(Cl)Cl)ccc1Cl] |
| F43 | 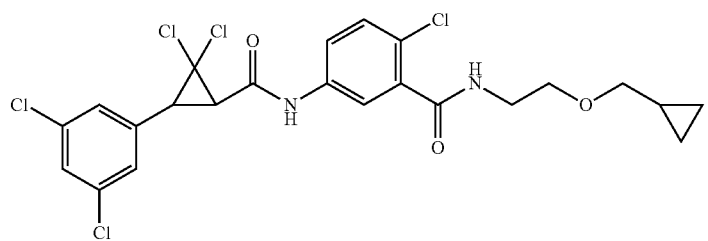 [SMILES: O=C(NCCOCC1CC1)c1cc(NC(=O)C2C(c3cc(Cl)cc(Cl)c3)C2(Cl)Cl)ccc1Cl] |

| No. | Structure |
|---|---|
| F44 | 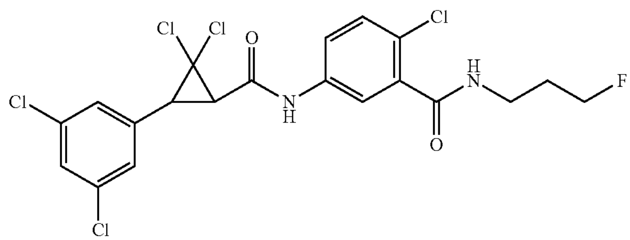 [SMILES: O=C(NCCCF)c1cc(NC(=O)C2C(c3cc(Cl)cc(Cl)c3)C2(Cl)Cl)ccc1Cl] |
| F45 | 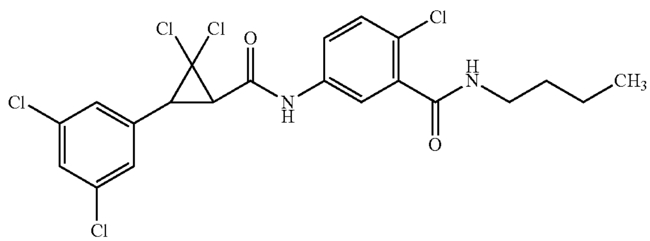 [SMILES: CCCCNC(=O)c1cc(NC(=O)C2C(c3cc(Cl)cc(Cl)c3)C2(Cl)Cl)ccc1Cl] |
| F46 | 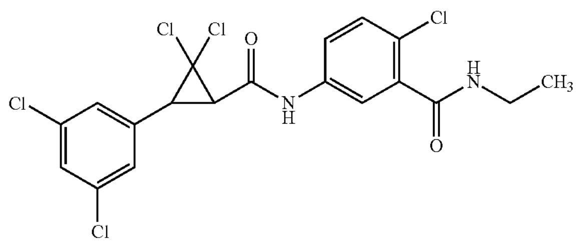 [SMILES: CCNC(=O)c1cc(NC(=O)C2C(c3cc(Cl)cc(Cl)c3)C2(Cl)Cl)ccc1Cl] |
| F47 | 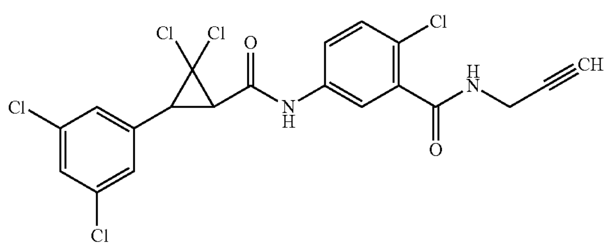 [SMILES: C#CCNC(=O)c1cc(NC(=O)C2C(c3cc(Cl)cc(Cl)c3)C2(Cl)Cl)ccc1Cl] |
| F48 | 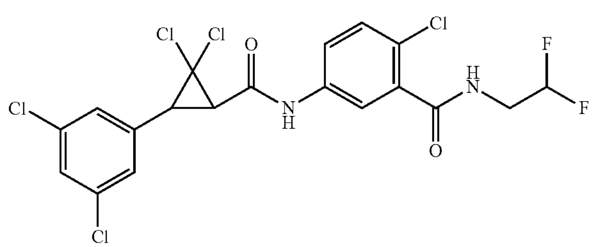 [SMILES: O=C(NCC(F)F)c1cc(NC(=O)C2C(c3cc(Cl)cc(Cl)c3)C2(Cl)Cl)ccc1Cl] |
| F49 | 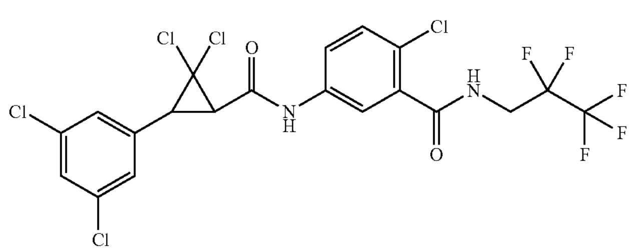 [SMILES: O=C(NCC(F)(F)C(F)(F)F)c1cc(NC(=O)C2C(c3cc(Cl)cc(Cl)c3)C2(Cl)Cl)ccc1Cl] |

-continued

| No. | Structure |
|---|---|
| F50 | 2-[2,2-dichloro-3-(3,5-dichlorophenyl)cyclopropanecarboxamido]-6-chloro-N-(4-(dimethylamino)butyl)benzamide |
| F51 | 2-[2,2-dichloro-3-(3,5-dichlorophenyl)cyclopropanecarboxamido]-6-chloro-N-(2-chloroethyl)benzamide |
| F52 | 2-[2,2-dichloro-3-(3,5-dichlorophenyl)cyclopropanecarboxamido]-6-chloro-N-(2-(methylthio)ethyl)benzamide |
| F53 | 2-[2,2-dichloro-3-(3,5-dichlorophenyl)cyclopropanecarboxamido]-6-chloro-N-(2-methoxyethyl)benzamide |
| F54 | 2-[2,2-dichloro-3-(3,5-dichlorophenyl)cyclopropanecarboxamido]-6-chloro-N-(2-ethoxyethyl)benzamide |
| F55 | 2-[2,2-dichloro-3-(3,5-dichlorophenyl)cyclopropanecarboxamido]-6-chloro-N-(2-acetamidoethyl)benzamide |

-continued
| No. | Structure |
|---|---|
| F56 | 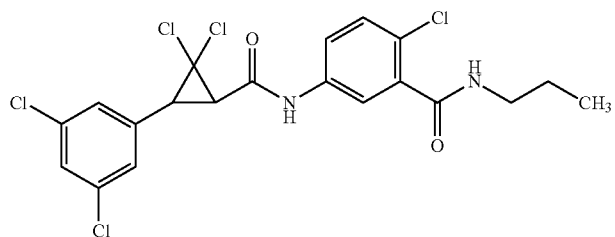 [SMILES: CCCNC(=O)c1cc(NC(=O)C2C(c3cc(Cl)cc(Cl)c3)C2(Cl)Cl)ccc1Cl] |
| F57 | 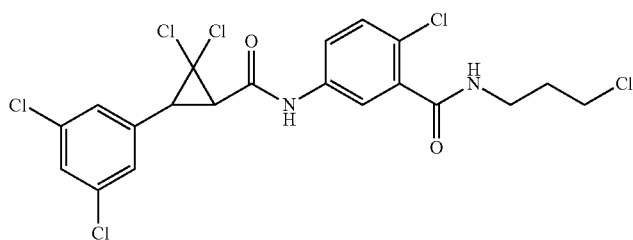 [SMILES: O=C(NCCCCl)c1cc(NC(=O)C2C(c3cc(Cl)cc(Cl)c3)C2(Cl)Cl)ccc1Cl] |
| F58 | 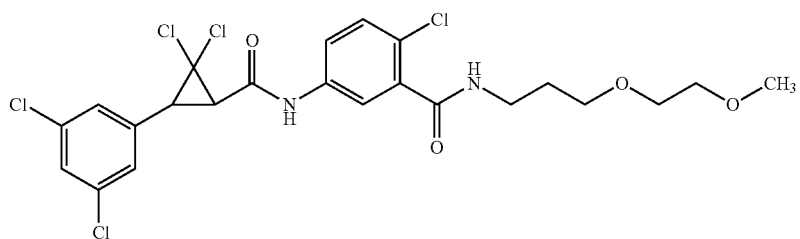 [SMILES: COCCOCCCNC(=O)c1cc(NC(=O)C2C(c3cc(Cl)cc(Cl)c3)C2(Cl)Cl)ccc1Cl] |
| F59 | 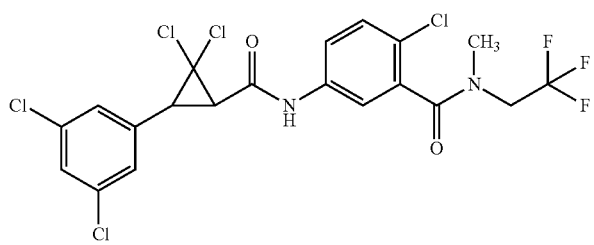 [SMILES: CN(CC(F)(F)F)C(=O)c1cc(NC(=O)C2C(c3cc(Cl)cc(Cl)c3)C2(Cl)Cl)ccc1Cl] |
| F60 | 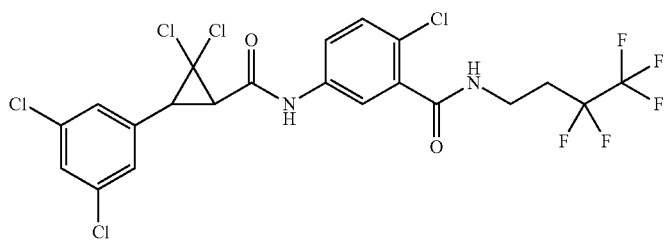 [SMILES: O=C(NCCC(F)(F)C(F)(F)F)c1cc(NC(=O)C2C(c3cc(Cl)cc(Cl)c3)C2(Cl)Cl)ccc1Cl] |
| F61 | 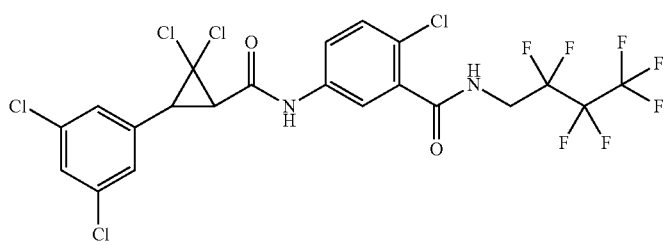 [SMILES: O=C(NCC(F)(F)C(F)(F)C(F)(F)F)c1cc(NC(=O)C2C(c3cc(Cl)cc(Cl)c3)C2(Cl)Cl)ccc1Cl] |

-continued
| No. | Structure |
|---|---|
| F62 | 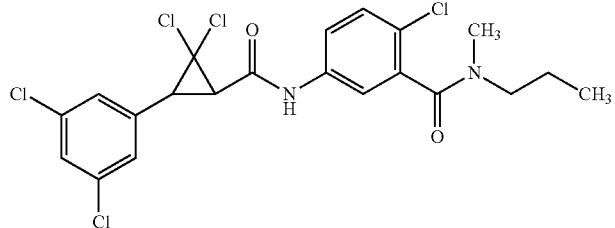 [SMILES: CCCN(C)C(=O)c1cc(NC(=O)C2C(c3cc(Cl)cc(Cl)c3)C2(Cl)Cl)ccc1Cl] |
| F63 | 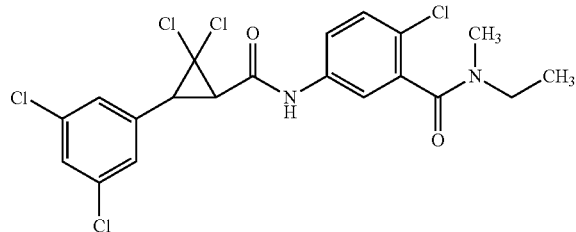 |
| F64 | 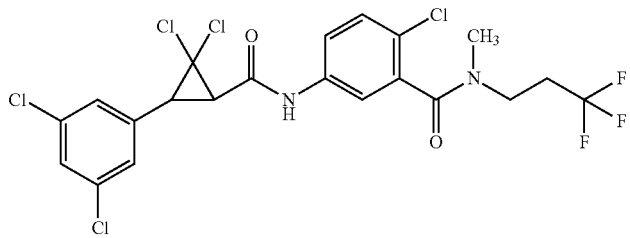 [SMILES: CN(CCC(F)(F)F)C(=O)c1cc(NC(=O)C2C(c3cc(Cl)cc(Cl)c3)C2(Cl)Cl)ccc1Cl] |
| F65 | 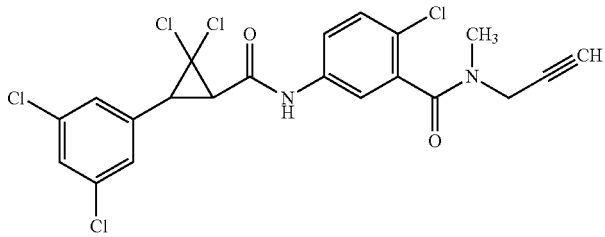 [SMILES: C#CCN(C)C(=O)c1cc(NC(=O)C2C(c3cc(Cl)cc(Cl)c3)C2(Cl)Cl)ccc1Cl] |
| F66 | 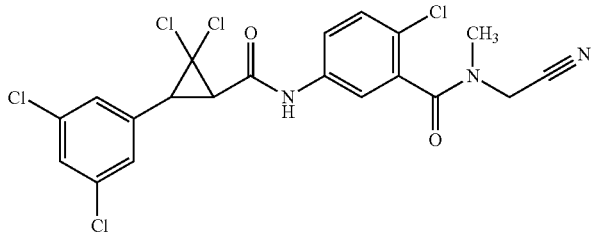 [SMILES: CN(CC#N)C(=O)c1cc(NC(=O)C2C(c3cc(Cl)cc(Cl)c3)C2(Cl)Cl)ccc1Cl] |
| F67 | 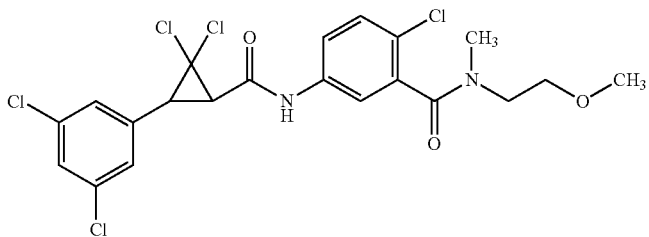 |

-continued
| No. | Structure |
|---|---|
| F68 | 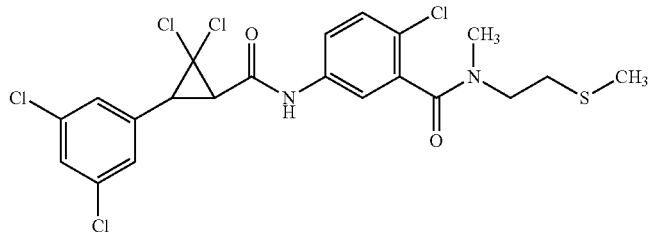 [SMILES: CSCCN(C)C(=O)c1cc(NC(=O)C2C(c3cc(Cl)cc(Cl)c3)C2(Cl)Cl)ccc1Cl] |
| F69 | 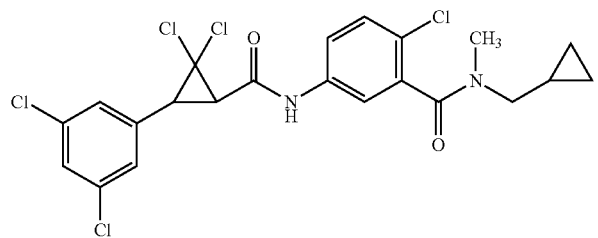 [SMILES: CN(CC1CC1)C(=O)c1cc(NC(=O)C2C(c3cc(Cl)cc(Cl)c3)C2(Cl)Cl)ccc1Cl] |
| F70 | 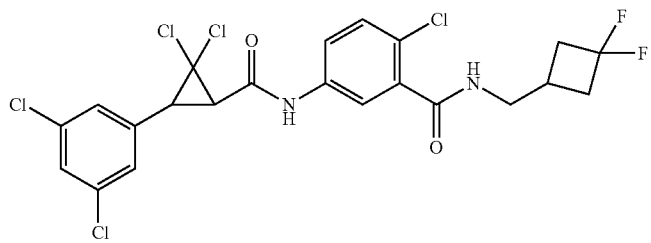 [SMILES: O=C(NCC1CC(F)(F)C1)c1cc(NC(=O)C2C(c3cc(Cl)cc(Cl)c3)C2(Cl)Cl)ccc1Cl] |
| F71 | 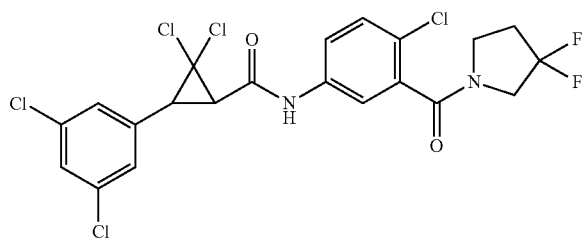 [SMILES: O=C(Nc1ccc(Cl)c(C(=O)N2CCC(F)(F)C2)c1)C1C(c2cc(Cl)cc(Cl)c2)C1(Cl)Cl] |
| F72 | 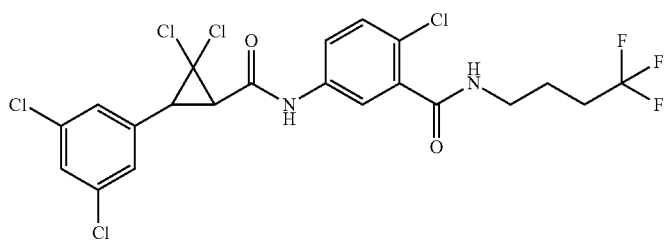 [SMILES: O=C(NCCCC(F)(F)F)c1cc(NC(=O)C2C(c3cc(Cl)cc(Cl)c3)C2(Cl)Cl)ccc1Cl] |
| F73 | 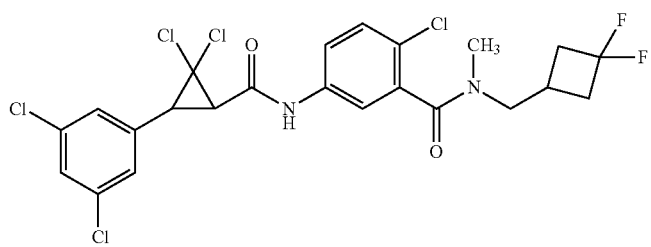 [SMILES: CN(CC1CC(F)(F)C1)C(=O)c1cc(NC(=O)C2C(c3cc(Cl)cc(Cl)c3)C2(Cl)Cl)ccc1Cl] |

-continued
| No. | Structure |
|---|---|
| F74 | 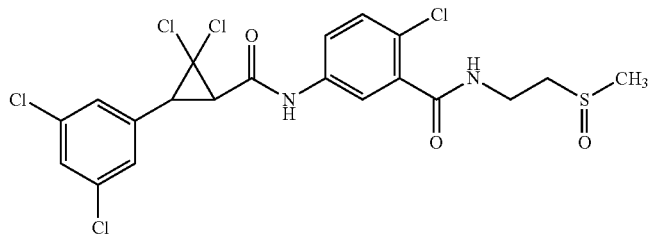 [SMILES: CS(=O)CCNC(=O)c1cc(NC(=O)C2C(c3cc(Cl)cc(Cl)c3)C2(Cl)Cl)ccc1Cl] |
| F75 | 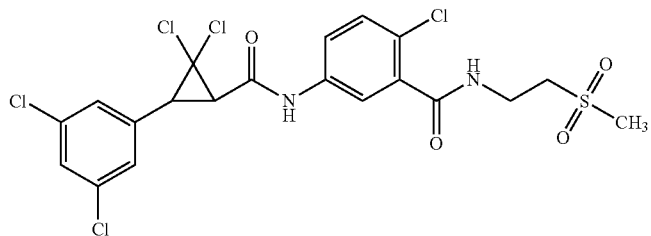 [SMILES: CS(=O)(=O)CCNC(=O)c1cc(NC(=O)C2C(c3cc(Cl)cc(Cl)c3)C2(Cl)Cl)ccc1Cl] |
| F78 | 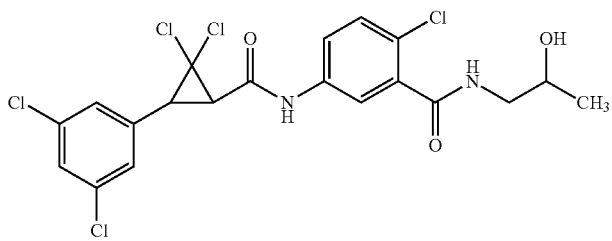 [SMILES: CC(O)CNC(=O)c1cc(NC(=O)C2C(c3cc(Cl)cc(Cl)c3)C2(Cl)Cl)ccc1Cl] |
| F79 | 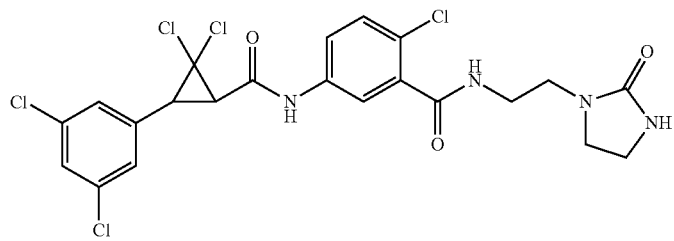 [SMILES: O=C(NCCN1CCNC1=O)c1cc(NC(=O)C2C(c3cc(Cl)cc(Cl)c3)C2(Cl)Cl)ccc1Cl] |
| F84 | 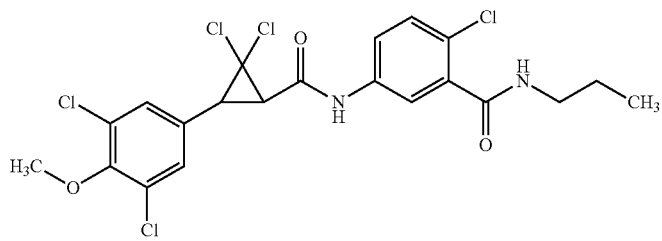 [SMILES: CCCNC(=O)c1cc(NC(=O)C2C(c3cc(Cl)c(OC)c(Cl)c3)C2(Cl)Cl)ccc1Cl] |
| F85 | 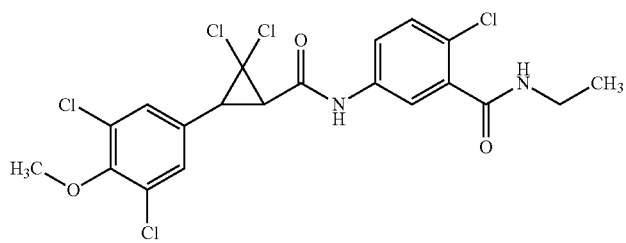 [SMILES: CCNC(=O)c1cc(NC(=O)C2C(c3cc(Cl)c(OC)c(Cl)c3)C2(Cl)Cl)ccc1Cl] |

| No. | Structure |
|---|---|
| F86 | 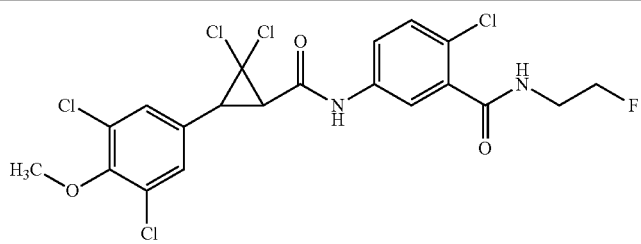 [SMILES: COc1c(Cl)cc(C2C(C(=O)Nc3ccc(Cl)c(C(=O)NCCF)c3)C2(Cl)Cl)cc1Cl] |
| F87 | 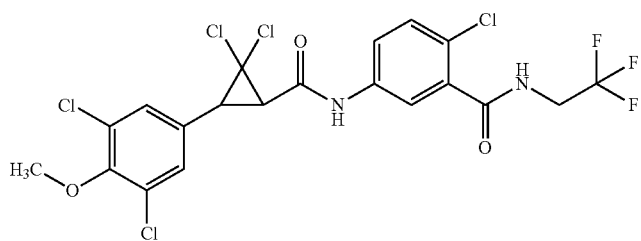 [SMILES: COc1c(Cl)cc(C2C(C(=O)Nc3ccc(Cl)c(C(=O)NCC(F)(F)F)c3)C2(Cl)Cl)cc1Cl] |
| F88 | 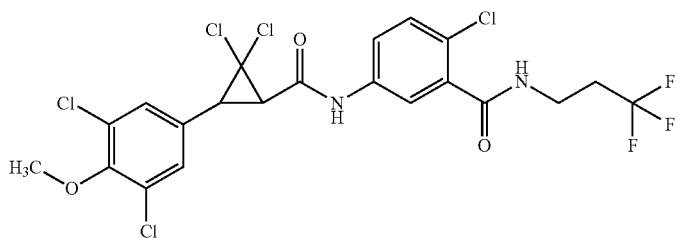 [SMILES: COc1c(Cl)cc(C2C(C(=O)Nc3ccc(Cl)c(C(=O)NCCC(F)(F)F)c3)C2(Cl)Cl)cc1Cl] |
| F91 | 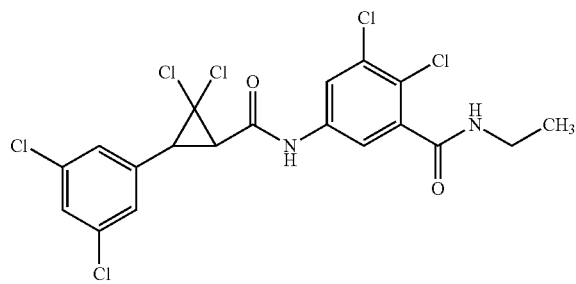 [SMILES: CCNC(=O)c1cc(NC(=O)C2C(c3cc(Cl)cc(Cl)c3)C2(Cl)Cl)cc(Cl)c1Cl] |
| F92 | 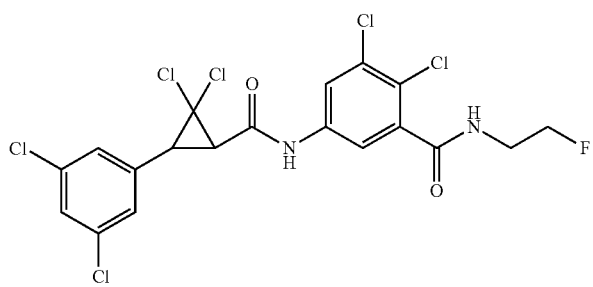 [SMILES: O=C(NCCF)c1cc(NC(=O)C2C(c3cc(Cl)cc(Cl)c3)C2(Cl)Cl)cc(Cl)c1Cl] |
| F93 | 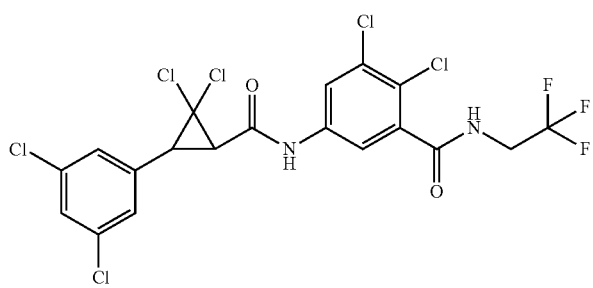 [SMILES: O=C(NCC(F)(F)F)c1cc(NC(=O)C2C(c3cc(Cl)cc(Cl)c3)C2(Cl)Cl)cc(Cl)c1Cl] |

| No. | Structure |
|---|---|
| F94 | 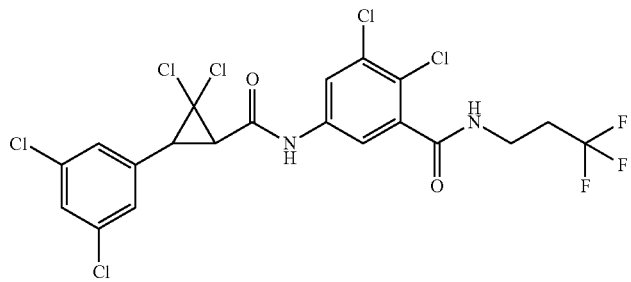 [SMILES: O=C(NCCC(F)(F)F)c1cc(NC(=O)C2C(c3cc(Cl)cc(Cl)c3)C2(Cl)Cl)cc(Cl)c1Cl] |
| F95 | 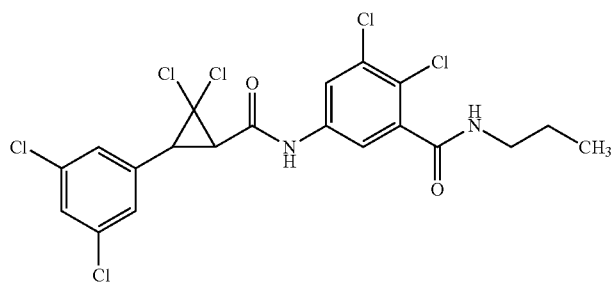 [SMILES: CCCNC(=O)c1cc(NC(=O)C2C(c3cc(Cl)cc(Cl)c3)C2(Cl)Cl)cc(Cl)c1Cl] |
| F96 | 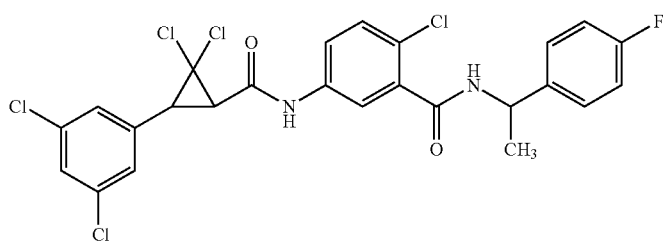 [SMILES: CC(NC(=O)c1cc(NC(=O)C2C(c3cc(Cl)cc(Cl)c3)C2(Cl)Cl)ccc1Cl)c1ccc(F)cc1] |
| F97 | 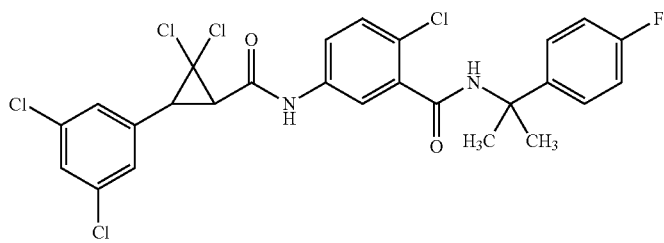 [SMILES: CC(C)(NC(=O)c1cc(NC(=O)C2C(c3cc(Cl)cc(Cl)c3)C2(Cl)Cl)ccc1Cl)c1ccc(F)cc1] |
| F98 | 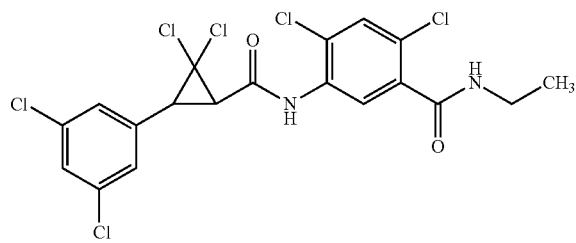 [SMILES: CCNC(=O)c1cc(NC(=O)C2C(c3cc(Cl)cc(Cl)c3)C2(Cl)Cl)c(Cl)cc1Cl] |
| F99 | 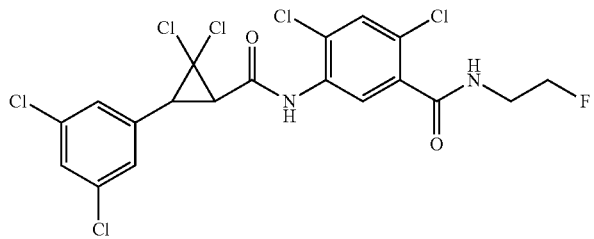 [SMILES: O=C(NCCF)c1cc(NC(=O)C2C(c3cc(Cl)cc(Cl)c3)C2(Cl)Cl)c(Cl)cc1Cl] |

| No. | Structure |
|---|---|
| F100 | 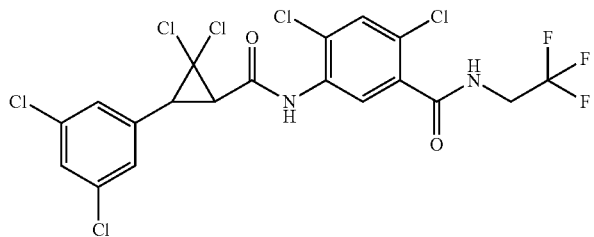 [SMILES: O=C(NCC(F)(F)F)c1cc(NC(=O)C2C(c3cc(Cl)cc(Cl)c3)C2(Cl)Cl)c(Cl)cc1Cl] |
| F102 | 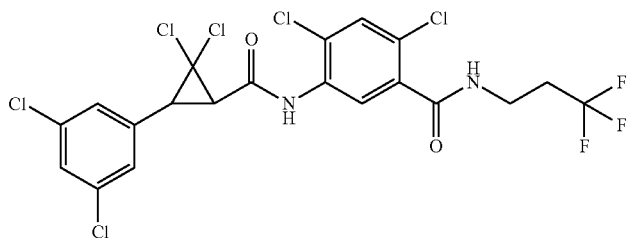 [SMILES: O=C(NCCC(F)(F)F)c1cc(NC(=O)C2C(c3cc(Cl)cc(Cl)c3)C2(Cl)Cl)c(Cl)cc1Cl] |
| F103 | 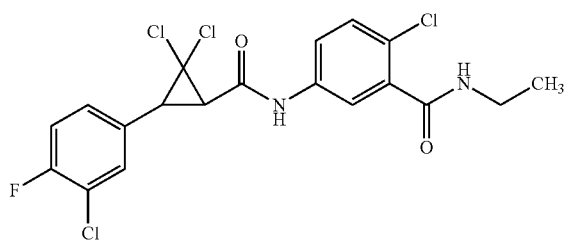 [SMILES: CCNC(=O)c1cc(NC(=O)C2C(c3ccc(F)c(Cl)c3)C2(Cl)Cl)ccc1Cl] |
| F104 | 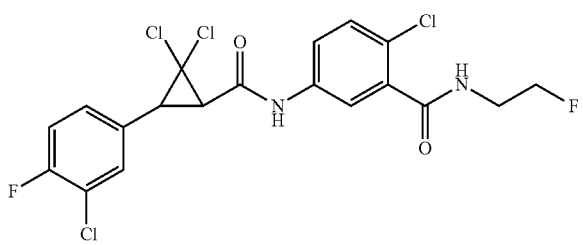 |
| F105 | 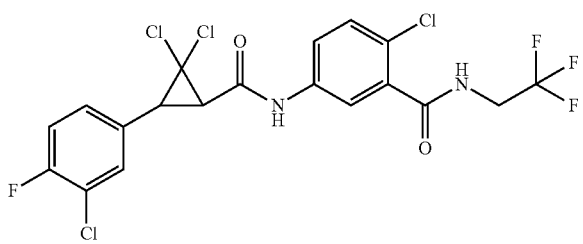 [SMILES: O=C(NCC(F)(F)F)c1cc(NC(=O)C2C(c3ccc(F)c(Cl)c3)C2(Cl)Cl)ccc1Cl] |
| F106 | 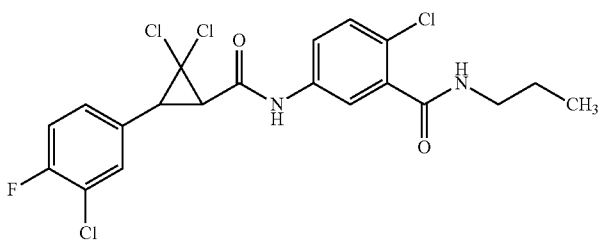 [SMILES: CCCNC(=O)c1cc(NC(=O)C2C(c3ccc(F)c(Cl)c3)C2(Cl)Cl)ccc1Cl] |

-continued
| No. | Structure |
|---|---|
| F107 | 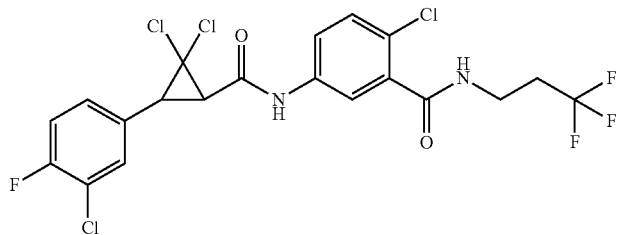 [SMILES: O=C(NCCC(F)(F)F)c1cc(NC(=O)C2C(c3ccc(F)c(Cl)c3)C2(Cl)Cl)ccc1Cl] |
| F108 | 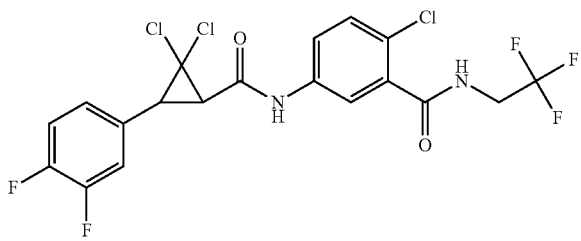 |
| F109 | 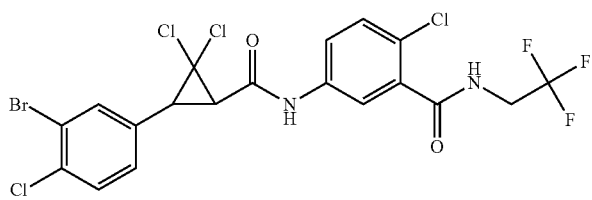 |
| F111 | 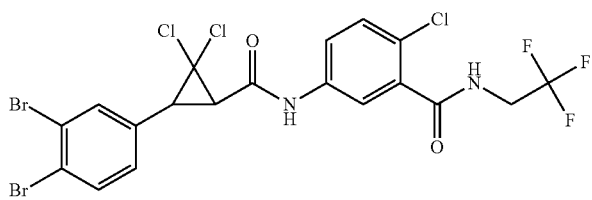 [SMILES: O=C(NCC(F)(F)F)c1cc(NC(=O)C2C(c3ccc(Cl)c(Br)c3)C2(Cl)Cl)ccc1Cl] |
| F112 | 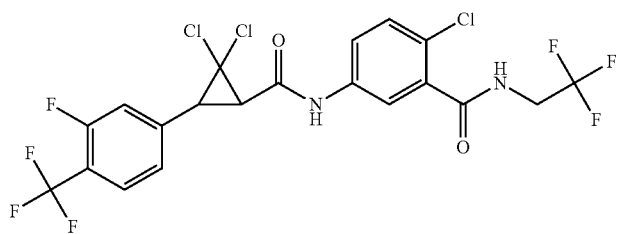 [SMILES: O=C(NCC(F)(F)F)c1cc(NC(=O)C2C(c3ccc(C(F)(F)F)c(F)c3)C2(Cl)Cl)ccc1Cl] |
| F113 | 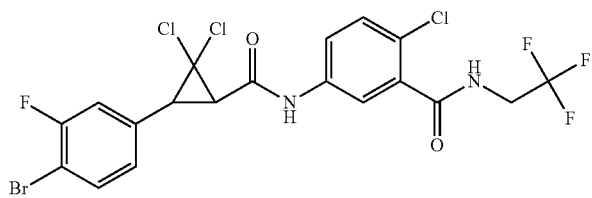 |
| F114 | 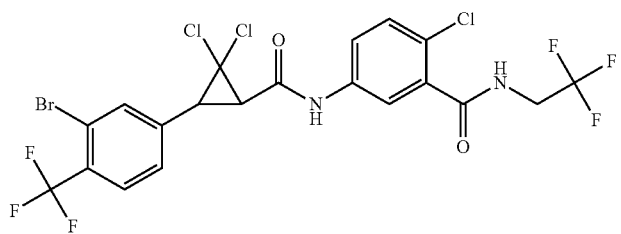 [SMILES: O=C(NCC(F)(F)F)c1cc(NC(=O)C2C(c3ccc(C(F)(F)F)c(Br)c3)C2(Cl)Cl)ccc1Cl] |

-continued
| No. | Structure |
|---|---|
| F115 | 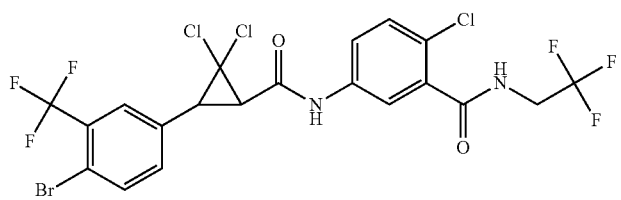 [SMILES: O=C(NCC(F)(F)F)c1cc(NC(=O)C2C(c3ccc(Br)c(C(F)(F)F)c3)C2(Cl)Cl)ccc1Cl] |
| F116 | 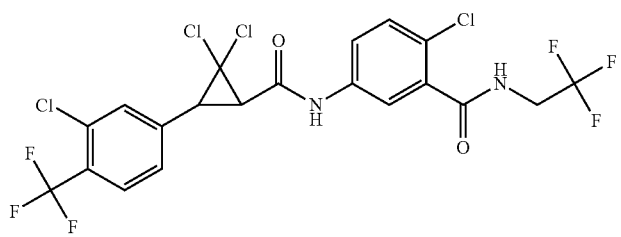 [SMILES: O=C(NCC(F)(F)F)c1cc(NC(=O)C2C(c3ccc(C(F)(F)F)c(Cl)c3)C2(Cl)Cl)ccc1Cl] |
| F117 | 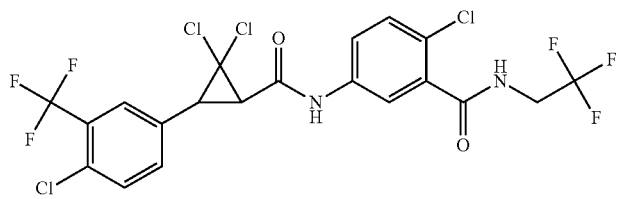 [SMILES: O=C(NCC(F)(F)F)c1cc(NC(=O)C2C(c3ccc(Cl)c(C(F)(F)F)c3)C2(Cl)Cl)ccc1Cl] |
| F118 | 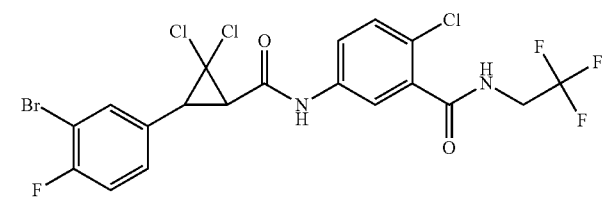 |
| F119 | 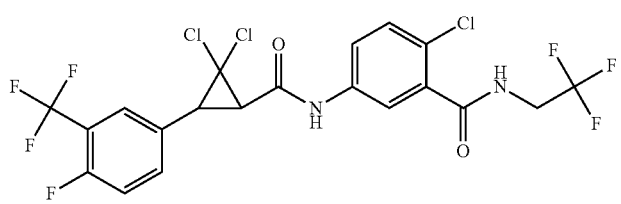 [SMILES: O=C(NCC(F)(F)F)c1cc(NC(=O)C2C(c3ccc(F)c(C(F)(F)F)c3)C2(Cl)Cl)ccc1Cl] |
| F120 | 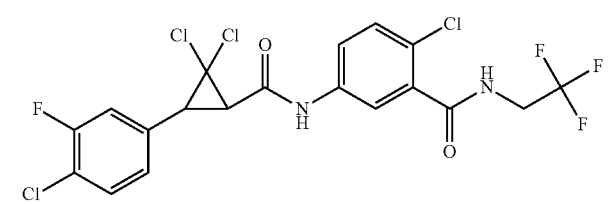 [SMILES: O=C(NCC(F)(F)F)c1cc(NC(=O)C2C(c3ccc(Cl)c(F)c3)C2(Cl)Cl)ccc1Cl] |
| F121 | 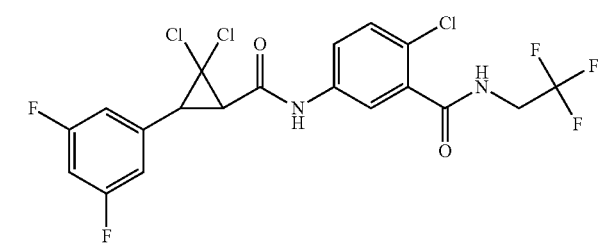 |

| No. | Structure |
|---|---|
| F122 | 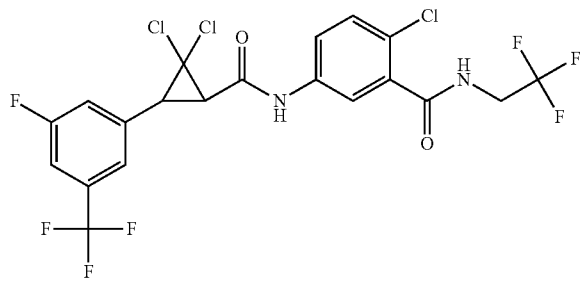 |
| F123 | 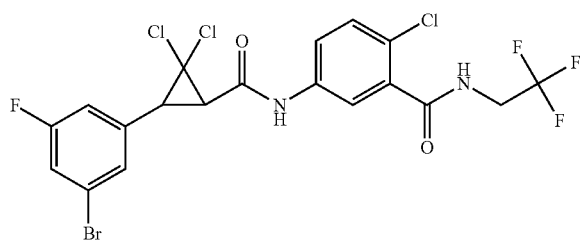 |
| F124 | 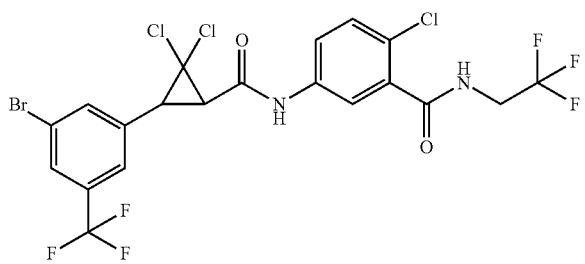 [SMILES: O=C(NCC(F)(F)F)c1cc(NC(=O)C2C(c3cc(Br)cc(C(F)(F)F)c3)C2(Cl)Cl)ccc1Cl] |
| F125 | 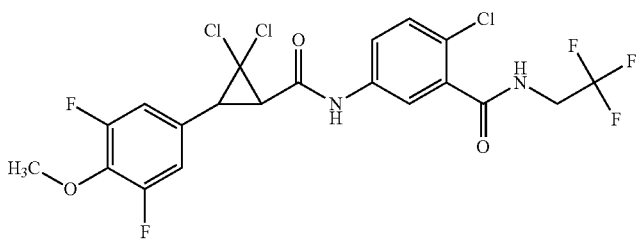 [SMILES: COc1c(F)cc(C2C(C(=O)Nc3ccc(Cl)c(C(=O)NCC(F)(F)F)c3)C2(Cl)Cl)cc1F] |
| F126 | 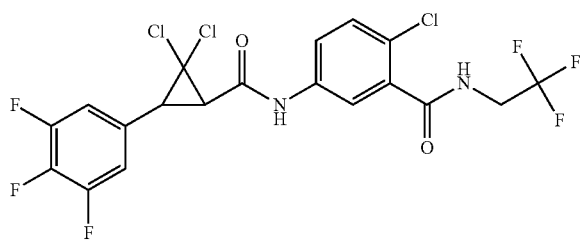 |
| F127 | 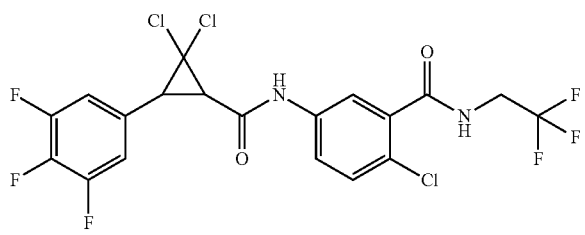 [SMILES: O=C(NCC(F)(F)F)c1cc(NC(=O)C2C(c3cc(F)c(F)c(F)c3)C2(Cl)Cl)ccc1Cl] |

| No. | Structure |
|---|---|
| F128 | 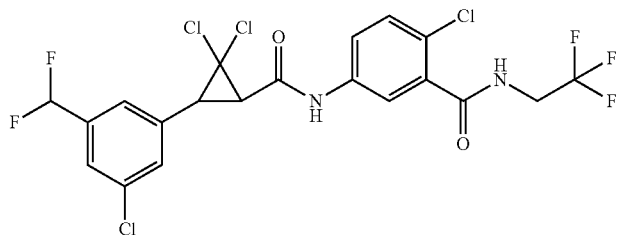 |
| F129 | 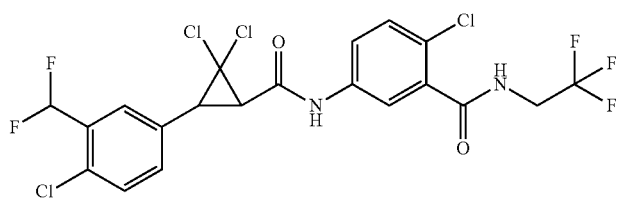 [SMILES: O=C(NCC(F)(F)F)c1cc(NC(=O)C2C(c3ccc(Cl)c(C(F)F)c3)C2(Cl)Cl)ccc1Cl] |
| F130 | 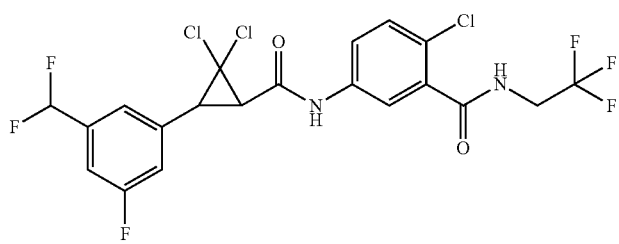 |
| F131 | 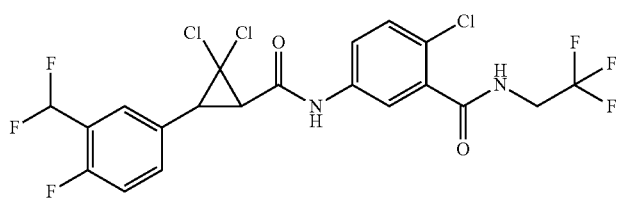 |
| F132 | 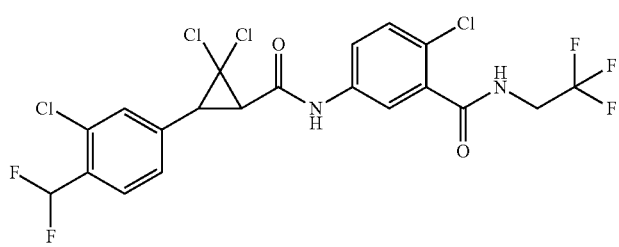 |
| F133 | 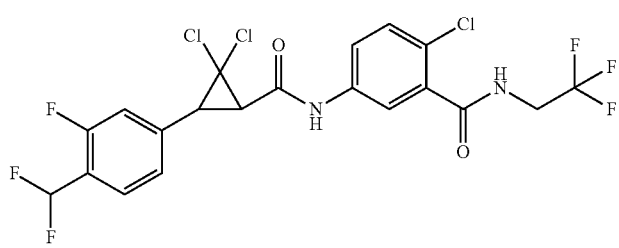 [SMILES: O=C(NCC(F)(F)F)c1cc(NC(=O)C2C(c3ccc(C(F)F)c(F)c3)C2(Cl)Cl)ccc1Cl] |
| F134 | 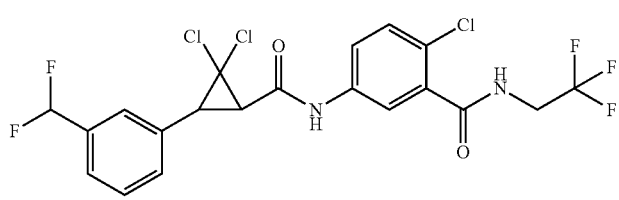 [SMILES: O=C(NCC(F)(F)F)c1cc(NC(=O)C2C(c3cccc(C(F)F)c3)C2(Cl)Cl)ccc1Cl] |

| No. | Structure |
|---|---|
| F135 | 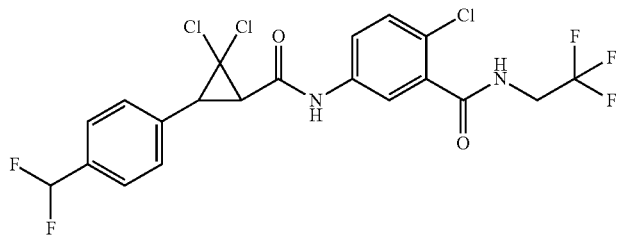 |
| PF1 | 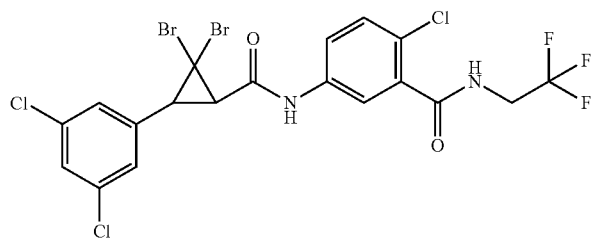 [SMILES: O=C(NCC(F)(F)F)c1cc(NC(=O)C2C(c3cc(Cl)cc(Cl)c3)C2(Br)Br)ccc1Cl] |
| PF2 | 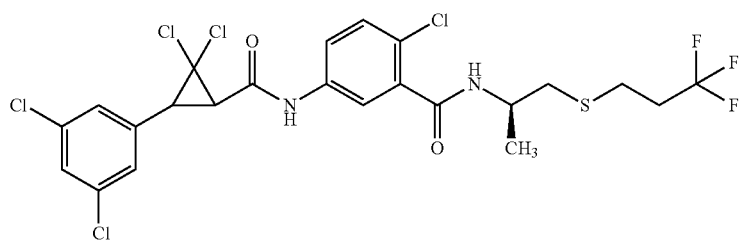 [SMILES: C[C@H](CSCCC(F)(F)F)NC(=O)c1cc(NC(=O)C2C(c3cc(Cl)cc(Cl)c3)C2(Cl)Cl)ccc1Cl] |
| PF3 | 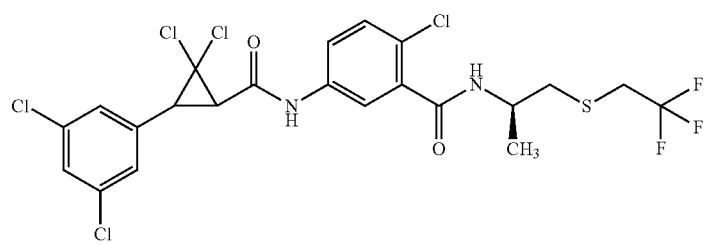 [SMILES: C[C@H](CSCC(F)(F)F)NC(=O)c1cc(NC(=O)C2C(c3cc(Cl)cc(Cl)c3)C2(Cl)Cl)ccc1Cl] |
| PF4 | 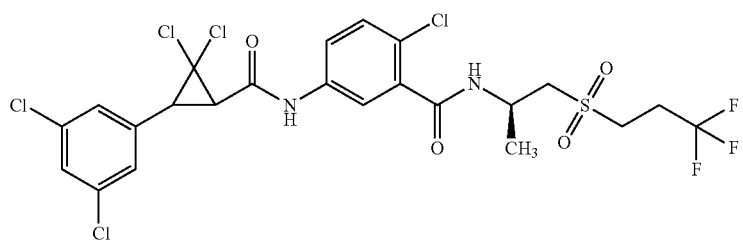 [SMILES: C[C@H](CS(=O)(=O)CCC(F)(F)F)NC(=O)c1cc(NC(=O)C2C(c3cc(Cl)cc(Cl)c3)C2(Cl)Cl)ccc1Cl] |
| PF5 | 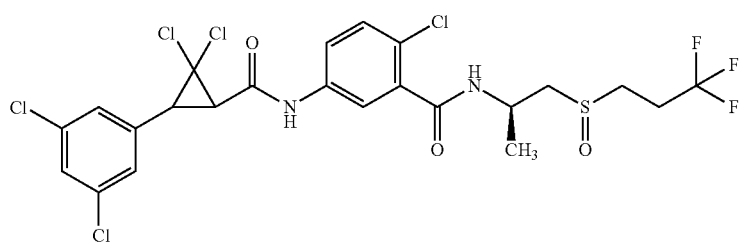 [SMILES: C[C@H](CS(=O)CCC(F)(F)F)NC(=O)c1cc(NC(=O)C2C(c3cc(Cl)cc(Cl)c3)C2(Cl)Cl)ccc1Cl] |

-continued
| No. | Structure |
|---|---|
| PF6 | 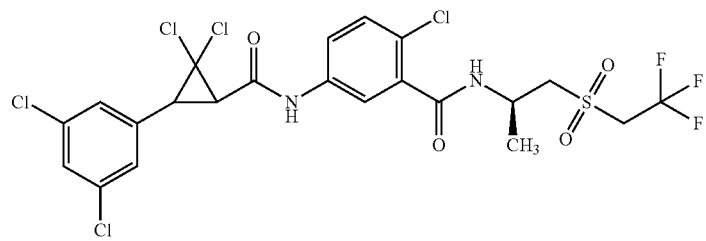 [SMILES: C[C@H](CS(=O)(=O)CC(F)(F)F)NC(=O)c1cc(NC(=O)C2C(c3cc(Cl)cc(Cl)c3)C2(Cl)Cl)ccc1Cl] |
| PF7 | 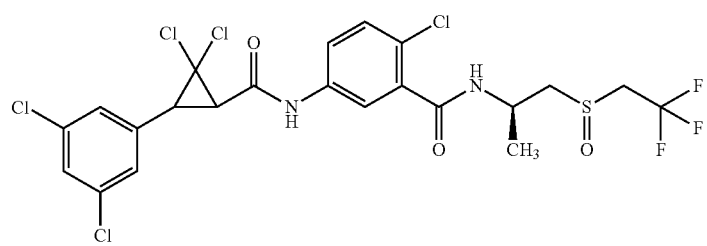 [SMILES: C[C@H](CS(=O)CC(F)(F)F)NC(=O)c1cc(NC(=O)C2C(c3cc(Cl)cc(Cl)c3)C2(Cl)Cl)ccc1Cl] |
| PF9 | 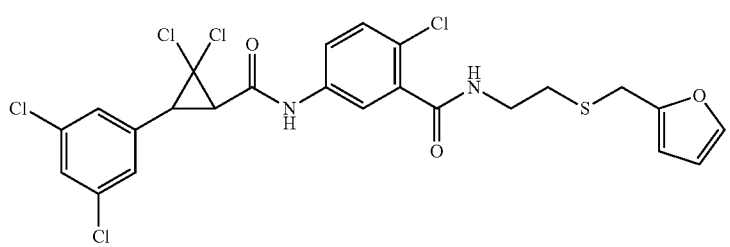 [SMILES: O=C(NCCSCc1ccco1)c1cc(NC(=O)C2C(c3cc(Cl)cc(Cl)c3)C2(Cl)Cl)ccc1Cl] |
| PF10 | 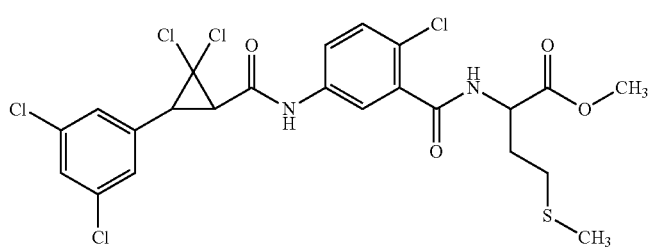 [SMILES: COC(=O)C(CCSC)NC(=O)c1cc(NC(=O)C2C(c3cc(Cl)cc(Cl)c3)C2(Cl)Cl)ccc1Cl] |
| PF11 | 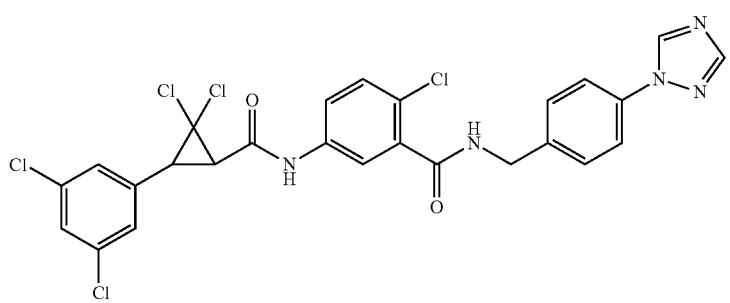 [SMILES: O=C(NCc1ccc(-n2cncn2)cc1)c1cc(NC(=O)C2C(c3cc(Cl)cc(Cl)c3)C2(Cl)Cl)ccc1Cl] |
| PF12 | 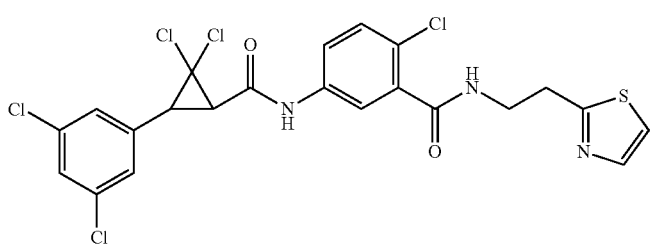 [SMILES: O=C(NCCc1nccs1)c1cc(NC(=O)C2C(c3cc(Cl)cc(Cl)c3)C2(Cl)Cl)ccc1Cl] |

-continued
| No. | Structure |
|---|---|
| PF13 | 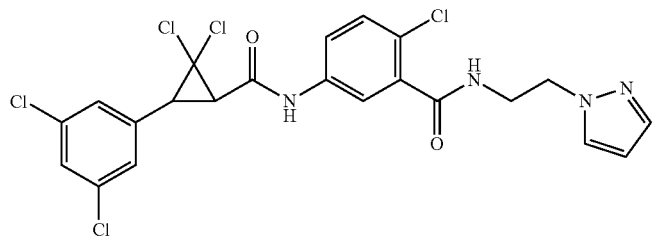 [SMILES: O=C(NCCn1cccn1)c1cc(NC(=O)C2C(c3cc(Cl)cc(Cl)c3)C2(Cl)Cl)ccc1Cl] |
| PF14 | 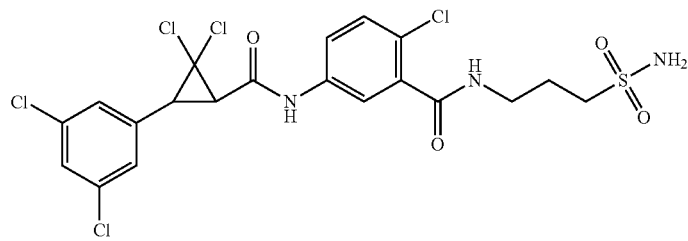 [SMILES: NS(=O)(=O)CCCNC(=O)c1cc(NC(=O)C2C(c3cc(Cl)cc(Cl)c3)C2(Cl)Cl)ccc1Cl] |
| PF15 | 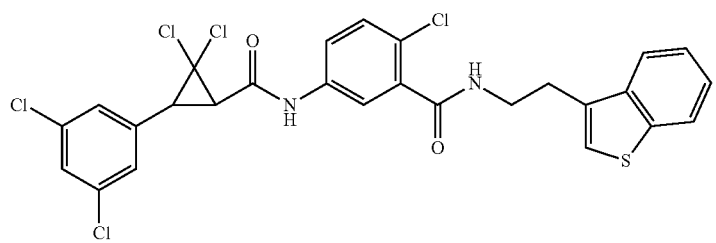 [SMILES: O=C(NCCc1csc2ccccc12)c1cc(NC(=O)C2C(c3cc(Cl)cc(Cl)c3)C2(Cl)Cl)ccc1Cl] |
| PF16 | 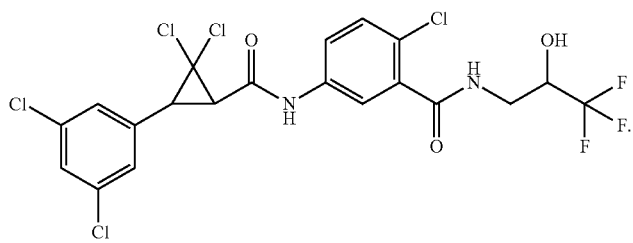 [SMILES: O=C(NCC(O)C(F)(F)F)c1cc(NC(=O)C2C(c3cc(Cl)cc(Cl)c3)C2(Cl)Cl)ccc1Cl] |
20. A molecule according to claim 1 wherein said molecule is selected from the following
| No. | Structure |
|---|---|
| F4 | 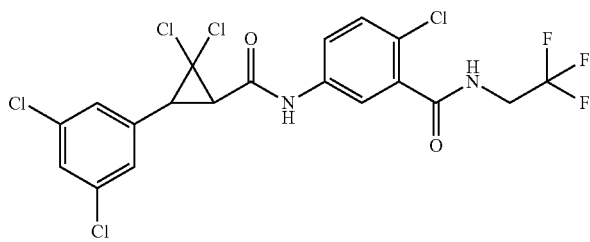 |

-continued
| No. | Structure |
|---|---|
| F15 | 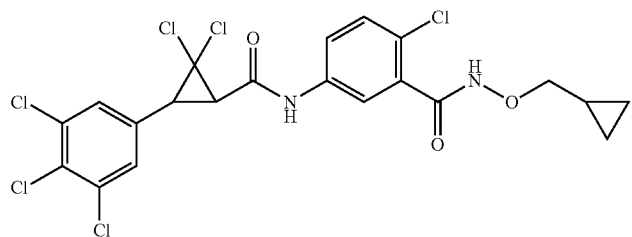 |
| F28 | 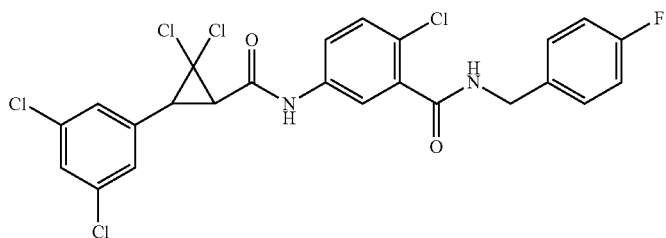 [SMILES: O=C(NCc1ccc(F)cc1)c1cc(NC(=O)C2C(c3cc(Cl)cc(Cl)c3)C2(Cl)Cl)ccc1Cl] |
| F30 | 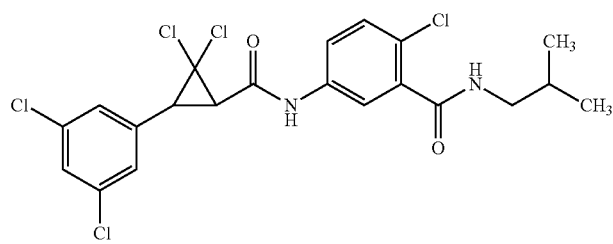 [SMILES: CC(C)CNC(=O)c1cc(NC(=O)C2C(c3cc(Cl)cc(Cl)c3)C2(Cl)Cl)ccc1Cl] |
| F35 | 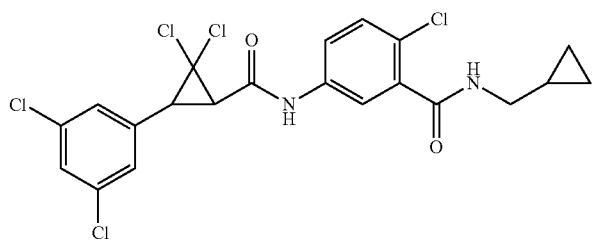 [SMILES: O=C(NCC1CC1)c1cc(NC(=O)C2C(c3cc(Cl)cc(Cl)c3)C2(Cl)Cl)ccc1Cl] |
| F38 | 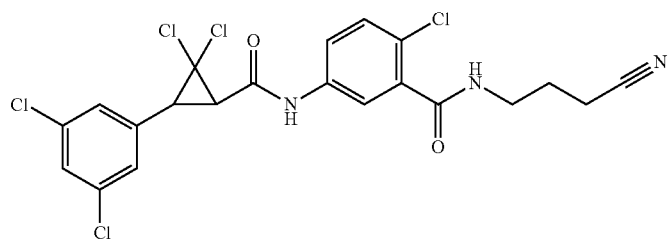 [SMILES: N#CCCCNC(=O)c1cc(NC(=O)C2C(c3cc(Cl)cc(Cl)c3)C2(Cl)Cl)ccc1Cl] |
| F39 | 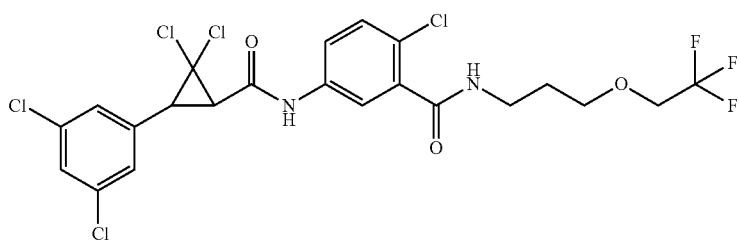 [SMILES: O=C(NCCCOCC(F)(F)F)c1cc(NC(=O)C2C(c3cc(Cl)cc(Cl)c3)C2(Cl)Cl)ccc1Cl] |

-continued

| No. | Structure |
|---|---|
| F40 | 2,2-dichloro-3-(3,5-dichlorophenyl)cyclopropanecarboxamide linked via NH to 2-chloro-5-aminobenzamide, N-(3,3,3-trifluoropropyl) |
| F45 | 2,2-dichloro-3-(3,5-dichlorophenyl)cyclopropanecarboxamide linked via NH to 2-chloro-5-aminobenzamide, N-butyl |
| F46 | 2,2-dichloro-3-(3,5-dichlorophenyl)cyclopropanecarboxamide linked via NH to 2-chloro-5-aminobenzamide, N-ethyl |
| F47 | 2,2-dichloro-3-(3,5-dichlorophenyl)cyclopropanecarboxamide linked via NH to 2-chloro-5-aminobenzamide, N-propargyl |
| F49 | 2,2-dichloro-3-(3,5-dichlorophenyl)cyclopropanecarboxamide linked via NH to 2-chloro-5-aminobenzamide, N-(2,2,3,3,3-pentafluoropropyl) |
| PF16 | 2,2-dichloro-3-(3,5-dichlorophenyl)cyclopropanecarboxamide linked via NH to 2-chloro-5-aminobenzamide, N-(3,3,3-trifluoro-2-hydroxypropyl) |

* * * * *